US012565490B2

(12) United States Patent
Lewis et al.

(10) Patent No.: US 12,565,490 B2
(45) Date of Patent: Mar. 3, 2026

(54) INHIBITORS OF RECEPTOR INTERACTING PROTEIN KINASE I FOR THE TREATMENT OF DISEASE

(71) Applicant: Board of Regents, The University of Texas System, Austin, TX (US)

(72) Inventors: Richard T. Lewis, Missouri City, TX (US); Matthew Hamilton, Missouri City, TX (US); William J. Ray, Houston, TX (US); Fernando Alvarez, Austin, TX (US); Naphtali Reyna, Arlington, TX (US); Suyambu Kesava Vijayan Ramaswamy, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 702 days.

(21) Appl. No.: 17/820,364

(22) Filed: Aug. 17, 2022

(65) Prior Publication Data

US 2023/0159508 A1 May 25, 2023

Related U.S. Application Data

(63) Continuation of application No. PCT/US2021/019797, filed on Feb. 26, 2021.

(60) Provisional application No. 62/983,356, filed on Feb. 28, 2020.

(51) Int. Cl.

| | |
|---|---|
| ***C07D 413/12*** | (2006.01) |
| ***C07D 213/61*** | (2006.01) |
| ***C07D 239/26*** | (2006.01) |
| ***C07D 403/12*** | (2006.01) |
| ***C07D 413/14*** | (2006.01) |
| ***C07D 471/04*** | (2006.01) |
| ***C07D 487/04*** | (2006.01) |
| ***C07D 491/107*** | (2006.01) |
| ***C07D 498/04*** | (2006.01) |

(52) U.S. Cl.

CPC ......... *C07D 413/12* (2013.01); *C07D 213/61* (2013.01); *C07D 239/26* (2013.01); *C07D 403/12* (2013.01); *C07D 413/14* (2013.01); *C07D 471/04* (2013.01); *C07D 487/04* (2013.01); *C07D 491/107* (2013.01); *C07D 498/04* (2013.01)

(58) Field of Classification Search

CPC .. C07D 413/12; C07D 213/61; C07D 239/26; C07D 403/12; C07D 413/14; C07D 471/04; C07D 487/04; C07D 491/107; C07D 498/04; C07D 213/81; C07D 239/28; C07D 401/12; C07D 519/00; A61P 25/00; A61P 27/02; A61P 29/00; A61P 35/00; A61P 43/00

See application file for complete search history.

(56) References Cited

U.S. PATENT DOCUMENTS

| | | | |
|---|---|---|---|
| 9,029,370 | B2 | 5/2015 | Galley |
| 2004/0072876 | A1 | 4/2004 | Kuroda |
| 2005/0032786 | A1 | 2/2005 | Kajino |

FOREIGN PATENT DOCUMENTS

| | | | |
|---|---|---|---|
| WO | 2014125444 | 8/2014 | |
| WO | 2016027253 | 2/2016 | |
| WO | WO-2017004500 A1 * | 1/2017 | ............. A61K 31/55 |
| WO | 2017136727 | 8/2017 | |
| WO | WO-2018039310 A1 * | 3/2018 | ......... A61K 31/4188 |
| WO | 2018073193 | 4/2018 | |
| WO | 2018109097 | 6/2018 | |
| WO | 2018154520 | 8/2018 | |
| WO | 2019204537 | 10/2019 | |
| WO | 2019213447 | 11/2019 | |
| WO | 2021173917 | 9/2021 | |

OTHER PUBLICATIONS

CAS Registry No. 2060583-29-9 (which entered the STN database on Jan. 27, 2017). (Year: 2017).*

International Application No. PCT/US2021/019797; International Search Report and Written Opinion of the International Searching Autority, date of mailing Jul. 8, 2021; 9 pages.

International Application No. PCT/US2021/019797; International Preliminary Report on Patentability, date of issuance Sep. 9, 2022; 6 pages.

* cited by examiner

*Primary Examiner* — Joseph K Mckane
*Assistant Examiner* — Meghan C Heasley
(74) *Attorney, Agent, or Firm* — Cynthia Hathaway; Michael Sertic

(57) ABSTRACT

Disclosed herein are compounds which inhibit RIPK1, pharmaceutical compositions, and methods of treatment of RIPK1-mediated diseases, such as neurodegenerative disorders, inflammatory disorders, and cancer.

31 Claims, No Drawings

INHIBITORS OF RECEPTOR INTERACTING PROTEIN KINASE I FOR THE TREATMENT OF DISEASE

This application is a bypass continuation of International Application No. PCT/US2021/019797, filed Feb. 26, 2021, which claims priority to, and the benefit of, U.S. Application No. 62/983,356, filed Feb. 28 2020, the contents of which are incorporated by reference as if written herein in their entireties.

The role of Receptor Interacting Protein Kinase I (RIPKI) in the regulation of apoptotic or necroptotic cell death pathways has been reported, and its emerging role in the mediation coordinating the response to pro-inflammatory signaling in a number of cell types and contexts is emerging. RIPKI consists of an N-terminal kinase domain, a RHIM (RIP homotypic interaction motif) domain, and a death domain, which collectively undergo extensive post-translational modification in response to signaling through various receptors such as tumor necrosis factor α receptors (TNFRs), toll-like receptors, NOD-like receptor, and others. RIPKI has been most extensively studied in the context of TNFRI signaling, which triggers its recruitment to the C-terminal domain of the receptor via the protein TRADD (TNF receptor associated death domain protein). There, RIPKI is ubiquitinated by the E3 ubiquitin ligases TNF receptor-associated factor 2 (TRAF2) or TRAF5 and the cellular inhibitor of apoptosis proteins (cIAPs) cIAPI and cIAP2. This molecular assembly is known as complex I. Cylindromatosis (CYLD) then mediates the deubiquitination of RIPKI to allow assembly of complex IIb, also known as the necrosome. The necrosome consists of the RIPKI homolog RIPK3 and the pseudokinase MLKL. The assembly and function of the necrosome is inhibited by caspase 8 such that only when caspase 8 activity is blocked is the necrosome functional. In that context the necrosome causes necroptosis, an inflammatory form of programmed cell death in which membrane lysis causes the release of cellular contents into the extracellular space.

RIPKI can also, in different contexts, regulate apoptosis and inflammation. When cIAPs are inhibited so that RIPKI ubiquitination does not occur, RIPKI participates in apoptosis. Ubiquitinated RIPKI can also recruit NF-KB essential modulator (NEMO) and TAKI binding protein 2 or 3 (TAB2/3), leading to activation of inhibitor of kappa B (IKB) kinase beta (IKK) and transforming growth factor beta (TGF)-activated kinase 1 (TAKI), which in turn promotes the NF-KB pro-inflammatory or pro-survival gene expression programs. Given its role in inflammation, RIPK1 has been implicated in many diseases featuring chronic and acute inflammatory signaling, including viral infections, sepsis, retinal degeneration, traumatic brain injury, ischemic stroke, intracerebral hemorrhage, amyotrophic lateral sclerosis, acute kidney injury, myocardial reperfusion injury, Alzheimer's disease, ulcerative colitis, osteoarthritis, and others. In animal models of these diseases, RIPK1 kinase inhibitors such as necrostatin-1 have shown to be effective, leading to the development of such molecules for clinical trials in a number of indications.

Provided herein is a compound of structural Formula (I):

(I)

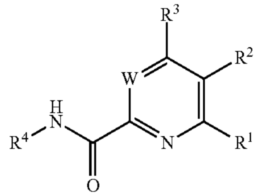

or a salt or tautomer thereof, wherein:

W is chosen from CH, $CR^5$, and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$.

$R^2$ and $R^3$ are independently chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$.

$R^4$ is chosen from alkyl, cycloalkyl, heterocycloalkyl, aryl, heteroaryl, (cycloalkyl)alkyl, (heterocycloalkyl) alkyl, (aryl)alkyl, and (heteroaryl)alkyl, any one of which is optionally substituted with one or more $R^{10}$;

$R^5$ is chosen from H, CN, halo, hydroxy, alkyl, and (alkyl)oxy;

each $R^6$, $R^7$, $R^8$, and $R^9$ is independently chosen from CN, halo, hydroxy, $NH_2$, oxo, alkyl, and (alkyl)oxy;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^2$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl) oxy, and oxo.

In certain embodiments,

W is chosen from CH, $CR^5$, and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$.

$R^2$ and $R^3$ are independently chosen from H, halo, cyano, alkyl, (alkyl)oxy, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^4$ is chosen from alkyl, cycloalkyl, heterocycloalkyl, aryl, heteroaryl, (cycloalkyl)alkyl, (heterocycloalkyl) alkyl, (aryl)alkyl, and (heteroaryl)alkyl, any one of which is optionally substituted with one or more $R^{10}$;

$R^5$ is chosen from H, CN, halo, hydroxy, alkyl, and (alkyl)oxy;

each $R^6$, $R^7$, $R^8$, and $R^9$ is independently chosen from CN, halo, hydroxy, oxo, alkyl, and (alkyl)oxy;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl) oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl) oxy, and oxo.

Also provided are pharmaceutical compositions comprising one or more compounds, salts or tautomers, disclosed herein together with a pharmaceutically acceptable carrier, as well as methods of making and using the compounds, salts, or tautomers, and compositions. Certain embodiments provide methods for inhibiting RIPK1. Certain embodiments provide methods for treating a RIPK1-mediated disorder in a patient in need of such treatment, comprising administering to said patient a therapeutically effective amount of a compound, or a salt or tautomer thereof, or composition as disclosed herein. Also provided is the use of certain compounds, salts or tautomers disclosed herein for use in the manufacture of a medicament for the treatment of a disease or condition ameliorated by the inhibition of RIPK1.

Also provided herein is a compound of structural Formula (Ia):

(Ia)

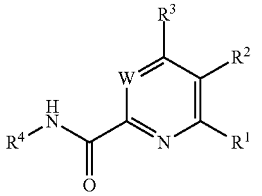

or a salt or tautomer thereof, wherein:

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$.

$R^2$ and $R^3$ are independently chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$.

$R^4$ is chosen from alkyl, cycloalkyl, heterocycloalkyl, aryl, heteroaryl, (cycloalkyl)alkyl, (heterocycloalkyl) alkyl, (aryl)alkyl, and (heteroaryl)alkyl, any one of which is optionally substituted with one or more $R^{10}$;

each $R^6$, $R^7$, $R^8$, and $R^9$ is independently chosen from CN, halo, hydroxy, $NH_2$, oxo, alkyl, and (alkyl)oxy;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl) $SO_2$, (heterocycloalkyl)$SO_2$, (aryl)$SO_2$, (heteroaryl) $SO_2$, (alkyl)NH, (cycloalkyl)NH, (heterocycloalkyl) NH, (aryl)NH, (heteroaryl)NH, (alkyl)oxy, (cycloalkyl) oxy, (heterocycloalkyl)oxy, (aryl)oxy, and (heteroaryl) oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl) oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl) oxy, and oxo.

In certain embodiments, $R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$;

$R^2$ and $R^3$ are independently chosen from H, halo, cyano, alkyl, (alkyl)oxy, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^4$ is chosen from alkyl, cycloalkyl, heterocycloalkyl, aryl, heteroaryl, (cycloalkyl)alkyl, (heterocycloalkyl) alkyl, (aryl)alkyl, and (heteroaryl)alkyl, any one of which is optionally substituted with one or more $R^{10}$;

$R^5$ is chosen from H, CN, halo, hydroxy, alkyl, and (alkyl)oxy;

each $R^6$, $R^7$, $R^8$, and $R^9$ is independently chosen from CN, halo, hydroxy, oxo, alkyl, and (alkyl)oxy;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments, $R^4$ is chosen from $C_{1-6}$alkyl, $C_{3-7}$cycloalkyl, 4- to 11-membered heterocycloalkyl, $C_{6-14}$aryl, 5- to 14-membered heteroaryl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, and (5- to 14-membered heteroaryl)$C_{1-6}$ alkyl, any one of which is optionally substituted with one or more $R^{10}$. In certain embodiments, $R^4$ is chosen from $C_{1-6}$alkyl, $C_{3-7}$cycloalkyl, 4- to 11-membered heterocycloalkyl, $C_{6-14}$aryl, 5- to 14-membered heteroaryl, ($C_{3-7}$cycloalkyl)methyl, (4- to 11-membered heterocycloalkyl)methyl, ($C_{6-10}$ aryl)methyl, (5- to 14-membered heteroaryl)methyl, any one of which is optionally substituted with one or more $R^{10}$. In certain embodiments, $R^4$ is chosen from $C_{1-6}$alkyl, cyclopropyl, cyclobutyl, phenyl, 2,3,4,5-tetrahydro-1H-benzo[b]azepinyl, 2,3,4,5-tetrahydrobenzo[b][1,4]oxazepinyl, 2,3,4,5-tetrahydropyrido[3,2-b][1,4]oxazepin-3-yl, 2,3,4,5-tetrahydro-1H-pyrido[3,4-b]azepin-3-yl, and 5,6,7,8-tetrahydro-4H-pyrazolo[1,5-a][1,3]diazepin-6-yl, any one of which is optionally substituted with one or more $R^{10}$.

In certain embodiments, $R^4$ is optionally substituted with one, two, or three $R^{10}$. In certain embodiments, $R^4$ is optionally substituted with one or two $R^{10}$. In certain embodiments, $R^4$ is substituted with one or two $R^{10}$.

In certain embodiments, $R^4$ is

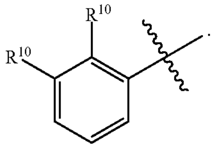

In certain embodiments:

$R^4$ is chosen from:

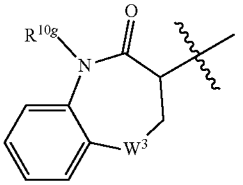,

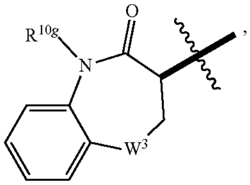,

-continued

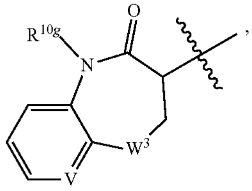,

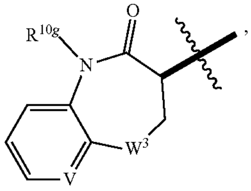,

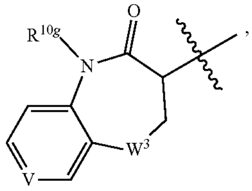,

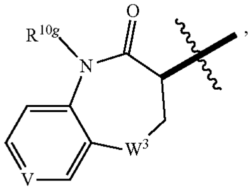,

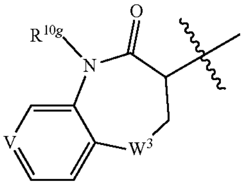,

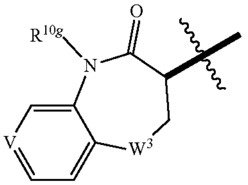,

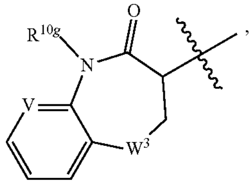,

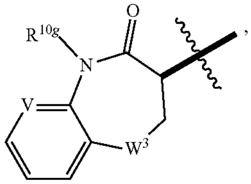,

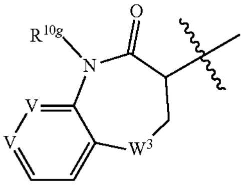,

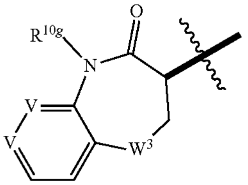,

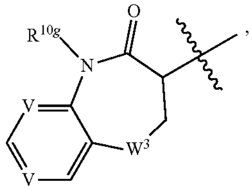,

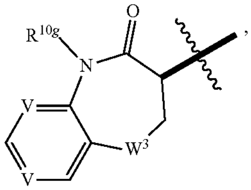,

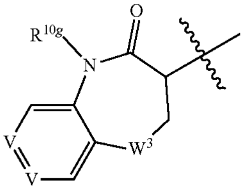,

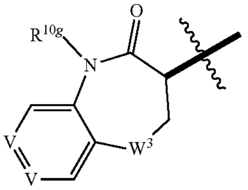,

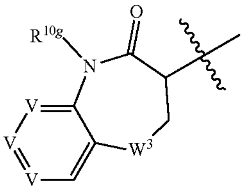,

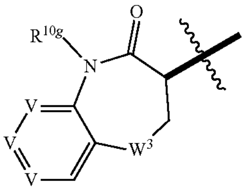,

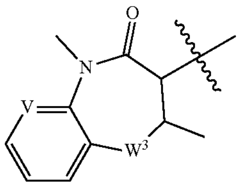, and

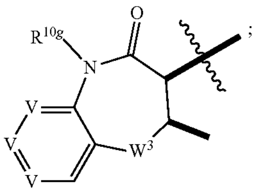;

each V is independently chosen from CH, $C(R^{10})$, and N;

$W^3$ is chosen from $CH_2$, NH, O, and S;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

In certain embodiments:

$R^4$ is chosen from:

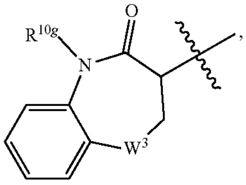,
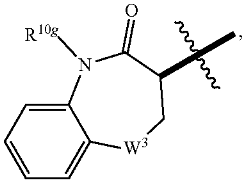,
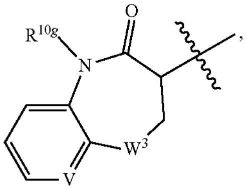,
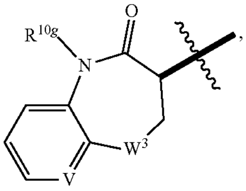,
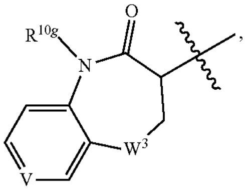,
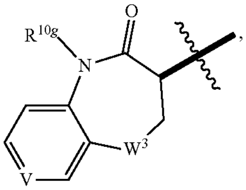,
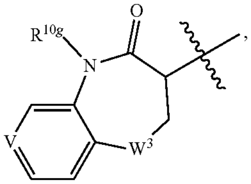,
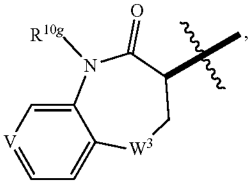,
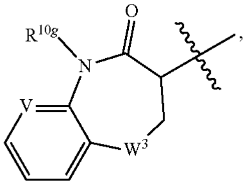,
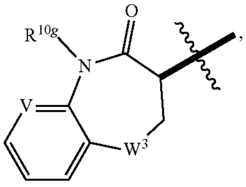, -continued

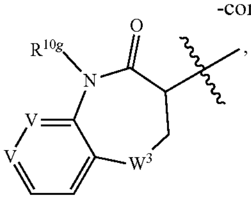,
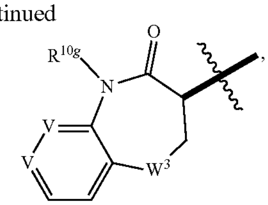,
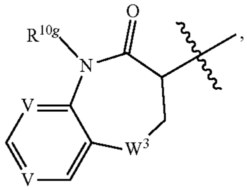,
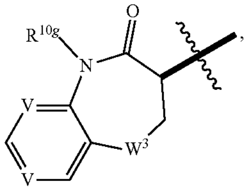,
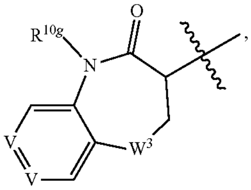,
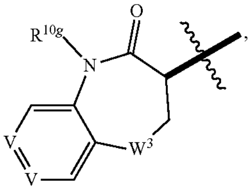,
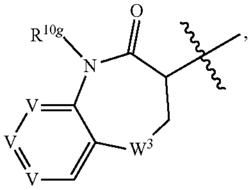, and
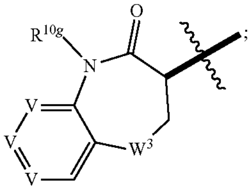;

each V is independently chosen from CH, $C(R^{10})$, and N;

$W^3$ is chosen from $CH_2$, NH, O, and S;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments:

$R^4$ is chosen from:

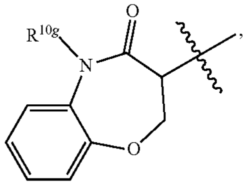,
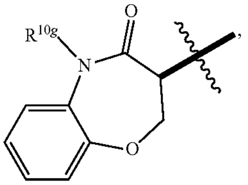,

-continued

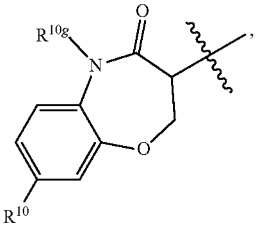
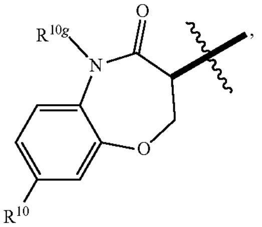
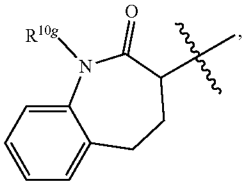
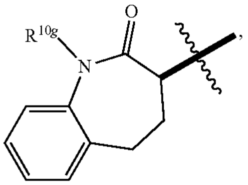
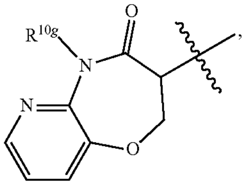
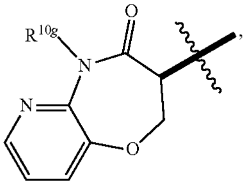
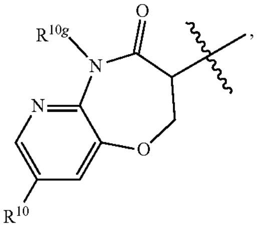
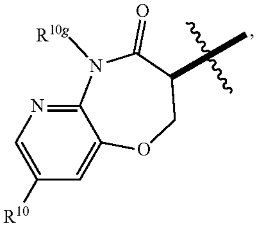
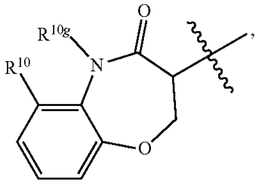
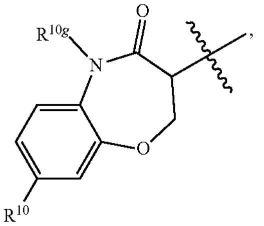
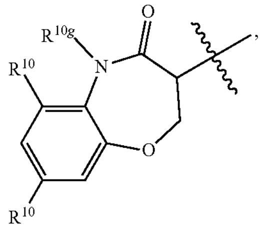
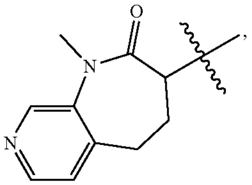
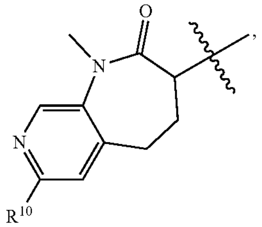
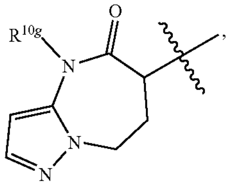
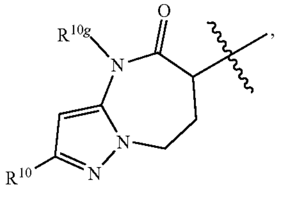

-continued

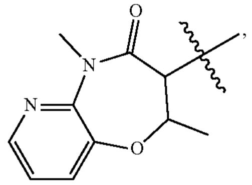
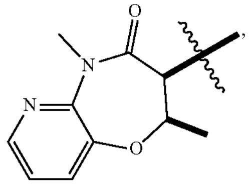
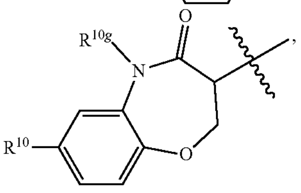
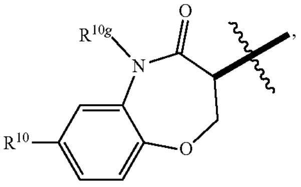
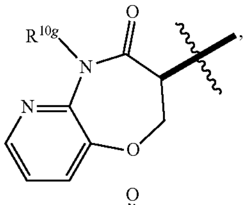
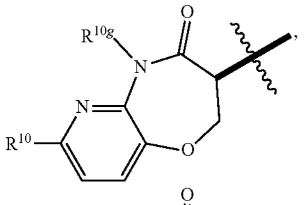
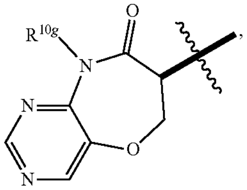
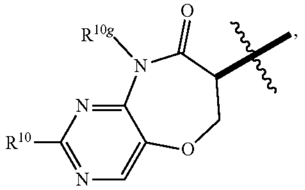
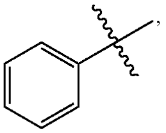
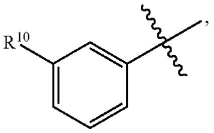
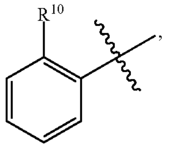

and

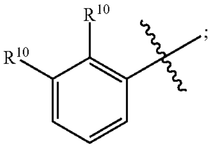

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

In certain embodiments:

$R^4$ is chosen from:

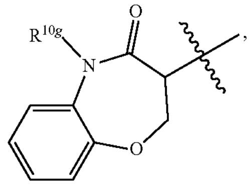,
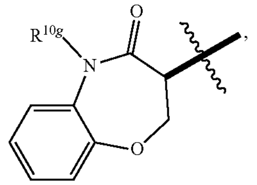,
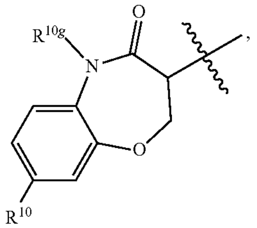,
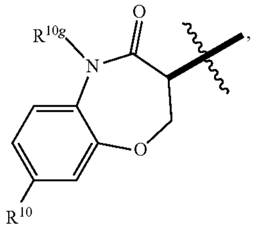,
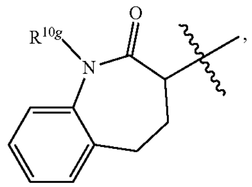,
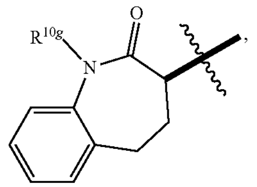,
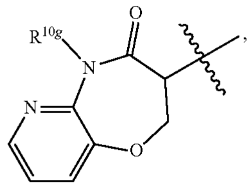,
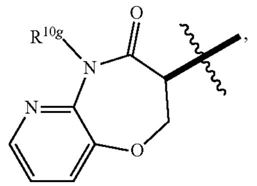,
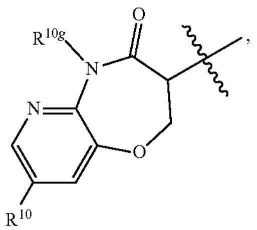,
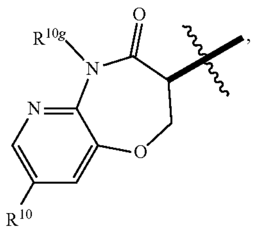,
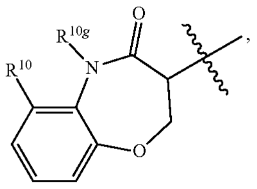,
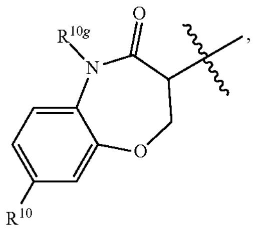, -continued

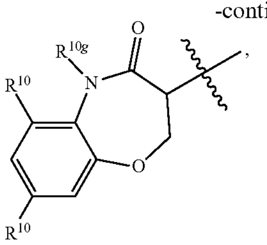,
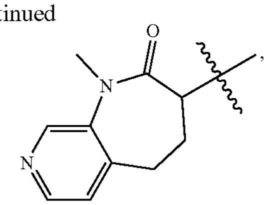,
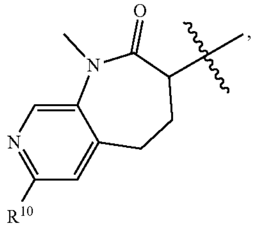,
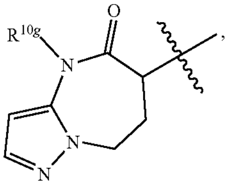,
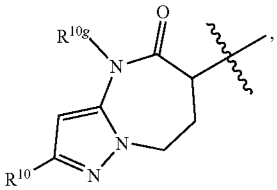,
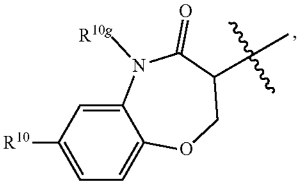,
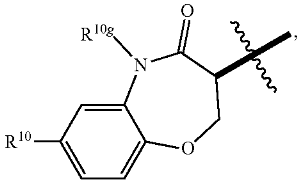,
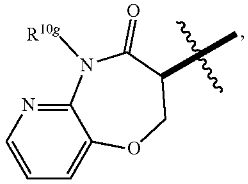,
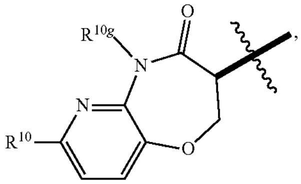,
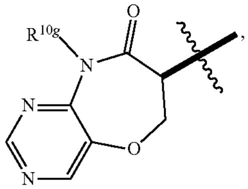,
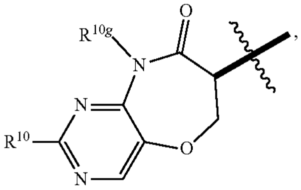,
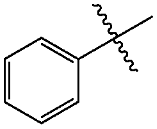,
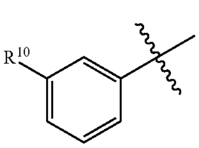,
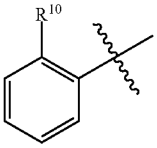, and
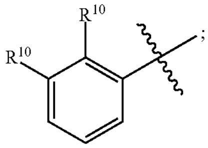;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments:

$R^4$ is chosen from:

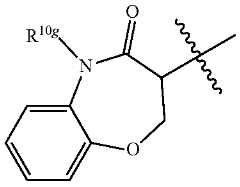,
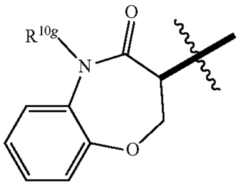,
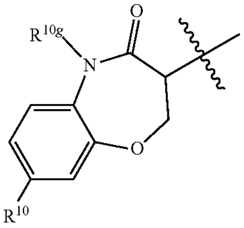,
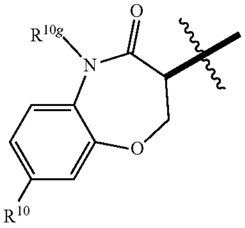,
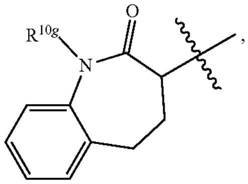,
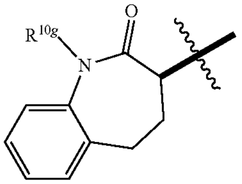,
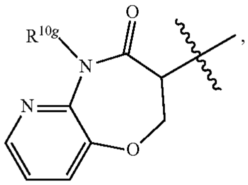,
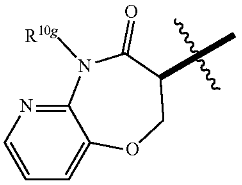,
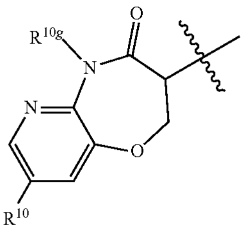,
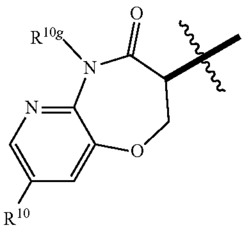, -continued

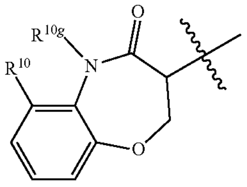,
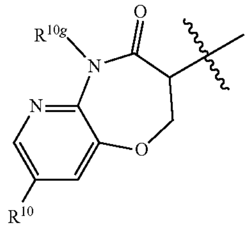,
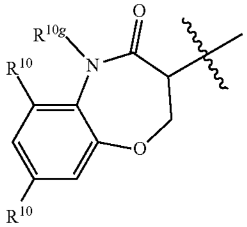,
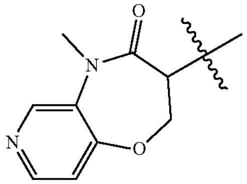,
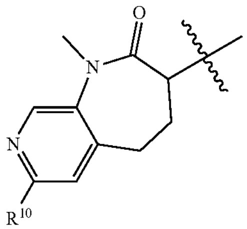,
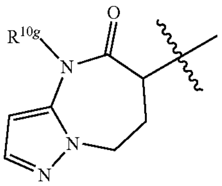,
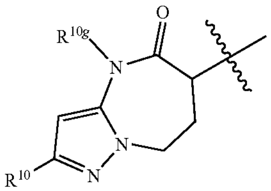,
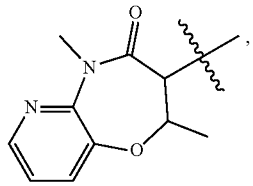,
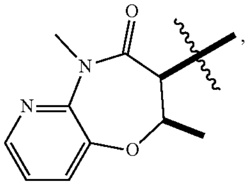,
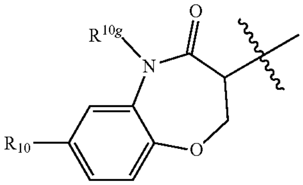,
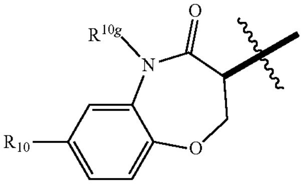,
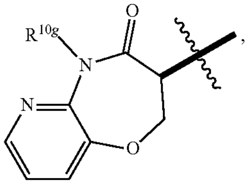,
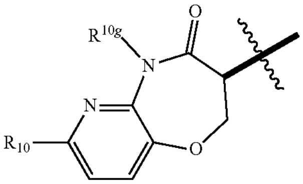, and
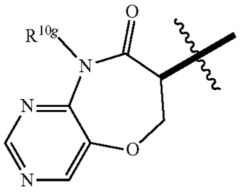

-continued

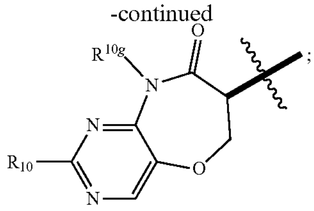;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

In certain embodiments:

$R^4$ is chosen from:

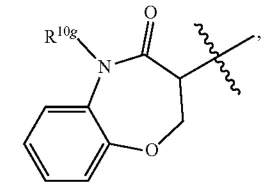,
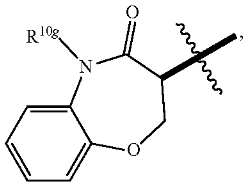,
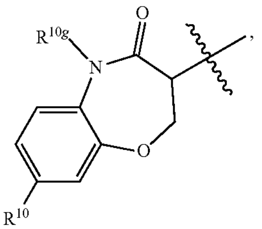,
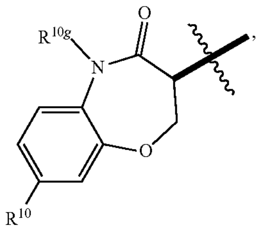,
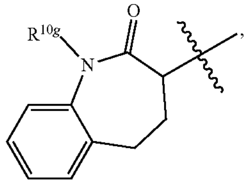,
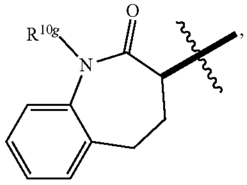,

-continued

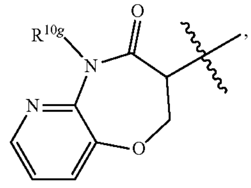,
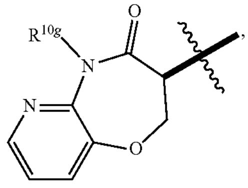,
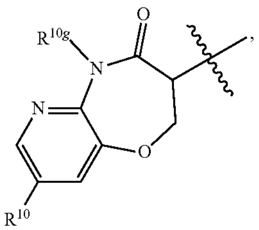,
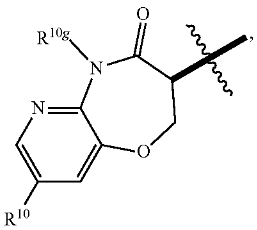,
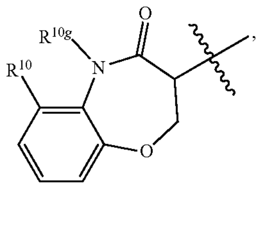,
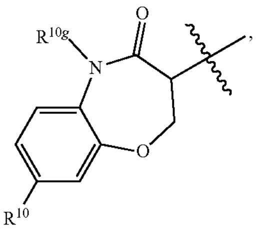,
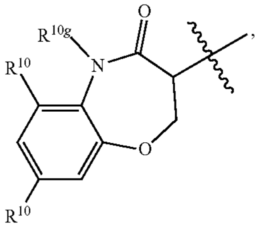,
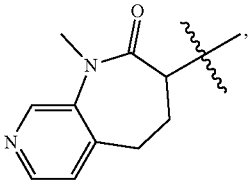,
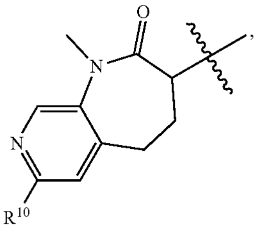,
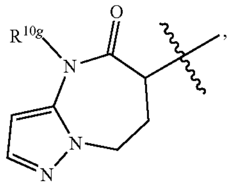,
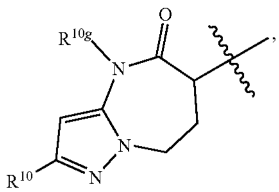,
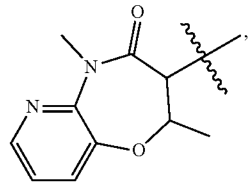,
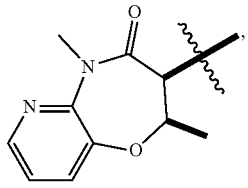,
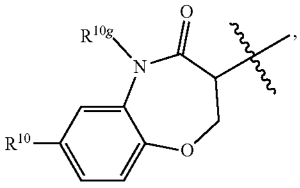, -continued

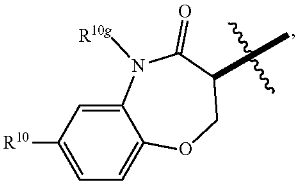

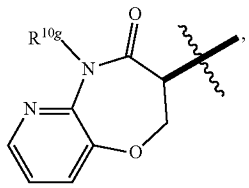

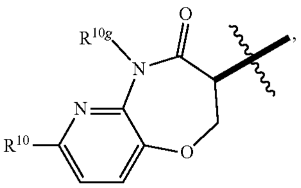

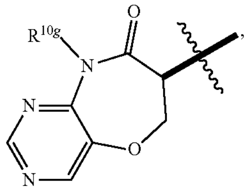

and

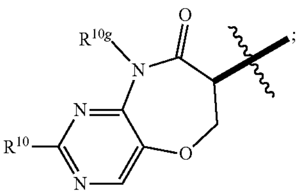

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments, $R^{10g}$ is chosen from H and alkyl. In certain embodiments, $R^{10g}$ is chosen from H and $C_{1-4}$alkyl. In certain embodiments, $R^{10g}$ is chosen from H, $CH_3$, $CD_3$, $CH_2CH_3$, $CH(CH_3)_2$, and $C(CH_3)_3$. In certain embodiments, $R^{10g}$ is chosen from H, $CH_3$, and $CD_3$. In certain embodiments, $R^{10g}$ is $CH_3$.

In certain embodiments, $R^{10g}$ is chosen from H, methyl, ethyl, and 2-propyl. In certain embodiments, $R^{10g}$ is chosen from H, methyl, and methyl-$d_3$. In certain embodiments, $R^{10g}$ is methyl.

In certain embodiments, $R^4$ is

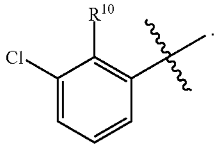

In certain embodiments, $R^4$ is

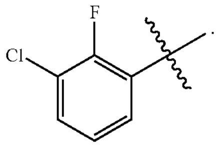 [SMILES: *c1cccc(Cl)c1F]

In certain embodiments:

$R^4$ is chosen from

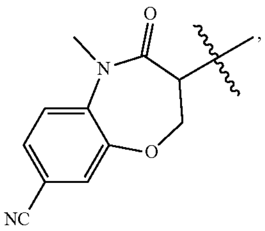

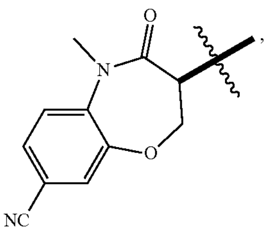

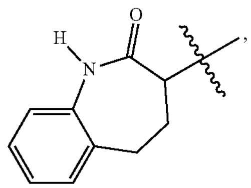

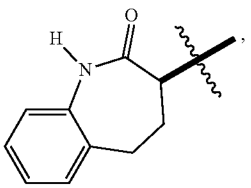

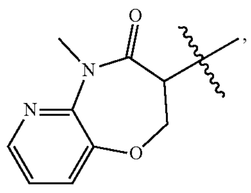

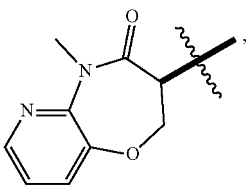

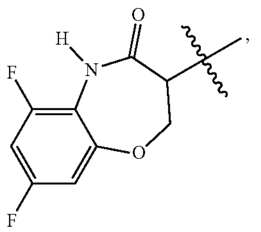

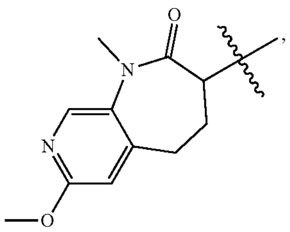

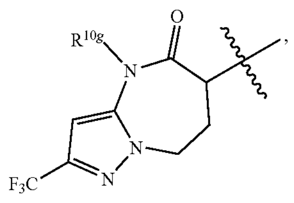

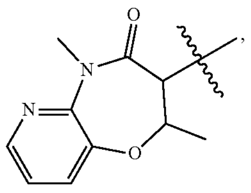

-continued
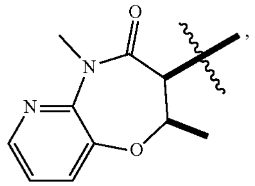
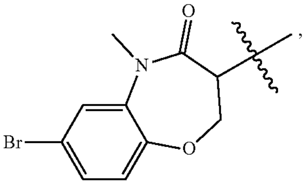
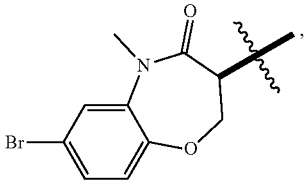
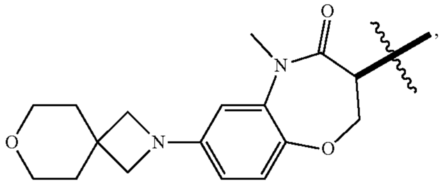
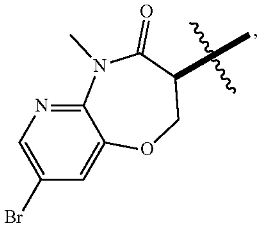
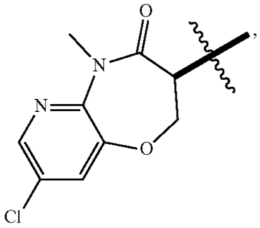
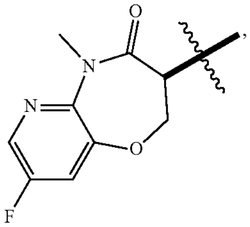
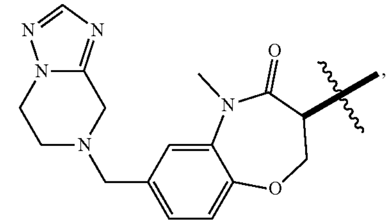
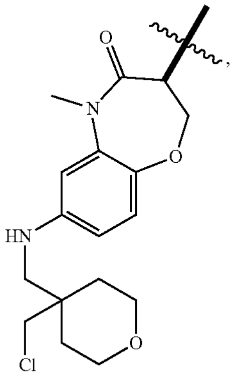
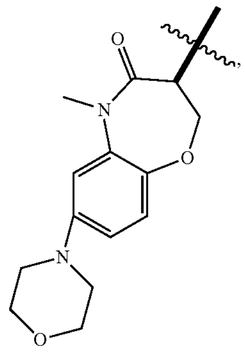
-continued
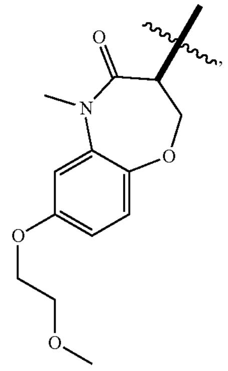
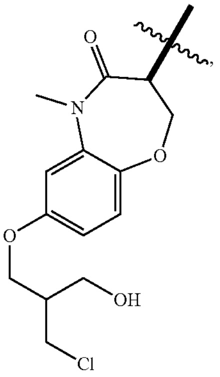
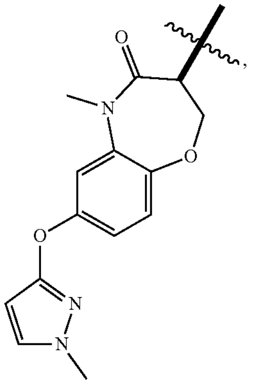
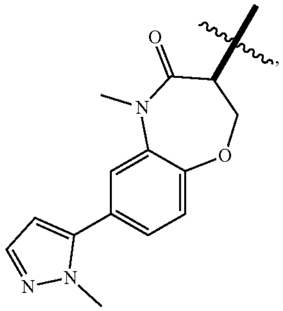
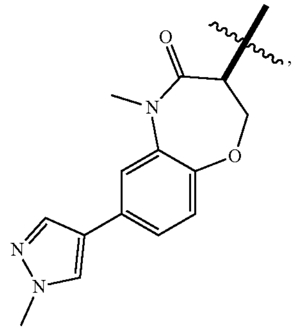
and
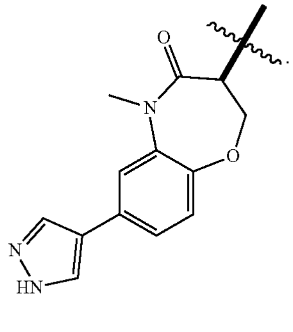

In certain embodiments:

$R^4$ is chosen from

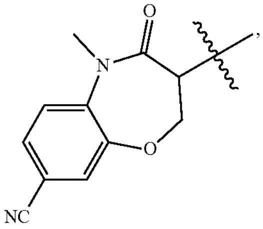
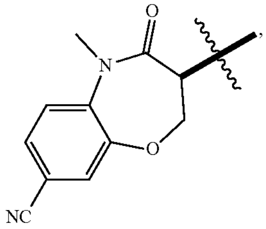
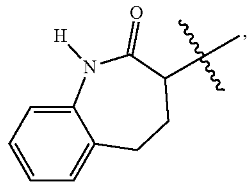
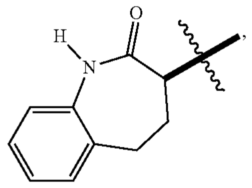
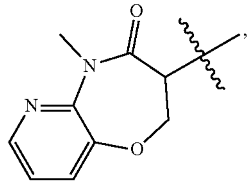
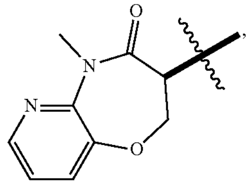
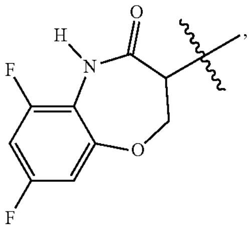
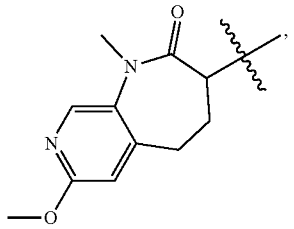
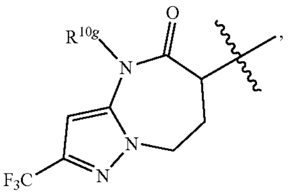
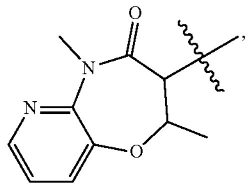
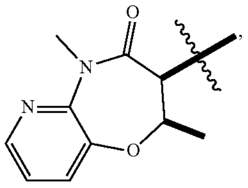
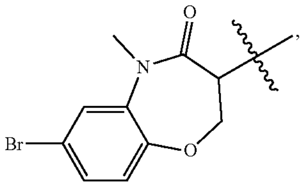
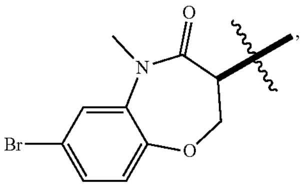
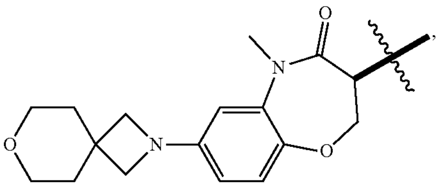

-continued

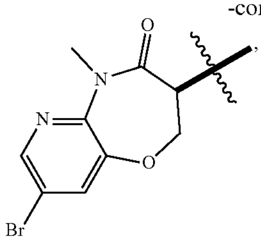
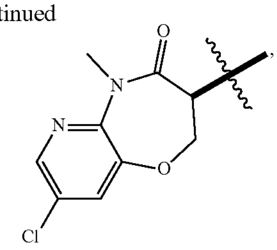
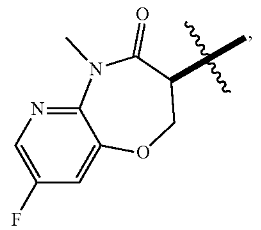

and

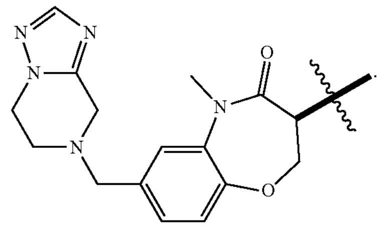

Also provided herein is a compound of structural Formula (II):

(II)

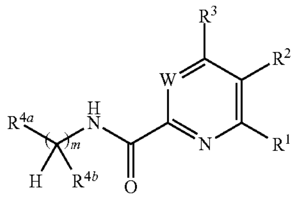

or a salt or tautomer thereof, wherein:

m is chosen from 0, 1, and 2;

W is chosen from CH, $CR^5$, and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$;

$R^2$ and $R^3$ are independently chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^{4a}$ is chosen from alkyl, cycloalkyl, heterocycloalkyl, aryl, and heteroaryl, any one of which is optionally substituted with one or more $R^{10}$;

each $R^{4b}$ is independently chosen from H and alkyl;

$R^5$ is chosen from H, CN, halo, hydroxy, alkyl, and (alkyl)oxy;

each $R^6$, $R^7$, $R^8$, and $R^9$ is independently chosen from CN, halo, hydroxy, $NH_2$, oxo, alkyl, and (alkyl)oxy;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

Also provided herein is a compound of structural Formula (II):

(II)

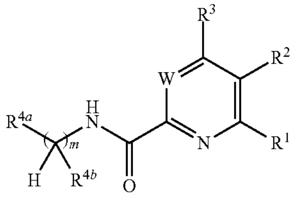

or a salt or tautomer thereof, wherein:

m is chosen from 0, 1, and 2;

W is chosen from CH, $CR^5$, and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^6$.

$R^2$ and $R^3$ are independently chosen from H, halo, cyano, alkyl, (alkyl)oxy, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^{4a}$ is chosen from alkyl, cycloalkyl, heterocycloalkyl, aryl, and heteroaryl, any one of which is optionally substituted with one or more $R^{10}$;

each $R^{4b}$ is independently chosen from H and alkyl;

$R^5$ is chosen from H, CN, halo, hydroxy, alkyl, and (alkyl)oxy;

each $R^6$, $R^7$, $R^8$, and $R^9$ is independently chosen from CN, halo, hydroxy, oxo, alkyl, and (alkyl)oxy;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments, $R^{4a}$ is chosen from $C_{1-6}$alkyl, $C_{3-7}$cycloalkyl, 4- to 11-membered heterocycloalkyl, $C_{6-14}$aryl, and 5- to 14-membered heteroaryl, any one of which is optionally substituted with one or more $R^{10}$. In certain embodiments, $R^{4a}$ is chosen from $C_{1-6}$alkyl, cyclopropyl, cyclobutyl, 2,3,4,5-tetrahydro-1H-benzo[b]azepinyl, 2,3,4,5-tetrahydro-benzo[b][1,4]oxazepinyl, phenyl, pyrrolyl, imidazolyl, pyrazolyl, thiazolyl, isothiazolyl, oxazolyl, isoxazoyl, 1,2,3-oxadiazolyl, 1,2,3-thiadiazolyl, 1,2,4-oxadiazolyl, 1,2,4-thiadiazolyl, pyridinyl, pyrazinyl, pyrimidinyl, pyridazinyl, quinolinyl, isoquinolinyl, indolinyl, acridinyl, pyrazolo[1,5-a]pyridinyl, benzo[d]thiazolyl, 1H-benzo[d]imidazolyl, and 1H-benzo[d][1,2,3]triazolyl, any one of which is optionally substituted with one or more $R^{10}$. In certain embodiments, $R^{4a}$ is chosen from 2,3,4,5-tetrahydro-1H-benzo[b]azepinyl, 2,3,4,5-tetrahydrobenzo[b][1,4]oxazepinyl, phenyl, pyrrolyl, imidazolyl, pyrazolyl, thiazolyl, isothiazolyl, oxazolyl, isoxazoyl, 1,2,3-oxadiazolyl, 1,2,3-thiadiazolyl, 1,2,4-oxadiazolyl, 1,2,4-thiadiazolyl, pyridinyl, pyrazinyl, pyrimidinyl, pyridazinyl, quinolinyl, isoquinolinyl, indolinyl, acridinyl, pyrazolo[1,5-a]pyridinyl, benzo[d]thiazolyl, 1H-benzo[d]imidazolyl, and 1H-benzo[d][1,2,3]triazolyl, any one of which is optionally substituted with one or more $R^{10}$.

In certain embodiments:

$R^{4a}$ is chosen from:

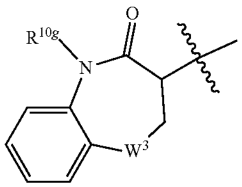, 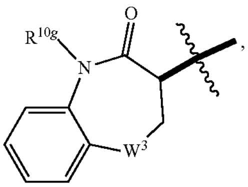,

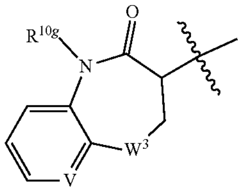, 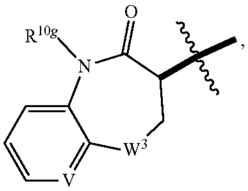,

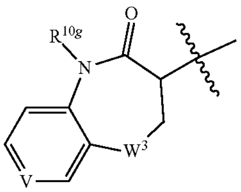, 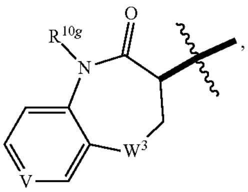,

-continued

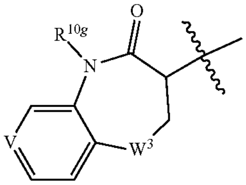, 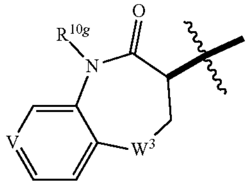,

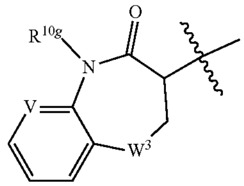, 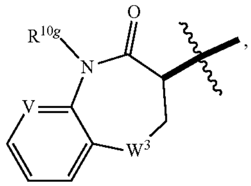,

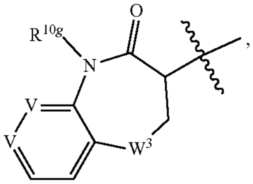, 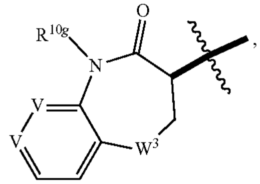,

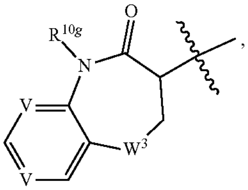, 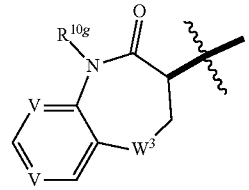,

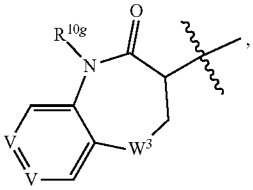, 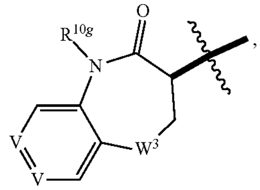,

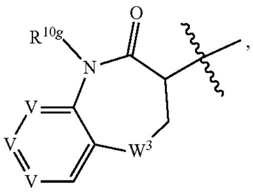, 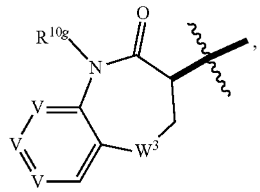,

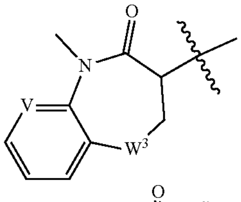, and

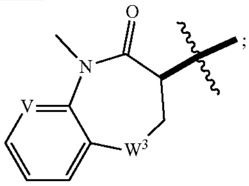;

each V is independently chosen from CH, C($R^{10}$), and N;

$W^3$ is chosen from $CH_2$, NH, O, and S;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

In certain embodiments:

$R^{4a}$ is chosen from:

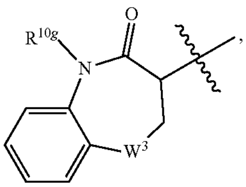, 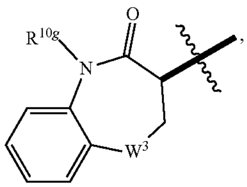,

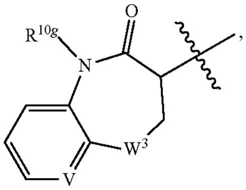, 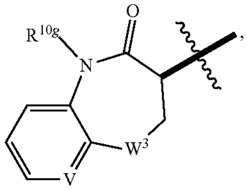,

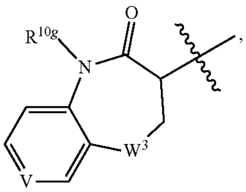, 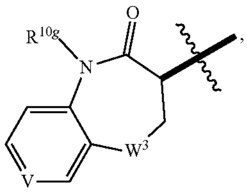,

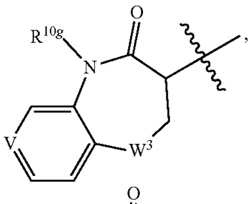, 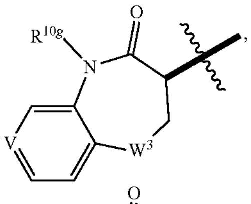,

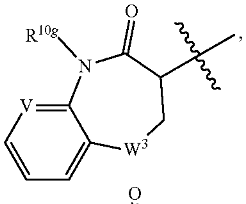, 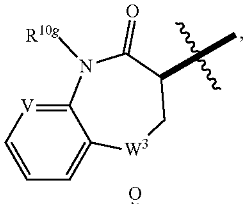,

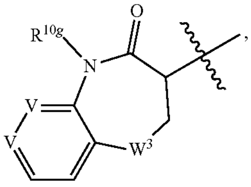, 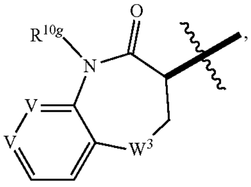,

-continued

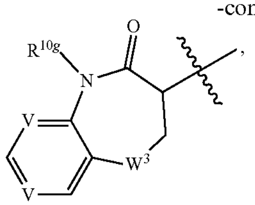

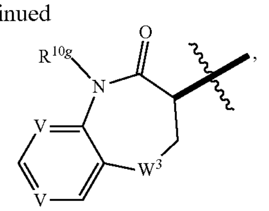

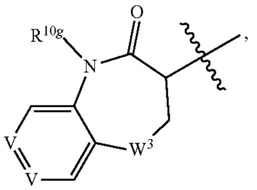

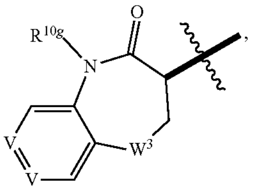

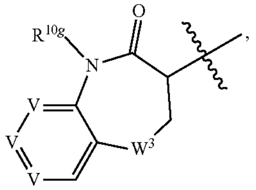

and

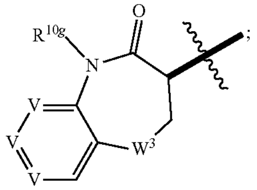

each V is independently chosen from CH, C($R^{10}$), and N;

$W^3$ is chosen from $CH_2$, NH, O, and S;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments:

$R^{4a}$ is chosen from

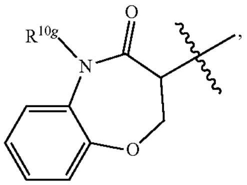

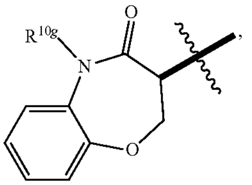

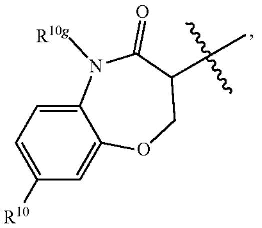

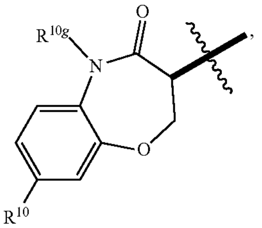

-continued

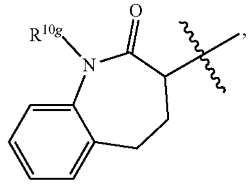

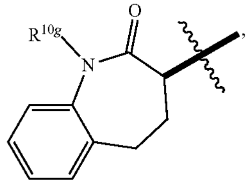

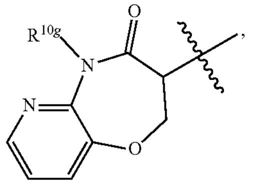

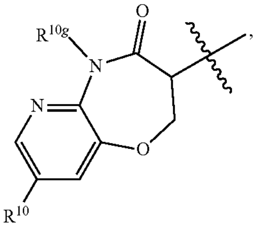

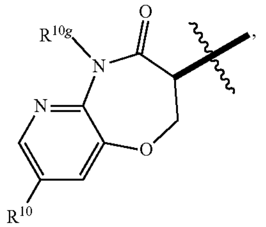

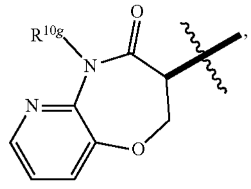

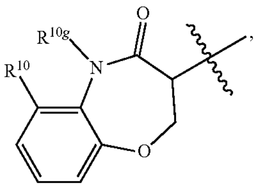

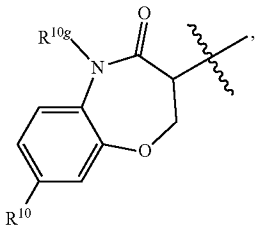

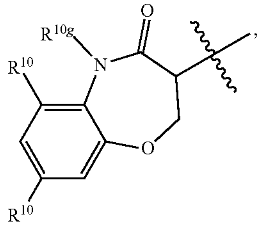

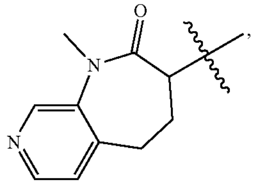

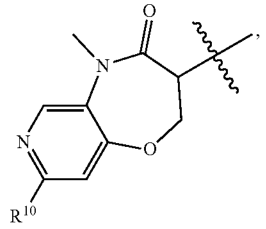

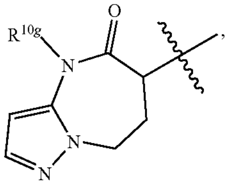

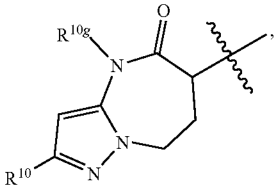

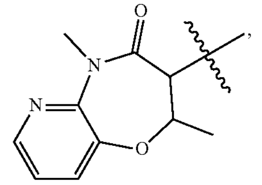

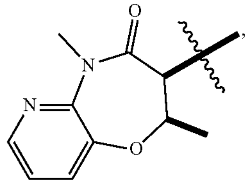

-continued

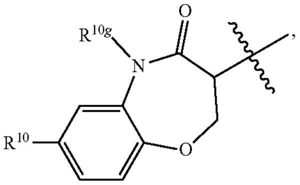

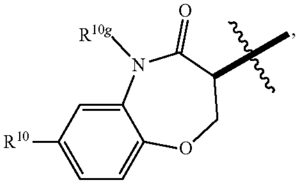

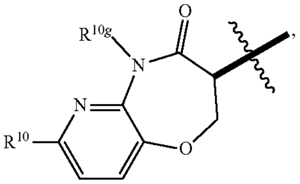

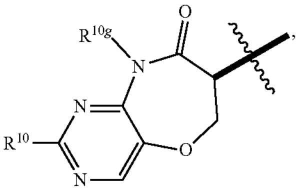

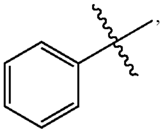 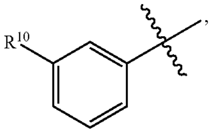

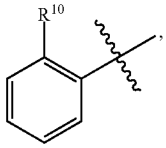 and

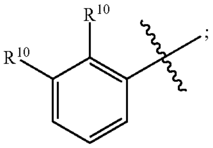

- $R^{10g}$ is chosen from H, alkyl, cycloalkyl, heterocycloalkyl, aryl, and heteroaryl, any one of which is optionally substituted with one or more $R^{11}$;
- each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;
- each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$,
- two $R^{11}$ can combine to form a $C_{5-7}$cycloalkyl or 5- to 7-membered heterocycloalkyl; and
- each $R^{12}$ is chosen from CN, halo, hydroxy, alkyl, (alkyl)oxy, and oxo.

In certain embodiments:

$R^{4a}$ is chosen from

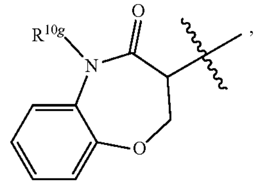 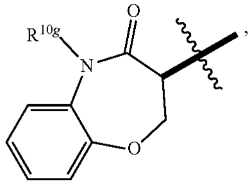

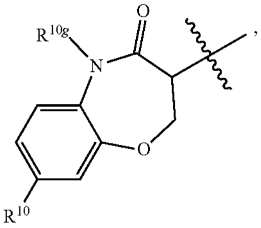 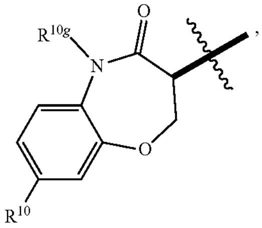

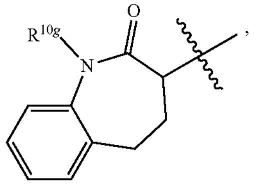 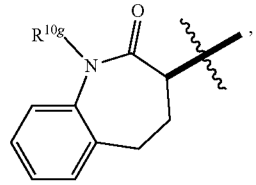

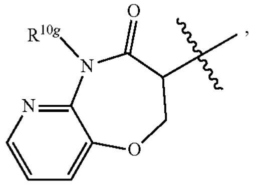 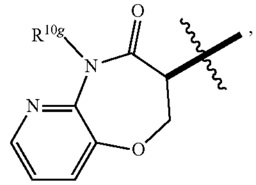

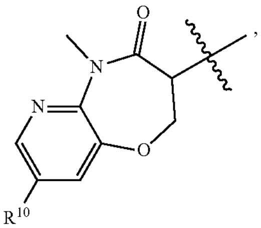 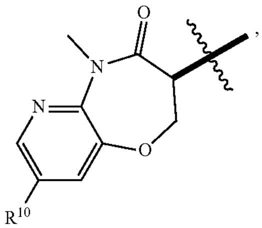

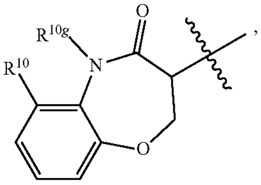 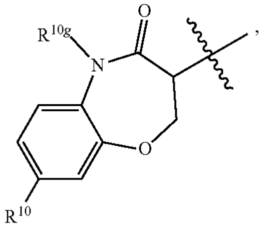

-continued

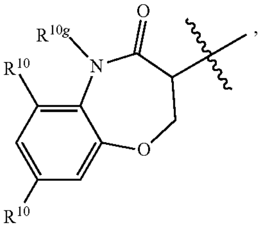 , 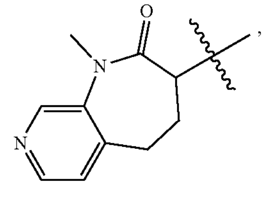 ,

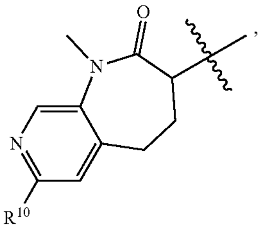 , 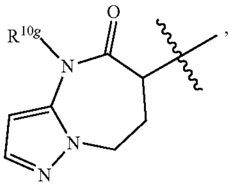 ,

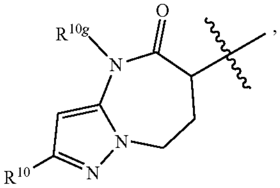 , 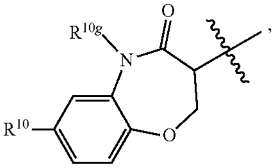 ,

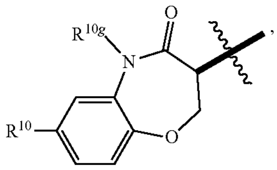 , 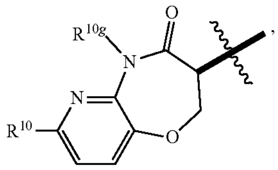 ,

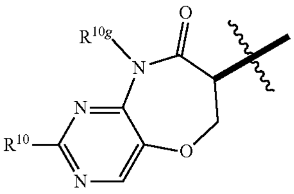 , 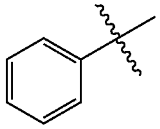 ,

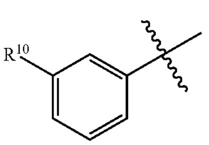 , 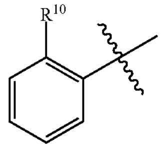 , and

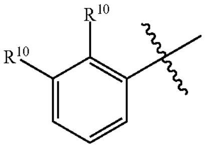 ;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments, $R^{10g}$ is chosen from H and alkyl. In certain embodiments, $R^{10g}$ is chosen from H and $C_{1-4}$alkyl. In certain embodiments, $R^{10g}$ is chosen from H, $CH_3$, $CD_3$, $CH_2CH_3$, $CH(CH_3)_2$, and $C(CH_3)_3$. In certain embodiments, $R^{10g}$ is chosen from H, $CH_3$, and $CD_3$. In certain embodiments, $R^{10g}$ is $CH_3$.

In certain embodiments, $R^{10g}$ is chosen from H, methyl, ethyl, and 2-propyl. In certain embodiments, $R^{10g}$ is chosen from H, methyl, and methyl-$d_3$. In certain embodiments, $R^{10g}$ is methyl.

Also provided herein is a compound of structural Formula (III):

(III)

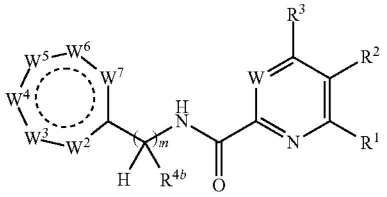

or a salt or tautomer thereof, wherein:

m is chosen from 0, 1, and 2;

W is chosen from CH, $CR^5$, and N;

$W^2$ is chosen from $CHR^{10a}$, $CR^{10a}$, $NR^{10a}$, N, O, and S;

$W^3$ is chosen from $CHR^{10b}$, $CR_{10b}$, $NR_{10b}$, N, O, and S;

$W^4$ is chosen from a bond, $CHR^{10c}$, $CR_{10c}$, $NR_{10c}$, N, O, and S;

$W^5$ is chosen from $CHR^{10d}$, $CR_{10d}$, $NR_{10d}$, N, O, and S;

$W^6$ is chosen from $CHR^{10e}$, $CR^{10e}$, $NR^{10e}$, N, O, and S;

$W^7$ is chosen from $CHR^{10f}$, $CR^{10f}$, $NR^{10f}$, N, O, and S;

$W^2$, $W^3$, $W^4$, $W_5$, $W^6$, and $W^7$, together with the intervening carbon, combine to form a 6- or 7-membered cycloalkyl, heterocycloalkyl, aryl, or heteroaryl;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^6$.

$R^2$ and $R^3$ are independently chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$.

each $R^{4b}$ is independently chosen from H and alkyl;

$R^5$ is chosen from H, CN, halo, hydroxy, alkyl, and (alkyl)oxy;

each $R^6$, $R^7$, $R^8$, and $R^9$ is independently chosen from CN, halo, hydroxy, $NH_2$, oxo, alkyl, and (alkyl)oxy;

$R^{10a}$ and $R^{10b}$ can combine, together with the intervening two atoms, to form a 5-, 6-, or 7-membered cycloalkyl, heterocycloalkyl, aryl, or heteroaryl, any one of which is optionally substituted with one or more $R^{10}$;

$R^{10c}$ and $R^{10d}$ can combine, together with the intervening two atoms, to form a 5-, 6-, or 7-membered cycloalkyl, heterocycloalkyl, aryl, or heteroaryl, any one of which is optionally substituted with one or more $R^{10}$;

$R^{10e}$ and $R^{10f}$ can combine, together with the intervening two atoms, to form a 5-, 6-, or 7-membered cycloalkyl, heterocycloalkyl, aryl, or heteroaryl, any one of which is optionally substituted with one or more $R^{10}$;

$R^{10a}$ and $R^{10e}$ can combine to form alkylene, which is optionally substituted with one or more $R^{10}$;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

$R^{10a}$, $R^{10b}$, $R^{10c}$, $R^{10d}$, $R^{10e}$, and $R^{10f}$, unless otherwise defined, are independently chosen from H, CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

Also provided herein is a compound of structural Formula (III):

(III)

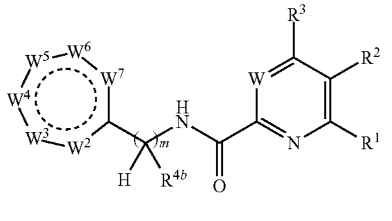

or a salt or tautomer thereof, wherein:

m is chosen from 0, 1, and 2;

W is chosen from CH, $CR^5$, and N;

$W^2$ is chosen from $CHR^{10a}$, $CR^{10a}$, $NR^{10a}$, N, O, and S;

$W^3$ is chosen from $CHR^{10b}$, $CR_{10b}$, $NR^{10b}$, N, O, and S;

$W^4$ is chosen from a bond, $CHR^{10c}$, $CR^{10c}$, $NR_{10c}$, N, O, and S;

$W^5$ is chosen from $CHR^{10d}$, $CR^{10d}$, $NR^{10d}$, N, O, and S;

$W^6$ is chosen from $CHR^{10e}$, $CR^{10e}$, $NR^{10e}$, N, O, and S;

$W^7$ is chosen from $CHR^{10f}$, $CR^{10f}$, $NR^{10f}$, N, O, and S;

$W^2$, $W^3$, $W^4$, $W^5$, $W^6$, and $W^7$, together with the intervening carbon, combine to form a 6- or 7-membered cycloalkyl, heterocycloalkyl, aryl, or heteroaryl;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^6$;

$R^2$ and $R^3$ are independently chosen from H, halo, cyano, alkyl, (alkyl)oxy, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

each $R^{4b}$ is independently chosen from H and alkyl;

$R^5$ is chosen from H, CN, halo, hydroxy, alkyl, and (alkyl)oxy;

each $R^6$, $R^7$, $R^8$, and $R^9$ is independently chosen from CN, halo, hydroxy, oxo, alkyl, and (alkyl)oxy;

$R^{10a}$ and $R^{10b}$ can combine, together with the intervening two atoms, to form a 5-, 6-, or 7-membered cycloalkyl, heterocycloalkyl, aryl, or heteroaryl, any one of which is optionally substituted with one or more $R^{10}$;

$R^{10c}$ and $R^{10a}$ can combine, together with the intervening two atoms, to form a 5-, 6-, or 7-membered cycloalkyl, heterocycloalkyl, aryl, or heteroaryl, any one of which is optionally substituted with one or more $R^{10}$;

$R^{10e}$ and $R^{10f}$ can combine, together with the intervening two atoms, to form a 5-, 6-, or 7-membered cycloalkyl, heterocycloalkyl, aryl, or heteroaryl, any one of which is optionally substituted with one or more $R^{10}$;

$R^{10e}$ and $R^{10f}$ can combine to form alkylene, which is optionally substituted with one or more $R^{10}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

$R^{10a}$, $R^{10b}$, $R^{10c}$, $R^{10d}$, $R^{10e}$, and $R^{10f}$, unless otherwise defined, are independently chosen from H, CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments, $W^7$ is C=O.

In certain embodiments, $W^6$ is chosen from NH and $N(CH_3)$.

In certain embodiments, $R^{10c}$ and $R^{10d}$ combine, together with the intervening two atoms, to form phenyl or a 5- or 6-membered heteroaryl, any one of which is optionally substituted with one or more $R^{10}$. In certain embodiments, $R^{10c}$ and $R^{10d}$ combine, together with the intervening two atoms, to form phenyl or a 6-membered heteroaryl, either one of which is optionally substituted with one or more $R^{10}$.

In certain embodiments, $R^{10c}$ and $R^{10d}$ combine, together with the intervening two atoms, to form phenyl, pyridinyl, pyridazinyl, pyrimidinyl, or pyrazinyl, any one of which is optionally substituted with one or two $R^{10}$. In certain embodiments, $R^{10c}$ and $R^{10d}$ combine, together with the intervening two atoms, to form phenyl or pyridinyleither one of which is optionally substituted with one or two $R^{10}$.

In certain embodiments, each $R^{4b}$ is independently chosen from H and $C_{1-6}$alkyl. In certain embodiments, each $R^{4b}$ is independently chosen from H, methyl, and ethyl. In certain embodiments, each $R^{4b}$ is independently chosen from H and methyl. In certain embodiments, at most one $R^{4b}$ is not H. In certain embodiments, $R^{4b}$ is H.

In certain embodiments, m is chosen from 0 and 1. In certain embodiments, m is 0.

In certain embodiments, $R^{10a}$, $R^{10b}$, $R^{10c}$, $R^{10d}$, $R^{10e}$, and $R^{10c}$ are independently chosen from H, CN, halo, hydroxy, oxo, $C_{1-6}$alkyl, $C_{3-7}$cycloalkyl, 5- to 14-membered heterocycloalkyl, $C_{6-14}$aryl, 5- to 14-membered heteroaryl, ($C_{1-6}$ alkyl)oxy, ($C_{3-7}$cycloalkyl)oxy, (5- to 14-membered heterocycloalkyl)oxy, ($C_{6-14}$aryl)oxy, and (5- to 14-membered heteroaryl)oxy, any one of which is optionally substituted with one or two $R^{11}$. In certain embodiments, $R^{10a}$, $R^{10b}$, $R^{10c}$, $R^{10d}$, $R^{10e}$, and $R^{10f}$ are independently chosen from H, CN, halo, hydroxy, oxo, methyl, ethyl, cyclopropyl, and cyclobutyl, any one of which is optionally substituted with one or two $R^{11}$.

In certain embodiments, $R^{10a}$, $R^{10b}$, $R^{10c}$, $R^{10d}$, $R^{10e}$, and $R^{10f}$ are optionally substituted with one $R^{11}$. In certain embodiments, at most one of $R^{10a}$, $R^{10b}$, $R^{10c}$, $R^{10d}$, $R^{10e}$, and $R^{10f}$ is substituted with an $R^{11}$.

In certain embodiments, exactly one of $R^{10a}$, $R^{10b}$, $R^{10c}$, $R^{10d}$, $R^{10e}$ and $R^{10f}$ is substituted with an $R^{11}$.

In certain embodiments, none of $R^{10a}$, $R^{10b}$, $R^{10c}$, $R^{10d}$, $R^{10e}$, and $R^{10f}$ is substituted with an $R^{11}$.

In certain embodiments, $R^{10a}$, $R^{10b}$, $R^{10c}$, $R^{10d}$, $R^{10e}$, and $R^{10f}$ are independently chosen from H, CN, halo, hydroxy, oxo, and methyl.

In certain embodiments, $W^4$ is chosen from $CHR^{10c}$, $CR^{10c}$, $NR^{10c}$, N, O, and S.

In certain embodiments:

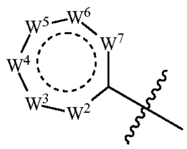

is chosen from

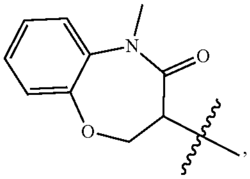

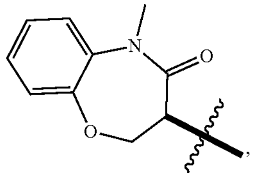

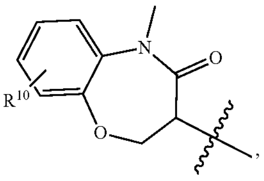

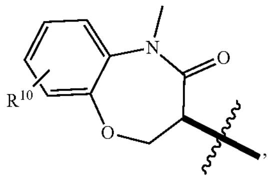

-continued

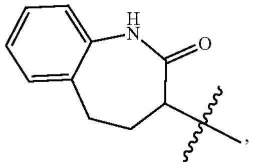

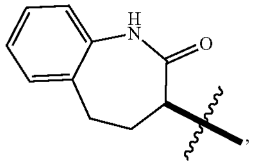

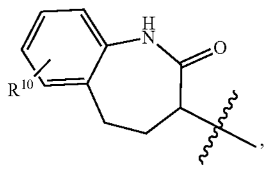

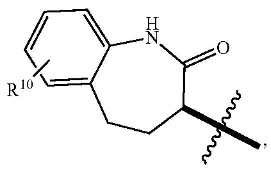

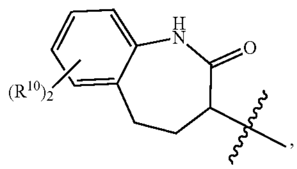

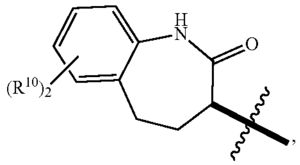

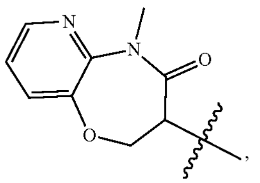

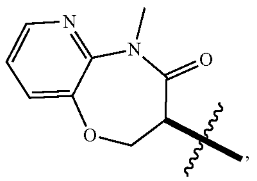

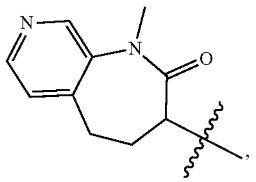

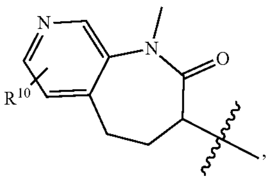

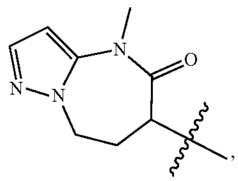

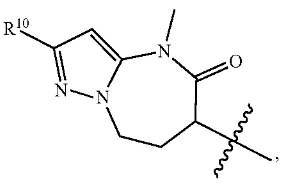

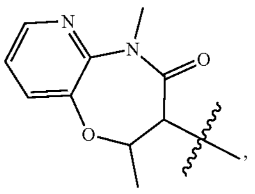

and

-continued
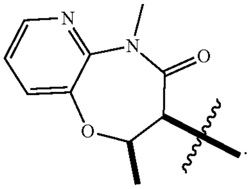.
In certain embodiments:
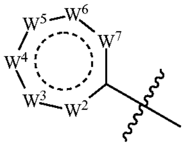
is chosen from
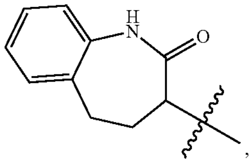, 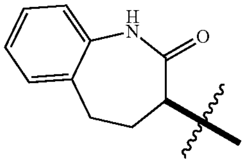, 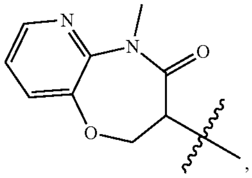, 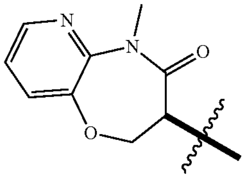, 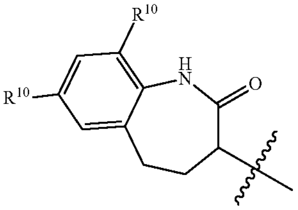, 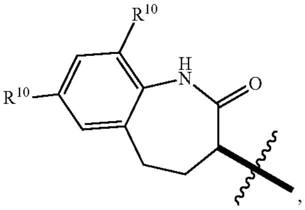, 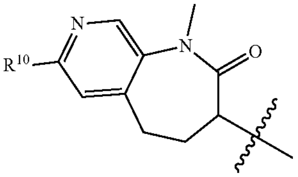, 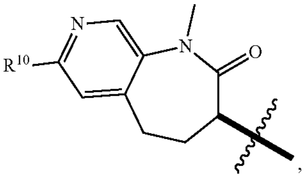,
-continued
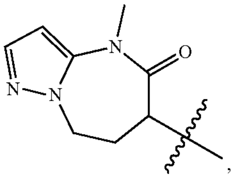, 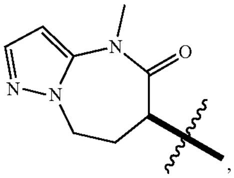, 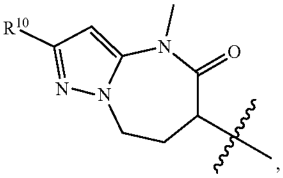, 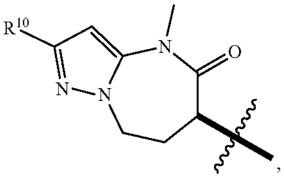, 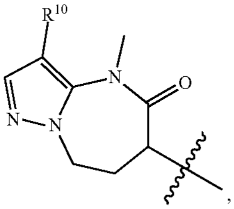, 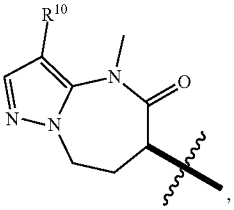, 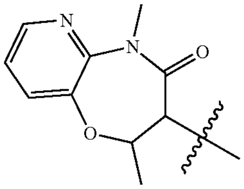, 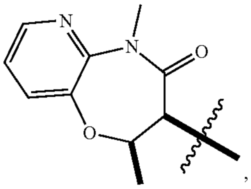, 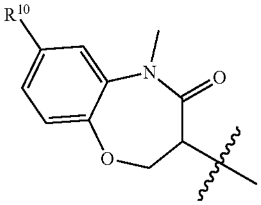, 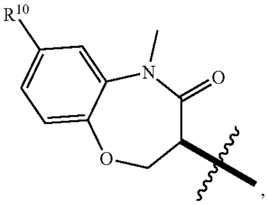, 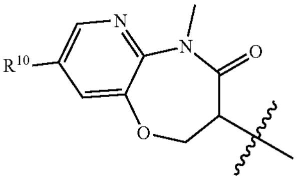, and 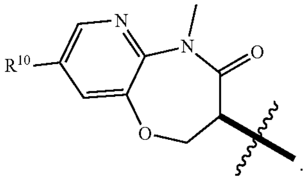.
In certain embodiments:
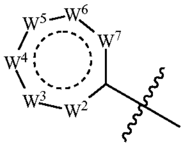

is chosen from
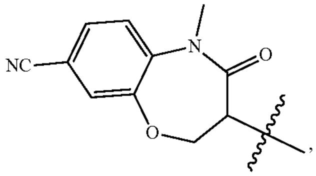,
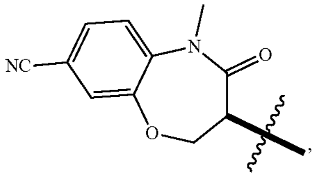,
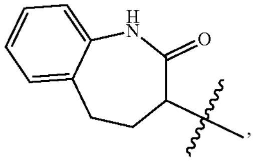,
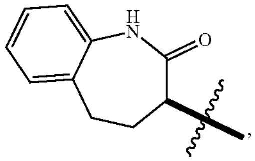,
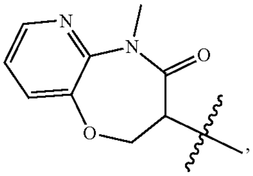,
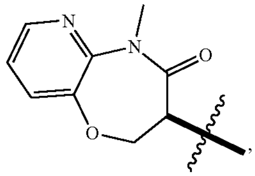,
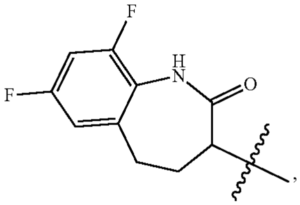,
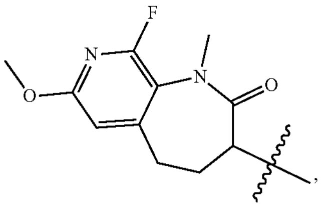,
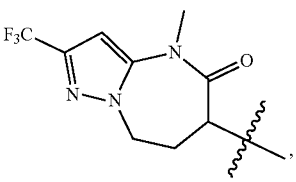,
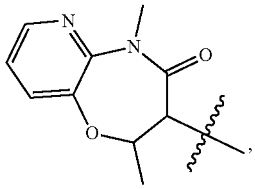,
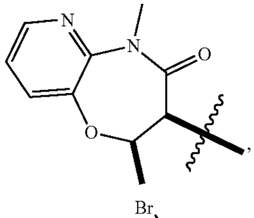,
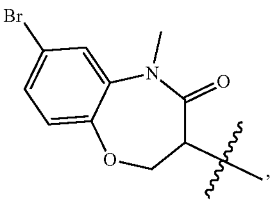,
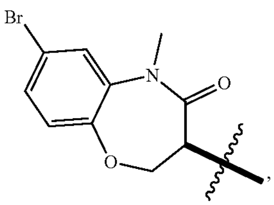,
-continued
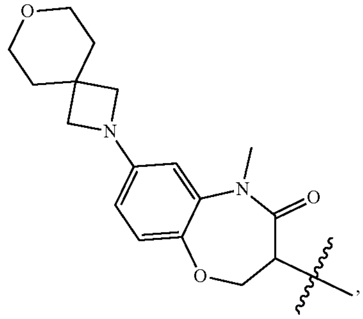,
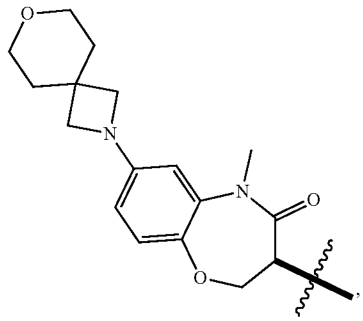,
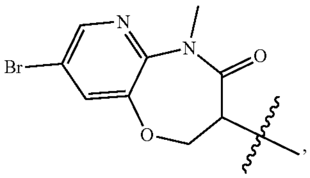,
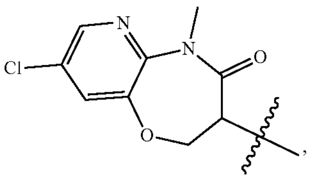,
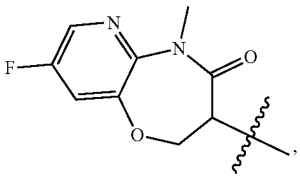,
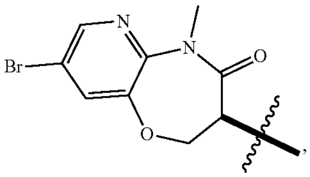,
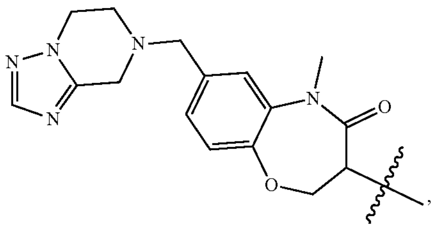, -continued

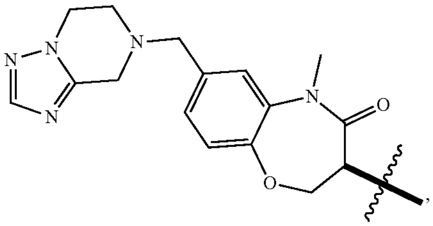

,

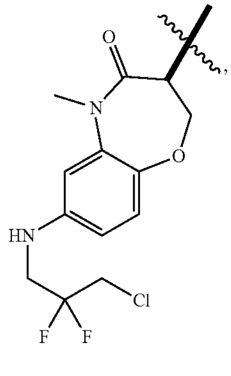

,

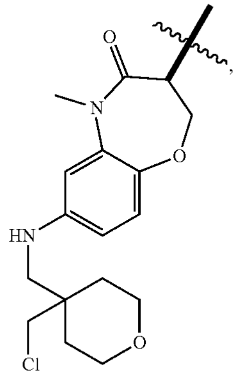

,

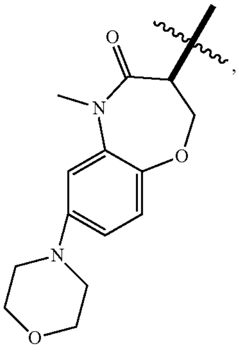

,

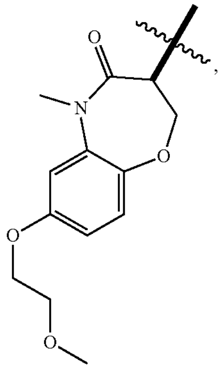

,

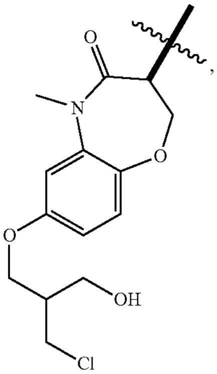

,

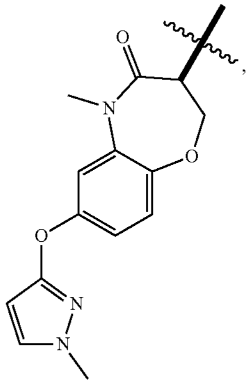

,

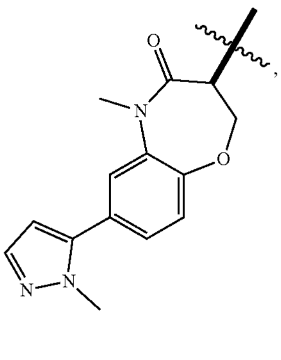

,

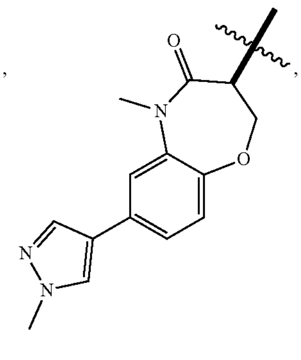

,

-continued

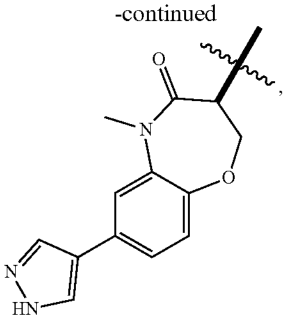

, and

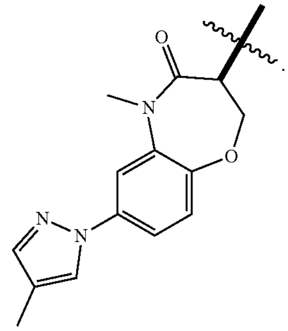

.

Also provided herein is a compound of structural Formula (IV):

(IV)

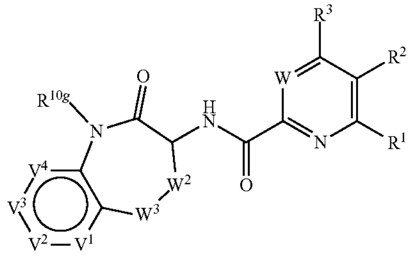

or a salt or tautomer thereof, wherein:

$V^1$ is chosen from a bond, CH, $CR^{10}$, N, NH, $NR^{10}$, O, and S;

$V^2$, $V^3$, and $V^4$ are independently chosen from CH, $CR^{10}$, N, NH, $NR^{10}$, O, and S;

$V^1$, $V^2$, $V^3$, and $V^4$, together with the intervening two carbons, combine to form a 5- or 6-membered aryl or heteroaryl;

W is chosen from CH, $CR^5$, and N;

$W^2$ and $W^3$ are independently chosen from $CH_2$, $CHR^{10}$, NH, O, and S;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$.

$R^2$ and $R^3$ are independently chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^5$ is chosen from H, CN, halo, hydroxy, alkyl, and (alkyl)oxy;

each $R^6$, $R^7$, $R^8$, and $R^9$ is independently chosen from CN, halo, hydroxy, $NH_2$, oxo, alkyl, and (alkyl)oxy;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

Also provided herein is a compound of structural Formula (IV):

(IV)

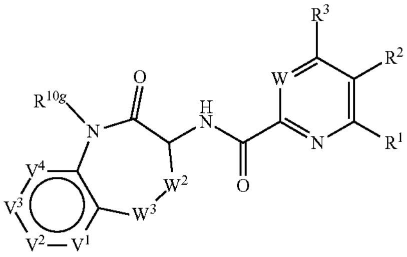

or a salt or tautomer thereof, wherein:

$V^1$ is chosen from a bond, CH, $CR^{10}$, N, NH, $NR^{10}$, O, and S;

$V^2$, $V^3$, and $V^4$ are independently chosen from CH, $CR^{10}$, N, NH, $NR^{10}$, O, and S;

$V^1$, $V^2$, $V^3$, and $V^4$, together with the intervening two carbons, combine to form a 5- or 6-membered aryl or heteroaryl;

W is chosen from CH, $CR^5$, and N;

$W^2$ and $W^3$ are independently chosen from $CH_2$, $CHR^{10}$, NH, O, and S;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^6$.

$R^2$ and $R^3$ are independently chosen from H, halo, cyano, alkyl, (alkyl)oxy, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$.

$R^5$ is chosen from H, CN, halo, hydroxy, alkyl, and (alkyl)oxy;

each $R^6$, $R^7$, $R^8$, and $R^9$ is independently chosen from CN, halo, hydroxy, oxo, alkyl, and (alkyl)oxy;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments, $W^2$ is $CH(R^{10})$. In certain embodiments, $W^2$ is $CH_2$.

In certain embodiments, $W^2$ is NH. In certain embodiments, $W^2$ is O. In certain embodiments, $W^2$ is S.

In certain embodiments, $W^3$ is $CH(R^{10})$. In certain embodiments, $W^3$ is $CH_2$.

In certain embodiments, $W^3$ is NH. In certain embodiments, $W^3$ is O. In certain embodiments, $W^3$ is S.

Also provided herein is a compound of structural Formula (IVa):

(IVa)

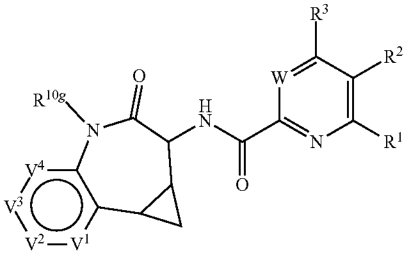

or a salt or tautomer thereof, wherein:

$V^1$ is chosen from a bond, CH, $CR^{10}$, N, NH, $NR^{10}$, O, and S;

$V^2$, $V^3$, and $V^4$ are independently chosen from CH, $CR^{10}$, N, NH, $NR^{10}$, O, and S;

$V^1$, $V^2$, $V^3$, and $V^4$, together with the intervening two carbons, combine to form a 5- or 6-membered aryl or heteroaryl;

W is chosen from CH, $CR^5$, and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$.

$R^2$ and $R^3$ are independently chosen from H, halo, cyano, alkyl, (alkyl)oxy, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$.

$R^5$ is chosen from H, CN, halo, hydroxy, alkyl, and (alkyl)oxy;

each $R^6$, $R^7$, $R^8$, and $R^9$ is independently chosen from CN, halo, hydroxy, oxo, alkyl, and (alkyl)oxy;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

Also provided herein is a compound of structural Formula (IVb):

(IVb)

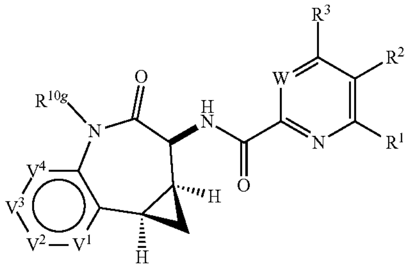

or a salt or tautomer thereof, wherein:

$V^1$ is chosen from a bond, CH, $CR^{10}$, N, NH, $NR^{10}$, O, and S;

$V^2$, $V^3$, and $V^4$ are independently chosen from CH, $CR^{10}$, N, NH, $NR^{10}$, O, and S;

$V^1$, $V^2$, $V^3$, and $V^4$, together with the intervening two carbons, combine to form a 5- or 6-membered aryl or heteroaryl;

W is chosen from CH, $CR^5$, and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$.

$R^2$ and $R^3$ are independently chosen from H, halo, cyano, alkyl, (alkyl)oxy, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^5$ is chosen from H, CN, halo, hydroxy, alkyl, and (alkyl)oxy;

each $R^6$, $R^7$, $R^8$, and $R^9$ is independently chosen from CN, halo, hydroxy, oxo, alkyl, and (alkyl)oxy;

$R^{10g}$ is chosen from H, alkyl, cycloalkyl, heterocycloalkyl, aryl, and heteroaryl, any one of which is optionally substituted with one or more $R^{11}$;

each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments, $R^{10g}$ is chosen from H and alkyl. In certain embodiments, $R^{10g}$ is chosen from H and $C_{1-4}$alkyl. In certain embodiments, $R^{10g}$ is chosen from H, $CH_3$, $CD_3$, $CH_2CH_3$, $CH(CH_3)_2$, and $C(CH_3)_3$. In certain embodiments, $R^{10g}$ is chosen from H, $CH_3$, and $CD_3$. In certain embodiments, $R^{10}$ is $CH_3$.

In certain embodiments, $R^{10g}$ is chosen from H, methyl, ethyl, and 2-propyl. In certain embodiments, $R^{10}$ is chosen from H, methyl, and methyl-$d_3$. In certain embodiments, $R^{10g}$ is methyl.

In certain embodiments, $R^{10g}$ is H.

In certain embodiments:

$V^1$, $V^2$, $V^3$, and $V^4$ are independently chosen from CH, $CR^{10}$, and N; and $V^1$, $V^2$, $V^3$, and $V^4$, together with the intervening two carbons, combine to form a 6-membered aryl or heteroaryl.

In certain embodiments, $V^1$, $V^2$, $V^3$, and $V^4$ are independently chosen from CH and N.

In certain embodiments, exactly one of $V^1$, $V^2$, $V^3$, and $V^4$ is N.

In certain embodiments, exactly two of $V^1$, $V^2$, $V^3$, and $V^4$ are N.

In certain embodiments:

$V^1$, $V^2$, $V^3$, and $V^4$ are chosen from CH and $CR^{10}$; and $V^1$, $V^2$, $V^3$, and $V^4$, together with the intervening two carbons, combine to form a 6-membered aryl.

In certain embodiments:

$V^1$ is a bond;

$V^2$, $V^3$, and $V^4$ are independently chosen from CH, $CR^{10}$, N, NH, $NR^{10}$, O, and S; and $V^2$, $V^3$, and $V^4$, together with the intervening two carbons, combine to form a 5-membered heteroaryl.

In certain embodiments, exactly one of $V^2$, $V^3$, and $V^4$ is chosen from O and S.

In certain embodiments, $V^2$, $V^3$, and $V^4$ are independently chosen from CH, $CR^{10}$, N, NH, and $NR^{10}$.

In certain embodiments, exactly one of $V^2$, $V^3$, and $V^4$ is chosen from N, NH, and $NR^{10}$.

In certain embodiments, exactly two of $V^2$, $V^3$, and $V^4$ are chosen from N, NH, and $NR^{10}$.

In certain embodiments:

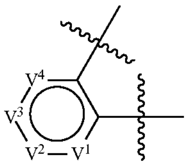

is chosen from

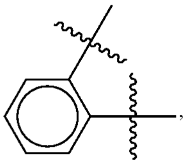
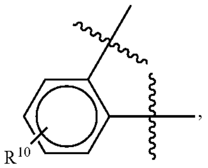
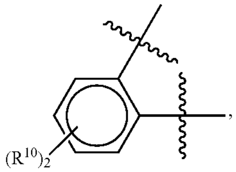
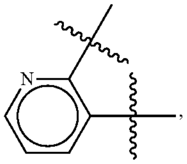
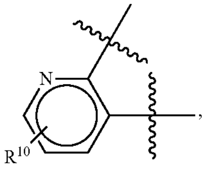
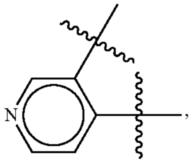
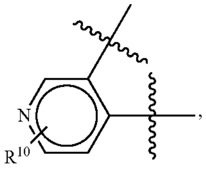
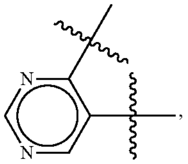
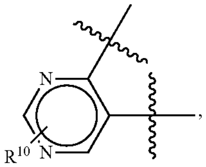
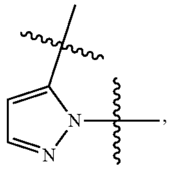
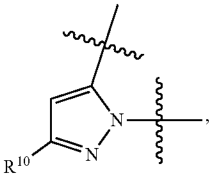

and

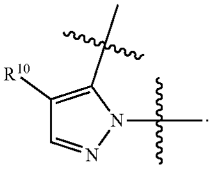

In certain embodiments:

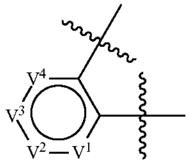

is chosen from

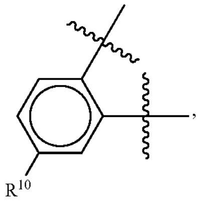
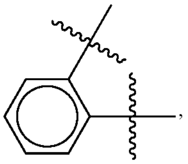
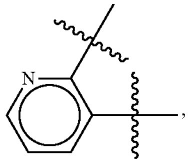
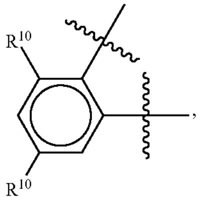
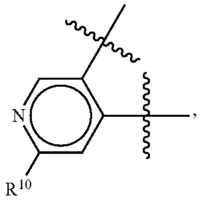
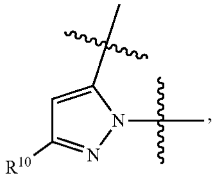
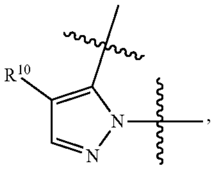
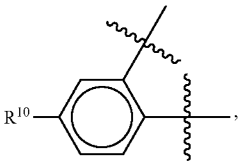
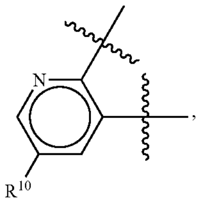
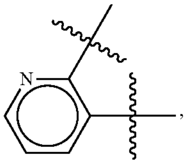
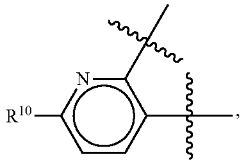
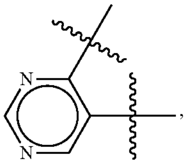
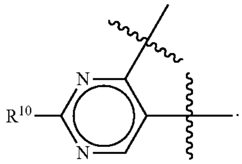

In certain embodiments:
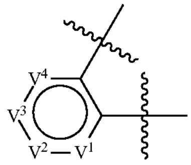
is chosen from
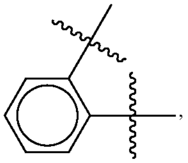
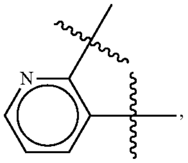
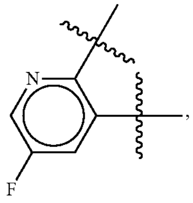
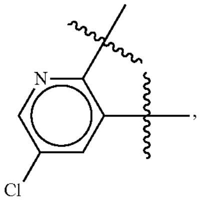
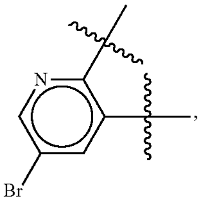
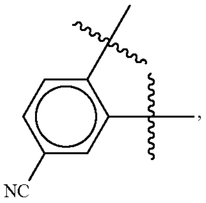
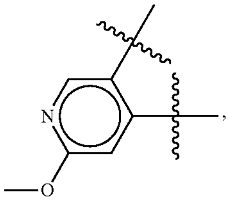
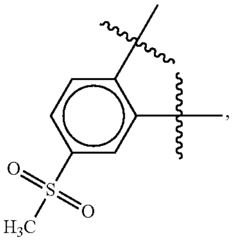
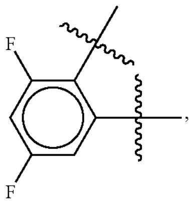
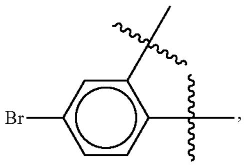
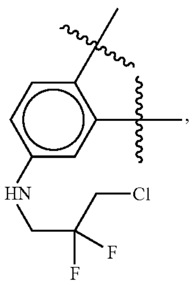
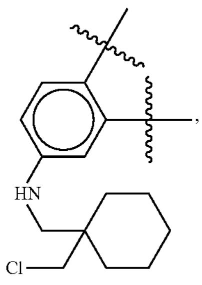
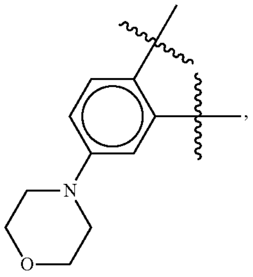
-continued
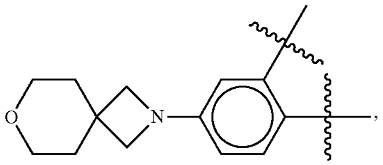
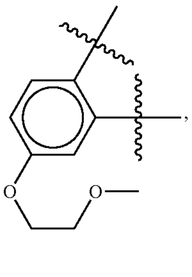
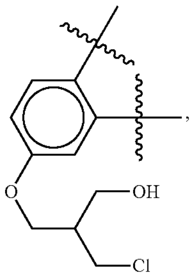
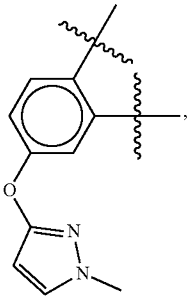
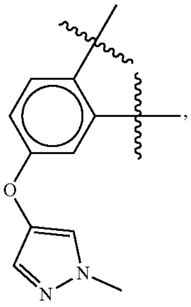
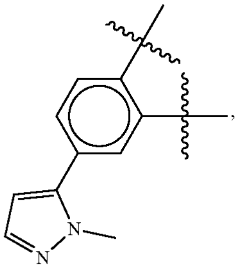
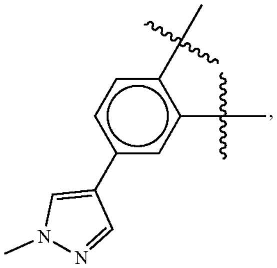
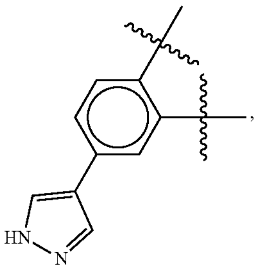
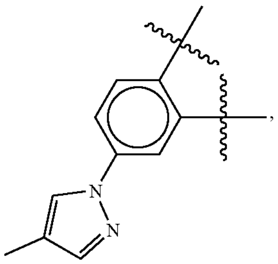

-continued

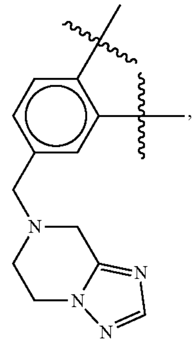

and

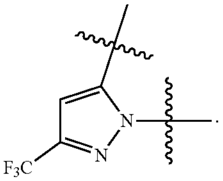

In certain embodiments:

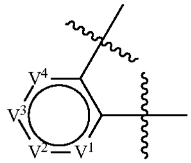

is chosen from

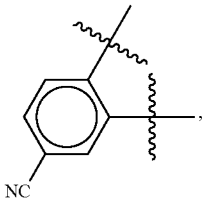

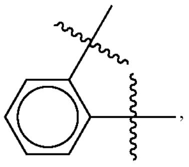

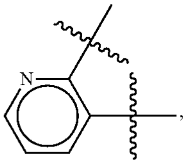

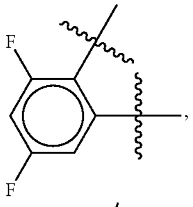

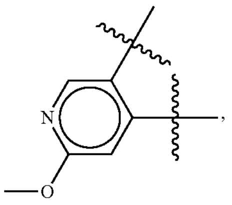

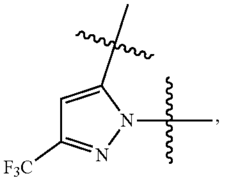

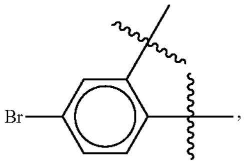

-continued

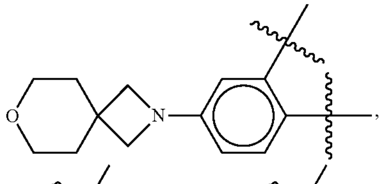

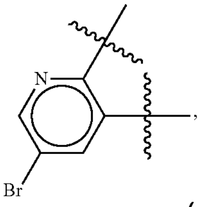

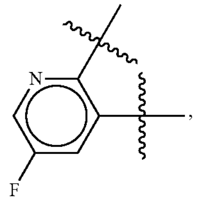

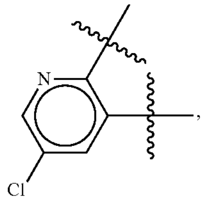

and

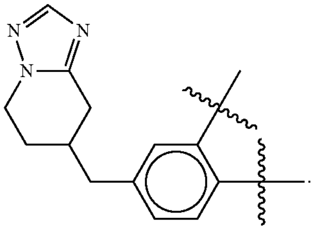

In certain embodiments, each $R^{10}$ is independently chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$.

In certain embodiments, each $R^{10}$ is independently chosen from CN, halo, hydroxy, oxo, $C_{1-6}$alkyl, $C_{3-7}$cycloalkyl, 5- to 14-membered heterocycloalkyl, $C_{6-14}$aryl, 5- to 14-membered heteroaryl, ($C_{3-7}$cycloalkyl)$CH_2$, (5- to 14-membered heterocycloalkyl)$CH_2$, ($C_{6-14}$aryl)$CH_2$, and (5- to 14-membered heteroaryl)$CH_2$, ($C_{1-6}$alkyl)$SO_2$, ($C_{3-7}$cycloalkyl)$SO_2$, (5- to 14-membered heterocycloalkyl)$SO_2$, ($C_{6-14}$aryl)$SO_2$, (5- to 14-membered heteroaryl)$SO_2$, ($C_{1-6}$alkyl)NH, ($C_{3-7}$ cycloalkyl)NH, (5- to 14-membered heterocycloalkyl)NH, ($C_{6-14}$aryl)NH, (5- to 14-membered heteroaryl)NH, ($C_{1-6}$ alkyl)oxy, ($C_{3-7}$cycloalkyl)oxy, (5- to 14-membered heterocycloalkyl)oxy, ($C_{6-14}$aryl)oxy, and (5- to 14-membered heteroaryl)oxy, any one of which is optionally substituted with one or two $R^{11}$.

In certain embodiments, each $R^{10}$ is independently chosen from $C_{1-6}$alkyl, $C_{3-7}$cycloalkyl, 5- to 14-membered heterocycloalkyl, $C_{6-14}$aryl, 5- to 14-membered heteroaryl, ($C_{3-7}$ cycloalkyl)$CH_2$, (5- to 14-membered heterocycloalkyl)$CH_2$, ($C_{6-14}$aryl)$CH_2$, and (5- to 14-membered heteroaryl)$CH_2$, ($C_{1-6}$alkyl)$SO_2$, ($C_{3-7}$cycloalkyl)$SO_2$, (5- to 14-membered heterocycloalkyl)$SO_2$, ($C_{6-14}$aryl)$SO_2$, (5- to 14-membered heteroaryl)$SO_2$, ($C_{1-6}$alkyl)NH, ($C_{3-7}$cycloalkyl)NH, (5- to 14-membered heterocycloalkyl)NH, ($C_{6-14}$aryl)NH, and (5- to 14-membered heteroaryl)NH, ($C_{1-6}$alkyl)oxy, ($C_{3-7}$cycloalkyl)oxy, (5- to 14-membered heterocycloalkyl)oxy, ($C_{6-14}$aryl)oxy, and (5- to 14-membered heteroaryl)oxy, any one of which is optionally substituted with one or two $R^{11}$.

In certain embodiments, each $R^{10}$ is independently chosen from $C_{1-6}$alkyl, $C_{3-7}$cycloalkyl, 5- to 14-membered heterocycloalkyl, $C_{6-14}$aryl, 5- to 14-membered heteroaryl, ($C_{1-6}$ alkyl)oxy, ($C_{3-7}$cycloalkyl)oxy, (5- to 14-membered heterocycloalkyl)oxy, ($C_{6-14}$aryl)oxy, and (5- to 14-membered heteroaryl)oxy, any one of which is optionally substituted with one or two $R^{11}$.

In certain embodiments, each $R^{10}$ is independently chosen from $C_{1-6}$alkyl, $C_{3-7}$cycloalkyl, 5- to 14-membered heterocycloalkyl, $C_{6-14}$aryl, and 5- to 14-membered heteroaryl, any one of which is optionally substituted with one or two $R^{11}$.

In certain embodiments, each $R^{10}$ is independently chosen from $C_{1-6}$alkyl, $C_{3-7}$cycloalkyl, and 5- to 14-membered heterocycloalkyl, any one of which is optionally substituted with one or two $R^{11}$.

In certain embodiments, each $R^{10}$ is optionally substituted with one $R^{11}$.

In certain embodiments, each $R^{10}$ is substituted with one $R^{11}$.

In certain embodiments, each $R^{10}$ is unsubstituted with an $R^{11}$.

In certain embodiments, each $R^{10}$ is independently chosen from H, $CH_3$, $CD_3$, F, Cl, Br, CN, $CF_3$, $OCH_3$,

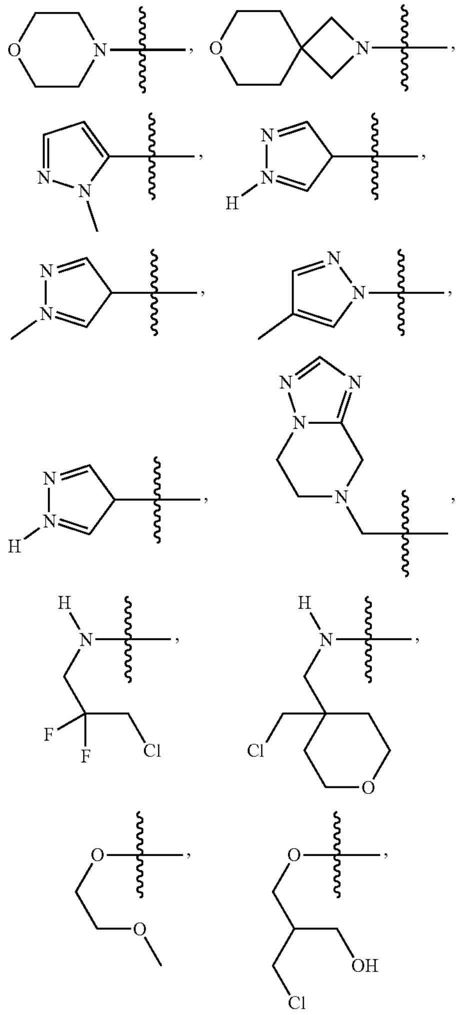

-continued

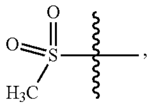

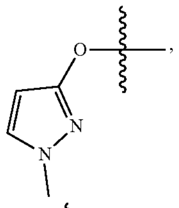

and

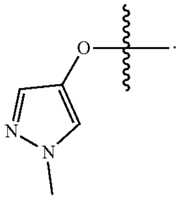

In certain embodiments, each $R^{10}$ is independently chosen from CN, halo, hydroxy, and oxo. In certain embodiments, each $R^{10}$ is independently chosen from CN and halo. In certain embodiments, each $R^{10}$ is independently chosen from F and Cl.

In certain embodiments, each $R^{10}$ is independently chosen from F, Cl, Br, CN, $CH_3$, $CH_2CH_3$, $CH(CH_3)_2$, $C(CH_3)_3$, $OCH_3$, and $CF_3$. In certain embodiments, each $R^{10}$ is independently chosen from $CH_3$ and $CH_2CH_3$.

Also provided herein is a compound of structural Formula (V):

(V)

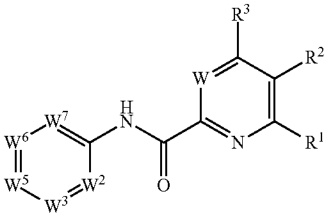

or a salt or tautomer thereof, wherein:

W is chosen from CH, $CR^5$, and N;

$W^2$ is chosen from $CR^{10a}$ and N;

$W^3$ is chosen from $CR^{10b}$ and N;

$W^5$ is chosen from $CR^{10d}$ and N;

$W^6$ is chosen from $CR^{10e}$ and N;

$W^7$ is chosen from $CR^{10f}$ and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$;

$R^2$ and $R^3$ are independently chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^5$ is chosen from H, CN, halo, hydroxy, alkyl, and (alkyl)oxy;

each $R^6$, $R^7$, $R^8$, and $R^9$ is independently chosen from CN, halo, hydroxy, $NH_2$, oxo, alkyl, and (alkyl)oxy;

$R^{10a}$, $R^{10b}$, $R^{10d}$, $R^{10e}$, and $R^{10f}$, unless otherwise defined, are independently chosen from H, CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

Also provided herein is a compound of structural Formula (V):

(V)

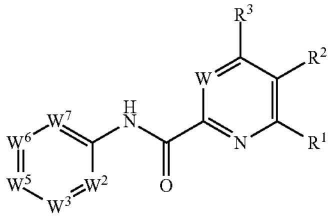

or a salt or tautomer thereof, wherein:

W is chosen from CH, $CR^5$, and N;

$W^2$ is chosen from $CR^{10a}$ and N;

$W^3$ is chosen from $CR^{10b}$ and N;

$W^5$ is chosen from $CR^{10d}$ and N;

$W^6$ is chosen from $CR^{10e}$ and N;

$W^7$ is chosen from $CR^{10f}$ and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^6$;

$R^2$ and $R^3$ are independently chosen from H, halo, cyano, alkyl, (alkyl)oxy, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^5$ is chosen from H, CN, halo, hydroxy, alkyl, and (alkyl)oxy;

each $R^6$, $R^7$, $R^8$, and $R^9$ is independently chosen from CN, halo, hydroxy, oxo, alkyl, and (alkyl)oxy;

$R^{10a}$, $R^{10b}$, $R^{10d}$, $R^{10e}$, and $R^{10f}$, unless otherwise defined, are independently chosen from H, CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$; and each $R^{12}$ is chosen from CN, halo, hydroxy, alkyl, (alkyl)oxy, and oxo.

In certain embodiments, W is chosen from N, CH and C(Cl). In certain embodiments, W is chosen from CH and $CR^5$. In certain embodiments, $R^5$ is chosen from H, CN, halo, hydroxy, $C_{1-6}$alkyl, and ($C_{1-6}$alkyl)oxy. In certain embodiments, $R^5$ is chosen from H, CN, F, Cl, Br, and hydroxy. In certain embodiments, $R^5$ is chosen from H and Cl. In certain embodiments, $R^5$ is H. In certain embodiments, W is N.

In certain embodiments, $R^{10a}$, $R^{10b}$, $R^{10d}$, $R^{10e}$, and $R^{10f}$ are independently chosen from H, CN, halo, hydroxy, oxo, $C_{1-6}$alkyl, $C_{3-7}$cycloalkyl, 5- to 14-membered heterocycloalkyl, $C_{6-14}$aryl, 5- to 14-membered heteroaryl, ($C_{1-6}$alkyl)oxy, ($C_{3-7}$cycloalkyl)oxy, (5- to 14-membered heterocycloalkyl)oxy, ($C_{6-14}$aryl)oxy, and (5- to 14-membered heteroaryl)oxy, any one of which is optionally substituted with one or two $R^{11}$. In certain embodiments, $R^{10a}$, $R^{10b}$, $R^{10d}$, $R^{10e}$, and $R^{10f}$ are independently chosen from H, $C_{1-6}$alkyl, $C_{3-7}$cycloalkyl, 5- to 14-membered heterocycloalkyl, $C_{6-14}$aryl, 5- to 14-membered heteroaryl, ($C_{1-6}$alkyl)oxy, ($C_{3-7}$cycloalkyl)oxy, (5- to 14-membered heterocycloalkyl)oxy, ($C_{6-14}$aryl)oxy, and (5- to 14-membered heteroaryl)oxy, any one of which is optionally substituted with one or two $R^{11}$. In certain embodiments, $R^{10a}$, $R^{10b}$, $R^{10d}$, $R^{10e}$, and $R^{10f}$ are independently chosen from H, CN, halo, hydroxy, $C_{1-6}$alkyl, $C_{3-7}$cycloalkyl, 5- to 14-membered heterocycloalkyl, $C_{6-14}$aryl, and 5- to 14-membered heteroaryl, any one of which is optionally substituted with one or two $R^{11}$. In certain embodiments, $R^{10a}$, $R^{10b}$, $R^{10d}$, $R^{10f}$, and $R^{10f}$ are independently chosen from H, $C_{1-6}$alkyl, $C_{3-7}$cycloalkyl, and 5- to 14-membered heterocycloalkyl, any one of which is optionally substituted with one $R^{11}$.

In certain embodiments, none of $R^{10a}$, $R^{10b}$, $R^{10d}$, $R^{10e}$, and $R^{10f}$ is substituted with an $R^{11}$.

In certain embodiments, $R^{10a}$, $R^{10b}$, $R^{10d}$, $R^{10e}$, and $R^{10f}$ are independently chosen from H, CN, halo, hydroxy, and oxo.

In certain embodiments, at least one of $R^{10a}$, $R^{10b}$, $R^{10d}$, $R^{10e}$, and $R^{10f}$ is not H. In certain embodiments, at least two of $R^{10a}$, $R^{10b}$, $R^{10d}$, $R^{10e}$, and $R^{10f}$ are not H.

In certain embodiments, at least one of $R^{10a}$, $R^{10b}$, $R^{10d}$, $R^{10e}$, and $R^{10f}$ is halo. In certain embodiments, at least two of $R^{10a}$, $R^{10b}$, $R^{10d}$, $R^{10e}$, and $R^{10f}$ are halo.

In certain embodiments, at least one of $R^{10a}$, $R^{10b}$, $R^{10d}$, $R^{10e}$, and $R^{10f}$ is Cl.

In certain embodiments, at least one of $R^{10a}$, $R^{10b}$, $R^{10d}$, $R^{10e}$, and $R^{10f}$ is Br.

In certain embodiments, none of $W^2$, $W^3$, $W^5$, $W^6$, and $W^7$ is N.

In certain embodiments, at least one of $W^2$, $W^3$, $W^5$, $W^6$, and $W^7$ is N. In certain embodiments, exactly one of $W^2$, $W^3$, $W^5$, $W^6$, and $W^7$ is N. In certain embodiments, exactly two of $W^2$, $W^3$, $W^5$, $W^6$, and $W^7$ are N.

In certain embodiments, $W^2$ is N.

In certain embodiments, $W^3$ is N.

In certain embodiments, $W^5$ is N.

In certain embodiments, $R^{10a}$, $R^{10b}$, $R^{10d}$, $R^{10e}$, and $R^{10f}$ are independently chosen from H, CN, halo, hydroxy, $C_{1-6}$alkyl, $C_{3-7}$cycloalkyl, and 5- to 14-membered heterocycloalkyl.

In certain embodiments, $R^{10a}$ is chosen from F, Cl, Br, and $CH_3$. In certain embodiments, $R^{10a}$ is F.

In certain embodiments, $R^{10b}$ is chosen from F, Cl, Br, and $CH_3$. In certain embodiments, $R^{10b}$ is Cl.

Also provided herein is a compound of structural Formula (VI):

(VI)

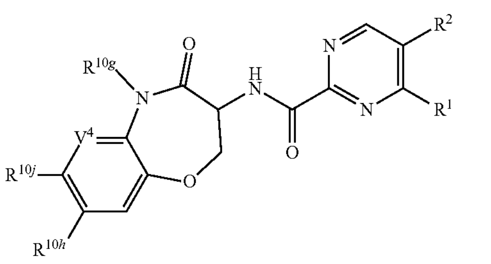

or a salt or tautomer thereof, wherein:

$V^4$ is chosen from CH and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$.

$R^2$ is chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$;

each $R^6$ and $R^7$ is independently chosen from CN, halo, hydroxy, $NH_2$, oxo, alkyl, and (alkyl)oxy;

$R^{10g}$ is chosen from H and alkyl;

$R^{10h}$ is chosen from H, F, Cl, and CN;

$R^{10j}$ is H or is chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl)$SO_2$, (heterocycloalkyl)$SO_2$, (aryl)$SO_2$, (heteroaryl)$SO_2$, (alkyl)NH, (cycloalkyl)NH, (heterocycloalkyl)NH, (aryl)NH, (heteroaryl)NH, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl) oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl) oxy, and oxo.

Also provided herein is a compound of structural Formula (VI):

(VI)

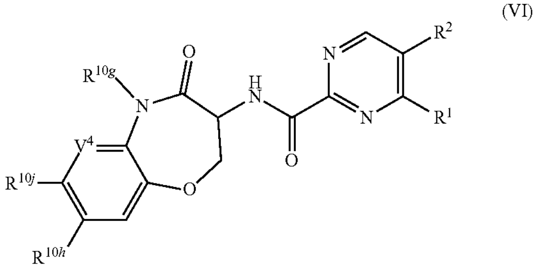

or a salt or tautomer thereof, wherein:

$V^4$ is chosen from CH and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$;

$R^2$ is chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$;

each $R^6$ and $R^7$ is independently chosen from CN, halo, hydroxy, oxo, alkyl, and (alkyl)oxy;

$R^{10g}$ is chosen from H and alkyl;

$R^{10h}$ is chosen from H, F, Cl, and CN;

$R^{10j}$ is H or is chosen from CN, halo, hydroxy, oxo, alkyl, cycloalkyl, heterocycloalkyl, aryl, heteroaryl, (alkyl) oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl) oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl) oxy, and oxo.

In certain embodiments, at least one of $R^{10h}$ and $R^{10g}$ is H.

In certain embodiments, $R^{10h}$ is H. In certain embodiments, $R^{10h}$ is chosen from F, Cl, and CN. In certain embodiments, $R^{10h}$ is chosen from H, F, and Cl.

In certain embodiments, $R^{10j}$ is H.

In certain embodiments, $R^{10g}$ is H or is chosen from $C_{1-6}$alkyl, $C_{3-7}$cycloalkyl, 5- to 10-membered heterocycloalkyl, $C_{6-10}$aryl, 5- to 7-membered heteroaryl, ($C_{3-7}$cycloalkyl)$CH_2$, (5- to 10-membered heterocycloalkyl)$CH_2$, ($C_{6-10}$aryl)$CH_2$, (5- to 7-membered heteroaryl)$CH_2$, ($C_{1-6}$ alkyl)$SO_2$, ($C_{3-7}$cycloalkyl)$SO_2$, (5- to 10-membered heterocycloalkyl)$SO_2$, ($C_{6-10}$aryl)$SO_2$, (5- to 7-membered heteroaryl)$SO_2$, ($C_{1-6}$alkyl)NH, ($C_{3-7}$cycloalkyl)NH, (5- to 10-membered heterocycloalkyl)NH, ($C_{6-10}$aryl)NH, (5- to 7-membered heteroaryl)NH, ($C_{1-6}$alkyl)oxy, ($C_{3-7}$cycloalkyl)oxy, (5- to 10-membered heterocycloalkyl)oxy, ($C_{6-10}$ aryl)oxy, and (5- to 7-membered heteroaryl)oxy, any one of which is optionally substituted with one or more $R^{11}$.

In certain embodiments, $R^{10j}$ is H or is chosen from

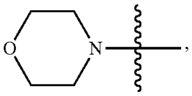, 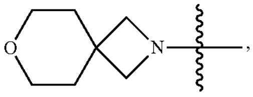, 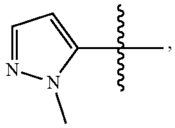, 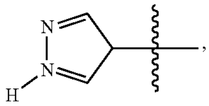, 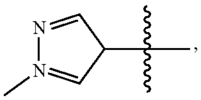, 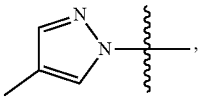, 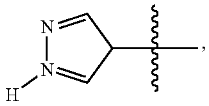, 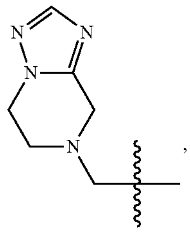, 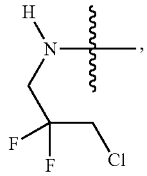, 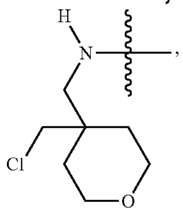, 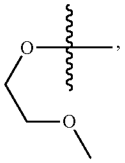, 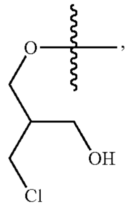, 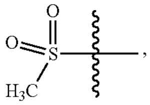, 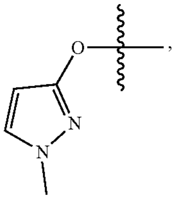, and 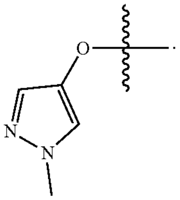.

In certain embodiments:

each $R^{11}$ is independently chosen from CN, halo, hydroxy, oxo, $C_{1-6}$alkyl, $C_{3-7}$cycloalkyl, 4- to 11-membered heterocycloalkyl, $C_{1-6}$alkylsulfonyl, halo$C_{1-6}$alkylsulfonyl, $C_{6-10}$aryl, 5- to 14-membered heteroaryl, ($C_{1-6}$alkyl)oxy, ($C_{3-7}$cycloalkyl)oxy, (4- to 11-membered heterocycloalkyl)oxy, ($C_{1-6}$alkylsulfonyl)oxy, (halo $C_{1-6}$alkylsulfonyl)oxy, ($C_{6-10}$ aryl)oxy, (5- to 14-membered heteroaryl)oxy, ($C_{1-6}$alkyl)NH, ($C_{3-7}$cycloalkyl)NH, (4- to 11-membered heterocycloalkyl)NH, ($C_{1-6}$alkylsulfonyl)NH, (halo $C_{1-6}$alkylsulfonyl)NH, ($C_{6-10}$aryl)NH, and (5- to 14-membered heteroaryl)NH, any one of which is optionally substituted with one or two $R^{12}$, and two $R^{11}$ can combine to form a $C_{5-7}$cycloalkyl or 5- to 7-membered heterocycloalkyl.

In certain embodiments:

each $R^{11}$ is independently chosen from CN, halo, hydroxy, oxo, $C_{1-6}$alkyl, $C_{3-7}$cycloalkyl, 4- to 11-membered heterocycloalkyl, $C_{1-6}$alkylsulfonyl, halo$C_{1-6}$alkylsulfonyl, $C_{6-10}$aryl, 5- to 14-membered heteroaryl, ($C_{1-6}$alkyl)oxy, ($C_{3-7}$cycloalkyl)oxy, (4- to 11-membered heterocycloalkyl)oxy, ($C_{1-6}$alkylsulfonyl)oxy, (halo $C_{1-6}$alkylsulfonyl)oxy, ($C_{6-10}$ aryl)oxy, (5- to 14-membered heteroaryl)oxy, ($C_{1-6}$alkyl)NH, ($C_{3-7}$cycloalkyl)NH, (4- to 11-membered heterocycloalkyl)NH, ($C_{1-6}$alkylsulfonyl)NH, (halo $C_{1-6}$alkylsulfonyl)NH, ($C_{6-10}$aryl)NH, and (5- to 14-membered heteroaryl)NH, any one of which is optionally substituted with one or two $R^{12}$.

In certain embodiments:

each $R^{11}$ is independently chosen from $C_{1-6}$alkyl, $C_{3-7}$cycloalkyl, 4- to 11-membered heterocycloalkyl, $C_{1-6}$alkylsulfonyl, halo$C_{1-6}$alkylsulfonyl, $C_{6-10}$aryl, 5- to 14-membered heteroaryl, ($C_{1-6}$alkyl)oxy, ($C_{3-7}$cycloalkyl)oxy, (4- to 11-membered heterocycloalkyl)oxy, ($C_{1-6}$alkylsulfonyl)oxy, (halo $C_{1-6}$alkylsulfonyl)oxy, ($C_{6-10}$aryl)oxy, and (5- to 14-membered heteroaryl)oxy, any one of which is optionally substituted with one or two $R^{12}$, and two $R^{11}$ can combine to form a $C_{5-7}$cycloalkyl or 5- to 7-membered heterocycloalkyl.

In certain embodiments:

each $R^{11}$ is independently chosen from $C_{1-6}$alkyl, $C_{3-7}$cycloalkyl, 4- to 11-membered heterocycloalkyl, $C_{1-6}$alkylsulfonyl, halo$C_{1-6}$alkylsulfonyl, $C_{6-10}$aryl, 5- to 14-membered heteroaryl, ($C_{1-6}$alkyl)oxy, ($C_{3-7}$cycloalkyl)oxy, (4- to 11-membered heterocycloalkyl)oxy, ($C_{1-6}$alkylsulfonyl)oxy, (halo $C_{1-6}$alkylsulfonyl)oxy, ($C_{6-10}$aryl)oxy, and (5- to 14-membered heteroaryl)oxy, any one of which is optionally substituted with one or two $R^{12}$.

In certain embodiments:

each $R^{11}$ is independently chosen from $C_{1-6}$alkyl, $C_{3-7}$cycloalkyl, 4- to 11-membered heterocycloalkyl, $C_{1-6}$alkylsulfonyl, halo$C_{1-6}$alkylsulfonyl, $C_{6-10}$aryl, and 5- to 14-membered heteroaryl, any one of which is optionally substituted with one or two $R^{12}$, and two $R^{11}$ can combine to form a $C_{5-7}$cycloalkyl or 5- to 7-membered heterocycloalkyl.

In certain embodiments:

each $R^{11}$ is independently chosen from $C_{1-6}$alkyl, $C_{3-7}$cycloalkyl, 4- to 11-membered heterocycloalkyl, $C_{1-6}$alkylsulfonyl, halo$C_{1-6}$alkylsulfonyl, $C_{6-10}$aryl, and 5- to 14-membered heteroaryl, any one of which is optionally substituted with one or two $R^{12}$.

In certain embodiments:

each $R^{11}$ is independently chosen from $C_{1-6}$alkyl, $C_{3-7}$cycloalkyl, 4- to 11-membered heterocycloalkyl, $C_{6-10}$aryl, and 5- to 14-membered heteroaryl, any one of which is optionally substituted with one or two $R^{12}$, and two $R^{11}$ can combine to form a $C_{5-7}$cycloalkyl or 5- to 7-membered heterocycloalkyl.

In certain embodiments:

each $R^{11}$ is independently chosen from $C_{1-6}$alkyl, $C_{3-7}$cycloalkyl, 4- to 11-membered heterocycloalkyl, $C_{6-10}$aryl, and 5- to 14-membered heteroaryl, any one of which is optionally substituted with one or two $R^{12}$.

In certain embodiments, two $R^{11}$, when attached directly to the same carbon atom, can combine to form a $C_{5-7}$cycloalkyl or 5- to 7-membered heterocycloalkyl. can combine to form a 5- to 7-membered heterocycloalkyl having heteroatoms selected from N, O, and S. In certain embodiments, two $R^{11}$, when attached directly to the same carbon atom, can combine to form a 5- to 7-membered heterocycloalkyl having 1 or 2 heteroatoms selected from N, O, and S. In certain embodiments, two $R^{11}$, when attached directly to the same carbon atom, can combine to form a 5- to 7-membered heterocycloalkyl having 1 heteroatom selected from N, O, and S. In certain embodiments, two $R^{11}$, when attached directly to the same carbon atom, can combine to form a 5- to 7-membered heterocycloalkyl having 1 heteroatom selected from N and O.

In certain embodiments, two $R^{11}$ can combine to form a 5- to 7-membered heterocycloalkyl having heteroatoms selected from N, O, and S. In certain embodiments, two $R^{11}$ can combine to form a 5- to 7-membered heterocycloalkyl having 1 or 2 heteroatoms selected from N, O, and S. In certain embodiments, two $R^{11}$ can combine to form a 5- to 7-membered heterocycloalkyl having 1 heteroatom selected from N, O, and S. In certain embodiments, two $R^{11}$ can combine to form a 5- to 7-membered heterocycloalkyl having 1 heteroatom selected from N and O. In certain embodiments, two $R^{11}$ can combine to form a 5- to 7-membered heterocycloalkyl chosen from piperidine, pyrrolidine, tetrahydrofuran, and tetrahydro-2H-pyran.

In certain embodiments, each $R^{11}$ is optionally substituted with one $R^{12}$. In certain embodiments, $R^{11}$ is substituted with one $R^{12}$.

In certain embodiments, each $R^{12}$ is chosen from CN, halo, hydroxy, $C_{1-6}$alkyl, ($C_{1-6}$alkyl)oxy, and oxo. In certain embodiments, each $R^{12}$ is chosen from CN, halo, hydroxy, and oxo. In certain embodiments, each $R^{12}$ is chosen from CN and halo.

In certain embodiments, each $R^{11}$ is unsubstituted with an $R^{12}$.

In certain embodiments, each $R^{11}$ is independently chosen from CN, halo, hydroxy, and oxo. In certain embodiments, each $R^{11}$ is independently chosen from CN and halo.

In certain embodiments, $R^1$ is chosen from $C_{1-6}$alkyl, $C_{3-7}$cycloalkyl, 4- to 11-membered heterocycloalkyl, $C_{6-14}$aryl, 5- to 14-membered heteroaryl, ($C_{3-7}$cycloalkyl)$C_{1-6}$alkyl, (4- to 11-membered heterocycloalkyl)$C_{1-6}$alkyl, ($C_{6-14}$aryl)$C_{1-6}$alkyl, and (5- to 14-membered heteroaryl)$C_{1-6}$ alkyl, any one of which is optionally substituted with one or more $R^6$.

In certain embodiments, $R^1$ is chosen from $C_{1-6}$alkyl, $C_{3-7}$cycloalkyl, 4- to 11-membered heterocycloalkyl, $C_{6-14}$aryl, 5- to 14-membered heteroaryl, ($C_{3-7}$cycloalkyl)methyl, (4- to 11-membered heterocycloalkyl)methyl, ($C_{6-14}$aryl)methyl, and (5- to 14-membered heteroaryl)methyl, any one of which is optionally substituted with one or more $R^6$.

In certain embodiments, $R^1$ is chosen from $C_{1-6}$alkyl, $C_{3-7}$cycloalkyl, 4- to 11-membered heterocycloalkyl, $C_{6-14}$aryl, and 5- to 14-membered heteroaryl, any one of which is optionally substituted with one or more $R^6$.

In certain embodiments, $R^1$ is chosen from $C_{1-6}$alkyl, $C_{3-7}$cycloalkyl, 4- to 7-membered heterocycloalkyl, phenyl, and 5- or 6-membered heteroaryl, any one of which is optionally substituted with one or more $R^6$.

In certain embodiments, $R^1$ is chosen from phenyl, pyridyl, pyridinyl, pyrazinyl, pyrimidinyl, and pyridazinyl, and is optionally substituted with one or more $R^6$.

In certain embodiments, $R^1$ is optionally substituted with one or two $R^6$. In certain embodiments, $R^1$ is optionally substituted with one $R^6$. In certain embodiments, $R^1$ is substituted with one $R^6$.

In certain embodiments:

$R^1$ is chosen from:

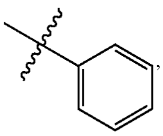, 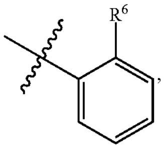,

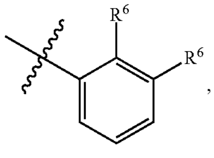, 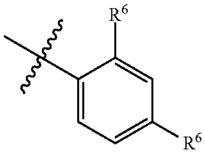,

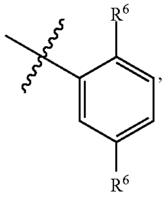, 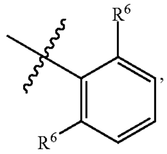,

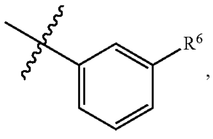, 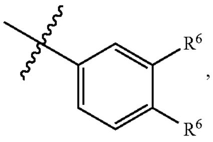,

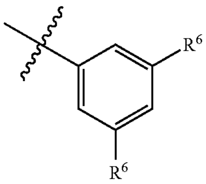, 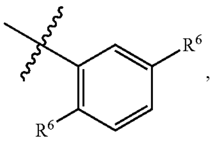,

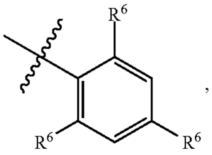, 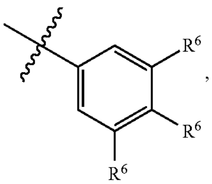,

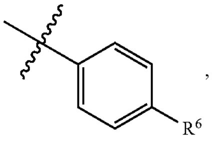, 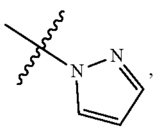,

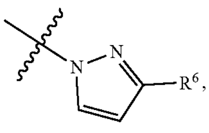, 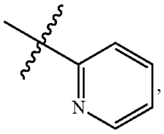,

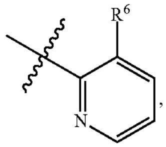, 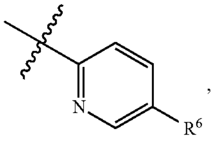,

-continued
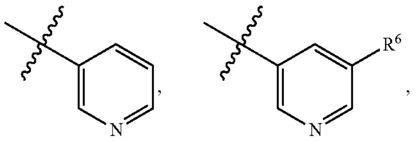
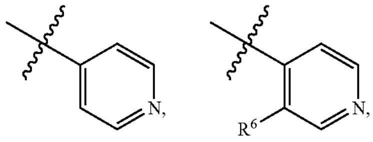
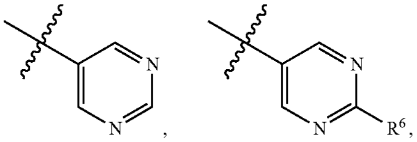
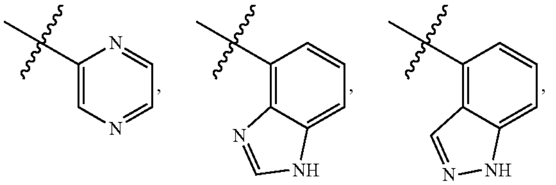
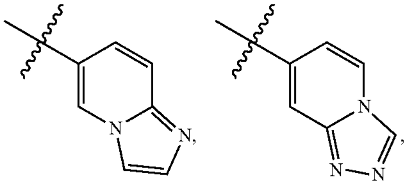
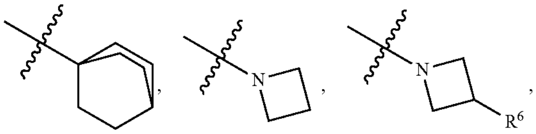
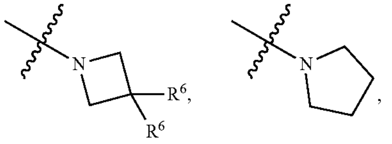
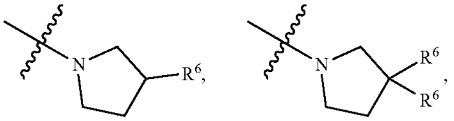
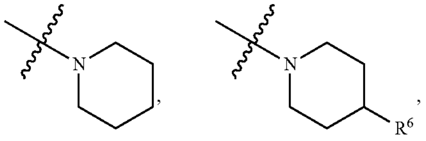
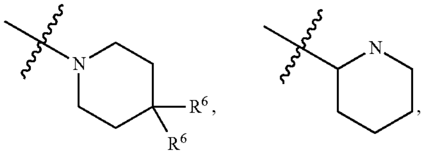
-continued
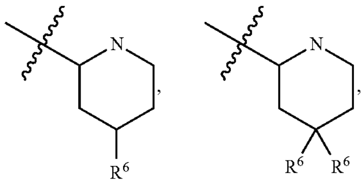
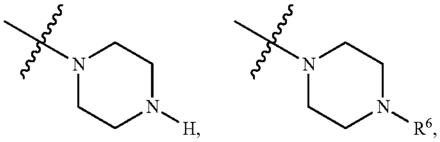
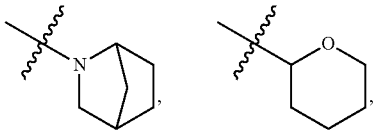
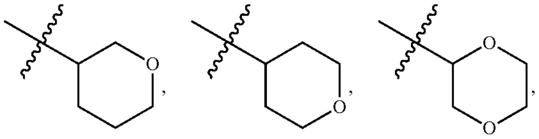
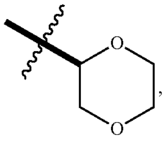
and
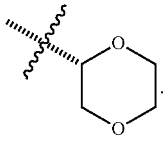
In certain embodiments:
$R^1$ is chosen from:
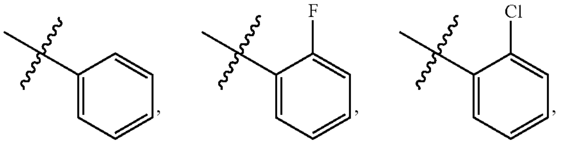
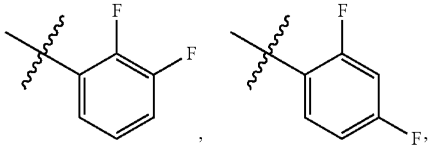
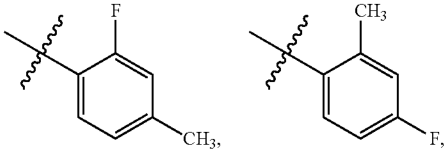
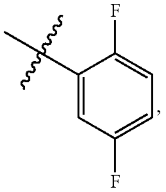
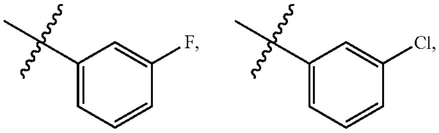

-continued
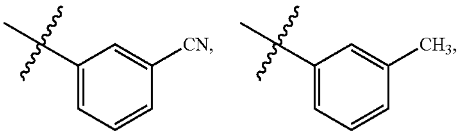
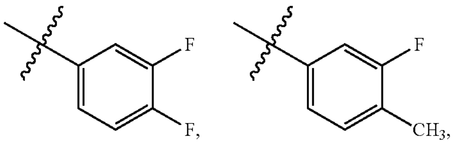
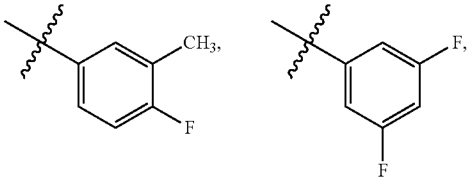
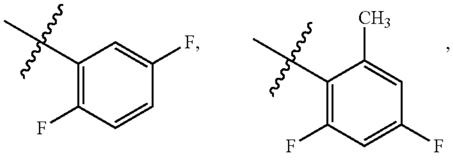
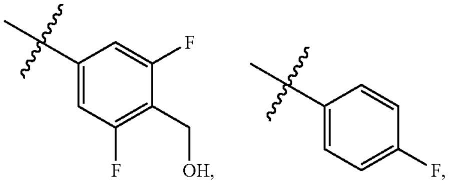
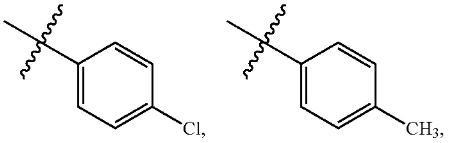
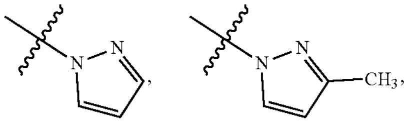
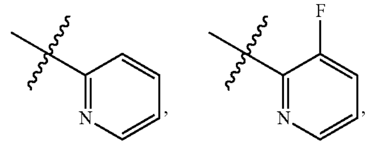
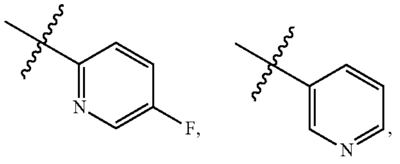
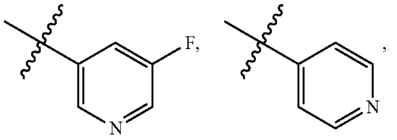
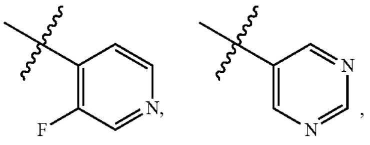
-continued
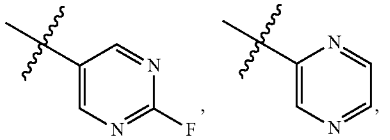
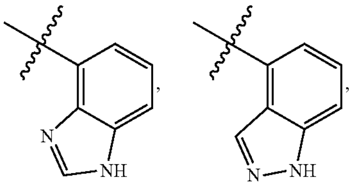
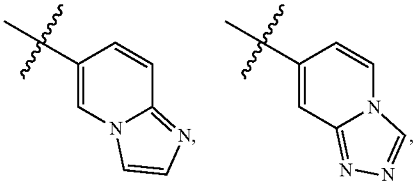
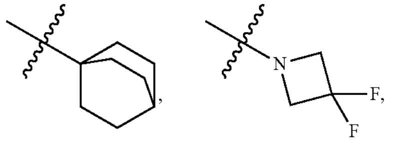
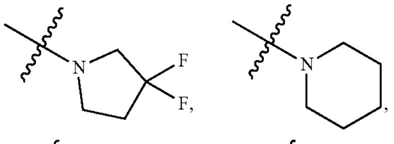
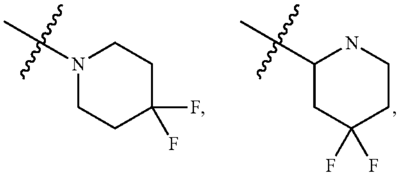
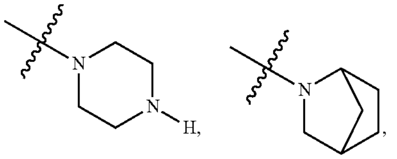
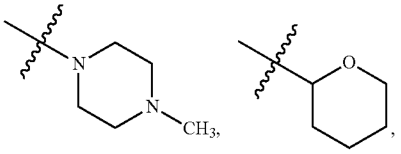
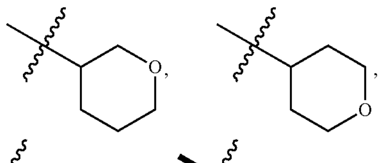
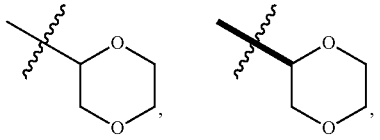
and
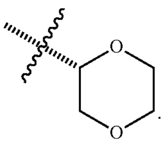

In certain embodiments:
$R^1$ is chosen from:
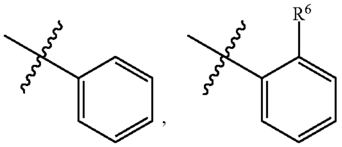,
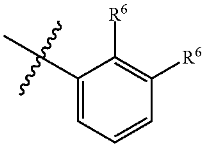,
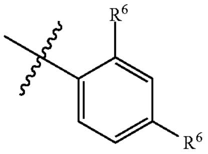,
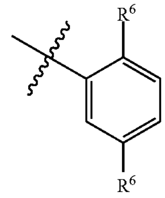,
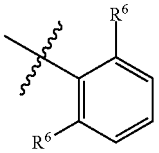,
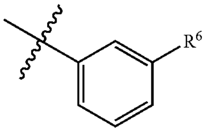,
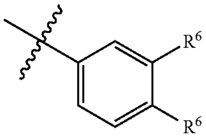,
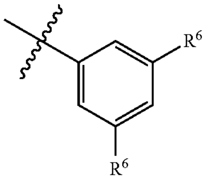,
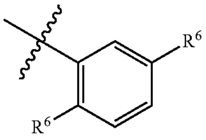,
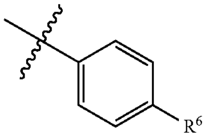,
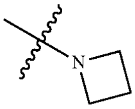,
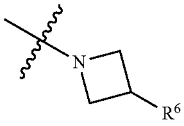,
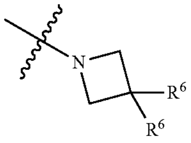,
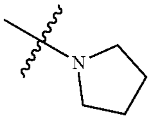,
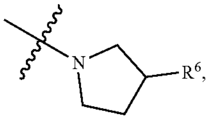
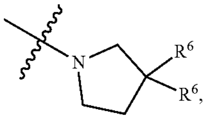
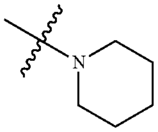,
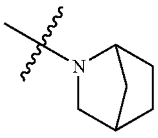,
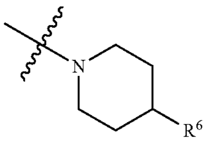,
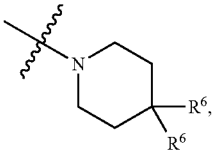,
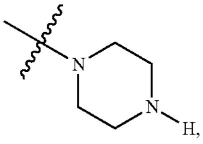
-continued
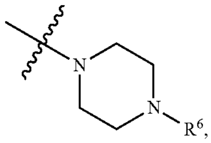 and
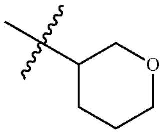.
In certain embodiments:
$R^1$ is chosen from:
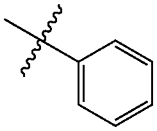,
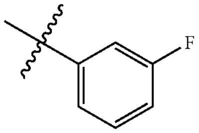,
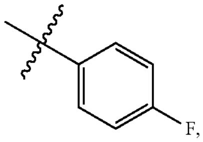
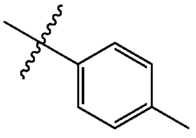,
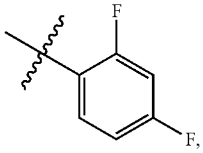
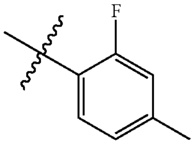,
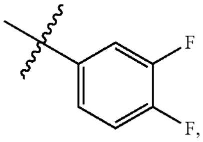
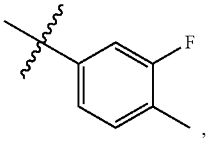,
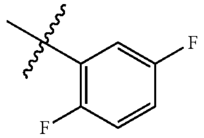,
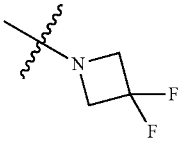,
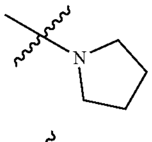,
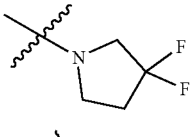,
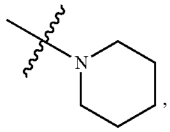,
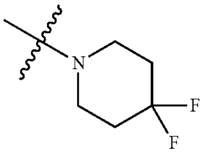
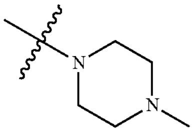,
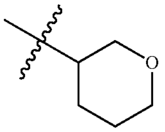, and
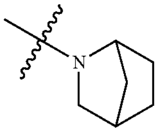.

In certain embodiments:

$R^1$ is chosen from:

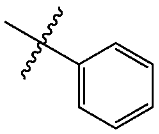,
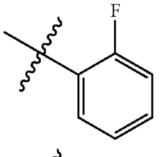,
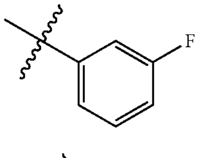,
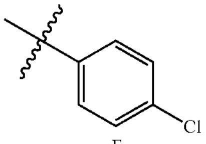,
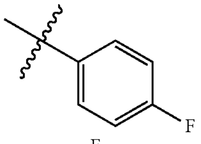,
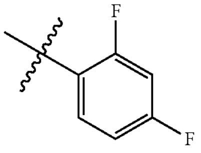,
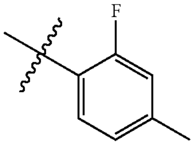,
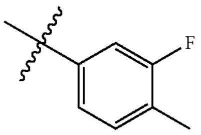, and
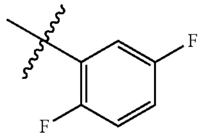.

In certain embodiments:

In certain embodiments, $R^1$ is unsubstituted with an $R^6$.

In certain embodiments, each $R^6$ is independently chosen from CN, halo, hydroxy, oxo, $C_{1-6}$alkyl, and ($C_{1-6}$alkyl)oxy. In certain embodiments, each $R^6$ is independently chosen from CN, F, Cl, Br, hydroxy, and $CH_3$. In certain embodiments, each $R^6$ is independently chosen from F, Cl, and $CH_3$. In certain embodiments, each $R^6$ is independently chosen from F and $CH_3$.

In certain embodiments, $R^2$ and $R^3$ are independently chosen from H, halo, cyano, alkyl, (alkyl)oxy, cycloalkyl, and (cycloalkyl)oxy, any one of which is optionally substituted with one or more $R^7$.

In certain embodiments, $R^2$ and $R^3$ are independently chosen from H, halo, cyano, alkyl, (alkyl)oxy, cycloalkyl, and (cycloalkyl)oxy, any one of which is optionally substituted with one or more $R^7$.

In certain embodiments, $R^2$ is chosen from alkyl, (alkyl) oxy, cycloalkyl, and (cycloalkyl)oxy, any one of which is optionally substituted with one or more $R^7$. In certain embodiments, $R^2$ is chosen from alkyl and cycloalkyl either one of which is optionally substituted with one or more $R^7$. In certain embodiments, $R^2$ is chosen from H, halo, cyclopropyl, $CH_3$, $CD_3$, and cyano. In certain embodiments, $R^2$ is chosen from Cl, $CH_3$, and $CD_3$. In certain embodiments, $R^2$ is chosen from Cl and $CH_3$.

In certain embodiments, $R^3$ is chosen from alkyl, (alkyl) oxy, cycloalkyl, and (cycloalkyl)oxy, any one of which is optionally substituted with one or more $R^7$. In certain embodiments, $R^3$ is chosen from H, halo, and cyano. In certain embodiments, $R^3$ is H.

In certain embodiments, each $R^7$ is independently chosen from CN, halo, hydroxy, oxo, $C_{1-6}$alkyl, and ($C_{1-6}$alkyl)oxy. In certain embodiments, each $R^7$ is independently chosen from CN, halo, and hydroxy.

In certain embodiments, $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$. In certain embodiments, $R^2$ and $R^3$, together with the intervening two carbons, combine to form a 5-7 membered cycloalkyl, heterocycloalkyl, aryl, or heteroaryl ring, any one of which is optionally substituted with one or two $R^8$ and is fused with a 6-membered aryl or heteroaryl ring, said 6-membered aryl or heteroaryl ring being optionally substituted with one or two $R^9$. In certain embodiments, $R^2$ and $R^3$, together with the intervening two carbons, combine to form a 5-7 membered cycloalkyl, heterocycloalkyl, aryl, or heteroaryl ring, any one of which is optionally substituted with one $R^8$ and is fused with a 6-membered aryl or heteroaryl ring, said 6-membered aryl or heteroaryl ring being optionally substituted with one or two $R^9$. In certain embodiments, $R^2$ and $R^3$, together with the intervening two carbons, combine to form a 5-7 membered cycloalkyl, heterocycloalkyl, aryl, or heteroaryl ring, any one of which is unsubstituted with an $R^8$ and is fused with a 6-membered aryl or heteroaryl ring, said 6-membered aryl or heteroaryl ring being optionally substituted with one or two $R^9$. In certain embodiments, $R^2$ and $R^3$, together with the intervening two carbons, combine to form a 5-7 membered cycloalkyl, heterocycloalkyl, aryl, or heteroaryl ring, any one of which is optionally substituted with one or two $R^8$. In certain embodiments, $R^2$ and $R^3$, together with the intervening two carbons, combine to form a 5-7 membered cycloalkyl, heterocycloalkyl, aryl, or heteroaryl ring, any one of which is optionally substituted with one $R^8$. In certain embodiments, $R^2$ and $R^3$, together with the intervening two carbons, combine to form a 5-7 membered cycloalkyl, heterocycloalkyl, aryl, or heteroaryl ring, any one of which is unsubstituted with an $R^8$.

In certain embodiments, each $R^9$ is independently chosen from CN, halo, hydroxy, oxo, $C_{1-6}$alkyl, and ($C_{1-6}$alkyl)oxy. In certain embodiments, each $R^9$ is independently chosen from CN, halo, and hydroxy.

In certain embodiments, each $R^8$ is independently chosen from CN, halo, hydroxy, oxo, $C_{1-6}$alkyl, and ($C_{1-6}$alkyl)oxy. In certain embodiments, each $R^8$ is independently chosen from CN, halo, and hydroxy.

Also provided is a compound chosen from:

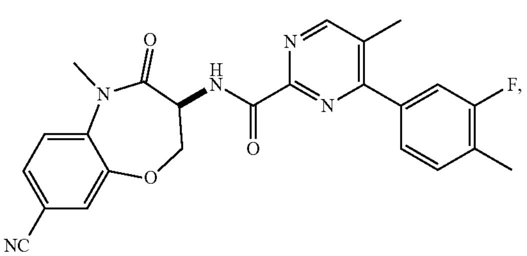

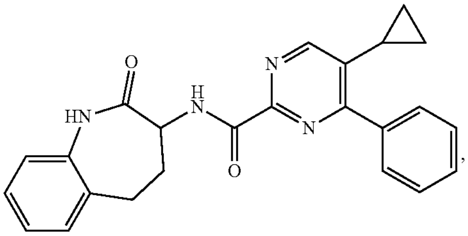,

-continued
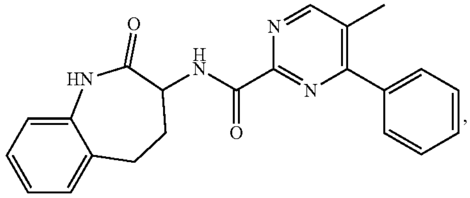
,
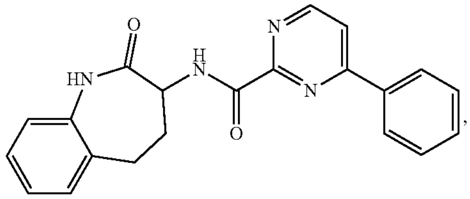
,
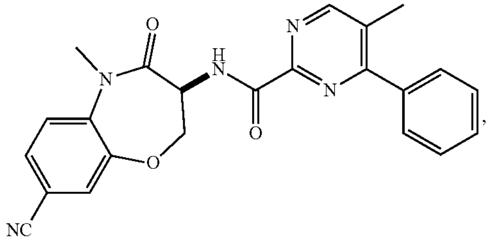
,
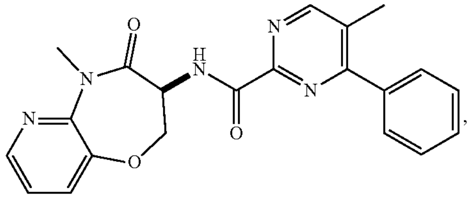
,
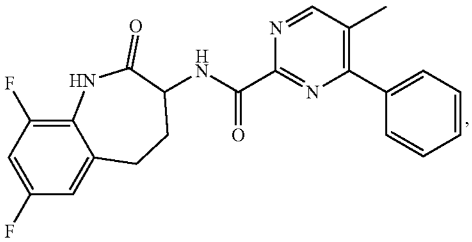
,
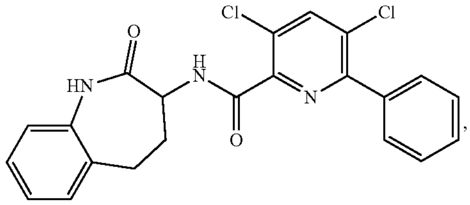
,
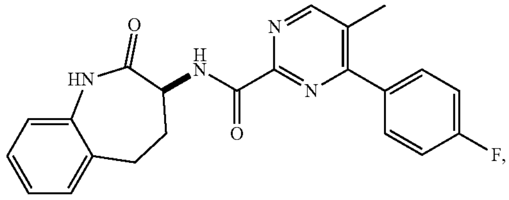
,
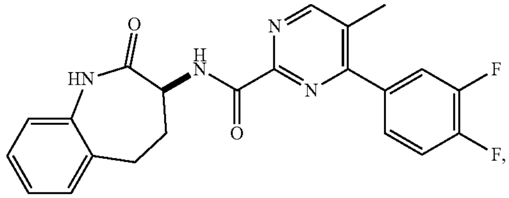
,
-continued
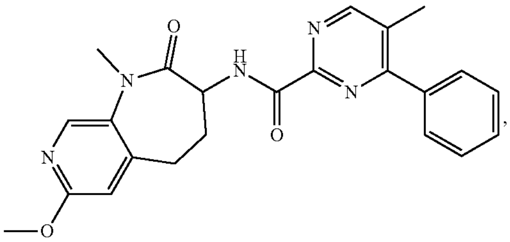
,
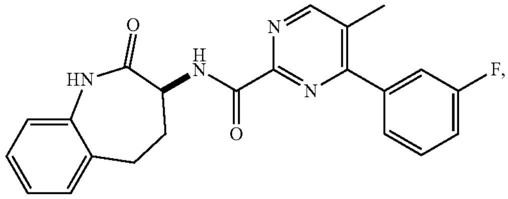
,
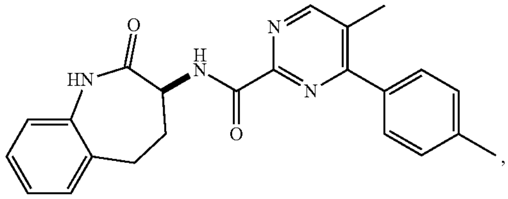
,
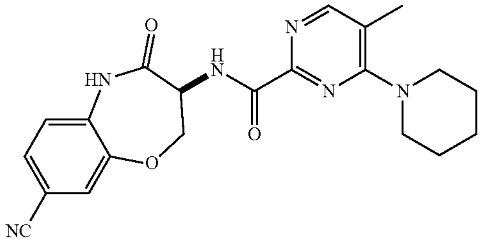
,
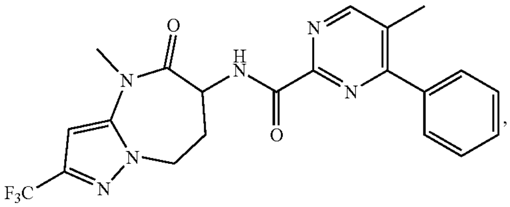
,
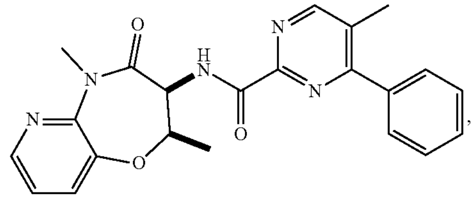
,
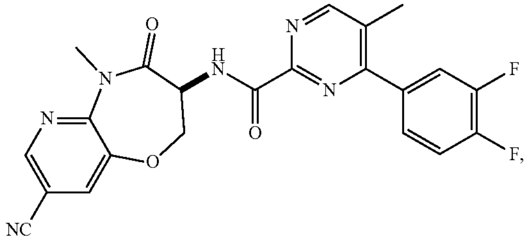
,
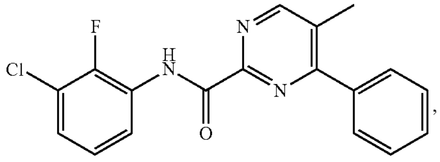
, -continued
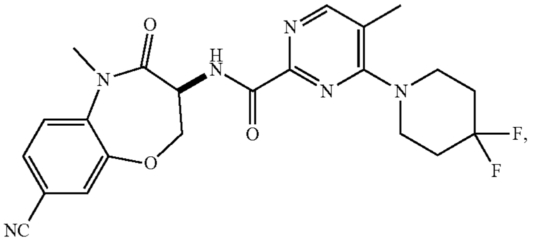,
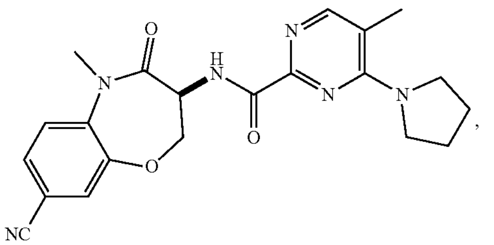,
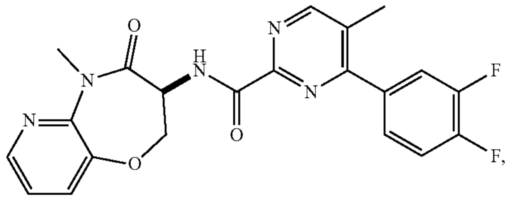,
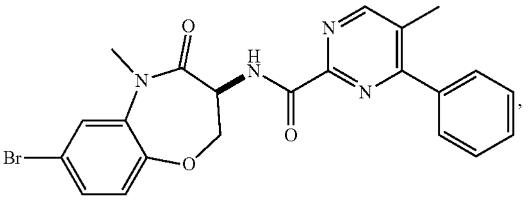,
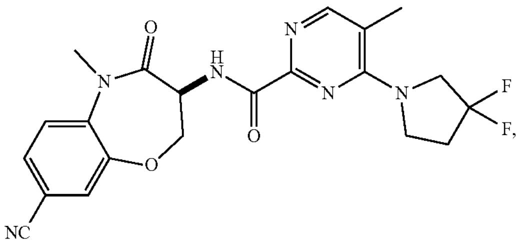,
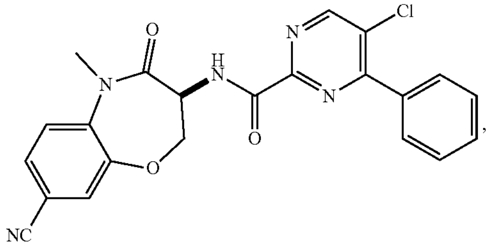,
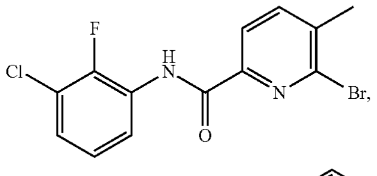,
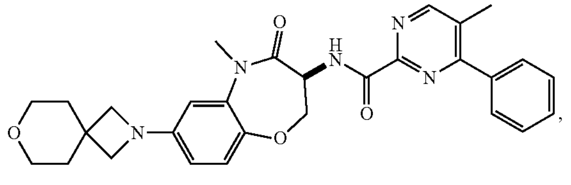,
-continued
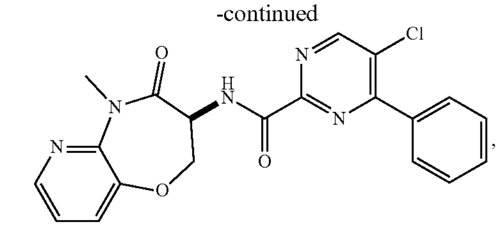,
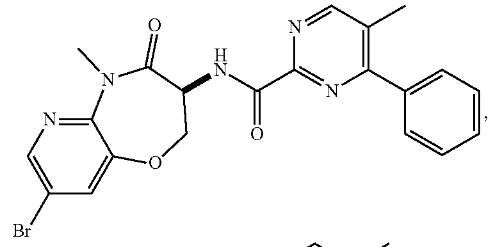,
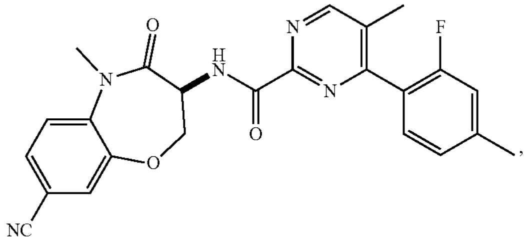,
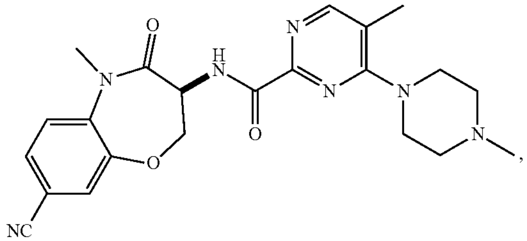,
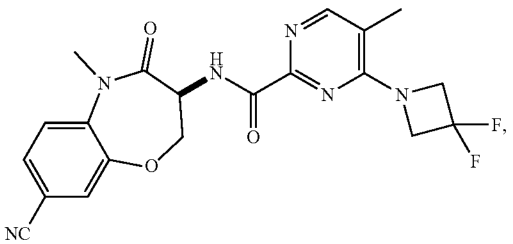,
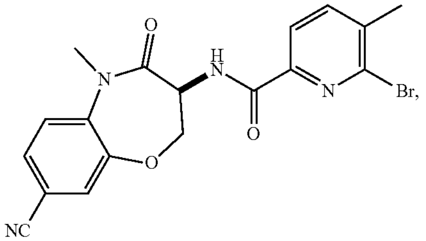,
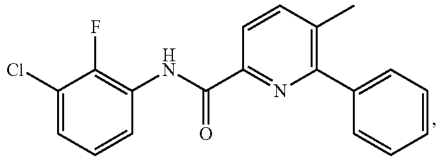,
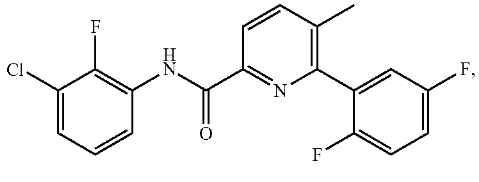, -continued
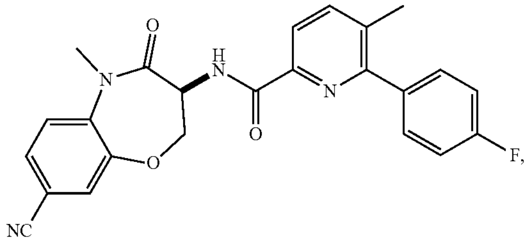
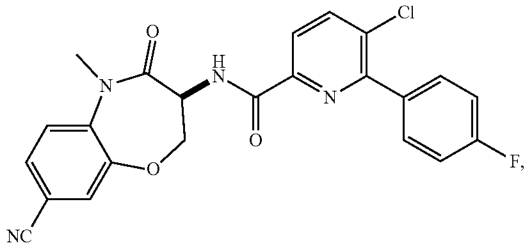
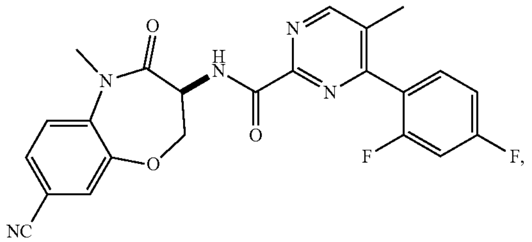
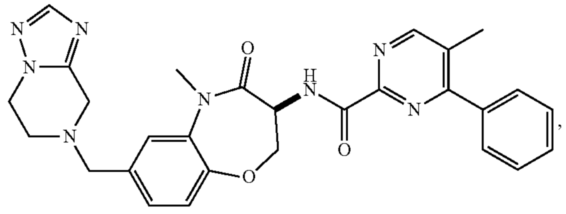
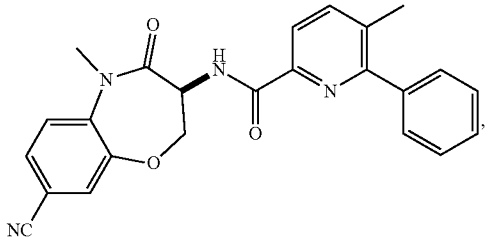
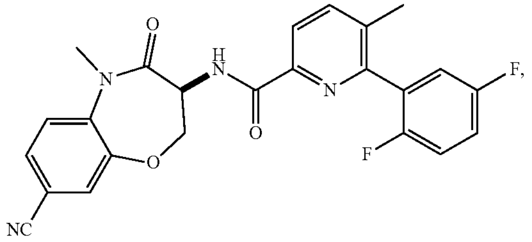
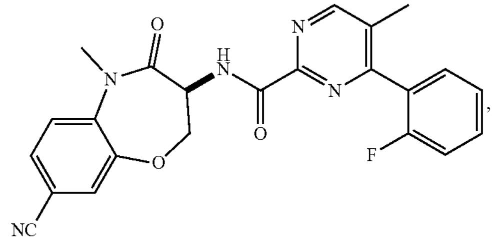
-continued
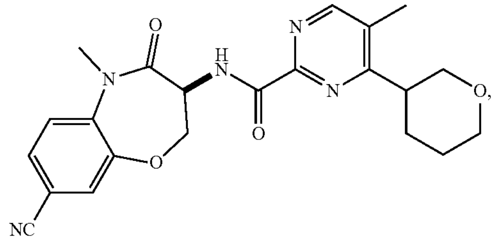
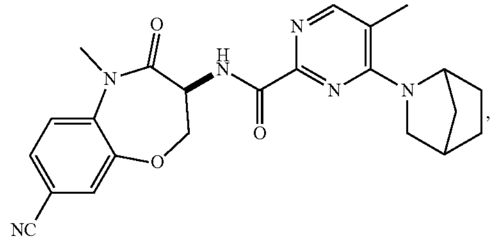
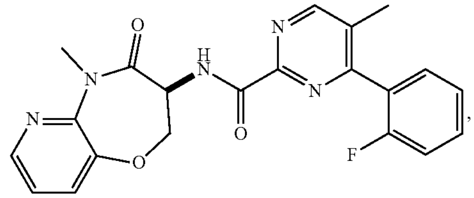
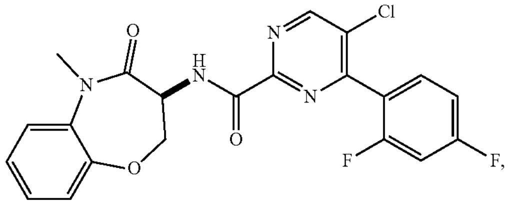
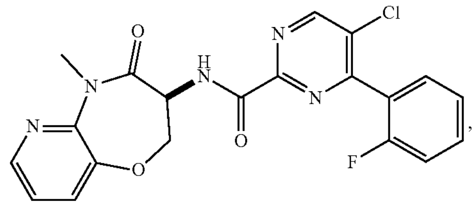
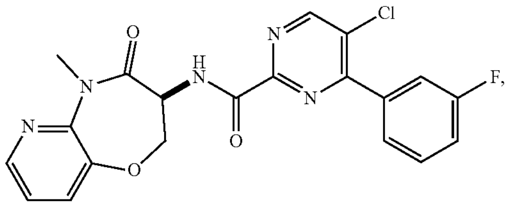
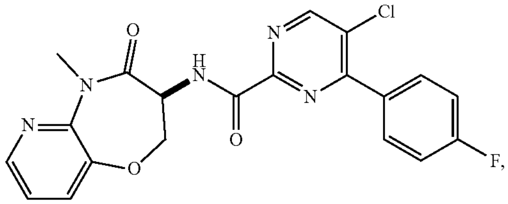
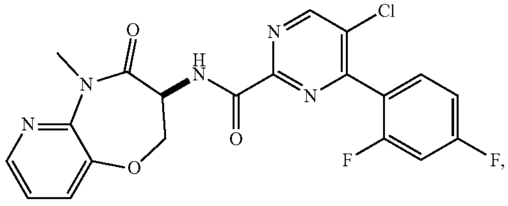

-continued
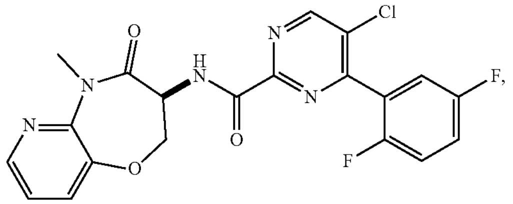
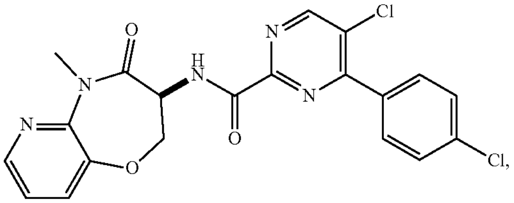
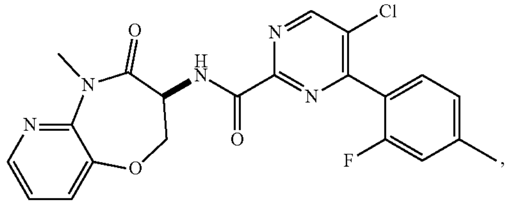
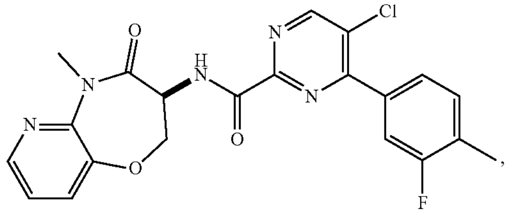
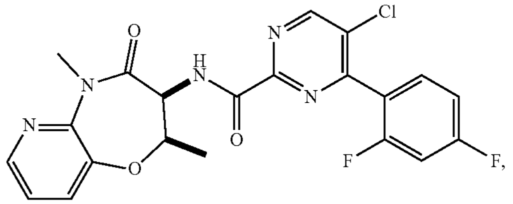
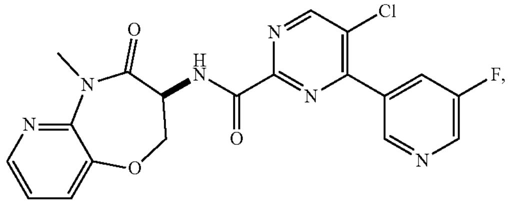
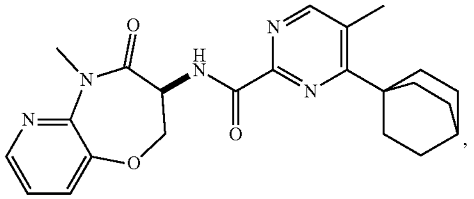
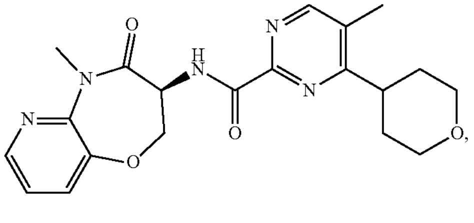
-continued
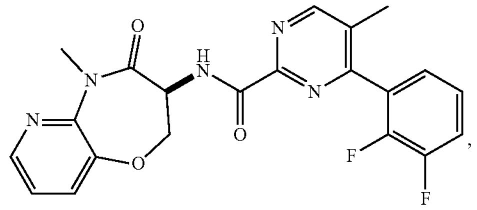
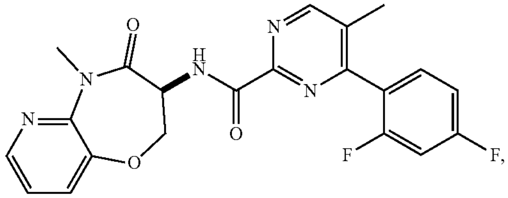
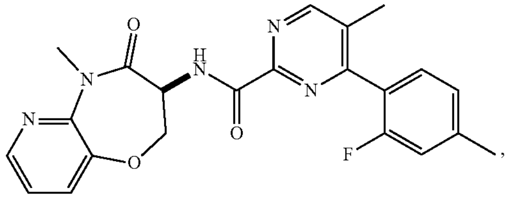
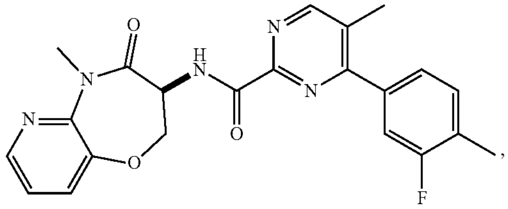
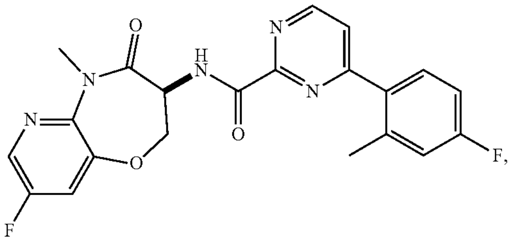
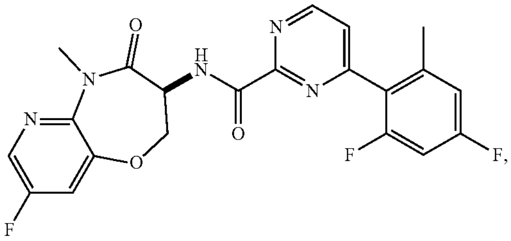
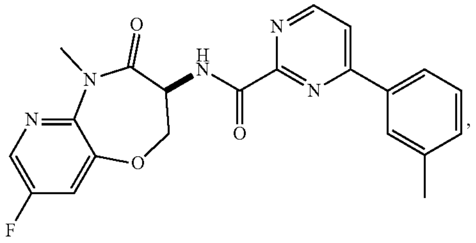

-continued
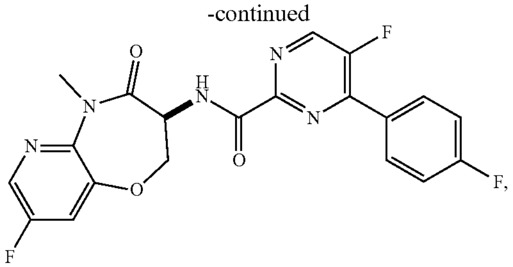
,
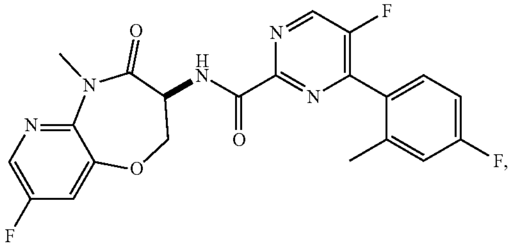
,
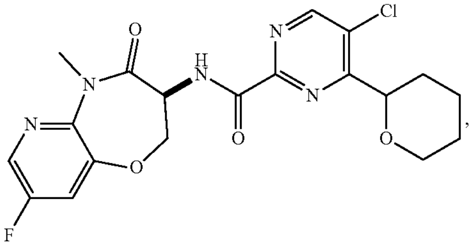
,
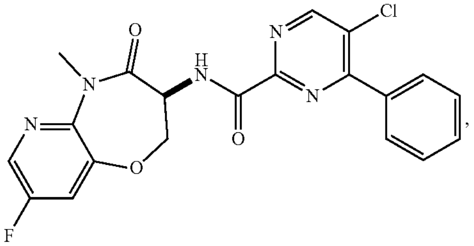
,
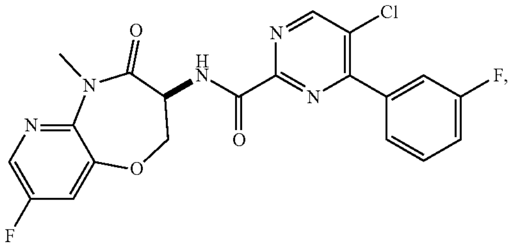
,
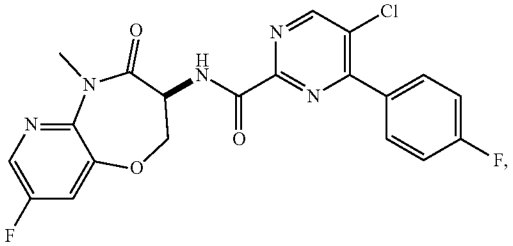
,
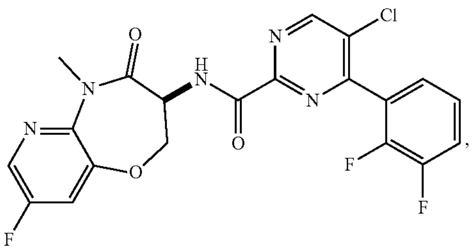
,
-continued
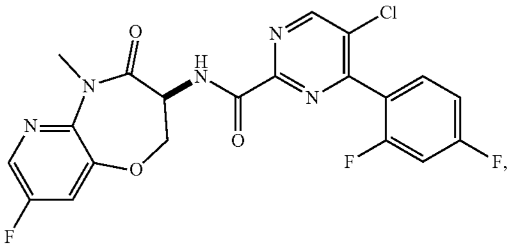
,
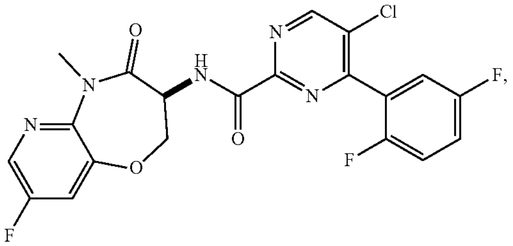
,
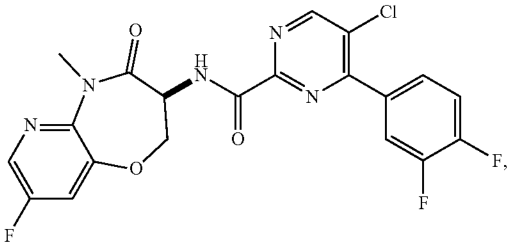
,
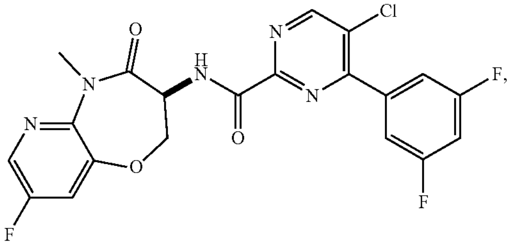
,
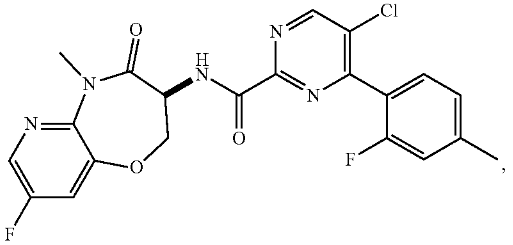
,
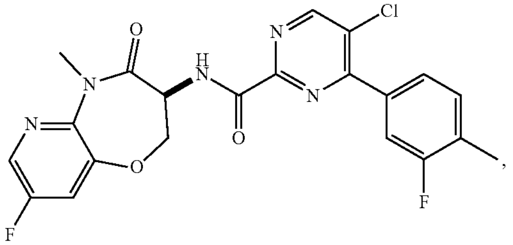
,
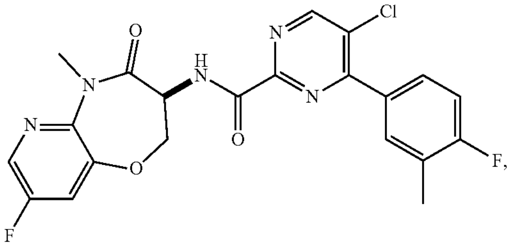
, -continued
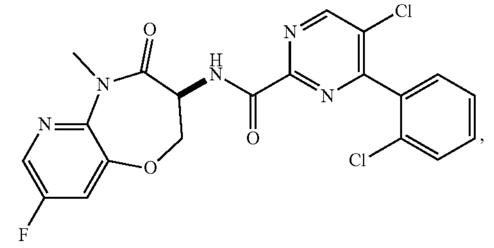
,
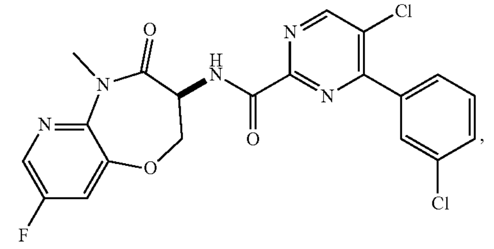
,
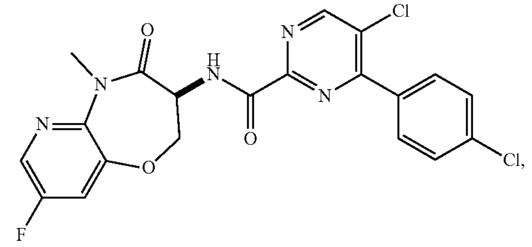
,
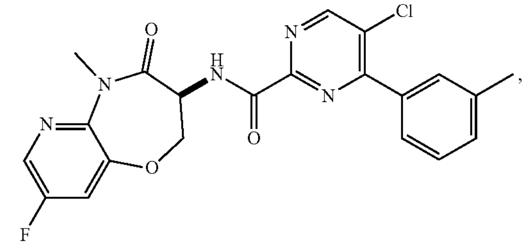
,
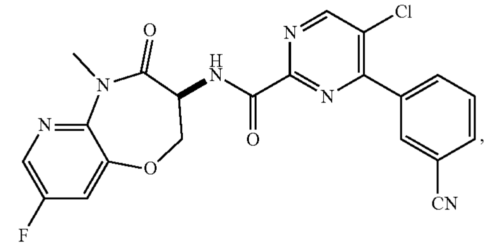
,
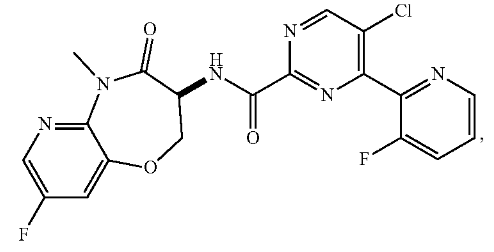
,
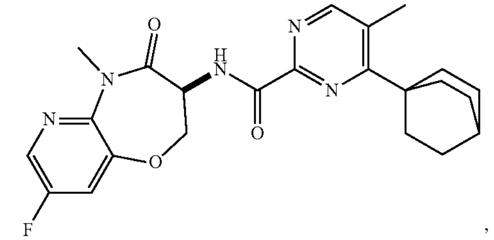
,
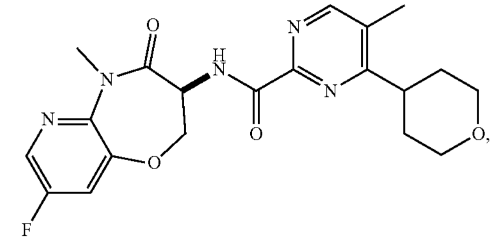
,
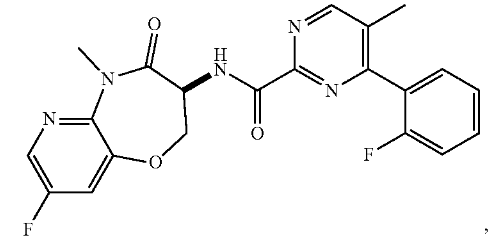
,
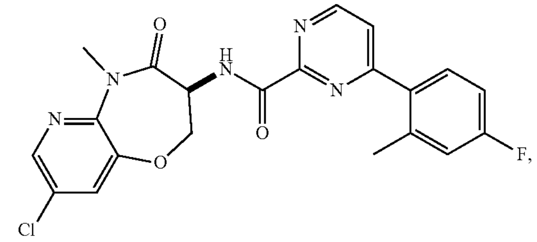
,
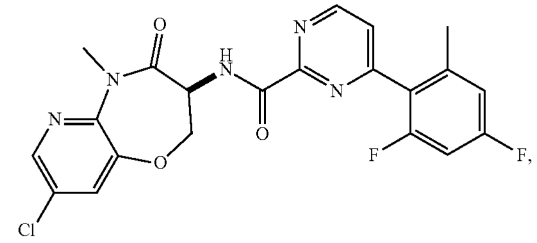
,
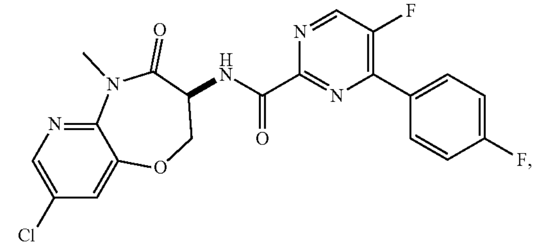
,
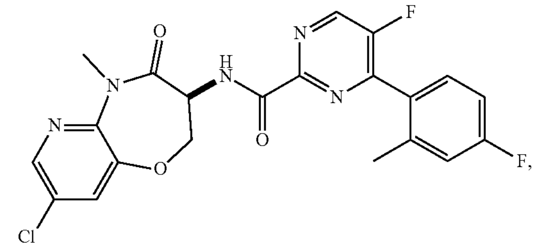
, -continued
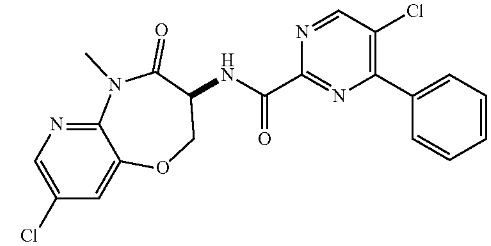
,
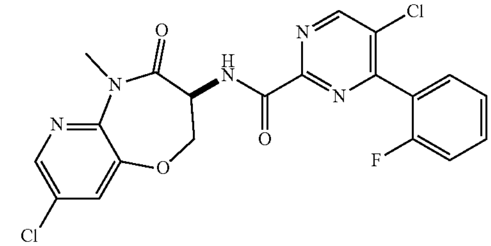
,
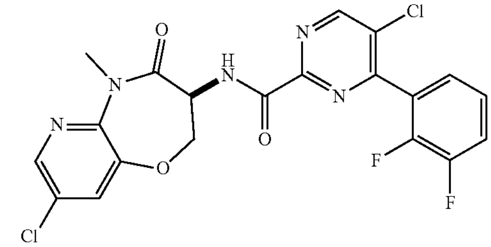
,
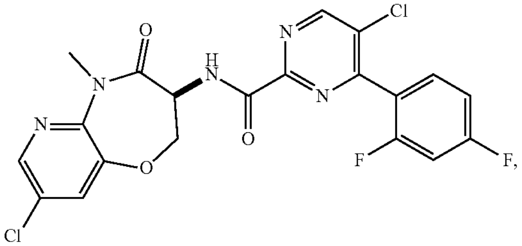
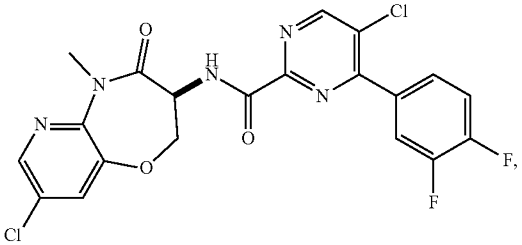
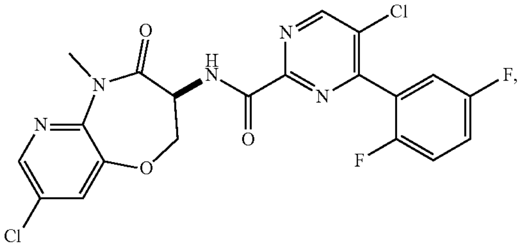
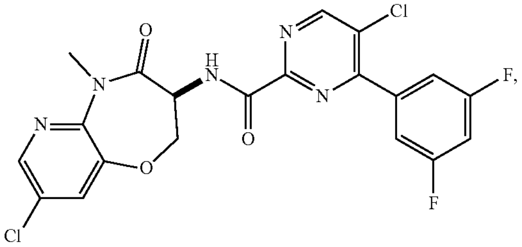
-continued
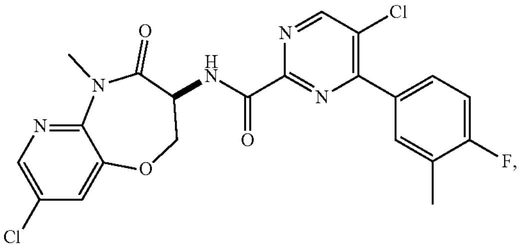
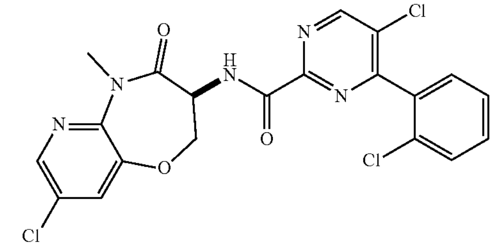
,
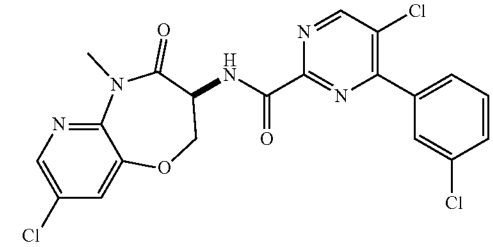
,
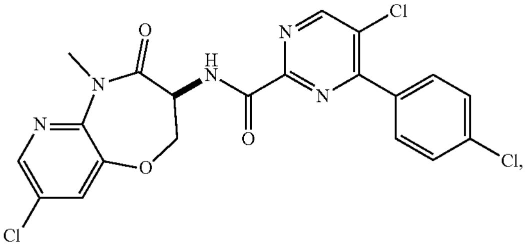
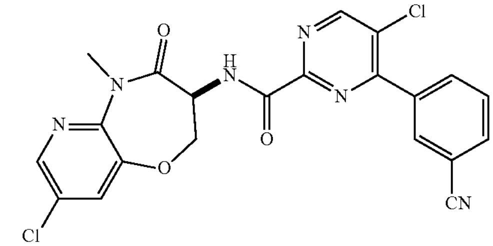
,
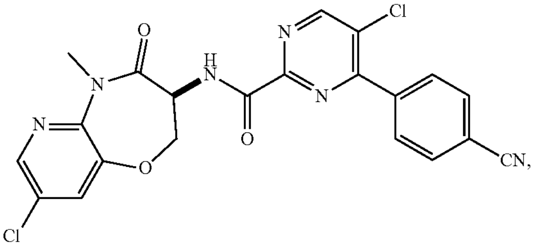
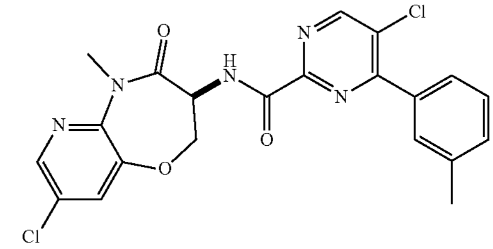
, -continued
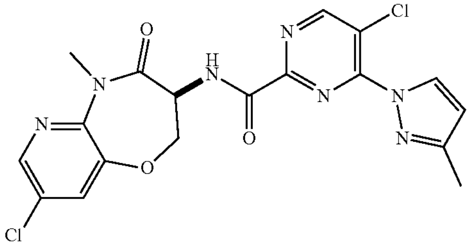
,
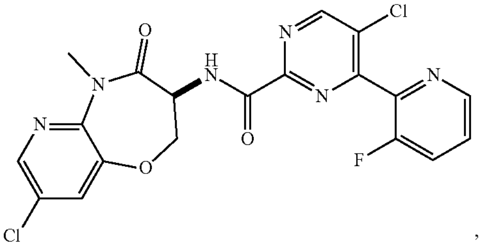
,
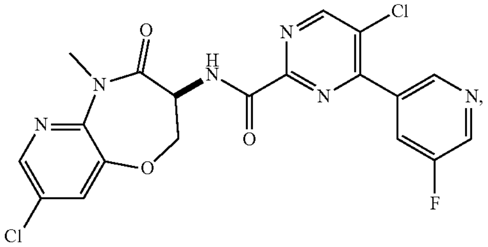
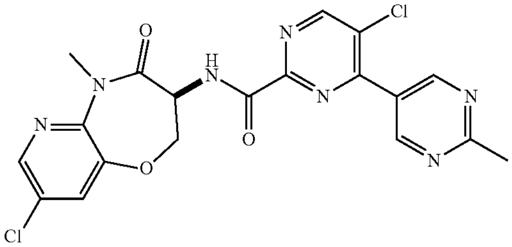
,
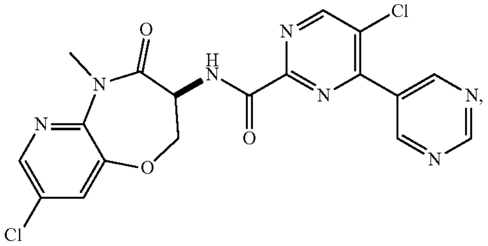
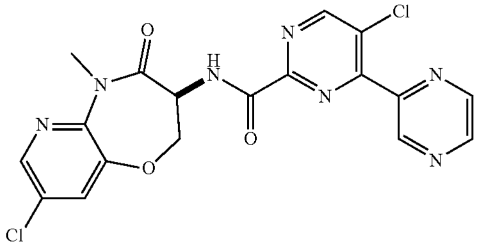
,
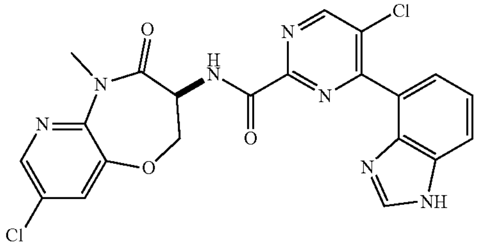
,
-continued
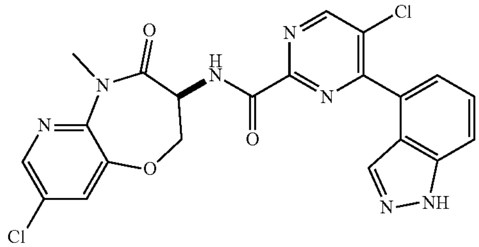
,
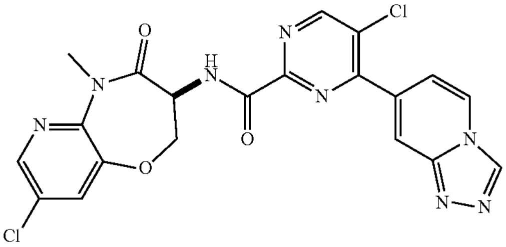
,
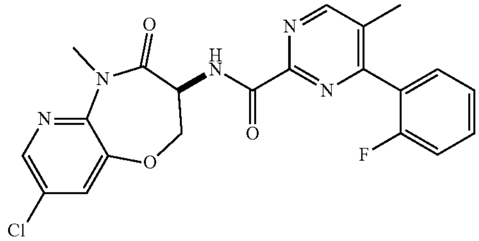
,
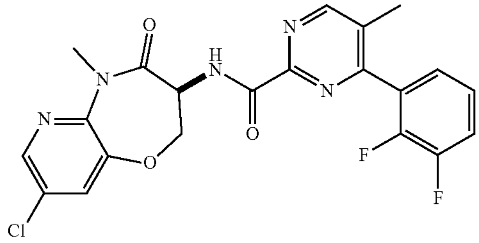
,
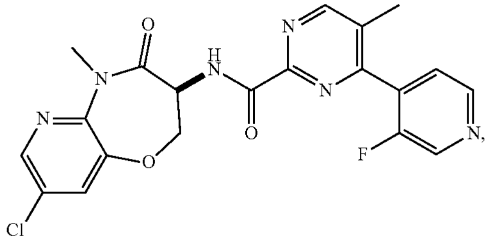
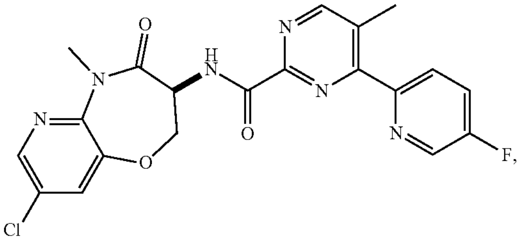
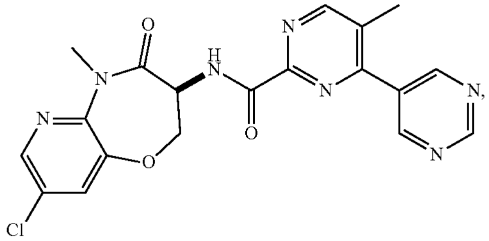

-continued
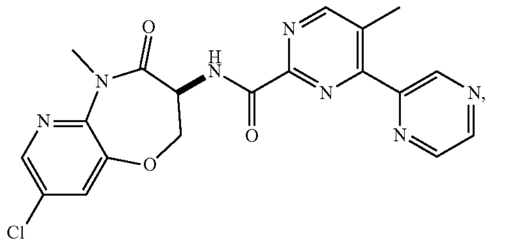
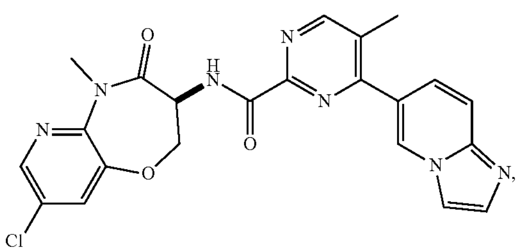
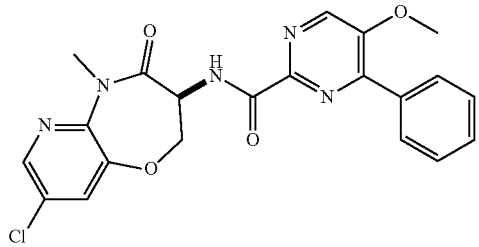
,
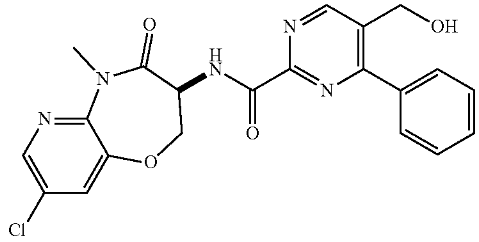
,
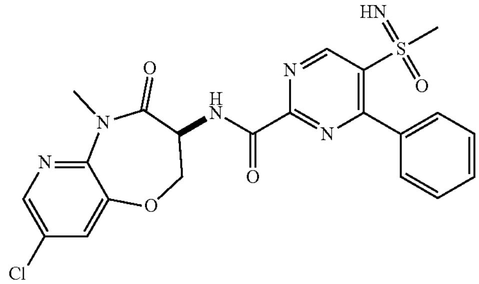
,
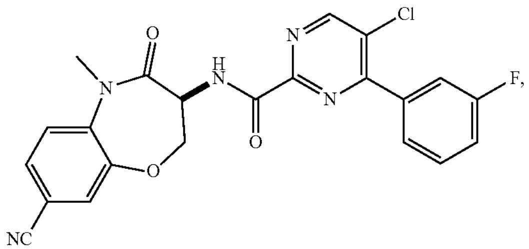
-continued
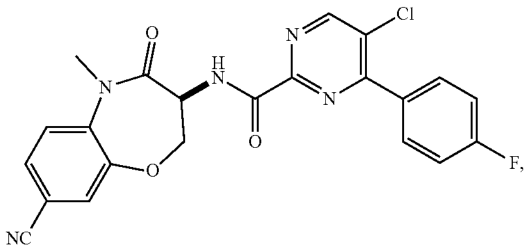
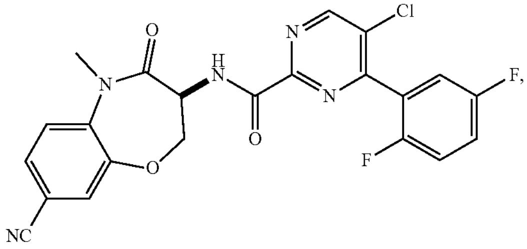
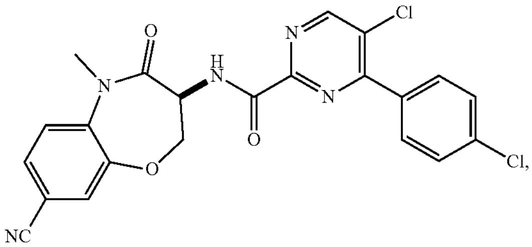
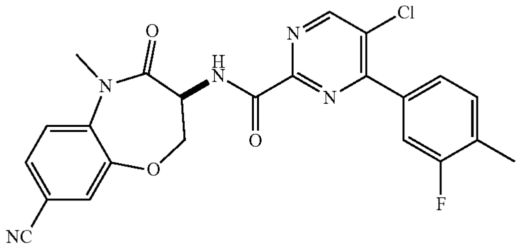
,
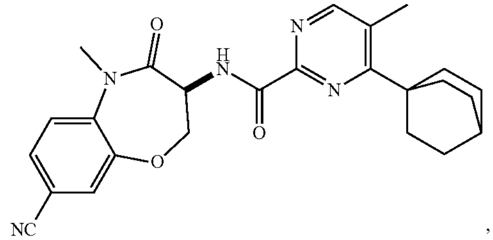
,
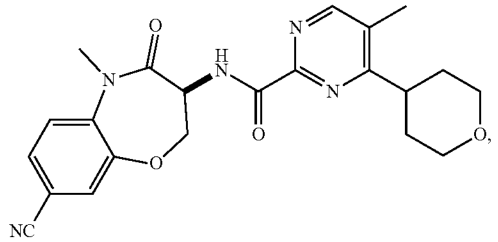
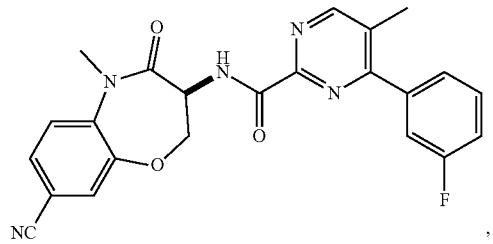
, -continued
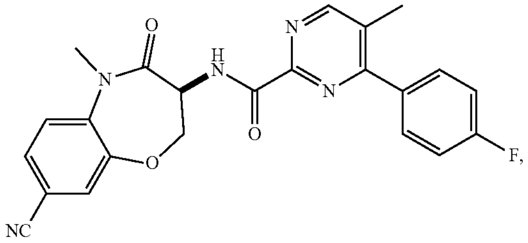
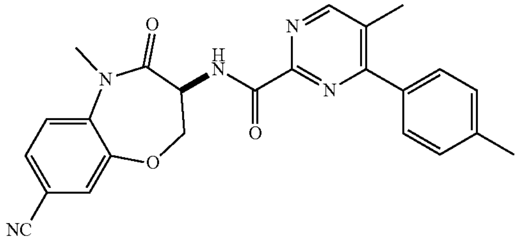
,
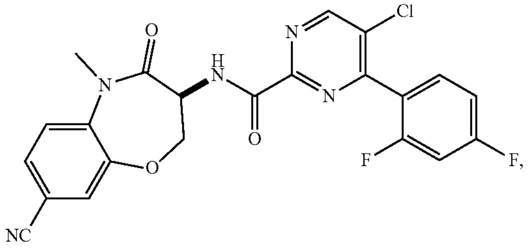
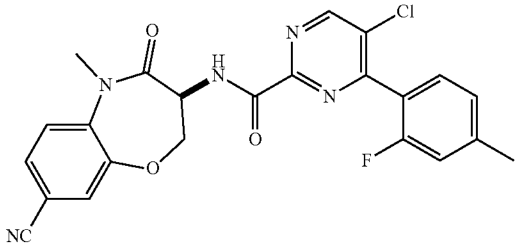
,
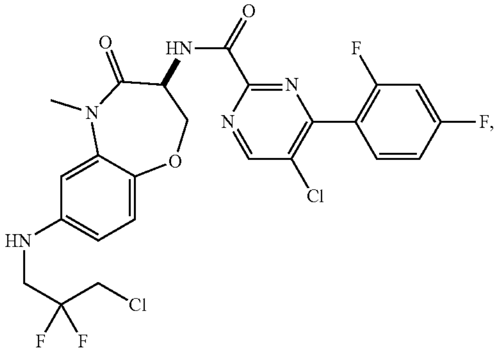
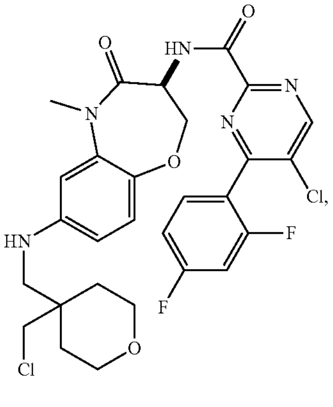
-continued
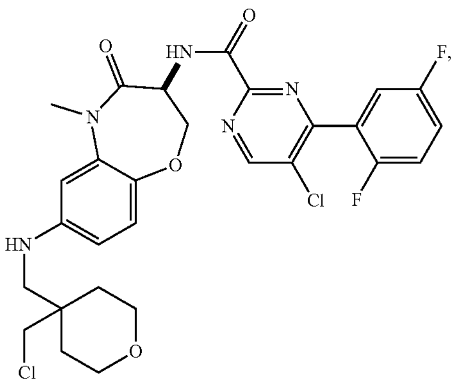
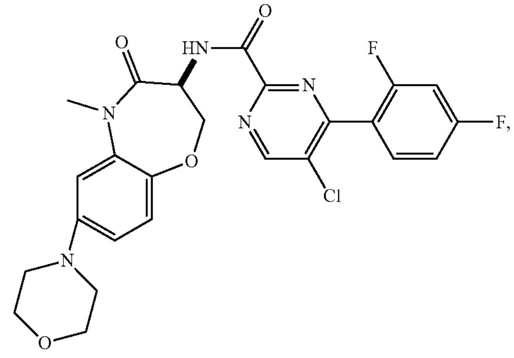
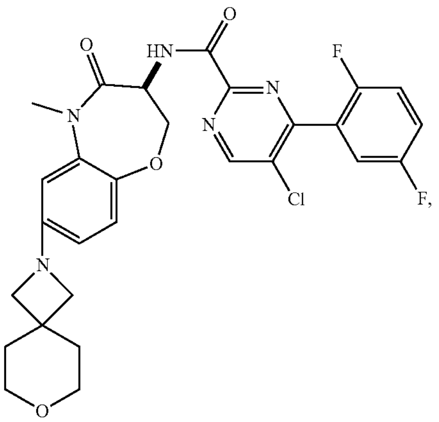
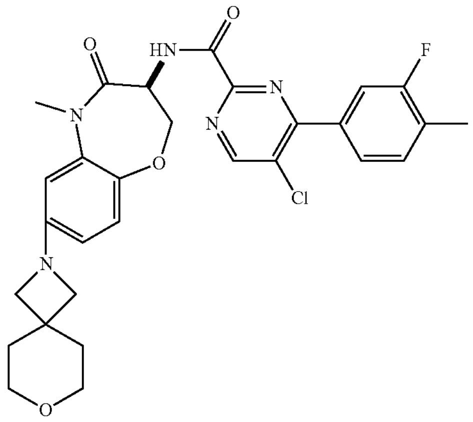
, -continued
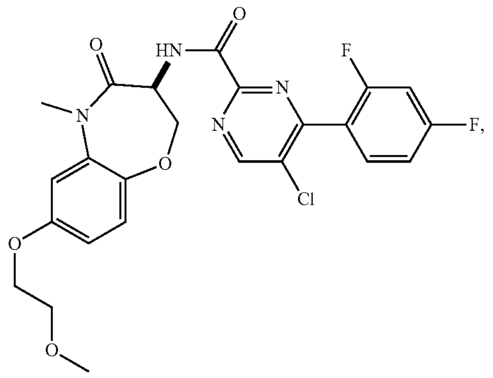
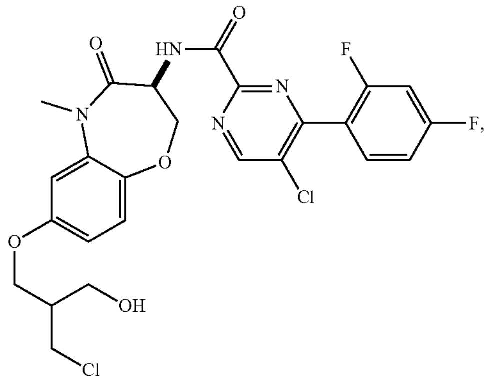
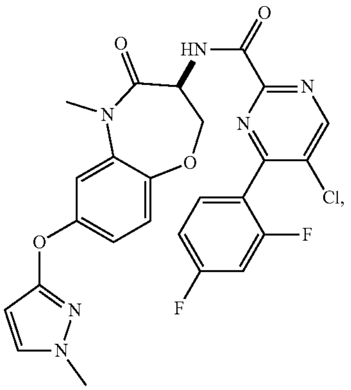
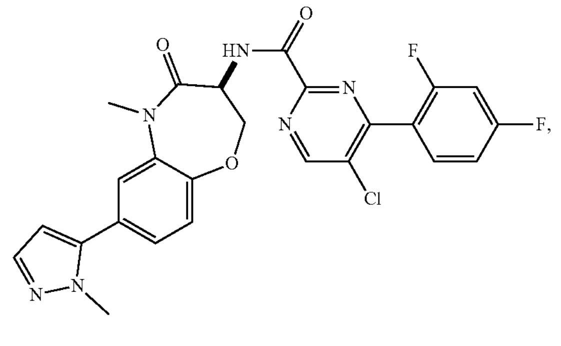
-continued
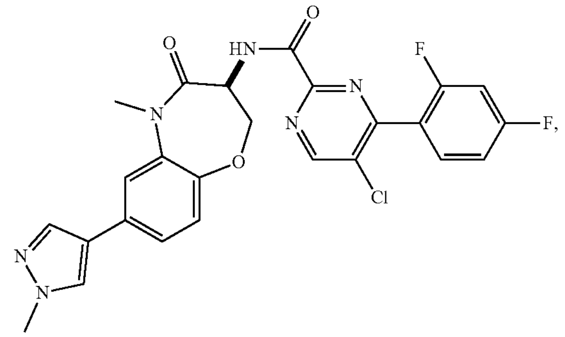
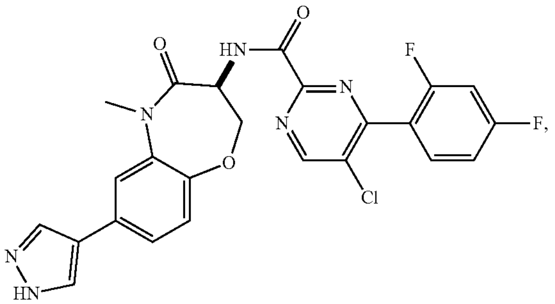
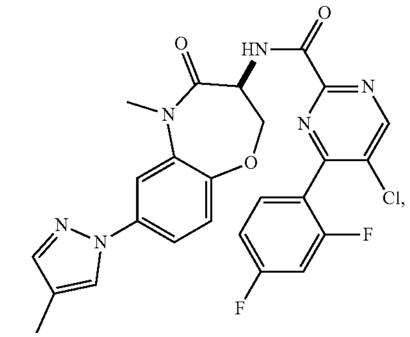
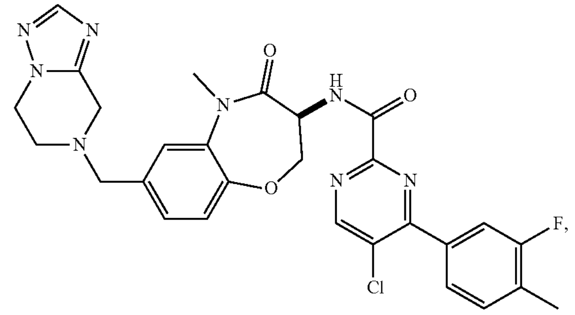
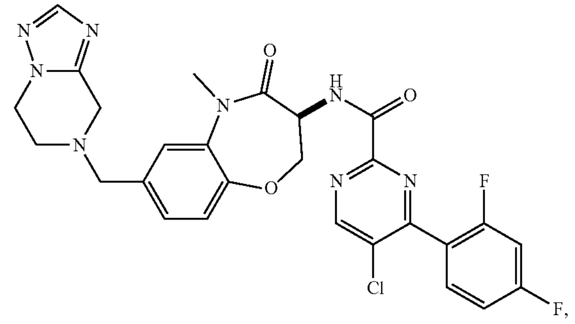

-continued
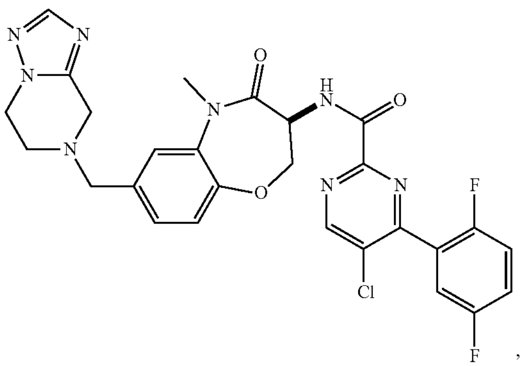
,
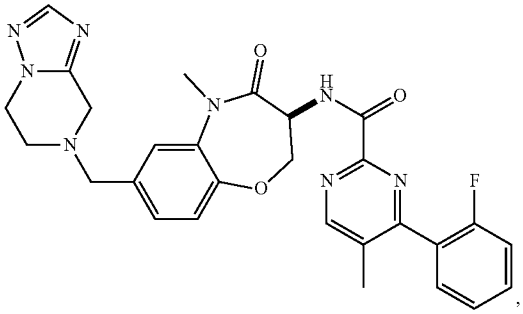
,
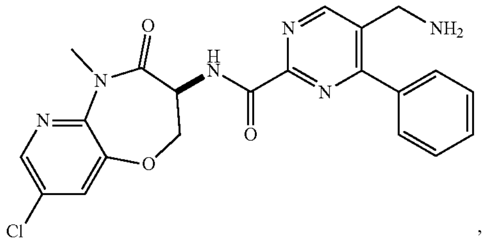
,
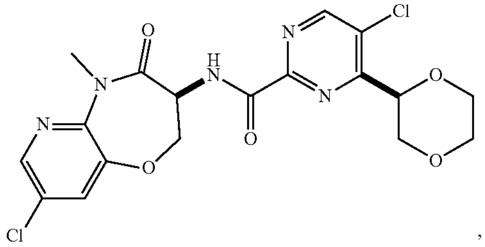
,
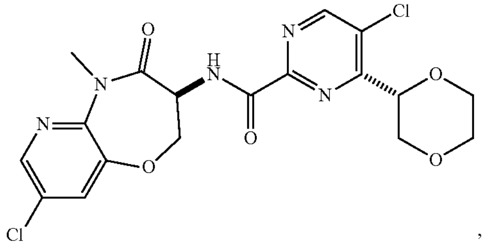
,
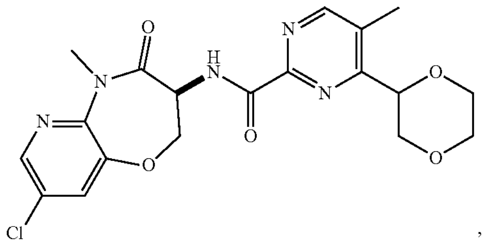
,
-continued
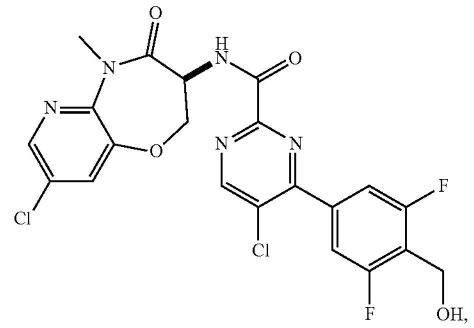
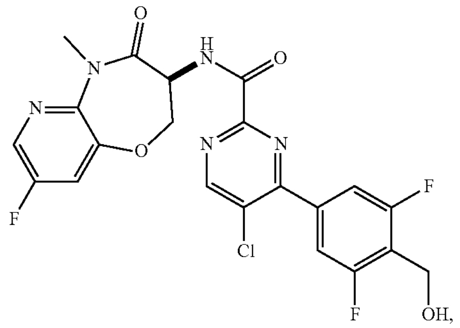
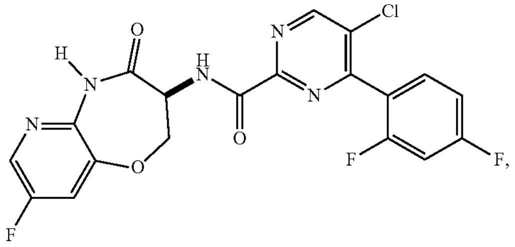
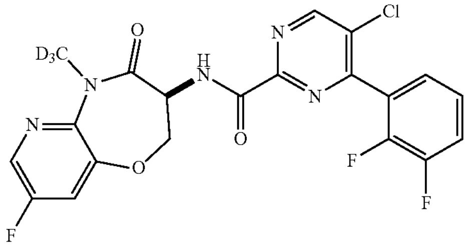
,
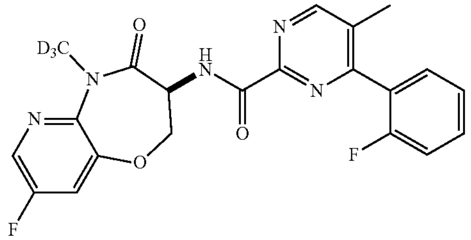
, and
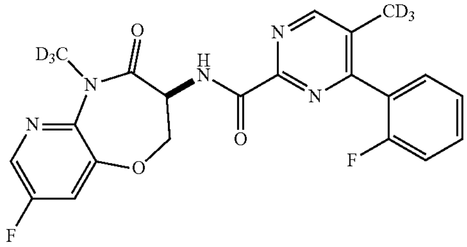
,
or a salt or tautomer thereof.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein, or a salt or tautomer thereof.

Also provided are methods of inhibiting at least one RIPK1 function comprising the step of contacting RIPK1 with a compound as described herein, or a salt or tautomer thereof. The cell phenotype, cell proliferation, activity of RIPK1, change in biochemical output produced by active RIPK1, expression of RIPK1, or binding of RIPK1 with a natural binding partner may be monitored. Such methods may be modes of treatment of disease, biological assays, cellular assays, biochemical assays, or the like.

Also provided herein are methods of treatment of a RIPK1-mediated disease comprising the administration of a therapeutically effective amount of a compound as disclosed herein, or a salt or tautomer thereof, to a patient in need thereof.

Also provided herein are methods of treatment of an inflammatory component of an RIPK1-mediated disease.

Also provided herein are methods of treatment of an apoptotic component of an RIPK1-mediated disease.

Also provided herein are methods of treatment of a necroptotic component of an RIPK1-mediated disease.

In certain embodiments, the disease is chosen from neurodegenerative disorders, inflammatory disorders, and cancer.

In certain embodiments, the disease is cancer. In certain embodiments, the cancer is treated by promoting an appropriate immune response to the tumor. In certain embodiments, the appropriate immune response to the tumor comprises, or results in, one or more of the following:

- an increase in the number or activity, or degree of tumor infiltration, of cytotoxic T-lymphocytes and/or natural killer cells;
- an increase in the number or activity of M1 macrophages in the tumor microenvironment and/or a decrease in the in the number or activity of M2 macrophages in the tumor microenvironment;
- a decrease in the number or activity of regulatory T cells; and
- a decrease in the number or activity of myeloid-derived suppressor cells.

In certain embodiments, the disease is a myelodysplastic syndrome (MDS). In certain embodiments, the myelodysplastic syndrome is chosen from myelodysplastic syndrome with unilineage dysplasia, myelodysplastic syndrome with multilineage dysplasia, myelodysplastic syndrome with ring sideroblasts, myelodysplastic syndrome associated with isolated del chromosome abnormality, myelodysplastic syndrome with excess blasts—type 1, and myelodysplastic syndrome with excess blasts—type 2. In certain embodiments the myelodysplastic syndrome is unclassifiable myelodysplastic syndrome.

In certain embodiments, the disease is acute myeloid leukemia (AML).

Also provided herein is a compound as disclosed herein, or a salt or tautomer thereof for use as a medicament.

Also provided herein is a compound as disclosed herein, or a salt or tautomer thereof for use as a medicament for the treatment of a RIPK1-mediated disease.

Also provided is the use of a compound as disclosed herein, or a salt or tautomer thereof as a medicament.

Also provided is the use of a compound as disclosed herein, or a salt or tautomer thereof as a medicament for the treatment of a RIPK1-mediated disease.

Also provided is a compound as disclosed herein, or a salt or tautomer thereof for use in the manufacture of a medicament for the treatment of a RIPK1-mediated disease.

Also provided is the use of a compound as disclosed herein, or a salt or tautomer thereof for the treatment of a RIPK1-mediated disease.

Also provided herein is a method of inhibition of RIPK1 comprising contacting RIPK1 with a compound as disclosed herein, or a salt or tautomer thereof.

Also provided herein is a method for achieving an effect in a patient comprising the administration of a therapeutically effective amount of a compound as disclosed herein, or a salt or tautomer thereof, to a patient wherein the effect is chosen from cognition enhancement.

Also provided is a method of modulation of a RIPK1-mediated function in a subject comprising the administration of a therapeutically effective amount of a compound as disclosed herein, or a salt or tautomer thereof.

Also provided is a pharmaceutical composition comprising a compound as disclosed herein, or a salt or tautomer thereof, together with a pharmaceutically acceptable carrier.

In certain embodiments, the pharmaceutical composition is formulated for oral administration.

In certain embodiments, the oral pharmaceutical composition is chosen from a tablet and a capsule.

Also provided is a method for the synthesis of a compound of Formula (I)

(I)

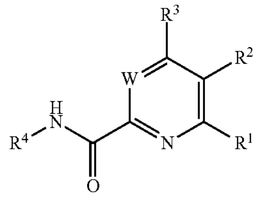

or a salt or tautomer thereof, comprising the step of contacting an acid of formula (I-A)

(I-A)

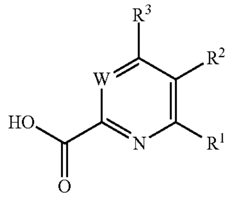

with a base of formula (I-B)

(I-A)

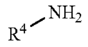

in the presence of an amide coupling agent, wherein:

W is chosen from CH, $CR^5$, and N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$;

$R^2$ and $R^3$ are independently chosen from H, halo, cyano, alkyl, (alkyl)oxy, (alkyl)thio, (alkyl)sulfonimidoyl, (alkyl)sulfonyl, cycloalkyl, and (cycloalkyl)oxy, any one of which is optionally substituted with one or more $R^7$, or $R^2$ and $R^3$, together with the intervening two carbons, combine to form a 5-7 membered cycloalkyl, heterocycloalkyl, aryl, or heteroaryl ring, any one of which is optionally substituted with one or more $R^8$ and optionally fused with a 6-membered aryl or heteroaryl ring, said 6-membered aryl or heteroaryl ring being optionally substituted with one or more $R^9$;

$R^4$ is chosen from alkyl, cycloalkyl, heterocycloalkyl, aryl, heteroaryl, (cycloalkyl)alkyl, (heterocycloalkyl) alkyl, (aryl)alkyl, and (heteroaryl)alkyl, any one of which is optionally substituted with one or more $R^{10}$;

$R^5$ is chosen from H, CN, halo, hydroxy, alkyl, and (alkyl)oxy;

each $R^6$, $R^7$, $R^8$, and $R^9$ is independently chosen from CN, halo, hydroxy, $NH_2$, oxo, alkyl, and (alkyl)oxy;

each $R^{10}$ is independently chosen from CN, halo, hydroxy, oxo, alkyl, cycloalkyl, heterocycloalkyl, aryl, heteroaryl, (cycloalkyl)$CH_2$, (heterocycloalkyl)$CH_2$, (aryl)$CH_2$, (heteroaryl)$CH_2$, (alkyl)$SO_2$, (cycloalkyl) $SO_2$, (heterocycloalkyl)$SO_2$, (aryl)$SO_2$, (heteroaryl) $SO_2$, (alkyl)NH, (cycloalkyl)NH, (heterocycloalkyl) NH, (aryl)NH, (heteroaryl)NH, (alkyl)oxy, (cycloalkyl) oxy, (heterocycloalkyl)oxy, (aryl)oxy, and (heteroaryl) oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl) oxy, (haloalkylsulfonyl)oxy, (aryl)oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl) oxy, and oxo.

In certain embodiments, the amide coupling agent is chosen from T3P and HATU.

In certain embodiments, the reaction is performed in the presence of an amine base. In certain embodiments, the amine base is chosen from $Et_3N$ and $iPr_2NEt$.

Definitions

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a $—C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy", and, interchangeably, "(alkyl)oxy", as used herein, alone or in combination, refers to an alkyl ether radical wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In certain embodiments, said alkyl will comprise from 1 to 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a straight chain saturated hydrocarbon attached at two or more positions, such as methylene ($—CH_2—$), ethylene ($—CH_2CH_2—$), and propylene ($—CH_2CH_2CH_2—$). "Alkylene" can thus be described as $—(CH_2)_n—$ with n being an positive integer. In some embodiments, n is chosen from 1 to 20. In some embodiments, n is chosen from 1 to 10. In some embodiments, n is chosen from 1 to 8. In some embodiments, n is chosen from 1 to 6. Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term “alkylthio,” as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term “alkynyl,” as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In certain embodiments, said alkynyl comprises from 2 to 4 carbon atoms. The term “alkynylene” refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term “alkynyl” may include “alkynylene” groups.

The terms “amido” and “carbamoyl,” as used herein, alone or in combination, refer to an amino group as described below attached to the parent molecular moiety through a carbonyl group, or vice versa. The term “C-amido” as used herein, alone or in combination, refers to a —C(O)N(RR') group with R and R' as defined herein or as defined by the specifically enumerated “R” groups designated. The term “N-amido” as used herein, alone or in combination, refers to a RC(O)N(R')— group, with R and R' as defined herein or as defined by the specifically enumerated “R” groups designated. The term “acylamino” as used herein, alone or in combination, embraces an acyl group attached to the parent moiety through an amino group. An example of an “acylamino” group is acetylamino ($CH_3C(O)NH$—).

The term “amino,” as used herein, alone or in combination, refers to —NRR' wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which is optionally substituted.

The term “aryl,” as used herein, alone or in combination, means a carbocyclic aromatic system containing one, two or three rings wherein such polycyclic ring systems are fused together. The term “aryl” embraces aromatic groups such as phenyl, naphthyl, anthracenyl, and phenanthryl.

The term “arylalkyl” or “aralkyl,” as used herein, alone or in combination, refers to an aryl group attached to the parent molecular moiety through an alkyl group.

The term “arylalkanoyl” or “aralkanoyl” or “aroyl,” as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms “benzo” and “benz,” as used herein, alone or in combination, refer to the divalent radical $C_6H_4$=derived from benzene. Examples include benzothiophene and benzimidazole.

The term “carbamate,” as used herein, alone or in combination, refers to an ester of carbamic acid (—NHCOO—) which may be attached to the parent molecular moiety from either the nitrogen or acid end, and which is optionally substituted as defined herein.

The term “O-carbamyl” as used herein, alone or in combination, refers to a —OC(O)NRR', group, with R and R' as defined herein.

The term “N-carbamyl” as used herein, alone or in combination, refers to a ROC(O)NR'— group, with R and R' as defined herein.

The term “carbonyl,” as used herein, when alone includes formyl [—C(O)H] and in combination is a —C(O)— group.

The term “carboxyl” or “carboxy,” as used herein, refers to —C(O)OH or the corresponding “carboxylate” anion, such as is in a carboxylic acid salt. An “O-carboxy” group refers to a RC(O)O— group, where R is as defined herein. A “C-carboxy” group refers to a —C(O)OR groups where R is as defined herein.

The term “cyano,” as used herein, alone or in combination, refers to —CN.

The term “cycloalkyl,” or, alternatively, “carbocycle,” as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. In certain embodiments, said cycloalkyl will comprise a spirocycle ring system. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. “Bicyclic” and “tricyclic” as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane.

The term “ester,” as used herein, alone or in combination, refers to a carboxy group bridging two moieties linked at carbon atoms.

The term “ether,” as used herein, alone or in combination, refers to an oxy group bridging two moieties linked at carbon atoms.

The term “halo,” or “halogen,” as used herein, alone or in combination, refers to fluorine, chlorine, bromine, or iodine.

The term “haloalkoxy,” as used herein, alone or in combination, refers to a haloalkyl group attached to the parent molecular moiety through an oxygen atom.

The term “haloalkyl,” as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and one, two, or three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In certain embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings wherein heteroaryl rings are fused with other heteroaryl rings wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridinyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic; saturated, partially unsaturated, or fully unsaturated (but not fully aromatic) bicyclic; or saturated, partially unsaturated, or fully unsaturated (but not fully aromatic) tricyclic heterocyclic group containing at least one heteroatom as a ring member wherein each said heteroatom may be independently chosen from nitrogen, oxygen, and sulfur. The term includes polycyclic groups which comprise at least one nonaromatic ring, such as 1,2-dihydroquinoline, 5,6-dihydroquinoline, and 2,3-dihydrobenzofuran. The term excludes polycyclic groups in which every ring is nonaromatic, such as indole, quinoline, and acridine.

In certain embodiments, said heterocycloalkyl will comprise a spirocycle ring system. In certain embodiments, said hetercycloalkyl will comprise from 1 to 4 heteroatoms as ring members. In certain embodiments, said hetercycloalkyl will comprise from 1 to 2 heteroatoms as ring members. In certain embodiments, said hetercycloalkyl will comprise from 3 to 8 ring members in each ring. In certain embodiments, said hetercycloalkyl will comprise from 3 to 7 ring members in each ring. In certain embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl or heteroaryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like.

The term "hydroxy," as used herein, alone or in combination, refers to —OH.

The term "hydroxyalkyl," as used herein, alone or in combination, refers to a hydroxy group attached to the parent molecular moiety through an alkyl group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR' wherein R and R' are independently chosen from hydrogen and lower alkyl, either of which is optionally substituted.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycle ring system" refers to a polycyclic ring system comprising two rings such that a single atom is common to both rings.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a $RS(=O)_2NR'$— group with R and R' as defined herein.

The term "S-sulfonamido" refers to a —$S(=O)_2NRR'$, group, with R and R' as defined herein.

The terms "thia" and "thio," as used herein, alone or in combination, refer to a —S-group or an ether wherein the oxygen is replaced with sulfur. The oxidized derivatives of the thio group, namely sulfinyl: —SO—, sulfonyl: —$SO_2$—, and sulfonimidoyl: —SO(NH)—, are included in the definition of thia and thio.

The term "thiol," as used herein, alone or in combination, refers to an —SH group.

The term "thiocyanato" refers to a —CNS group.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which is optionally substituted. Such R and R' groups should be understood to be optionally substituted as defined herein. Whether an R group has a number designation or not, every R group, including R, R' and $R^n$ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds, salts, and tautomers disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds, salts, and tautomers can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds, salts, and tautomers of particular stereochemistry are either commercially available or can be made and resolved by techniques known in the art. Additionally, the compounds, salts, and tautomers disclosed herein may exist as geometric isomers. The present invention includes all cis, trans, syn, anti, entgegen (E), and zusammen (Z) isomers as well as the appropriate mixtures thereof.

The term "tautomers", as used herein, alone or in combination, refers to a pair of compounds which differ in the attachment of a hydrogen and disposition of a double bond, and which rapidly interconvert in conventional media. Tautomeric pairs that are recognized to the person of skill include, but are not limited to, keto/enol tautomers, 2-hydroxypyridine /2-pyridone tautomers, lactam/lactim tautomers, and imine/enamine tautomers.

Compounds disclosed herein may exist as tautomers; all tautomeric isomers are provided with this disclosure. For example, 2-hydroxypyridines will be recognized by those skilled in the art to exist in tautomeric equilibrium with the corresponding 2-pyridone, as represented by the following equilibrium:

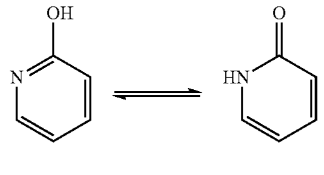 [SMILES: Oc1ccccn1 ; O=c1cccc[nH]1]

A similar equilibrium exists for 4-hydroxypyridines. The relative amount of 2-hydroxypyridine and 2-pyridone (and, respectively, 4-hydroxypyridine and 4-pyridone) is controlled by the various groups around the heteroaryl ring, as well as the particulars of the solvent media. A person of skill will appreciate that compounds that exist in tautomeric equilibria, including, but not limited to the above equilibria, are generally not isolated in either of the two tautomeric forms, but rather as a mixture.

Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"RIPK1 binder" is used herein to refer to a compound, or a salt or tautomer thereof, that exhibits an $K_d$ with respect to RIPK1 of no more than about 100 μM and more typically not more than about 50 μM, as measured in the RIPK1 binding assay described generally herein. The RIPK1 binding assay measures the $K_d$ (dissociation constant) for the binding of a compound, or a salt or tautomer thereof with the active site of RIPK1. Certain compounds disclosed herein, or a salt or tautomer thereof, have been discovered to bind to RIPK1. In certain embodiments, compounds, or salts or tautomers thereof, will exhibit an $K_d$ with respect to RIPK1 of no more than about 10 μM; in certain embodiments, compounds, or salts or tautomers thereof, will exhibit a $K_d$ with respect to RIPK1 of no more than about 1 μM; in certain embodiments, compounds, or salts or tautomers thereof, will exhibit a $K_d$ with respect to RIPK1 of not more than about 0.1 μM; in certain embodiments, compounds, or salts or tautome thereof, will exhibit a $K_d$ with respect to RIPK1 of not more than about 10 nM, as measured in the RIPK1 assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, or tautomers thereof) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

Salts and Polymorphs

The compounds disclosed herein can exist as therapeutically acceptable salts. The present invention includes compounds listed above, and tautomers thereof, in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and tautomers thereof, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

While it may be possible for the compounds, salts, and tautomers of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, or tautomers thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

Formulations

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound, salt, or tautomer of the subject invention or a pharmaceutically acceptable salt, or tautomer thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds, or salts or tautomers thereof disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound, or a salt or tautomer thereof, moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds, or salts or tautomers thereof, may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses, or salts or tautomers thereof.

The compounds, or a salt or tautomer thereof, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds, or a salt or tautomer thereof, which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds, or salts or tautomer thereof, to allow for the preparation of highly concentrated solutions.

In addition to the formulations described previously, the compounds, or salts or tautomers thereof, may also be formulated as a depot preparation. Such long acting formulations may be administered by implantation (for example subcutaneously or intramuscularly) or by intramuscular injection. Thus, for example, the compounds, or salts or tautomers thereof, may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds, or salts or tautomers thereof, may also be formulated in rectal compositions such as suppositories or retention enemas, e.g., containing conventional suppository bases such as cocoa butter, polyethylene glycol, or other glycerides.

Certain compounds, or salts or tautomers thereof, disclosed herein may be administered topically, that is by non-systemic administration. This includes the application of a compound, or a salt or tautomer thereof, disclosed herein externally to the epidermis or the buccal cavity and the instillation of such a compound, or a salt or tautomer thereof, into the ear, eye and nose, such that the compound (or salt or tautomers thereof) does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds, or salts or tautomers thereof, may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds, salts, and tautomers according to the invention may take the form of a dry powder composition, for example a powder mix of the compound, or salt or tautomer thereof, and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Administration and Treatment

Compounds, or salts or tautomers thereof, may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds, or salts or tautomers thereof, which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds, or salts or tautomers thereof, can be administered in various modes, e.g. orally, topically, or by injection. The precise amount of compound, or salt or tautomer thereof, administered to a patient will be the responsibility of the attendant physician. The specific dose level for any particular patient will depend upon a variety of factors including the activity of the specific compound employed, or salt or tautomer thereof, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, or tautomer thereof) in combination with another therapeutic agent. By way of example only, if one of the side effects experienced by a patient upon receiving one of the compounds herein, or salt or tautomer thereof, is hypertension, then it may be appropriate to administer an anti-hypertensive agent in combination with the initial therapeutic agent. Or, by way of example only, the therapeutic effectiveness of one of the compounds described herein, or salts or tautomers thereof, may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein, or salts or tautomers thereof, with another therapeutic agent (which also includes a therapeutic regimen) that also has therapeutic benefit. By way of example only, in a treatment for diabetes involving administration of one of the compounds described herein, or salts or tautomers thereof, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds, salts, and tautomers of the invention with: donepezil, rivastigmine, galantamine, and memantine. Further examples include anti-amyloid antibodies and vaccines, anti-Ab antibodies and vaccines, anti-tau antibodies and vaccines, β-secretase inhibitors, 5-HT4 agonists, 5-HT6 antagonists, 5-HT1a antagonists, α7 nicotinic receptor agonists, 5-HT3 receptor antagonists, PDE4 inhibitors, O-glycnacase inhibitors, and other medicines approved for the treatment of Alzheimer's disease. Further examples include metformin, minocycline, tissue plasminogen activator, and other therapies that improve neuronal survival.

In any case, the multiple therapeutic agents (at least one of which is a compound disclosed herein, or a salt or tautomer thereof) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating RIPK1-mediated disorders in a human or animal subject in need of such treatment comprising administering to said subject an amount of a compound disclosed herein, or a salt or tautomer thereof, effective to reduce or prevent said disorder in the subject, in combination with at least one additional agent for the treatment of said disorder that is known in the art. In a related aspect, certain embodiments provide therapeutic compositions comprising at least one compound disclosed herein, or salt or tautomer thereof, in combination with one or more additional agents for the treatment of RIPK1-mediated disorders.

For use in cancer and neoplastic diseases a RIPK1 inhibitor may be optimally used together with one or more of the following non-limiting examples of anti-cancer agents:

1) inhibitors or modulators of a protein involved in one or more of the DNA damage repair (DDR) pathways such as:
   a. PARP1/2, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;
   c. checkpoint kinase 2 (CHK2), including, but not limited to: PV1019, NSC 109555, and VRX0466617;
   d. dual CHK1/CHK2, including, but not limited to: XL-844, AZD7762, and PF-473336;
   e. WEE1, including, but not limited to: MK-1775 and PD0166285;
   f. ATM, including, but not limited to KU-55933,
   g. DNA-dependent protein kinase, including, but not limited to NU7441 and M3814; and
   h. Additional proteins involved in DDR;
2) Inhibitors or modulators of one or more immune checkpoints, including, but not limited to:
   a. PD-1 inhibitors such as nivolumab (OPDIVO), pembrolizumab (KEYTRUDA), pidilizumab (CT-011), and AMP-224 (AMPLIMMUNE);
   b. PD-L1 inhibitors such as Atezolizumab (TECENTRIQ), Avelumab (Bavencio), Durvalumab (Imfinzi), MPDL3280A (Tecentriq), BMS-936559, and MEDI4736;
   c. anti-CTLA-4 antibodies such as ipilimumab (YERVOY) and CP-675,206 (TREMELIMUMAB);
   d. inhibitors of T-cell immunoglobulin and mucin domain 3 (Tim-3);
   e. inhibitors of V-domain Ig suppressor of T cell activation (Vista);
   f. inhibitors of band T lymphocyte attenuator (BTLA);
   g. inhibitors of lymphocyte activation gene 3 (LAG3); and
   h. inhibitors of T cell immunoglobulin and immunoreceptor tyrosine-based inhibitory motif domain (TIGIT);
3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;
7) antimitotic, which are often plant alkaloids and terpenoids, or derivatives thereof including but limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);
8) topoisomerase inhibitors, including, but not limited to: amacrine, camptothecin (CTP), genistein, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);
9) DNA replication inhibitors, including, but not limited to: fludarabine (FLUDARA), aphidicolin, ganciclovir, and cidofovir;
10) ribonucleoside diphosphate reductase inhibitors, including, but not limited to: hydroxyurea;
11) transcription inhibitors, including, but not limited to: actinomycin D (dactinomycin, COSMEGEN) and plicamycin (mithramycin);
12) DNA cleaving agents, including, but not limited to: bleomycin (BLENOXANE), idarubicin,
13) cytotoxic antibiotics, including, but not limited to: actinomycin D (dactinomycin, COSMEGEN),
14) aromatase inhibitors, including, but not limited to: aminoglutethimide, anastrozole (ARIMIDEX), letrozole (FEMARA), vorozole (RIVIZOR), and exemestane (AROMASIN);

15) angiogenesis inhibitors, including, but not limited to: genistein, sunitinib (SUTENT), and bevacizumab (AVASTIN);
16) anti-steroids and anti-androgens, including, but not limited to: aminoglutethimide (CYTADREN), bicalutamide (CASODEX), cyproterone, flutamide (EULEXIN), nilutamide (NILANDRON);
17) tyrosine kinase inhibitors, including, but not limited to: imatinib (GLEEVEC), erlotinib (TARCEVA), lapatininb (TYKERB), sorafenib (NEXAVAR), and axitinib (INLYTA);
18) mTOR inhibitors, including, but not limited to: everolimus, temsirolimus (TORISEL), and sirolimus;
19) monoclonal antibodies, including, but not limited to: trastuzumab (HERCEPTIN) and rituximab (RITUXAN);
20) apoptosis inducers such as cordycepin;
21) protein synthesis inhibitors, including, but not limited to: clindamycin, chloramphenicol, streptomycin, anisomycin, and cycloheximide;
22) antidiabetics, including, but not limited to: metformin and phenformin;
23) antibiotics, including, but not limited to:
    a. tetracyclines, including, but not limited to: doxycycline;
    b. erythromycins, including, but not limited to: azithromycin;
    c. glycylglycines, including, but not limited to: tigecycline;
    d. antiphrastic, including, but not limited to: pyrvinium pamoate;
    e. beta-lactams, including, but not limited to the penicillins and cephalosporins;
    f. anthracycline antibiotics, including, but not limited to: daunorubicin and doxorubicin;
    g. other antibiotics, including, but not limited to: chloramphenicol, mitomycin C, and actinomycin;
24) antibody therapeutic agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and
25) other agents, such as *Bacillus* Calmette-Gudrin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

An RIPK1 inhibitor may be optimally used together with one or more of the following therapeutics for myelodysplastic syndromes:

1) growth factors, such as epoetin (EPOGEN®, PROCRIT®), darbepoetin alfa (ARANESP®), luspatercept (REBLOZYL®), filgrastim (NEUPOGEN®), pegfilgrastim (NEULASTA®), romiplostim (NPLATE®), eltrombopag (PROMACTA®), and oprelvekin (NEUMEGA);
2) hypomethylating agents, such as azacitidine (ONUREG®, VIDAZA®);
3) antineoplastics, such as idarubicin (IDAMYCIN®), daunorubicin (CERUBIDINE®).

An RIPK1 inhibitor may be optimally used together with one or more of the following non-limiting examples of CNS agents:

1) catecholamine agents such as L-DOPA;
2) acetylcholinesterase inhibitors such as donepezil (ARICEPT®);
3) edaravone (RADICAVA®);
4) riluzole (RILUTEK®);
5) glaucoma medications, including:
    a. beta blockers, such as timolol;
    b. alpha agonists, such as brimonidine (ALPHAGAN®) and apraclonidine (IOPIDINE®);
    c. rho kinase inhibitors, such as netarsudil (RHOPRESSA®, RHOKIINSA®); and
    d. carbonic anhydrase inhibitors, such as dorzolamide (TRUSOPT®), brinzolamide (AZOPT®), acetazolamide (DIAMOX®), and methazolamide (NEPTAZANE®);
6) multiple sclerosis medications, including:
    a. immunomodulators, such as glatiramer (COPAXONE®), ofatumumab (KESIMPTA®), and interferon and its derivatives;
    b. monoclonal antibodies, such as alemtuzumab (LEMTRADA®), ocrelizumab (OCREVUS®), and natalizumab (TYSABRI®); abd
    c. other agents, such as teriflunomide (Aubagio®), monomethyl fumarate (BAFIERTAM™), dimethyl fumarate (TECFIDERA®), fingolimod (GILENYA®), cladribine (MAVENCLAD®), siponimod (MAYZENT®), diroximel (VUMERITY®), ozanimod (ZEPOSIA®), and mitoxantrone (NOVANTRONE®);
7) epilepsy/anti-seizure medications, including brivaracetam (BRIVIACT®), carbamazepine (CARBATROL®), diazepam (VALIUM®), lorazepam (ATIVAN®), clonazepam (KLONOPIN®), eslicarbazepine (APTIOM®), ethosuximide (ZARONTIN®), felbamate (FELBATOL®), fenfluramine (FINTEPLA®), lacosamide (VIMPAT®), lamotrigine (LAMICTAL®), levetiracetam (KEPPRA®), oxcarbazepine (OXTELLAR®), perampanel (FYCOMPA®), and phenobarbital;

In certain embodiments, the compounds, salts, or tautomers, compositions, and methods disclosed herein may be useful for the treatment of a disorder associated with an inflammatory component of cellular stress. In certain embodiments, the disorder is chosen from multiple sclerosis, Neimanm-Pick disease, Alzheimers disease, Parkinson's disease, amyotrophic lateral sclerosis, Lewy body dementia, frontotemporal dementia, glutamine expansion diseases such as Huntington's disease, Kennedy's disease, and spinocerebellar ataxia.

In certain embodiments, the compounds, salts, tautomers, compositions, and methods disclosed herein may be useful for the treatment of neuropathy. In certain embodiments, the neuropathy is chosen from diabetic neuropathy and chemotherapy induced neuropathy.

In certain embodiments, the compounds, salts, tautomers, compositions, and methods disclosed herein may be useful for the treatment of a retinal disease. In certain embodiments, the retinal disease is chosen from macular degeneration and retinitis.

In certain embodiments, the compounds, salts, tautomers, compositions, and methods disclosed herein may be useful for the treatment of an injury to the CNS. In certain embodiments, the injury is chosen from a traumatic brain injury and stroke.

In certain embodiments, the compounds, salts, tautomers, compositions, and methods disclosed herein may be useful for the treatment of an autoimmune disorder. In certain embodiments, the autoimmune disorder is chosen from ulcerative colitis, rheumatoid arthritis, psoriasis, lupus, inflammatory bowel disease.

In certain embodiments, the compounds, salts, tautomers, compositions, and methods disclosed herein may be useful for the treatment of viral infections.

In certain embodiments, the compounds, salts, tautomers, compositions, and methods disclosed herein may be useful for the treatment of sepsis.

In certain embodiments, the compounds, salts, tautomers, compositions, and methods disclosed herein may be useful for the treatment of retinal degeneration.

In certain embodiments, the compounds, salts, tautomers, compositions, and methods disclosed herein may be useful for the treatment of ischemic stroke.

In certain embodiments, the compounds, salts, tautomers, compositions, and methods disclosed herein may be useful for the treatment of intracerebral hemorrhage.

In certain embodiments, the compounds, salts, tautomers, compositions, and methods disclosed herein may be useful for the treatment of amyotrophic lateral sclerosis.

In certain embodiments, the compounds, salts, tautomers, compositions, and methods disclosed herein may be useful for the treatment of an acute kidney injury.

In certain embodiments, the compounds, salts, tautomers, compositions, and methods disclosed herein may be useful for the treatment of a myocardial reperfusion injury.

In certain embodiments, the compounds, salts, tautomers, compositions, and methods disclosed herein may be useful for the treatment of Alzheimer's disease.

In certain embodiments, the compounds, salts, tautomers, compositions, and methods disclosed herein may be useful for the treatment of ulcerative colitis.

In certain embodiments, the compounds, salts, tautomers, compositions, and methods disclosed herein may be useful for the treatment of osteoarthritis.

In certain embodiments, the compounds, salts, tautomers, compositions, and methods disclosed herein may be useful for the treatment of myelodysplastic syndrome. In certain embodiments, the compounds, salts, tautomers, compositions, and methods disclosed herein may be useful for the treatment of myelodysplastic syndrome at any stage of the disease, and to retard progression of the disease, including progression to acute myeloid leukemia. In certain embodiments, the compounds, salts, tautomers, compositions, and methods disclosed herein may be effective to maintain the disease in complete or partial remission following treatment for such remission, for example bone marrow transplant or chemotherapy.

In certain embodiments, the compounds, salts, tautomers, compositions, and methods disclosed herein may be useful for the treatment of one or more sub-classifications of myelodysplastic syndrome, as defined by either the FAB or WHO classifications, including refractory anemia with or without ringed sideroblasts, 5q-syndrome with or without ringed sideroblasts, refactory anemia with multilineage dysplasia with or without ringed sideroblasts, refactory anemia with excess blasts I and II, refractory anemia with excess blasts in transformation, chronic myelo-monocytic leukemia, and unclassifiable myelodysplastic syndrome.

In certain embodiments, the compounds, salts, tautomers, compositions, and methods disclosed herein may be useful to treat patients within one of the classifications defined by the International Prognostic Scoring System, including the low, intermediate-1, intermediate-2 and high risk classifications. In certain embodiments, the compounds, salts, tautomers, compositions, and methods disclosed herein may be particularly beneficial in treating patients who are within the intermediate and high risk classifications and are at increased risk of death or progression of the disease to acute myeloid leukemia.

In certain embodiments, the compounds, salts, tautomers, compositions, and methods disclosed herein may be useful for the treatment of acute myeloid leukemia. In certain embodiments, the compounds, salts, tautomers, compositions, and methods disclosed herein may be useful both for the treatment of the active disease, and for maintenance of the disease in complete or partial remission following treatment for such remission, for example bone marrow transplant or chemotherapy.

In certain embodiments, the compounds, salts, tautomers, compositions, and methods disclosed herein may be useful for the treatment of one or more sub-classifications of acute myeloid leukemia, as defined by either the FAB or WHO classifications, including minimally differentiated myeloid leukemia (MO), acute myeloid leukemia without maturation (M1), acute myeloid leukemia with maturation (M2), acute myeloid leukemia with maturation with t(8;21), acute promyelocytic leukemia (M3), hypergranular type acute myeloid leukemia, micro granular type acute myeloid leukemia. acute myelomonocytic leukemia (M4), acute myelomonocytic leukemia with increased marrow eosinophils (M4EO), acute Monocytic Leukemia (M5), acute monoblastic leukemia (M5a), acute monocytic leukemia with maturation (M5b), erythroleukemia, erythroid/myeloid leukemia (M6a), pure erythroid leukemia (M6b), acute megakaryoblastic leukemia (M7), acute megakaryoblastic leukemia associated with t(1;22), acute basophilic leukemia, acute myelofibrosis (acute myelodysplasia with myelofibrosis), acute leukemia and transient myeloproliferative disorder in Down's Syndrome, hypocellular acute myeloid leukemia, and myeloid sarcoma.

In certain embodiments, the the compounds, salts, tautomers, compositions, and methods disclosed herein may be coadministered with another therapeutic agent.

Besides being useful for human treatment, certain compounds salts, tautomers, and formulations disclosed herein may also be useful for veterinary treatment of companion animals, exotic animals and farm animals, including mammals, rodents, and the like. More preferred animals include horses, dogs, and cats.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; BPD=bis(pinacolato)diboron=4,4,5,5-tetramethyl-2-(4,4,5,5-tetramethyl-1,3,2-dioxaborolan-2-yl)-1,3,2-dioxaborolane; Bu=butyl; $Bu_3SnH$=tributyltin hydride; $CD_3OD$=deuterated methanol; $CDCl_3$=deuterated chloroform; CDI=1,1'-carbonyldiimidazole; DAST=(diethylamino)sulfur trifluoride; dba=dibenzylideneacetone DBU=1,8-diazabicyclo[5.4.0]undec-7-ene; DCE=1,2-dichloroethane; DCM=dichloromethane; DEAD=diethyl azodicarboxylate; DtBAD=di-t-butyl azodicarboxylate; DHP=3,4-dihydro-2H-pyran; DIBAL-H=di-iso-butyl aluminium hydride; DIEA=DIPEA=N,N-diisopropylethylamine; DMAP=4-dimethylaminopyridine; DMF=N,N-dimethyl-formamide; DMFDMA=dimethylformamide dimethyl acetal; DMSO-$d_6$=deuterated dimethyl sulfoxide; DMSO=dimethyl sulfoxide; DPPA=diphenylphosphoryl azide; dppp=1,3-bis(diphenylphosphino)propane; dppf=1,1'-bis(diphenylphosphino)ferrocene; EDC·HCl=EDCI·HCl=1-ethyl-3-(3-dimethylaminopropyl) carbodiimide hydrochloride; Et=ethyl; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; iPr=i-Pr=isopropyl=2-propyl; iPrOH=i-PrOH=isopropanol; LAH=lithium aluminiumhydride; LDA=lithium diisopropyl amide; LiHMDS=Lithium bis(t-rimethylsilyl)amide; MeCN=acetonitrile; MeI=methyl iodide; MeOH=methanol; MP-carbonate resin=macroporous triethylammonium methylpolystyrene carbonate resin; MsCl=mesyl chloride; MTBE=methyl tert-butyl ether; n-BuLi=n-butyllithium; NaHMDS=Sodium bis(trimethylsilyl)amide; NaOEt=sodium ethoxide; NaOMe=sodium methoxide; NaOtBu=sodium t-butoxide; NBS=N-bromosuccinimide; NCS=N-chlorosuccinimide; NIS=N-iodosuccinimide; NMP=N-Methyl-2-pyrrolidone; $Pd(Ph_3)_4$=tetrakis(triphenylphosphine)palladium(0); $Pd_2(dba)_3$=tris(dibenzylideneacetone)dipalladium(0); $PdCl_2(PPh_3)_2$=bis(triphenylphosphine)palladium(II) dichloride; PG=protecting group; Ph=phenyl; prep-HPLC=preparative high-performance liquid chromatography; PMB=para-methoxybenzyl; PMBCl=para-methoxybenzyl chloride; PMBOH=para-methoxybenzyl alcohol; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=1,1-dimethylethyl; TBAF=tetrabutylammonium fluoride; TBDPS=t-butyldiphenylsilyl; t-BuOH=tBuOH=tert-butanol; T3P=Propylphosphonic Anhydride; TEA=$Et_3N$=triethylamine; TFA=trifluoroacetic acid; TFAA=trifluoroacetic anhydride; THF=tetrahydrofuran; TIPS=triisopropylsilyl; Tol=toluene; TsCl=tosyl chloride; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

General Synthetic Methods for Preparing Compounds

The following schemes can be used to practice the present invention.

Scheme I

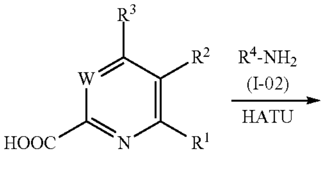

I-01

-continued

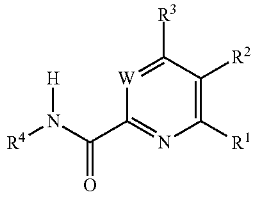

I-03

Example 1, and similar compounds, can be synthesized by using the general synthetic procedure set forth in Scheme I. Carboxylic acid I-01 is coupled with primary amine I-02, using HATU or another suitable coupling agent known in the art, such as $T_3P$, to afford amide I-03. Syntheses of certain compounds may include deprotection steps for one or more of groups $R^1$, $R^2$, $R^3$, and $R^4$, using methods known in the art.

Scheme II

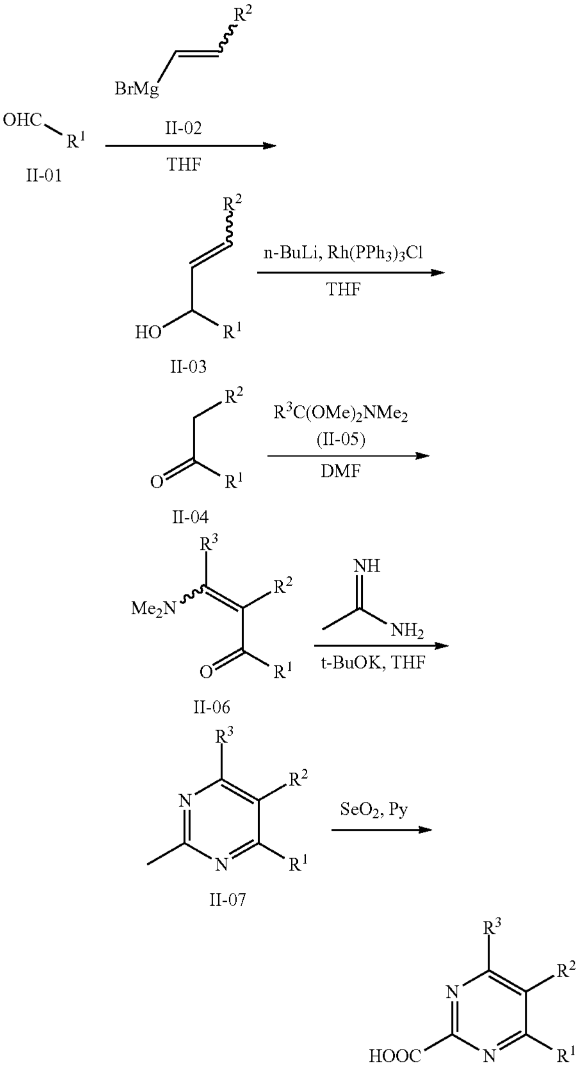

II-08

Example 1, and similar compounds, can be synthesized using the general synthetic procedure set forth in Scheme II. Carboxaldehyde II-01 is reacted with vinyl Grignard II-02 to afford secondary alcohol II-03. Allylic rearrangement provides ketone II-04. Condensation with amide acetal II-05 provides enone II-06, which is further reacted with acetamidine to give pyrimidine II-07. Oxidation of the activated 2-methyl group gives carboxylic acid II-08, which is suitable for incorporation into Scheme I. Syntheses of certain compounds may include deprotection steps for one or more of groups $R^1$, $R^2$, $R^3$, and $R^4$, using methods known in the art.

The invention is further illustrated by the following examples.

INTERMEDIATE A-1

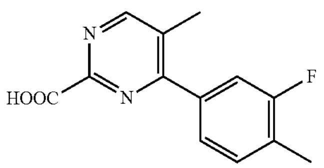

4-(3-fluoro-4-methylphenyl)-5-methylpyrimidine-2-carboxylic acid

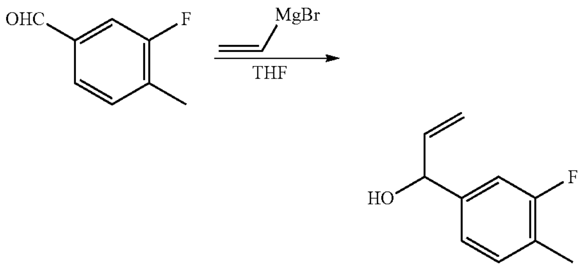

1-(3-Fluoro-4-methyl-phenyl)prop-2-en-1-ol To a solution of 3-fluoro-4-methyl-benzaldehyde (15 g, 108.59 mmol, 13.27 mL, 1 eq) in THF (200 mL) was added vinylmagnesium bromide (1 M, 119.45 mL, 1.1 eq) dropwise at 0° C. After stirring at 25° C. under $N_2$ for 16 h, the reaction was quenched with 1 N HCl (20 mL) and diluted with $H_2O$ (50 mL) and EtOAc (50 mL). The organic layer was separated, and the aqueous layer was extracted with EtOAc (2×50 mL). The combined organic layers were dried over $Na_2SO_4$, filtered, and concentrated to obtain a residue which was purified by flash silica gel chromatography (ISCO®; 40 g SepaFlash® Silica Flash Column, Eluent of 0~15% EtOAc/PE gradient @30 mL/min) to yield the title compound (11 g, 66 mmol, 61% yield) as light yellow oil. $^1H$ NMR (400 MHz, $CDCl_3$) δ=7.25-7.13 (m, 2H), 7.04-6.95 (m, 1H), 6.11-5.99 (m, 1H), 5.41-5.32 (m, 1H), 5.26-5.12 (m, 2H), 2.29 (d, J=1.6 Hz, 3H).

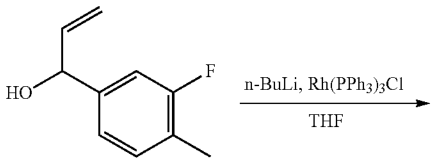

-continued

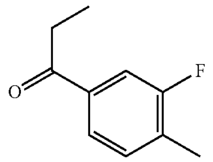

1-(3-Fluoro-4-methyl-phenyl)propan-1-one To a solution of the product from the previous step (7 g, 42.12 mmol, 1 eq) in THF (60 mL) was added n-BuLi (2.5 M, 18.53 mL, 1.1 eq) at 0° C., and the mixture was stirred at 0° C. for 30 min. To the mixture was added a solution of tris(triphenylphosphine)rhodium (I) chloride (1.95 g, 2.11 mmol, 0.05 eq) in THF (20 mL) at 0° C. After stirring at 60° C. under $N_2$ for 16 h, the mixture was poured into water (50 mL), extracted with EtOAc (50 mL×3), dried over $Na_2SO_4$, filtered and concentrated under reduced pressure to obtain a residue which was purified by flash silica gel chromatography (ISCO®; 40 g SepaFlash® Silica Flash Column, Eluent of 0~10% EtOAc/PE gradient @30 mL/min) to yield 1-(3-fluoro-4-methyl-phenyl)propan-1-one (3.5 g, 21.06 mmol, 50% yield) as a white solid. $^1H$ NMR (400 MHz, $CDCl_3$) δ=7.87-7.83 (m, 1H), 7.83-7.77 (m, 1H), 7.10-7.03 (m, 1H), 3.04-2.94 (m, 2H), 2.36-2.31 (d, 3H, J=2.0 Hz), 1.26-1.19 (t, 3H, J=2.0 Hz).

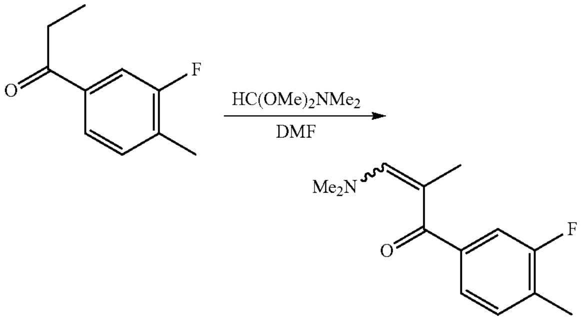

(Z)-3-(dimethylamino)-1-(3-fluoro-4-methyl-phenyl)-2-methyl-prop-2-en-1-one To a solution of the product from the previous step (3.5 g, 21.06 mmol, 4.55 mL, 1 eq) in DMF (20 mL) was added DMFDMA (10.0 g, 84.24 mmol, 11.19 mL, 4 eq). After stirring at 160° C. for 2 h, the mixture was poured into water (20 mL), extracted with EtOAc (20 mL), dried over $Na_2SO_4$, filtered and concentrated under reduced pressure to obtain the title compound as a yellow solid, which was used directly without further purification. MS(ES+) $C_{13}H_{16}ONF$ requires:221, found: 222 $[M+H]^+$.

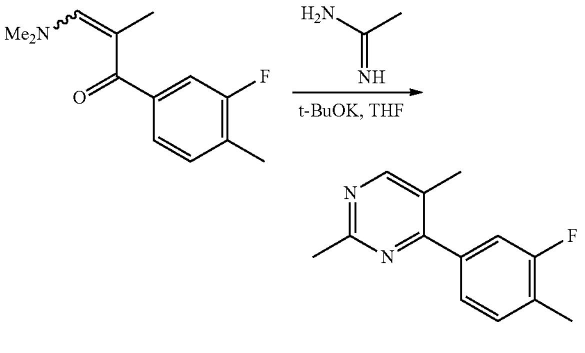

4-(3-Fluoro-4-methyl-phenyl)-2,5-dimethyl-pyrimidine To a solution of acetamidine HCl (2.99 g, 31.59 mmol, 1.5 eq) in THF (30 mL) was added t-BuOK (3.54 g, 31.59 mmol, 1.5 eq). The mixture was stirred at 70° C. for 1 hr. Then to the mixture was added a solution of the product from the previous step (4.66 g, 21.06 mmol, 1 eq) in THF (10 mL). After stirring at 60° C. for 16 hr, the mixture was poured into water (50 mL), extracted with EtOAc (50 mL×3), dried over $Na_2SO_4$, filtered and concentrated under reduced pressure to obtain a residue which was purified by flash silica gel chromatography (ISCO®; 40 g SepaFlash® Silica Flash Column, Eluent of 0-10% EtOAc/PE gradient @30 mL/min) to yield the title compound (2.1 g, 9.13 mmol, 43% yield) as light yellow oil. MS(ES+) $C_{13}H_{13}N_2F$ requires:216, found: 217 $[M+H]^+$.

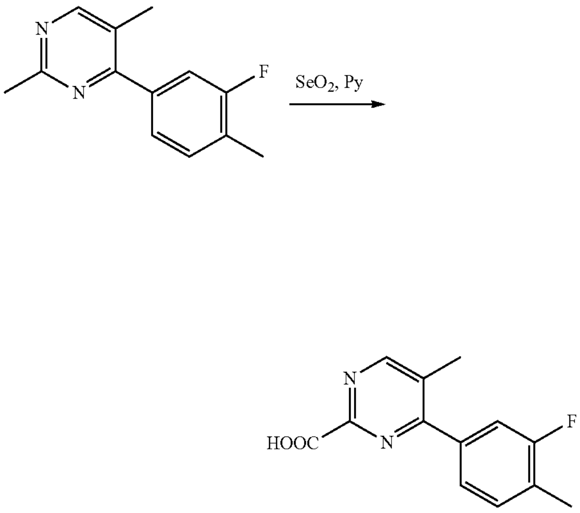 [SMILES: Cc1ncc(C)c(-c2ccc(C)c(F)c2)n1 ; Cc1ccc(-c2nc(C(=O)O)ncc2C)cc1F]

4-(3-fluoro-4-methyl-phenyl)-5-methyl-pyrimidine-2-carboxylic acid To a solution of the product from the previous step (2.1 g, 9.71 mmol, 1 eq) in pyridine (15 mL) was added $SeO_2$ (3.77 g, 33.99 mmol, 3.70 mL, 3.5 eq). The mixture was stirred at 120° C. for 16 hr. To the mixture was added to NaOH (1 M) aqueous solution to adjust pH to 13, extracted with EtOAc (10 mL). To the aqueous phase was added HCl (1 M) to adjust the pH to 1, then extracted with EtOAc (10 mL), washed with brine (10 mL), dried over $Na_2SO_4$, filtered and concentrated under reduced pressure to obtain a residue which was triturated with EtOAc at 25° C. for 30 min to yield the title compound (1.47 g, 5.85 mmol, 60% yield) as a brown solid.

MS(ES+) $C_{13}H_{11}N_2FO_2$ requires:246, found: 247 $[M+H]^+$. $^1H$ NMR (400 MHz, DMSO-$d_6$) δ=8.90-8.84 (s, 1H), 7.69-7.64 (m, 1H), 7.62-7.56 (m, 1H), 7.35-7.27 (m, 1H), 2.45-2.38 (s, 3H), 2.35-2.30 (s, 3H).

INTERMEDIATE A-2

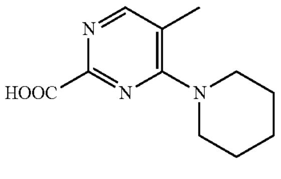

5-methyl-4-(piperidin-1-yl)pyrimidine-2-carboxylic acid

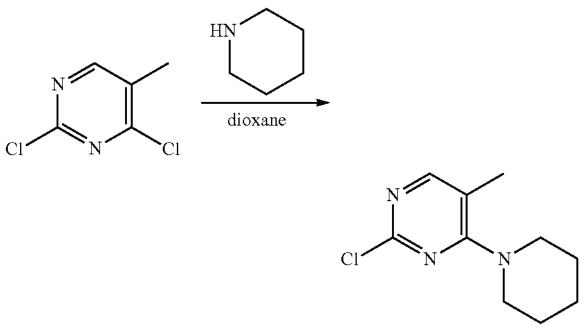

2-chloro-5-methyl-4-(1-piperidyl)pyrimidine To a solution of 2,4-dichloro-5-methylpyrimidine (3 g, 18.40 mmol, 1 eq) in dioxane (3 mL) was added a solution of piperidine (3.13 g, 36.81 mmol, 3.64 mL, 2 eq) in dioxane (3 mL) at 0° C. The mixture was stirred at 0° C. for 2 h. The mixture was poured into water (20 mL), extracted with EtOAc (20 mL×3), dried over $Na_2SO_4$, filtered and concentrated under reduced pressure to obtain a residue which was purified by flash silica gel chromatography (ISCO®; 10 g SepaFlash® Silica Flash Column, Eluent of 0~10% EtOAc/PE gradient @30 mL/min) to afford the title compound (2.6 g, 12.28 mmol, 66% yield) as a colorless oil. MS(ES+)$C_{10}H_{14}ClN_3$ requires:211, found: 212 $[M+H]^+$.

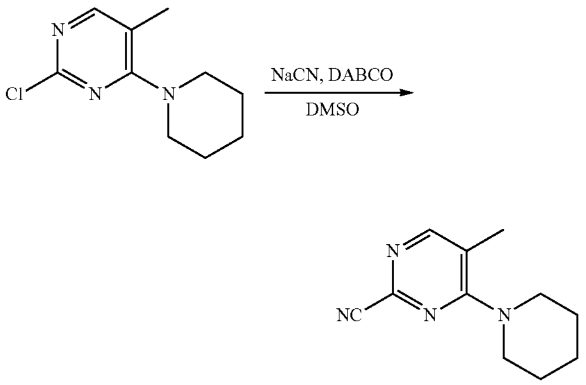

5-methyl-4-(1-piperidyl)pyrimidine-2-carbonitrile To a solution of the product from the previous step (2 g, 9.45 mmol, 1 eq) in DMSO (10 mL) was added NaCN (694.55 mg, 14.17 mmol, 1.5 eq) and DABCO (211.95 mg, 1.89 mmol, 207.79 uL, 0.2 eq). The mixture was stirred at 120° C. for 16 hr. To the mixture was added water (70 mL) and extracted with EtOAc (100 mL×3), the organic phase was washed with brine (100 mL×3), dried over $Na_2SO_4$, filtered and concentrated under reduced pressure to give a residue which was purified by column chromatography ($SiO_2$, Petroleum ether/EtOAc=20/1 to 5/1) to afford the title compound (1.2 g, 5.87 mmol, 62% yield) as a white solid.

MS(ES+)$C_{11}H_{14}N_4$ requires:202, found: 203 $[M+H]^+$. $^1H$ NMR (400 MHz, $CDCl_3$) δ=7.99 (s, 1H), 3.46-3.44 (m, 4H), 2.2 (s, 3H), 1.67-1.57 (m, 6H).

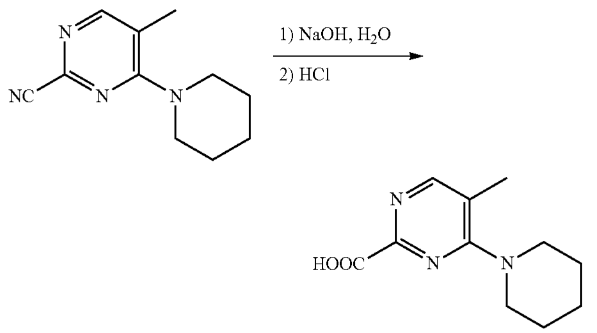

5-methyl-4-(1-piperidyl)pyrimidine-2-carboxylic acid To a solution of the product from the previous step (1.2 g, 5.87 mmol, 1 eq) in dioxane (7 mL) was added a solution of NaOH (704.80 mg, 17.62 mmol, 3 eq) in $H_2O$ (21 mL). The mixture was stirred at 60° C. for 2 hr. To the mixture was added aqueous HCl solution and the pH was adjusted to 7, the mixture was concentrated under reduced pressure to give a residue which was purified by prep-HPLC (column: Phenomenex luna C18 (250*70 mm, 15 um); mobile phase: [water (0.1% TFA)-$CH_3CN$]; B %: 1 $CH_3CN$ %-30 $CH_3CN$ %, 30 min), the eluent was concentrated and then freeze dried to afford the title compound (1.16 g, 5.23 mmol, 89% yield) as a white solid.

MS(ES+) $C_{11}H_{15}N_3O_2$ requires:221, found: 222 $[M+H]^+$. $^1H$ NMR (400 MHz, $CDCl_3$) δ=8.3 (s, 1H), 3.96-3.91 (m, 4H), 2.43 (s, 3H), 1.83-1.75 (m, 6H).

INTERMEDIATE A-3

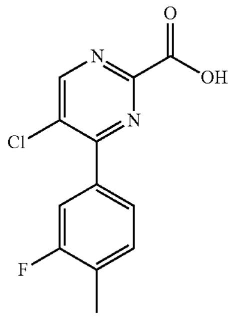

5-Chloro-4-(3-fluoro-4-methylphenyl)pyrimidine-2-carboxylic acid

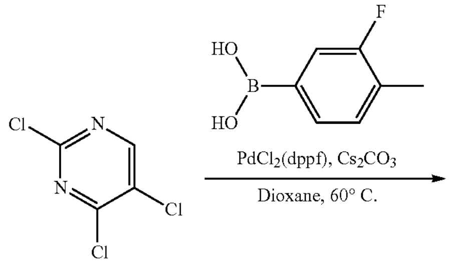

-continued

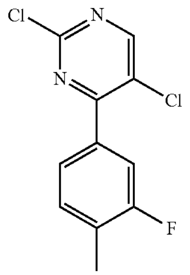

2,5-dichloro-4-(3-fluoro-4-methylphenyl)pyrimidine To a solution of 2,4,5-trichloropyrimidine (1 g, 5.45 mmol) in dioxane (20 ml) were added (3-fluoro-4-methylphenyl)boronic acid (1.007 g, 6.54 mmol), $Cs_2CO_3$ (5.33 g, 16.36 mmol) and $PdCl_2(dppf)$-$CH_2Cl_2$ adduct (0.445 g, 0.545 mmol) and the resulting mixture was stirred at 60° C. overnight. The reaction mixture was filtered through CELITE®, the filter pad was washed with MeOH, and the combined filtrate was concentrated under reduced pressure. The residue was purified via silica gel chromatography (0-70% EtOAc in hexanes) to give the title compound (947 mg, 3.68 mmol, 67.6% yield) as a pale yellow liquid.

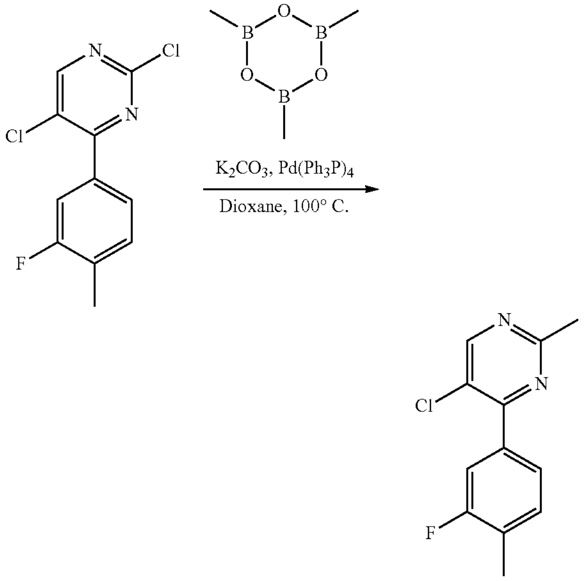

5-chloro-4-(3-fluoro-4-methylphenyl)-2-methylpyrimidine A mixture of the product from the previous step (430 mg, 1.673 mmol), $K_2CO_3$ (462 mg, 3.35 mmol) and $Pd(Ph_3P)_4$ (193 mg, 0.167 mmol) in dioxane (8363 μl) was degassed with $N_2$ for 5 minutes. 2,4,6-trimethyl-1,3,5,2,4,6-trioxatriborinane (252 mg, 2.007 mmol) was added. The reaction mixture was heated at 100° C. and stirred for 16 h. $H_2O$ was added, and the layers were separated. The aqueous phase was extracted with EtOAc (3×), and the combined organic layers were washed with sat NaCl, dried over $Na_2SO_4$, filtered and concentrated under reduced pressure. The residue was purified via silica gel chromatography (0-50% EtOAc in hexanes) to give the title compound (140 mg, 0.592 mmol, 35.4% yield) as an orange oil.

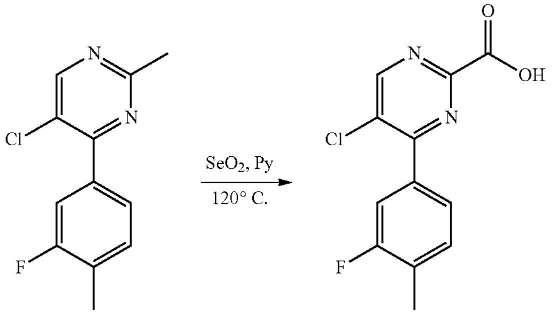 [SMILES: Cc1ncc(Cl)c(-c2ccc(C)c(F)c2)n1 ; Cc1ccc(-c2nc(C(=O)O)ncc2Cl)cc1F]

5-chloro-4-(3-fluoro-4-methylphenyl)pyrimidine-2-carboxylic acid To a solution of the product from the previous step (140 mg, 0.592 mmol) in pyridine (657 μl) was added $SeO_2$ (164 mg, 1.479 mmol), and the resulting mixture was stirred at 120° C. for 48 hrs. The reaction mixture was filtered through CELITE®, the filter pad was washed with MeOH, and the combined filtrate was concentrated under reduced pressure to afford the title compound (127 mg, 0.476 mmol, 81% yield).

INTERMEDIATE A-4

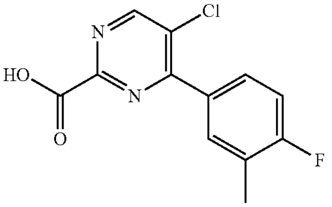

5-Chloro-4-(4-fluoro-3-methylphenyl)pyrimidine-2-carboxylic acid

This compound was obtained using a procedure similar to that used for Intermediate A-3.

INTERMEDIATE A-5

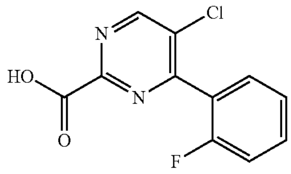

5-chloro-4-(2-fluorophenyl)pyrimidine-2-carboxylic acid

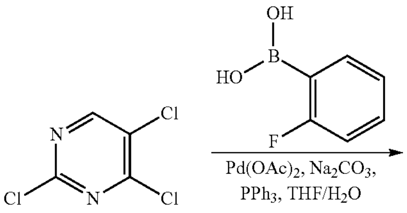

-continued

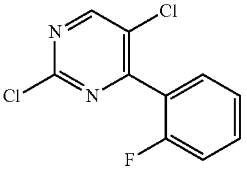

2,5-Dichloro-4-(2-fluorophenyl)pyrimidine To a solution of 2,4,5-trichloropyrimidine (3 g, 16.36 mmol, 1 eq) in THF (30 mL) and $H_2O$ (6 mL) were added (2-fluorophenyl) boronic acid (2.29 g, 16.36 mmol, 1 eq), $Na_2CO_3$ (3.47 g, 32.71 mmol, 2 eq), $PPh_3$ (214.50 mg, 817.78 μmol, 0.05 eq) and $Pd(OAc)_2$ (183.60 mg, 817.78 μmol, 0.05 eq) under $N_2$. After stirring at 60° C. for 12 h, the mixture was diluted with water (30 mL), extracted with EtOAc (30 mL×3), dried over $Na_2SO_4$, filtered and concentrated under $N_2$. The residue was purified by chromatography on silica gel (eluent EtOAC/Petroleum ether=2%~20%) to afford the title compound (3.8 g, 15.63 mmol, 95% yield) as light yellow oil. MS (ES+) $C_{10}H_5Cl_2FN_2$, requires: 242 and 244, found: 243 and 245 $[M+H]^+$.

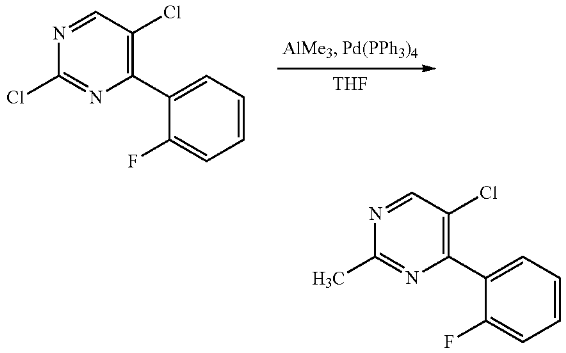

5-Chloro-4-(2-fluorophenyl)-2-methylpyrimidine To a solution of the product from the previous step (3.8 g, 12.51 mmol, 80% purity, 1 eq), $AlMe_3$ (1.35 g, 18.76 mmol, 9 mL, 2 M in toluene, 1.5 eq) in THF (38 mL) was added $Pd(PPh_3)_4$ (1.45 g, 1.25 mmol, 0.1 eq) under $N_2$. After stirring at 60° C. for 16 h, the mixture was quenched with a saturated $NH_4Cl$ aqueous solution, diluted with water (30 mL), extracted with EtOAc (30 mL×3), washed with brine (20 mL×3), dried over $Na_2SO_4$, filtered and concentrated under reduced pressure. The residue was purified by chromatography on silica gel (eluent EtOAC/Petroleum ether=10%~50%) to afford the title compound (1.9 g, 8.41 mmol, 67% yield) as a light yellow solid. MS (ES+) $C_{11}H_8ClFN_2$, requires: 222 and 224, found: 223 and 225 $[M+H]^+$.

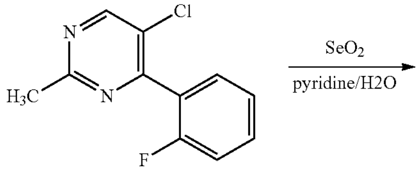

-continued

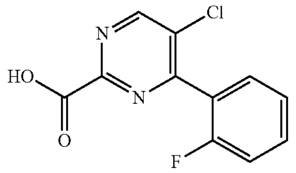

5-Chloro-4-(2-fluorophenyl)pyrimidine-2-carboxylic acid To a solution of the product from the previous step (1.9 g, 8.53 mmol, 1 eq) in pyridine (25 mL) and $H_2O$ (2.5 mL) was added $SeO_2$ (9.47 g, 85.34 mmol, 10 eq). After stirring at 120° C. for 48 h, the mixture was filtered, the filtrate was concentrated, diluted with $H_2O$ (20 mE), basified with NaOH (10%) to pH 8~10, extracted with EtOAc (20 mL×2). The aqueous layer was acidified with HCl (1 N) to pH 3~5, the suspension was filtered, washed with $H_2O$ (15 mL×2). The filtered cake was triturated with MeOH (5 mL), filtered, concentrated to afford the title compound (1.8 g, 7.13 mmol, 83% yield) as a light yellow solid.

MS (ES+) $C_{11}H_6ClFN_2O_2$, requires: 252 and 254, found: 253 amd 255 $[M+H]^+$. $^1H$ NMR (400 MHz, DMSO-$d_6$) δ=14.44-13.35 (br s, 1H), 9.21 (s, 1H), 7.71-7.57 (m, 2H), 7.49-7.37 (m, 2H).

The following pyrimidine-2-carboxylic acids were obtained by procedures similar to that used for Intermediate A-5.

TABLE 1

Pyrimidine-2-carboxylic acids. I.

| Int. | Chloro pyrimidine | Arylboronic acid | Structure IUPAC name | MS (ES+) $^1H$ NMR |
|---|---|---|---|---|
| A-6 | 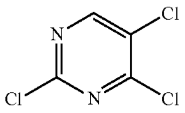 | 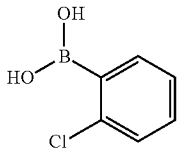 | 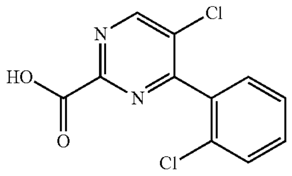 [SMILES: O=C(O)c1ncc(Cl)c(-c2ccccc2Cl)n1] 5-chloro-4-(2-chlorophenyl)pyrimidine-2-carboxylic acid | $C_{11}H_6Cl_2N_2O_2$ requires: 268 and 270, found: 269 and 271 $[M + H]^+$. (400 MHz, DMSO-$d_6$) δ = 13.59 (br s, 1H), 9.27-9.22 (m, 1H), 7.69-7.65 (m, 1H), 7.63-7.57 (m, 1H), 7.57-7.53 (m, 2H). |
| A-7 | 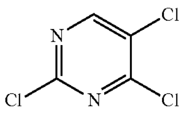 | 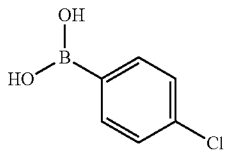 | 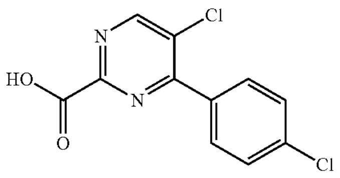 [SMILES: O=C(O)c1ncc(Cl)c(-c2ccc(Cl)cc2)n1] 5-chloro-4-(4-chlorophenyl)pyrimidine-2-carboxylic acid | $C_{11}H_6Cl_2N_2O_2$ requires: 268 and 270, found: 269 and 271 $[M + H]^+$. (400 MHz, DMSO-d6) δ ppm = 9.15 (s, 1 H), 7.92-7.87 (m, 2 H), 7.69-7.64 (m, 2 H). |
| A-8 | 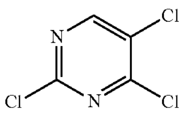 | 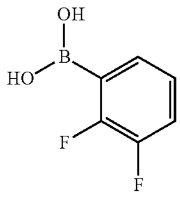 | 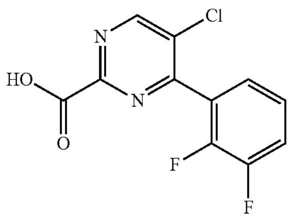 [SMILES: O=C(O)c1ncc(Cl)c(-c2cccc(F)c2F)n1] 5-chloro-4-(2,3-difluorophenyl)pyrimidine-2-carboxylic acid | $C_{11}H_5ClN_2O_2F_2$ requires: 270 and 272, found: 271 and 273 $[M + H]^+$. (400 MHz, DMSO-$d_6$) δ = 13.84 (br s, 1H), 9.26 (s, 1H), 7.79-7.66 (m, 1H), 7.49-7.41 (m, 2H) |
| A-9 | 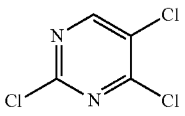 | 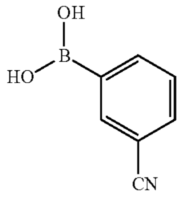 | 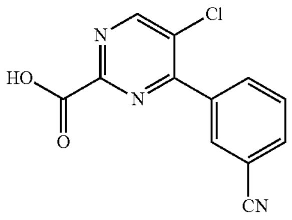 [SMILES: N#Cc1cccc(-c2nc(C(=O)O)ncc2Cl)c1] 5-chloro-4-(3-cyanophenyl)pyrimidine-2-carboxylic acid | MS (ES+) $C_{12}H_6N_3O_2Cl$ requires: 259 and 261, found: 260 and 262 $[M + H]^+$. (400 MHz, DMSO-$d_6$) δ = 9.21 (s, 1H), 8.28 (t, J = 1.4 Hz, 1H), 8.20-8.13 (m, 1H), 8.11-8.05 (m, 1H), 7.81 (t, J = 7.9 Hz, 1H). |

TABLE 1-continued

| Pyrimidine-2-carboxylic acids. I. | | | | |
|---|---|---|---|---|
| Int. | Chloro pyrimidine | Arylboronic acid | Structure IUPAC name | MS (ES+) $^1$H NMR |
| A-10 | 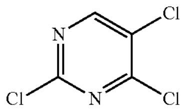 | 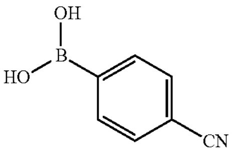 | 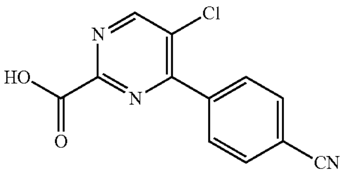 [SMILES: N#Cc1ccc(-c2nc(C(=O)O)ncc2Cl)cc1] 5-chloro-4-(4-cyanophenyl)pyrimidine-2-carboxylic acid | $C_{12}H_6N_3ClO_2$ requires: 259 and 261, found: 260 and 262 $[M + H]^+$. (400 MHz, DMSO-$d_6$) δ = δ = 9.12 (s, 1H), 8.08-8.04 (m, 2H), 8.03-7.97 (m, 2H). |
| A-11 | 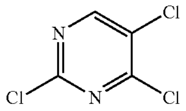 | 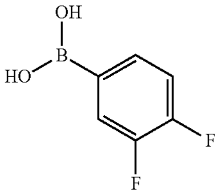 | 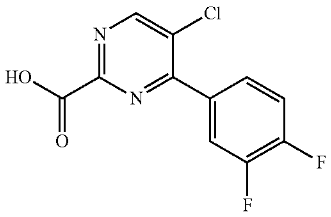 [SMILES: O=C(O)c1ncc(Cl)c(-c2ccc(F)c(F)c2)n1] 5-chloro-4-(3,4-difluorophenyl)pyrimidine-2-carboxylic acid | MS (ES+) $C_{11}H_5ClF_2N_2O_2$ requires: 270 and 272, found: 271 and 273 $[M + H]^+$. (400 MHz, DMSO-$d_6$) δ = 9.18 (s, 1H), 8.07-7.89 (m, 1H), 7.81-7.60 (m, 2H). |
| A-12 | 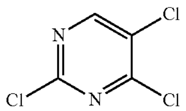 | 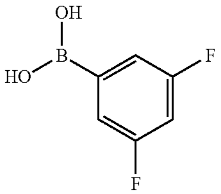 | 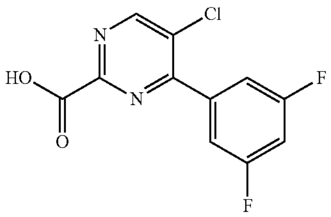 [SMILES: O=C(O)c1ncc(Cl)c(-c2cc(F)cc(F)c2)n1] 5-chloro-4-(3,5-difluorophenyl)pyrimidine-2-carboxylic acid | $C_{11}H_5ClN_2O_2F_2$ requires: 270 and 272, found: 271 and 273 $[M + H]^+$. (400 MHz, DMSO-$d_6$) δ = 13.80 (br s, 1H), 9.25-9.19 (s, 1H), 7.61-7.52 (m, 3H). |
| A-13 | 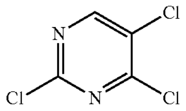 | 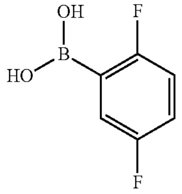 | 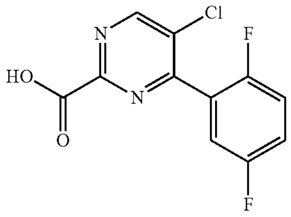 [SMILES: O=C(O)c1ncc(Cl)c(-c2cc(F)ccc2F)n1] 5-chloro-4-(2,5-difluorophenyl)pyrimidine-2-carboxylic acid | $C_{11}H_5ClF_2N_2O_2$ requires: 270 and 272, found: 271 and 273 $[M + H]^+$. (400 MHz, DMSO-$d_6$) δ ppm = 9.23 (br s, 1 H), 7.65-7.45 (m, 3 H). |
| A-14 | 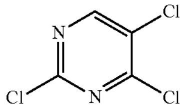 | 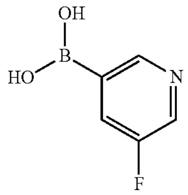 | 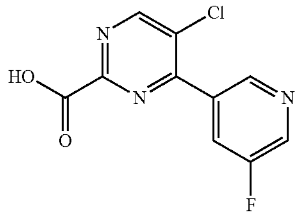 [SMILES: O=C(O)c1ncc(Cl)c(-c2cncc(F)c2)n1] 5-chloro-4-(5-fluoropyridin-3-yl)-pyrimidine-2-carboxylic acid | $C_{10}H_5ClFN_3O_2$, requires: 253 and 255, found: 254 and 256. (400 MHz, DMSO-$d_6$) δ = 14.36-13.58 (br s, 1H), 9.24 (s, 1H), 8.90 (t, J = 1.6 Hz, 1H), 8.82 (d, J = 2.8 Hz, 1H), 8.24-8.17 (m, 1H) |

TABLE 1-continued

Pyrimidine-2-carboxylic acids. I.

| Int. | Chloro pyrimidine | Arylboronic acid | Structure IUPAC name | MS (ES+) $^1$H NMR |
|---|---|---|---|---|
| A-15 | 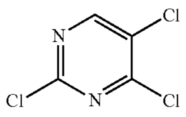 | 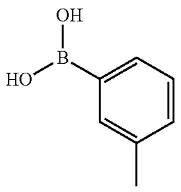 | 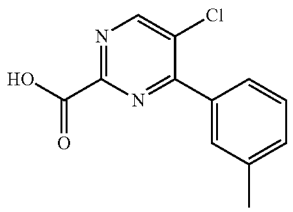 [SMILES: Cc1cccc(-c2nc(C(=O)O)ncc2Cl)c1] 5-chloro-4-(m-tolyl)-pyrimidine-2-carboxylic acid | $C_{12}H_9ClN_2O_2$ requires: 248 and 250, found: 249 and 251 $[M + H]^+$. (400 MHz, DMSO-$d_6$) δ = 13.79 (br s, 1H), 9.14 (s, 1H), 7.69-7.60 (m, 2H), 7.53-7.36 (m, 2H), 2.42 (s, 3H) |
| A-16 | 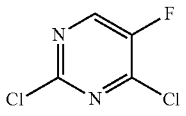 | 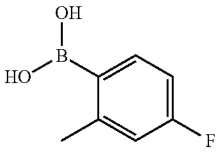 | 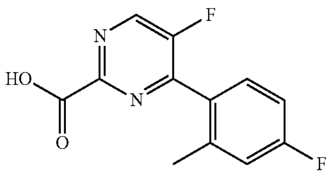 [SMILES: Cc1cc(F)ccc1-c1nc(C(=O)O)ncc1F] 5-fluoro-4-(4-fluoro-2-methylphenyl)pyrimidine-2-carboxylic acid | $C_{12}H_8F_2N_2O_2$ requires: 250, found: 251 $[M + H]^+$. (400 MHz, DMSO-$d_6$) δ = 9.08 (s, 1H), 7.53 (dd, J = 6.3, 8.1 Hz, 1H), 7.32-7.18 (m, 2H), 2.27 (s, 3H). |
| A-17 | 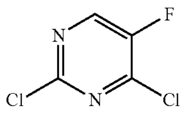 | 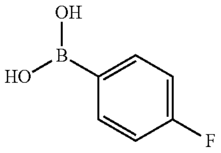 | 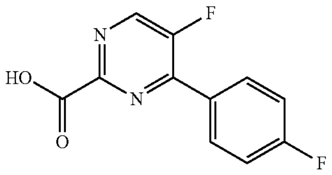 [SMILES: O=C(O)c1ncc(F)c(-c2ccc(F)cc2)n1] 5-fluoro-4-(4-fluorophenyl)pyrimidine-2-carboxylic acid | $C_{12}H_8F_2N_2O_2$ requires: 236, found: 237 $[M + H]^+$. (400 MHz, DMSO-$d_6$) δ = 9.00 (d, J = 3.3 Hz, 1H), 8.18 (dd, J = 5.6, 8.2 Hz, 2H), 7.43-7.36 (m, 2H). |
| A-18 | 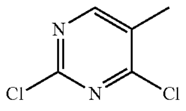 | 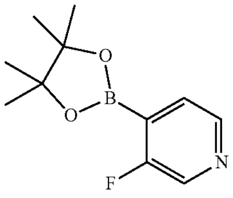 | 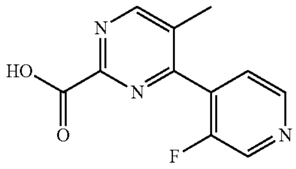 [SMILES: Cc1cnc(C(=O)O)nc1-c1ccncc1F] 4-(3-fluoropyridin-4-yl)-5-methylpyrimidine-2-carboxylic acid | $C_{11}H_8N_3O_2F$ requires: 233, found: 234 $[M + H]^+$. (400 MHz, DMSO-$d_6$) δ = 9.02 (s, 1H), 8.85-8.77 (m, 1H), 8.69-8.60 (m, 1H), 7.68-7.62 (m, 1H), 2.27 (s, 3H). |

INTERMEDIATE A-19

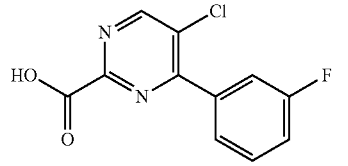

5-Chloro-4-(3-fluorophenyl)pyrimidine-2-carboxylic acid

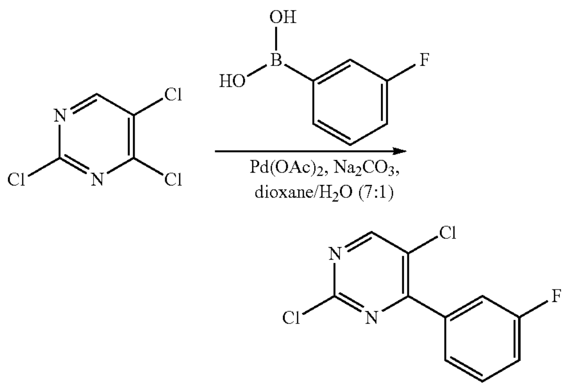

2,5-Dichloro-4-(3-fluorophenyl)pyrimidine To a solution of 2,4,5-trichloropyrimidine (2 g, 10.90 mmol, 1 eq), (3-fluorophenyl)boronic acid (1.60 g, 11.45 mmol, 1.05 eq) in THF (80 mL), $H_2O$ (20 mL) were added $Na_2CO_3$ (1.81 g, 17.08 mmol, 1.57 eq), $PPh_3$ (114.40 mg, 436.15 μmol, 0.04 eq) and $Pd(OAc)_2$ (48.96 mg, 218.08 μmol, 0.02 eq) at 25° C. under $N_2$. After stirring at 60° C. for 6 h, the mixture was diluted with EtOAc (50 mL), dried over $Na_2SO_4$, filtered and concentrated. The residue which was purified by silica gel chromatography (ISCO®; 25 g SepaFlash® Silica Flash Column, Eluent 0~30% EtOAC/Petroleum ether gradient @40 mL/min) to afford the title compound (2.4 g, 9.48 mmol, 87% yield) as a white solid. MS (ES+) $C_{10}H_5Cl_2FN_2$ requires: 242 and 244, found: 243 and 245 $[M+H]^+$.

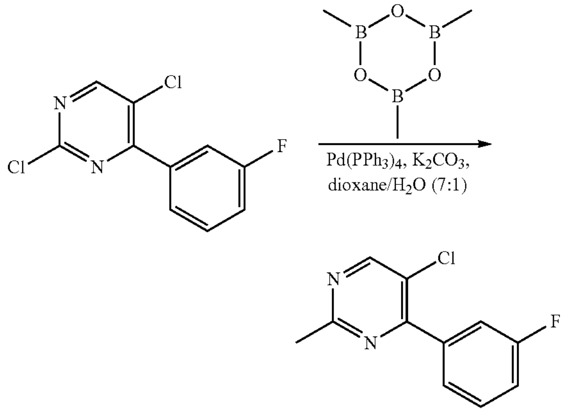

5-Chloro-4-(3-fluorophenyl)-2-methylpyrimidine To a solution of the product from the previous step (4.4 g, 18.10 mmol, 1 eq) in $H_2O$ (10 mL) and dioxane (70 mL) were added 2,4,6-trimethyl-1,3,5,2,4,6-trioxatriborinane (5.09 g, 20.27 mmol, 5.67 mL of a 50% solution in THF, 1.12 eq), $K_2CO_3$ (6.25 g, 45.26 mmol, 2.5 eq) and $Pd(PPh_3)_4$ (418.36 mg, 362.04 μmol, 0.02 eq) at 25° C. under $N_2$. After stirring at 100° C. for 16 h, the mixture was diluted with EtOAc (50 mL), dried over $Na_2SO_4$, filtered and concentrated. The residue was purified by silica gel chromatography (ISCO®; 40 g SepaFlash® Silica Flash Column, Eluent 0~15% EtOAC/Petroleum ether gradient @100 mL/min) to afford the title compound (2.7 g, 11.40 mmol, 63% yield) as brown oil. MS (ES+) $C_{18}H_8ClFN_2$ requires: 222 and 224, found: 223 and 225 $[M+H]^+$.

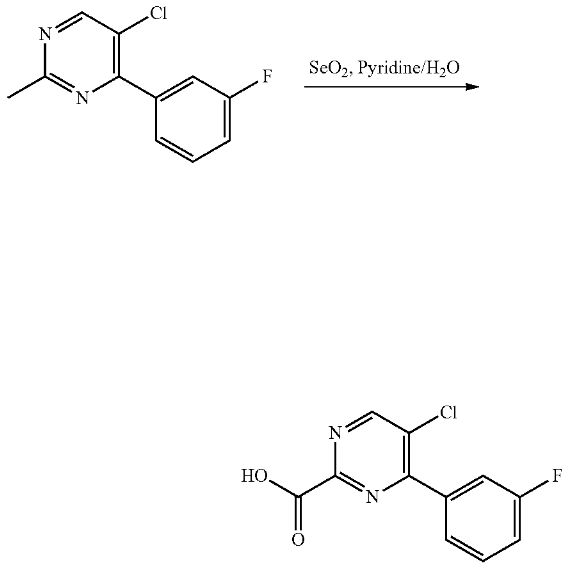

5-Chloro-4-(3-fluorophenyl)pyrimidine-2-carboxylic acid To a solution of the product from the previous step (2.6 g, 11.68 mmol, 1 eq) in pyridine (50 mL) was added $SeO_2$ (6.48 g, 58.39 mmol, 5 eq) at 25° C. After stirring at 120° C. for 16 h, $H_2O$ (4 mL) and $SeO_2$ (3.89 g, 35.03 mmol, 3 eq) were added to the reaction mixture at 25° C. After stirring at 120° C. for another 12 h, the mixture was cooled to 25° C., basified by NaOH (1 M) aqueous solution to adjust pH to 13, extracted with EtOAc (50 mL×3). The aqueous phase was acidified by HCl (1 M) to adjust the pH to 1, then extracted with EtOAc (50 mL×3), washed with brine (20 mL×3), dried over $Na_2SO_4$, filtered and concentrated under reduced pressure. The residue was triturated with petroleum ether:EtOAc (20:1, 20 mL) at 25° C. for 1 h to afford the title compound (1.21 g, 4.80 mmol, 41% yield) as a yellow solid.

MS (ES+) $C_{11}H_6ClFN_2O_2$ requires: 252 and 254, found: 253 and 255 $[M+H]^+$. $^1H$ NMR (400 MHz, DMSO-$d_6$) δ=13.85 (br s, 1H), 9.18 (s, 1H), 7.73-7.59 (m, 3H), 7.65-7.45 (m, 1H).

The following pyrimidine-2-carboxylic acids were obtained by procedures similar to that used for Intermediate A-19.

TABLE 2

Pyrimidine-2-carboxylic acids. II.

| Int. | Chloro pyrimidine | Arylboronic acid | Structure IUPAC name | MS (ES+) $^1$H NMR |
|---|---|---|---|---|
| A-20 | 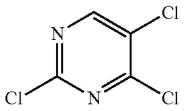 | 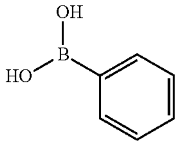 | 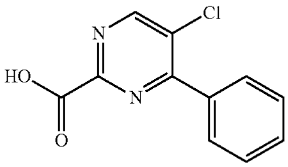 [SMILES: O=C(O)c1ncc(Cl)c(-c2ccccc2)n1] 5-chloro-4-phenylpyrimidine-2-carboxylic acid | $C_{11}H_7N_2ClO_2$ requires: 234 and 236, found: 235 and 237 $[M + H]^+$. (400 MHz, DMSO-$d_6$) δ = 9.00 (s, 1H), 7.86-7.79 (m, 2H), 7.60-7.52 (m, 3H). |
| A-21 | 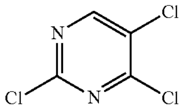 | 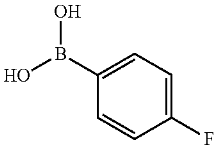 | 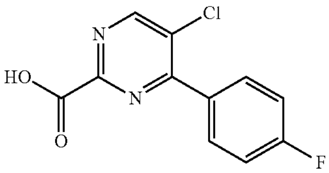 [SMILES: O=C(O)c1ncc(Cl)c(-c2ccc(F)cc2)n1] 5-chloro-4-(4-fluorophenyl)pyrimidine-2-carboxylic acid | $C_{11}H_6ClFN_2O_2$ requires: 252 and 254, found: 253 and 255 $[M + H]^+$. (400MHz, DMSO-$d_6$) δ = 13.49-12.34 (m, 1H), 9.14 (s, 1H), 7.97-7.91 (m, 2H), 7.43 (t, J = 8.9 Hz, 2H). |
| A-22 | 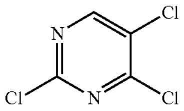 | 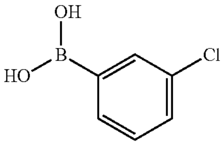 | 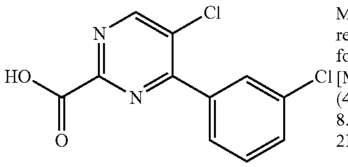 5-chloro-4-(3-chlorophenyl)pyrimidine-2-carboxylic acid | MS (ES+) $C_{11}H_6Cl_2N_2O_2$ requires:268 and 270, found: 269 and 271 $[M + H]^+$. (400 MHz, DMSO-$d_6$) δ = 8.82 (s, 1H), 7.85-7.72 (m, 2H), 7.67-7.54 (m, 2H). |
| A-23 | 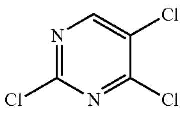 | 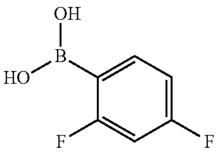 | 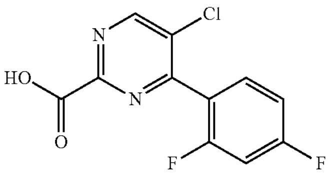 [SMILES: O=C(O)c1ncc(Cl)c(-c2ccc(F)cc2F)n1] 5-chloro-4-(2,4-difluorophenyl)pyrimidine-2-carboxylic acid | $C_{11}H_5ClF_2N_2O_2$ requires: 270 and 272, found: 271 and 273 $[M + H]^+$. (400 MHz, DMSO-$d_6$) δ = 13.50 (br s, 1H), 9.22 (s, 1H), 7.75-7.64 (m, 1H), 7.56-7.47 (m, 1H), 7.35-7.33 (m, 1H). |
| A-24 | 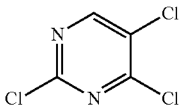 | 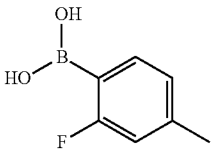 | 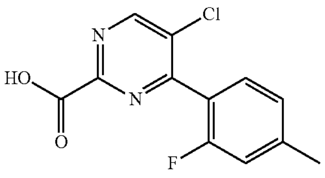 [SMILES: Cc1ccc(-c2nc(C(=O)O)ncc2Cl)c(F)c1] 5-chloro-4-(2-fluoro-4-methylphenyl)pyrimidine-2-carboxylic acid | $C_{12}H_8N_2ClO_2F$ requires: 266 and 268, found: 267 and 269 $[M + H]^+$. (400 MHz, DMSO-$d_6$) δ = 9.02 (s, 1H), 7.47-7.41 (m, 1H), 7.27-7.19 (m, 2H), 2.41 (s, 3H). |

TABLE 2-continued

Pyrimidine-2-carboxylic acids. II.

| Int. | Chloro pyrimidine | Arylboronic acid | Structure IUPAC name | MS (ES+) $^1$H NMR |
|---|---|---|---|---|
| A-25 | 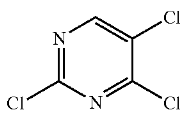 | 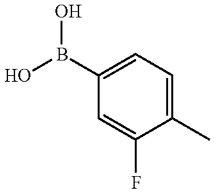 | 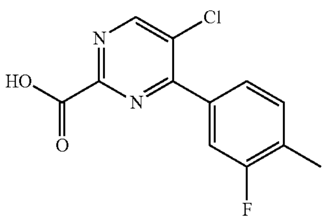 [SMILES: Cc1ccc(-c2nc(C(=O)O)ncc2Cl)cc1F] 5-chloro-4-(3-fluoro-4-methylphenyl)pyrimidine-2-carboxylic acid | $C_{12}H_8N_2ClO_2F$ requires: 266 and 268, found: 267 and 269 [M + H]$^+$. (400 MHz, DMSO-$d_6$) δ = 8.79 (s, 1H), 7.64-7.52 (m, 2H), 7.47-7.37 (m, 1H), 2.32 (s, 3H). |

INTERMEDIATE A-26

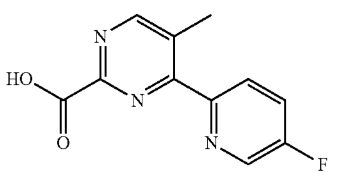

4-(5-fluoropyridin-2-yl)-5-methylpyrimidine-2-carboxylic acid

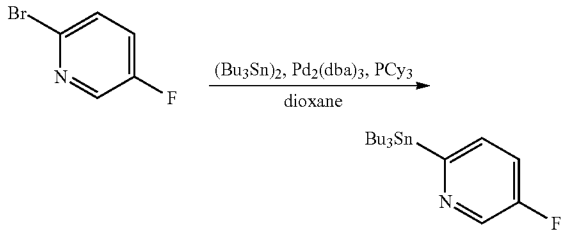

5-Fluoro-2-(tributylstannyl)pyridine To a solution of 2-bromo-5-fluoro-pyridine (4 g, 22.73 mmol, 1 eq) in dioxane (40 mL) were added tributyl(tributylstannyl)stannane (15.82 g, 27.27 mmol, 13.64 mL, 1.2 eq), tricyclohexylphosphane (318.69 mg, 1.14 mmol, 368.43 uL, 0.05 eq) and $Pd_2(dba)_3$ (1.04 g, 1.14 mmol, 0.05 eq) under $N_2$. After stirring at 100° C. for 16 h, the mixture was concentrated under reduced pressure to afford the title compound (8.8 g, crude) as black oil which was used directly. MS (ES+) $C_{17}H_{30}NFSn$ requires:387, found: 388 [M+H]$^+$.

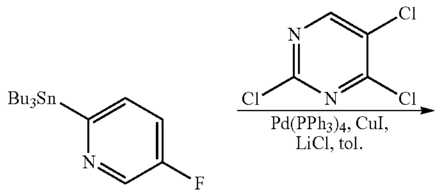

-continued

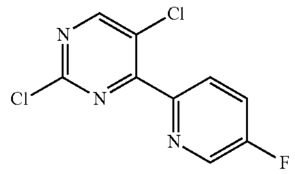

2,5-Dichloro-4-(5-fluoropyridin-2-yl)pyrimidine To a solution of the product from the previous step (8.8 g, 22.79 mmol, 1 eq) in toluene (60 mL) were added 2,4,5-trichloropyrimidine (4.18 g, 22.79 mmol, 2.61 mL, 1 eq), $Pd(PPh_3)_4$ (790.06 mg, 683.70 μmol, 0.03 eq), LiCl (1.93 g, 45.58 mmol, 933.49 μL, 2 eq) and CuI (868.07 mg, 4.56 mmol, 0.2 eq) under $N_2$. After stirring at 100° C. for 16 h, the mixture was concentrated under reduced pressure, diluted with $H_2O$ (50 mL) and extracted with EtOAc (50 mL×2). The combined organic layer was dried over $Na_2SO_4$, filtered and concentrated under reduced pressure. The residue was purified by prep-HPLC (column: Phenomenex Synergi Max-RP 250*50 mm*10 um; mobile phase: [water (0.05% HCl)—$CH_3CN$]; B %: 25 $CH_3CN$ %-55 $CH_3CN$ %, 23 min), and the eluent was concentrated under reduced pressure and freeze dried to afford the title compound (300 mg, 1.23 mmol, 5% yield) as a white solid. $^1$H NMR (400 MHz, DMSO-$d_6$) δ=9.06 (s, 1H), 8.81-8.77 (m, 1H), 8.10-8.04 (m, 1H), 8.03-7.96 (m, 1H).

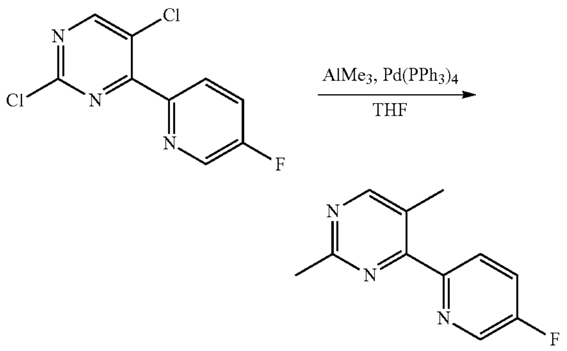

4-(5-Fluoropyridin-2-yl)-2,5-dimethylpyrimidine To a solution of the product from the previous step (250 mg, 1.02 mmol, 1 eq) in THF (10 mL) were added $Pd(PPh_3)_4$ (118.37 mg, 102.44 μmol, 0.1 eq) and $AlMe_3$ (2 M in toluene, 1.54 mL, 3 eq) under $N_2$. After stirring at 80° C. for 16 h, the mixture was poured into $H_2O$ (20 mL) and extracted with EtOAc (20 mL×2). The combined organic layer was dried over $Na_2SO_4$, filtered and concentrated under reduced pressure, the residue was purified by prep-TLC (Petroleum ether/EtOAc=2/1) to afford the title compound (90 mg, 403.02 μmol, 39% yield) as a white solid.

MS (ES+) $C_{11}H_{10}N_3F$ requires:203, found: 204 $[M+H]^+$. $^1H$ NMR (400 MHz, DMSO-$d_6$) δ=8.72 (d, J=2.9 Hz, 1H), 8.66 (s, 1H), 8.16 (dd, J=4.7, 8.8 Hz, 1H), 7.96-7.89 (m, 1H), 2.65 (s, 3H), 2.46 (s, 3H).

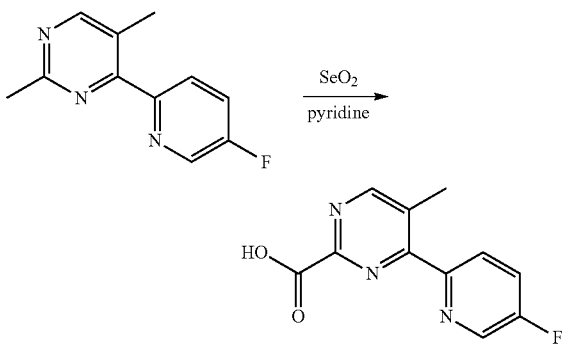

4-(5-fluoropyridin-2-yl)-5-methylpyrimidine-2-carboxylic acid To a solution of the product from the previous step (90 mg, 442.88 μmol, 1 eq) in pyridine (5 mL) and $H_2O$ (0.5 mL) was added $SeO_2$ (245.71 mg, 2.21 mmol, 5 eq). After stirring at 120° C. for 16 h, the mixture was filtered and the filtrate was concentrated under reduced pressure to afford the title compound (120 mg, crude) as a yellow oil which was used directly. MS (ES+) $C_{11}H_8N_3FO_2$ requires: 233, found: 234 $[M+H]^+$.

INTERMEDIATE A-27

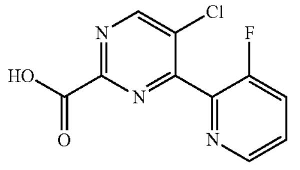

5-Chloro-4-(3-fluoropyridin-2-yl)pyrimidine-2-carboxylic acid

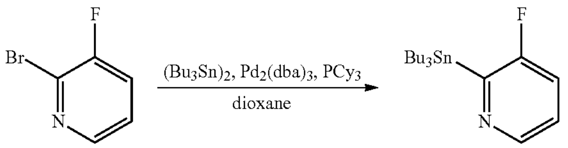

3-Fluoro-2-(tributylstannyl)pyridine A mixture of 2-bromo-3-fluoro-pyridine (10 g, 56.82 mmol, 1 eq), tricyclohexylphosphane (1.59 g, 5.68 mmol, 1.84 mL, 0.1 eq), tributyl (tributylstannyl) stannane (49.44 g, 85.23 mmol, 42.62 mL, 1.5 eq) and $Pd_2(dba)_3$ (5.20 g, 5.68 mmol, 0.1 eq) in dioxane (100 mL) was degassed and purged with $N_2$ 3 times. After stirring at 100° C. for 16 h, the mixture was filtered and concentrated under reduced pressure to obtain the title compound (64 g, crude) as black oil which was used directly without further purification. MS $(ES^+)$ $C_{17}H_{30}NFSn$ requires: 387 and 385, found: 388 and 386 $[M+H]^+$.

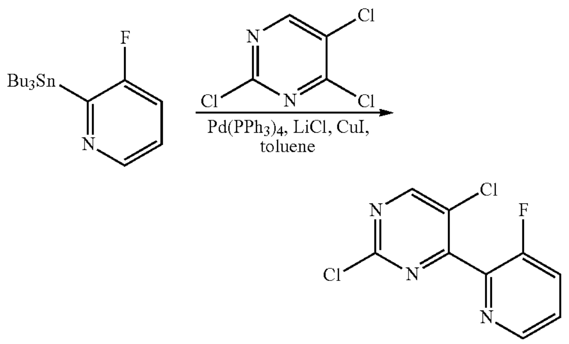

2,5-Dichloro-4-(3-fluoropyridin-2-yl)pyrimidine To a solution of the product from the previous step (78 g, 64.64 mmol, 32% purity, 1 eq) in toluene (150 mL) were added 2,4,5-trichloropyrimidine (11.86 g, 64.64 mmol, 1 eq), $Pd(PPh_3)_4$ (3.73 g, 3.23 mmol, 0.05 eq), LiCl (5.48 g, 129.28 mmol, 2.65 mL, 2 eq) and CuI (4.92 g, 25.86 mmol, 0.4 eq) under $N_2$. After stirring at 100° C. for 16 h, the mixture was filtered, the combined organic phase was dried over $Na_2SO_4$, filtered and concentrated under reduced pressure. The residue was purified by silica gel chromatography (ISCO®; 80 g SepaFlash® Silica Flash Column, Eluent 0~10% EtOAC/Petroleum ether gradient @50 mL/min) to afford the title compound (6 g, 22.37 mmol, 34% yield) as a brown solid.

MS $(ES^+)$ $C_9H_4N_3Cl_2F$ requires: 243 and 245, found: 244 and 246 $[M+H]^+$. $^1H$ NMR (400 MHz, $CDCl_3$) δ=8.77 (s, 1H), 8.67-8.60 (m, 1H), 7.69-7.59 (m, 1H), 7.57-7.50 (in, 1H).

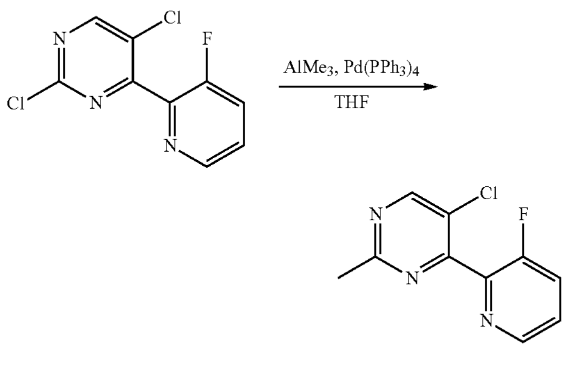

5-Chloro-4-(3-fluoropyridin-2-yl)-2-methylpyrimidine To a solution of the product from the previous step (5.3 g, 21.72 mmol, 1 eq) in THF (50 mL) were added $Pd(PPh_3)_4$ (2.51 g, 2.17 mmol, 0.1 eq) and $AlMe_3$ (2 M in toluene, 16.29 mL, 1.5 eq) under $N_2$. After stirring at 100° C. for 16 h, the mixture was poured into ice water (60 mL), extracted with EtOAc (60 mL×3), the organic phase was washed with brine (60 mL×3), dried over $Na_2SO_4$, filtered and concentrated under reduced pressure. The residue was purified by silica gel chromatography (ISCO®; 40 g SepaFlash® Silica Flash Column, Eluent 0~20% EtOAC/Petroleum ether gradient @50 mL/min) to afford the title compound (2.6 g, 11.63 mmol, 53% yield) as a yellow solid.

MS ($ES^+$) $C_{10}H_7N_3ClF$ requires: 223 and 225, found: 224 and 226 $[M+H]^+$. $^1H$ NMR (400 MHz, $CDCl_3$) δ=8.75 (s, 1H), 8.62 (d, J=4.4 Hz, 1H), 7.64-7.55 (m, 1H), 7.53-7.45 (m, 1H), 2.82 (s, 3H).

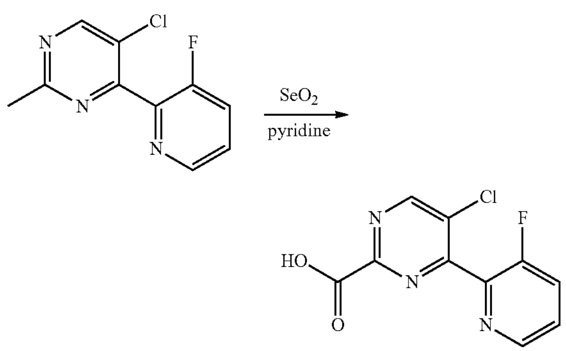

5-Chloro-4-(3-fluoropyridin-2-yl)pyrimidine-2-carboxylic acid To a solution of the product from the previous step (2.6 g, 11.63 mmol, 1 eq) in pyridine (20 mL) and $H_2O$ (2 mL) was added $SeO_2$ (5.16 g, 46.50 mmol, 4 eq). After stirring at 120° C. for 16 h, the mixture was poured into water (30 mL), extracted with EtOAc (30 mLx3), the combined organic phase was washed by brine (30 mLx3) dried over $Na_2SO_4$, filtered and concentrated under reduced pressure. The residue was triturated with EtOAc at 25° C. for 30 min, the filter cake was collected to afford the title compound (2.1 g, 7.78 mmol, 66% yield) as a yellow solid.

MS ($ES^+$) $C_{10}H_5ClFN_3O_2$ requires: 253 and 255, found: 254 and 256 $[M+H]^+$. $^1H$ NMR (400 MHz, DMSO-$d_6$) δ=8.94 (s, 1H), 8.61 (td, J=1.6, 4.6 Hz, 1H), 7.99 (m, 1H), 7.75-7.66 (m, 1H).

INTERMEDIATE A-28

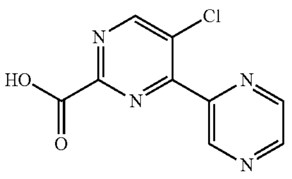

5-chloro-4-(pyrazin-2-yl)pyrimidine-2-carboxylic acid

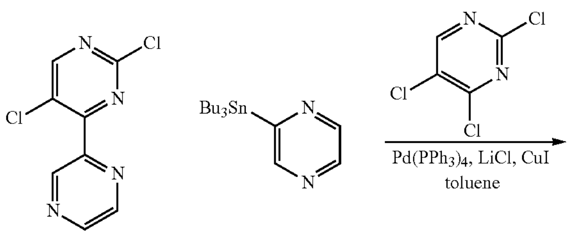

-continued

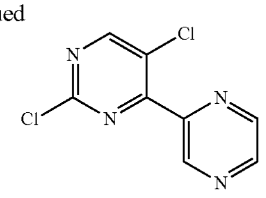

2,5-Dichloro-4-(pyrazin-2-yl)pyrimidine To a solution of 2,4,5-trichloropyrimidine (2 g, 10.90 mmol, 1.25 mL, 1 eq) in xylene (10 mL) were added $Pd(PPh_3)_4$ (630.00 mg, 545.19 umol, 0.05 eq) and 2-(tributylstannyl)pyrazine (4.02 g, 10.90 mmol, 1 eq) under $N_2$. After stirring at 120° C. for 16 h, the mixture was quenched with saturated KF aqueous solution (40 mL) and extracted with EtOAc (40 mLx2). The combined organic layer was concentrated and then purified by chromatography on silica gel (eluent Petroleum ether/EtOAc=20/1) to afford the title compound (280 mg, 1.17 mmol, 10% yield) as an orange solid. MS(ES+) $C_8H_4N_4Cl_2$ requires:226 and 228, found: 227 and 229 $[M+H]^+$.

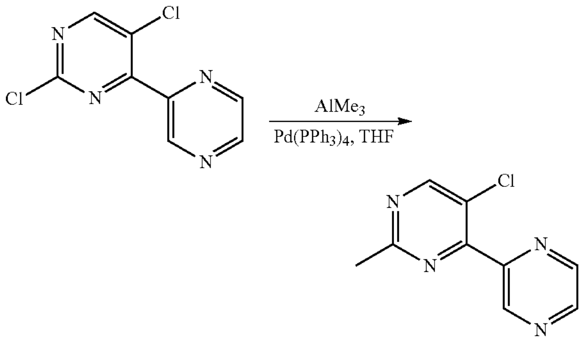

5-Chloro-2-methyl-4-(pyrazin-2-yl)pyrimidine To a solution of the product from the previous step (280 mg, 1.23 mmol, 1 eq) in THF (6 mL) were added $AlMe_3$ (2 M in toluene, 924.91 uL, 1.5 eq) and $Pd(PPh_3)_4$ (71.25 mg, 61.66 umol, 0.05 eq) under $N_2$. After stirring at 60° C. for 16 h, the mixture was quenched with $H_2O$ (10 mL) and extracted with EtOAc (10 mLx2). The combined organic layer was dried over $Na_2SO_4$, filtered and concentrated under reduced pressure to obtain a residue which was purified by prep-TLC (Petroleum ether:EtOAc=2:1) to afford the title compound (100 mg, 479.11 umol, 38% yield) as a yellow solid.

MS(ES+) $C_9H_7N_4Cl$ requires:206 and 208, found: 207 and 209 $[M+H]^+$. $^1H$ NMR (400 MHz, DMSO-$d_6$) δ=9.14 (s, 1H), 9.00 (s, 1H), 8.85-8.84 (m, 2H), 2.72 (s, 3H).

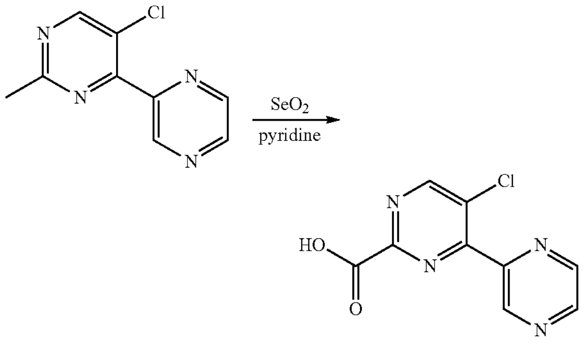

5-Chloro-4-(pyrazin-2-yl)pyrimidine-2-carboxylic acid To a solution of the product from the previous step (100 mg, 483.95 umol, 1 eq) in pyridine (2 mL) and $H_2O$ (0.2 mL) was added $SeO_2$ (268.50 mg, 2.42 mmol, 5 eq). After stirring at 120° C. for 16 h, the mixture was filtered and the filtrate was concentrated and then diluted with $H_2O$ (5 mL) and extracted with EtOAc (5 mL×2). The aqueous phase was acidified HCl (1 M) to adjust the pH to 2, then extracted with EtOAc (5 mL×2). The combined organic layer was concentrated to afford the title compound (30 mg, 106.50 umol, 22% yield) as a yellow solid. MS(ES+) $C_9H_5N_4O_2Cl$ requires:236 and 238, found: 237 and 239 $[M+H]^+$.

INTERMEDIATE A-29

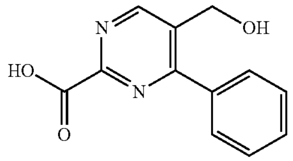

5-(hydroxymethyl)-4-phenylpyrimidine-2-carboxylic acid and

INTERMEDIATE A-30

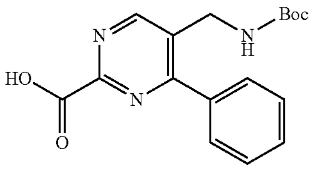

5-(((tert-Butoxycarbonyl)amino)methyl)-4-phenylpyrimidine-2-carboxylic acid

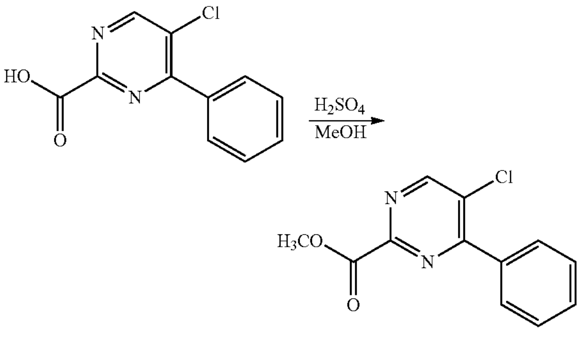

Methyl 5-chloro-4-phenylpyrimidine-2-carboxylate To a solution of 5-chloro-4-phenylpyrimidine-2-carboxylic acid (600 mg, 2.56 mmol, 1 eq) in MeOH (6 mL) was added $H_2SO_4$ (920.00 mg, 9.38 mmol, 0.5 mL, 3.67 eq). After stirring at 60° C. for 1 h, the mixture was concentrated as a yellow oil, diluted with $H_2O$ (10 mL) and extracted with EtOAc (10 mL×2). The combined organic layer was washed with brine (20 mL×3), dried over $Na_2SO_4$, filtered and concentrated under reduced pressure to afford the title compound (540 mg, 1.95 mmol, 76% yield) as a yellow oil.

MS (ES+) $C_{12}H_9N_2ClO_2$ requires: 248 and 250, found: 249 and 251 $[M+H]^+$. $^1H$ NMR (400 MHz, DMSO-$d_6$) δ=9.18 (s, 1H), 7.93-7.77 (m, 2H), 7.70-7.51 (m, 3H), 3.94 (s, 3H).

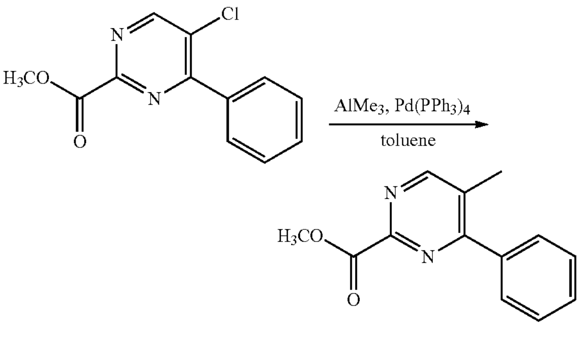

Methyl 5-methyl-4-phenylpyrimidine-2-carboxylate To a solution of the product from the previous step (540 mg, 2.17 mmol, 1 eq) in THF (10 mL) were added $Pd(PPh_3)_4$ (125.47 mg, 108.58 μmol, 0.05 eq) and $AlMe_3$ (2 M in toluene, 2.71 mL, 2.5 eq) under $N_2$. After stirring at 80° C. for 3 h, the mixture was quenched with $H_2O$ (20 mL) and extracted with EtOAc (20 mL×2). The combined organic layer was washed with brine (20 mL×3), dried over $Na_2SO_4$, filtered and concentrated under reduced pressure. The residue was purified by prep-TLC (eluent Petroleum ether/EtOAc=1/1) to afford the title compound (260 mg, 797.38 μmol, 36% yield) as a white solid.

MS (ES+) $C_{13}H_{12}N_2O_2$ requires: 228, found: 229 $[M+H]^+$. $^1H$ NMR (400 MHz, DMSO-$d_6$) δ=9.04 (s, 1H), 7.85-7.80 (m, 2H), 7.71-7.67 (m, 3H), 4.04 (s, 3H), 2.56 (s, 3H).

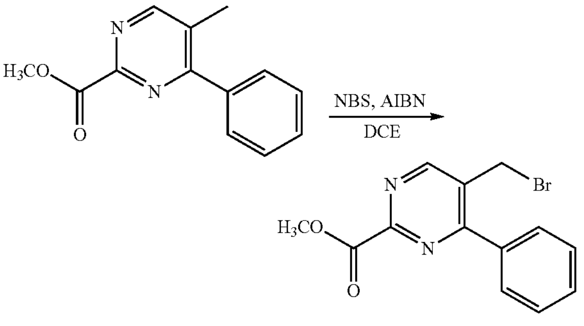

Methyl 5-(bromomethyl)-4-phenylpyrimidine-2-carboxylate To a solution of the product from the previous step (260 mg, 797.38 μmol, 70% purity, 1 eq) in DCE (6 mL) were added NBS (283.84 mg, 1.59 mmol, 2 eq) and AIBN (52.37 mg, 318.95 μmol, 0.4 eq). After stirring at 80° C. for 16 h, the mixture was diluted with $H_2O$ (20 mL) and extracted with $CH_2Cl_2$ (20 mL×2). The combined organic layer was washed with brine (20 mL×3), dried over $Na_2SO_4$, filtered and concentrated under reduced pressure. The residue was purified by prep-TLC (eluent Petroleum ether/EtOAc=1/1) to afford the title compound (100 mg, 293.02 μmol, 36% yield) as a white solid.

MS (ES+) $C_{13}H_{11}N_2O_2Br$ requires: 306 and 308, found: 307 and 309 $[M+H]^+$. $^1H$ NMR (400 MHz, DMSO-$d_6$) δ=9.19 (s, 1H), 7.79-7.70 (m, 2H), 7.65-7.58 (m, 3H), 4.81 (s, 2H), 3.93 (s, 3H).

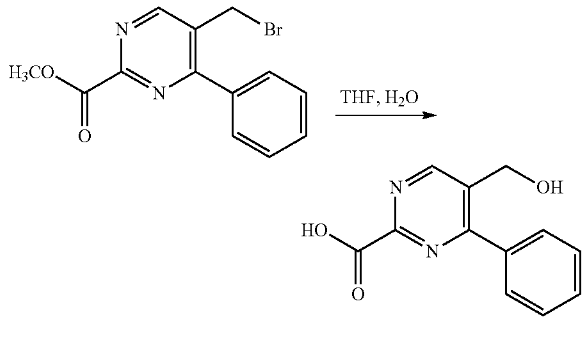

5-(Hydroxymethyl)-4-phenylpyrimidine-2-carboxylic acid (Intermediate A-29

A mixture of the product from the previous step (250 mg, 691.86 μmol, 1 eq) in THF (5 mL) and $H_2O$ (5 mL) was stirred at 80° C. for 16 h, the mixture was concentrated under reduced pressure to afford the title compound (300 mg, crude) as a yellow solid. MS (ES+) $C_{12}H_{10}N_2O_3$ requires: 230, found: 231 $[M+H]^+$.

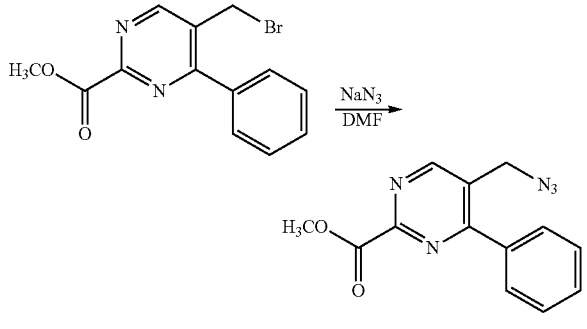

Methyl 5-(azidomethyl)-4-phenylpyrimidine-2-carboxylate To a solution of the product from the previous step (100 mg, 325.58 umol, 1 eq) in DMF (2 mL) was added NaN3 (70 mg, 1.08 mmol, 3.31 eq). After stirring at 25° C. for 16 h, the mixture was diluted with $H_2O$ (10 mL) and extracted with EtOAc (10 mL×2). The combined organic layer was washed with brine (20 mL×3), dried over $Na_2SO_4$, filtered and concentrated to the title compound (80 mg, crude) as a yellow oil. MS (ES+) $C_{13}H_{11}N_5O_2$ requires: 269, found: 270 $[M+H]^+$.

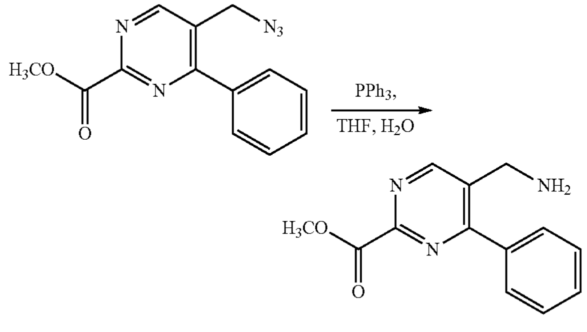

Methyl 5-(aminomethyl)-4-phenylpyrimidine-2-carboxylate To a solution of the product from the previous step (80 mg, 297.11 μmol, 1 eq) in THF (4 mL) were added $PPh_3$ (155.86 mg, 594.23 μmol, 2 eq) and $H_2O$ (0.4 mL). After stirring at 25° C. for 1 h, the mixture was concentrated as a yellow oil to afford the title compound (120 mg, crude). MS (ES+) $C_{13}H_{13}N_3O_2$ requires: 243, found: 244 $[M+H]^+$.

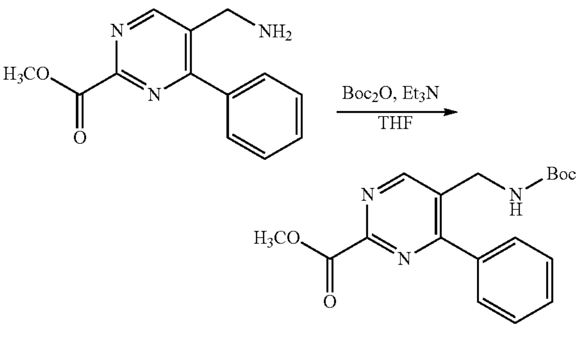

Methyl 5-(((tert-butoxycarbonyl)amino)methyl)-4-phenylpyrimidine-2-carboxylate To a solution of the product from the previous step (80 mg, 328.87 μmol, 1 eq) in THF (3 mL) were added $Boc_2O$ (143.55 mg, 657.73 μmol, 151.10 μL, 2 eq) and $Et_3N$ (133.11 mg, 1.32 mmol, 183.10 μL, 4 eq). After stirring at 25° C. for 2 h, the mixture was concentrated under reduced pressure. The residue was purified by prep-TLC (eluent Petroleum ether/EtOAc=1/1) to afford the title compound (30 mg, 61.16 μmol, 18% yield) as a colorless oil. MS (ES+) $C_{18}H_{21}N_3O_4$ requires: 343, found: 344 $[M+H]^+$.

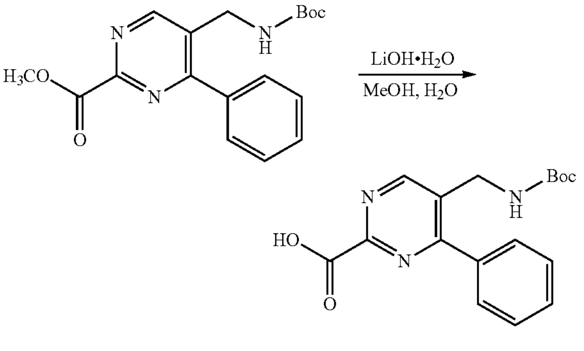

5-(((tert-Butoxycarbonyl)amino)methyl)-4-phenylpyrimidine-2-carboxylic acid (Intermediate A-30) To a solution of the product from the previous step (30 mg, 87.37 μmol, 1 eq) in MeOH (1.5 mL) and $H_2O$ (1.5 mL) was added $LiOH \cdot H_2O$ (7.33 mg, 174.74 μmol, 2 eq). After stirring at 25° C. for 1 h, the mixture was concentrated to afford the title compound (40 mg, crude) as a white solid. MS (ES+) $C_{17}H_{19}N_3O_4$ requires: 329, found: 330 $[M+H]^+$.

INTERMEDIATE A-31

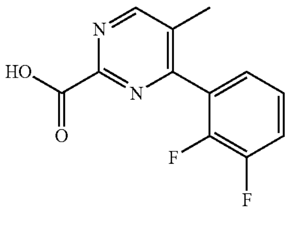

4-(2,3-Difluorophenyl)-5-methylpyrimidine-2-carboxylic acid

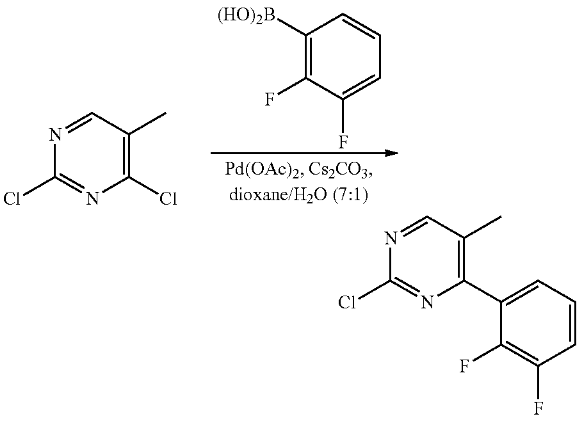

2-Chloro-4-(2,3-difluorophenyl)-5-methylpyrimidineTo a solution of 2,4-dichloro-5-methylpyrimidine (4.3 g, 26.38 mmol, 1 eq) in THF (50 mL) and $H_2O$ (5 mL) were added (2,3-difluorophenyl) boronic acid (5.00 g, 31.66 mmol, 1.2 eq), $Pd(OAc)_2$ (118.45 mg, 0.52 mmol, 0.02 eq), $Na_2CO_3$ (2.80 g, 26.38 mmol, 1 eq) and $PPh_3$ (276.76 mg, 1.06 mmol, 0.04 eq) under $N_2$. After stirring at 60° C. for 16 h, the reaction mixture was diluted with $H_2O$ (50 mL) and extracted with EtOAc (50×3 mL), washed with brine (100 mL), dried over $Na_2SO_4$, filtered and concentrated under reduced pressure to obtain a residue which was purified by flash silica gel chromatography (80 g SepaFlash® Silica Flash Column, Eluent of 30~40% EtOAC/Petroleum ether gradient @100 mL/min) to yield the title compound (5 g, 20.78 mmol, 78% yield) as a white solid. MS (ES+) $C_{11}H_7ClF_2N_2$ requires: 240, found: 241 $[M+H]^+$

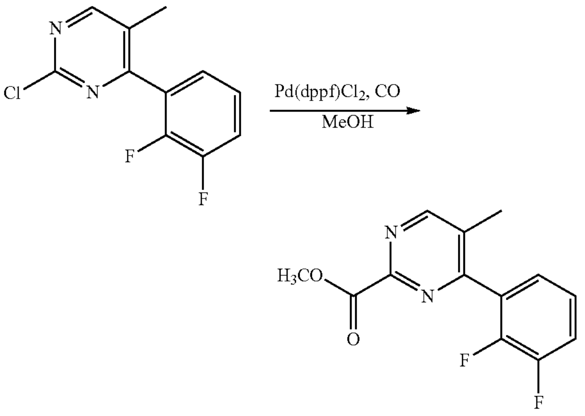

Methyl 4-(2,3-difluorophenyl)-5-methylpyrimidine-2-carboxylate To a solution of the product from the previous step (2 g, 8.31 mmol, 1 eq) in MeOH (20 mL) were added $Pd(dppf)Cl_2$ (608.14 mg, 0.83 mmol, 0.1 eq) and $Et_3N$ (2.52 g, 24.93 mmol, 3.47 mL, 3 eq) under $N_2$. The suspension was degassed under vacuum and purged with CO several times. After stirring under CO (®50 psi) at 60° C. for 16 h, the reaction mixture was filtered and concentrated under reduced pressure to give a residue which was purified by silica gel chromatography (45 g SepaFlash® Silica Flash Column, Eluent of 40~50% EtOAC/Petroleum ether gradient @80 mL/min) to yield the title compound (2 g, 7.49 mmol, 90% yield) as a white solid. MS (ES+) $C_{13}H_{10}F_2N_2O_2$ requires: 264, found: 265 $[M+H]^+$.

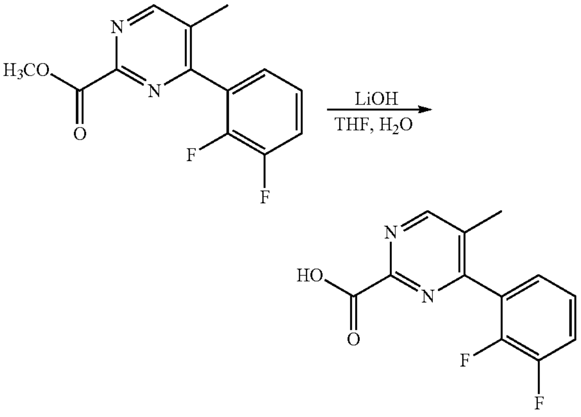

4-(2,3-Difluorophenyl)-5-methylpyrimidine-2-carboxylic acid To a solution of the product from the previous step (2 g, 7.57 mmol, 1 eq) in THF (20 mL) and $H_2O$ (5 mL) was added $LiOH \cdot H_2O$ (953 mg, 22.71 mmol, 3 eq). After stirring at 25° C. for 16 h, the mixture was acidified with aqueous HCl until pH=2 and concentrated under reduced pressure to obtain a residue which was triturated with water (40 mL) to yield the title compound (2 g, 7.43 mmol, 98% yield) as a white solid.

MS (ES+) $C_{12}H_8F_2N_2O_2$ requires: 250, found: 251 $[M+H]^+$. $^1H$ NMR (400 MHz, DMSO-$d_6$) δ=14.58-12.44 (br s, 1H), 8.97 (s, 1H), 7.70-7.59 (m, 1H), 7.46-7.32 (m, 2H), 2.26 (s, 3H).

The following pyrimidine-2-carboxylic acids were obtained using procedures similar to that used for Intermediate A-31.

TABLE 3

| Pyrimidine-2-carboxylic acids. III. | | |
|---|---|---|
| Int. | Structure | IUPAC name |
| A-32 | 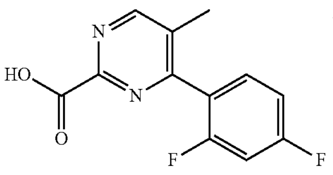 [SMILES: Cc1cnc(C(=O)O)nc1-c1ccc(F)cc1F] | 4-(2,4-Difluorophenyl)-5-methylpyrimidine-2-carboxylic acid |
| A-33 | 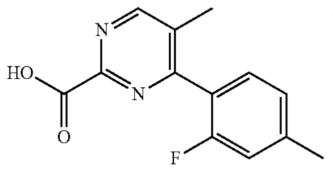 [SMILES: Cc1ccc(-c2nc(C(=O)O)ncc2C)c(F)c1] | 4-(2-Fluoro-4-methylphenyl)-5-methylpyrimidine-2-carboxylic acid |
| A-34 | 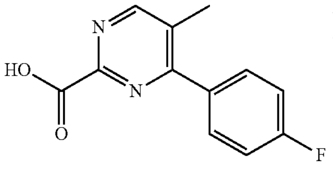 [SMILES: Cc1cnc(C(=O)O)nc1-c1ccc(F)cc1] | 4-(4-Fluorophenyl)-5-methylpyrimidine-2-carboxylic acid |

TABLE 3-continued

| Pyrimidine-2-carboxylic acids. III. | | |
|---|---|---|
| Int. | Structure | IUPAC name |
| A-35 | 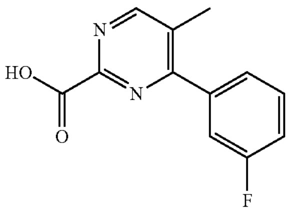 [SMILES: Cc1cnc(C(=O)O)nc1-c1cccc(F)c1] | 4-(3-Fluorophenyl)-5-methylpyrimidine-2-carboxylic acid |
| A-36 | 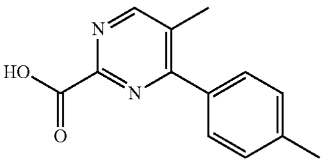 [SMILES: Cc1ccc(-c2nc(C(=O)O)ncc2C)cc1] | 5-Methyl-4-(p-tolyl)-pyrimidine-2-carboxylic acid |

INTERMEDIATE A-37

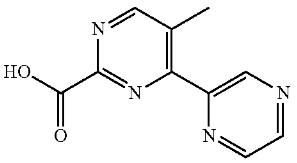

5-Methyl-4-(pyrazin-2-yl)pyrimidine-2-carboxylic acid

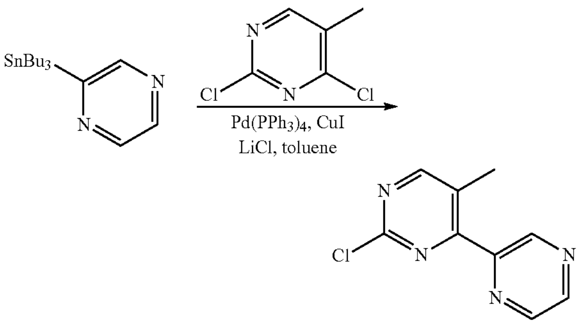

2-Chloro-5-methyl-4-(pyrazin-2-yl)pyrimidine A mixture of tributyl (pyrazin-2-yl)stannane (2 g, 5.42 mmol, 1 eq), 2,4-dichloro-5-methylpyrimidine (883.18 mg, 5.42 mmol, 1 eq), $Pd(PPh_3)_4$ (626.10 mg, 541.81 μmol, 0.1 eq), CuI (412.75 mg, 2.17 mmol, 0.4 eq) and LiCl (459.39 mg, 10.84 mmol, 221.93 μL, 2 eq) in toluene (20 mL) was degassed and purged with $N_2$ for 3 times, and then the mixture was stirred at 60° C. for 16 h under $N_2$. The reaction mixture was filtered and concentrated under reduced pressure. The residue was purified by silica gel chromatography (40 g SepaFlash® Silica Flash Column, Eluent 30~50% EtOAC/Petroleum ether gradient @50 mL/min) to afford the title compound (900 mg, 3.88 mmol, 71% yield) as a red solid. MS (ES+) $C_9H_7ClN_4$ requires: 206 and 208, found: 207 and 209 $[M+H]^+$,

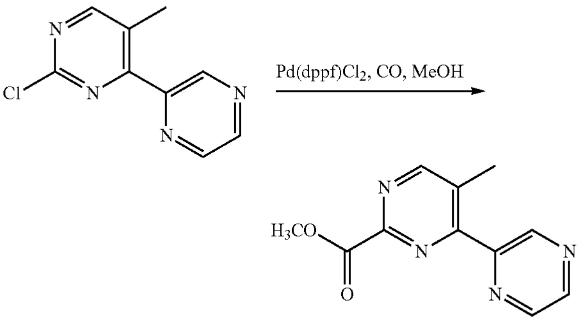

Methyl 5-methyl-4-(pyrazin-2-yl)pyrimidine-2-carboxylate To a solution of the product from the previous step (900 mg, 4.36 mmol, 1 eq) in methanol (20 mL) were added $Pd(dppf)Cl_2$ (318.70 mg, 435.56 μmol, 0.1 eq) and $Et_3N$ (1.32 g, 13.07 mmol, 1.82 mL, 3 eq) under $N_2$. The suspension was degassed under vacuum and purged with CO 3 times. After stirring under CO (50 psi) at 70° C. for 16 h, the reaction mixture was filtered and concentrated under reduced pressure. The residue was purified by silica gel chromatography (40 g SepaFlash® Silica Flash Column, Eluent 50~80% EtOAC/Petroleum ether gradient @60 mL/min) to afford the title compound (600 mg, 2.01 mmol, 46% yield) as a red solid. MS (ES+) $C_{11}H_{10}N_4O_2$ requires: 230, found: 231 $[M+H]^+$.

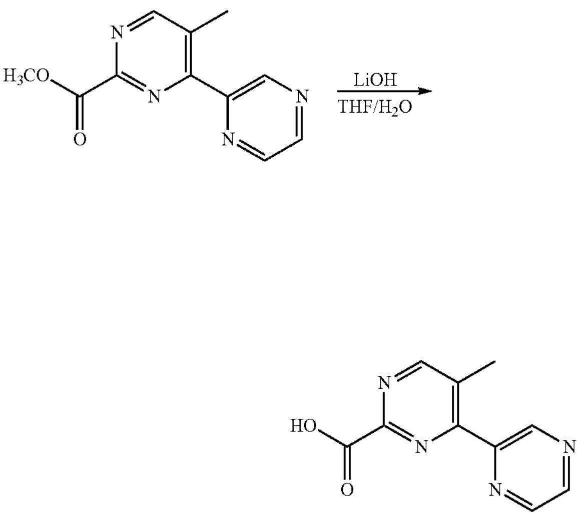

5-Methyl-4-(pyrazin-2-yl)pyrimidine-2-carboxylic acid To a solution of the product from the previous step (600 mg, 2.61 mmol, 1 eq) in THF (10 mL) and $H_2O$ (2 mL) was added $LiOH \cdot H_2O$ (328.07 mg, 7.82 mmol, 3 eq). The mixture was stirred at 25° C. for 16 h, the mixture was acidified with aqueous HCl (1 M) to pH=6 and concentrated under reduced pressure. The residue was triturated with water and the filter cake was collected. To the filter cake was added deionized water (5 mL) and the mixture was freeze-dried to afford the title compound (200 mg, 370.03 μmol, 14% yield) as a yellow solid.

MS (ES+) $C_{10}H_8N_4O_2$ requires: 216, found: 217 $[M+H]^+$. $^1H$ NMR (400 MHz, DMSO-$d_6$) δ=13.60 (br s, 1H), 9.32 (s, 1H), 9.00 (s, 1H), 8.88-8.78 (m, 2H), 2.60 (s, 3H).

INTERMEDIATE A-38

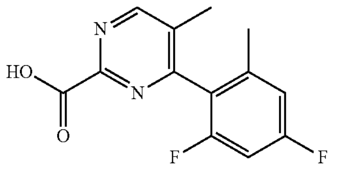

4-(2,4-Difluoro-6-methylphenyl)-5-methylpyrimidine-2-carboxylic acid

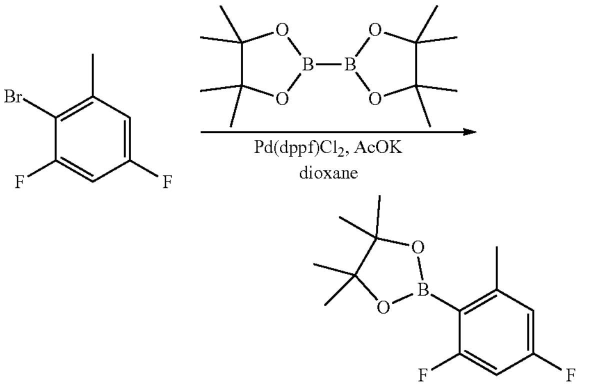

2-(2,4-Difluoro-6-methylphenyl)-4,4,5,5-tetramethyl-1,3,2-dioxaborolane To a solution of the product from the previous step (1.5 g, 7.25 mmol, 1 eq) in dioxane (20 mL) was added BPD (3.68 g, 14.49 mmol, 2 eq), Pd(dppf) $Cl_2$ (530.18 mg, 724.58 μmol, 0.1 eq), KOAc (1.07 g, 10.87 mmol, 1.5 eq) under $N_2$. After stirring at 120° C. for 16 h, the mixture was concentrated under reduced pressure to give a residue which was purified by column chromatography ($SiO_2$, Petroleum ether/EtOAc=100/1 to 50/1) to afford the title compound (1 g, 3.74 mmol, 51% yield) as a yellow oil. $^1H$ NMR (400 MHz, DMSO-$d_6$) δ=7.02-6.76 (m, 2H), 2.39 (s, 3H), 1.30 (s, 12H).

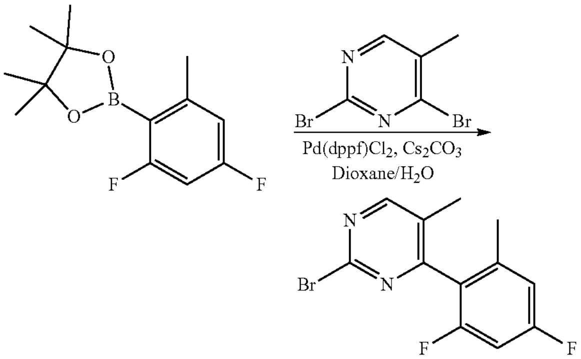

2-bromo-4-(2,4-difluoro-6-methylphenyl)-5-methylpyrimidine To a solution of the product from the previous step (1.6 g, 6.30 mmol, 1 eq) in dioxane (20 mL) and $H_2O$ (5 mL) were added 2,4-dibromopyrimidine (1.50 g, 6.30 mmol, 1 eq), $Cs_2CO_3$ (6.16 g, 18.89 mmol, 3 eq) and Pd(dppf) $Cl_2$ (230.39 mg, 314.86 μmol, 0.05 eq) under $N_2$. After stirring at 100° C. for 16 h, the reaction mixture was diluted with $H_2O$ (50 mL) and extracted with EtOAc (25 mL×2). The combined organic layer was dried over $Na_2SO_4$, filtered and concentrated under reduced pressure to give a residue which was purified by column chromatography ($SiO_2$, Petroleum ether/EtOAc=100/1 to 5/1) to afford the title compound (1.2 g, 3.37 mmol, 53.47% yield, 80% purity)) as a yellow solid.

MS (ES+) $C_{11}H_7F_2BrN_2$ requires: 284 and 286, found: 285 and 287 $[M+H]^+$. $^1H$ NMR (400 MHz, DMSO-$d_6$) δ=8.90 (d, J=5.1 Hz, 1H), 7.84-7.82 (m, 1H), 7.37-7.30 (m, 1H), 7.25-7.20 (m, 1H), 2.30 (s, 3H).

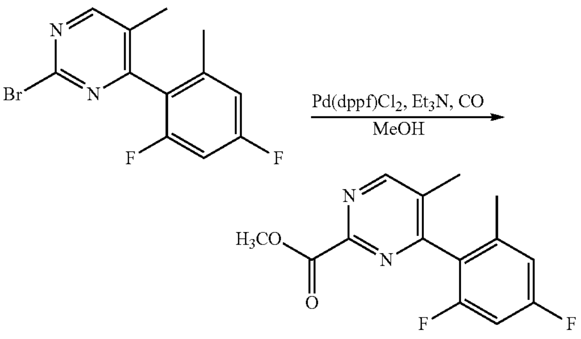

Methyl 4-(2,4-difluoro-6-methylphenyl)-5-methylpyrimidine-2-carboxylate

To a solution of the product from the previous step (1.2 g, 4.21 mmol, 1 eq) in MeOH (30 mL) were added Pd(dppf) $Cl_2$ (154.00 mg, 210.46 μmol, 0.05 eq) and $Et_3N$ (851.86 mg, 8.42 mmol, 1.17 mL, 2 eq). After stirring at 60° C. for 30 h under an atmosphere of CO (®50 psi), the mixture was concentrated, diluted with water (20 mL) and extracted with EtOAc (10 mL×2). The combined organic layers were dried over $Na_2SO_4$, filtered and concentrated under reduced pressure to obtain a residue which was purified by column chromatography ($SiO_2$, Petroleum ether/EtOAc=100/1 to 1/1) to afford the title compound (730 mg, 2.76 mmol, 65% yield) as a white solid.

MS (ES+) $C_{13}H_{10}F_2N_2O_2$ requires:264, found: 265 $[M+H]^+$. $^1H$ NMR (400 MHz, DMSO-$d_6$) δ=9.11 (d, J=5.1 Hz, 1H), 7.89 (dd, J=1.6, 5.1 Hz, 1H), 7.29 (s, 1H), 7.19 (dd, J=0.7, 9.6 Hz, 1H), 3.93 (s, 3H), 2.23 (s, 3H).

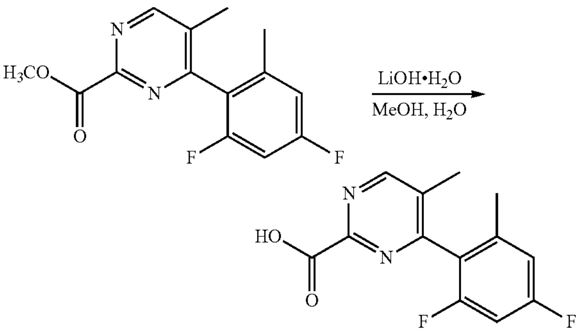

4-(2,4-Difluoro-6-methylphenyl)-5-methylpyrimidine-2-carboxylic acid To a solution of the product from the previous step (730 mg, 2.76 mmol, 1 eq) in MeOH (10 mL) and $H_2O$ (10 mL) was added LiOH·$H_2O$ (348 mg, 8.29 mmol, 3 eq). After stirring at 25° C. for 2 h, the mixture was concentrated, adjusted pH to 11 with NaOH (1 M) and extracted with EtOAc (10 mL). The aqueous layer was adjusted pH to 3 with HCl (1 M) and extracted with EtOAc (10 mL). The organic layer was dried over $Na_2SO_4$, filtered and concentrated to afford the title compound (670 mg, 2.68 mmol, 97% yield) as a white solid.

MS (ES+) $C_{12}H_8F_2N_2O_2$ requires: 250, found: 251 $[M+H]^+$. $^1H$ NMR (400 MHz, DMSO-$d_6$) δ=13.68 (s, 1H), 9.08 (d, J=5.1 Hz, 1H), 7.83 (dd, J=1.6, 5.1 Hz, 1H), 7.34-7.23 (m, 1H), 7.18 (dd, J=0.7, 9.6 Hz, 1H), 2.22 (s, 3H).

INTERMEDIATE A-39

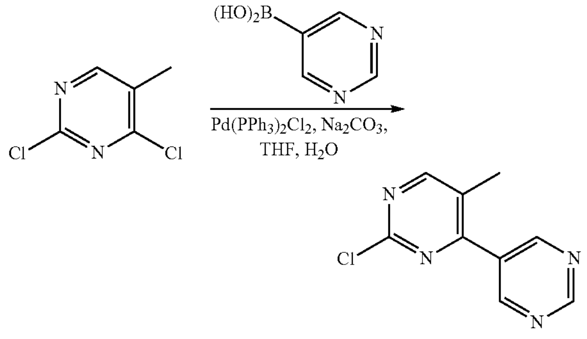

2-Chloro-5-methyl-4,5'-bipyrimidine To a solution of 2,4-dichloro-5-methyl-pyrimidine (2 g, 12.27 mmol, 1 eq) in THF (21 mL) and $H_2O$ (7 mL) were added pyrimidin-5-ylboronic acid (1.67 g, 13.50 mmol, 1.1 eq), $Pd(dppf)Cl_2$ (448.89 mg, 613.48 umol, 0.05 eq) and $Na_2CO_3$ (3.90 g, 36.81 mmol, 3 eq) under $N_2$. After stirring at 70° C. for 16 h, the mixture was diluted with $H_2O$ (50 mL) and extracted with EtOAc (50 mL×2). The combined organic layer was washed with brine, dried over anhydrous $Na_2SO_4$ and filtrated. The filtrate was concentrated and purified by chromatography on silica gel (eluent Petroleum ether/EtOAc=1:1) to afford the title compound (3.8 g, crude) as an orange solid. $^1H$ NMR (400 MHz, DMSO-$d_6$) δ=9.35 (s, 1H), 9.15 (s, 2H), 8.81 (s, 1H), 2.40 (s, 3H).

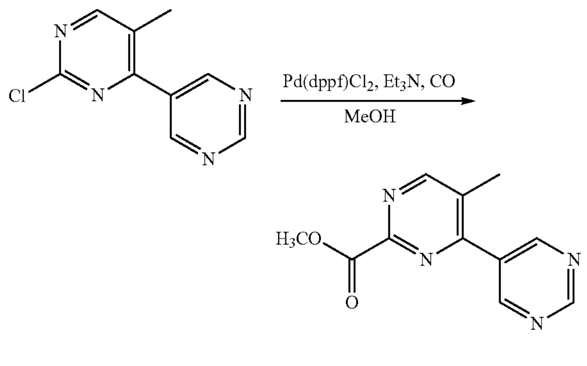

Methyl 5-methyl-[4,5'-bipyrimidine]-2-carboxylate To a solution of the product from the previous step (3.8 g, 18.39 mmol, 1 eq) in MeOH (40 mL) were added $Et_3N$ (3.72 g, 36.78 mmol, 5.12 mL, 2 eq) and $Pd(dppf)Cl_2$ (672.81 mg, 919.51 umol, 0.05 eq), the suspension was stirred at 70° C. under CO (45 psi) for 16 h, the mixture was concentrated. The resulting brown solid was purified by chromatography on silica gel (eluent Petroleum ether/EtOAc=0:1) to afford the title compound (630 mg, 2.65 mmol, 14% yield) as a red solid.

MS (ES+) $C_{11}H_{10}N_4O_2$ requires: 230, found: 231 $[M+H]^+$. $^1H$ NMR (400 MHz, DMSO-$d_6$) δ=9.37 (s, 1H), 9.17 (s, 2H), 9.01 (s, 1H), 3.93 (s, 3H), 2.49 (s, 3H).

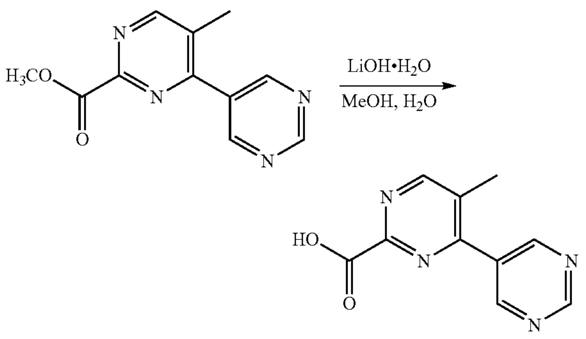

5-Methyl-[4,5'-bipyrimidine]-2-carboxylic acid To a solution of the product from the previous step (30 mg, 130.31 umol, 1 eq) in MeOH (1 mL) and $H_2O$ (1 mL) was added $LiOH·H_2O$ (8.20 mg, 195.46 umol, 1.5 eq). After stirring at 25° C. for 10 min. The pH of mixture was adjusted to 7 with 1M HCl aqueous solution. The residue was concentrated under reduced pressure to afford the title compound (30 mg, crude) as a yellow oil.

MS(ES+) $C_{10}H_8N_4O_2$ requires: 216, found: 217 $[M+H]^+$. $^1H$ NMR (400 MHz, DMSO-$d_6$) δ=9.32 (s, 1H), 9.18 (s, 2H), 8.84 (s, 1H), 2.41 (s, 3H).

INTERMEDIATE A-40

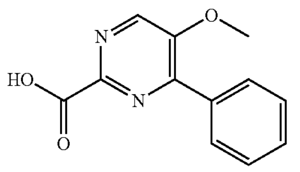

5-Methoxy-4-phenylpyrimidine-2-carboxylic acid

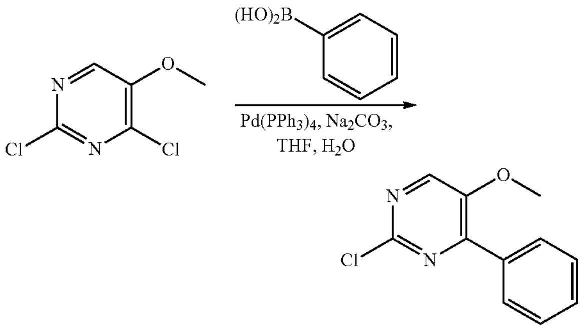

2-Chloro-5-methoxy-4-phenylpyrimidine To a solution of 2,4-dichloro-5-methoxypyrimidine in THF (20 mL) and $H_2O$ (5 mL) (2 g, 11.17 mmol, 1 eq) were added phenylboronic acid (1.36 g, 11.17 mmol, 1 eq), $Pd(OAc)_2$ (50.17 mg, 223.46 μmol, 0.02 eq), $Na_2CO_3$ (2.37 g, 22.35 mmol, 2 eq) and $PPh_3$ (117.22 mg, 446.92 μmol, 0.04 eq) under $N_2$. After stirring at 60° C. for 16 h, the mixture was diluted with $H_2O$ (20 mL) and extracted with EtOAc (20 mL×2), dried over $Na_2SO_4$, filtered and concentrated under reduced pressure. The residue was purified by chromatography on silica gel (eluent Petroleum ether/EtOAc=10/to 5/1) to afford the title compound as a white solid (1.9 g, 5.86 mmol, 52% yield).

MS (ES+) $C_{11}H_9ClN_2O$ requires: 220 and 222, found: 221 and 223 $[M+H]^+$. $^1H$ NMR (400 MHz, DMSO-$d_6$) δ=8.66 (s, 1H), 8.06-7.98 (m, 2H), 7.57-7.48 (m, 3H), 4.00 (s, 3H).

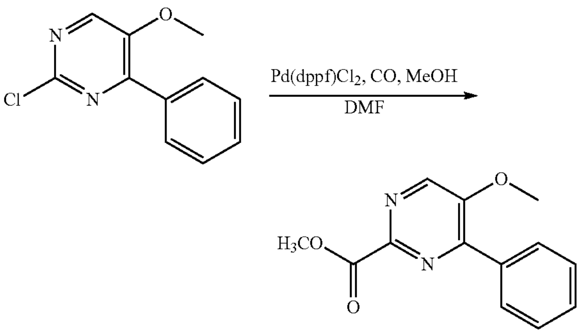

Methyl 5-methoxy-4-phenylpyrimidine-2-carboxylate To a solution of the product from the previous step (1.8 g, 8.16 mmol, 1 eq), in MeOH (40 mL) and DMF (8 mL) were added $Et_3N$ (2.48 g, 24.47 mmol, 3.41 mL, 3.00 eq) and Pd(dppf)$Cl_2$ (895.34 mg, 1.22 mmol, 0.15 eq) under $N_2$. The suspension was degassed under vacuum and purged with CO 3 times. After stirring at 80° C. under CO atmosphere (45 psi) for 16 h, the mixture was diluted with $H_2O$ (50 mL), extracted with EtOAc (50 mL×2) and concentrated under reduced pressure. The residue was purified by chromatography on silica gel (eluent Petroleum ether/EtOAc=5/1 to 2/1) to afford the title compound (1.7 g, 6.26 mmol, 76% yield) as a white solid.

MS (ES+) $C_{13}H_{12}N_2O_3$ requires: 244, found: 245 $[M+H]^+$. $^1H$ NMR (400 MHz, DMSO-$d_6$) δ=8.82 (s, 1H), 8.09-8.02 (m, 2H), 7.57-7.50 (m, 3H), 4.08 (s, 3H), 3.90 (s, 3H).

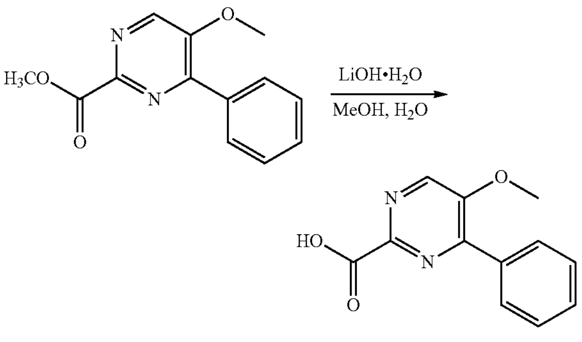

5-Methoxy-4-phenylpyrimidine-2-carboxylic acid To a solution of the product from the previous step (1.7 g, 6.96 mmol, 1 eq) in MeOH (10 mL) and $H_2O$ (10 mL) was added $LiOH \cdot H_2O$ (876.23 mg, 20.88 mmol, 3 eq). After stirring at 25° C. for 16 h, the mixture was diluted with water (50 mL), extracted with EtOAc (50 mL×2) and concentrated under reduced pressure. The residue was purified by chromatography on silica gel (eluent Petroleum ether/EtOAc=10/1 to 2/1) to afford the title compound (1.3 g, 5.65 mmol, 81% yield).

MS (ES+) $C_{12}H_{10}N_2O_3$ requires: 230, found: 231 $[M+H]^+$. $^1H$ NMR (400 MHz, DMSO-$d_6$) δ=8.80 (s, 1H), 8.10-8.05 (m, 2H), 7.56-7.50 (m, 3H), 4.07 (s, 3H).

INTERMEDIATE A-41

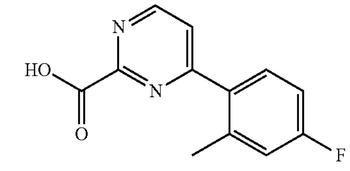

4-(4-Fluoro-2-methylphenyl)pyrimidine-2-carboxylic acid

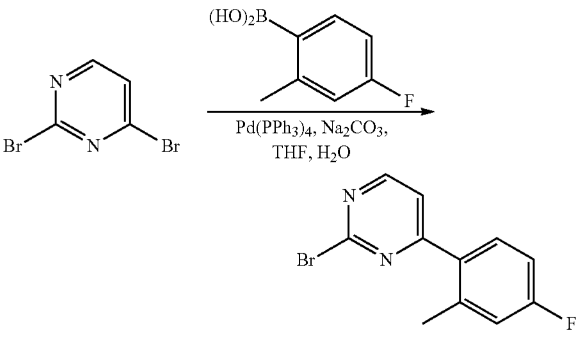

2-Bromo-4-(4-fluoro-2-methylphenyl)pyrimidine To a solution of 2,4-dibromopyrimidine (5 g, 21.02 mmol, 1 eq) and (4-fluoro-2-methylphenyl) boronic acid (3.24 g, 21.02 mmol, 1 eq) in THF (60 mL) and $H_2O$ (20 mL) were added $Na_2CO_3$ (6.68 g, 63.06 mmol, 3 eq) and $Pd(PPh_3)_4$ (1.21 g, 1.05 mmol, 0.05 eq) under $N_2$. After stirring at 60° C. for 16 h, the mixture was diluted with water (50 mL) and extracted with EtOAc (100 mL×2). The combined organic phase was dried over $Na_2SO_4$, filtered and concentrated under reduced pressure. The residue was purified by chromatography on silica gel (eluent Petroleum ether/EtOAc=100/1 to 5/1) to afford the title compound (3.5 g, 11.79 mmol, 56% yield) as a white solid.

MS (ES+) $C_{11}H_8N_2FBr$ requires: 266 and 268, found: 267 and 269 $[M+H]^+$. $^1H$ NMR (400 MHz, DMSO-$d_6$) δ=8.77 (d, J=5.1 Hz, 1H), 7.82 (d, J=5.1 Hz, 1H), 7.61 (dd, J=6.0, 8.5 Hz, 1H), 7.32-7.16 (m, 2H), 2.43 (s, 3H).

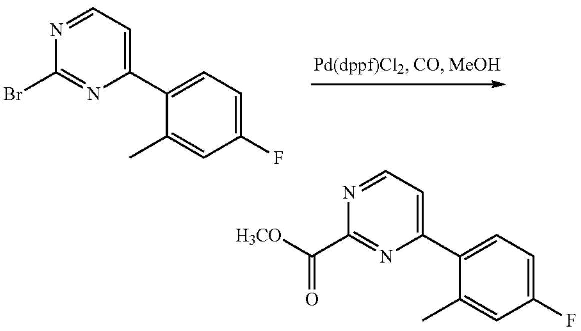

Methyl 4-(4-fluoro-2-methylphenyl)pyrimidine-2-carboxylate To a solution of the product from the previous step (3.5 g, 13.10 mmol, 1 eq) in MeOH (50 mL) was added $Pd(dppf)Cl_2$ (479.41 mg, 655.19 μmol, 0.05 eq) and $Et_3N$ (2.65 g, 26.21 mmol, 3.65 mL, 2 eq). The suspension stirred under CO atomsphere (50 psi) at 60° C. for 16 h, then the reaction was concentrated under reduced pressure. The residue was purified by chromatography on silica gel (eluent Petroluem ether/EtOAc=5/1) to afford the title compound (2.8 g, 10.23 mmol, 78% yield) as a yellow solid. MS (ES+) $C_{13}H_{11}FN_2O_2$ requires: 246, found: 247 $[M+H]^+$

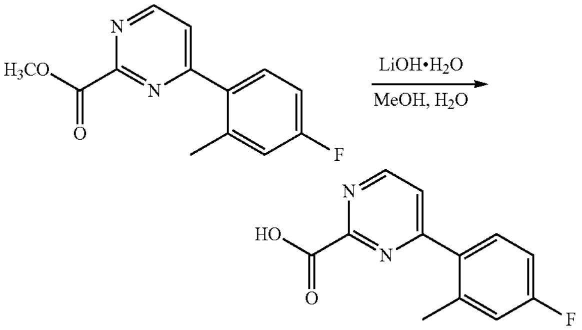

4-(4-Fluoro-2-methylphenyl)pyrimidine-2-carboxylic acid To a solution of the product from the previous step (400 mg, 1.54 mmol, 1 eq) in THF (10 mL) and $H_2O$ (5 mL) was added $LiOH{\cdot}H_2O$ (122.94 mg, 3.07 mmol, 2 eq). After stirring at 25° C. for 2 h, the mixture was concentrated under reduced pressure to remove THF. The mixture was acidified with HCl (1 M) aqueous solution to adjust pH to 2, diluted with water (5 mL), extracted with EtOAc (5 mL×3). The combined organic phase was dried over $Na_2SO_4$, filtered and concentrated under reduced pressure. The residue was triturated with EtOAc at 25° C. for 10 min, and filter cake was collected and dried under reduced pressure to afford the title compound (220 mg, 900.05 μmol, 58% yield) as a white solid.

MS (ES+) $C_{12}H_9N_2O_2F$ requires: 232, found: 233 $[M+H]^{+1}$H NMR (400 MHz, DMSO-$d_6$) δ=13.60 (br s, 1H), 8.90 (br d, J=5.0 Hz, 1H), 7.73 (d, J=5.1 Hz, 1H), 7.59 (dd, J=6.1, 8.5 Hz, 1H), 7.31-7.14 (m, 2H), 2.42 (s, 3H).

INTERMEDIATE A-42

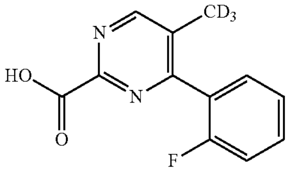

4-(2-Fluorophenyl)-5-(methyl-$d_3$)pyrimidine-2-carboxylic acid

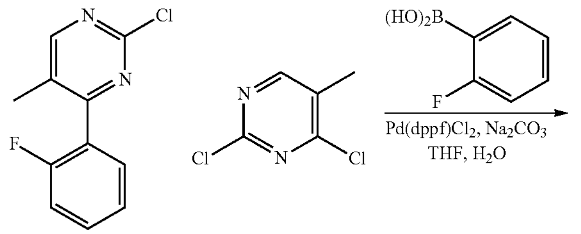

-continued

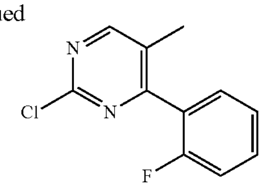

2-Chloro-4-(2-fluorophenyl)-5-methylpyrimidine To a solution of 2,4-dichloro-5-methylpyrimidine (6 g, 36.81 mmol, 1 eq) in THF (60 mL) and $H_2O$ (20 mL) were added (2-fluorophenyl)boronic acid (5.15 g, 36.81 mmol, 1 eq), $Na_2CO_3$ (7.80 g, 73.62 mmol, 2 eq) and $Pd(dppf)Cl_2$ (807.99 mg, 1.10 mmol, 0.03 eq) under $N_2$. After stirring at 70° C. for 16 h, the mixture was diluted with $H_2O$ (100 mL) and extracted with EtOAc (100 mL×2). The combined organic layer was washed with brine, dried over anhydrous $Na_2SO_4$ and filtrated. The filtrate was concentrated and purified by chromatography on silica gel (eluent Petroleum ether/EtOAc=1:1) to afford the title compound (8 g, crude) as a white solid.

MS(ES+) $C_{11}H_8N_2ClF$ requires:222 and 224, found: 223 and 225 $[M+H]^+$. $^1$H NMR (400 MHz, DMSO-$d_6$) δ=8.77 (s, 1H), 7.64-7.58 (m, 1H), 7.56-7.50 (m, 1H), 7.42-7.36 (m, 2H), 2.17 (s, 3H).

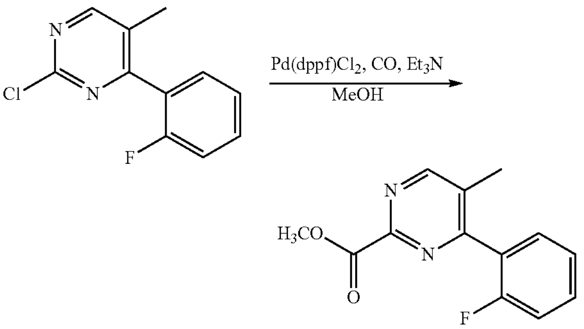

Methyl 4-(2-fluorophenyl)-5-methylpyrimidine-2-carboxylate To a solution of the product from the previous step (8 g, 35.93 mmol, 1 eq) in MeOH (80 mL) were added $Pd(dppf)Cl_2$ (1.31 g, 1.80 mmol, 0.05 eq) and $Et_3N$ (10.91 g, 107.79 mmol, 15.00 mL, 3 eq). The suspension was stirred at 70° C. under CO (45 psi) for 16 h, the mixture was concentrated to remove MeOH, then diluted with $H_2O$ (200 mL) and extracted with EtOAc (200 mL×2). The combined organic layer was washed with brine, dried over $Na_2SO_4$ and filtered. The filtrate was concentrated and purified by chromatography on silica gel (eluent Petroleum ether/EtOAc=1:1) to afford the title compound (6 g, 24.37 mmol, 67% yield) as a white solid.

MS(ES+) $C_{13}H_{11}N_2FO_2$ requires:246, found: 247 $[M+H]^+$. $^1$H NMR (400 MHz, DMSO-$d_6$) δ=8.97 (s, 1H), 7.66-7.58 (m, 1H), 7.56-7.50 (m, 1H), 7.44-7.36 (m, 2H), 3.91 (s, 3H), 2.25 (d, J=1.1 Hz, 3H).

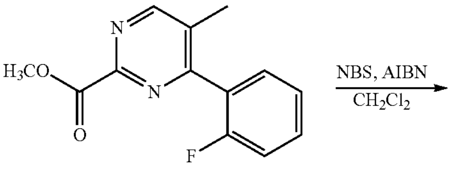

-continued

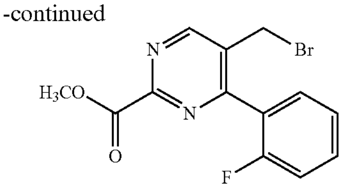

Methyl 5-(bromomethyl)-4-(2-fluorophenyl)pyrimidine-2-carboxylate To a solution of the product from the previous step (500 mg, 2.03 mmol, 1 eq) in DCE (10 mL) were added AIBN (66.69 mg, 406.11 umol, 0.2 eq) and NBS (542.11 mg, 3.05 mmol, 1.5 eq). After stirring at 80° C. for 16 h, the mixture was concentrated to remove DCE, then diluted with $H_2O$ (10 mL) and extracted with EtOAc (10 mL×2). The combined organic layer was washed with brine, dried over $Na_2SO_4$ and filtered. The filtrate was concentrated and purified by prep-TLC (eluent Petroleum ether/EtOAc=1:1) to afford the title compound (151 mg, 413.34 umol, 20% yield) as a white solid. MS(ES+) $C_{13}H_{10}N_2O_2FBr$ requires: 324 and 326, found: 325 and 327 $[M+H]^+$.

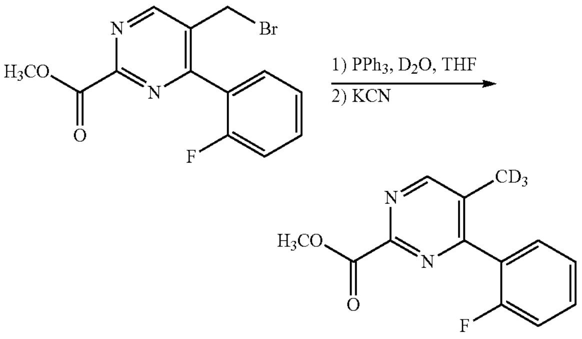

Methyl 4-(2-fluorophenyl)-5-(methyl-$d_3$)pyrimidine-2-carboxylate To a solution of the product from the previous step (80 mg, 228.83 umol, 93% purity, 1 eq) in $D_2O$ (1 mL) and THF (1 mL) was added $PPh_3$ (72.02 mg, 274.60 umol, 1.2 eq). The mixture was stirred at 15° C. for 12 h. Then to the mixture was added KCN (0.03 g, 460.72 umol, 2.01 eq) and the mixture was stirred at 50° C. for 13 h. The mixture was diluted with $H_2O$ (5 mL) and extracted with EtOAc (5 mL×2). The combined organic layer was washed with brine, dried over $Na_2SO_4$ and filtered. The filtrate was concentrated and purified by prep-TLC (eluent Petroleum ether/EtOAc=1:2) to afford the title compound (25 mg, 92.27 umol, 40% yield) as a white solid. MS(ES+) $C_{13}H_8D_3N_2O_2F$ requires:249, found: 250 $[M+H]^+$.

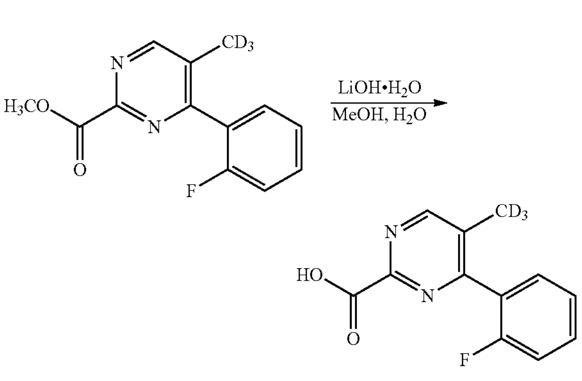

4-(2-Fluorophenyl)-5-(methyl-$d_3$)pyrimidine-2-carboxylic acid To a solution of the product from the previous step (25 mg, 100.30 umol, 1 eq) in MeOH (1.5 mL) and $H_2O$ (1.5 mL) was added $LiOH{\cdot}H_2O$ (12.63 mg, 300.90 umol, 3 eq). The mixture was stirred at 15° C. for 30 min. The pH of the mixture was adjusted to 7 with 1M HCl aqueous solution, the mixture was concentrated to afford the title compound (30 mg, crude) as a white solid. MS(ES+) $C_{12}H_6D_3N_2O_2F$ requires:235, found: 236 $[M+H]^+$.

INTERMEDIATE A-43

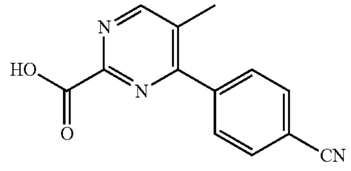

4-(4-Cyanophenyl)-5-methylpyrimidine-2-carboxylic acid

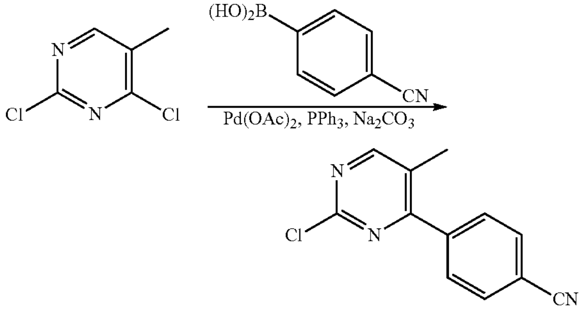

4-(2-chloro-5-methylpyrimidin-4-yl)benzonitrile To a solution of 2,4-dichloro-5-methylpyrimidine (3 g, 18.40 mmol, 1 eq), (4-cyanophenyl)boronic acid (2.70 g, 18.40 mmol, 1 eq) in THF (40 mL) and $H_2O$ (4 mL) were added $Pd(OAc)_2$ (82.64 mg, 368.09 μmol, 0.02 eq), $PPh_3$ (193.09 mg, 736.18 μmol, 0.04 eq) and $Na_2CO_3$ (1.95 g, 18.40 mmol, 1 eq) at 25° C. under $N_2$. After stirring at 60° C. for 16 h, the mixture was diluted with $H_2O$ (30 mL), extracted with EtOAc (50 mL×3), dried over $Na_2SO_4$, filtered and concentrated under reduced pressure. The residue was purified by chromatography on silica gel (eluent Petroleum ether/EtOAc=0 to 20/1) to afford the title compound (2.5 g, 10.12 mmol, 55% yield) as a white solid.

MS (ES+) $C_{12}H_8ClN_3$ requires: 229 and 231, found 230 and 232 $[M+H]^+$. $^1H$ NMR (400 MHz, $CDCl_3$) δ=8.59 (s, 1H), 7.85-7.81 (m, 2H), 7.80-7.74 (m, 2H), 2.41 (s, 3H).

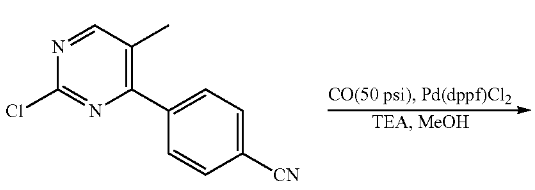

-continued

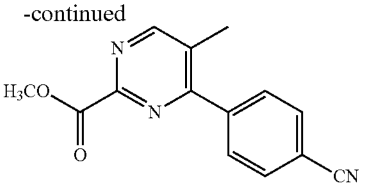

Methyl 4-(4-cyanophenyl)-5-methylpyrimidine-2-carboxylate To a solution of the product from the previous step (1.5 g, 6.53 mmol, 1 eq) in MeOH (20 mL) were added Pd(dppf) $Cl_2$ (238.95 mg, 326.56 μmol, 0.05 eq), $Et_3N$ (1.32 g, 13.06 mmol, 1.82 mL, 2 eq) under $N_2$. The suspension was degassed under vacuum and purged with CO several times. After stirring at 60° C. for 20 h under CO (50 psi), the mixture was diluted with $H_2O$ (30 mL), extracted with EtOAc (50 mL×3), dried over $Na_2SO_4$, filtered and concentrated under reduced pressure. The residue was purified by chromatography on silica gel (eluent Petroleum ether/EtOAc=5/1 to 1/1) to afford the title compound (300 mg, 1.15 mmol, 17% yield) as a red solid.

MS (ES+) $C_{14}H_{11}N_3O_2$ requires: 253, found 254 $[M+H]^+$. $^1H$ NMR (400 MHz, DMSO-$d_6$) δ=8.98 (s, 1H), 8.04 (d, J=8.4 Hz, 2H), 7.90 (d, J=8.4 Hz, 2H), 3.92 (s, 3H), 2.42 (s, 3H).

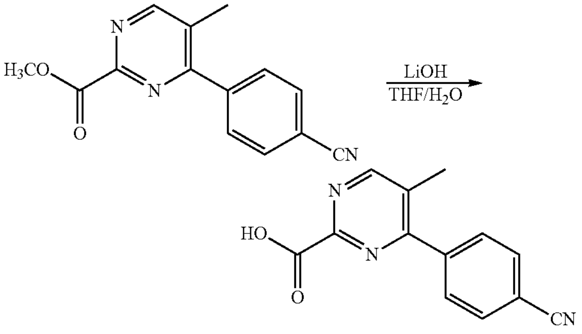

4-(4-Cyanophenyl)-5-methylpyrimidine-2-carboxylic acid To a solution of the product from the previous step (100 mg, 394.86 μmol, 1 eq) in THF (1 mL) and $H_2O$ (0.1 mL) was added LiOH (9.46 mg, 394.86 μmol, 1 eq). After stirring at 25° C. for 3 h, the reaction mixture was concentrated under reduced pressure. The residue was diluted with water (20 mL), basified with NaOH (1 M) aqueous solution to adjust pH to 10 and extracted with EtOAc (20 mL×3). Then the aqueous phase was acidified with HCl (1 M) aqueous solution to adjust pH to 2, extracted with EtOAc (20 mL×3), dried over $Na_2SO_4$, filtered and concentrated under reduced pressure to afford the title compound (90 mg, 376.21 μmol, 95% yield) as a white solid.

MS (ES+) $C_{13}H_9N_3O_2$ requires: 239, found 240 $[M+H]^+$. $^1H$ NMR (400 MHz, DMSO-$d_6$) δ=8.75 (br s, 1H), 8.02 (d, J=8.3 Hz, 2H), 7.87 (d, J=8.4 Hz, 2H), 2.34 (s, 3H).

INTERMEDIATE A-44

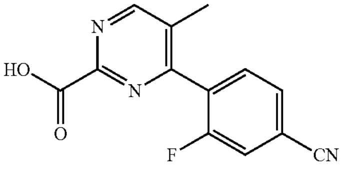

4-(4-cyano-2-fluorophenyl)-5-methylpyrimidine-2-carboxylic acid

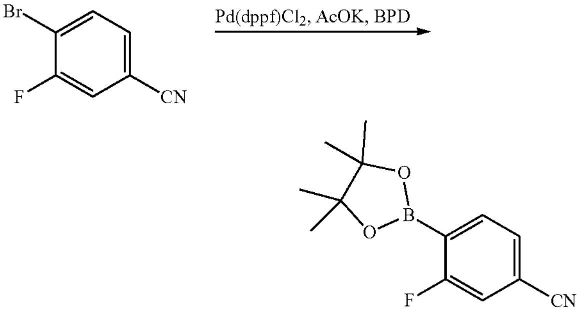 [SMILES: N#Cc1ccc(Br)c(F)c1 ; "Pd(dppf)Cl2, AcOK, BPD" ; CC1(C)OB(c2ccc(C#N)cc2F)OC1(C)C]

3-Fluoro-4-(4,4,5,5-tetramethyl-1,3,2-dioxaborolan-2-yl)benzonitrile To a solution of 4-bromo-3-fluorobenzonitrile (5 g, 25.00 mmol, 1 eq) in dioxane (50 mL) were added Pd(dppf)$Cl_2$ (914.60 mg, 1.25 mmol, 0.05 eq), AcOK (4.91 g, 50.00 mmol, 2 eq) and BPD (7.62 g, 30.00 mmol, 1.2 eq) under $N_2$. After stirring at 110° C. for 16 h, the mixture was concentrated under reduced pressure to afford the title compound (12 g, crude) as a crude black solid.

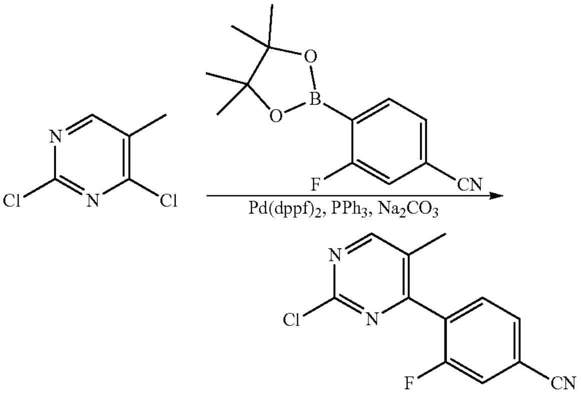

4-(2-Chloro-5-methylpyrimidin-4-yl)-3-fluorobenzonitrile To a solution of 2,4-dichloro-5-methylpyrimidine (3 g, 18.40 mmol, 1 eq) and the product from the previous step (5.46 g, 22.09 mmol, 1.2 eq) in THF (32 mL) and $H_2O$ (8 mL) were added $Pd(OAc)_2$ (82.64 mg, 368.09 μmol, 0.02 eq), $PPh_3$ (193.09 mg, 736.18 μmol, 0.04 eq) and $Na_2CO_3$ (3.90 g, 36.81 mmol, 2 eq) under $N_2$. After stirring at 60° C. for 16 h, the mixture was diluted with water (50 mL), extracted with EtOAc (50 mL×3), dried over anhydrous $Na_2SO_4$, filtered and concentrated under reduced pressure. The mixture was purified by chromatography on silica gel (eluent Petroleum ether/EtOAc=0:1) and triturated with petroleum ether and EtOAc (60 mL, Petroleum ether/EtOAc=5:1). The mixture was filtered and filter cake was collected to afford the title compound (2.7 g, 10.90 mmol, 59% yield) as a white solid. MS (ES+) $C_{12}H_7ClFN_3$ requires: 247 and 249, found 248 and 250 $[M+H]^+$. $^1H$ NMR (400 MHz, DMSO-$d_6$) δ=8.85 (s, 1H), 8.12 (dd, J=1.2, 10.0 Hz, 1H), 7.95-7.88 (m, 1H), 7.84-7.75 (m, 1H), 2.18 (d, J=0.9 Hz, 3H).

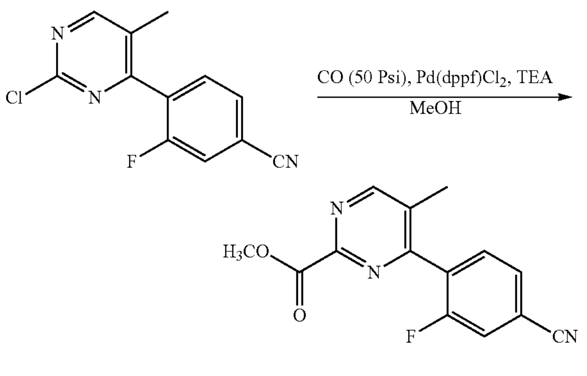

Methyl 4-(4-cyano-2-fluorophenyl)-5-methylpyrimidine-2-carboxylate To a solution of the product from the previous step (2.7 g, 10.90 mmol, 1 eq) in MeOH (30 mL) were added Pd(dppf)$Cl_2$ (398.86 mg, 545.11 μmol, 0.05 eq) and $Et_3N$ (2.21 g, 21.80 mmol, 3.03 mL, 2 eq) under $N_2$. After degassing and purging with CO for 5 min, the mixture was stirred under CO (50 psi) atmosphere at 70° C. for 16 h. Then the mixture was concentrated under reduced pressure to remove MeOH, then diluted with $H_2O$ (50 mL) and extracted with EtOAc (50 mL×2). The combined organic layer was washed with brine (50 mL), dried over anhydrous $Na_2SO_4$ and filtered and concentrated under reduced pressure. The residue was purified by chromatography on silica gel (eluent Petroleum ether/EtOAc=1:1) to afford the title compound (650 mg, 1.75 mmol, 16% yield) as a yellow solid.

MS (ES+) $C_{14}H_{10}N_3O_2F$ requires: 271, found 272 $[M+H]^+$. $^1H$ NMR (400 MHz, DMSO-$d_6$) δ=9.03 (s, 1H), 8.12 (dd, J=1.2, 9.9 Hz, 1H), 7.92 (dd, J=1.3, 7.9 Hz, 1H), 7.78 (t, J=7.6 Hz, 1H), 3.91 (s, 3H), 2.26 (s, 3H).

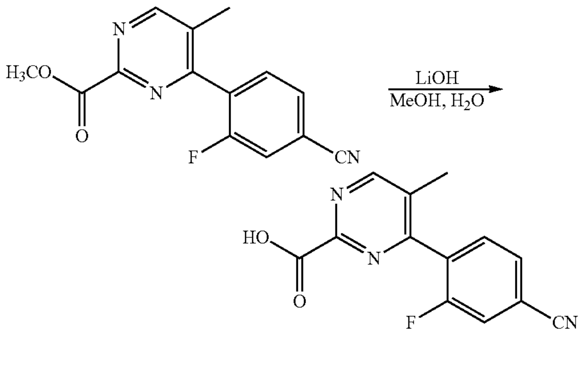

4-(4-cyano-2-fluorophenyl)-5-methylpyrimidine-2-carboxylic acid To a solution of the product from the previous step (600 mg, 1.61 mmol, 1 eq) in $H_2O$ (6 mL) and MeOH (6 mL) was added LiOH·$H_2O$ (203.28 mg, 4.84 mmol, 3 eq). After stirring at 15° C. for 1 h, the mixture was diluted with $H_2O$ (20 mL) and the pH of aqueous layer was adjusted to 6 with 1M HCl aqueous solution. The mixture was extracted with EtOAc (20 mL×2). The combined organic layer was washed with brine (20 mE), dried over anhydrous $Na_2SO_4$ and filtered. The filtrate was concentrated under reduced pressure to afford the title compound (200 mg, crude) as an orange solid. MS (ES+) $C_{13}H_8FN_3O_2$ requires: 257, found 258 $[M+H]^+$.

INTERMEDIATE A-45

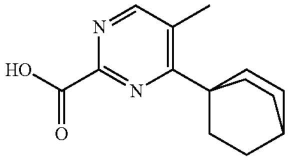

4-(Bicyclo[2.2.2]octan-1-yl)-5-methylpyrimidine-2-carboxylic acid

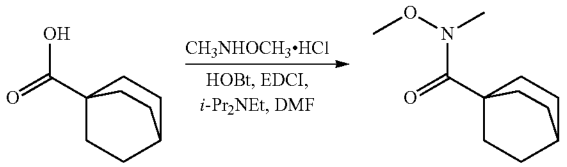

N-methoxy-N-methylbicyclo[2.2.2]octane-1-carboxamide To a solution of bicyclo[2.2.2]octane-4-carboxylic acid (4.5 g, 29.18 mmol, 1 eq) in DMF (50 mL) were added N-methoxymethanamine hydrochloride (3.42 g, 35.02 mmol, 1.2 eq), HOBt (4.73 g, 35.02 mmol, 1.2 eq), EDCI (6.71 g, 35.02 mmol, 1.2 eq) and i-$Pr_2NEt$ (11.31 g, 87.55 mmol, 15.25 mL, 3 eq). After stirring at 15° C. for 2 h, the mixture was diluted with $H_2O$ (200 mL) and extracted with EtOAc (200 mL×2), washed with brine (100 mL×3). The combined organic phase was dried over $Na_2SO_4$, filtered and concentrated under reduced pressure to afford the title compound (6.12 g, crude) as a colorless oil.

MS (ES+) $C_{11}H_{19}NO_2$ requires: 197, found: 198 $[M+H]^+$. $^1H$ NMR (400 MHz, $CDCl_3$) δ=3.58 (s, 3H), 3.07 (s, 3H), 1.84-1.69 (m, 6H), 1.58-1.46 (m, 7H).

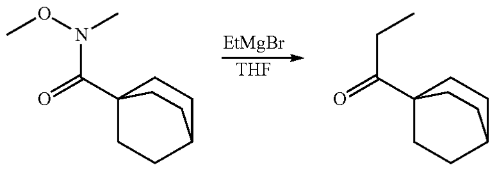

1-(Bicyclo[2.2.2]octan-1-yl)propan-1-one To a solution of the product from the previous step (6.12 g, 31.02 mmol, 1 eq) in THF (60 mL) was added EtMgBr (3 M, 11.38 mL, 1.1 eq) at 0° C. under $N_2$. After stirring at 25° C. for 4 h, the mixture was poured into 1 M HCl (100 mL) and extracted with EtOAc (100 mL×2). The combined organic layer was dried over $Na_2SO_4$, filtered and concentrated under reduced pressure, and the residue was purified by chromatography on silica gel (eluent Petroleum ether/EtOAc=20/1) to afford the title compound (2.8 g, 15.16 mmol, 48% yield) as a yellow oil. $^1H$ NMR (400 MHz, $CD_3OD$) δ=2.49 (q, J=7.3 Hz, 2H), 1.73-1.58 (m, 13H), 0.95 (t, J=7.2 Hz, 3H).

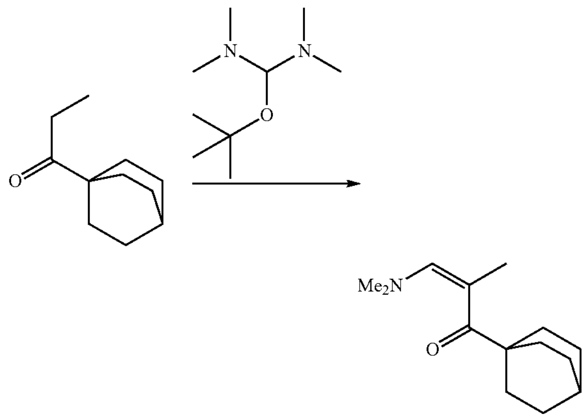

(E)-1-(bicyclo[2.2.2]octan-1-yl)-3-(dimethylamino)-2-methylprop-2-en-1-one

To 1-tert-butoxy-N,N,N',N'-tetramethyl-methanediamine (4.22 g, 24.21 mmol, 5 mL, 2.24 eq) was added the product from the previous step (1.8 g, 10.83 mmol, 1 eq). After stirring at 120° C. for 16 h, the residue was diluted with $H_2O$ (20 mL) and extracted with EtOAc (20 mL×2). The combined organic phase was dried over $Na_2SO_4$, filtered and concentrated to afford the title compound (2.3 g, crude) as a yellow solid. $^1H$ NMR (400 MHz, $CD_3OD$) δ=7.41 (s, 1H), 2.98 (s, 6H), 1.80 (s, 3H), 1.76-1.69 (m, 6H), 1.57-1.49 (m, 7H).

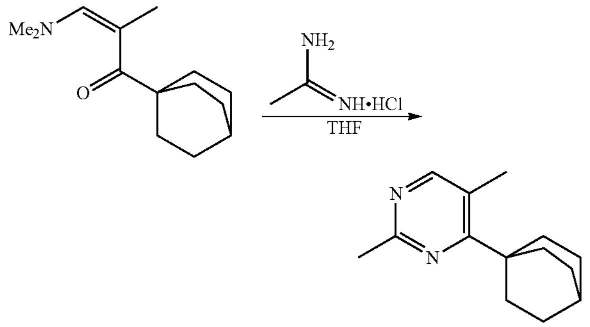

4-(bicyclo[2.2.2]octan-1-yl)-2,5-dimethylpyrimidine To a solution of acetamidine (905.33 mg, 15.59 mmol, 1.5 eq) in THF (30 mL) was added t-BuOK (1.75 g, 15.59 mmol, 1.5 eq) under $N_2$. After stirring at 60° C. for 15 min, to the mixture was added the product from the previous step (2.3 g, 10.39 mmol, 1 eq) and the mixture was stirred at 60° C. for 16 h. The mixture was diluted with $H_2O$ (60 mL) and extracted with EtOAc (60 mL×2). The combined organic layer was dried over $Na_2SO_4$, filtered and concentrated under reduced pressure, and the residue was purified by chromatography on silica gel (eluent Petroleum ether/EtOAc=2/1) to afford the title compound (0.8 g, 2.92 mmol, 28% yield) as a yellow solid.

MS (ES+) $C_{14}H_{20}N_2$ requires: 216, found: 217 $[M+H]^+$. $^1H$ NMR (400 MHz, $CD_3OD$) δ=8.23 (s, 1H), 2.58 (s, 3H), 2.46 (s, 3H), 2.07-1.94 (m, 6H), 1.78-1.67 (m, 7H).

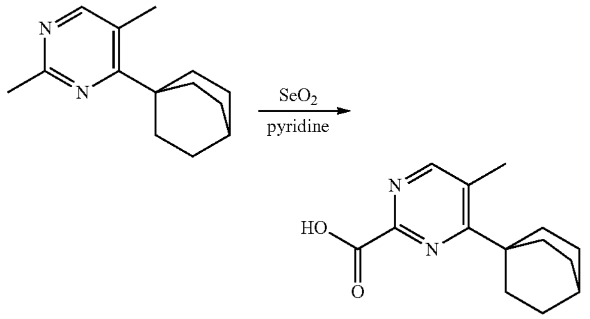

4-(Bicyclo[2.2.2]octan-1-yl)-5-methylpyrimidine-2-carboxylic acid To a solution of the product from the previous step (800 mg, 2.92 mmol, 79% purity, 1 eq) in pyridine (10 mL) was added $SeO_2$ (1.13 g, 10.23 mmol, 3.5 eq). After stirring at 120° C. for 48 h, the mixture was filtered and the filtrate was concentrated. And the residue was purified by prep-HPLC (column: Phenomenex luna C18 150*25 mm*10 um; mobile phase: [water (0.05% HCl)—$CH_3CN$]; B %: 33%-63%, 10 min). The eluent was concentrated under reduced pressure and freeze-dried to afford the title compound (500.7 mg, 1.99 mmol, 68% yield) as a white solid.

MS (ES+) $C_{14}H_{18}N_2O_2$ requires: 246, found: 247 $[M+H]^+$. $^1H$ NMR (400 MHz, $CD_3OD$) δ: 8.54 (s, 1H), 2.58 (s, 3H), 2.14-1.99 (m, 6H), 1.79-1.68 (m, 7H).

INTERMEDIATE A-46

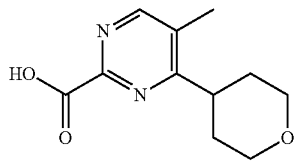

5-Methyl-4-(tetrahydro-2H-pyran-4-yl)pyrimidine-2-carboxylic acid

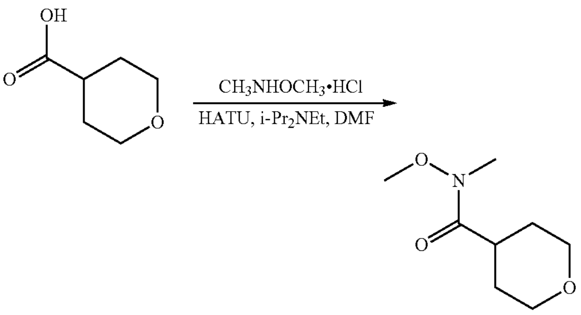

N-methoxy-N-methyltetrahydro-2H-pyran-4-carboxamide To a solution of tetrahydro-2H-pyran-4-carboxylic acid (15 g, 115.26 mmol, 1 eq) and N-methoxymethanamine (13.49 g, 138.31 mmol, 1.20 eq, HCl) in DMF (150 mL) were added HATU (65.74 g, 172.89 mmol, 1.5 eq) and i-$Pr_2$NEt (44.69 g, 345.78 mmol, 60.23 mL, 3 eq) at 25° C. After stirring at 25° C. for 16 h, the mixture was poured into ice-water (200 mL) and extracted with EtOAc (200 mL×3). The combined organic phase was washed with brine (200 mL×3), dried over $Na_2SO_4$, filtered and concentrated under reduced pressure. The residue was purified by silica gel chromatography (ISCO®; 120 g SepaFlash® Silica Flash Column, Eluent 20-50% EtOAC/Petroleum ether gradient @100 mL/min) to afford the title compound (14 g, 80.83 mmol, 70% yield) as light yellow oil.

MS (ES+) $C_8H_{15}NO_3$ requires: 173, found: 174 $[M+H]^+$. $^1H$ NMR (400 MHz, DMSO-$d_6$) δ=3.90-3.80 (m, 2H), 3.68 (s, 3H), 3.42-3.32 (m, 2H), 3.09 (s, 3H), 2.98-2.85 (m, 1H), 1.63-1.52 (m, 4H).

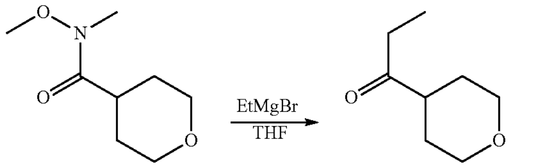

1-(tetrahydro-2H-pyran-4-yl)propan-1-one To a solution of the product from the previous step (13 g, 75.05 mmol, 1 eq) in THF (150 mL) was added EtMgBr (3 M, 27.52 mL, 1.1 eq) at 0° C. under $N_2$. After stirring at 25° C. for 4 h, the mixture was quenched with saturated $NH_4Cl$ aqueous solution (100 mL) and extracted with EtOAc (200 mL×3). The combined organic phase was washed with brine (200 mL×2), dried over $Na_2SO_4$, filtered and concentrated under reduced pressure. The residue was purified by silica gel chromatography (ISCO®; 80 g SepaFlash® Silica Flash Column, Eluent 0~15% EtOAC/Petroleum ether gradient @50 mL/min) to afford the title compound (9.2 g, 64.70 mmol, 86% yield) as a colorless liquid.

MS (ES+) $C_8H_{14}O_2$ requires: 142, found: 143 $[M+H]^+$. $^1H$ NMR (400 MHz, $CDCl_3$) δ=4.03-3.96 (m, 2H), 3.46-3.38 (m, 2H), 2.60-2.43 (m, 3H), 1.80-1.65 (m, 4H), 1.05 (t, J=7.2 Hz, 3H).

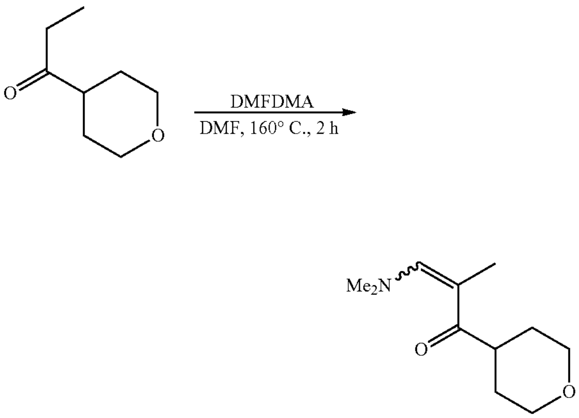

3-(dimethylamino)-2-methyl-1-(tetrahydro-2H-pyran-4-yl)prop-2-en-1-one To a solution of the product from the previous step (2.4 g, 16.88 mmol, 1 eq) in DMF (10 mL) was added DMFDMA (8.04 g, 67.51 mmol, 8.97 mL, 4 eq). After stirring at 160° C. for 2 h, the mixture was poured into water (50 mL), extracted with $CH_2Cl_2$ (50 mL×3), dried over $Na_2SO_4$, filtered and concentrated under reduced pressure to obtain the title compound (3.33 g, 16.88 mmol, 100% yield) as light yellow oil.

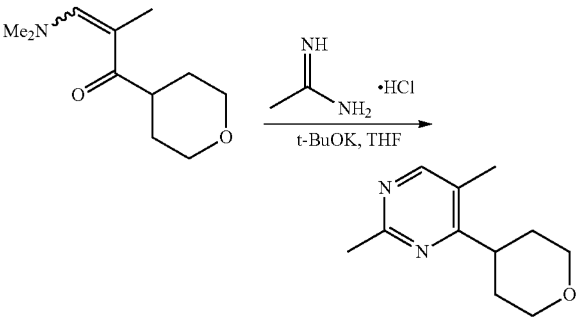

2,5-Dimethyl-4-(tetrahydro-2H-pyran-4-yl)pyrimidine To a solution of acetamidine hydrochloride (2.37 g, 25.09 mmol, 1.5 eq) in THF (20 mL) was added t-BuOK (2.82 g, 25.09 mmol, 1.5 eq) under $N_2$. After stirring at 60° C. for 1 h, to the mixture was added a solution of the product from the previous step (3.3 g, 16.73 mmol, 1 eq) in THF (10 mL). After stirring at 60° C. for 16 h, the mixture was dried over $Na_2SO_4$, filtered, the organic phase was concentrated under reduced pressure. The residue was purified by silica gel chromatography (ISCO®; 20 g SepaFlash® Silica Flash Column, Eluent 0~50% EtOAC/Petroleum ether gradient @30 mL/min) to afford the title compound (320 mg, 1.66 mmol, 9% yield) as a brown solid.

$^1H$ NMR (400 MHz, $CDCl_3$) δ=8.24 (s, 1H), 4.16-4.07 (m, 2H), 3.52-3.43 (m, 2H), 3.01-2.91 (m, 1H), 2.59 (s, 3H), 2.19 (s, 3H), 2.10-1.93 (m, 2H), 1.56-1.50 (m, 2H).

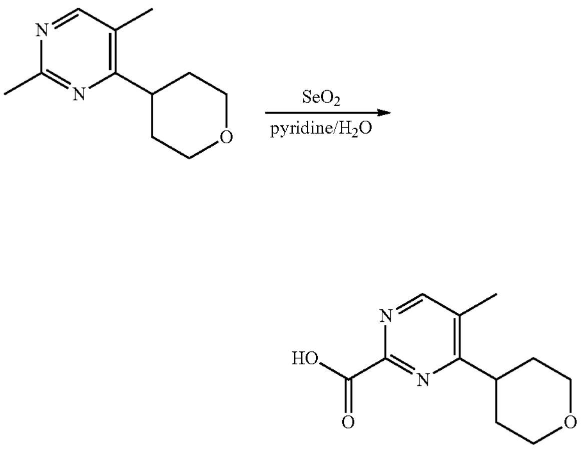

5-Methyl-4-(tetrahydro-2H-pyran-4-yl)pyrimidine-2-carboxylic acid To a solution of the product from the previous step (320 mg, 1.66 mmol, 1 eq) in pyridine (6 mL) and $H_2O$ (0.06 mL) was added $SeO_2$ (646.40 mg, 5.83 mmol, 3.5 eq). After stirring at 120° C. for 16 h, the mixture was filtered and concentrated under reduced pressure. The residue was purified by prep-HPLC (column: Zhongpu RD-C18 150*25 mm*3 um; mobile phase: [water (0.225% FA) —$CH_3CN$]; B %: 3%-33%, 10 min). The eluent was concentrated and freeze-dried to afford the title compound (70 mg, 314.97 μmol, 18% yield) as a white solid. $^1H$ NMR (400 MHz, $CDCl_3$) δ=8.62 (br s, 1H), 4.07 4.14-3.99 (m, 2H), 3.58-3.42 (m, 2H), 3.22-3.06 (m, 1H), 2.39 (s, 3H), 2.15-1.98 (m, 2H), 1.69-1.49 (m, 2H).

INTERMEDIATE A-47

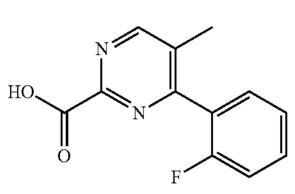

4-(2-Fluorophenyl)-5-methylpyrimidine-2-carboxylic acid

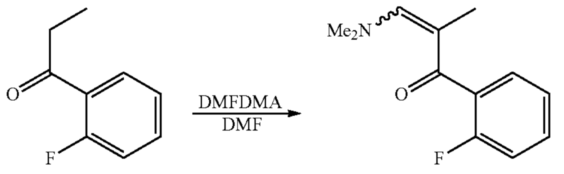

3-(Dimethylamino)-1-(2-fluorophenyl)-2-methylprop-2-en-1-one To a solution of 1-(2-fluorophenyl)propan-1-one (6 g, 39.43 mmol, 1 eq) in DMF (30 mL) was added DMFDMA (18.79 g, 157.72 mmol, 20.95 mL, 4 eq). The mixture was stirred at 160° C. for 2 hours. To the mixture was added water (100 mL) and extracted with EtOAc (100 mL×3), the organic phase was washed with brine (100 mL×3), dried over $Na_2SO_4$, filtered and concentrated under reduced pressure. The residue was purified by silica gel chromatography (ISCO®; 20 g SepaFlash® Silica Flash Column, Eluent 0~100% EtOAC/Petroleum ether gradient @100 mL/min), the eluent was concentrated to afford the title compound (7.47 g, 36.04 mmol, 91% yield) as a brown solid.

MS(ES+) $C_{12}H_{14}OFN$ requires: 207, found: 208 $[M+H]^+$, $^1H$ NMR (400 MHz, DMSO-$d_6$) δ=7.44-7.38 (m, 1H), 7.27-7.18 (m, 3H), 6.74 (s, 1H), 3.02 (s, 6H), 2.02 (s, 3H).

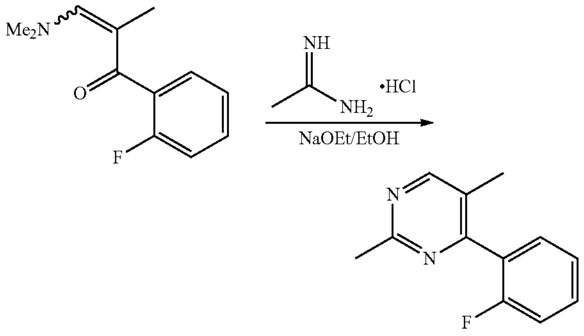

4-(2-Fluorophenyl)-2,5-dimethylpyrimidine To EtOH (10 mL) was added Na (1.33 g, 57.90 mmol, 3 eq). The mixture was stirred at 20° C. under $N_2$ for 20 min. Then to the mixture was added a solution of acetamidine hydrochloride (2.74 g, 28.95 mmol, 1.5 eq) in EtOH (10 mL). The mixture was stirred at 0° C. under $N_2$ for 20 min. Then to the mixture was added a solution of the product from the previous step (4 g, 19.30 mmol, 1 eq) in EtOH (10 mL). The mixture was stirred at 70° C. for 5 h. To the mixture was added water (80 mL) and extracted with EtOAc (50 mL×3), the organic phase was washed with brine (50 mL×2), dried over $Na_2SO_4$, filtered and concentrated under reduced pressure.

The residue was purified by silica gel chromatography (ISCO®; 25 g SepaFlash® Silica Flash Column, Eluent 0~100% EtOAC/Petroleum ether gradient @50 mL/min), the eluent was concentrated to afford the title compound (3.16 g, 15.63 mmol, 80% yield) was as a yellow oil.

MS(ES+) $C_{12}H_{11}N_2F$ requires: 202, found: 203 $[M+H]^+$. $^1H$ NMR (400 MHz, DMSO-$d_6$) δ=8.66 (s, 1H), 7.59-7.53 (m, 1H), 7.49-7.45 (m, 1H), 7.38-7.33 (m, 2H), 2.62 (s, 3H), 2.11 (s, 3H).

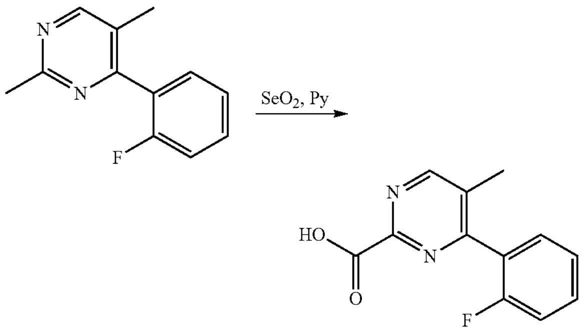

4-(2-Fluorophenyl)-5-methylpyrimidine-2-carboxylic acid To a solution of the product from the previous step (1.5 g, 7.42 mmol, 1 eq) in Pyridine (15 mL) was added $SeO_2$ (4.94 g, 44.50 mmol, 6 eq). The mixture was stirred at 120° C. for 16 h. To the mixture was added water (20 mL) and extracted with EtOAc (20 mL×3), the organic phase was washed with brine (20 mL), dried over $Na_2SO_4$, filtered and concentrated under reduced pressure. The residue was purified by prep-HPLC (column: Phenomenex luna C18 (250*70 mm, 15 um); mobile phase: [water (0.1% TFA)-$CH_3CN$]; B %: 20 $CH_3CN$ %-50 $CH_3CN$ %, 30 min), the eluent was concentrated and then freeze dried to afford the title compound (360.7 mg, 1.55 mmol, 20% yield) as a yellow solid.

MS(ES+) $C_{12}H_9N_2FO_2$ requires:232, found: 233 $[M+H]^+$. $^1H$ NMR (400 MHz, DMSO-$d_6$) δ=13.55 (s, 1H), 8.94 (s, 1H), 7.65-7.60 (m, 1H), 7.57-7.53 (s, 1H), 7.44-7.39 (m, 2H), 2.25 (s, 3H).

INTERMEDIATE A-48

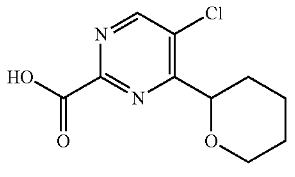

5-Chloro-4-(tetrahydro-2H-pyran-2-yl)pyrimidine-2-carboxylic acid

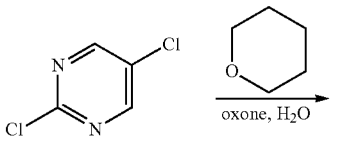

-continued

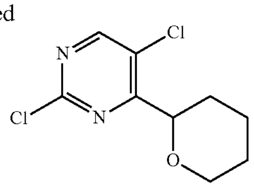

2,5-Dichloro-4-(tetrahydro-2H-pyran-2-yl)pyrimidine To a solution of 2,5-dichloropyrimidine (2.5 g, 16.78 mmol, 1 eq) in $CH_3CN$ (40 mL) and $H_2O$ (20 mL) were added tetrahydropyran (28.91 g, 335.62 mmol, 20 eq) and OXONE® (13.61 g, 50.34 mmol, 10.08 mL, 3 eq). After stirring at 120° C. for 6 h under $N_2$, the mixture was poured into water (30 mL), extracted with EtOAc (50 mL×3), dried over $Na_2SO_4$, filtered and concentrated under reduced pressure. The residue was purified by silica gel chromatography (ISCO®; 12 g SepaFlash® Silica Flash Column, Eluent 0~10% EtOAC/Petroleum ether gradient @50 mL/min) to afford the title compound (1.0 g, 4.29 mmol, 25% yield) as colourless oil.

MS ($ES^+$) $C_9H_{10}N_2Cl_2O$ requires: 232 and 234, found: 233 and 235 $[M+H]^+$. $^1H$ NMR (400 MHz, $CDCl_3$) δ=8.53 (s, 1H), 4.77 (dd, J=2.4, 10.4 Hz, 1H), 4.26-4.18 (m, 1H), 4.16-4.08 (m, 1H), 4.07-3.98 (m, 1H), 3.70-3.59 (m, 2H), 3.59-3.41 (m, 1H), 2.08-1.91 (m, 2H).

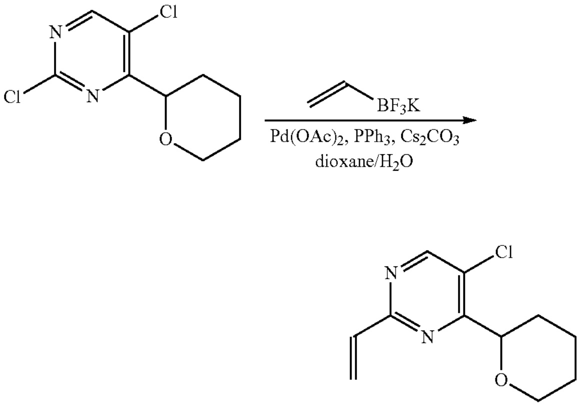

5-Chloro-4-(tetrahydro-2H-pyran-2-yl)-2-vinylpyrimidine To a solution of the product from the previous step (900 mg, 3.86 mmol, 1 eq) in dioxane (4 mL) and $H_2O$ (0.4 mL) were added $Cs_2CO_3$ (2.52 g, 7.72 mmol, 2 eq), potassium (vinyl)trifluoroborate (620.46 mg, 4.63 mmol, 1.2 eq), $Pd(OAc)_2$ (130.03 mg, 579.00 μmol, 0.15 eq) and $PPh_3$ (303.81 mg, 1.16 mmol, 0.3 eq). After stirring at 105° C. for 16 h, the mixture was concentrated under reduced pressure. The residue was purified by silica gel chromatography (ISCO®; 12 g SepaFlash® Silica Flash Column, Eluent 0~10% EtOAC/Petroleum ether gradient @30 mL/min) to afford the title compound (300 mg, 1.34 mmol, 34% yield) as a colourless oil.

MS ($ES^+$) $C_{11}H_{13}N_2ClO$ requires: 224 and 226, found: 225 and 227 $[M+H]^{+1}$H NMR (400 MHz, $CDCl_3$) δ=8.52 (s, 1H), 6.86 (dd, J=10.6, 17.3 Hz, 1H), 6.55 (dd, J=1.7, 17.3 Hz, 1H), 5.67 (dd, J=1.7, 10.6 Hz, 1H), 4.78-4.67 (m, 1H), 4.20-4.11 (m, 1H), 3.64-3.54 (m, 1H), 1.99-1.90 (m, 1H), 1.87-1.49 (m, 5H).

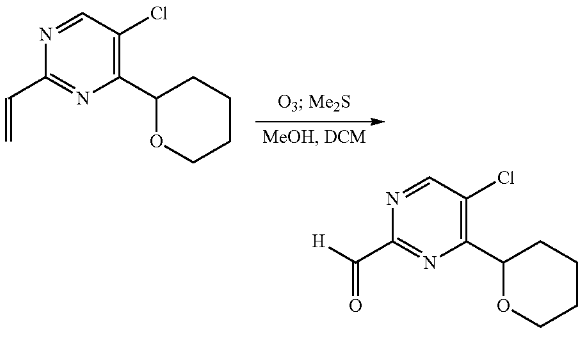

5-Chloro-4-(tetrahydro-2H-pyran-2-yl)pyrimidine-2-carbaldehyde A stream of $O_3$ was bubbled into a solution of the product from the previous step (280 mg, 1.25 mmol, 1 eq) in $CH_2Cl_2$ (4 mL) and MeOH (4 mL) at −78° C. for 10 minutes. After excess 03 was purged by $N_2$, $Me_2S$ (774.30 mg, 12.46 mmol, 915.25 μL, 10 eq) was added at 25° C. After stirring at 25° C. for 2 h, the mixture was diluted with $H_2O$ (10 mL), extracted with EtOAc (10 mL×3), washed with brine (10 mL×3). The combined organic phase was dried over by $Na_2SO_4$, filtered and concentrated under reduced pressure. The residue was purified by chromatography on silica gel (eluent Petroleum ether/EtOAc=2/1) to afford the title compound (200 mg, 882.38 μmol, 70% yield) as colourless oil.

MS ($ES^+$) $C_{10}H_{11}ClN_2O_2$ requires: 226 and 227, found: 227 and 228 $[M+H]^+$. $^1H$ NMR (400 MHz, $CDCl_3$) δ=10.18 (s, 1H), 8.90 (s, 1H), 4.99-4.87 (m, 1H), 4.31-4.25 (m, 1H), 3.78-3.65 (m, 1H), 1.96-1.68 (m, 6H).

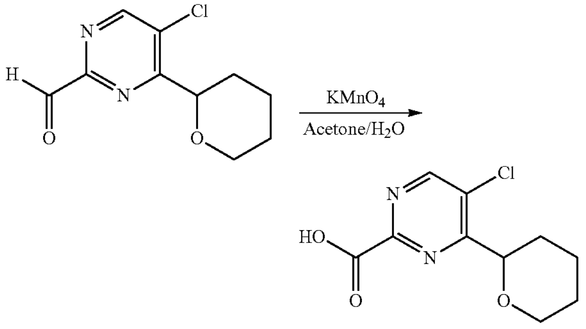

5-Chloro-4-(tetrahydro-2H-pyran-2-yl)pyrimidine-2-carboxylic acid To a solution of the product from the previous step (180 mg, 794.14 μmol, 1 eq) in acetone (4 mL) and $H_2O$ (1 mL) was added $KMnO_4$ (125.50 mg, 794.14 μmol, 1 eq). After stirring at 25° C. for 1 h, the mixture was extracted with EtOAc (10 mL) and water (10 mL), dried over $Na_2SO_4$, filtered and concentrated under reduced pressure. The residue was purified by prep-HPLC (column: Shim-pack C18 150*25*10 um; mobile phase: [water (0.225% FA) —$CH_3CN$]; B %: 15%-35%, 11 min), and the eluent was concentrated and freeze-dried to obtain the title compound (20 mg, 81.60 μmol, 10.27% yield, 99% purity) as a white solid.

MS (ES+) $C_{10}H_{11}N_2ClO_3$ requires: 242 and 244, found: 243 and 245 $[M+H]^+$. $^1H$ NMR (400 MHz, $CDCl_3$) δ=8.81 (s, 1H), 4.83 (dd, J=2.3, 10.4 Hz, 1H), 4.21-4.09 (m, 1H), 3.67-3.56 (m, 1H), 2.04-1.93 (m, 1H), 1.92-1.82 (m, 1H), 1.80-1.56 (m, 4H).

INTERMEDIATE A-49

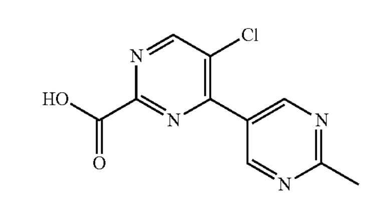

5-Chloro-2'-methyl-[4,5'-bipyrimidine]-2-carboxylic acid

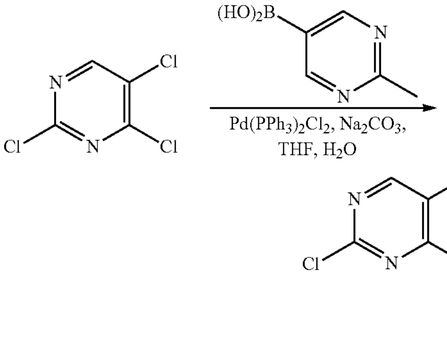

2,5-Dichloro-2'-methyl-4,5'-bipyrimidine To a solution of 2,4,5-trichloropyrimidine (2 g, 10.90 mmol, 1.25 mL, 1 eq) in THF (21 mL) and $H_2O$ (7 mL) were added (2-methylpyrimidin-5-yl) boronic acid (1.50 g, 10.90 mmol, 1 eq), $Pd(PPh_3)_2Cl_2$ (382.67 mg, 545.19 μmol, 0.05 eq) and $Na_2CO_3$ (3.47 g, 32.71 mmol, 3 eq) under $N_2$. After stirring at 70° C. for 16 h, the mixture was diluted with $H_2O$ (50 mL) and extracted with EtOAc (50 mL×2), dried over $Na_2SO_4$, filtered and concentrated under reduced pressure. The residue was purified by chromatography on silica gel (eluent Petroleum ether/EtOAc=2/1) to afford the title compound (2 g, 5.89 mmol, 54% yield) as a white solid.

MS (ES+) $C_9H_6Cl_2N_4$ requires: 240 and 242, found: 241 and 243 $[M+H]^+$. $^1H$ NMR (400 MHz, DMSO-$d_6$) δ=9.14 (s, 2H), 9.08 (s, 1H), 2.74 (s, 3H).

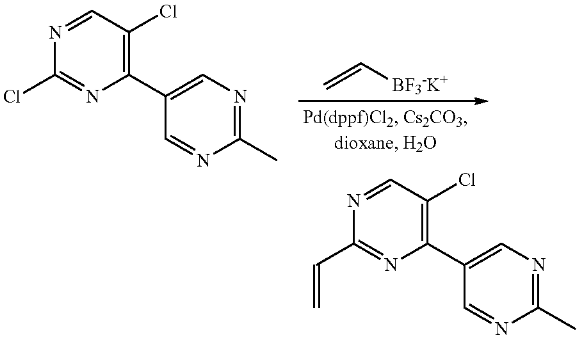

5-Chloro-2'-methyl-2-vinyl-4,5'-bipyrimidine To a solution of the product from the previous step (1.9 g, 5.60 mmol, 1 eq) and potassium (vinyl)trifluoroborate (899.46 mg, 6.71 mmol, 1.2 eq) in dioxane (40 mL) and $H_2O$ (10 mL) were added Pd(dppf) $Cl_2$ (204.72 mg, 279.79 μmol, 0.05 eq) and $Cs_2CO_3$ (5.47 g, 16.79 mmol, 3 eq) under $N_2$. After stirring at 80° C. for 16 h, the mixture was diluted with $H_2O$ (100 mL), extracted with EtOAc (100 mL×2), dried over $Na_2SO_4$, filtered and concentrated under reduced pressure. The residue was purified by chromatography on silica gel (eluent Petroleum ether/EtOAc=2/1) to afford the title compound (1.1 g, 4.02 mmol, 71% yield) as a white solid.

MS (ES+) $C_{11}H_9N_4C_1$ requires: 232 and 234, found: 233 and 235 $[M+H]^+$. $^1H$ NMR (400 MHz, DMSO-$d_6$) δ=9.16 (s, 2H), 9.03 (s, 1H), 7.01-6.78 (m, 1H), 6.62 (d, J=17.2 Hz, 1H), 5.87 (d, J=10.4 Hz, 1H), 2.73 (s, 3H).

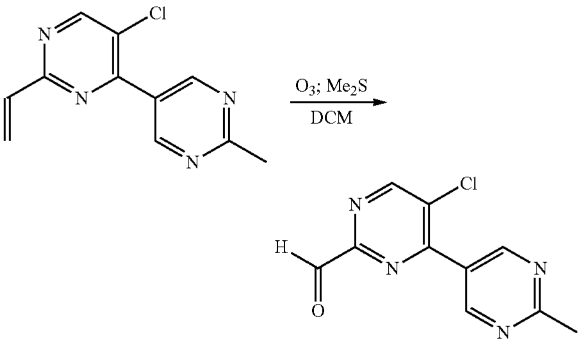

5-Chloro-2'-methyl-[4,5'-bipyrimidine]-2-carbaldehyde A stream of 03 was passed through a solution of the product from the previous step (1.1 g, 4.02 mmol, 1 eq) in $CH_2Cl_2$ (3 mL) and MeOH (1 mL) at −78° C. After stirred at 25° C. for 10 min, $Me_2S$ (3.45 g, 55.53 mmol, 4.08 mL, 13.82 eq) was added. The mixture was poured into water (20 mL), extracted with EtOAc (20 mL×3), washed with brine (20 mL×3), dried over $Na_2SO_4$, filtered and concentrated under reduced pressure. The residue was purified by chromatography on silica gel (eluent Petroleum ether/EtOAc=1/1) to afford the title compound (870 mg, 3.45 mmol, 85% yield) as a white solid. MS (ES+) $C_{10}H_7N_4ClO$ requires:234 and 236, found: 235 and 237 $[M+H]^+$.

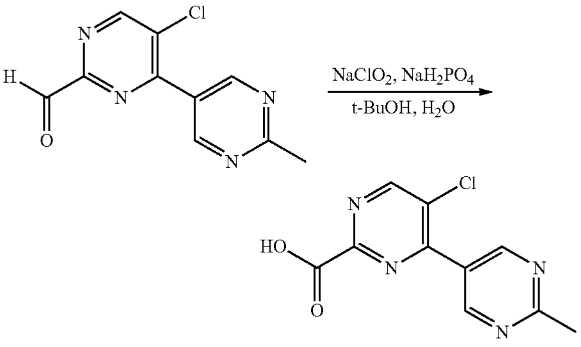

5-Chloro-2'-methyl-[4,5'-bipyrimidine]-2-carboxylic acid To a solution of the product from the previous step (0.87 g, 3.71 mmol, 1 eq) in t-BuOH (8 mL) was added $NaClO_2$ (1.01 g, 11.12 mmol, 3 eq) and $NaH_2PO_4$ (355.88 mg, 2.97 mmol, 0.8 eq) in $H_2O$ (2 mL). After stirring at 25° C. for 3 h, the mixture was quenched with saturated $Na_2SO_3$ aqueous solution (10 mL) and extracted with EtOAc (10 mL×2), dried over $Na_2SO_4$, filtered and concentrated under reduced pressure to afford the title compound (220 mg, 868.97 μmol, 23% yield).

MS (ES+) $C_{10}H_7N_4O_2C_1$ requires: 250 and 252, found: 251 and 253 $[M+H]^+$. $^1H$ NMR (400 MHz, DMSO-$d_6$) δ=9.14 (s, 2H), 8.97 (s, 1H), 2.72 (s, 3H).

INTERMEDIATE A-50

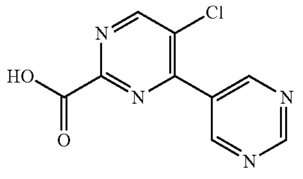

5-chloro-[4,5'-bipyrimidine]-2-carboxylic acid

This compound was obtained using a procedure similar to that used for Intermediate A-49.

INTERMEDIATE A-51

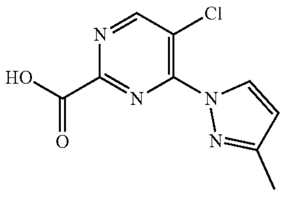

5-Chloro-4-(3-methyl-1H-pyrazol-1-yl)pyrimidine-2-carboxylic acid

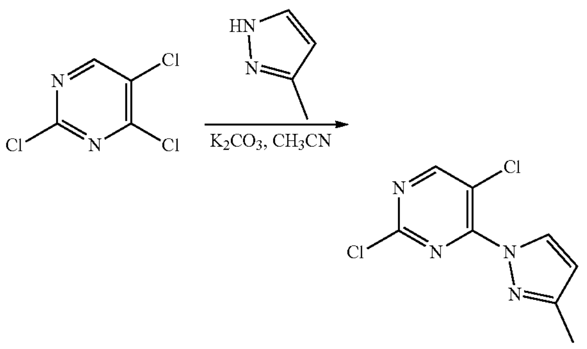

2,5-Dichloro-4-(3-methyl-1H-pyrazol-1-yl)pyrimidine To a solution of 2,4,5-trichloropyrimidine (3.58 g, 19.52 mmol, 1 eq) in $CH_3CN$ (50 mL) were added 3-methyl-1H-pyrazole (1.60 g, 19.52 mmol, 1 eq) and $K_2CO_3$ (4.05 g, 29.28 mmol, 1.5 eq) at 25° C. After stirring at 25° C. for 16 h, the mixture was diluted with $H_2O$ (30 mL), extracted with EtOAc (50 mL×3), dried over $Na_2SO_4$, filtered and concentrated under reduced pressure. The residue was purified by chromatography on silica gel (eluent Petroleum ether/EtOAc=0 to 20/1) to afford the title compound (2.5 g, 10.04 mmol, 51% yield) as a white solid. MS (ES+) $C_8H_6N_4Cl_2$ requires: 228 and 230, found: 229 and 231 $[M+H]^+$. $^1H$ NMR (400 MHz, $CDCl_3$) δ=8.63 (s, 1H), 8.45 (d, J=2.7 Hz, 1H), 6.35 (d, J=2.7 Hz, 1H), 2.41 (s, 3H).

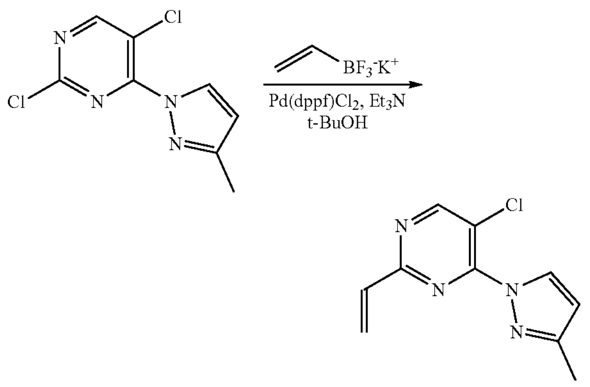

5-Chloro-4-(3-methyl-1H-pyrazol-1-yl)-2-vinylpyrimidine To a solution of the product from the previous step (2.5 g, 10.91 mmol, 1 eq) in t-BuOH (30 mL) were added $Pd(dppf)Cl_2$ (399.29 mg, 545.69 μmol, 0.05 eq), potassium (vinyl)trifluoroborate (1.75 g, 13.10 mmol, 1.2 eq) and $Et_3N$ (1.66 g, 16.37 mmol, 2.28 mL, 1.5 eq) at 25° C. under $N_2$. After stirring at 60° C. for 16 h, the mixture was diluted with $H_2O$ (30 mL), extracted with EtOAc (50 mL×3), dried over $Na_2SO_4$, filtered and concentrated under reduced pressure. The residue was purified by chromatography on silica gel (eluent Petroleum ether/EtOAc=0 to 20/1) to afford the title compound (1.5 g, 3.33 mmol, 30 yield).

MS (ES+) $C_{10}H_9ClN_4$ requires: 220 and 222, found: 221 and 223 $[M+H]^+$. $^1H$ NMR (400 MHz, $CDCl_3$) δ=8.74 (s, 1H), 8.47 (d, J=2.4 Hz, 1H), 6.90-6.82 (m, 1H), 6.70-6.63 (m, 1H), 6.35 (d, J=2.8 Hz, 1H), 5.81 (dd, J=1.6, 10.4 Hz, 1H), 2.43 (s, 3H)

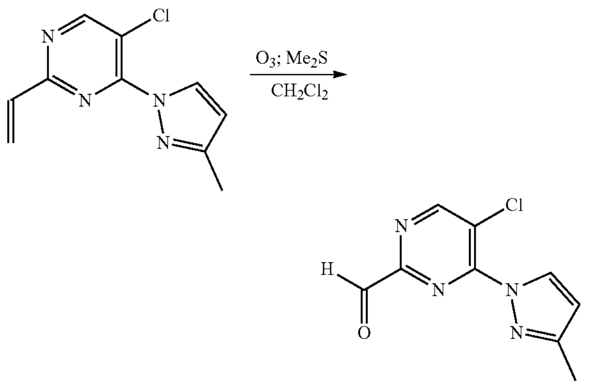

5-Chloro-4-(3-methyl-1H-pyrazol-1-yl)pyrimidine-2-carbaldehyde A stream of $O_3$ was bubbled into a solution of the product from the previous step (1.5 g, 3.33 mmol, 49% purity, 1 eq) in $CH_2Cl_2$ (15 mL) at −78° C. for 0.5 h. After excess $O_3$ was purged by $N_2$, $Me_2S$ (2.07 g, 33.31 mmol, 2.45 mL, 10 eq) was added at 25° C. After stirring at 25° C. for 20 h, the mixture was diluted with $H_2O$ (30 mL), extracted with EtOAc (50 mL×3), dried over $Na_2SO_4$, filtered and concentrated under reduced pressure. The residue was purified by chromatography on silica gel (eluent Petroleum ether/EtOAc=20/1 to 10/1) to afford the title compound (400 mg, 1.51 mmol, 45% yield) as a yellow oil. MS (ES+) $C_9H_7N_4ClO$ requires: 222 and 224, found: 223 and 225 $[M+H]^+$.

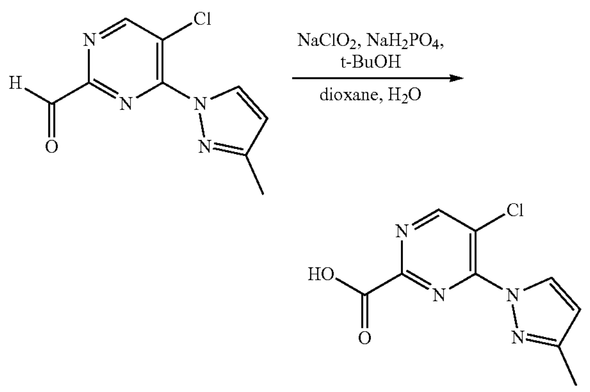

5-Chloro-4-(3-methyl-1H-pyrazol-1-yl)pyrimidine-2-carboxylic acid To a solution of the product from the previous step (400 mg, 1.80 mmol, 1 eq) in t-BuOH (2 mL), $H_2O$ (0.5 mL), and dioxane (2 mL) were added $NaH_2PO_4$ (172.45 mg, 1.44 mmol, 0.8 eq) and $NaClO_2$ (487.49 mg, 5.39 mmol, 3 eq). After stirring at 25° C. for 3 h, the reaction mixture was concentrated under reduced pressure. The residue was purified by prep-HPLC (column: Phenomenex luna $C_{18}$ 250*50 mm*15 um; mobile phase: [water (0.225% FA)—$CH_3CN$]; B %: 18%-48%, 10 min). The eluent was concentrated and freeze-dried to afford the title compound (100 mg, 419.06 μmol, 23% yield) as a white solid.

MS (ES+) $C_9H_7N_4ClO_2$ requires: 238 and 240, found: 239 and 241 $[M+H]^+$. $^1H$ NMR (400 MHz, $CDCl_3$) δ=8.94 (s, 1H), 8.62 (d, J=2.8 Hz, 1H), 6.42 (d, J=2.8 Hz, 1H), 2.44 (s, 3H).

INTERMEDIATE A-52

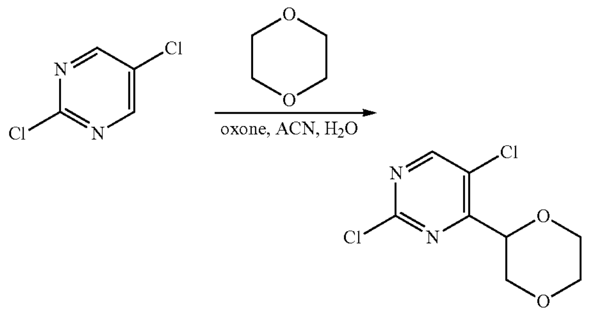

2,5-Dichloro-4-(1,4-dioxan-2-yl)pyrimidine To a solution of 2,5-dichloropyrimidine (2.5 g, 16.78 mmol, 1 eq) and dioxane (29.57 g, 335.62 mmol, 28.71 mL, 20 eq) in $CH_3CN$ (50 mL) was added OXONE® (13.61 g, 50.34 mmol, 10.08 mL, 3 eq) at 25° C. under $N_2$. After stirring at 120° C. for 16 h, the mixture was diluted with $H_2O$ (30 mL), extracted with EtOAc (50 mL×3), dried over $Na_2SO_4$, filtered and concentrated under reduced pressure. The residue was purified by chromatography on silica gel (eluent Petroleum ether/EtOAc=0 to 20/1) to afford the title compound (2 g, 8.51 mmol, 50% yield) as a white solid. MS (ES+) $C_8H_8N_2Cl_2O_2$ requires: 234 and 236, found: 235 and 237 $[M+H]^+$. $^1H$ NMR (400 MHz, $CDCl_3$) δ=8.50 (s, 1H), 5.00 (dd, J=2.6, 9.8 Hz, 1H), 4.00-3.95 (m, 1H), 3.95-3.83 (m, 2H), 3.76 (dd, J=2.3, 8.1 Hz, 2H), 3.68 (dd, J=9.8, 11.5 Hz, 1H)

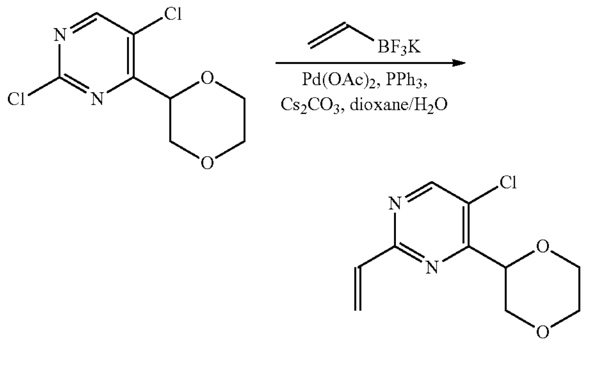

5-Chloro-4-(1,4-dioxan-2-yl)-2-vinylpyrimidine To a solution of the product from the previous step (1.4 g, 5.96 mmol, 1 eq), potassium (vinyl)trifluoroborate (1.20 g, 8.93 mmol, 1.5 eq) in dioxane (15 mL) were added $PPh_3$ (468.64 mg, 1.79 mmol, 0.3 eq), $Cs_2CO_3$ (3.88 g, 11.91 mmol, 2 eq) and $Pd(OAc)_2$ (200.57 mg, 893.36 μmol, 0.15 eq) at 25° C. under $N_2$. After stirring at 60° C. for 16 h, the mixture was diluted with $H_2O$ (30 mE), extracted with EtOAc (50 mL×3), dried over $Na_2SO_4$, filtered and concentrated under reduced pressure. The residue was purified by chromatography on silica gel (eluent Petroleum ether/EtOAc=0 to 20/1) to afford the title compound (1 g, 4.41 mmol, 74% yield) as a white solid. MS (ES+) $C_{10}H_{11}N_2ClO_2$ requires: 226 and 228, found: 227 and 229 $[M+H]^+$.

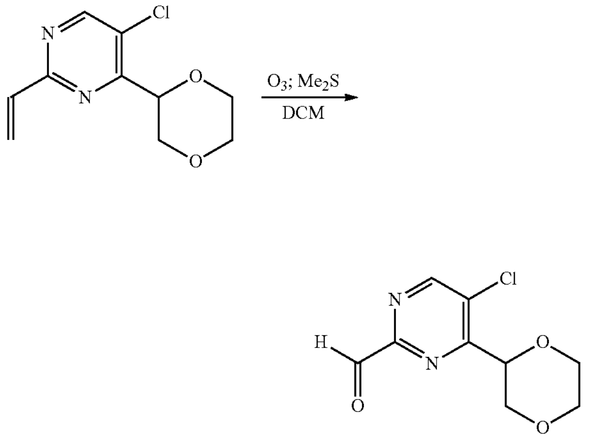

5-Chloro-4-(1,4-dioxan-2-yl)pyrimidine-2-carbaldehyde A stream of $O_3$ was bubbled into a solution of the product from the previous step (1 g, 4.41 mmol, 100% purity, 1 eq) in $CH_2Cl_2$ (15 mL) at −78° C. for 30 minutes. After excess $O_3$ was purged by $N_2$, $Me_2S$ (2.74 g, 44.12 mmol, 3.24 mL, 10 eq) was added at 25° C. After stirring at 25° C. for 20 h, the mixture was diluted with $H_2O$ (30 mL), extracted with EtOAc (50 mL×3). The combined organic phase was dried over $Na_2SO_4$, filtered and concentrated under reduced pressure. The residue was purified by chromatography on silica gel (eluent Petroleum ether/EtOAc=20/1 to 10/1) to afford the title compound as a yellow oil.

MS (ES+) $C_9H_9N_2ClO_3$ requires:228 and 230, found: 229 and 231 $[M+H]^+$. $^1H$ NMR (400 MHz, $CDCl_3$) δ=10.15 (s, 1H), 8.93 (s, 1H), 5.20 (dd, J=2.7, 9.7 Hz, 1H), 4.14-4.05 (m, 4H), 3.90-3.87 (m, 2H).

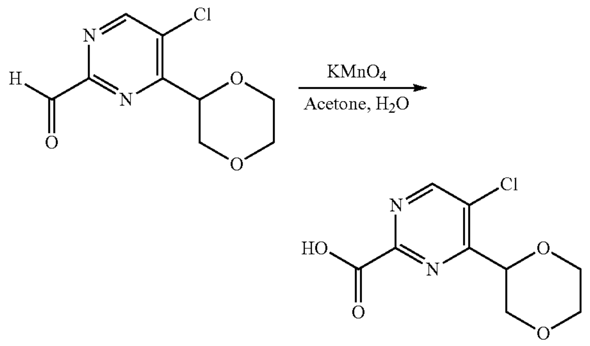

5-Chloro-4-(1,4-dioxan-2-yl)pyrimidine-2-carboxylic acid To a solution of the product from the previous step (120 mg, 524.86 μmol, 1 eq) in t-BuOH (1.2 mL) $H_2O$ (0.3 mL) were added $NaH_2PO_4$ (50.38 mg, 419.89 μmol, 0.8 eq), and $NaClO_2$ (142.41 mg, 1.57 mmol, 3 eq) at 25° C. After stirring at 50° C. for 16 h, the reaction mixture was concentrated under reduced pressure. The residue was purified by prep-HPLC (column: Phenomenex Synergi $C_{18}$ 150*25 mm*10 um; mobile phase: [water (0.1% TFA) —$CH_3CN$]; B %: 8%-38%, 10 min) to afford the title compound (65 mg, 265.71 μmol, 50% yield) as a white solid.

MS (ES+) $C_9H_9N_2ClO_4$ requires: 244 and 246, found: 245 and 247 $[M+H]^+$. $^1H$ NMR (400 MHz, DMSO-$d_6$) δ=13.84 (br s, 1H), 9.08 (s, 1H), 4.99 (dd, J=2.6, 9.7 Hz, 1H), 3.94 (dt, J=2.5, 11.2 Hz, 2H), 3.84-3.74 (m, 3H), 3.69-3.60 (m, 1H).

INTERMEDIATE A-53

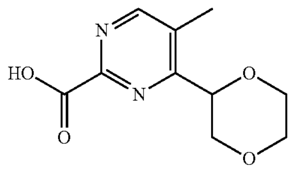

4-(1,4-Dioxan-2-yl)-5-methylpyrimidine-2-carboxylic acid

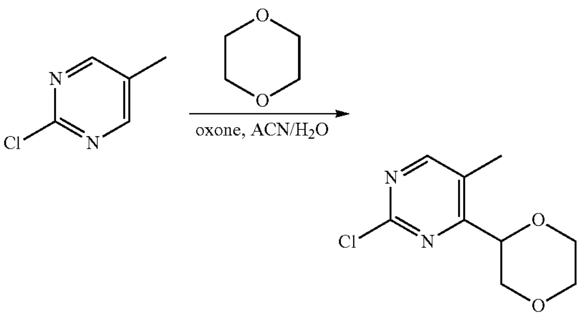

2-Chloro-4-(1,4-dioxan-2-yl)-5-methylpyrimidine To a solution of the product from the previous step (0.5 g, 3.89 mmol, 1 eq) in $H_2O$ (5 mL) and $CH_3CN$ (10 mL) were added dioxane (6.85 g, 77.78 mmol, 6.65 mL, 20 eq) and OXONE® (3.15 g, 11.67 mmol, 3 eq) under $N_2$. After stirring at 120° C. for 16 h, the mixture was cooled to 25° C. and diluted with water (20 mL) and extracted with EtOAc (20 mL×3). The combined organic phase was dried over $Na_2SO_4$, filtered and concentrated under reduced pressure. The residue was purified by silica gel chromatography (ISCO®; 14 g SepaFlash® Silica Flash Column, Eluent 0~20% EtOAC/Petroleum ether gradient @30 mL/min) to afford the title compound (400 mg, 1.86 mmol, 47% yield) as a white solid.

$^1H$ NMR (400 MHz, CDCl3) δ=8.33 (s, 1H), 4.71 (dd, J=2.8, 9.8 Hz, 1H), 3.94-3.87 (m, 2H), 3.87-3.79 (m, 2H), 3.76-3.68 (m, 2H), 2.31 (s, 3H).

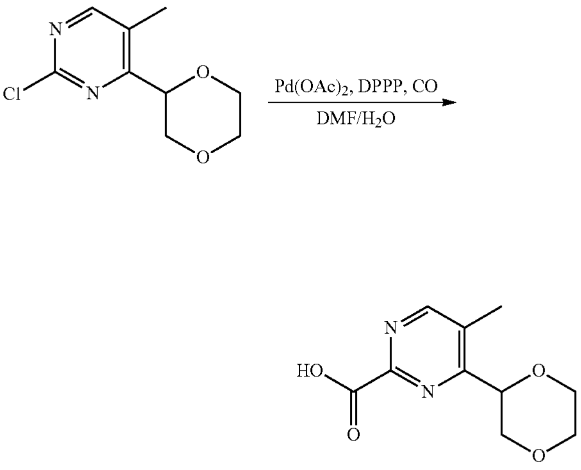

4-(1,4-Dioxan-2-yl)-5-methylpyrimidine-2-carboxylic acid To a mixture of the product from the previous step (400 mg, 1.86 mmol, 1 eq) in DMF (6 mL) and $H_2O$ (1 mL) were added dppp (76.86 mg, 186.35 μmol, 0.1 eq), $Pd(OAc)_2$ (41.84 mg, 186.35 μmol, 0.1 eq) and $Et_3N$ (377.13 mg, 3.73 mmol, 518.75 μL, 2 eq) under $N_2$. The suspension was degassed under vacuum and purged with CO 3 times. After stirring under CO (45 psi) at 80° C. for 16 h, the mixture was concentrated under reduced pressure. The residue was diluted with water (20 mL), basified with NaOH (1 M) aqueous solution to adjust pH to 13, extracted with EtOAc (20 mL×3). The aqueous phase was acidified by HCl (1 M) to adjust the pH to 1, then extracted with EtOAc (20 mL×3), washed with brine (20 mL×3), dried over $Na_2SO_4$, filtered and concentrated under reduced pressure to afford the title compound (600 mg, crude) as a gray solid.

MS (ES+) $C_{10}H_{12}N_2O_4$ requires: 224, found: 225 $[M+H]^+$. $^1H$ NMR (400 MHz, DMSO-$d_6$) δ=12.90 (br s, 1H), 8.78 (s, 1H), 4.85 (dd, J=2.4, 9.7 Hz, 1H), 4.07-3.71 (m, 5H), 3.68-3.55 (m, 1H), 2.43 (s, 3H).

INTERMEDIATE A-54

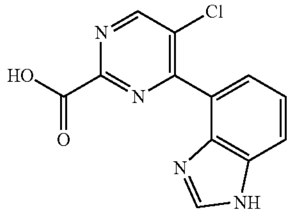

4-(1H-benzo[d]imidazol-4-yl)-5-chloropyrimidine-2-carboxylic acid

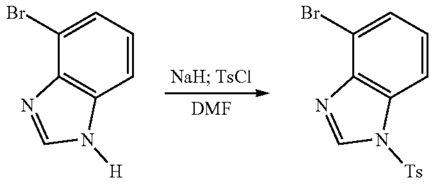

4-Bromo-1-(p-toluenesulfonyl)-1H-benzo[d]imidazole To a solution of 4-bromo-1H-benzo[d]imidazole (4 g, 20.30 mmol, 1 eq) in THF (40 mL) was added NaH (1.22 g, 30.45 mmol, 60% wt dispersion, 1.5 eq) at 0° C. After stirring at 0° C. for 30 min under $N_2$, 4-methylbenzenesulfonyl chloride (4.64 g, 24.36 mmol, 1.2 eq) was added to the reaction mixture. After stirring at 25° C. for 16 hr, the reaction mixture was quenched with saturated aqueous $NH_4Cl$ solution (10 mL) and then extracted with EtOAc (50 mL×3). The combined organic phase was dried over $Na_2SO_4$, filtered and concentrated under reduced pressure. The residue was purified by chromatography on silica gel (eluent Petroleum ether/EtOAc=0 to 20/1) to afford the title compound (4 g, 11.39 mmol, 56% yield) as a white solid.

MS (ES+) $C_{14}HIIN_2SO_2Br$ requires 350 and 352, found: 351 and 353 [M+H$^+$]. $^1$H NMR (400 MHz, $CDCl_3$) δ=8.37 (s, 1H), 7.80 (d, J=8.4 Hz, 2H), 7.75 (d, J=8.3 Hz, 1H), 7.48 (d, J=7.9 Hz, 1H), 7.25 (d, J=8.3 Hz, 2H), 7.21 (s, 1H), 2.33 (s, 3H).

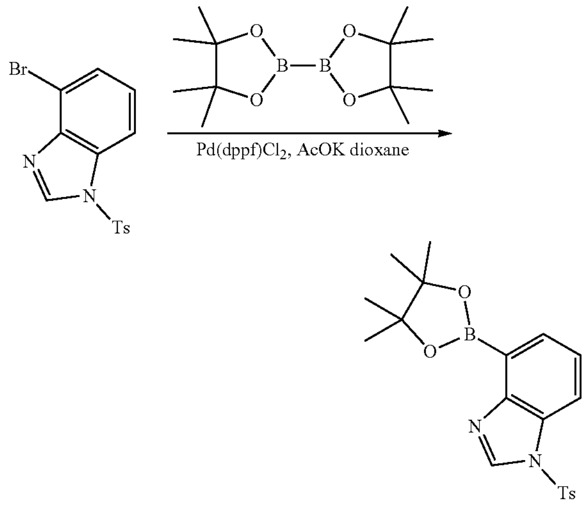

4-(4,4,5,5-tetramethyl-1,3,2-dioxaborolan-2-yl)-1-(p-toluenesulfonyl)-1H-benzo[d]imidazole To a solution of the product from the previous step (2 g, 5.69 mmol, 1 eq) in dioxane (20 mL) were added BPD (1.74 g, 6.83 mmol, 1.2 eq), Pd(dppf) $Cl_2$ (208.33 mg, 284.72 μmol, 0.05 eq) and AcOK (838.30 mg, 8.54 mmol, 1.5 eq) at 25° C. After stirring at 120° C. for 16 hr under $N_2$, the mixture was concentrated under reduced pressure to afford the title compound (4.0 g, crude) MS (ES+) $C_{20}H_{23}N_2SO_4B$ requires: 398, found: 399 [M+H]$^+$.

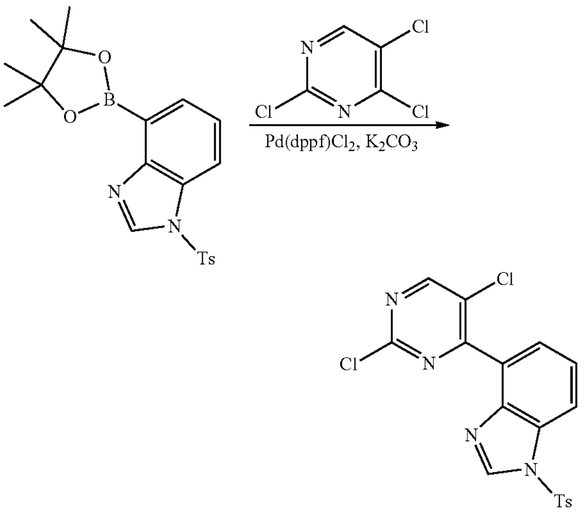

4-(2,5-Dichloropyrimidin-4-yl)-1-(p-toluenesulfonyl)-1H-benzo[d]imidazole

To a solution of the product from the previous step (4 g, 10.04 mmol, 1 eq), 2,4,5-trichloropyrimidine (1.84 g, 10.04 mmol, 1 eq) in THF (40 mL) and $H_2O$ (4 mL) were added $Na_2CO_3$ (1.06 g, 10.04 mmol, 1 eq) and $Pd(PPh_3)_4$ (11.61 g, 10.04 mmol, 1 eq) at 25° C. After stirring at 60° C. for 16 h under $N_2$, the mixture was diluted with $H_2O$ (30 mL) and then extracted with EtOAc (50 mL×3). The combined organic phase was dried over $Na_2SO_4$, filtered and concentrated under reduced pressure. The residue was purified by chromatography on silica gel (eluent Petroleum ether/EtOAc=0 to 20/1) to afford the title compound (3.7 g, 7.59 mmol, 75% yield) as a yellow oil. MS (ES+) $C_{18}H_{12}N_4Cl_2SO_2$ requires: 418 and 420 found: 419 and 421 [M+H]$^+$.

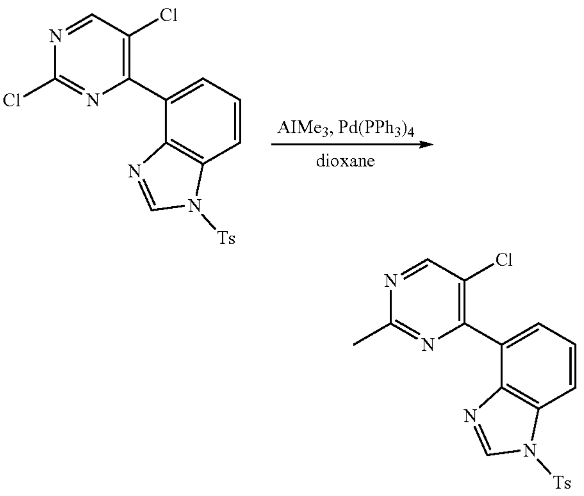

4-(5-Chloro-2-methylpyrimidin-4-yl)-1-(p-toluenesulfonyl)-1H-benzo[d]imidazole To a solution of the product from the previous step (3.7 g, 8.82 mmol, 1 eq) in THF (40 mL) were added $Pd(PPh_3)_4$ (509.87 mg, 441.23 μmol, 0.05 eq) and $Al(CH_3)_3$ (2 M solution in toluene, 8.82 mL, 2 eq)

at 25° C. After stirring at 100° C. for 5 h under $N_2$, the mixture was diluted with $H_2O$ (30 mL) and then extracted with EtOAc (50 mL×3). The combined organic phase was dried over $Na_2SO_4$, filtered and concentrated under reduced pressure. The residue was purified by chromatography on silica gel (eluent Petroleum ether/EtOAc=0 to 20/1) to afford the title compound (1.5 g, 3.01 mmol, 34% yield) as a yellow oil.

MS (ES+) $C_{19}H_{15}N_4ClSO_2$ MS (ES+) requires: 398 and 400, found: 399 and 401[M+H$^+$]. $^1$H NMR (400 MHz, $CDCl_3$) δ=8.73 (s, 1H), 8.42 (s, 1H), 8.01 (dd, J=1.4, 7.9 Hz, 1H), 7.90 (d, J=8.4 Hz, 2H), 7.72-7.63 (m, 1H), 7.57-7.53 (m, 1H), 7.34 (d, J=8.2 Hz, 2H), 2.77 (s, 3H), 2.41 (s, 3H).

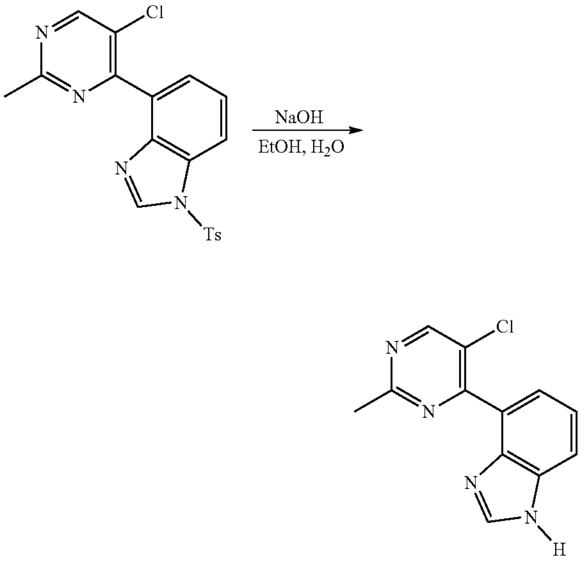

4-(5-Chloro-2-methylpyrimidin-4-yl)-1H-benzo[d]imidazole To a solution of the product from the previous step (1.5 g, 3.76 mmol, 1 eq) in ethanol (15 mL) and $H_2O$ (1.5 mL) was added NaOH (752.13 mg, 18.80 mmol, 5 eq) at 25° C. After stirring at 60° C. for 1 h, the mixture was diluted with $H_2O$ (30 mL) and then extracted with EtOAc (50 mL×3). The combined organic phase was dried over $Na_2SO_4$, filtered and concentrated under reduced pressure. The residue was purified by chromatography on silica gel (eluent Petroleum ether/EtOAc=20/1 to 10/1) to afford the title compound (630 mg, 2.32 mmol, 61% yield) as a white solid.

MS (ES+) $C_{12}H_9N_4Cl$ requires 244 and 246, found: 245 and 247[M+H]$^+$. $^1$H NMR (400 MHz, $CDCl_3$) δ=8.81-8.72 (m, 1H), 8.35 (d, J=7.8 Hz, 1H), 8.28 (s, 1H), 7.99 (d, J=7.9 Hz, 1H), 7.47-7.41 (m, 1H), 2.85 (s, 3H).

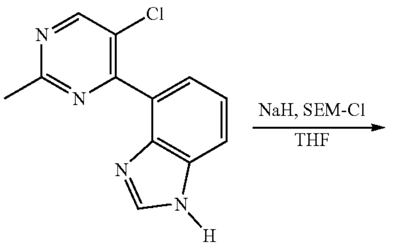

-continued

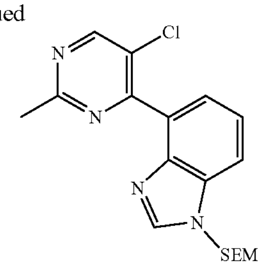

4-(5-chloro-2-methylpyrimidin-4-yl)-1-((2-(trimethylsilyl)ethoxy)methyl)-1H-benzo[d]imidazole To a solution of the product from the previous step (600 mg, 2.45 mmol, 1 eq) in THF (6 mL) was added NaH (147.13 mg, 3.68 mmol, 60% purity, 1.5 eq) at 0° C. After stirring at 0° C. for 30 min, SEM-Cl (490.60 mg, 2.94 mmol, 520.80 μL, 1.2 eq) was added to the reaction mixture. After stirring at 25° C. for 16 h, the reaction mixture was quenched with saturated $NH_4Cl$ (5 mL) solution at 0° C. and then diluted with $H_2O$ (20 mL) and extracted with EtOAc (50 mL×3). The combined organic phase was dried over $Na_2SO_4$, filtered and concentrated under reduced pressure. The residue was purified by chromatography on silica gel (eluent Petroleum ether/EtOAc=20/1 to 10/1) to afford the title compound (700 mg, 1.59 mmol, 64% yield) as a yellow solid.

MS (ES+) $C_{18}H_{23}N_4ClSiO$ requires 374 and 376, found: 375 and 377[M+H]$^+$. $^1$H NMR (400 MHz, $CDCl_3$) δ=8.76 (s, 1H), 8.18 (s, 1H), 7.99 (d, J=7.8 Hz, 1H), 7.44 (d, J=7.8 Hz, 1H), 7.42-7.38 (m, 1H), 5.35 (s, 2H), 3.14-3.07 (m, 2H), 2.8 (s, 3H), 0.67-0.60 (m, 2H), 0.11 (s, 9H).

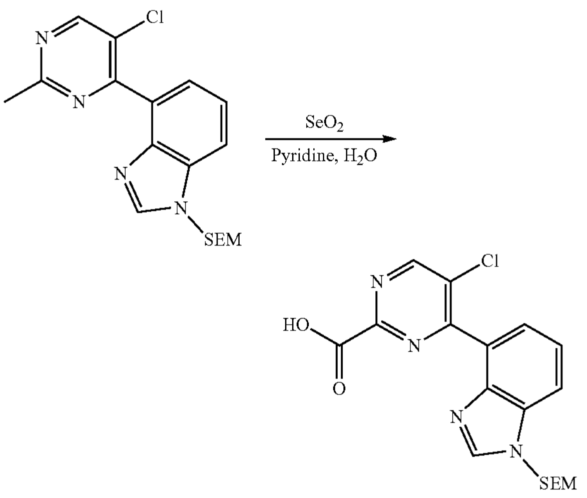

5-Chloro-4-(1-((2-(trimethylsilyl)ethoxy)methyl)-1H-benzo[d]imidazol-4-yl)-pyrimidine-2-carboxylic acid To a solution of the product from the previous step (0.7 g, 1.87 mmol, 1 eq) in pyridine (7 mL) and $H_2O$ (1.5 mL) was added $SeO_2$ (725.06 mg, 6.53 mmol, 3.5 eq). After stirring at 120° C. for 144 hr, the reaction mixture was concentrated under reduced pressure. The residue was diluted with $H_2O$ (20 mL). The pH of the mixture was adjusted to 10 with NaOH (1 M) aqueous solution. After being washed with EtOAc (20 mL×3), the pH of the aqueous phase was adjusted to 2 with HCl (1 M) aqueous solution. The aqueous phase was extracted with EtOAc (20 mL×3). The combined organic phase was dried over $Na_2SO_4$, filtered and concentrated under reduced pressure to afford the title compound (100 mg, 219.80 μmol, 11% yield) as a yellow solid.

MS (ES+) $C_{18}H_{21}N_4ClO_3Si$ requires: 404 and 406, found: 405 and 407 $[M+H]^+$. $^1H$ NMR (400 MHz, DMSO-$d_6$) δ=9.24 (s, 1H), 8.43 (s, 1H), 7.90 (dd, J=1.2, 7.8 Hz, 1H), 7.48-7.44 (m, 1H), 7.13-7.08 (m, 1H), 5.38 (s, 2H), 2.69-2.64 (m, 2H), 1.23-1.19 (m, 2H), 0.18 (s, 9H).

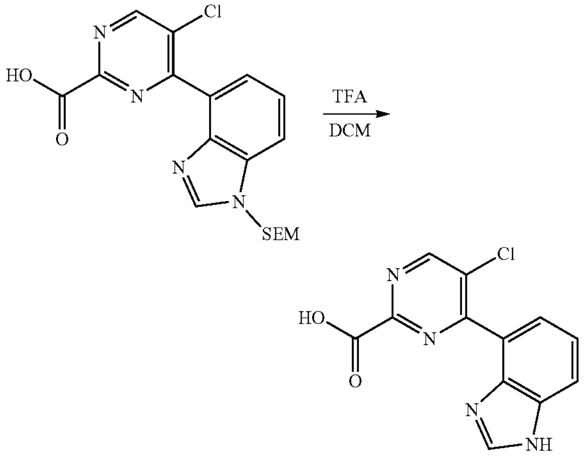

4-(1H-benzo[d]imidazol-4-yl)-5-chloropyrimidine-2-carboxylic acid To a solution of the product from the previous step (100.00 mg, 246.96 μmol, 1 eq) in $CH_2Cl_2$ (1 mL) was added TFA (1.13 g, 9.88 mmol, 731.41 μL, 40 eq). After stirring at 25° C. for 16 hr, the reaction mixture was concentrated under reduced pressure. The residue was triturated with EtOAc (1 mL) at 25° C. for 30 min and the solid was removed by filtration to afford the title compound (40 mg, 116.51 μmol, 47% yield) was obtained as a colourless solid.

$^1H$ NMR (400 MHz, DMSO-$d_6$) δ=10.92 (br s, 0.5H), 10.64 (br s, 0.5H), 9.28 (s, 1H), 8.02 (d, J=8.2 Hz, 1H), 7.82 (d, J=7.3 Hz, 1H), 7.72-7.62 (m, 1H), 7.11 (s, 1H).

INTERMEDIATE A-55

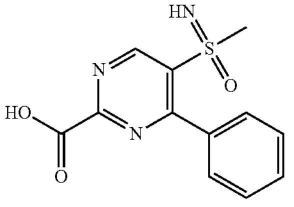

5-(S-methylsulfonimidoyl)-4-phenylpyrimidine-2-carboxylic acid

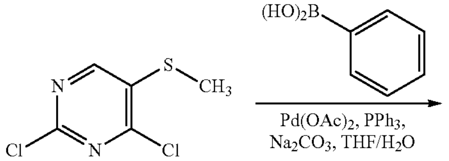

-continued

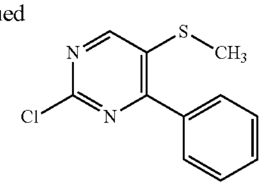

2-Chloro-5-(methylthio)-4-phenylpyrimidine To a solution of 2,4-dichloro-5-(methylthio)pyrimidine (4.7 g, 24.09 mmol, 1 eq) and phenylboronic acid (3.53 g, 28.91 mmol, 1.2 eq) in THF (50 mL) and $H_2O$ (5 mL) were added $Na_2CO_3$ (2.55 g, 24.09 mmol, 1 eq), $PPh_3$ (252.78 mg, 963.76 μmol, 0.04 eq) and $Pd(OAc)_2$ (108.19 mg, 481.88 μmol, 0.02 eq) at 25° C. under $N_2$. After stirring at 60° C. for 16 h, the mixture was diluted with $H_2O$ (30 mL), extracted with EtOAc (50 mL×3), dried over $Na_2SO_4$, filtered and concentrated under reduced pressure. The residue was purified by chromatography on silica gel (eluent ether/EtOAc=0 to 20/1) to afford the title compound (4.2 g, 14.73 mmol, 61% yield) as a yellow solid.

MS (ES+) $C_{11}H_9ClN_2S$ requires 236 and 238, found: 237 and 239$[M+H^+]$. $^1H$ NMR (400 MHz, $CDCl_3$) δ=8.49 (s, 1H), 7.82-7.78 (m, 2H), 7.54-7.50 (m, 3H), 2.47 (s, 3H).

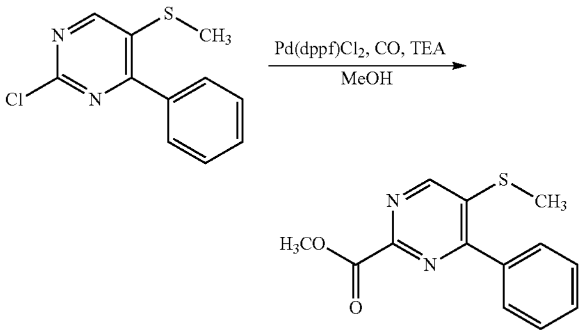

Methyl 5-(methylthio)-4-phenylpyrimidine-2-carboxylate To a solution of the product from the previous step (1.5 g, 6.34 mmol, 1 eq) in MeOH (20 mL) were added Pd(dppf)$Cl_2$ (231.83 mg, 316.83 μmol, 0.05 eq) and $Et_3N$ (1.28 g, 12.67 mmol, 1.76 mL, 2 eq) at 25° C. The mixture was stirred under a CO atmosphere (45 psi) at 60° C. for 16 h, then diluted with $H_2O$ (30 mL), extracted with EtOAc (50 mL×3), dried over $Na_2SO_4$, filtered and concentrated under reduced pressure. The residue was purified by chromatography on silica gel (eluent Petroleum ether/EtOAc=0 to 20/1) to afford the title compound (700 mg, 2.18 mmol, 34% yield) as a yellow solid.

MS (ES+) $C_{13}H_{12}N_2O_2S$ requires 260, found: 261 $[M+H]^+$. $^1H$ NMR (400 MHz, $CDCl_3$) δ=8.61 (s, 1H), 7.74-7.67 (m, 2H), 7.47-7.39 (m, 3H), 4.00-3.96 (m, 3H), 2.47 (s, 3H)

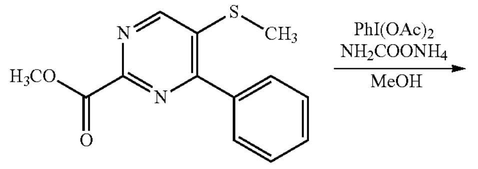

-continued

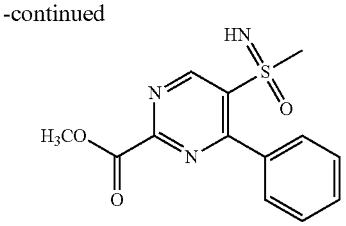

Methyl 5-(S-methylsulfonimidoyl)-4-phenylpyrimidine-2-carboxylate To a solution of the product from the previous step (100 mg, 384.16 μmol, 1 eq) in MeOH (1 mL) in THF (20 mL) were added $PhI(OAc)_2$ (247.47 mg, 768.31 μmol, 2 eq), and ammonium carbamate (89.97 mg, 1.15 mmol, 3 eq) at 25° C. under $N_2$. After stirring at 60° C. for 20 h, the mixture was diluted with $H_2O$ (30 mL) and then extracted with EtOAc (50 mL×3), dried over $Na_2SO_4$, filtered and concentrated under reduced pressure. The residue was purified by chromatography on silica gel (eluent Petroleum ether/EtOAc=20/1 to 10/1) to afford the title compound (60 mg, 199.78 μmol, 52% yield) as a white solid.

MS (ES+) $C_{13}H_{13}N_3SO_3$ requires: 291, found: 292 $[M+H]^+$. $^1H$ NMR (400 MHz, DMSO-$d_6$) δ=9.51 (s, 1H), 7.71-7.66 (m, 2H), 7.62-7.52 (m, 3H), 4.99 (br s, 1H), 3.95 (s, 3H), 2.92 (s, 3H).

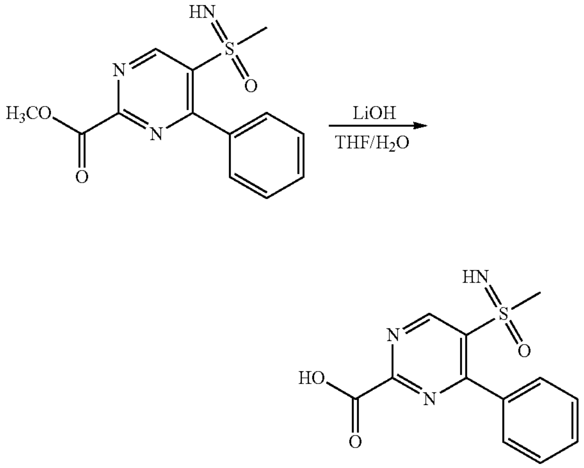

5-(S-methylsulfonimidoyl)-4-phenylpyrimidine-2-carboxylic acid To a solution of the product from the previous step (50 mg, 171.63 μmol, 1 eq) in THF (1 mL) and $H_2O$ (0.5 mL) was added LiOH (8.22 mg, 343.26 μmol, 2 eq). After stirring at 25° C. for 1 h, the reaction mixture was concentrated under reduced pressure. The residue was diluted with water (20 mL), basified with NaOH (1 M) aqueous solution to adjust pH to 10 and extracted with EtOAc (20 mL×3). Then the aqueous phase was acidified with HCl (1 M) aqueous solution to adjust pH to 2, extracted with EtOAc (20 mL×3), dried over $Na_2SO_4$, filtered and concentrated under reduced pressure to afford the title compound (30 mg, 97.37 μmol, 56% yield) as a white solid.

MS (ES+) $C_{12}H_{11}N_3SO_3$ requires: 277, found: 278 $[M+H]^+$. $^1H$ NMR (400 MHz, DMSO-$d_6$) δ=9.47 (s, 1H), 7.72-7.66 (m, 2H), 7.58-7.50 (m, 3H), 4.94 (br s, 1H), 2.92 (s, 3H).

INTERMEDIATE A-56

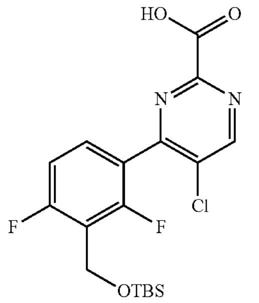

4-(3-(((tert-butyldimethylsilyl)oxy)methyl)-2,4-difluorophenyl)-5-chloropyrimidine-2-carboxylic acid

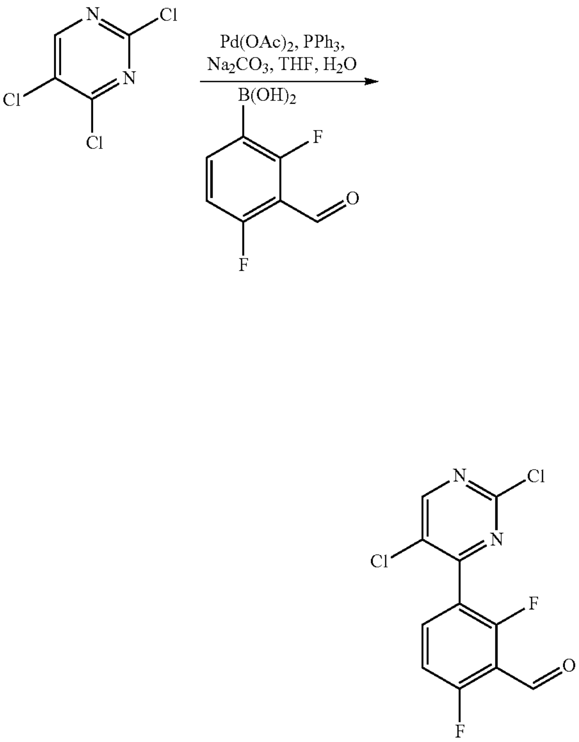

3-(2,5-Dichloropyrimidin-4-yl)-2,6-difluorobenzaldehyde To a solution of (2,4-difluoro-3-formylphenyl)boronic acid (5 g, 26.89 mmol, 1 eq), and 2,4,5-trichloropyrimidine (4.93 g, 26.89 mmol, 3.08 mL, 1 eq) in THF (80 mL) and $H_2O$ (20 mL) were added $Pd(OAc)_2$ (120.75 mg, 537.86 μmol, 0.02 eq), $PPh_3$ (282.15 mg, 1.08 mmol, 0.04 eq) and $Na_2CO_3$ (5.70 g, 53.79 mmol, 2 eq) under $N_2$. After stirring at 60° C. for 16 h, the reaction mixture was concentrated to remove THF, then diluted with $H_2O$ (100 mL), extracted with EtOAc (100 mL×2), dried over $Na_2SO_4$, filtered and concentrated under reduced pressure. The residue was purified by chromatography on silica gel (eluent Petroluem ether/EtOAc=40/1) to afford the title compound (2.6 g, 7.92 mmol, 29% yield) as a yellow oil. MS (ES+) $C_{11}H_4F_2ON_2Cl_2$ requires: 288 and 290, found: 289 and 291 $[M+H]^+$.

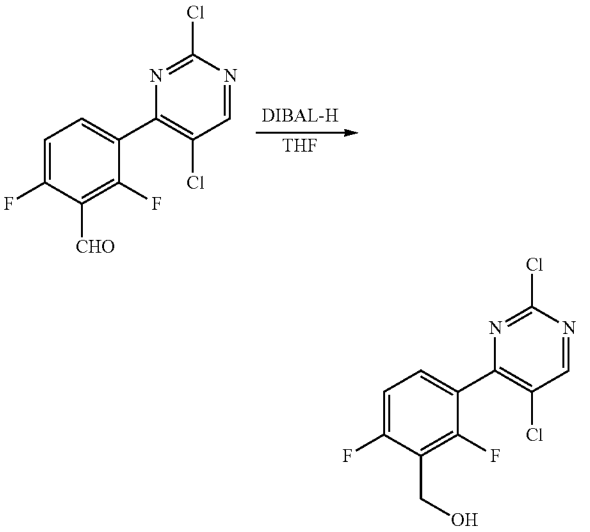

(3-(2,5-Dichloropyrimidin-4-yl)-2,6-difluorophenyl) methanol To a solution of the product from the previous step (2.3 g, 7.00 mmol, 1 eq) in THF (40 mL) was added DIBAL-H (1 M in toluene, 21.01 mL, 3 eq) at 0° C. under $N_2$. After stirring at 0° C. for 2 h, the mixture was quenched with $H_2O$ (100 mL), extracted with EtOAc (100 mL×2), dried over $Na_2SO_4$, filtered and concentrated under reduced pressure. The residue was purified by chromatography on silica gel (eluent Petroleum ether/EtOAc=5/1) to afford the title compound (1.5 g, 4.07 mmol, 58% yield) as a colorless oil. MS (ES+) $C_{11}H_6F_2ON_2Cl_2$ requires: 290 and 292, found: 291 and 293 $[M+H]^+$. $^1H$ NMR (400 MHz, DMSO-$d_6$) δ=9.09 (s, 1H), 7.72-7.55 (m, 1H), 7.41-7.24 (m, 1H), 4.58 (s, 2H).

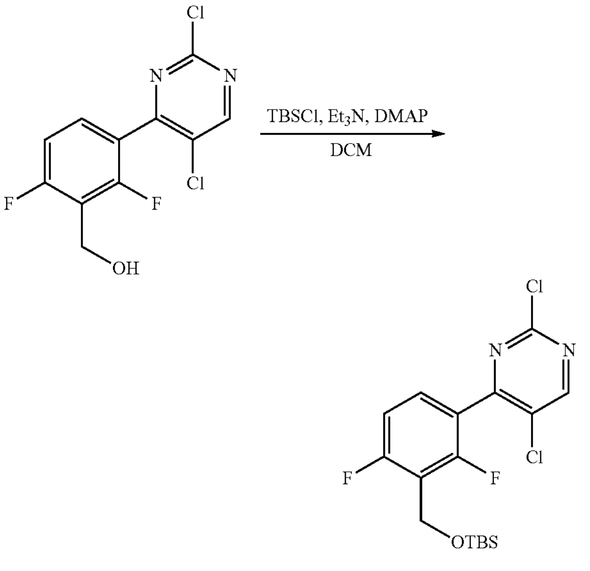

4-(3-(((tert-butyldimethylsilyl)oxy)methyl)-2,4-difluorophenyl)-2,5-dichloropyrimidine To a solution of the product from the previous step (1.4 g, 3.80 mmol, 79% purity, 1 eq) in $CH_2Cl_2$ (20 mL) were added DMAP (92.84 mg, 759.93 μmol, 0.2 eq), $Et_3N$ (768.96 mg, 7.60 mmol, 1.06 mL, 2 eq) and TBSCl (1.15 g, 7.60 mmol, 931.20 μL, 2 eq). After stirring at 25° C. for 16 h, the mixture was diluted with $H_2O$ (50 mL) and extracted with $CH_2Cl_2$ (50 mL×2), dried over $Na_2SO_4$, filtered and concentrated under reduced pressure. The residue was purified by chromatography on silica gel (eluent Petroleum ether/EtOAc=2/1) to afford the title compound (1.6 g, 3.75 mmol, 98% yield) as a colorless oil.

MS (ES+) $C_{17}H_{20}N_2OF_2Cl_2Si$ requires: 404 and 406, found: 405 and 407 $[M+H]^+$. $^1H$ NMR (400 MHz, DMSO-$d_6$) δ=9.01 (s, 1H), 7.65-7.51 (m, 1H), 7.27 (t, J=8.6 Hz, 1H), 4.71 (s, 2H), 0.79-0.74 (m, 9H), 0.00 (s, 6H).

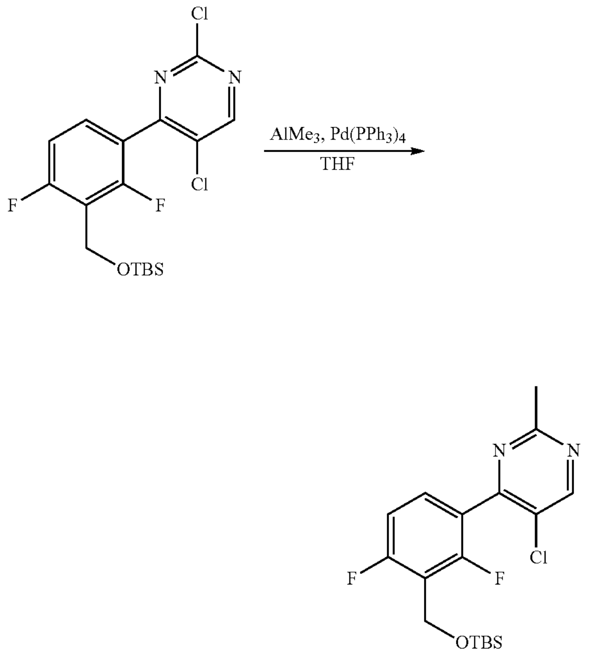

4-(3-(((tert-butyldimethylsilyl)oxy)methyl)-2,4-difluorophenyl)-5-chloro-2-methylpyrimidine To a solution of the product from the previous step (1.6 g, 3.95 mmol, 1 eq) in THF (20 mL) were added $AlMe_3$ (2 M in toluene, 2.96 mL, 1.5 eq) and $Pd(PPh_3)_4$ (228.07 mg, 197.36 μmol, 0.05 eq) in $N_2$. After stirring at 60° C. for 16 h under $N_2$, the mixture was quenched with $H_2O$ (50 mL) and extracted with EtOAc (50 mL×2), dried over $Na_2SO_4$, filtered and concentrated under reduced pressure. The residue was purified by chromatography on silica gel (eluent Petroluem ether/EtOAc=10/1) to afford the title compound (1.2 g, 2.96 mmol, 75% yield) as a colorless oil. MS (ES+) $C_{18}H_{23}N_2OClF_2Si$ requires: 384 and 386, found: 385 and 387 $[M+H]^+$.

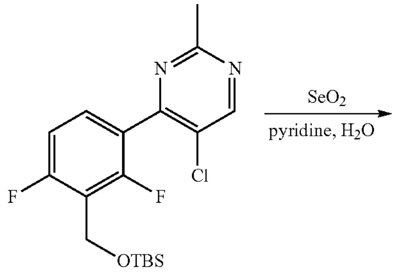

-continued

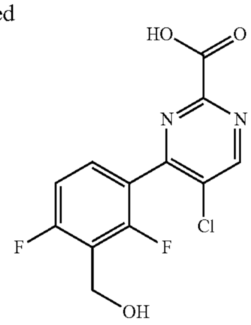

5-chloro-4-(2,4-difluoro-3-(hydroxymethyl)phenyl)pyrimidine-2-carboxylic acid To a solution of the product from the previous step (1.2 g, 3.12 mmol, 1 eq) in pyridine (10 mL) and $H_2O$ (1 mL) was added $SeO_2$ (1.73 g, 15.59 mmol, 5 eq). After stirring at 120° C. for 16 h, the mixture was filtrated and the filtrate was concentrated. The residue was diluted with $H_2O$ (50 mL), acidified with HCl (1 M) aqueous solution to adjust pH to 2-3 and extracted with EtOAc (50 mL×2). The combined organic layer was dried over $Na_2SO_4$, filtered and concentrated to afford the title compound (1.86 g, crude) as a yellow oil.

MS (ES+) $C_{12}H_7N_2O_3ClF_2$ requires: 300 and 302, found: 301 and 303 $[M+H]^+$. $^1H$ NMR (400 MHz, DMSO-$d_6$) δ=9.22 (s, 1H), 7.68-7.58 (m, 1H), 7.32 (t, J=8.8 Hz, 1H), 4.59 (s, 2H).

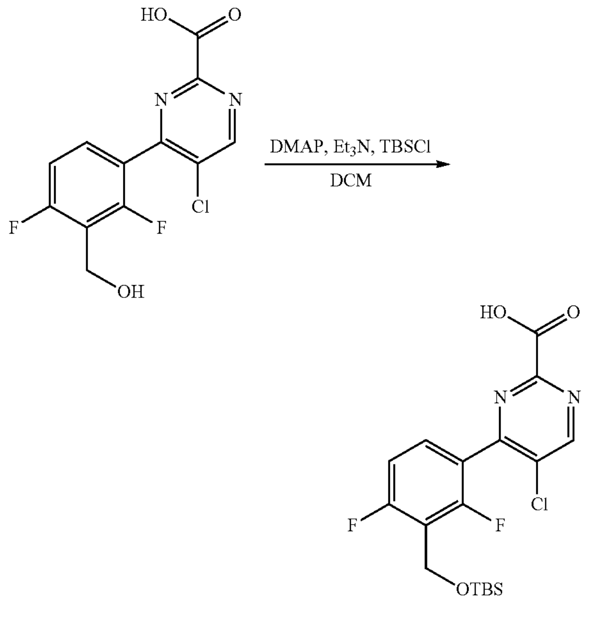

4-(3-(((tert-butyldimethylsilyl)oxy)methyl)-2,4-difluorophenyl)-5-chloropyrimidine-2-carboxylic acid To a solution of the product from the previous step (1.86 g, 6.19 mmol, 1 eq) in $CH_2Cl_2$ (20 mL) were added DMAP (151.16 mg, 1.24 mmol, 0.2 eq), $Et_3N$ (1.25 g, 12.37 mmol, 1.72 mL, 2 eq) and TBSCl (1.86 g, 12.37 mmol, 1.52 mL, 2 eq). After stirring at 25° C. for 16 h, the mixture was concentrated to remove $CH_2Cl_2$, diluted with $H_2O$ (40 mL) and extracted with EtOAc (40 mL×2). The combined organic layer was dried over $Na_2SO_4$, filtered and concentrated under reduced pressure. The residue was purified by chromatography on silica gel ($CH_2Cl_2$/Methanol=10/1) to afford the title compound (600 mg, 1.45 mmol, 23% yield) as a white solid.

MS (ES+) $C_{18}H_{21}N_2O_3ClF_2Si$ requires: 414 and 416, found: 415 and 417 $[M+H]^+$. $^1H$ NMR (400 MHz, DMSO-$d_6$) δ=8.96 (s, 1H), 7.70-7.47 (m, 1H), 7.32 (t, J=8.6 Hz, 1H), 4.78 (s, 2H), 0.85 (s, 9H), 0.08 (s, 6H).

INTERMEDIATE A-57

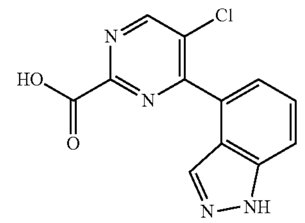

5-Chloro-4-(1H-indazol-4-yl)pyrimidine-2-carboxylic acid

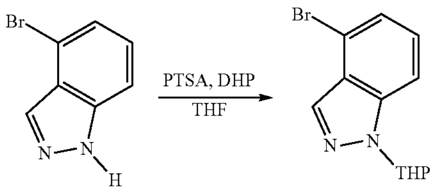

4-Bromo-1-(tetrahydro-2H-pyran-2-yl)-1H-indazole To a solution of 4-bromo-1H-indazole (5 g, 25.38 mmol, 1 eq) in THF (40 mL) were added 4-methylbenzenesulfonic acid (436.99 mg, 2.54 mmol, 0.1 eq) and DHP (4.27 g, 50.75 mmol, 4.64 mL, 2 eq). After stirring at 70° C. for 16 h, the mixture was concentrated under reduced pressure. The residue was purified by silica gel chromatography (ISCO®; 40 g SepaFlash® Silica Flash Column, Eluent 0-30% EtOAC/Petroleum ether gradient @30 mL/min) to afford the title compound (7 g, 24.90 mmol, 98% yield) as colourless oil.

$^1H$ NMR (400 MHz, $CDCl_3$) δ=8.06 (s, 1H), 7.57 (d, J=8.4 Hz, 1H), 7.40-7.31 (m, 1H), 7.29-7.21 (m, 1H), 5.73 (dd, J=2.8, 9.2 Hz, 1H), 4.09-3.95 (m, 1H), 3.87-3.66 (m, 1H), 2.68-2.47 (m, 1H), 2.25-2.07 (m, 2H), 1.94-1.60 (m, 3H).

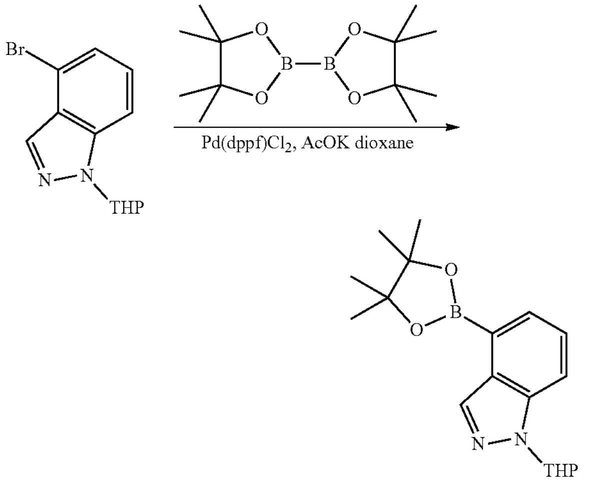

1-(Tetrahydro-2H-pyran-2-yl)-4-(4,4,5,5-tetramethyl-1,3,2-dioxaborolan-2-yl)-1H-indazole To a solution of the product from the previous step (7 g, 24.90 mmol, 1 eq) in dioxane (70 mL) were added BPD (9.48 g, 37.35 mmol, 1.5 eq), AcOK (7.33 g, 74.69 mmol, 3 eq) and $Pd(dppf)Cl_2 \cdot CH_2Cl_2$ (1.02 g, 1.24 mmol, 0.05 eq) under $N_2$. After being stirred at 100° C. for 3 h, the mixture was concentrated under reduced pressure to afford the title compound (8.17 g, 24.89 mmol, 100% yield) as black oil. MS (ES+) $C_{18}H_{25}BN_2O_3$ requires: 328, found: 329 $[M+H]^+$.

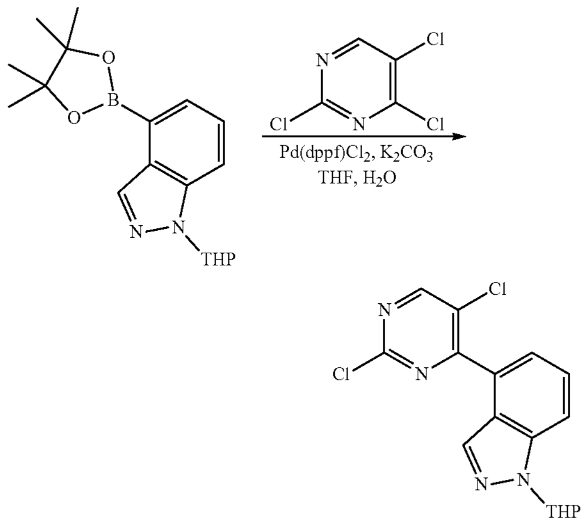

To a solution of 1-tetrahydropyran-2-yl-4-(4, 4, 5, 5-tetramethyl-1, 3, 2-dioxaborolan-2-yl) indazole (8.17 g, 24.89 mmol, 1 eq) in dioxane (80 mL) and $H_2O$ (15 mL) were added 2,4,5-trichloropyrimidine (5.48 g, 29.87 mmol, 1.2 eq), $Pd(dppf)Cl_2$ (1.82 g, 2.49 mmol, 0.1 eq) and $K_2CO_3$ (10.32 g, 74.68 mmol, 3 eq) under $N_2$. After stirring at 60° C. for 16 h, the mixture was diluted with water (100 mL), extracted with EtOAc (100 mL×3). The combined organic phase was dried over $Na_2SO_4$, filtered and concentrated under reduced pressure. The residue was purified by silica gel chromatography (ISCO®; 40 g SepaFlash® Silica Flash Column, Eluent 0~20% EtOAC/Petroleum ether gradient @50 mL/min) to afford the title compound (7.9 g, 22.62 mmol, 90% yield) as a white solid.

$^1H$ NMR (400 MHz, $CDCl_3$) δ=8.75 (s, 1H), 8.19 (d, J=0.6 Hz, 1H), 7.83 (d, J=8.5 Hz, 1H), 7.70 (d, J=6.7 Hz, 1H), 7.53 (dd, J=7.3, 8.4 Hz, 1H), 5.82 (dd, J=2.8, 9.0 Hz, 1H), 4.08-4.01 (m, 1H), 3.89-3.68 (m, 1H), 2.74-2.48 (m, 1H), 2.32-2.08 (m, 2H), 1.89-1.58 (m, 3H).

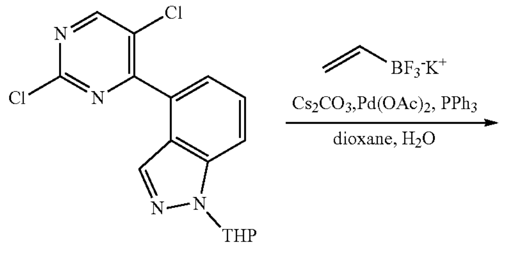

-continued

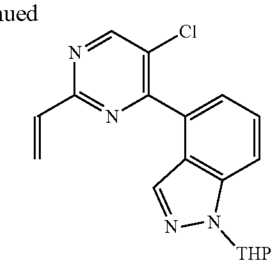

4-(5-Chloro-2-vinylpyrimidin-4-yl)-1-(tetrahydro-2H-pyran-2-yl)-1H-indazole To a solution of the product from the previous step (3 g, 8.59 mmol, 1 eq) in dioxane (30 mL) and $H_2O$ (6 mL) were added potassium (vinyl)trifluoroborate (1.38 g, 10.31 mmol, 1.2 eq), $Cs_2CO_3$ (5.60 g, 17.18 mmol, 2 eq), $Pd(OAc)_2$ (289.30 mg, 1.29 mmol, 0.15 eq) and $PPh_3$ (675.97 mg, 2.58 mmol, 0.3 eq) under $N_2$. After stirring at 110° C. for 16 h, the mixture was diluted with water (50 mL), extracted with EtOAc (50 mL×3), dried over $Na_2SO_4$, filtered and concentrated under reduced pressure. The residue was purified by silica gel chromatography (ISCO®; 40 g SepaFlash® Silica Flash Column, Eluent 0~20% EtOAC/Petroleum ether gradient @50 mL/min) to afford the title compound (0.9 g, 2.64 mmol, 30% yield) as colourless oil.

$^1H$ NMR (400 MHz, $CDCl_3$) δ=8.82 (s, 1H), 8.19 (s, 1H), 7.79 (d, J=8.5 Hz, 1H), 7.69 (d, J=7.2 Hz, 1H), 7.53 (dd, J=7.3, 8.4 Hz, 1H), 6.96 (dd, J=10.5, 17.3 Hz, 1H), 6.71 (dd, J=1.6, 17.3 Hz, 1H), 5.87-5.76 (m, 2H), 4.10-4.02 (m, 1H), 3.84-3.75 (m, 1H), 2.74-2.55 (m, 1H), 2.30-2.09 (m, 2H), 1.91-1.65 (m, 3H).

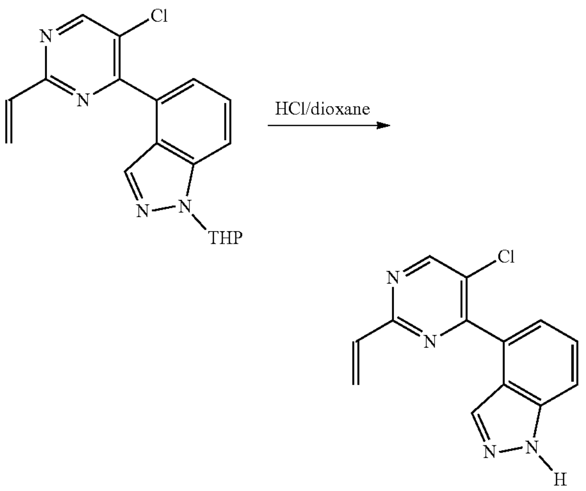

4-(5-Chloro-2-vinylpyrimidin-4-yl)-1H-indazole To a solution of the product from the previous step (800 mg, 2.35 mmol, 1 eq) in $CH_2Cl_2$ (10 mL) was added TfOH (5 mL). After stirring at 25° C. for 2 h, the mixture was neutralized with saturated $Na_2CO_3$ aqueous solution (20 mL) and, extracted with EtOAc (20 mL×3), the combined organic phase washed with brine (50 mL×3), dried over $Na_2SO_4$, filtered and concentrated under reduced pressure to afford the title compound (1.7 g, crude) as a yellow solid. MS (ES+) $C_{13}H_9N_4Cl$ requires: 256 and 258, found: 257 and 259 $[M+H]^+$,

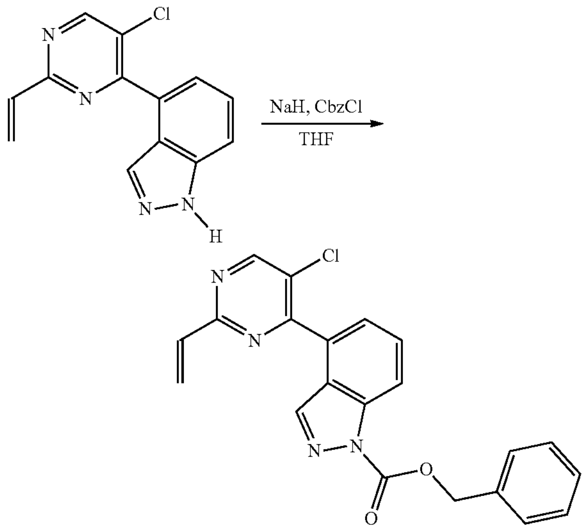

Benzyl 4-(5-chloro-2-vinylpyrimidin-4-yl)-1H-indazole-1-carboxylate To a solution of the product from the previous step (1.7 g, 6.62 mmol, 1 eq) in THF (10 mL) was added NaH (317.86 mg, 7.95 mmol, 60% in mineral oil, 1.2 eq) at 0° C. under $N_2$. After stirring at 0° C. for 0.5 hr, CbzCl (1.69 g, 9.93 mmol, 1.41 mL, 1.5 eq) was added into the mixture. After stirring at 25° C. for 3 h, the mixture was quenched with saturated $NH_4Cl$ aqueous solution (10 mL), the mixture was extracted with EtOAc (10 mL×3), the combined organic phase was dried over $Na_2SO_4$, filtered and the filtrate was concentrated under reduced pressure. The residue was purified by silica gel chromatography (ISCO®; 10 g SepaFlash® Silica Flash Column, Eluent 0~20% EtOAC/Petroleum ether gradient @30 mL/min) to afford the title compound (0.9 g, 2.30 mmol, 34% yield) as colourless oil. $^1$H NMR (400 MHz, $CDCl_3$) δ=8.84 (s, 1H), 8.44 (d, J=8.5 Hz, 1H), 8.38 (s, 1H), 7.85 (d, J=7.5 Hz, 1H), 7.69 (dd, J=7.5, 8.3 Hz, 1H), 7.61-7.56 (m, 2H), 7.48-7.30 (m, 3H), 6.95 (dd, J=10.5, 17.3 Hz, 1H), 6.70 (dd, J=1.6, 17.4 Hz, 1H), 5.83 (dd, J=1.5, 10.5 Hz, 1H), 5.60 (s, 2H).

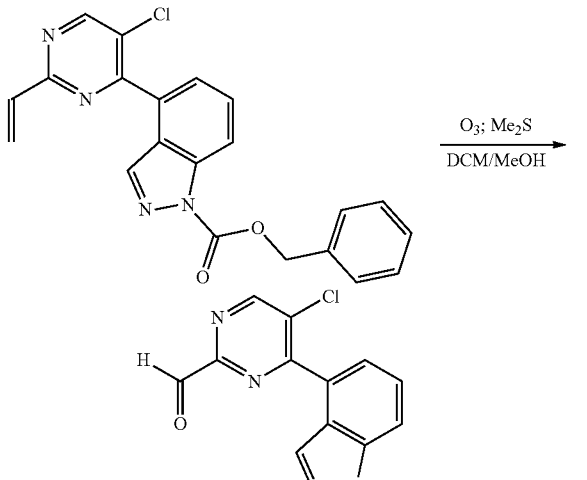

Benzyl 4-(5-chloro-2-formylpyrimidin-4-yl)-1H-indazole-1-carboxylate A stream of 03 was passed through a cooled (−78° C.) solution of the product from the previous step (900 mg, 2.30 mmol, 1 eq) in MeOH (3 mL) and $CH_2Cl_2$ (10 mL). After stirring at −78° C. for 15 min, the mixture was purged with $N_2$ then $Me_2S$ (1.78 g, 28.65 mmol, 2.10 mL, 12.44 eq) was added to the mixture, which was then stirred at 25° C. for 3 h. The mixture was concentrated under reduced pressure, diluted with EtOAc (10 mL), washed with brine (10 mL×3), dried over $Na_2SO_4$, filtered, and concentrated under reduced pressure. The residue was purified by silica gel chromatography (ISCO®; 10 g SepaFlash® Silica Flash Column, Eluent 0~50% EtOAC/Petroleum ether gradient @50 mL/min) to afford the title compound (300 mg, crude) as colourless oil. MS (ES+) $C_{20}H_{13}N_4ClO_3$ requires: 392 and 394, found: 393 and 395 $[M+H]^+$.

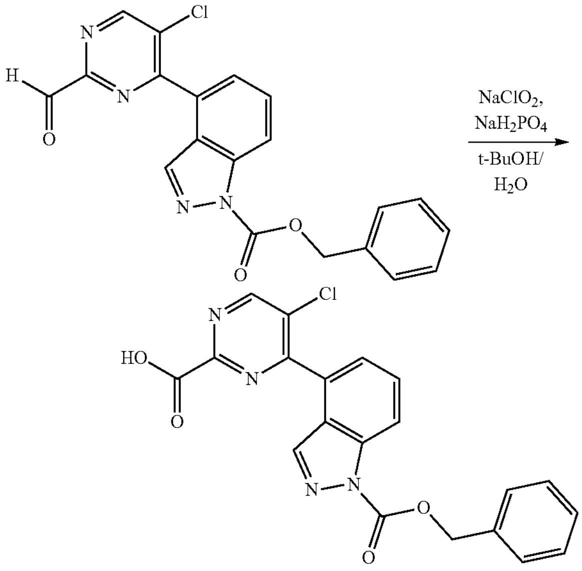

4-(1-((Benzyloxy)carbonyl)-1H-indazol-4-yl)-5-chloropyrimidine-2-carboxylic acid To a solution of the product from the previous step (250 mg, 636.46 μmol, 1 eq) in t-BuOH (6 mL) and $H_2O$ (1.5 mL) were added $NaH_2PO_4$ (61.09 mg, 509.17 μmol, 0.8 eq) and sodium chlorite (172.69 mg, 1.91 mmol, 3 eq). After stirring at 25° C. for 3 h, the mixture was poured into water (10 mL), extracted by EtOAc (10 mL×3), the combined organic phase was concentrated under reduced pressure to afford the title compound (100 mg, 244.62 μmol, 38% yield) as a white solid. $^1$H NMR (400 MHz, $CDCl_3$) δ=8.93-8.86 (m, 1H), 8.46 (d, J=2.1 Hz, 1H), 8.32 (dd, J=2.1, 6.8 Hz, 1H), 7.78 (d, J=7.1 Hz, 2H), 7.61-7.53 (m, 2H), 7.49-7.35 (m, 3H), 5.56 (s, 2H).

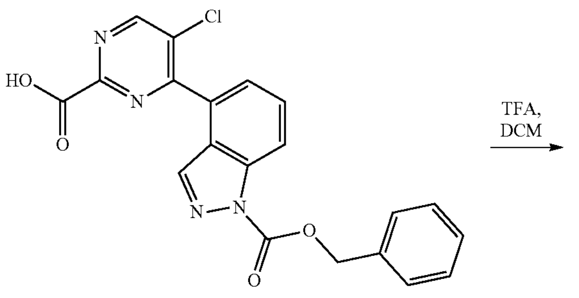

-continued

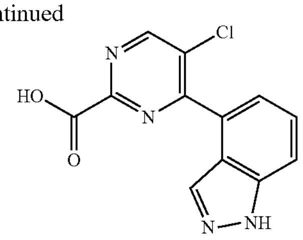

5-Chloro-4-(1H-indazol-4-yl)pyrimidine-2-carboxylic acid To a solution of the product from the previous step (100 mg, 244.62 μmol, 1 eq) in $CH_2Cl_2$ (0.2 mL) was added TFA (2.79 g, 24.46 mmol, 1.81 mL, 100 eq). After stirring at 40° C. for 0.5 h, the mixture was concentrated under reduced pressure to obtain the trifluoroacetic acid salt of the title compound (90 mg, 231.55 μmol, 94% yield) as a brown solid. $^1H$ NMR (400 MHz, DMSO-$d_6$) δ=13.42 (s, 1H), 9.10 (s, 1H), 8.17 (s, 1H), 7.77 (br d, J=8.4 Hz, 1H), 7.60 (br d, J=7.0 Hz, 1H), 7.57-7.48 (m, 1H).

INTERMEDIATE A-58

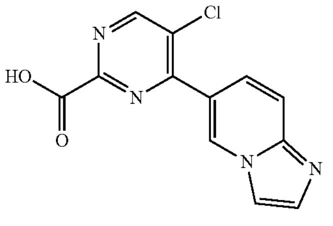

5-Chloro-4-(imidazo[1,2-a]pyridin-6-yl)pyrimidine 2-carboxylic acid

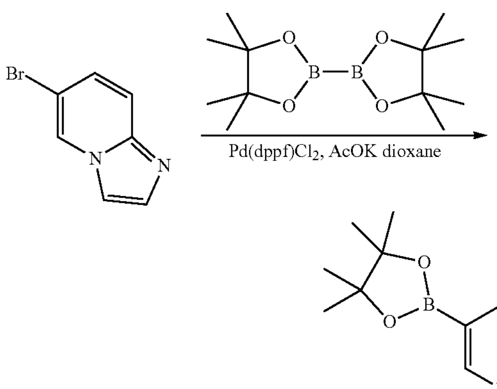

6-(4,4,5,5-Tetramethyl-1,3,2-dioxaborolan-2-yl)imidazo [1,2-a]pyridine A mixture of 6-bromoimidazo[1,2-a]pyridine (5 g, 25.38 mmol, 1 eq), BPD (7.09 g, 27.91 mmol, 1.1 eq), $Pd(dppf)Cl_2$ (1.86 g, 2.54 mmol, 0.1 eq) and AcOK (7.47 g, 76.13 mmol, 3 eq) in dioxane (50 mL) was degassed and purged with $N_2$ 3 times, and then the mixture was stirred at 90° C. for 6 h under $N_2$. The reaction mixture was filtered and the filter cake was washed with EtOAc (50 mL), The filtrate was concentrated under reduced pressure to afford the title compound (6 g, crude) as a brown solid. MS (ES+) $C_{13}H_{17}BN_{2}02$ requires: 162, found: 163 [M-pinacol+H]$^+$.

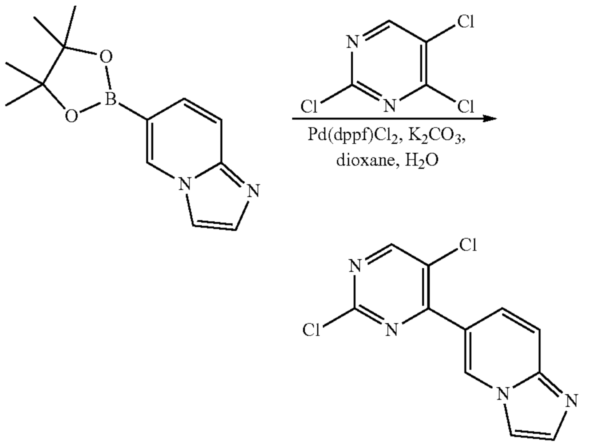

6-(2,5-Dichloropyrimidin-4-yl)imidazo[1,2-a]pyridine A mixture of 2,4,5-trichloropyrimidine (5.41 g, 29.50 mmol, 1.2 eq), the product from the previous step (6 g, 24.58 mmol, 1 eq), $K_2CO_3$ (10.19 g, 73.74 mmol, 3 eq) and Pd(dppf) $Cl_2$ (1.80 g, 2.46 mmol, 0.1 eq) in water (10 mL) and dioxane (100 mL) was degassed and purged with $N_2$ 3 times, and then the mixture was stirred at 60° C. for 16 h under $N_2$. The mixture was diluted with EtOAc (200 mL), dried over $Na_2SO_4$, filtered and concentrated under reduced pressure. The residue was purified by silica gel chromatography (80 g SepaFlash® Silica Flash Column, Eluent 80~90% EtOAC/Petroleum ether gradient @100 mL/min) to afford the title compound (700 mg, 2.11 mmol, 8% yield) as a yellow solid. MS (ES+) $C_{11}H_6Cl_2N_4$ requires: 264 and 266, found: 265 and 267 [M+H]$^+$,

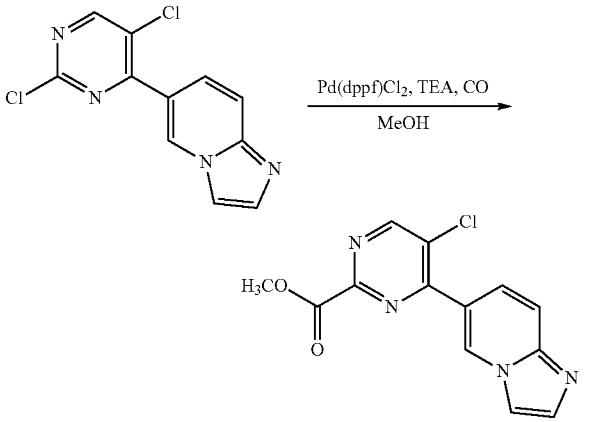

Methyl 5-chloro-4-(imidazo[1,2-a]pyridin-6-yl)pyrimidine-2-carboxylate To a solution of the product from the previous step (200 mg, 754.44 μmol, 1 eq) in MeOH (4 mL) were added $Pd(dppf)Cl_2$ (55.20 mg, 75.44 μmol, 0.1 eq) and $Et_3N$ (229.02 mg, 2.26 mmol, 315.03 μL, 3 eq) under $N_2$. The suspension was degassed under vacuum and purged with CO 3 times. After stirring under CO (15 psi) at 50° C. for 5 h, the reaction mixture was concentrated under reduced pressure. The residue was purified by prep-HPLC (column: Phenomenex Gemini-NX C18 75*30 mm*3 um; mobile phase: [water (0.225% FA) —$CH_3CN$]; B %: 0%-10%, 7 min). The eluent was concentrated and freeze-dried to afford the title compound (80 mg, 271.57 μmol, 36% yield) as a white solid. MS (ES+) $C_{13}H_9ClN_4O_2$ requires: 288 and 290, found: 289 and 291 $[M+H]^+$.

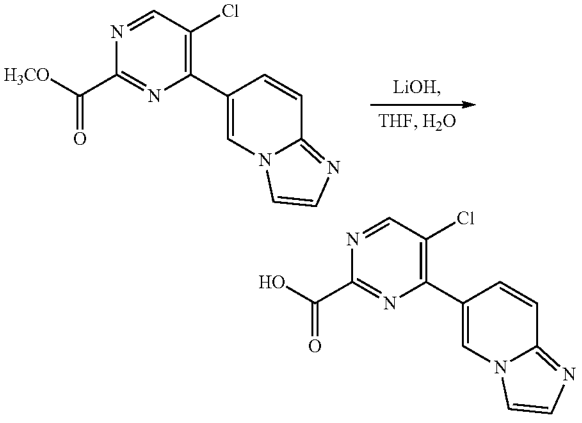

5-Chloro-4-(imidazo[1,2-a]pyridin-6-yl)pyrimidine-2-carboxylic acid To a solution of the product from the previous step (50 mg, 173.20 μmol, 1 eq) in THF (1 mL) and $H_2O$ (0.2 mL) was added $LiOH{\cdot}H_2O$ (21.80 mg, 519.59 μmol, 3 eq). After stirring at 20° C. for 2 h, the mixture was neutralized with aqueous HCl solution (1 M) to pH=6, concentrated under reduced pressure to afford the title compound (50 mg, crude) as a white solid. MS (ES+) $C_{12}H_7ClN_4O_2$ requires: 274 and 276, found: 275 and 277 $[M+H]^+$. $^1H$ NMR (400 MHz, DMSO-$d_6$) δ=9.35-9.30 (m, 1H), 9.18 (s, 1H), 8.27-8.23 (m, 1H), 7.84-7.74 (m, 3H)

INTERMEDIATE A-59

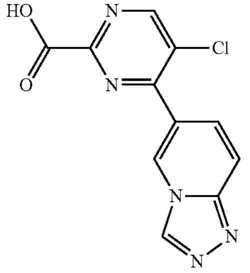

4-([1,2,4]triazolo[4,3-a]pyridin-6-yl)-5-chloropyrimidine-2-carboxylic acid

This compound was obtained using a procedure similar to that used for Intermediate A-58.

INTERMEDIATE A-60

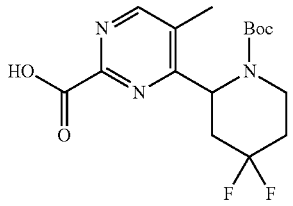

4-(1-(tert-butoxycarbonyl)-4,4-difluoropiperidin-2-yl)-5-methylpyrimidine-2-carboxylic acid

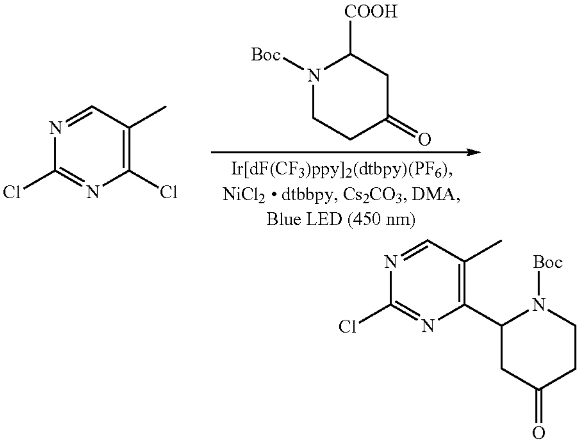

tert-Butyl 2-(2-chloro-5-methylpyrimidin-4-yl)-4-oxopiperidine-1-carboxylate

To an oven-dried 40 mL vial equipped with magnetic stir bar were charged with 2,4-dichloro-5-methylpyrimidine (500 mg, 3.07 mmol, 1 eq), 1-tert-butoxycarbonyl-4-oxopiperidine-2-carboxylic acid (970.01 mg, 3.99 mmol, 1.3 eq), $Ir[dF(CF_3)ppy]_2(dtbpy)(PF_6)$ (34.41 mg, 30.67 μmol, 0.01 eq), $NiCl_2{\cdot}dtbbpy$ (61.04 mg, 153.37 μmol, 0.05 eq), $Cs_2CO_3$ (1.50 g, 4.60 mmol, 1.5 eq), and DMA (35 mL) under $N_2$. Then the reaction mixture was stirred and irradiated with two 34 W blue LED lamps (at approximately 7 cm away) from the light source to maintain the reaction temperature at 25° C. for 14 h. The mixture was diluted with water (50 mL) and extracted with EtOAc (50 mL×2). The combined organic layers were washed with brine (50 mL×3), dried over $Na_2SO_4$, filtered and concentrated under reduced pressure. The residue was purified by silica gel chromatography (40 g SepaFlash® Silica Flash Column, Eluent 10-25% EtOAC/Petroleum ether gradient @60 mL/min) to afford the title compound (390 mg, 1.20 mmol, 78% yield) as a yellow oil.

MS (ES+) $C_{15}H_{20}ClN_3O_3$ requires: 325 and 327, found 326 and 328 $[M+H]^+$. $^1H$ NMR (400 MHz, $CDCl_3$) δ=8.39 (s, 1H), 5.88-5.45 (m, 1H), 4.23-4.11 (m, 1H), 3.70-3.43 (m, 1H), 2.75-2.64 (m, 3H), 2.59-2.44 (m, 1H), 2.35 (s, 3H), 1.43 (s, 9H).

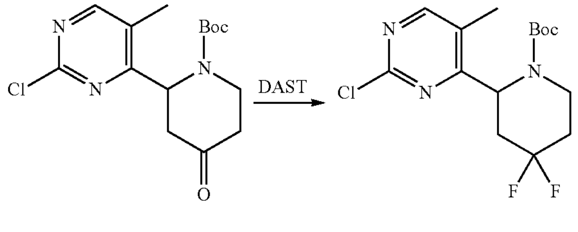

tert-Butyl 2-(2-chloro-5-methylpyrimidin-4-yl)-4,4-difluoropiperidine-1-carboxylate A solution of the product from the previous step (340 mg, 1.04 mmol, 1 eq) in DAST (3.66 g, 22.71 mmol, 3 mL, 21.76 eq) was stirred at −20° C. for 0.5 h. The mixture was warmed to 20° C. and stirred for 6 h. The reaction mixture was quenched by addition of aqueous $Na_2CO_3$ solution (100 mL, 1 M) at 0° C. and extracted with EtOAc (50 mL×2). The combined organic layers were washed with brine (30 mL×2), dried over $Na_2SO_4$, filtered and concentrated under reduced pressure. The residue was purified by silica gel chromatography (20 g SepaFlash® Silica Flash Column, Eluent 10~30% EtOAC/Petroleum ether gradient @30 mL/min) to afford the title compound (100 mg, 287.53 μmol, 27% yield) as a yellow oil. MS (ES+) $C_{15}H_{20}ClF_2N_3O_2$ requires: 347 and 349, found 348 and 350 $[M+H]^+$.

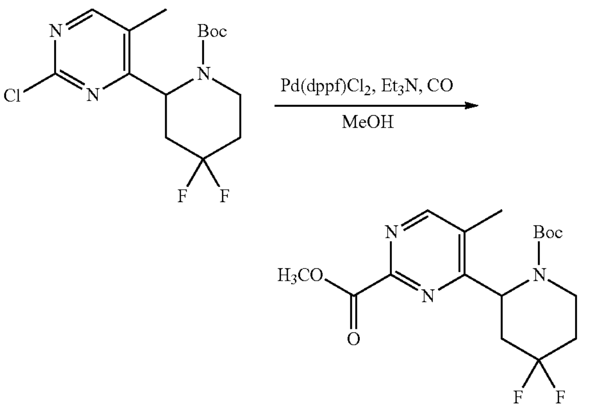

Methyl 4-(1-(tert-butoxycarbonyl)-4,4-difluoropiperidin-2-yl)-5-methylpyrimidine-2-carboxylate To a solution of the product from the previous step (80 mg, 230.03 μmol, 1 eq) in MeOH (5 mL) were added $Pd(dppf)Cl_2$ (16.83 mg, 23.00 μmol, 0.1 eq) and $Et_3N$ (69.83 mg, 690.08 μmol, 96.05 μL, 3 eq) under $N_2$. The suspension was degassed under vacuum and purged with CO several times. The mixture was stirred under CO (15 psi) at 50° C. for 6 h. The reaction mixture was filtered and the filtrate was concentrated under reduced pressure. The residue was purified by silica gel chromatography (10 g SepaFlash® Silica Flash Column, Eluent 20~40% EtOAC/Petroleum ether gradient @30 mL/min) to afford the title compound (80 mg, 202.49 μmol, 88% yield) as yellow oil.

MS (ES+) $C_{17}H_{23}F_2N_3O_4$ requires: 371, found 372 $[M+H]^+$. $^1H$ NMR (400 MHz, $CDCl_3$) δ=8.61 (s, 1H), 5.54-5.37 (m, 1H), 4.23-4.12 (m, 2H), 4.02 (s, 3H), 2.51-2.43 (m, 2H), 2.42 (s, 3H), 2.22-2.07 (m, 2H), 1.34 (s, 9H).

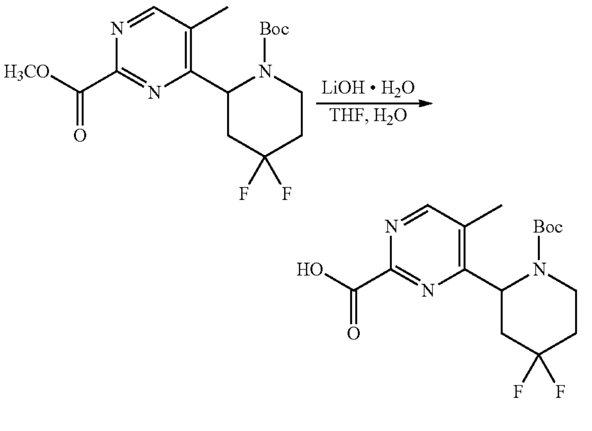

4-(1-(tert-butoxycarbonyl)-4,4-difluoropiperidin-2-yl)-5-methylpyrimidine-2-carboxylic acid To a solution of the product from the previous step (40 mg, 107.71 μmol, 1 eq) in THF (1 mL) was added a solution of $LiOH \cdot H_2O$ (13.56 mg, 323.12 μmol, 3 eq) in $H_2O$ (0.2 mL). After stirring at 20° C. for 2 h, the mixture was neutralized with aqueous solution of HCl (1 M) to pH=7 and concentrated under reduced pressure to afford the title compound (crude) as a white solid. MS (ES+) $C_{16}H_{21}F_2N_3O_4$ requires: 357, found 358 $[M+H]^+$. $^1H$ NMR (400 MHz, DMSO-$d_6$) δ=8.52 (s, 1H), 5.44-5.30 (m, 1H), 4.19-3.96 (m, 2H), 2.48-2.30 (m, 5H), 2.28-2.07 (m, 2H), 1.28 (s, 9H).

INTERMEDIATE A-61

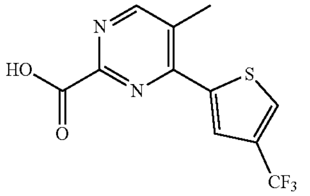

5-methyl-4-(4-(trifluoromethyl)thiophen-2-yl)pyrimidine-2-carboxylic acid

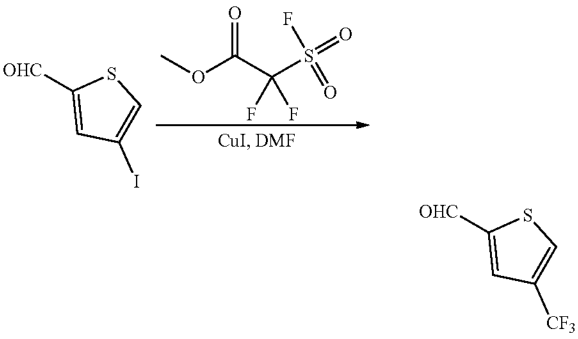

4-(trifluoromethyl)thiophene-2-carbaldehyde To a solution of 4-iodothiophene-2-carbaldehyde (4.3 g, 18.06 mmol, 1 eq) in DMF (30 mL) were added methyl 2,2-difluoro-2-(fluorosulfonyl)acetate (3.47 g, 18.06 mmol, 2.30 mL, 1 eq) and CuI (3.44 g, 18.06 mmol, 1 eq) under $N_2$. After stirring at 100° C. for 16 h, the mixture was diluted with $H_2O$ (100 mL) and extracted with EtOAc (100 mL×2). The combined organic layer was washed with brine (100 mL), dried over anhydrous $Na_2SO_4$ and filtered. The filtrate was concentrated to afford the title compound (2.7 g, crude) as a yellow solid. $^1H$ NMR (400 MHz, DMSO-$d_6$) δ=9.97 (d, J=1.2 Hz, 1H), 8.80 (d, J=1.0 Hz, 1H), 8.32 (t, J=1.3 Hz, 1H).

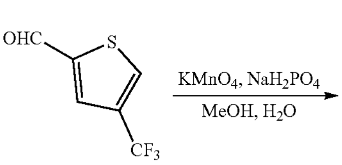

-continued

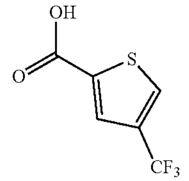

4-(Trifluoromethyl)thiophene-2-carboxylic acid To a solution of the product from the previous step (2.6 g, 14.43 mmol, 1 eq) in $H_2O$ (20 mL) and MeOH (20 mL) were added $KMnO_4$ (2.28 g, 14.43 mmol, 1 eq) and $NaH_2PO_4$ (1.73 g, 14.43 mmol, 1 eq). After stirring at 15° C. for 2 h, the mixture was diluted with $H_2O$ (100 mL) and extracted with EtOAc (100 mL×2). The combined organic layer was washed with brine (100 mL), dried over anhydrous $Na_2SO_4$ and filtered. The filtrate was concentrated to afford the title compound (1.75 g, crude) as a white solid. $^1H$ NMR (400 MHz, DMSO-$d_6$) δ=13.25 (br s, 1H), 8.59-8.53 (m, 1H), 7.93 (d, J=1.1 Hz, 1H).

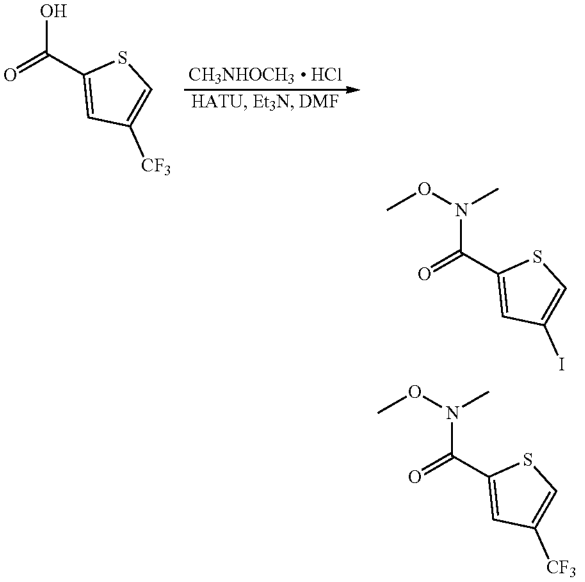

N-methoxy-N-methyl-4-(trifluoromethyl)thiophene-2-carboxamide and 4-iodo-N-methoxy-N-methylthiophene-2-carboxamide To a solution of the product from the previous step (1.65 g, 8.41 mmol, 1 eq) and N-methoxymethanamine hydrochloride salt (902.60 mg, 9.25 mmol, 1.1 eq) in DMF (15 mL) were added $Et_3N$ (2.55 g, 25.24 mmol, 3.51 mL, 3 eq) and HATU (4.80 g, 12.62 mmol, 1.5 eq). After stirring at 10° C. for 2 h, the mixture was diluted with $H_2O$ (100 mL) and extracted with EtOAc (100 mL×2). The combined organic layer was washed with brine (100 mL), dried over anhydrous $Na_2SO_4$ and filtered. The filtrate was concentrated to afford a mixture of N-methoxy-N-methyl-4-(trifluoromethyl)thiophene-2-carboxamide and 4-iodo-N-methoxy-N-methylthiophene-2-carboxamide (1.9 g, crude) as yellow oil. MS (ES+) $C_8H_8NO_2SF_3$ requires: 239, found 240 $[M+H]^+$, MS (ES+) $C_7H_8NO_2SI$ requires: 297, found 298 $[M+H]^+$.

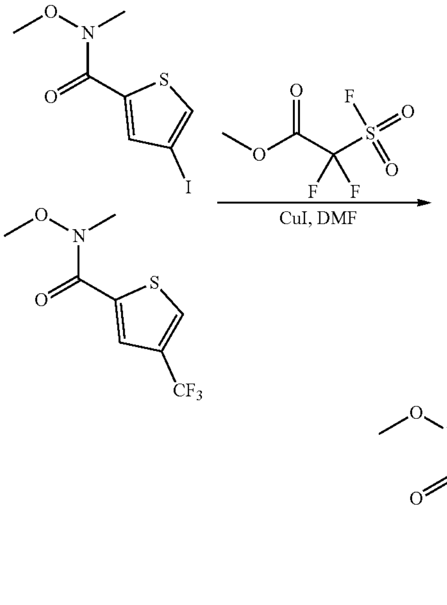

N-methoxy-N-methyl-4-(trifluoromethyl)thiophene-2-carboxamide To a solution of the above mixture (1.9 g, 6.39 mmol, 1 eq) in DMF (20 mL) were added methyl 2,2-difluoro-2-(fluorosulfonyl)acetate (1.23 g, 6.39 mmol, 813.61 μL, 1 eq) and CuI (1.22 g, 6.39 mmol, 1 eq) under $N_2$. After stirring at 100° C. for 32 h, the mixture was diluted with $H_2O$ (100 mL) and extracted with EtOAc (100 mL×2). The combined organic layer was washed with brine (100 mL), dried over anhydrous $Na_2SO_4$ and filtered and concentrated under reduced pressure. The residue was purified by chromatography on silica gel (eluent Petroleum ether/EtOAc=1:1) to afford the title compound (1.8 g) as yellow oil. $^1H$ NMR (400 MHz, DMSO-$d_6$) δ=8.58 (s, 1H), 7.98 (s, 1H), 3.80 (s, 3H), 3.32 (s, 3H).

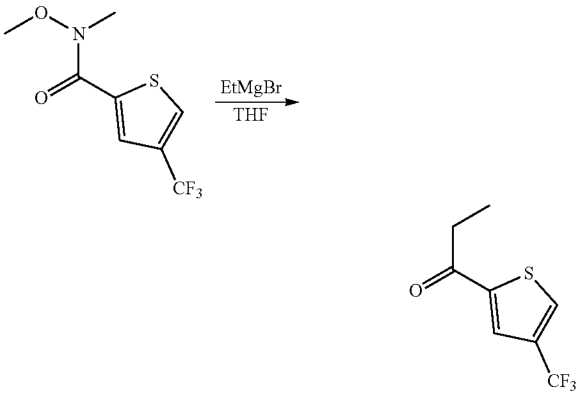

1-(4-(Trifluoromethyl)thiophen-2-yl)propan-1-one To a solution of the product from the previous step (1.7 g, 7.11 mmol, 1 eq) in THF (20 mL) was added EtMgBr (3 M in diethyl ether, 3.55 mL, 1.5 eq) under $N_2$. After stirring at 0° C. for 1 h, the mixture was poured into 1M HCl aqueous solution (40 mL) and extracted with EtOAc (40 mL×2). The combined organic layer was washed with brine (40 mL), dried over anhydrous $Na_2SO_4$ and filtered and concentrated under reduced pressure. The residue was purified by chromatography on silica gel (eluent Petroleum ether/EtOAc=5:1) to afford the title compound (1 g, 4.80 mmol, 67% yield) as a white solid.

MS (ES+) $C_8H_7OSF_3$ requires: 208, found 209 $[M+H]^+$. $^1H$ NMR (400 MHz, DMSO-$d_6$) δ=8.71 (s, 1H), 8.33 (s, 1H), 3.12 (q, J=7.2 Hz, 2H), 1.15 (t, J=7.2 Hz, 3H).

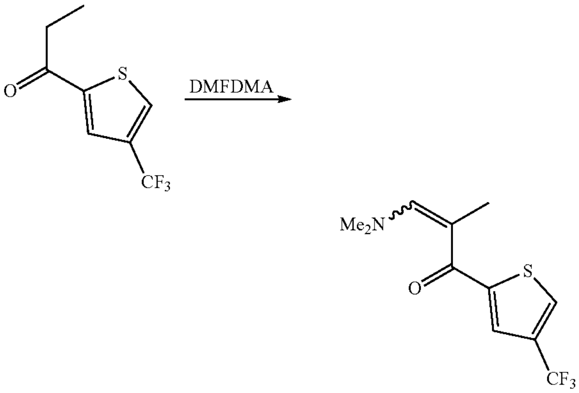

3-(Dimethylamino)-2-methyl-1-(4-(trifluoromethyl)thiophen-2-yl)prop-2-en-1-one A mixture of DMFDMA (10 mL) and the product from the previous step (750 mg, 3.60 mmol, 1 eq) was stirred at 120° C. for 2 h. The mixture was concentrated under reduced pressure to afford the title compound (950 mg, crude) as a yellow oil. MS (ES+) $C_{11}H_{12}NOSF_3$ requires: 263, found 264 $[M+H]^+$.

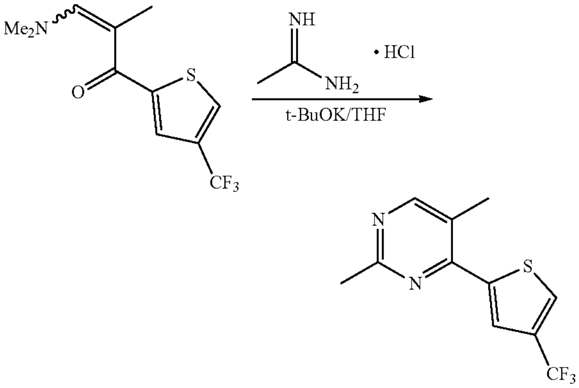

2,5-Dimethyl-4-(4-(trifluoromethyl)thiophen-2-yl)pyrimidine To a solution of acetamidine hydrochloride (511.72 mg, 5.41 mmol, 1.5 eq) in THF (10 mL) was added t-BuOK (607.34 mg, 5.41 mmol, 1.5 eq). The mixture was stirred at 60° C. for 15 min. Then to the mixture was added the product from the previous step (950 mg, 3.61 mmol, 1 eq) and the mixture was stirred at 60° C. for 6 h. The mixture was concentrated to remove THF, diluted with $H_2O$ (30 mL) and extracted with EtOAc (30 mL×2). The combined organic phase was washed with brine (30 mL), dried over anhydrous $Na_2SO_4$ and filtered and the filtrate was concentrated under reduced pressure. The residue was purified by prep-TLC ($SiO_2$, eluent Petroleum ether/EtOAc=1:1) to afford the title compound (40 mg, 122.36 μmol, 3% yield) as a yellow solid. MS (ES+) $C_{11}H_9N_2SF_3$ requires: 258, found 259 $[M+H]^+$.

5-methyl-4-[4-(trifluoromethyl)-2-thienyl]pyrimidine-2-carboxylic acid

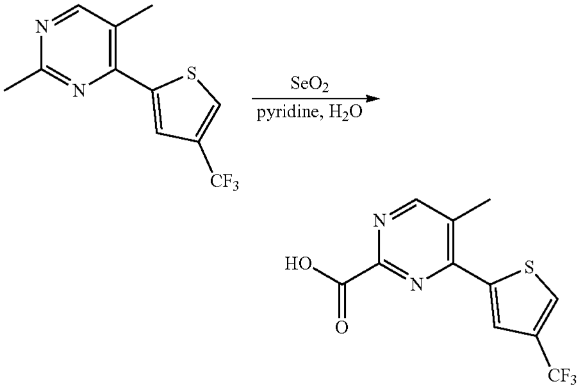

5-Methyl-4-(4-(trifluoromethyl)thiophen-2-yl)pyrimidine-2-carboxylic acid

To a solution of the product from the previous step (40 mg, 122.36 μmol, 1 eq) in pyridine (2 mL) and $H_2O$ (0.2 mL) was added $SeO_2$ (67.88 mg, 611.78 μmol, 66.55 μL, 5 eq). After stirring at 120° C. for 16 h, the mixture was filtered and the filtrate was concentrated to afford the title compound (45 mg, crude) as a yellow oil. MS (ES+) $C_{11}H_7N_2O_2SF_3$ requires: 288, found 289 $[M+H]^+$.

INTERMEDIATE A-62

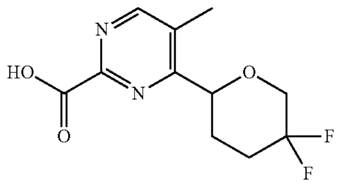

4-(5,5-difluorotetrahydro-2H-pyran-2-yl)-5-methylpyrimidine-2-carboxylic acid

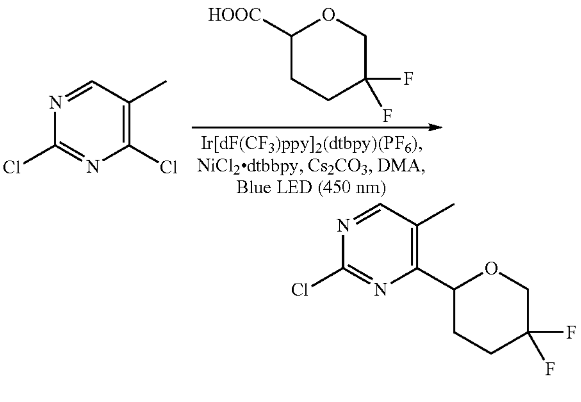

2-Chloro-4-(5,5-difluorotetrahydro-2H-pyran-2-yl)-5-methylpyrimidine To a solution of 2,4-dichloro-5-methylpyrimidine (75 mg, 0.46 mmol, 1 eq) in DMA (10 mL) were added 5,5-difluorotetrahydropyran-2-carboxylic acid (100 mg, 0.78 mmol, 1.3 eq), $Ir[dF(CF_3)ppy]_2(dtbpy)(PF_6)$ (5.6 mg, 0.46 µmol, 0.01 eq), $NiCl_2{\cdot}dtbbpy$ (10 mg, 0.023 mmol, 0.05 eq) and $Cs_2CO_3$ (224.38 mg, 0.69 mmol, 1.5 eq) under $N_2$. Then the mixture was stirred and irradiated with two 34 W blue LED lamps (at approximately 7 cm away) from the light source to keep the reaction temperature at 25° C. for 14 h. Another batch photo reaction (75 mg scale) was set up under the same conditions, and two batches were combined for work-up. The combined reaction mixture was diluted with water (20 mL), extracted with EtOAc (20 mL×3), washed with brine (20 mL×3), dried over $Na_2SO_4$, filtered and concentrated under reduced pressure. The residue was purified by silica gel chromatography (ISCO®; 10 g SepaFlash® Silica Flash Column, Eluent 0~20% EtOAC/Petroleum ether gradient @50 mL/min) to afford the title compound (50 mg, 201.61 µmol, 21% yield) as colourless oil. $^1H$ NMR (400 MHz, $CDCl_3$) δ=8.34 (s, 1H), 4.54 (dd, J=2.1, 10.8 Hz, 1H), 4.01-3.92 (m, 1H), 3.66-3.52 (m, 1H), 2.43-2.30 (m, 4H), 2.30-2.19 (m, 1H), 2.10-1.89 (m, 2H).

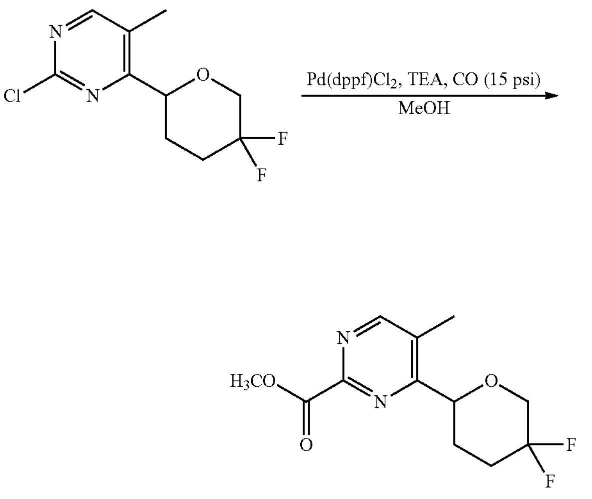

Methyl 4-(5,5-difluorotetrahydro-2H-pyran-2-yl)-5-methylpyrimidine-2-carboxylate To a solution of the product from the previous step (50 mg, 201.08 µmol, 1 eq) in MeOH (1 mL) were added Pd(dppf) $Cl_2$ (7.36 mg, 10.05 µmol, 0.05 eq) and $Et_3N$ (40.69 mg, 402.16 µmol, 55.98 µL, 2 eq) under $N_2$. The suspension was degassed under vacuum and purged with CO several times. After stirring under CO (15 psi) at 60° C. for 32 h, the mixture was concentrated under reduced pressure. The residue was purified by silica gel chromatography (ISCO®; 4 g SepaFlash® Silica Flash Column, Eluent 0~50% EtOAC/Petroleum ether gradient @30 mL/min) to afford the title compound (30 mg, 110.19 µmol, 54% yield) as a white solid. MS ($ES^+$) $C_{12}H_{14}N_2O_3F_2$ requires: 272, found 273 $[M+H]^+$.

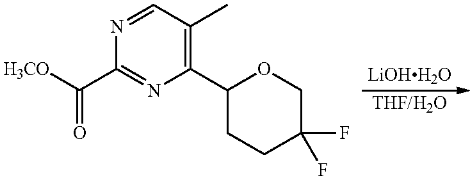

-continued

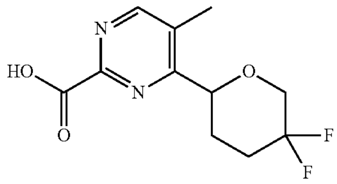

4-(5,5-difluorotetrahydro-2H-pyran-2-yl)-5-methylpyrimidine-2-carboxylic acid To a solution of the product from the previous step (25 mg, 91.83 µmol, 1 eq) in MeOH (1 mL) and $H_2O$ (0.3 mL) was added $LiOH{\cdot}H_2O$ (11.56 mg, 275.48 µmol, 3 eq). After stirring at 25° C. for 16 h, the mixture was neutralized with HCl aqueous solution (1 M) to adjust pH to 7, and concentrated under reduced pressure to afford the title compound (40 mg, crude) as a white solid. MS ($ES^+$) $C_{11}H_{12}N_2O_3F_2$ requires: 258, found 259 $[M+H]^+$.

The following compounds were obtained using procedures reported in the literature.

TABLE 4

Amino oxazepine intermediates. I.

| Int. | Structure | IUPAC name |
|---|---|---|
| B-1 | 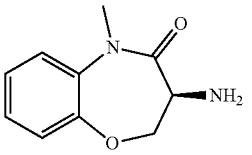 | (S)-3-amino-5-methyl-2,3-dihydrobenzo[b][1,4]oxazepin-4(5H)-one |
| B-2 | 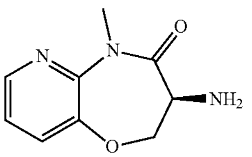 | (S)-3-amino-5-methyl-2,3-dihydropyrido[3,2-b][1,4]oxazepin-4(5H)-one |
| B-3 | 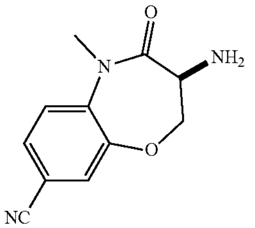 [SMILES: CN1C(=O)[C@@H](N)COc2cc(C#N)ccc21] | (S)-3-amino-5-methyl-4-oxo-2,3,4,5-tetrahydrobenzo[b][1,4]oxazepine-8-carbonitrile |

INTERMEDIATE B-4

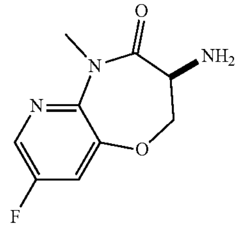

(S)-3-amino-8-fluoro-5-methyl-2,3-dihydropyrido[3,2-b][1,4]oxazepin-4 (5H)-one

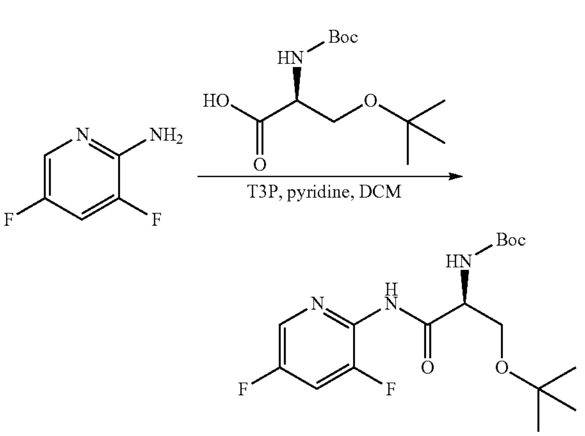

tert-Butyl (S)-(3-(tert-butoxy)-1-((3,5-difluoropyridin-2-yl)amino)-1-oxopropan-2-yl)carbamate To a solution of N-(tert-butoxycarbonyl)-O-(tert-butyl)-L-serine (5 g, 19.13 mmol, 1 eq) and 3, 5-difluoropyridin-2-amine (4.98 g, 38.27 mmol, 2 eq) in $CH_2Cl_2$ (50 mL) was added pyridine (4.54 g, 57.40 mmol, 4.63 mL, 3 eq). After stirring at 0° C. for 5 min, to the mixture was added $T_3P$ (24.35 g, 38.27 mmol, 22.76 mL of a 50% solution in EtOAc, 2 eq) dropwise and stirred at 0° C. for 1 h. The mixture was diluted with $H_2O$ (200 mL) and extracted with $CH_2Cl_2$ (200 mL×2). The combined organic layer was dried over $Na_2SO_4$, filtered, concentrated under reduced pressure, and the residue was purified by chromatography on silica gel (eluent Petroleum ether/EtOAc=1/1) to afford the title compound (7.5 g, 18.08 mmol, 94% yield) as a yellow oil. MS (ES+) $C_{17}H_{25}N_3O_4F_2$ requires: 373, found: 374 $[M+H]^+$.

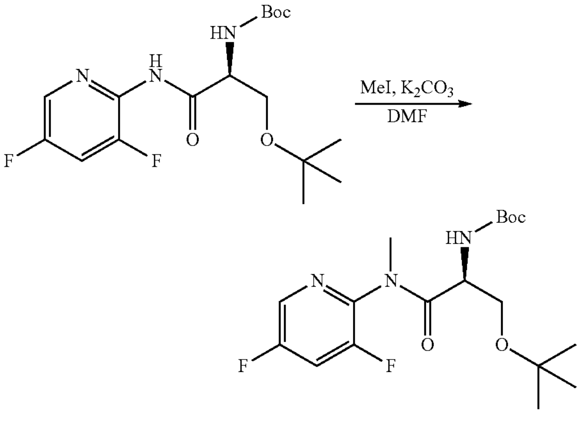

tert-Butyl (S)-(3-(tert-butoxy)-1-((3,5-difluoropyridin-2-yl)(methyl)amino)-1-oxopropan-2-yl)carbamate To a solution of the product from the previous step (3.5 g, 9.37 mmol, 1 eq) in THF (40 mL) were added $K_2CO_3$ (2.10 g, 18.75 mmol, 2 eq) and $CH_3I$ (2.66 g, 18.75 mmol, 1.17 mL, 2 eq). After stirring at 20° C. for 2 h, the mixture was diluted with $H_2O$ (100 mL) and extracted with EtOAc (100 mL×2). The combined organic layer was dried over $Na_2SO_4$, filtered, concentrated under reduced pressure, and the residue was purified by chromatography on silica gel (eluent Petroleum ether/EtOAc=1/1) to afford the title compound (2.7 g, 6.90 mmol, 73% yield) as a yellow oil. MS (ES+) $C_{18}H_{27}N_3O_4F_2$ requires:387, found: 388 $[M+H]^+$.

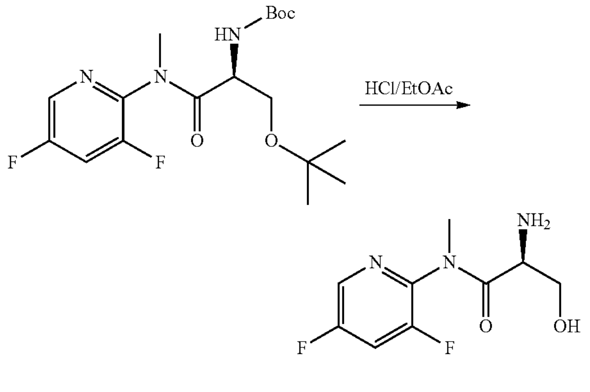

(S)-2-amino-N-(3,5-difluoropyridin-2-yl)-3-hydroxy-N-methylpropanamide

To HCl/EtOAc (4 M, 30 mL, 17.22 eq) was added the product from the previous step (2.7 g, 6.97 mmol, 1 eq) at 0° C. After stirring at 0° C. for 2 h, the mixture was concentrated to afford the HCl salt of the title compound (1.9 g) as a brown solid. MS (ES+) $C_9H_{11}N_3O_2F_2$ requires: 231, found: 232 $[M+H]^+$.

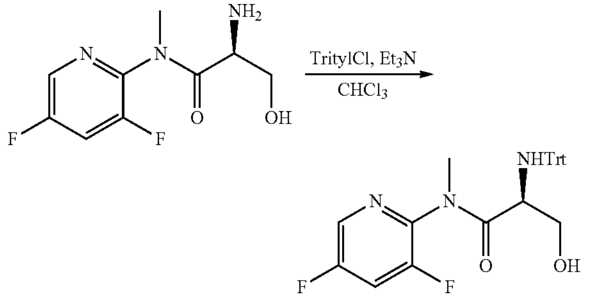

(S)—N-(3,5-difluoropyridin-2-yl)-3-hydroxy-N-methyl-2-(tritylamino)-propanamide To a solution of the HCl salt of the product from the previous step (1.8 g, 7.79 mmol, 1 eq) in chloroform (30 mL) was added [chloro(diphenyl)methyl]benzene (3.26 g, 11.68 mmol, 1.5 eq) and $Et_3N$ (3.15 g, 31.14 mmol, 4.33 mL, 4 eq) at 0° C. After stirring at 25° C. for 16 h, the mixture was dried over $Na_2SO_4$, filtered and concentrated under reduced pressure. The residue was purified by silica gel chromatography (ISCO®; 40 g SepaFlash® Silica Flash Column, Eluent of 0~50% EtOAC/Petroleum ether gradient @40 mL/min) to afford the title compound (1.3 g, 2.75 mmol, 35% yield) as colourless oil. $^1H$ NMR (400 MHz, $CDCl_3$) δ=7.98 (s, 1H), 7.37 (br s, 7H), 7.28-7.07 (m, 9H), 4.52 (br d, J=3.4 Hz, 1H), 4.07-3.91 (m, 1H), 3.78-3.67 (m, 2H), 3.51 (s, 3H).

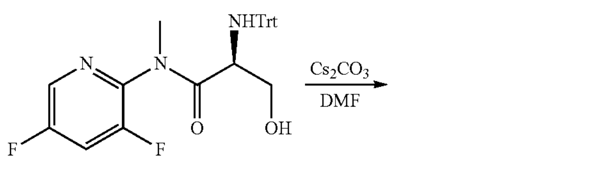

-continued

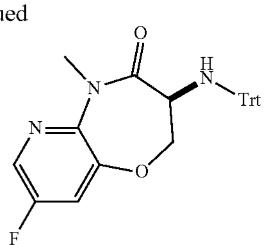

(S)-8-fluoro-5-methyl-3-(tritylamino)-2,3-dihydropyrido[3,2-b][1,4]oxazepin-4 (5H)-one To a solution of the product from the previous step (1.1 g, 2.32 mmol, 1 eq) in DMF (5 mL) was added $Cs_2CO_3$ (2.65 g, 8.13 mmol, 3.5 eq). After stirring at 110° C. for 16 hr, the mixture was diluted with water (20 mL), extracted with EtOAc (20 mL×3), the organic phase was washed with brine (50 mL×3), dried over $Na_2SO_4$, filtered and concentrated under reduced pressure. The residue was purified by silica gel chromatography (ISCO®; 25 g SepaFlash® Silica Flash Column, Eluent of 0~50% EtOAC/Petroleum ether gradient @50 mL/min) to obtain the title compound (750 mg, 1.65 mmol, 71% yield) as a white solid. $^1H$ NMR (400 MHz, $CDCl_3$) δ=8.03-7.97 (m, 1H), 7.40-7.32 (m, 3H), 7.32-7.29 (m, 3H), 7.22-7.00 (m, 10H), 4.55-4.42 (m, 1H), 4.39-4.29 (m, 1H), 3.54-3.42 (m, 1H), 3.29 (d, J=8.4 Hz, 1H), 2.88 (s, 3H).

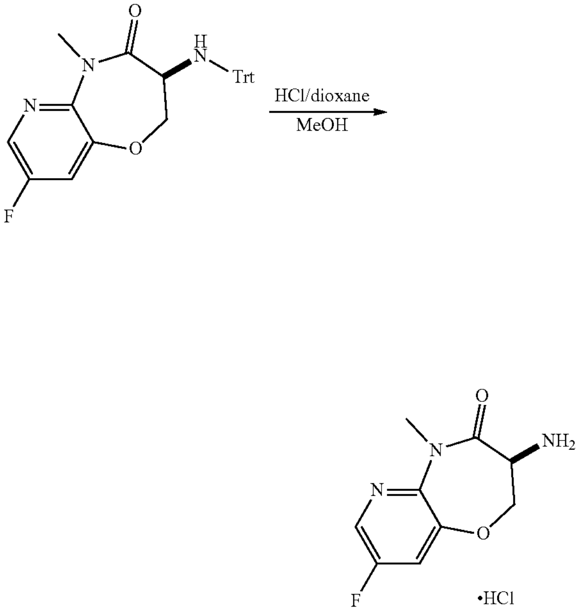

(3S)-3-amino-8-fluoro-5-methyl-2, 3-dihydropyrido[3, 2-b][1, 4]oxazepin-4-one To a solution of the product from the previous step (650 mg, 1.43 mmol, 1 eq) in dioxane (20 mL) and MeOH (2.25 mL) was added HCl/dioxane (4 M, 1.15 mL, 3.2 eq). After stirring at 25° C. for 16 hr, the mixture was concentrated under reduced pressure. The residue which was triturated with $CH_2Cl_2$ at 25° C. for 30 min to afford the HCl salt of the title compound (250 mg, 879.93 μmol, 61% yield) as a white solid. $^1H$ NMR (400 MHz, DMSO-$d_6$) δ=8.35 (d, J=2.6 Hz, 1H), 7.72 (dd, J=2.6, 8.8 Hz, 1H), 4.38 (dd, J=7.2, 9.9 Hz, 1H), 4.12 (dd, J=10.0, 11.5 Hz, 1H), 3.70 (dd, J=7.1, 11.6 Hz, 1H), 3.34 (s, 3H).

INTERMEDIATE B-5

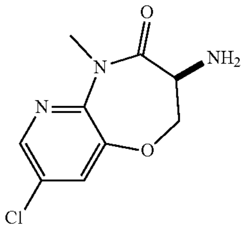

(S)-3-amino-8-chloro-5-methyl-2,3-dihydropyrido[3,2-b][1,4]oxazepin-4 (5H)-one

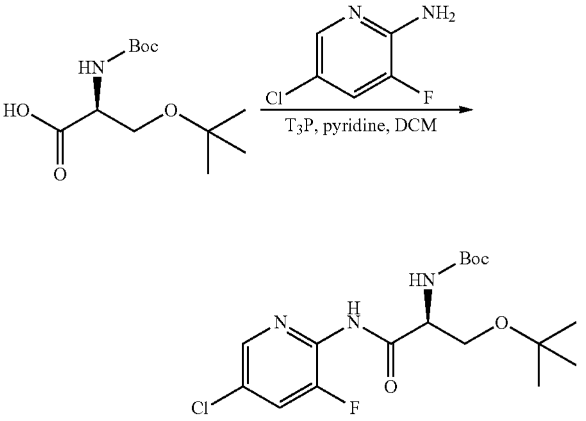

tert-Butyl (S)-(3-(tert-butoxy)-1-((5-chloro-3-fluoropyridin-2-yl)amino)-1-oxopropan-2-yl)carbamate To a solution of 5-chloro-3-fluoro-pyridin-2-amine (14 g, 50.63 mmol, 53% purity, 1 eq) and N-(tert-butoxycarbonyl)-O-(tert-butyl)-L-serine (22.49 g, 86.07 mmol, 1.7 eq) in $CH_2Cl_2$ (150 mL) were added pyridine (12.01 g, 151.89 mmol, 12.26 mL, 3 eq) and $T_3P$ (64.44 g, 101.26 mmol, 60.22 mL of a 50% solution in EtOAc, 2 eq). After stirring at 25° C. for 16 h, the reaction mixture was diluted with water (100 mL) and extracted with $CH_2Cl_2$ (100 mL×2). The combined organic phase was dried over $Na_2SO_4$, filtered and concentrated under reduced pressure. The residue was purified by chromatography on silica gel (eluent Petroleum ether/EtOAc=100/1 to 5/1) to afford the title compound (6 g, 15.39 mmol, 30% yield) as a white solid.

MS (ES+) $C_{17}H_{25}N_3FO_4Cl$ requires: 389, found: 390 $[M+H]^+$. $^1H$ NMR (400 MHz, DMSO-$d_6$) δ=10.36 (s, 1H), 8.35 (d, J=2.1 Hz, 1H), 8.10 (dd, J=2.1, 9.6 Hz, 1H), 6.76-6.65 (m, 1H), 4.42-4.26 (m, 1H), 3.60-3.50 (m, 2H), 1.39 (s, 9H), 1.12 (s, 9H).

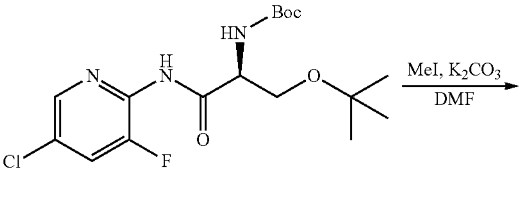

-continued

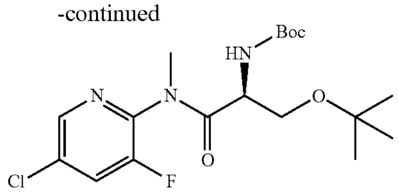

tert-Butyl (S)-(3-(tert-butoxy)-1-((5-chloro-3-fluoropyridin-2-yl)(methyl)amino)-1-oxopropan-2-yl)carbamate To a solution of the product from the previous step (6 g, 15.39 mmol, 1 eq) in THF (60 mL) were added $K_2CO_3$ (8.51 g, 61.56 mmol, 4 eq) and MeI (8.74 g, 61.56 mmol, 3.83 mL, 4 eq). After stirring at 60° C. for 16 h, the mixture was concentrated under reduced pressure to remove THF. The residue was diluted with water (50 mL), extracted with EtOAc (50 mL×2). And the combined organic phase was dried over $Na_2SO_4$, filtered and concentrated under reduced pressure. The residue was purified by chromatography on silica gel (eluent Petroleum ether/EtOAc=5/1) to afford the title compound (5.9 g, 10.96 mmol, 71% yield) as a yellow oil.

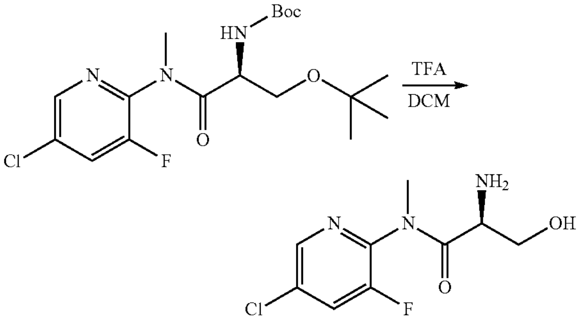

(S)-2-amino-N-(5-chloro-3-fluoropyridin-2-yl)-3-hydroxy-N-methylpropanamide To a solution of the product from the previous step (5.9 g, 14.61 mmol, 1 eq) in $CH_2Cl_2$ (30 mL) was added TFA (1.67 g, 14.61 mmol, 1.08 mL, 1 eq) at 0° C. After stirring at 25° C. for 16 h, the mixture was concentrated under reduced pressure to afford the trifluoroacetic acid salt of the title compound (3 g, 12.11 mmol, 82% yield) as a yellow solid. MS (ES+) $C_9H_{11}N_3FO_2C_1$ requires: 247, found: 248 [M+H]+.

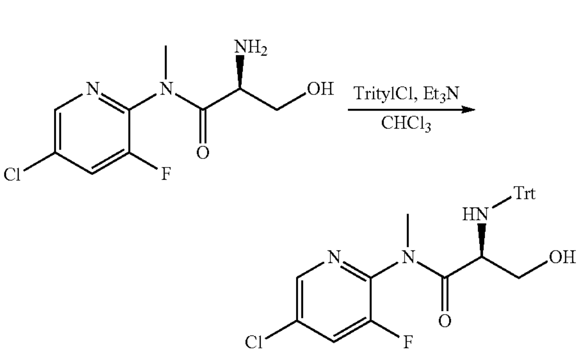

(S)—N-(5-chloro-3-fluoropyridin-2-yl)-3-hydroxy-N-methyl-2-(tritylamino)-propenamide To a solution of the TFA salt of the product from the previous step (3 g, 12.11 mmol, 1 eq) in $CHCl_3$ (60 mL) were added [chloro(diphenyl)methyl]benzene (5.07 g, 18.17 mmol, 1.5 eq) and $Et_3N$ (6.13 g, 60.57 mmol, 8.43 mL, 5 eq) at 0° C. After stirring at 25° C. for 16 h, the mixture was concentrated under reduced pressure to remove $CHCl_3$. The residue was diluted with water (50 mL) and extracted with EtOAc (25 mL×2), and the combined organic phase was dried over $Na_2SO_4$, filtered and concentrated under reduced pressure. The residue was purified by chromatography on silica gel (eluent Petroleum ether/EtOAc=100/1 to 1/1) to the title compound (1.4 g, 2.57 mmol, 21% yield) as a yellow oil. $^1H$ NMR400 MHz, DMSO-$d_6$) δ=8.43-7.94 (m, 2H), 7.57-7.15 (m, 15H), 3.84-3.39 (m, 3H), 2.88 (s, 3H).

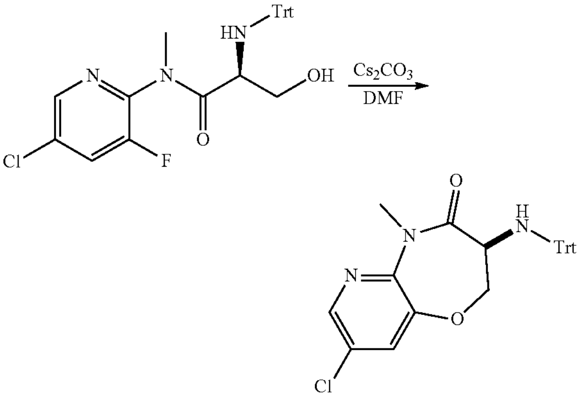

(S)-8-chloro-5-methyl-3-(tritylamino)-2,3-dihydropyrido[3,2-b][1,4]oxazepin-4 (5H)-one To a solution of the product from the previous step (1.4 g, 2.86 mmol, 1 eq) in DMF (30 mL) was added $Cs_2CO_3$ (3.26 g, 10.00 mmol, 3.5 eq). After stirring at 80° C. for 16 h, the mixture was diluted with water (50 mL) and extracted with EtOAc (25 mL×2). The combined organic phase was washed with brine (50 mL×3), dried over $Na_2SO_4$, filtered and concentrated under reduced pressure. The residue was purified by chromatography on silica gel (eluent Petroleum ether/EtOAc=100/1 to 10/1) to afford the title compound (1 g, 1.92 mmol, 67% yield) as a yellow oil. $^1H$ NMR (400 MHz, DMSO-$d_6$) δ=8.28 (d, J=2.3 Hz, 1H), 7.76 (d, J=2.3 Hz, 1H), 7.55-7.05 (m, 16H), 4.55-4.45 (m, 2H), 3.55-3.40 (m, 1H), 2.85 (s, 3H).

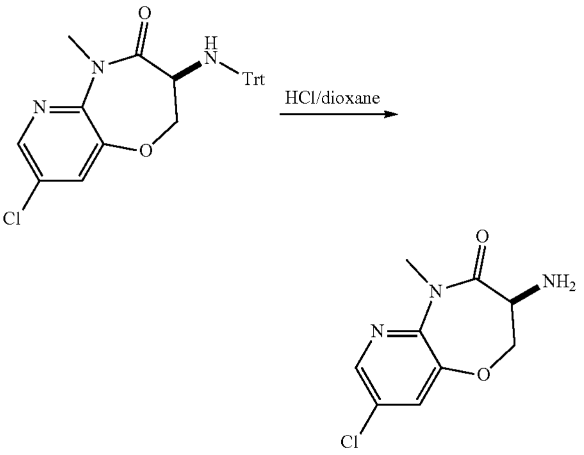

(S)-3-amino-8-chloro-5-methyl-2,3-dihydropyrido[3,2-b][1,4]oxazepin-4 (5H)-one To a solution of the product from the previous step (1 g, 2.13 mmol, 1 eq) in dioxane (5 mL) was added HCl/dioxane (4 M, 5 mL, 9.4 eq). After stirring at 0° C. for 1 h, the mixture was concentrated under reduced pressure. The residue was triturated with EtOAc (10 mL) and dried under reduced pressure to afford the hydrochloride salt of the title compound (700 mg) as a yellow solid.

MS (ES+) $C_9H_{10}ClN_3O_2$ requires: 227 and 229, found: 228 and 230 $[M+H]^+$. $^1H$ NMR (400 MHz, DMSO-$d_6$) δ=8.88 (br s, 3H), 8.43 (d, J=2.3 Hz, 1H), 7.99 (d, J=2.3 Hz, 1H), 4.81-4.72 (m, 1H), 4.85-4.70 (m, 2H), 3.36 (s, 3H).

INTERMEDIATE B-6

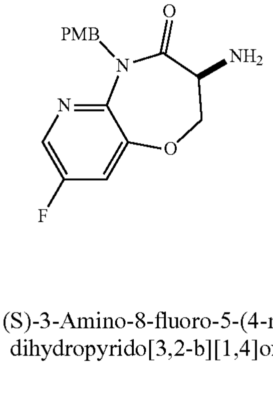

(S)-3-Amino-8-fluoro-5-(4-methoxybenzyl)-2,3-dihydropyrido[3,2-b][1,4]oxazepin-4 (5H)-one

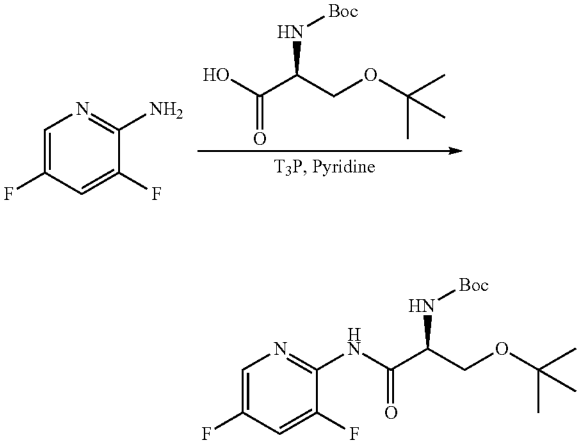

tert-Butyl (S)-(3-(tert-butoxy)-1-((3,5-difluoropyridin-2-yl)amino)-1-oxopropan-2-yl)carbamate To a solution of (2S)-3-tert-butoxy-2-(tert-butoxycarbonylamino) propanoic acid (60.26 g, 230.60 mmol, 1.2 eq) in DCE (250 mL) were added 3, 5-difluoropyridin-2-amine (25 g, 192.17 mmol, 1 eq), pyridine (45.60 g, 576.50 mmol, 46.53 mL, 3 eq) and $T_3P$ (293.49 g, 461.20 mmol, 274.29 mL of a 50% solution in EtOAc, 2.4 eq). After stirring at 60° C. for 16 h, the mixture was concentrated under reduced pressure. The residue was purified by silica gel chromatography (ISCO®; 40 g SepaFlash® Silica Flash Column, Eluent 0~10% EtOAC/Petroleum ether gradient @50 mL/min) to afford the title compound (14 g, 37.49 mmol, 19% yield) as colourless oil. $^1H$ NMR (400 MHz, $CDCl_3$) δ=9.15 (br s, 1H), 8.17 (d, J=2.5 Hz, 1H), 7.34-7.24 (m, 1H), 5.59 (br s, 1H), 4.42 (br s, 1H), 3.97-3.82 (m, 1H), 3.57-3.41 (m, 1H), 1.47 (s, 9H), 1.25 (s, 9H).

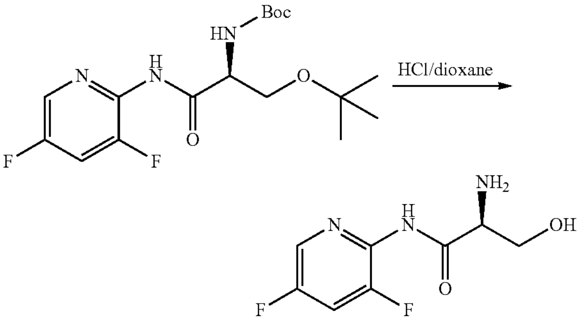

(S)-2-amino-N-(3,5-difluoropyridin-2-yl)-3-hydroxypropanamide To a solution of the product from the previous step (14 g, 28.12 mmol, 1 eq) in dioxane (70 mL) was added HCl/dioxane (70 mL, 4M solution) at 25° C. After stirring at 25° C. for 16 h, the mixture was concentrated under reduced pressure to afford the HCl salt of the title compound (6 g, 23.66 mmol, 84% yield) as colourless oil. MS (ES+) $C_8H_9N_3F_2O_2$ requires: 217, found: 218 $[M+H]^+$.

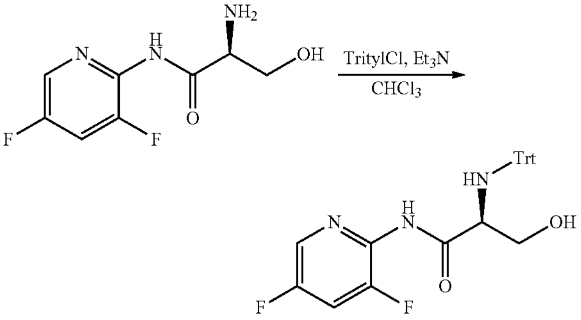

(S)—N-(3,5-difluoropyridin-2-yl)-3-hydroxy-2-(tritylamino)propenamide To a solution of the HCl salt of the product from the previous step (6 g, 27.63 mmol, 1 eq) and [chloro (diphenyl) methyl]benzene (11.55 g, 41.44 mmol, 1.5 eq) in THF (30 mL) and $H_2O$ (4.29 mL) was added $Et_3N$ (13.98 g, 138.14 mmol, 19.23 mL, 5 eq) at 25° C. After stirring at 25° C. for 16 h, the mixture was diluted with $H_2O$ (30 mL) and then extracted with EtOAc (50 mL×3), dried over $Na_2SO_4$, filtered and concentrated under reduced pressure. The residue was purified by chromatography on silica gel (eluent Petroleum ether/EtOAc=0 to 20/1) to afford the title compound as a yellow oil.

MS (ES+) $C_{27}H_{23}N_3F_2O_2$ requires: 459, found: 482 $[M+Na]^+$. $^1H$ NMR (400 MHz, $CDCl_3$) δ=10.22-9.78 (m, 1H), 8.19-8.13 (m, 1H), 7.51-7.44 (m, 7H), 7.32-7.29 (m, 5H), 7.24-7.19 (m, 4H), 3.79 (br d, J=10.0 Hz, 1H), 3.53 (br d, J=1.7 Hz, 1H), 3.38 (br s, 1H), 2.70 (br d, J=1.8 Hz, 1H), 2.37 (br s, 1H)

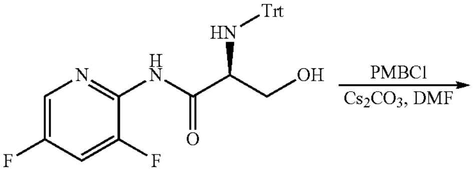

-continued

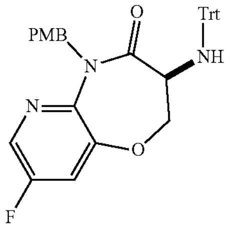

(S)-8-fluoro-5-(4-methoxybenzyl)-3-(tritylamino)-2,3-dihydropyrido[3,2-b][1,4]oxazepin-4 (5H)-one To a solution of the product from the previous step (7.8 g, 12.73 mmol, 1 eq) in DMF (150 mL) were added PMBCl (2.19 g, 14.00 mmol, 1.91 mL, 1.1 eq) and $Cs_2CO_3$ (8.30 g, 25.46 mmol, 2 eq) at 25° C. under $N_2$. After stirring at 80° C. for 16 h, the mixture was diluted with $H_2O$ (30 mL) and then extracted with EtOAc (50 mL×3). The combined organic phase was dried over $Na_2SO_4$, filtered and concentrated under reduced pressure. The residue was purified by chromatography on silica gel (eluent Petroleum ether/EtOAc=0 to 20/1) to afford the title compound (5.7 g, 8.66 mmol, 68% yield) as a white solid.

MS (ES+) $C_{35}H_{30}N_3O_3F$ requires: 559, found: 582 $[M+Na]^+$. $^1H$ NMR (400 MHz, $CDCl_3$) δ=8.09 (d, J=2.6 Hz, 1H), 7.46-7.41 (m, 6H), 7.35-7.27 (m, 3H), 7.27-7.19 (m, 6H), 7.08 (dd, J=2.6, 8.0 Hz, 1H), 7.02 (d, J=8.7 Hz, 2H), 6.73-6.67 (m, 2H), 4.75-4.62 (m, 2H), 4.56-4.44 (m, 2H), 3.72 (s, 3H), 3.68-3.58 (m, 1H), 3.45 (br d, J=7.6 Hz, 1H).

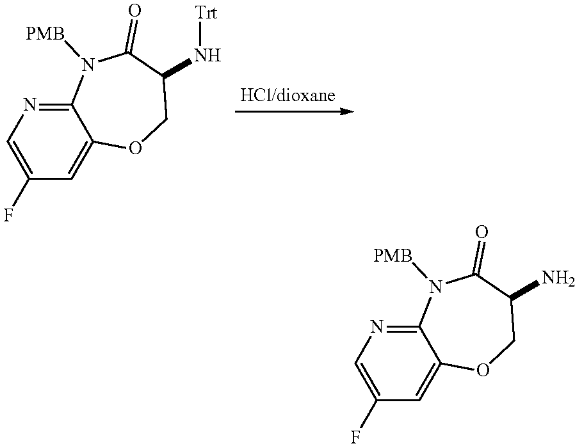

(S)-3-Amino-8-fluoro-5-(4-methoxybenzyl)-2,3-dihydropyrido[3,2-b][1,4]oxazepin-4 (5H)-one A solution of (the product from the previous step (500 mg, 670.09 μmol, 1 eq) in HCl/dioxane (10 mL, 4M) under $N_2$ was stirred at 25° C. for 3 h, then the mixture was filtered, and the filter cake was washed with dioxane (5 mL×3), then dried under reduced pressure to afford the HCl salt of the title compound (250 mg, 627.82 μmol, 93% yield) as a white solid.

MS (ES+) $C_{16}H_{16}FN_3O_3$ requires: 317, found: 318 $[M+H]^+$. $^1H$ NMR (400 MHz, $CDCl_3$) δ=9.05 (br s, 3H), 8.07 (d, J=2.6 Hz, 1H), 7.14 (br dd, J=2.6, 7.8 Hz, 1H), 7.06 (br d, J=8.4 Hz, 2H), 6.64 (br d, J=8.6 Hz, 2H), 5.19 (br d, J=14.7 Hz, 1H), 5.04-4.83 (m, 2H), 4.64 (br t, J=10.9 Hz, 1H), 4.30-4.11 (m, 1H), 3.62 (s, 3H).

INTERMEDIATE B-7

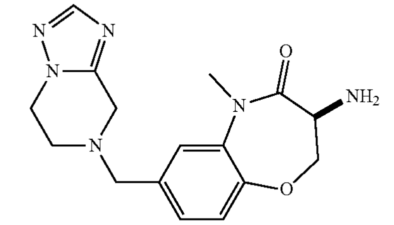

(S)-3-amino-7-((5,6-dihydro-[1,2,4]triazolo[1,5-a]pyrazin-7 (8H)-yl)methyl)-5-methyl-2,3-dihydrobenzo[b][1,4]oxazepin-4 (5H)-one

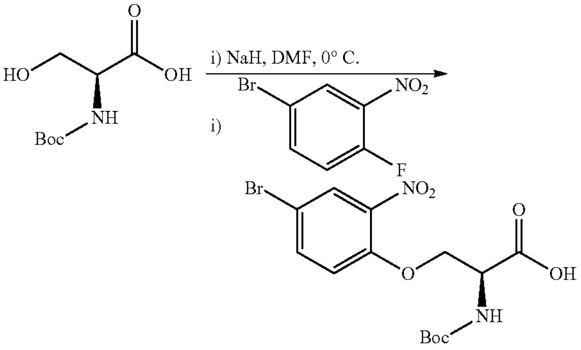

O-(4-bromo-2-nitrophenyl)-N-(tert-butoxycarbonyl)-L-serine To a solution of (tert-butoxycarbonyl)-L-serine (0.933 g, 4.55 mmol) in DMF (20 ml) at 0° C. were added NaH (0.364 g, 9.09 mmol) and stirred for 30 mins then 4-bromo-1-fluoro-2-nitrobenzene (1 g, 4.55 mmol) was added and the resulting mixture was allowed to reach roomtemp and stirred overnight. 1M HCl (4.55 ml, 4.55 mmol) was added until pH~3-4, and the layers were separated. The aqueous phase was extracted with EtOAc (3×), the combined organic layers were washed with sat NaCl, dried over $Na_2SO_4$, filtered and concentrated under reduced pressure. The residue was purified via silica gel chromatography (20-100% EtOAc in hexanes to afford the title compound (1.5 g, 3.70 mmol, 81% yield) as a yellow liquid. MS ($ES^+$) $C_{14}H_{17}BrN_2O_7$ requires: 405, found: 305 M-$Boc^+$.

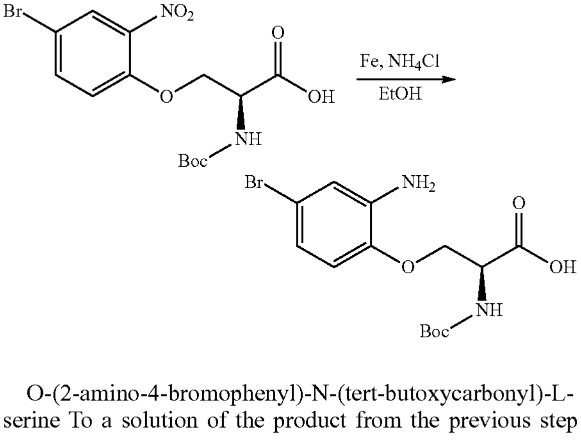

O-(2-amino-4-bromophenyl)-N-(tert-butoxycarbonyl)-L-serine To a solution of the product from the previous step (1.5 g, 3.70 mmol) in EtOH (4.23 ml)/Water (1.058 ml) were added ammonium chloride (1.980 g, 37.0 mmol) and iron (2.067 g, 37.0 mmol) and the resulting mixture was stirred at 80° C. for 4 hrs. The reaction mixture was filtered through CELITE® and washed with MeOH, and the filtrate was concentrated under reduced pressure. $H_2O$ and EtOAc was added, and the layers were separated. The aqueous phase was extracted with EtOAc (3×), the combined organic layers were washed with sat NaCl, dried over $Na_2SO_4$, filtered and concentrated under reduced pressure. The residue was purified via silica gel chromatography (0-15% MeOH in EtOAc to give the title compound (370 mg, 0.986 mmol, 26.6% yield) as a brown liquid. MS ($ES^+$) $C_{14}H_{19}BrN_2O_5$ requires: 375, found: 275 M-$Boc^+$.

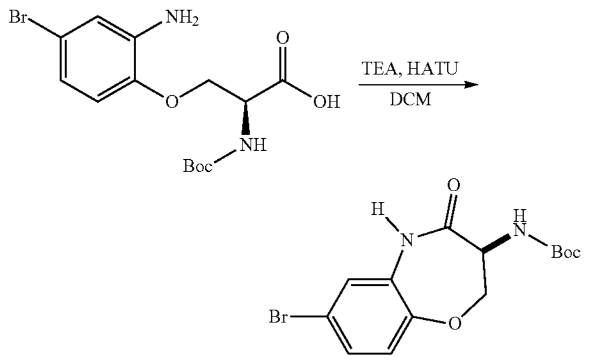

tert-Butyl (S)-(7-bromo-4-oxo-2,3,4,5-tetrahydrobenzo[b][1,4]oxazepin-3-yl)carbamate To a solution of the product from the previous step (370 mg, 0.986 mmol) in $CH_2Cl_2$ (30 ml) were added HATU (412 mg, 1.085 mmol) and $Et_3N$ (0.344 ml, 2.465 mmol) and the resulting mixture was stirred at 25° C. overnight. The volatiles were removed under reduced pressure. The residue was purified via silica gel chromatography (0-80% EtOAc in hexanes to give the title compound (136 mg, 0.381 mmol, 38.6% yield) as a pale yellow amorphous material.

MS ($ES^+$) $C_{14}H_{17}BrN_2O_4$ requires: 357, found: 257 M-Boc+. $^1$H NMR (600 MHz, DMSO-$d_6$) δ 10.02 (s, 1H), 7.29-7.24 (m, 2H), 7.13 (d, J=8.2 Hz, 1H), 7.08 (d, J=8.5 Hz, 1H), 4.39-4.31 (m, 2H), 4.31-4.23 (m, 1H), 1.36 (s, 9H).

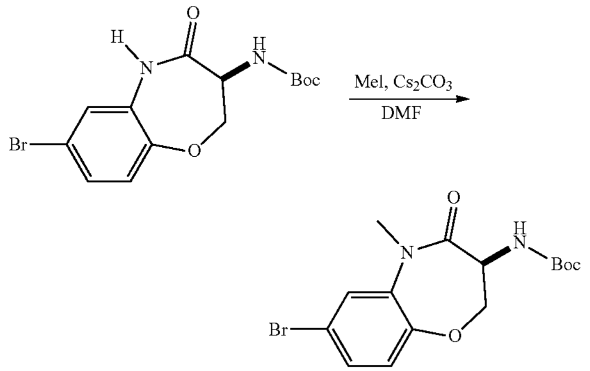

tert-Butyl (S)-(7-bromo-5-methyl-4-oxo-2,3,4,5-tetrahydrobenzo[b][1,4]-oxazepin-3-yl)carbamate To a solution of the product from the previous step (136 mg, 0.381 mmol) in DMF (2 ml) were added $Cs_2CO_3$ (186 mg, 0.571 mmol) and iodomethane (0.029 ml, 0.457 mmol) and the resulting mixture was stirred at 25° C. overnight. $H_2O$ was added, and the layers were separated. The aqueous phase was extracted with EtOAc (3×), the combined organic layers were washed with sat NaCl, dried over $Na_2SO_4$, filtered and concentrated under reduced pressure to afford the title compound, which was carried on to the next step without further purification.

MS ($ES^+$) $C_{15}H_{19}BrN_2O_4$ requires: 371, found: 272 M-$Boc^+$. $^1$H NMR (600 MHz, DMSO-$d_6$) δ 7.74 (s, 1H), 7.44 (d, J=8.5 Hz, 1H), 7.19 (d, J=8.6 Hz, 1H), 7.15 (d, J=8.5 Hz, 1H), 4.40-4.33 (m, 1H), 4.33-4.26 (m, 2H), 3.27 (s, 3H), 1.34 (s, 9H).

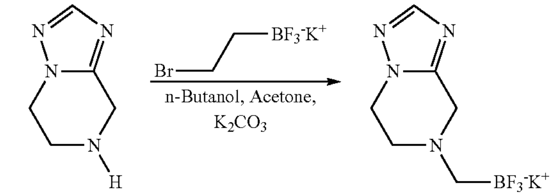

Potassium ((5,6-dihydro-[1,2,4]triazolo[1,5-a]pyrazin-7(8H)-yl)methyl)trifluoroborate To a solution of the product from the previous step (50 mg, 0.403 mmol) in butan-1-ol (2 ml) were added potassium (bromomethyl)trifluoroborate (97 mg, 0.483 mmol) and the resulting mixture was stirred at 110° C. overnight. The volatiles were removed under reduced pressure. The residue was dissolved in Acetone (15 ml) and $K_2CO_3$ (66.8 mg, 0.483 mmol) was added and stirred for 30 mins. by which time a precipitate was observed. The reaction mixture was filtered through CELITE®, and the filtrate was concentrated under reduced pressure to yield the title compound (90 mg, 0.369 mmol, 92% yield) as a off-white amorphous material, which was used in the next step without further purification.

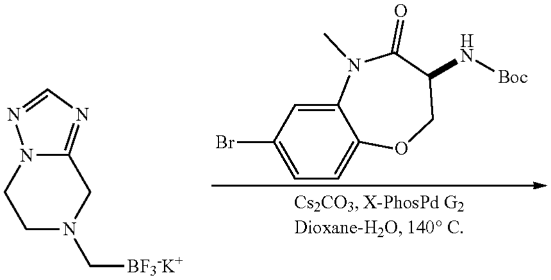

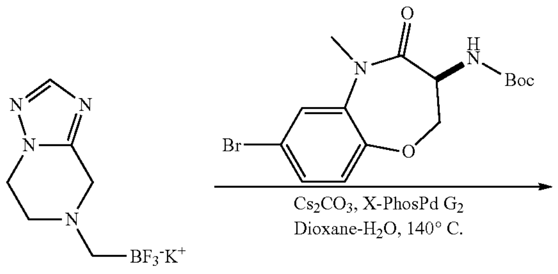

-continued

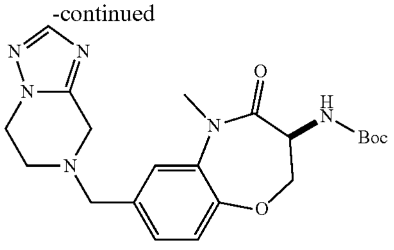

tert-Butyl (S)-(7-((5,6-dihydro-[1,2,4]triazolo[1,5-a]pyrazin-7 (8H)-yl)methyl)-5-methyl-4-oxo-2,3,4,5-tetrahydrobenzo[b][1,4]oxazepin-3-yl)carbamate A microwave vial was charged with tert-butyl (S)-(7-bromo-5-methyl-4-oxo-2,3,4,5-tetrahydrobenzo[b][1,4]oxazepin-3-yl) carbamate (66 mg, 0.178 mmol), potassium ((5,6-dihydro-[1,2,4]triazolo[1,5-a]pyrazin-7 (8H)-yl)methyl)trifluoroborate (60.7 mg, 0.249 mmol), $Cs_2CO_3$ (174 mg, 0.533 mmol) and dioxane (1.32 ml) and $H_2O$ (0.66 ml). The reaction mixture was degassed with $N_2$ for 10 min. then (2'-amino-[1,1'-biphenyl]-2-yl)(dicyclohexyl(2',4',6'-triisopropyl-[1,1'-biphenyl]-2-yl)-15-phosphaneyl)palladium(II) chloride (X-PhosPd G2) (7.00 mg, 8.89 μmol) was added to the mixture. The vial was sealed and the reaction mixture was heated to 140° C. in the microwave reactor for 1 hr. The mixture was diluted with EtOAc, $H_2O$ was added, and the layers were separated. The aqueous phase was extracted with EtOAc (3×), the combined organic layers were washed with sat NaCl, dried over $Na_2SO_4$, filtered and concentrated under reduced pressure. The residue was purified via silica gel chromatography (0-15% MeOH in EtOAc to the title compound (30 mg, 0.070 mmol, 39.4% yield) as a brown amorphous material. $^1H$ NMR (500 MHz, $CDCl_3$) δ 7.88 (s, 1H), 7.23-7.14 (m, 2H), 7.14-7.05 (m, 1H), 5.51 (d, J=7.4 Hz, 1H), 4.67 (dt, J=11.3, 7.2 Hz, 1H), 4.58 (dd, J=9.7, 7.3 Hz, 1H), 4.24-4.09 (m, 2H), 3.88-3.65 (m, 4H), 3.40 (s, 3H), 3.00 (dt, J=10.9, 5.6 Hz, 2H), 1.40 (s, 9H).

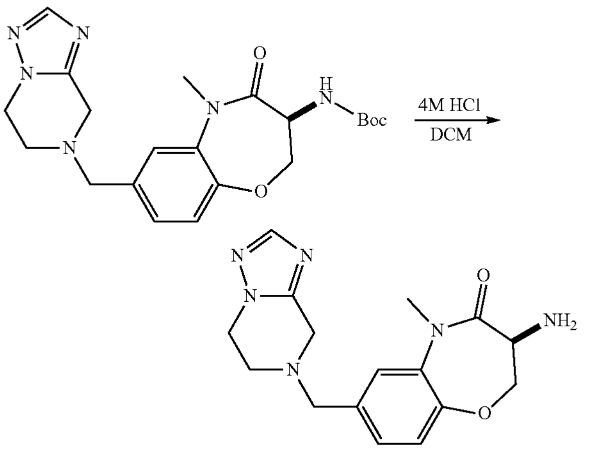

(S)-3-amino-7-((5,6-dihydro-[1,2,4]triazolo[1,5-a]pyrazin-7 (8H)-yl)methyl)-5-methyl-2,3-dihydrobenzo[b][1,4]oxazepin-4 (5H)-one To a solution of the product from the previous step (30 mg, 0.070 mmol) in Dioxane (0.2 ml) were added 4M HCl in dioxane (0.088 ml, 0.350 mmol) and the resulting mixture was stirred at 25° C. for 4 hrs. The volatiles were removed under reduced pressure to yield the title compound as a white powder, which was used without further purification.

INTERMEDIATE B-8

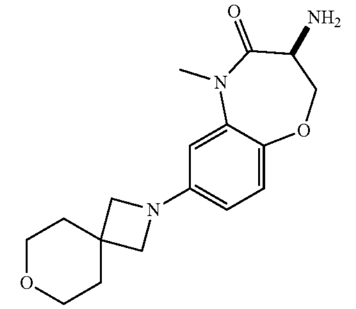

(S)-3-amino-5-methyl-7-(7-oxa-2-azaspiro[3.5]nonan-2-yl)-2,3-dihydrobenzo[b][1,4]oxazepin-4 (5H)-one

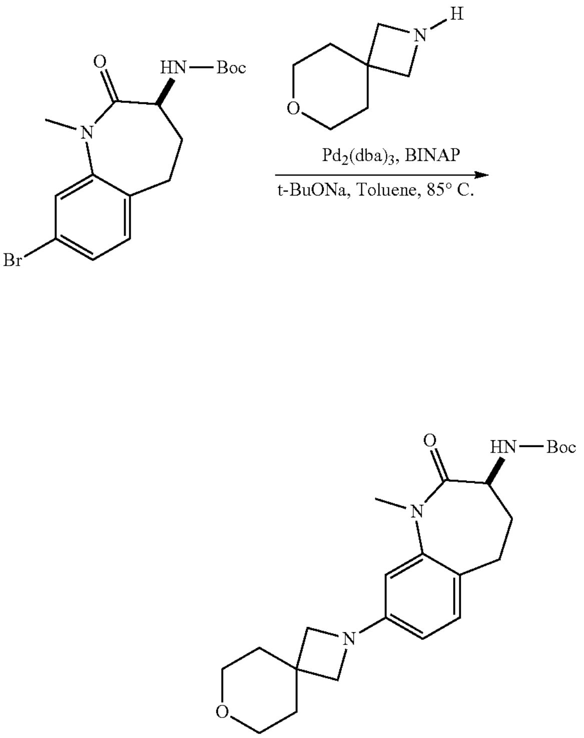

tert-Butyl (S)-(5-methyl-4-oxo-7-(7-oxa-2-azaspiro[3.5]nonan-2-yl)-2,3,4,5-tetrahydrobenzo[b][1,4]oxazepin-3-yl) carbamate To a solution of the product from the previous step (150 mg, 0.404 mmol) in toluene (4 ml) were added 7-oxa-2-azaspiro[3.5]nonane hydrochloride (86 mg, 0.525 mmol), $Pd_2(dba)_3$ (22.20 mg, 0.024 mmol), BINAP (37.7 mg, 0.061 mmol) and sodium tert-butoxide (97 mg, 1.010 mmol) and the resulting mixture was stirred at 85° C. overnight. The reaction mixture was filtered through CELITE® washed with EtOAc, and the filtrate was concentrated under reduced pressure. The residue was purified via silica gel chromatography (10-100% EtOAc in hexanes to give the title compound (50 mg, 0.120 mmol, 29.5% yield) as a brown amorphous material.

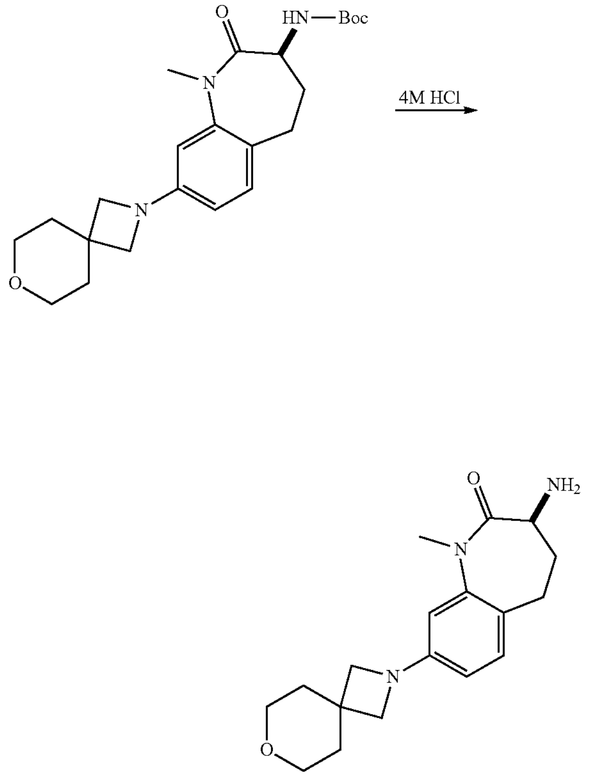

(S)-3-amino-5-methyl-7-(7-oxa-2-azaspiro[3.5]nonan-2-yl)-2,3-dihydrobenzo[b][1,4]oxazepin-4 (5H)-one To a solution of the product from the previous step (50 mg, 0.120 mmol) in Dioxane (0.5 ml) were added 4M HCl in dioxane (0.150 ml, 0.599 mmol) and the resulting mixture was stirred at 25° C. overnight. The volatiles were removed under reduced pressure to yield the HCl salt of the title compound (40 mg, 0.113 mmol, 94% yield) as a white solid, which was used without further purification MS ($ES^+$) $C_{17}H_{23}N_3O_3$ requires: 317, found: 318 $[M+H]^+$.

INTERMEDIATE B-9

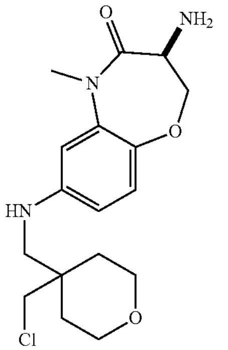

(S)-3-amino-7-(((4-(chloromethyl)tetrahydro-2H-pyran-4-yl)methyl)amino)-5-methyl-2,3-dihydrobenzo[b][1,4]oxazepin-4 (5H)-one This compound was obtained as a byproduct from the synthesis of Intermediate B-8.

Intermediate B-10

(S)-7-bromo-5-methyl-3-(tritylamino)-2,3-dihydrobenzo[b][1,4]oxazepin-4 (5H)-one

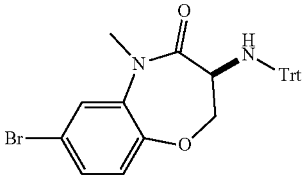

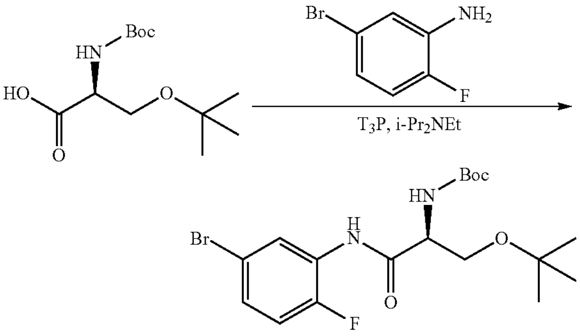

tert-Butyl (S)-(1-((5-bromo-2-fluorophenyl)amino)-3-(tert-butoxy)-1-oxopropan-2-yl)carbamate To a solution of N-(tert-butoxycarbonyl)-O-(tert-butyl)-L-serine (20 g, 76.54 mmol, 1 eq) in $CH_2Cl_2$ (200 mL) were added $T_3P$ (58.45 g, 91.84 mmol, 54.62 mL of a 50% solution in EtOAc, 1.2 eq), i-$Pr_2$NEt (19.78 g, 153.07 mmol, 26.66 mL, 2 eq) and 5-bromo-2-fluoroaniline (8.73 g, 45.92 mmol, 0.6 eq). After stirring at 25° C. for 16 h, the mixture diluted with water (200 mL), extracted with $CH_2Cl_2$ (200 mL×3), dried over $Na_2SO_4$, filtered and concentrated under reduced pressure. The residue was purified by silica gel chromatography (ISCO®; 120 g SepaFlash® Silica Flash Column, Eluent 0~20% EtOAC/Petroleum ether gradient @50 mL/min) to afford the title compound (14 g, 32.31 mmol, 42% yield) as a colourless oil. $^1H$ NMR (400 MHz, DMSO-$d_6$) δ=9.81 (br s, 1H), 8.21-8.06 (m, 1H), 7.35-7.18 (m, 2H), 6.97-6.74 (m, 1H), 4.32 (br s, 1H), 3.53 (br d, J=6.0 Hz, 2H), 1.39 (s, 9H), 1.14-1.07 (m, 9H).

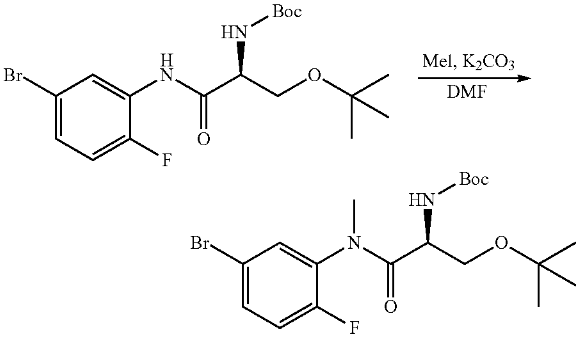

tert-Butyl (S)-(1-((5-bromo-2-fluorophenyl)(methyl)amino)-3-(tert-butoxy)-1-oxopropan-2-yl)carbamate To a solution of the product from the previous step (11 g, 25.39 mmol, 1 eq) in DMF (50 mL) was added $Cs_2CO_3$ (9.93 g, 30.46 mmol, 1.2 eq) followed by MeI (3.60 g, 25.39 mmol, 1.58 mL, 1 eq). After stirring at 25° C. for 16 h, the mixture was diluted with water (50 mL), extracted with EtOAc (50 mL×3), washed with brine (50 mL×3). The combined organic phase was dried over $Na_2SO_4$, filtered and concentrated under reduced pressure. The residue was purified by silica gel chromatography (ISCO®; 120 g SepaFlash® Silica Flash Column, Eluent 0~20% EtOAC/Petroleum ether gradient @50 mL/min) to afford the title compound (11 g, 24.59 mmol, 96% yield) as colourless oil. MS (ES+) $C_{19}H_{28}FN_2O_4Br$ requires: 446 and 448, found 391 and 393 [M-isobutene+H]$^+$.

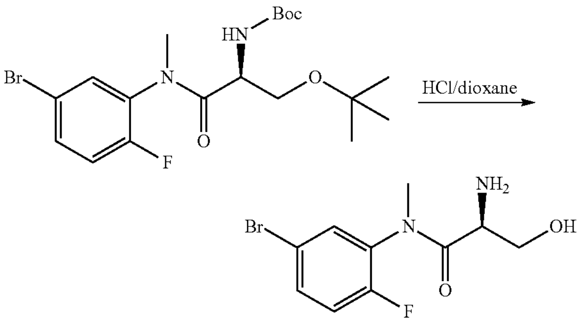

(S)-2-amino-N-(5-bromo-2-fluorophenyl)-3-hydroxy-N-methylpropanamide

To a solution of the product from the previous step (11 g, 24.59 mmol, 1 eq) in $CH_2Cl_2$ (90 mL) was added HCl/dioxane (4 M, 30 mL). After stirring at 30° C. for 3 h, the mixture was concentrated under reduced pressure to afford the title compound (10 g, 22.28 mmol, 90% yield) as colourless oil. MS (ES+) $C_{10}H_{12}FN_2O_2Br$ requires: 290 and 292, found 291 and 293 [M+H]$^+$.

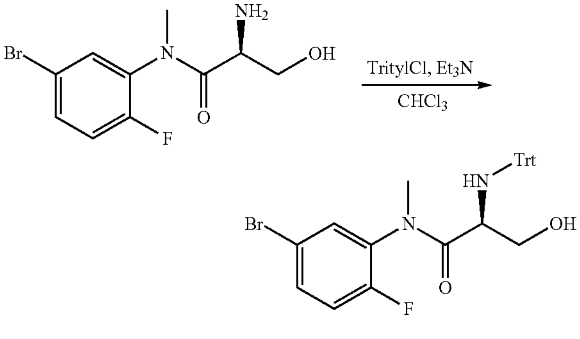

(S)—N-(5-bromo-2-fluorophenyl)-3-hydroxy-N-methyl-2-(tritylamino)-propanamide To a solution of the product from the previous step (2.00 g, 5.02 mmol, 73% purity, 1 eq) in $CHCl_3$ (20 mL) were added $Et_3N$ (1.22 g, 12.04 mmol, 1.68 mL, 2.4 eq) and [chloro(diphenyl)methyl]benzene (1.68 g, 6.02 mmol, 1.2 eq). After stirring at 25° C. for 16 h, the mixture was diluted with $H_2O$ (20 mL), extracted with $CH_2Cl_2$ (20 mL×3), dried over $Na_2SO_4$, filtered and concentrated under reduced pressure. The residue was purified by silica gel chromatography (ISCO®; 40 g SepaFlash® Silica Flash Column, Eluent 0~30% EtOAC/Petroleum ether gradient @50 mL/min) to afford the title compound (2 g, 3.75 mmol, 74% yield) as colourless oil. MS (ES+) $C_{29}H_{26}FN_2O_2Br$ requires: 532 and 534, found 555 and 557 [M+Na]$^+$.

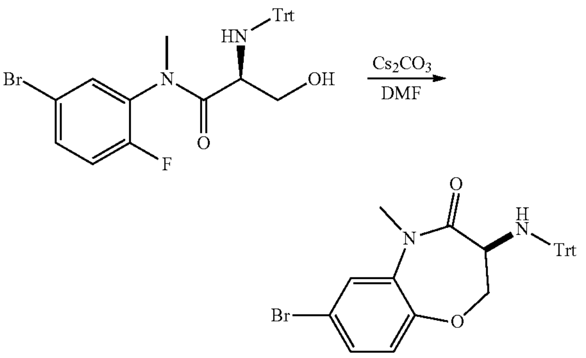

(S)-7-bromo-5-methyl-3-(tritylamino)-2,3-dihydrobenzo[b][1,4]oxazepin-4 (5H)-one To a solution of the product from the previous step (1.5 g, 2.81 mmol, 1 eq) in DMF (32.5 mL) was added $Cs_2CO_3$ (2.75 g, 8.44 mmol, 3 eq). After stirring at 50° C. for 16 h, the mixture was diluted with $H_2O$ (50 mL), extracted with EtOAc (50 mL×3), washed with brine (50 mL×3), dried over $Na_2SO_4$, filtered and concentrated under reduced pressure to afford the title compound (1.3 g, 2.53 mmol, 90% yield) as a white solid. $^1H$ NMR (400 MHz, DMSO-$d_6$) δ=7.38 (d, J=2.4 Hz, 1H), 7.33-7.23 (m, 13H), 7.22-7.16 (m, 3H), 7.04 (d, J=8.5 Hz, 1H), 4.47-4.28 (m, 2H), 3.45-3.35 (m, 1H), 3.18 (d, J=8.8 Hz, 1H), 2.81 (s, 3H).

INTERMEDIATE B-11

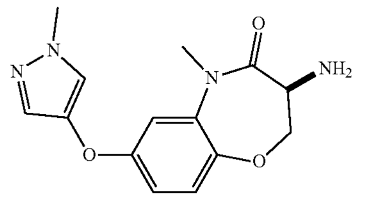

(S)-3-amino-5-methyl-7-((1-methyl-1H-pyrazol-4-yl)oxy)-2,3-dihydrobenzo[b][1,4]oxazepin-4 (5H)-one

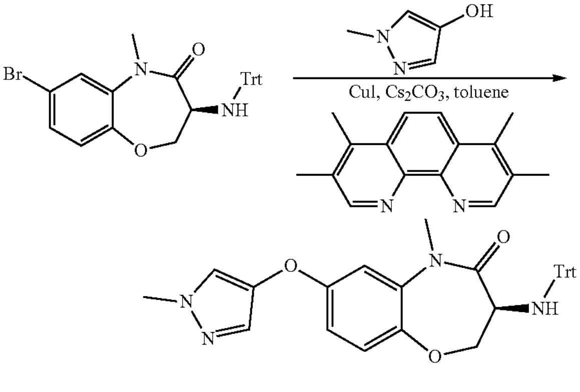

(S)-5-methyl-7-((l-methyl-1H-pyrazol-4-yl)oxy)-3-(tritylamino)-2,3-dihydrobenzo[b][1,4]oxazepin-4 (5H)-one To a solution of Intermediate B-10 (0.7 g, 1.36 mmol, 1 eq) in toluene (4.55 mL) were added 1-methylpyrazol-4-ol (200.63 mg, 2.05 mmol, 1.5 eq) and $Cs_2CO_3$ (888.44 mg, 2.73 mmol, 2 eq) under $N_2$. Then CuI (51.93 mg, 272.68 μmol, 0.2 eq) and 3, 4, 7, 8-tetramethyl-1,10-phenanthroline (64.44 mg, 272.68 μmol, 0.2 eq) were added and mixture was degassed with $N_2$ for 5 min. After stirring at 100° C. for 16 h, the mixture was filtered and concentrated under reduced pressure. The residue was purified by silica gel chromatography (ISCO®; 10 g SepaFlash® Silica Flash Column, Eluent 0~100% EtOAC/Petroleum ether gradient @50 mL/min) to afford the title compound (220 mg, 414.61 μmol, 30% yield) as a white solid. $^1H$ NMR (400 MHz, $CDCl_3$) δ=7.48-7.39 (m, 6H), 7.36 (br d, J=0.6 Hz, 1H), 7.30-7.10 (m, 10H), 6.95 (d, J=8.8 Hz, 1H), 6.70 (dd, J=2.9, 8.8 Hz, 1H), 6.58 (d, J=2.8 Hz, 1H), 4.52 (dd, J=7.3, 9.8 Hz, 1H), 4.36 (dd, J=9.8, 11.6 Hz, 1H), 3.92 (s, 3H), 3.63-3.51 (m, 1H), 3.34 (br d, J=8.1 Hz, 1H), 2.86 (s, 3H).

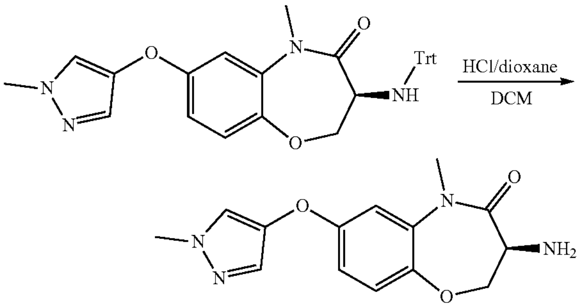

(S)-3-amino-5-methyl-7-((1-methyl-1H-pyrazol-4-yl) oxy)-2,3-dihydrobenzo[b][1,4]oxazepin-4 (5H)-one To a solution of the product from the previous step (220 mg, 414.61 μmol, 1 eq) in $CH_2Cl_2$ (1 mL) was added HCl/dioxane (4 M, 310.96 μL, 3 eq). After stirring at 25° C. for 4 h, the mixture was concentrated under reduced pressure. The residue was triturated with 5 mL EtOAc:petroleum ether (v/v 1:3). The mixture was filtered and the filter cake was collected to afford the HCl salt of the title compound (140 mg, 387.57 μmol, 93% yield) as a white solid. $^1H$ NMR (400 MHz, DMSO-$d_6$) δ=8.64 (br d, J=3.5 Hz, 3H), 7.78 (s, 1H), 7.39 (s, 1H), 7.27-7.15 (m, 2H), 6.88 (dd, J=2.9, 8.8 Hz, 1H), 4.66-4.51 (m, 1H), 4.45-4.36 (m, 1H), 4.34-4.16 (m, 1H), 3.82 (s, 3H), 3.32 (s, 3H).

INTERMEDIATE B-12

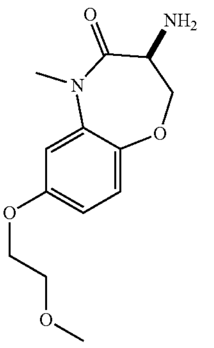

(S)-3-amino-7-(2-methoxyethoxy)-5-methyl-2,3-dihydrobenzo[b][1,4]oxazepin-4 (5H)-one

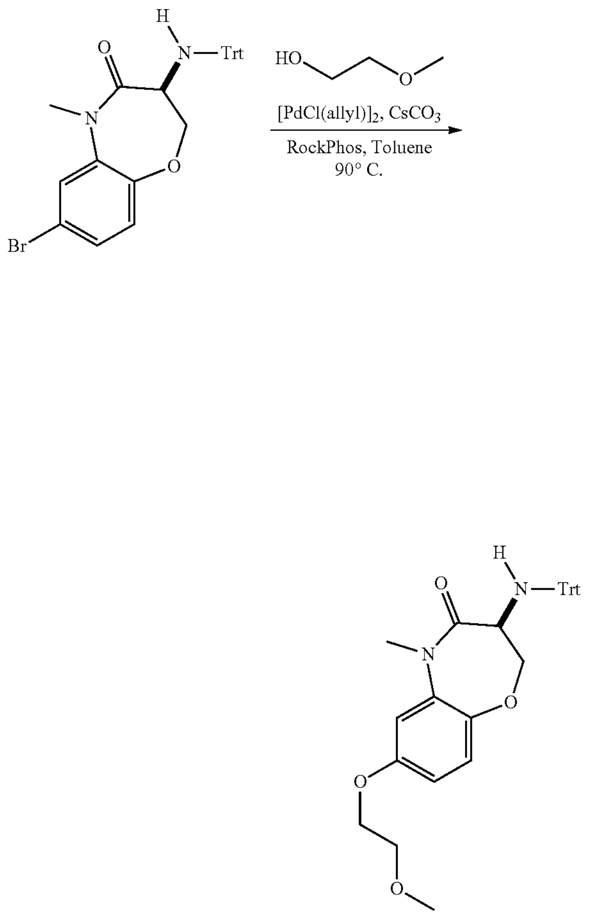

(S)-7-(2-methoxyethoxy)-5-methyl-3-(tritylamino)-2,3-dihydrobenzo[b][1,4]-oxazepin-4 (5H)-one A solution of Intermediate B-10 (100 mg, 0.195 mmol), 2-methoxyethan-1-ol (29.6 mg, 0.390 mmol) and $Cs_2CO_3$ (127 mg, 0.390 mmol) in Toluene (390 μl) was degassed with $N_2$ for 5 minutes. Di-tert-butyl(2',4',6'-triisopropyl-3-methoxy-6-methyl-[1,1'-biphenyl]-2-yl)phosphane (RockPhos, 13.69 mg, 0.029 mmol) and allylpalladium(II) chloride (3.56 mg, 9.74 μmol) were added and the mixture was degassed with $N_2$ for an additional 5 minutes. The reaction mixture was heated to 90° C. overnight. The reaction mixture was filtered through CELITE® with EtOAc, and the filtrate was concentrated under reduced pressure. The residue was purified via silica gel chromatography (5-80% EtOAc in hexanes to give the title compound (83 mg, 0.163 mmol, 84% yield) as a yellow liquid.

MS ($ES^+$) $C_{22}H_{31}N_3O_5$ requires: 508, found: 531 M+$Na^+$. $^1H$ NMR (500 MHz, CDCl3) δ 7.44-7.36 (m, 8H), 7.25-7.19 (m, 6H), 7.17-7.13 (m, 2H), 6.97-6.90 (m, 1H), 6.60 (dd, J=8.8, 2.9 Hz, 1H), 6.49 (d, J=2.9 Hz, 1H), 4.49-4.40 (m, 1H), 4.30 (dd, J=11.6, 9.8 Hz, 1H), 4.12-4.01 (m, 2H), 3.80-3.70 (m, 2H), 3.46 (s, 3H), 3.32-3.25 (m, 1H), 2.85 (s, 3H).

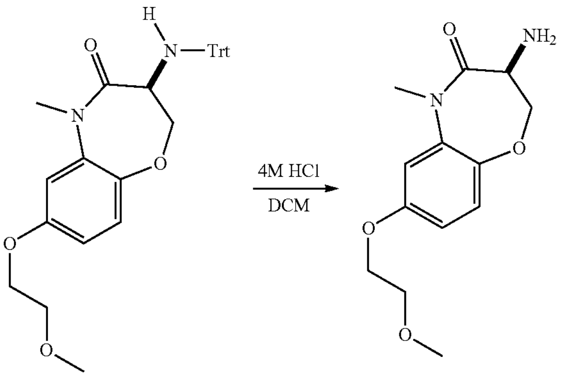

(S)-3-amino-7-(2-methoxyethoxy)-5-methyl-2,3-dihydrobenzo[b][1,4]-oxazepin-4 (5H)-one To a solution of the product from the previous step (80 mg, 0.157 mmol) in $CH_2Cl_2$ (1 ml) were added 4M HCl in dioxane (0.118 ml, 0.472 mmol) and the resulting mixture was stirred at 25° C. overnight. The volatiles were removed under reduced pressure. The residue was triturated with $CH_2Cl_2$ and hexanes. The resulting solid was filtered and collected to afford the HCl salt of the title compound, which was used without further purification.

MS ($ES^+$) $C_{13}H_{18}N_2O_4$ requires: 266, found: 267 $[M+H]^+$. $^1H$ NMR (500 MHz, CDCl3) δ 8.75 (s, 3H), 7.07 (d, J=8.8 Hz, 1H), 6.81-6.72 (m, 2H), 4.83 (t, J=9.0 Hz, 1H), 4.71 (t, J=10.7 Hz, 1H), 4.43 (s, 1H), 4.10 (s, 2H), 3.75 (s, 2H), 3.45 (s, 3H), 3.29 (s, 3H).

INTERMEDIATE B-13

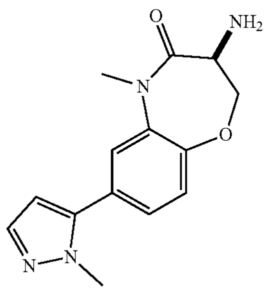

(S)-3-amino-5-methyl-7-(1-methyl-1H-pyrazol-5-yl)-2,3-dihydrobenzo[b][1,4]oxazepin-4 (5H)-one

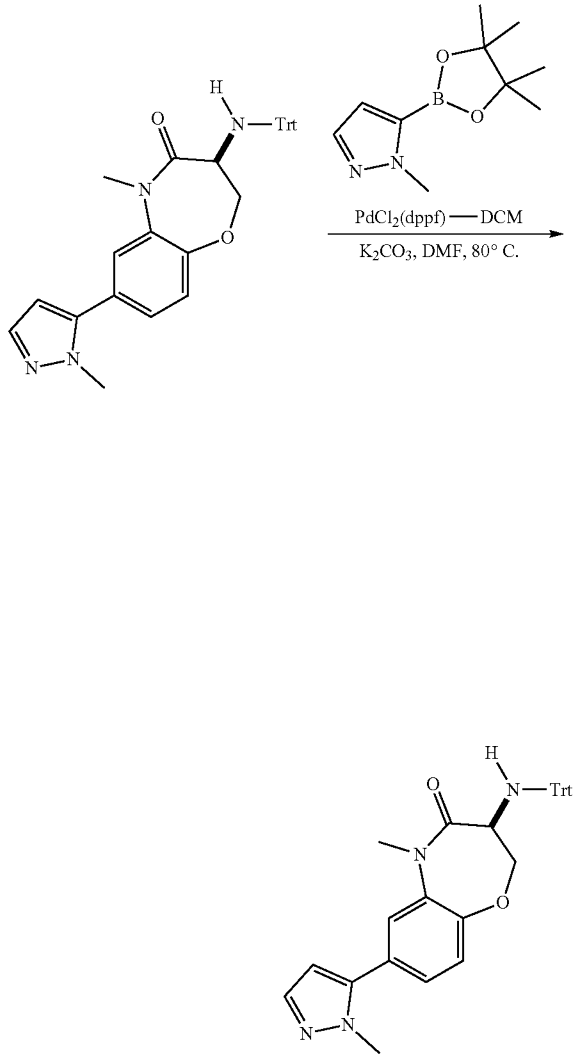

(S)-5-methyl-7-(1-methyl-1H-pyrazol-5-yl)-3-(tritylamino)-2,3-dihydrobenzo[b][1,4]oxazepin-4 (5H)-one A solution of Intermediate B-10 (50 mg, 0.097 mmol), 1-methyl-5-(4,4,5,5-tetramethyl-1,3,2-dioxaborolan-2-yl)-1H-pyrazole (20.26 mg, 0.097 mmol) and $K_2CO_3$ (26.9 mg, 0.195 mmol) in DMF (0.75 ml) was degassed with $N_2$ for 5 minutes. PdCl2(dppf)-$CH_2Cl_2$ Adduct (7.95 mg, 9.74 μmol) were added and the mixture was degassed with $N_2$ for an additional 5 minutes. The reaction mixture was heated to 80° C. and stirred overnight. The reaction mixture was filtered through CELITE® and washed with EtOAc, and the filtrate was concentrated under reduced pressure. The residue was purified via silica gel chromatography (10-100% EtOAc in hexanes to give the title compound (50 mg, 0.097 mmol, 100% yield) as a off-white amorphous material.

MS ($ES^+$) $C_{33}H_{30}N_4O_2$ requires: 514, found: 515 $[M+H]^+$. $^1H$ NMR (600 MHz, CDCl3) δ 7.53 (s, 1H), 7.41 (d, J=8.1 Hz, 6H), 7.22 (t, J=7.5 Hz, 6H), 7.19-7.15 (m, 3H), 7.14-7.07 (m, 2H), 6.89 (s, 1H), 6.29 (s, 1H), 4.61-4.55 (m, 1H), 4.43 (dd, J=11.7, 9.8 Hz, 1H), 3.87 (s, 3H), 3.62-3.55 (m, 1H), 3.37 (d, J=8.7 Hz, 1H), 2.92 (s, 3H).

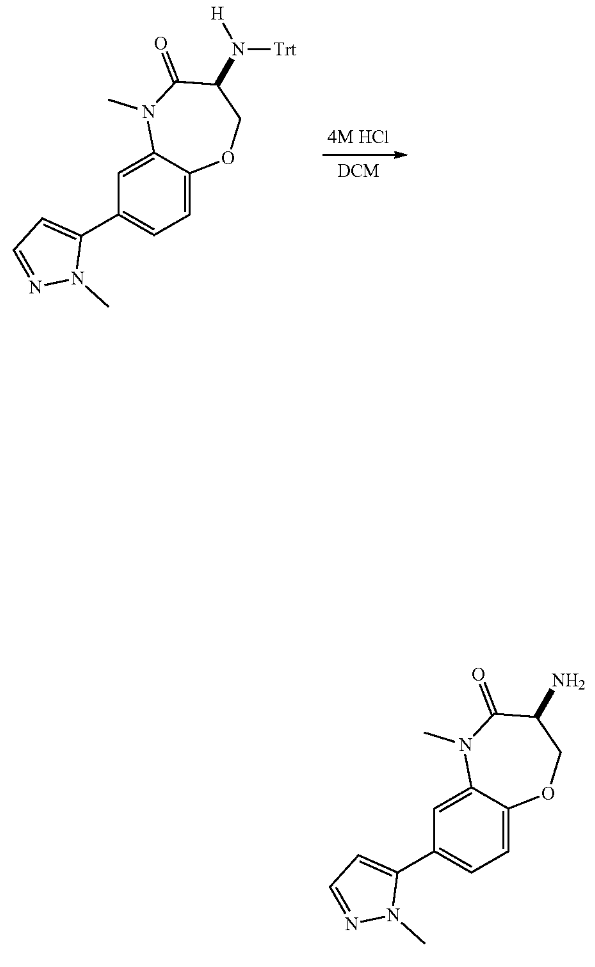

(S)-3-amino-5-methyl-7-(1-methyl-1H-pyrazol-5-yl)-2,3-dihydrobenzo[b][1,4]-oxazepin-4 (5H)-one To a solution of (S)-5-methyl-7-(1-methyl-1H-pyrazol-5-yl)-3-(tritylamino)-2,3-dihydrobenzo[b][1,4]oxazepin-4 (5H)-one (50 mg, 0.097 mmol) in $CH_2C_{12}$ (0.5 ml) were added 4M HCl in dioxane (0.073 ml, 0.291 mmol) and the resulting mixture was stirred at 25° C. overnight. The volatiles were removed under reduced pressure. The residue was triturated with $CH_2Cl_2$ and hexanes. The resulting solid was filtered and collected to afford the HCl salt of the title compound, and used without further purification. MS ($ES^+$) $C_{14}H_{16}N_4O_2$ requires: 272, found: 273 $[M+H]^+$.

INTERMEDIATE B-14

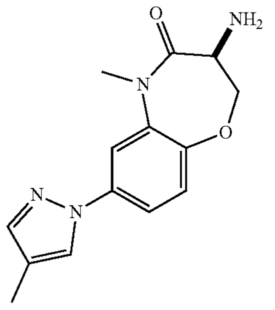

(S)-3-amino-5-methyl-7-(4-methyl-1H-pyrazol-1-yl)-2,3-dihydrobenzo[b][1,4]oxazepin-4 (5H)-one

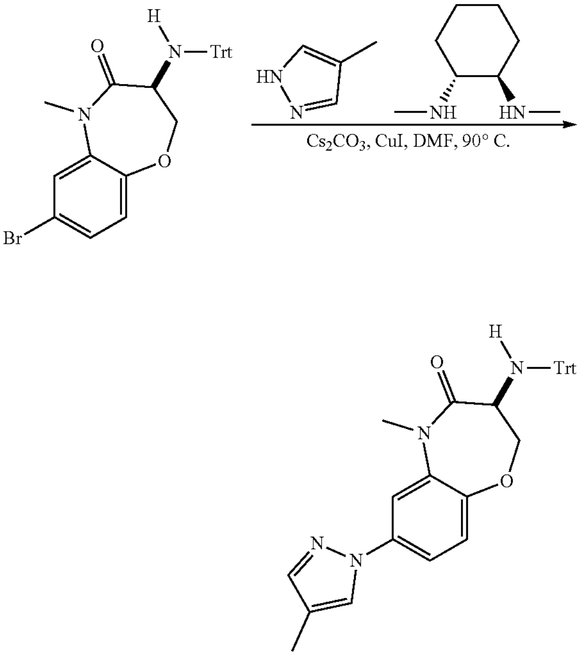

(S)-5-methyl-7-(4-methyl-1H-pyrazol-1-yl)-3-(tritylamino)-2,3-dihydrobenzo[b][1,4]oxazepin-4 (5H)-one A solution of Intermediate B-10 (100 mg, 0.195 mmol), 4-methyl-1H-pyrazole (20.79 mg, 0.253 mmol) and $Cs_2CO_3$ (127 mg, 0.390 mmol) in DMF (0.5 ml) was degassed with $N_2$ for 5 minutes. CuI (3.71 mg, 0.019 mmol) and (1R,2R)—N1,N2-dimethylcyclohexane-1,2-diamine (4.16 mg, 0.029 mmol) were added and the mixture was degassed with $N_2$ for an additional 5 minutes. The reaction mixture was heated to 90° C. and stirred overnight. The volatiles were removed under reduced pressure. $H_2O$ was added, and the layers were separated. The aqueous phase was extracted with EtOAc (3×), the combined organic layers were washed with sat NaCl, dried over $Na_2SO_4$, filtered and concentrated under reduced pressure. The residue was purified via silica gel chromatography (10-100% EtOAc in hexanes to give the title compound (45 mg, 0.087 mmol, 44.9% yield) as a yellow liquid. MS ($ES^+$) $C_{33}H_{30}N_4O_2$ requires: 514, found: 537 $M+Na^+$.

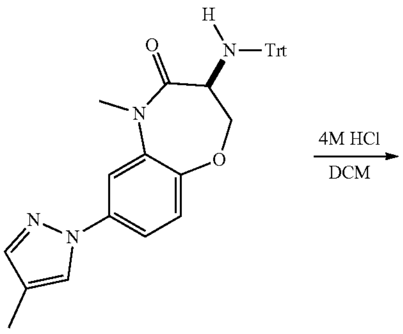

-continued

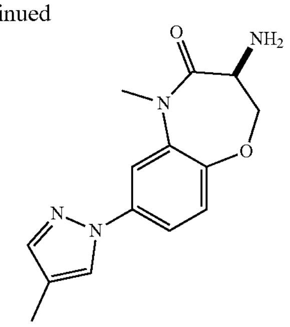

(S)-3-amino-5-methyl-7-(4-methyl-1H-pyrazol-1-yl)-2,3-dihydrobenzo[b][1,4]-oxazepin-4 (5H)-one To a solution of the product from the previous step (45 mg, 0.087 mmol) in $CH_2Cl_2$ (0.5 ml) were added 4M HCl in dioxane (0.066 ml, 0.262 mmol) and the resulting mixture was stirred at 25° C. overnight. The volatiles were removed under reduced pressure to afford the HCl salt of the title compound, which was used without further purification. MS ($ES^+$) $C_{14}H_{16}N_4O_2$ requires: 272, found: 273 $[M+H]^+$.

INTERMEDIATE B-15

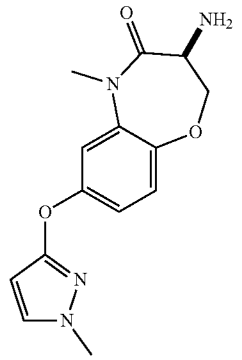

(S)-3-amino-5-methyl-7-((1-methyl-1H-pyrazol-3-yl)oxy)-2,3-dihydrobenzo[b][1,4]-oxazepin-4 (5H)-one

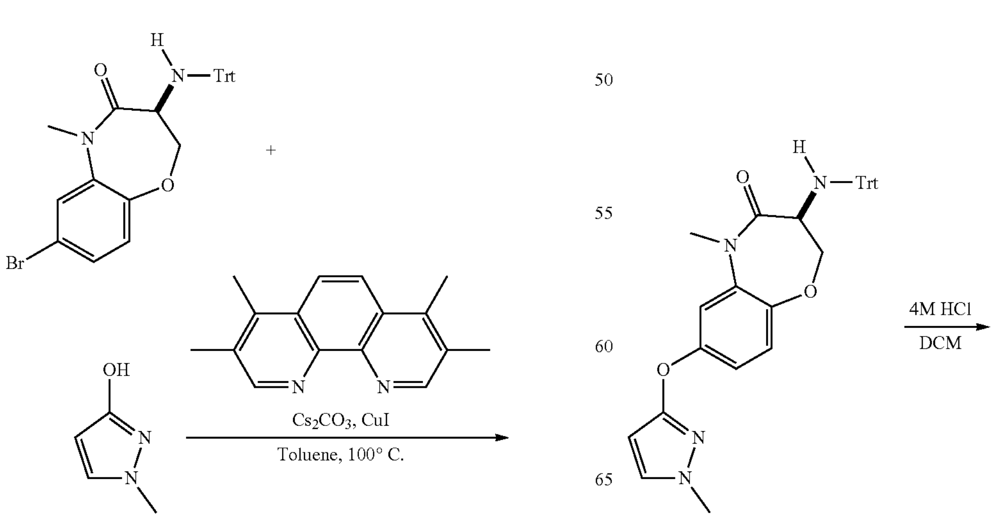

-continued

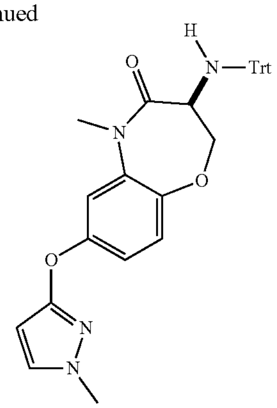

(S)-5-methyl-7-((1-methyl-1H-pyrazol-3-yl)oxy)-3-(tritylamino)-2,3-dihydrobenzo[b][1,4]oxazepin-4 (5H)-one A solution of Intermediate B-10 (100 mg, 0.195 mmol), 1-methyl-1H-pyrazol-4-ol (28.7 mg, 0.292 mmol) and $Cs_2CO_3$ (127 mg, 0.390 mmol) in Toluene (649 μl) was degassed with $N_2$ for 5 minutes. 3,4,7,8-tetramethyl-1,10-phenanthroline (9.21 mg, 0.039 mmol) and CuI (7.42 mg, 0.039 mmol) were added and the mixture was degassed with $N_2$ for an additional 5 minutes. The reaction mixture was heated to 100° C. overnight. The reaction mixture was filtered through CELITE®, and the filtrate was concentrated under reduced pressure. The residue was purified via silica gel chromatography (10-100% EtOAc in hexanes to give the title compound (62 mg, 0.117 mmol, 60.0% yield) as a pale yellow liquid.

MS ($ES^+$) $C_{33}H_{30}N_4O_3$ requires: 530, found: 553 $M+Na^+$. $^1H$ NMR (600 MHz, CDCl3) δ 7.40 (d, J=7.8 Hz, 6H), 7.33 (s, 1H), 7.25 (s, 1H), 7.24-7.19 (m, 6H), 7.16 (t, J=8.2 Hz, 3H), 6.92 (d, J=8.9 Hz, 1H), 6.70-6.65 (m, 1H), 6.57-6.53 (m, 1H), 4.49 (t, J=7.9, 7.3 Hz, 1H), 4.37-4.30 (m, 1H), 3.90 (s, 3H), 3.58-3.51 (m, 1H), 3.31 (d, J=8.1 Hz, 1H), 2.84 (s, 3H).

-continued

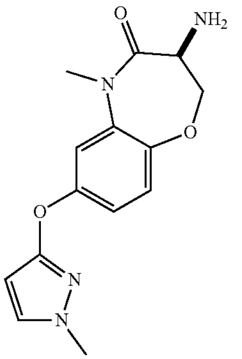

(S)-3-amino-5-methyl-7-((1-methyl-1H-pyrazol-3-yl)oxy)-2,3-dihydrobenzo[b][1,4]oxazepin-4 (5H)-one To a solution of the product from the previous step (62 mg, 0.117 mmol) in $CH_2Cl_2$ (0.5 ml) were added 4M HCl in dioxane (0.088 ml, 0.351 mmol) and the resulting mixture was stirred at 25° C. overnight. The volatiles were removed under reduced pressure to afford the HCl salt of the title compound, which was used without further purification. MS ($ES^+$) $C_{14}H_{16}N_4O_3\cdot ClH$ requires: 288, found: 289 $[M+H]^+$. Rt: 0.8 min

INTERMEDIATE B-16

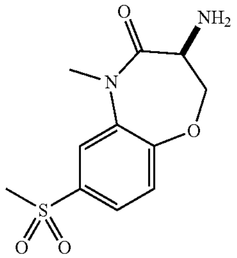

(S)-3-amino-5-methyl-7-(methylsulfonyl)-2,3-dihydrobenzo[b][1,4]oxazepin-4 (5H)-one

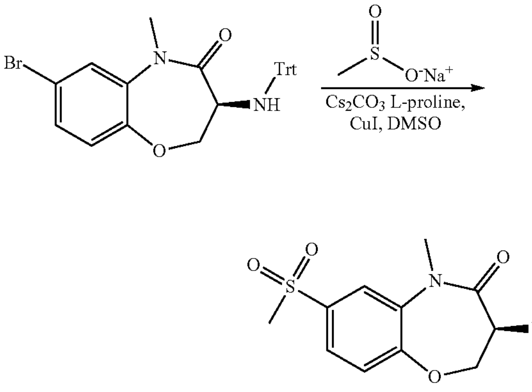

(S)-5-methyl-7-(methylsulfonyl)-3-(tritylamino)-2,3-dihydrobenzo[b]-[1,4]oxazepin-4 (5H)-one To a solution of Intermediate B-10 (200 mg, 389.54 μmol, 1 eq) in DMSO (2.5 mL) were added sodium methanesulfinate (79.54 mg, 779.08 μmol, 2 eq), (2S)-pyrrolidine-2-carboxylic acid (17.94 mg, 155.82 μmol, 0.4 eq), CuI (14.84 mg, 77.91 μmol, 0.2 eq) and $Cs_2CO_3$ (50.77 mg, 155.82 μmol, 0.4 eq) under $N_2$. After stirring at 140° C. for 2 h in a microwave reactor, the mixture was diluted with $H_2O$ (10 mL) and extracted with EtOAc (10 mL×2). The combined organic layer was washed with brine (10 mL), dried over anhydrous $Na_2SO_4$ and filtered. The filtrate was concentrated to afford the title compound (160 mg, crude) as yellow oil. $^1H$ NMR (400 MHz, DMSO-$d_6$) δ=7.69 (dd, J=1.9, 8.3 Hz, 1H), 7.61 (d, J=1.9 Hz, 1H), 7.36-7.15 (m, 17H), 4.57-4.40 (m, 2H), 3.43-3.36 (m, 1H), 3.28 (s, 3H), 2.88 (s, 3H).

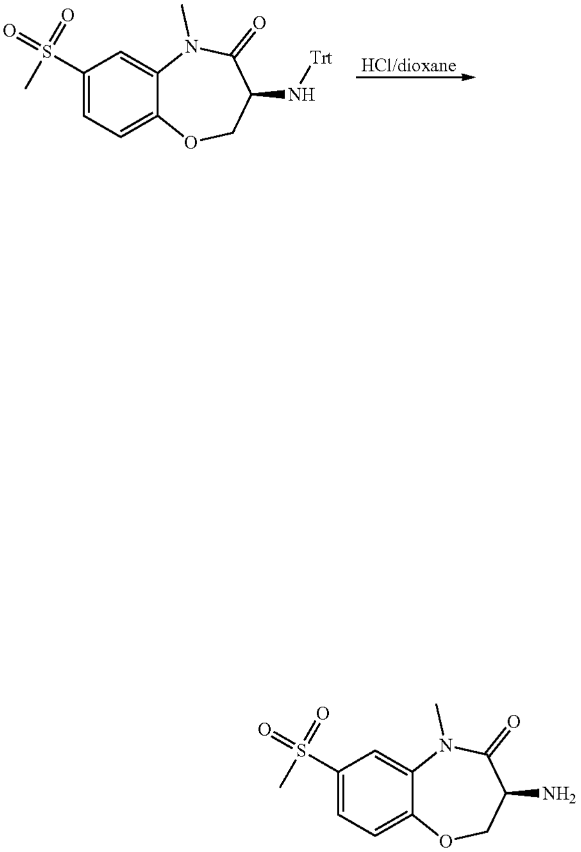

(S)-3-amino-5-methyl-7-(methylsulfonyl)-2,3-dihydrobenzo[b][1,4]oxazepin-4 (5H)-one hydrochloride A mixture of the product from the previous step (80 mg, 156.06 umol, 1 eq) and HCl/dioxane (4 M, 2 mL, 51.26 eq) was stirred at 15° C. for 1 h. The mixture was concentrated under reduced pressure to afford the HCl salt of the title compound (48 mg, crude) as a yellow solid. MS (ES+) $C_{11}H_{14}N_2O_4S$ requires: 270, found 271 $[M+H]^+$.

The following intermediates were obtained, as the respective HCl salts, using synthetic procedures as described above.

TABLE 5

| Amino oxazepine intermediates. II. | | | |
|---|---|---|---|
| Int. | Structure | IUPAC Name | Proc. of |
| B-17 | 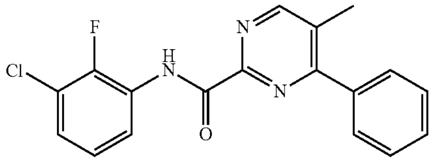 [SMILES: Cc1cnc(C(=O)Nc2cccc(Cl)c2F)nc1-c1ccccc1] | (2R,3S)-3-amino-2,5-dimethyl-2,3-dihydropyrido[3,2-b][1,4]oxazepin-4(5H)-one | B-4 |
| B-18 | 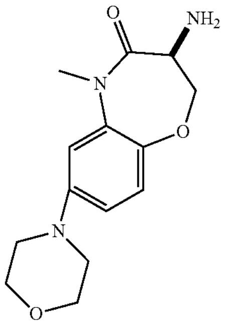 [SMILES: CN1C(=O)[C@@H](N)COc2ccc(N3CCOCC3)cc21] | (S)-3-amino-5-methyl-7-morpholino-2,3-dihydrobenzo[b][1,4]oxazepin-4(5H)-one | B-8 |
| B-19 | 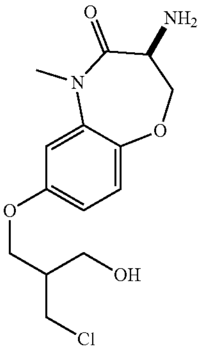 [SMILES: CN1C(=O)[C@@H](N)COc2ccc(OCC(CO)CCl)cc21] | (3S)-3-amino-7-(3-chloro-2-(hydroxymethyl)propoxy)-5-methyl-2,3-dihydrobenzo[b][1,4]oxazepin-4(5H)-one | B-8 |
| B-20 | 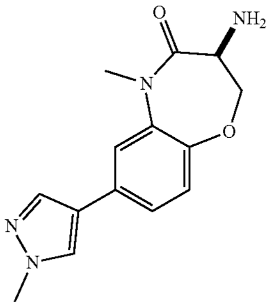 [SMILES: CN1C(=O)[C@@H](N)COc2ccc(-c3cnn(C)c3)cc21] | (S)-3-amino-5-methyl-7-(1-methyl-1H-pyrazol-4-yl)-2,3-dihydrobenzo[b][1,4]oxazepin-4(5H)-one | B-13 |
| B-21 | 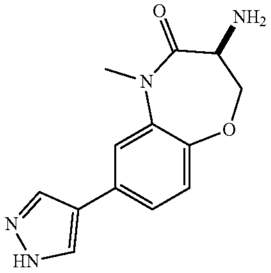 [SMILES: CN1C(=O)[C@@H](N)COc2ccc(-c3cn[nH]c3)cc21] | (S)-3-amino-5-methyl-7-(1H-pyrazol-4-yl)-2,3-dihydrobenzo[b][1,4]oxazepin-4(5H)-one | B-13 |

EXAMPLE 1

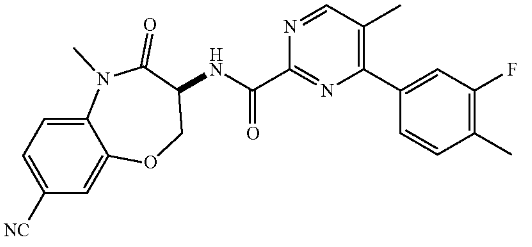

(S)—N-(8-cyano-5-methyl-4-oxo-2,3,4,5-tetrahydrobenzo[b][1,4]oxazepin-3-yl)-4-(3-fluoro-4-methylphenyl)-5-methylpyrimidine-2-carboxamide

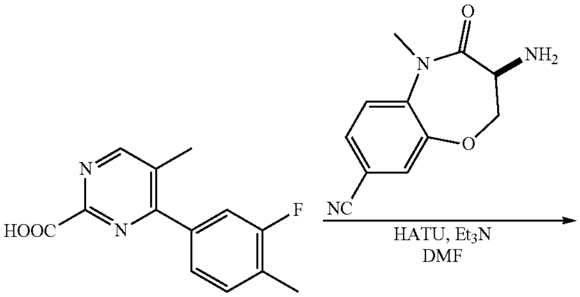

-continued

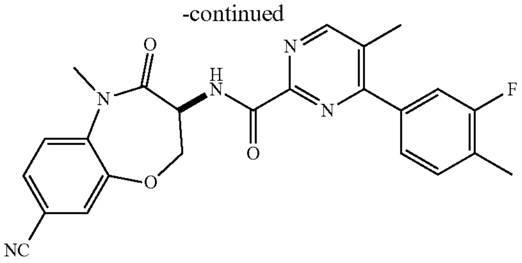

To a solution of 4-(3-fluoro-4-methylphenyl)-5-methylpyrimidine-2-carboxylic acid (28 mg, 0.12 mmol) in DMF (0.5 ml) were added HATU (53 mg, 0.14 mmol), Intermediate B-3 (25 mg, 0.12 mmol), and $Et_3N$ (20 μl, 0.14 mmol) and the resulting mixture was stirred at room temperature for 2 hr. Sat $NaHCO_3$ was added, and the aqueous phase was extracted with EtOAc (3×), the combined organic layers were washed with sat NaCl, dried over $Na_2SO_4$, filtered and concentrated under reduced pressure. The residue was purified by mass-triggered preparative HPLC (Mobile phase: A=0.1% TFA/$H_2O$, B=0.1% TFA/MeCN; Gradient: B=10-90%; 12 min; Column: C18) to give the title compound (3.4 mg, 8 μmol, 7% yield) as an off-white solid.

MS ($ES^+$) $C_{24}H_{20}FN_5O_3$ requires: 445, found: 446 $[M+H]^+$. $^1H$ NMR (500 MHz, DMSO-$d_6$) δ 9.04-9.01 (m, 1H), 8.91-8.89 (m, 1H), 7.86-7.79 (m, 2H), 7.73-7.70 (m, 1H), 7.70-7.67 (m, 1H), 7.66-7.59 (m, 1H), 7.37-7.30 (m, 1H), 4.97-4.88 (m, 1H), 4.74-4.66 (m, 1H), 4.60-4.53 (m, 1H), 3.36 (s, 3H), 2.43 (s, 3H), 2.36-2.32 (m, 3H).

TABLE 6

RIPK1 inhibitors. I.

| Ex. No. | Structure | Name |
| --- | --- | --- |
| 2 | 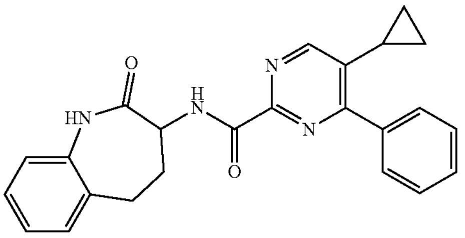 [SMILES: O=C(NC1CCc2ccccc2NC1=O)c1ncc(C2CC2)c(-c2ccccc2)n1] | 5-cyclopropyl-N-(2-oxo-2,3,4,5-tetrahydro-1H-benzo[b]azepin-3-yl)-4-phenylpyrimidine-2-carboxamide |
| 3 | 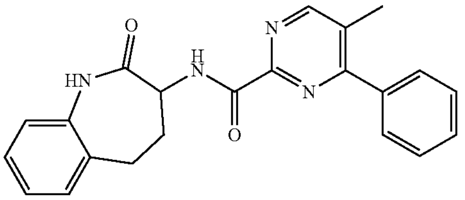 [SMILES: Cc1cnc(C(=O)NC2CCc3ccccc3NC2=O)nc1-c1ccccc1] | 5-methyl-N-(2-oxo-2,3,4,5-tetrahydro-1H-benzo[b]azepin-3-yl)-4-phenylpyrimidine-2-carboxamide |
| 4 | 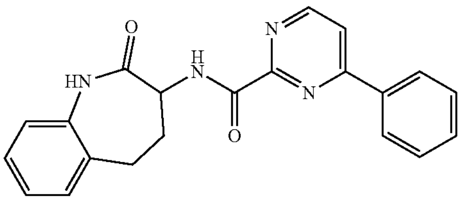 [SMILES: O=C(NC1CCc2ccccc2NC1=O)c1nccc(-c2ccccc2)n1] | N-(2-oxo-2,3,4,5-tetrahydro-1H-benzo[b]azepin-3-yl)-4-phenylpyrimidine-2-carboxamide |

TABLE 6-continued

| RIPK1 inhibitors. I. | | |
|---|---|---|
| Ex. No. | Structure | Name |
| 5 | 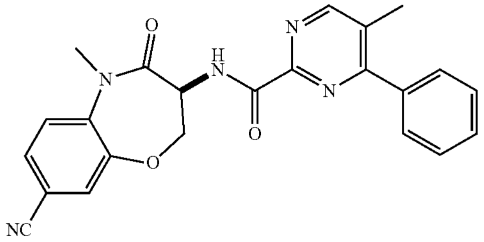 | (S)-N-(8-cyano-5-methyl-4-oxo-2,3,4,5-tetrahydro-benzo[b][1,4]oxazepin-3-yl)-5-methyl-4-phenylpyrimidine-2-carboxamide |
| 6 | 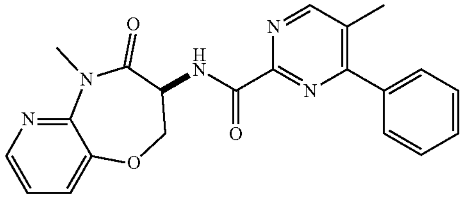 [SMILES: Cc1cnc(C(=O)N[C@H]2COc3cccnc3N(C)C2=O)nc1-c1ccccc1] | (S)-5-methyl-N-(5-methyl-4-oxo-2,3,4,5-tetrahydropyrido[3,2-b][1,4]oxazepin-3-yl)-4-phenylpyrimidine-2-carboxamide |
| 7 | 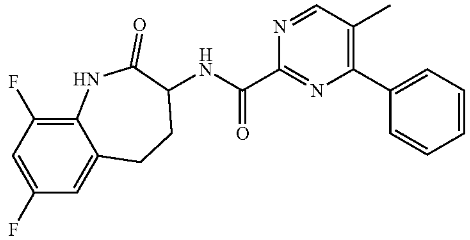 [SMILES: Cc1cnc(C(=O)NC2CCc3cc(F)cc(F)c3NC2=O)nc1-c1ccccc1] | N-(7,9-difluoro-2-oxo-2,3,4,5-tetrahydro-1H-benzo[b]azepin-3-yl)-5-methyl-4-phenylpyrimidine-2-carboxamide |
| 8 | 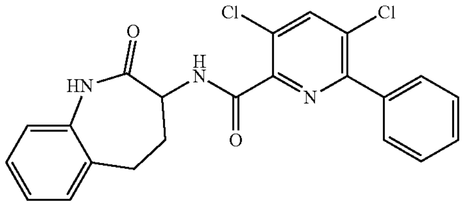 [SMILES: O=C(NC1CCc2ccccc2NC1=O)c1nc(-c2ccccc2)c(Cl)cc1Cl] | 3,5-dichloro-N-(2-oxo-2,3,4,5-tetrahydro-1H-benzo[b]azepin-3-yl)-6-phenylpicolinamide |
| 9 | 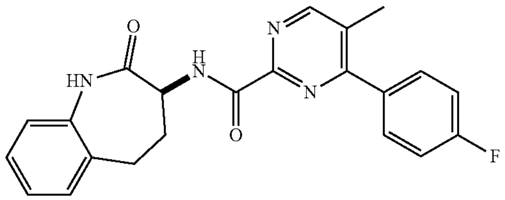 [SMILES: Cc1cnc(C(=O)N[C@H]2CCc3ccccc3NC2=O)nc1-c1ccc(F)cc1] | (S)-4-(4-fluorophenyl)-5-methyl-N-(2-oxo-2,3,4,5-tetrahydro-1H-benzo[b]azepin-3-yl)pyrimidine-2-carboxamide |
| 10 | 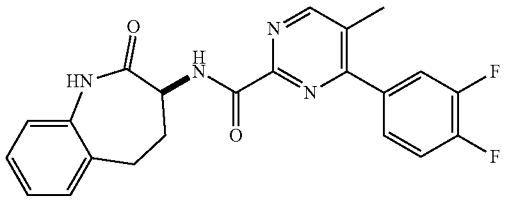 [SMILES: Cc1cnc(C(=O)N[C@H]2CCc3ccccc3NC2=O)nc1-c1ccc(F)c(F)c1] | (S)-4-(3,4-difluorophenyl)-5-methyl-N-(2-oxo-2,3,4,5-tetrahydro-1H-benzo[b]azepin-3-yl)pyrimidine-2-carboxamide |

TABLE 6-continued

| RIPK1 inhibitors. I. | | |
|---|---|---|
| Ex. No. | Structure | Name |
| 11 | 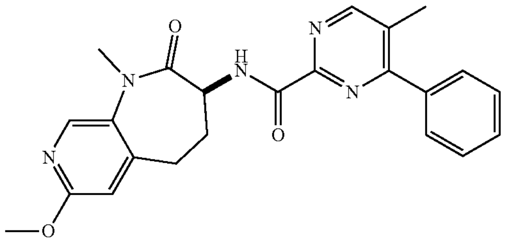 [SMILES: COc1cc2c(cn1)N(C)C(=O)[C@@H](NC(=O)c1ncc(C)c(-c3ccccc3)n1)CC2] | N-(7-methoxy-1-methyl-2-oxo-2,3,4,5-tetrahydro-1H-pyrido[3,4-b]azepin-3-yl)-5-methyl-4-phenylpyrimidine-2-carboxamide |
| 12 | 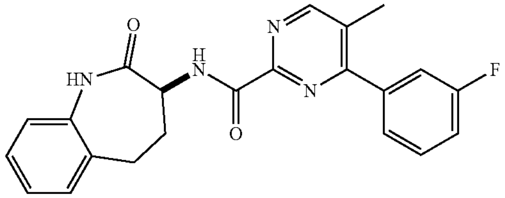 [SMILES: Cc1cnc(C(=O)N[C@H]2CCc3ccccc3NC2=O)nc1-c1cccc(F)c1] | (S)-4-(3-fluorophenyl)-5-methyl-N-(2-oxo-2,3,4,5-tetrahydro-1H-benzo[b]azepin-3-yl)pyrimidine-2-carboxamide |
| 13 | 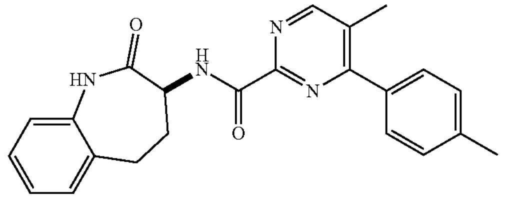 [SMILES: Cc1ccc(-c2nc(C(=O)N[C@H]3CCc4ccccc4NC3=O)ncc2C)cc1] | (S)-5-methyl-N-(2-oxo-2,3,4,5-tetrahydro-1H-benzo[b]azepin-3-yl)-4-(p-tolyl)pyrimidine-2-carboxamide |
| 14 | 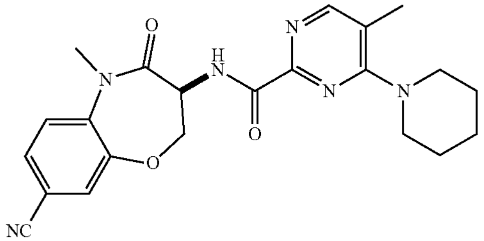 [SMILES: Cc1cnc(C(=O)N[C@H]2COc3cc(C#N)ccc3N(C)C2=O)nc1N1CCCCC1] | (S)-N-(8-cyano-5-methyl-4-oxo-2,3,4,5-tetrahydro-benzo[b][1,4]oxazepin-3-yl)-5-methyl-4-(piperidin-1-yl)-pyrimidine-2-carboxamide |
| 15 | 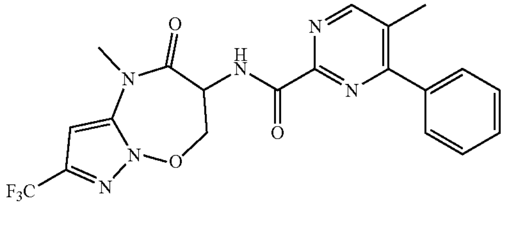 [SMILES: Cc1cnc(C(=O)NC2COn3nc(C(F)(F)F)cc3N(C)C2=O)nc1-c1ccccc1] | 5-methyl-N-(4-methyl-5-oxo-2-(trifluoromethyl)-5,6,7,8-tetrahydro-4H-pyrazolo[1,5-a][1,3]diazepin-6-yl)-4-phenyl-pyrimidine-2-carboxamide |
| 16 | 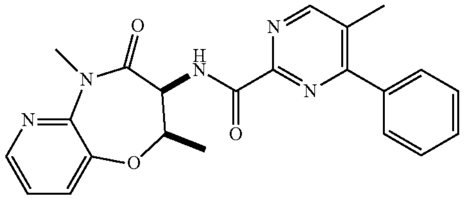 [SMILES: Cc1cnc(C(=O)N[C@@H]2C(=O)N(C)c3ncccc3O[C@@H]2C)nc1-c1ccccc1] | N-((2R,3S)-2,5-dimethyl-4-oxo-2,3,4,5-tetrahydropyrido[3,2-b][1,4]oxazepin-3-yl)-5-methyl-4-phenylpyrimidine-2-carboxamide |

TABLE 6-continued

| RIPK1 inhibitors. I. | | |
|---|---|---|
| Ex. No. | Structure | Name |
| 17 | 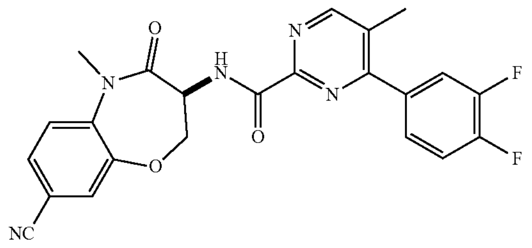 [SMILES: Cc1cnc(C(=O)N[C@H]2COc3cc(C#N)ccc3N(C)C2=O)nc1-c1ccc(F)c(F)c1] | (S)-N-(8-cyano-5-methyl-4-oxo-2,3,4,5-tetrahydro-benzo[b][1,4]oxazepin-3-yl)-4-(3,4-difluorophenyl)-5-methyl-pyrimidine-2-carboxamide |
| 18 | 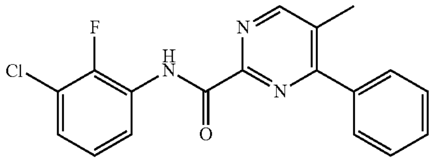 [SMILES: Cc1cnc(C(=O)Nc2cccc(Cl)c2F)nc1-c1ccccc1] | N-(3-chloro-2-fluorophenyl)-5-methyl-4-phenylpyrimidine-2-carboxamide |
| 19 | 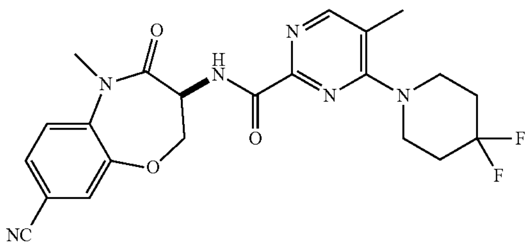 [SMILES: Cc1cnc(C(=O)N[C@H]2COc3cc(C#N)ccc3N(C)C2=O)nc1N1CCC(F)(F)CC1] | (S)-N-(8-cyano-5-methyl-4-oxo-2,3,4,5-tetrahydro-benzo[b][1,4]oxazepin-3-yl)-4-(4,4-difluoropiperidin-1-yl)-5-methylpyrimidine-2-carboxamide |
| 20 | 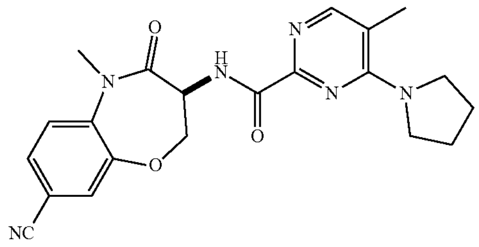 [SMILES: Cc1cnc(C(=O)N[C@H]2COc3cc(C#N)ccc3N(C)C2=O)nc1N1CCCC1] | (S)-N-(8-cyano-5-methyl-4-oxo-2,3,4,5-tetrahydro-benzo[b][1,4]oxazepin-3-yl)-5-methyl-4-(pyrrolidin-1-yl)-pyrimidine-2-carboxamide |
| 21 | 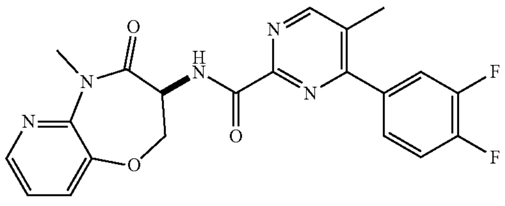 [SMILES: Cc1cnc(C(=O)N[C@H]2COc3cccnc3N(C)C2=O)nc1-c1ccc(F)c(F)c1] | (S)-4-(3,4-difluorophenyl)-5-methyl-N-(5-methyl-4-oxo-2,3,4,5-tetrahydropyrido[3,2-b][1,4]oxazepin-3-yl)pyrimidine-2-carboxamide |
| 22 | 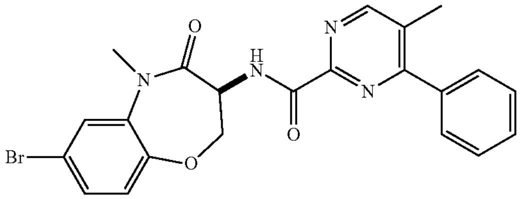 [SMILES: Cc1cnc(C(=O)N[C@H]2COc3ccc(Br)cc3N(C)C2=O)nc1-c1ccccc1] | (S)-N-(7-bromo-5-methyl-4-oxo-2,3,4,5-tetrahydro-benzo[b][1,4]oxazepin-3-yl)-5-methyl-4-phenylpyrimidine-2-carboxamide |

TABLE 6-continued

| RIPK1 inhibitors. I. | | |
|---|---|---|
| Ex. No. | Structure | Name |
| 23 | 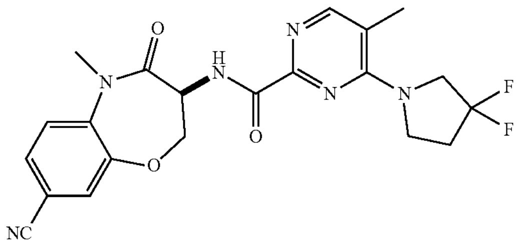 [SMILES: Cc1cnc(C(=O)N[C@H]2COc3cc(C#N)ccc3N(C)C2=O)nc1N1CCC(F)(F)C1] | (S)-N-(8-cyano-5-methyl-4-oxo-2,3,4,5-tetrahydro-benzo[b][1,4]oxazepin-3-yl)-4-(3,3-difluoropyrrolidin-1-yl)-5-methylpyrimidine-2-carboxamide |
| 24 | 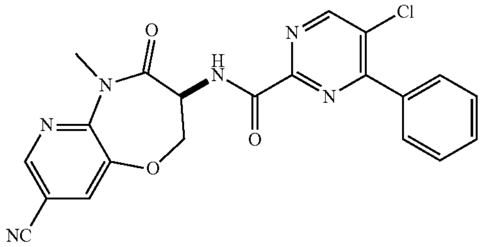 [SMILES: CN1C(=O)[C@@H](NC(=O)c2ncc(Cl)c(-c3ccccc3)n2)COc2cc(C#N)cnc21] | (S)-5-chloro-N-(8-cyano-5-methyl-4-oxo-2,3,4,5-tetrahydro-benzo[b][1,4]oxazepin-3-yl)-4-phenylpyrimidine-2-carboxamide |
| 25 | 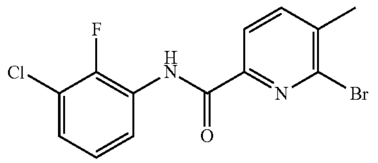 [SMILES: Cc1ccc(C(=O)Nc2cccc(Cl)c2F)nc1Br] | 6-bromo-N-(3-chloro-2-fluorophenyl)-5-methyl-picolinamide |
| 26 | 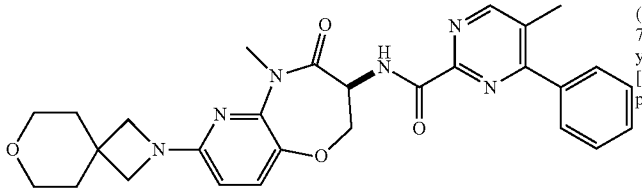 | (S)-5-methyl-N-(5-methyl-4-oxo-7-(7-oxa-2-azaspiro[3.5]nonan-2-yl)-2,3,4,5-tetrahydrobenzo[b]-[1,4]oxazepin-3-yl)-4-phenyl-pyrimidine-2-carboxamide |
| 27 | 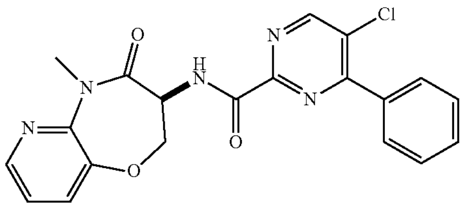 [SMILES: CN1C(=O)[C@@H](NC(=O)c2ncc(Cl)c(-c3ccccc3)n2)COc2cccnc21] | (S)-5-chloro-N-(5-methyl-4-oxo-2,3,4,5-tetrahydropyrido[3,2-b][1,4]oxazepin-3-yl)-4-phenylpyrimidine-2-carboxamide |
| 28 | | |
| 29 | 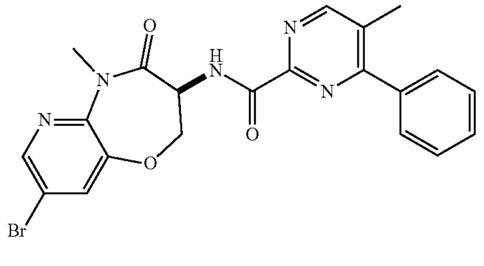 | (S)-N-(8-bromo-5-methyl-4-oxo-2,3,4,5-tetrahydropyrido[3,2-b][1,4]oxazepin-3-yl)-5-methyl-4-phenylpyrimidine-2-carboxamide |

TABLE 6-continued

RIPK1 inhibitors. I.

| Ex. No. | Structure | Name |
|---|---|---|
| 30 | 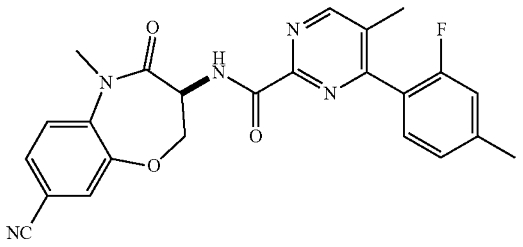 [SMILES: Cc1ccc(-c2nc(C(=O)N[C@H]3COc4cc(C#N)ccc4N(C)C3=O)ncc2C)c(F)c1] | (S)-N-(8-cyano-5-methyl-4-oxo-2,3,4,5-tetrahydro-benzo[b][1,4]oxazepin-3-yl)-4-(2-fluoro-4-methylphenyl)-5-methylpyrimidine-2-carboxamide |
| 31 | 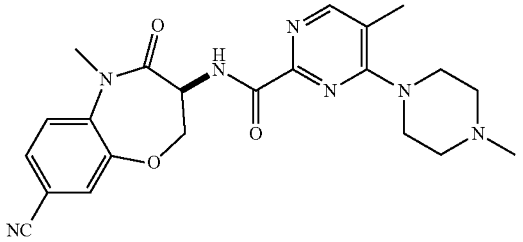 [SMILES: Cc1cnc(C(=O)N[C@H]2COc3cc(C#N)ccc3N(C)C2=O)nc1N1CCN(C)CC1] | (S)-N-(8-cyano-5-methyl-4-oxo-2,3,4,5-tetrahydro-benzo[b][1,4]oxazepin-3-yl)-5-methyl-4-(4-methylpiperazin-1-yl)pyrimidine-2-carboxamide |
| 32 | 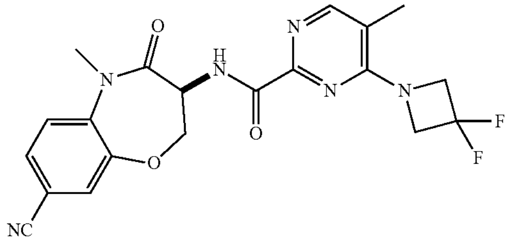 [SMILES: Cc1cnc(C(=O)N[C@H]2COc3cc(C#N)ccc3N(C)C2=O)nc1N1CC(F)(F)C1] | (S)-N-(8-cyano-5-methyl-4-oxo-2,3,4,5-tetrahydro-benzo[b][1,4]oxazepin-3-yl)-4-(3,3-difluoroazetidin-1-yl)-5-methylpyrimidine-2-carboxamide |
| 33 | 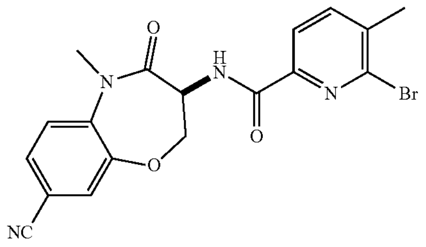 [SMILES: Cc1ccc(C(=O)N[C@H]2COc3cc(C#N)ccc3N(C)C2=O)nc1Br] | (S)-6-bromo-N-(8-cyano-5-methyl-4-oxo-2,3,4,5-tetrahydro-benzo[b][1,4]oxazepin-3-yl)-5-methylpicolinamide |
| 34 | 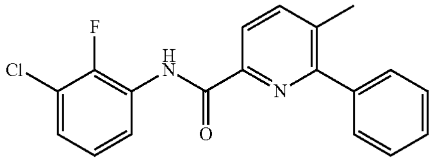 [SMILES: Cc1ccc(C(=O)Nc2cccc(Cl)c2F)nc1-c1ccccc1] | N-(3-chloro-2-fluorophenyl)-5-methyl-6-phenylpicolinamide |
| 35 | 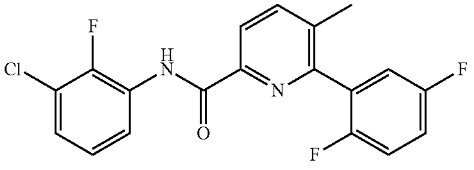 [SMILES: Cc1ccc(C(=O)Nc2cccc(Cl)c2F)nc1-c1cc(F)ccc1F] | N-(3-chloro-2-fluorophenyl)-6-(2,5-difluorophenyl)-5-methylpicolinamide |

TABLE 6-continued

| RIPK1 inhibitors. I. | | |
|---|---|---|
| Ex. No. | Structure | Name |
| 36 | 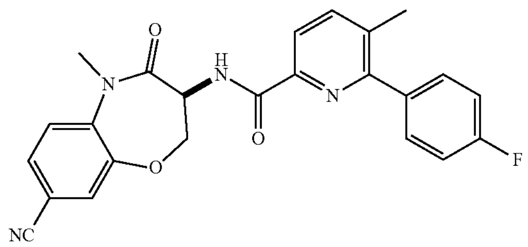 [SMILES: Cc1ccc(C(=O)N[C@H]2COc3cc(C#N)ccc3N(C)C2=O)nc1-c1ccc(F)cc1] | (S)-N-(8-cyano-5-methyl-4-oxo-2,3,4,5-tetrahydro-benzo[b][1,4]oxazepin-3-yl)-6-(4-fluorophenyl)-5-methyl-picolinamide |
| 37 | 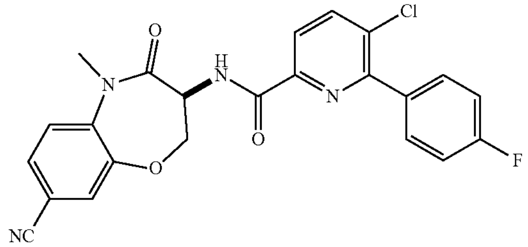 [SMILES: CN1C(=O)[C@@H](NC(=O)c2ccc(Cl)c(-c3ccc(F)cc3)n2)COc2cc(C#N)ccc21] | (S)-5-chloro-N-(8-cyano-5-methyl-4-oxo-2,3,4,5-tetrahydro-benzo[b][1,4]oxazepin-3-yl)-6-(4-fluorophenyl)picolinamide |
| 38 | 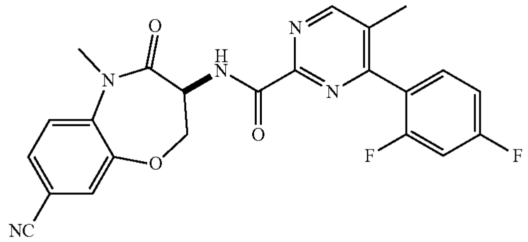 [SMILES: Cc1cnc(C(=O)N[C@H]2COc3cc(C#N)ccc3N(C)C2=O)nc1-c1ccc(F)cc1F] | (S)-N-(8-cyano-5-methyl-4-oxo-2,3,4,5-tetrahydro-benzo[b][1,4]oxazepin-3-yl)-4-(2,4-difluorophenyl)-5-methyl-pyrimidine-2-carboxamide |
| 39 | 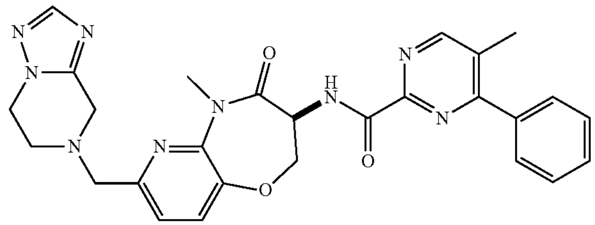 [SMILES: Cc1cnc(C(=O)N[C@H]2COc3ccc(CN4CCn5ncnc5C4)nc3N(C)C2=O)nc1-c1ccccc1] | (S)-N-(7-((5,6-dihydro-[1,2,4]triazolo[1,5-a]pyrazin-7(8H)-yl)methyl)-5-methyl-4-oxo-2,3,4,5-tetrahydro-benzo[b][1,4]oxazepin-3-yl)-5-methyl-4-phenylpyrimidine-2-carboxamide |
| 40 | 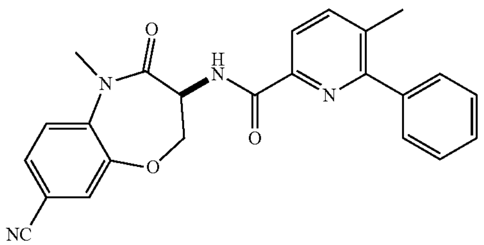 [SMILES: Cc1ccc(C(=O)N[C@H]2COc3cc(C#N)ccc3N(C)C2=O)nc1-c1ccccc1] | (S)-N-(8-cyano-5-methyl-4-oxo-2,3,4,5-tetrahydro-benzo[b][1,4]oxazepin-3-yl)-5-methyl-6-phenylpicolinamide |
| 41 | 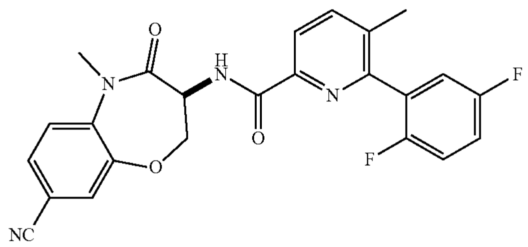 [SMILES: Cc1ccc(C(=O)N[C@H]2COc3cc(C#N)ccc3N(C)C2=O)nc1-c1cc(F)ccc1F] | (S)-N-(8-cyano-5-methyl-4-oxo-2,3,4,5-tetrahydro-benzo[b][1,4]oxazepin-3-yl)-6-(2,5-difluorophenyl)-5-methylpicolinamide |

TABLE 6-continued

RIPK1 inhibitors. I.

| Ex. No. | Structure | Name |
|---|---|---|
| 42 | 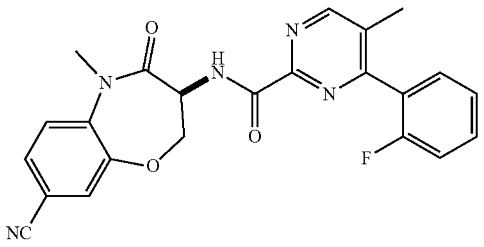 [SMILES: Cc1cnc(C(=O)N[C@H]2COc3cc(C#N)ccc3N(C)C2=O)nc1-c1ccccc1F] | (S)-N-(8-cyano-5-methyl-4-oxo-2,3,4,5-tetrahydro-benzo[b][1,4]oxazepin-3-yl)-4-(2-fluorophenyl)-5-methylpyrimidine-2-carboxamide |
| 43 | 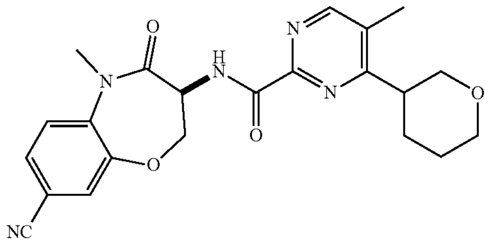 [SMILES: Cc1cnc(C(=O)N[C@H]2COc3cc(C#N)ccc3N(C)C2=O)nc1C1CCCOC1] | N-((S)-8-cyano-5-methyl-4-oxo-2,3,4,5-tetrahydro-benzo[b][1,4]oxazepin-3-yl)-5-methyl-4-(tetrahydro-2H-pyran-3-yl)pyrimidine-2-carboxamide |

| Ex. No. | Structure | Name |
|---|---|---|
| 44 | 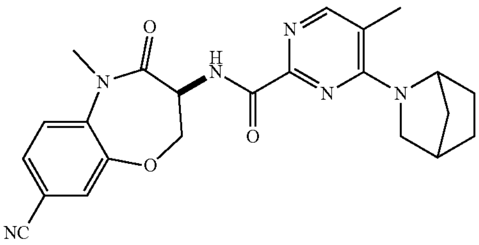 [SMILES: Cc1cnc(C(=O)N[C@H]2COc3cc(C#N)ccc3N(C)C2=O)nc1N1CC2CCC1C2] | 4-(2-azabicyclo[2.2.1]heptan-2-yl)-N-((S)-8-cyano-5-methyl-4-oxo-2,3,4,5-tetrahydro-benzo[b][1,4]oxazepin-3-yl)-5-methylpyrimidine-2-carboxamide |
| 45 | 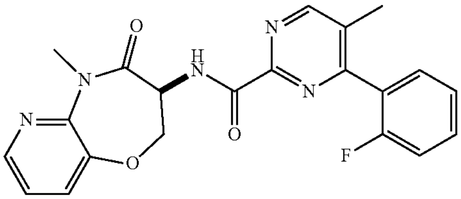 [SMILES: Cc1cnc(C(=O)N[C@H]2COc3cccnc3N(C)C2=O)nc1-c1ccccc1F] | (S)-4-(2-fluorophenyl)-5-methyl-N-(5-methyl-4-oxo-2,3,4,5-tetrahydropyrido[3,2-b][1,4]oxazepin-3-yl)pyrimidine-2-carboxamide |

TABLE 7

RIPK1 inhibitors. II.

| Ex. No. | | | Structure | Name |
|---|---|---|---|---|
| 46 | A-23 | B-1 | 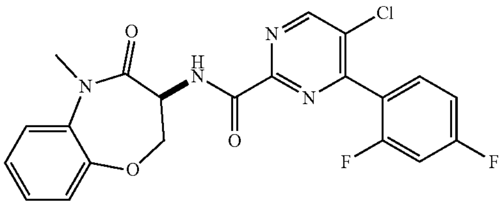 [SMILES: CN1C(=O)[C@@H](NC(=O)c2ncc(Cl)c(-c3ccc(F)cc3F)n2)COc2ccccc21] | (S)-5-chloro-4-(2,4-difluorophenyl)-N-(5-methyl-4-oxo-2,3,4,5-tetrahydrobenzo[b]-[1,4]oxazepin-3-yl)pyrimidine-2-carboxamide |

TABLE 7-continued

RIPK1 inhibitors. II.

| Ex. No. | | | Structure | Name |
|---|---|---|---|---|
| 47 | A-5 | B-2 | 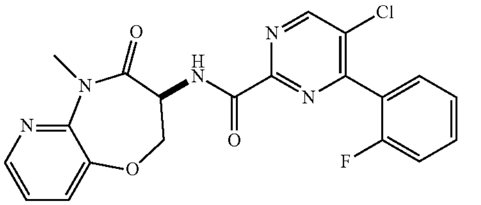 [SMILES: CN1C(=O)[C@@H](NC(=O)c2ncc(Cl)c(-c3ccccc3F)n2)COc2cccnc21] | (S)-5-chloro-4-(2-fluorophenyl)-N-(5-methyl-4-oxo-2,3,4,5-tetrahydro-pyrido[3,2-b][1,4]oxazepin-3-yl)pyrimidine-2-carboxamide |
| 48 | A-19 | B-2 | 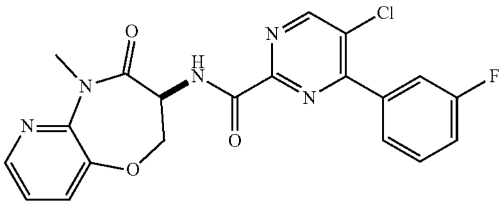 [SMILES: CN1C(=O)[C@@H](NC(=O)c2ncc(Cl)c(-c3cccc(F)c3)n2)COc2cccnc21] | (S)-5-chloro-4-(3-fluorophenyl)-N-(5-methyl-4-oxo-2,3,4,5-tetrahydro-pyrido[3,2-b][1,4]oxazepin-3-yl)pyrimidine-2-carboxamide |
| 49 | A-21 | B-2 | 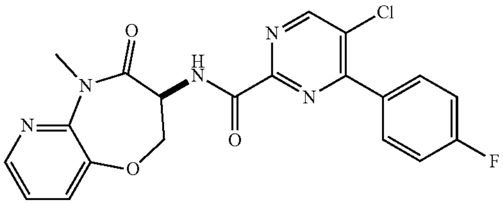 [SMILES: CN1C(=O)[C@@H](NC(=O)c2ncc(Cl)c(-c3ccc(F)cc3)n2)COc2cccnc21] | (S)-5-chloro-4-(4-fluorophenyl)-N-(5-methyl-4-oxo-2,3,4,5-tetrahydro-pyrido[3,2-b][1,4]oxazepin-3-yl)pyrimidine-2-carboxamide |
| 50 | A-23 | B-2 | 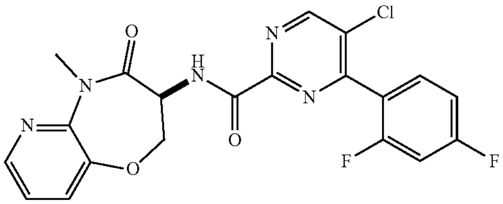 [SMILES: CN1C(=O)[C@@H](NC(=O)c2ncc(Cl)c(-c3ccc(F)cc3F)n2)COc2cccnc21] | (S)-5-chloro-4-(2,4-difluorophenyl)-N-(5-methyl-4-oxo-2,3,4,5-tetrahydro-pyrido[3,2-b][1,4]oxazepin-3-yl)pyrimidine-2-carboxamide |
| 51 | A-13 | B-2 | 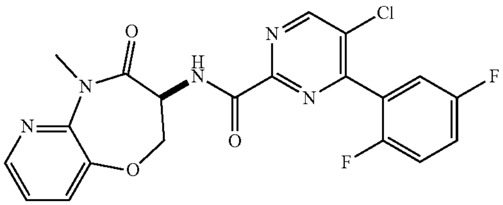 [SMILES: CN1C(=O)[C@@H](NC(=O)c2ncc(Cl)c(-c3cc(F)ccc3F)n2)COc2cccnc21] | (S)-5-chloro-4-(2,5-difluorophenyl)-N-(5-methyl-4-oxo-2,3,4,5-tetrahydro-pyrido[3,2-b][1,4]oxazepin-3-yl)pyrimidine-2-carboxamide |
| 52 | A-7 | B-2 | 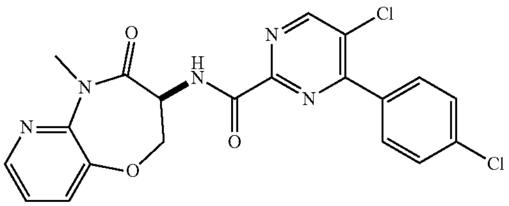 [SMILES: CN1C(=O)[C@@H](NC(=O)c2ncc(Cl)c(-c3ccc(Cl)cc3)n2)COc2cccnc21] | (S)-5-chloro-4-(4-chlorophenyl)-N-(5-methyl-4-oxo-2,3,4,5-tetrahydro-pyrido[3,2-b][1,4]oxazepin-3-yl)pyrimidine-2-carboxamide |
| 53 | A-24 | B-2 | 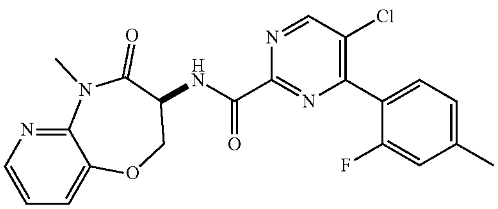 [SMILES: Cc1ccc(-c2nc(C(=O)N[C@H]3COc4cccnc4N(C)C3=O)ncc2Cl)c(F)c1] | (S)-5-chloro-4-(2-fluoro-4-methylphenyl)-N-(5-methyl-4-oxo-2,3,4,5-tetrahydro-pyrido[3,2-b][1,4]oxazepin-3-yl)pyrimidine-2-carboxamide |

TABLE 7-continued

RIPK1 inhibitors. II.

| Ex. No. | | | Structure | Name |
|---|---|---|---|---|
| 54 | A-25 | B-2 | 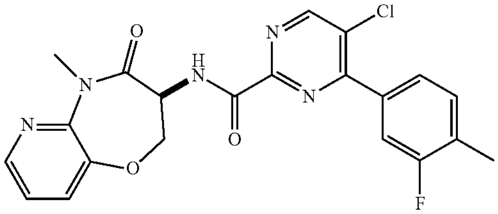 [SMILES: Cc1ccc(-c2nc(C(=O)N[C@H]3COc4cccnc4N(C)C3=O)ncc2Cl)cc1F] | (S)-5-chloro-4-(3-fluoro-4-methylphenyl)-N-(5-methyl-4-oxo-2,3,4,5-tetrahydro-pyrido[3,2-b][1,4]oxazepin-3-yl)pyrimidine-2-carboxamide |
| 55 | A-23 | B-17 | 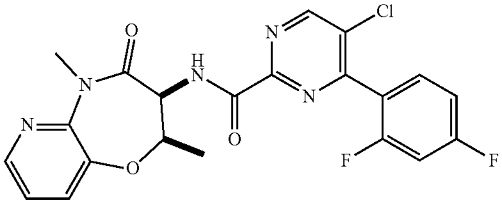 [SMILES: C[C@H]1Oc2cccnc2N(C)C(=O)[C@H]1NC(=O)c1ncc(Cl)c(-c2ccc(F)cc2F)n1] | 5-chloro-4-(2,4-difluorophenyl)-N-((2R,3S)-2,5-dimethyl-4-oxo-2,3,4,5-tetrahydropyrido[3,2-b]-[1,4]oxazepin-3-yl)pyrimidine-2-carboxamide |
| 56 | A-14 | B-2 | 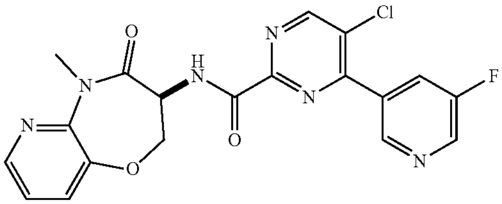 [SMILES: CN1C(=O)[C@@H](NC(=O)c2ncc(Cl)c(-c3cncc(F)c3)n2)COc2cccnc21] | (S)-5-chloro-4-(5-fluoropyridin-3-yl)-N-(5-methyl-4-oxo-2,3,4,5-tetrahydropyrido[3,2-b]-[1,4]oxazepin-3-yl)pyrimidine-2-carboxamide |
| 57 | A-45 | B-2 | 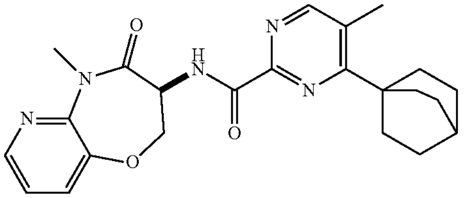 [SMILES: Cc1cnc(C(=O)N[C@H]2COc3cccnc3N(C)C2=O)nc1C12CCC(CC1)CC2] | (S)-4-(bicyclo[2.2.2]octan-1-yl)-5-methyl-N-(5-methyl-4-oxo-2,3,4,5-tetrahydro-pyrido[3,2-b][1,4]oxazepin-3-yl)pyrimidine-2-carboxamide |
| 58 | A-46 | B-2 | 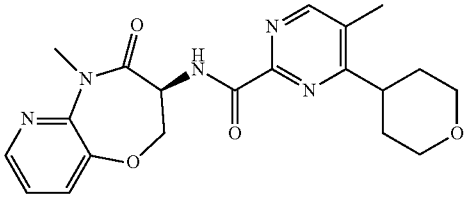 [SMILES: Cc1cnc(C(=O)N[C@H]2COc3cccnc3N(C)C2=O)nc1C1CCOCC1] | (S)-5-methyl-N-(5-methyl-4-oxo-2,3,4,5-tetrahydro-pyrido[3,2-b][1,4]oxazepin-3-yl)-4-(tetrahydro-2H-pyran-4-yl)pyrimidine-2-carboxamide |
| 59 | A-31 | B-2 | 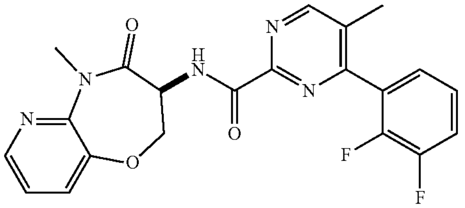 [SMILES: Cc1cnc(C(=O)N[C@H]2COc3cccnc3N(C)C2=O)nc1-c1cccc(F)c1F] | (S)-4-(2,3-difluorophenyl)-5-methyl-N-(5-methyl-4-oxo-2,3,4,5-tetrahydropyrido[3,2-b]-[1,4]oxazepin-3-yl)pyrimidine-2-carboxamide |
| 60 | A-32 | B-2 | 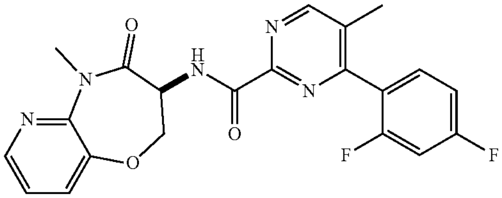 [SMILES: Cc1cnc(C(=O)N[C@H]2COc3cccnc3N(C)C2=O)nc1-c1ccc(F)cc1F] | (S)-4-(2,4-difluorophenyl)-5-methyl-N-(5-methyl-4-oxo-2,3,4,5-tetrahydropyrido[3,2-b]-[1,4]oxazepin-3-yl)pyrimidine-2-carboxamide |

TABLE 7-continued

RIPK1 inhibitors. II.

| Ex. No. | | | Structure | Name |
|---|---|---|---|---|
| 61 | A-33 | B-2 | 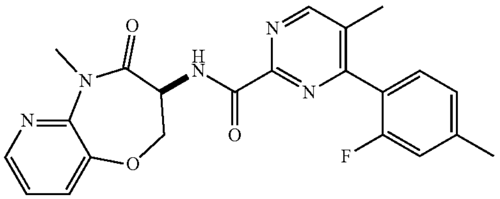 [SMILES: Cc1ccc(-c2nc(C(=O)N[C@H]3COc4cccnc4N(C)C3=O)ncc2C)c(F)c1] | (S)-4-(2-fluoro-4-methylphenyl)-5-methyl-N-(5-methyl-4-oxo-2,3,4,5-tetrahydropyrido[3,2-b]-[1,4]oxazepin-3-yl)pyrimidine-2-carboxamide |
| 62 | A-1 | B-2 | 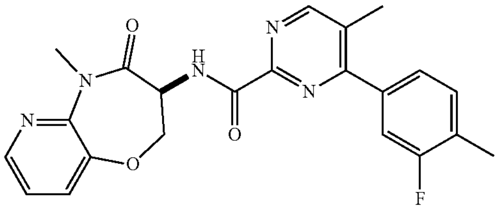 [SMILES: Cc1ccc(-c2nc(C(=O)N[C@H]3COc4cccnc4N(C)C3=O)ncc2C)cc1F] | (S)-4-(3-fluoro-4-methylphenyl)-5-methyl-N-(5-methyl-4-oxo-2,3,4,5-tetrahydropyrido[3,2-b]-[1,4]oxazepin-3-yl)pyrimidine-2-carboxamide |
| 63 | A-41 | B-4 | 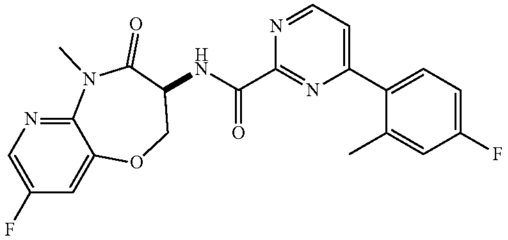 [SMILES: Cc1cc(F)ccc1-c1ccnc(C(=O)N[C@H]2COc3cc(F)cnc3N(C)C2=O)n1] | (S)-4-(4-fluoro-2-methylphenyl)-N-(8-fluoro-5-methyl-4-oxo-2,3,4,5-tetrahydropyrido[3,2-b]-[1,4]oxazepin-3-yl)pyrimidine-2-carboxamide |
| 64 | A-38 | B-4 | 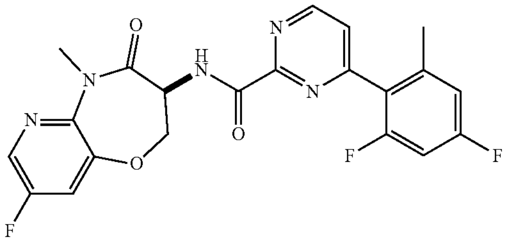 [SMILES: Cc1cc(F)cc(F)c1-c1ccnc(C(=O)N[C@H]2COc3cc(F)cnc3N(C)C2=O)n1] | (S)-4-(2,4-difluoro-6-methylphenyl)-N-(8-fluoro-5-methyl-4-oxo-2,3,4,5-tetrahydropyrido[3,2-b]-[1,4]oxazepin-3-yl)pyrimidine-2-carboxamide |
| 65 | A-15 | B-4 | 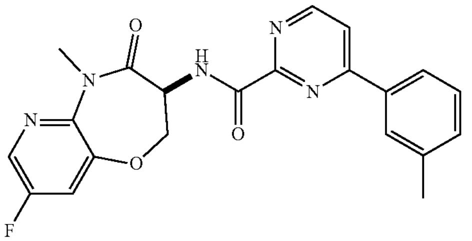 [SMILES: Cc1cccc(-c2ccnc(C(=O)N[C@H]3COc4cc(F)cnc4N(C)C3=O)n2)c1] | (S)-N-(8-fluoro-5-methyl-4-oxo-2,3,4,5-tetrahydro-pyrido[3,2-b][1,4]oxazepin-3-yl)-4-(m-tolyl)pyrimidine-2-carboxamide |
| 66 | A-17 | B-4 | 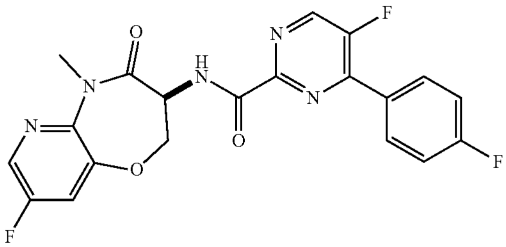 [SMILES: CN1C(=O)[C@@H](NC(=O)c2ncc(F)c(-c3ccc(F)cc3)n2)COc2cc(F)cnc21] | (S)-5-fluoro-N-(8-fluoro-5-methyl-4-oxo-2,3,4,5-tetrahydropyrido[3,2-b]-[1,4]oxazepin-3-yl)-4-(4-fluorophenyl)pyrimidine-2-carboxamide |

TABLE 7-continued

| Ex. No. | | | Structure | Name |
|---|---|---|---|---|
| | | | RIPK1 inhibitors. II. | |
| 67 | A-41 | B-4 | 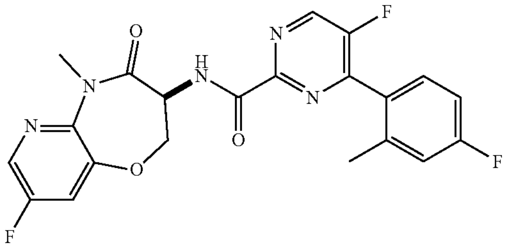 [SMILES: Cc1cc(F)ccc1-c1nc(C(=O)N[C@H]2COc3cc(F)cnc3N(C)C2=O)ncc1F] | (S)-5-fluoro-4-(4-fluoro-2-methylphenyl)-N-(8-fluoro-5-methyl-4-oxo-2,3,4,5-tetrahydropyrido[3,2-b]-[1,4]oxazepin-3-yl)pyrimidine-2-carboxamide |
| 68 | A-48 | B-4 | 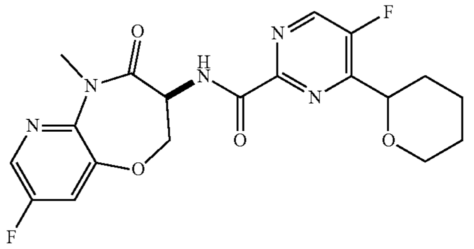 [SMILES: CN1C(=O)[C@@H](NC(=O)c2ncc(F)c(C3CCCCO3)n2)COc2cc(F)cnc21] | 5-chloro-N-((S)-8-fluoro-5-methyl-4-oxo-2,3,4,5-tetrahydropyrido[3,2-b]-[1,4]oxazepin-3-yl)-4-(tetrahydro-2H-pyran-2-yl)-pyrimidine-2-carboxamide |
| 69 | A-20 | B-4 | 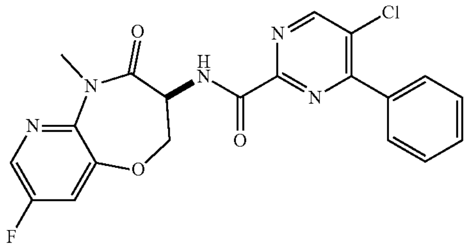 [SMILES: CN1C(=O)[C@@H](NC(=O)c2ncc(Cl)c(-c3ccccc3)n2)COc2cc(F)cnc21] | (S)-5-chloro-N-(8-fluoro-5-methyl-4-oxo-2,3,4,5-tetrahydropyrido[3,2-b]-[1,4]oxazepin-3-yl)-4-phenylpyrimidine-2-carboxamide |
| 70 | A-19 | B-4 | 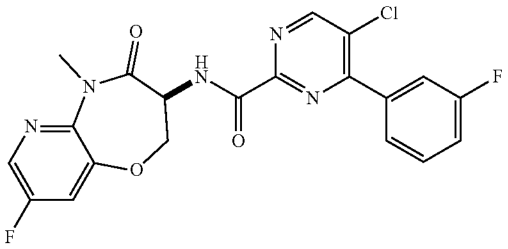 [SMILES: CN1C(=O)[C@@H](NC(=O)c2ncc(Cl)c(-c3cccc(F)c3)n2)COc2cc(F)cnc21] | (S)-5-chloro-N-(8-fluoro-5-methyl-4-oxo-2,3,4,5-tetrahydropyrido[3,2-b]-[1,4]oxazepin-3-yl)-4-(3-fluorophenyl)pyrimidine-2-carboxamide |
| 71 | A-21 | B-4 | 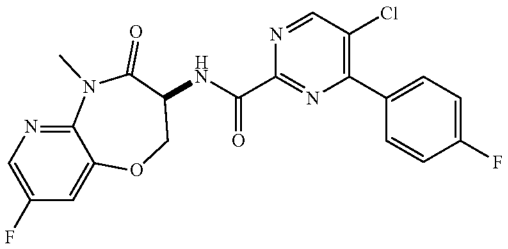 [SMILES: CN1C(=O)[C@@H](NC(=O)c2ncc(Cl)c(-c3ccc(F)cc3)n2)COc2cc(F)cnc21] | (S)-5-chloro-N-(8-fluoro-5-methyl-4-oxo-2,3,4,5-tetrahydropyrido[3,2-b]-[1,4]oxazepin-3-yl)-4-(4-fluorophenyl)pyrimidine-2-carboxamide |
| 72 | A-8 | B-4 | 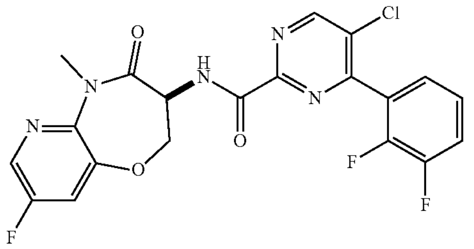 [SMILES: CN1C(=O)[C@@H](NC(=O)c2ncc(Cl)c(-c3cccc(F)c3F)n2)COc2cc(F)cnc21] | (S)-5-chloro-4-(2,3-difluorophenyl)-N-(8-fluoro-5-methyl-4-oxo-2,3,4,5-tetrahydropyrido[3,2-b]-[1,4]oxazepin-3-yl)pyrimidine-2-carboxamide |

TABLE 7-continued

| RIPK1 inhibitors. II. | | | | |
|---|---|---|---|---|
| Ex. No. | | | Structure | Name |
| 73 | A-23 | B-4 | 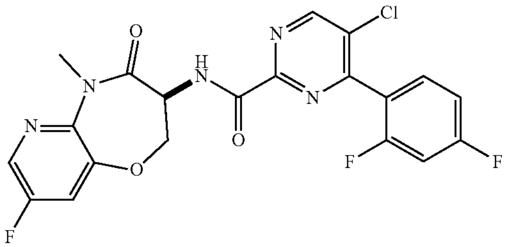 [SMILES: CN1C(=O)[C@@H](NC(=O)c2ncc(Cl)c(-c3ccc(F)cc3F)n2)COc2cc(F)cnc21] | (S)-5-chloro-4-(2,4-difluorophenyl)-N-(8-fluoro-5-methyl-4-oxo-2,3,4,5-tetrahydropyrido[3,2-b]-[1,4]oxazepin-3-yl)pyrimidine-2-carboxamide |
| 74 | A-13 | B-4 | 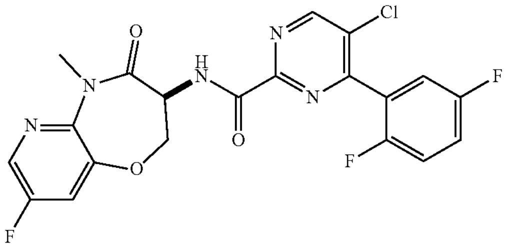 [SMILES: CN1C(=O)[C@@H](NC(=O)c2ncc(Cl)c(-c3cc(F)ccc3F)n2)COc2cc(F)cnc21] | (S)-5-chloro-4-(2,5-difluorophenyl)-N-(8-fluoro-5-methyl-4-oxo-2,3,4,5-tetrahydropyrido[3,2-b]-[1,4]oxazepin-3-yl)pyrimidine-2-carboxamide |
| 75 | A-11 | B-4 | 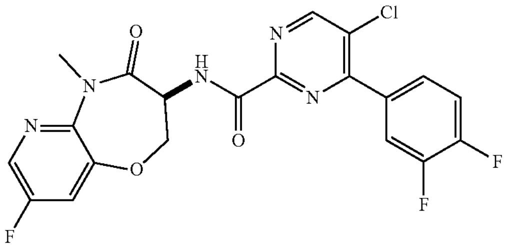 [SMILES: CN1C(=O)[C@@H](NC(=O)c2ncc(Cl)c(-c3ccc(F)c(F)c3)n2)COc2cc(F)cnc21] | (S)-5-chloro-4-(3,4-difluorophenyl)-N-(8-fluoro-5-methyl-4-oxo-2,3,4,5-tetrahydropyrido[3,2-b]-[1,4]oxazepin-3-yl)pyrimidine-2-carboxamide |
| 76 | A-12 | B-4 | 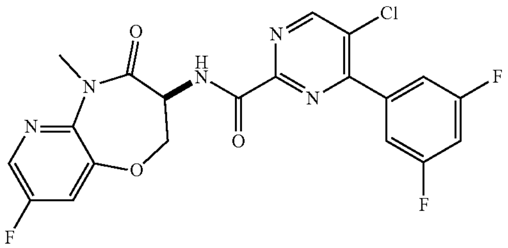 [SMILES: CN1C(=O)[C@@H](NC(=O)c2ncc(Cl)c(-c3cc(F)cc(F)c3)n2)COc2cc(F)cnc21] | (S)-5-chloro-4-(3,5-difluorophenyl)-N-(8-fluoro-5-methyl-4-oxo-2,3,4,5-tetrahydropyrido [3,2-b]-[1,4]oxazepin-3-yl)pyrimidine-2-carboxamide |
| 77 | A-24 | B-4 | 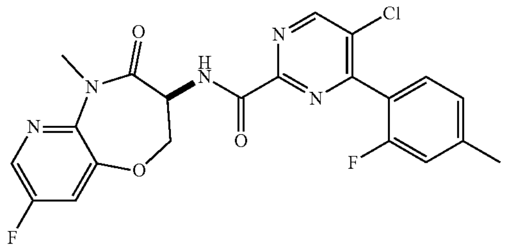 [SMILES: Cc1ccc(-c2nc(C(=O)N[C@H]3COc4cc(F)cnc4N(C)C3=O)ncc2Cl)c(F)c1] | (S)-5-chloro-4-(2-fluoro-4-methylphenyl)-N-(8-fluoro-5-methyl-4-oxo-2,3,4,5-tetrahydropyrido[3,2-b]-[1,4]oxazepin-3-yl)pyrimidine-2-carboxamide |
| 78 | A-25 | B-4 | 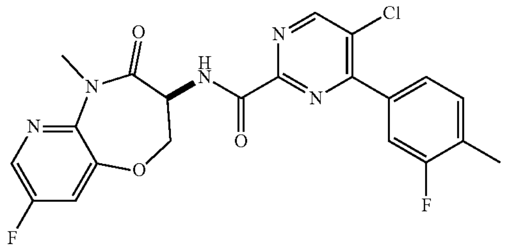 [SMILES: Cc1ccc(-c2nc(C(=O)N[C@H]3COc4cc(F)cnc4N(C)C3=O)ncc2Cl)cc1F] | (S)-5-chloro-4-(3-fluoro-4-methylphenyl)-N-(8-fluoro-5-methyl-4-oxo-2,3,4,5-tetrahydropyrido[3,2-b]-[1,4]oxazepin-3-yl)pyrimidine-2-carboxamide |

TABLE 7-continued

| Ex. No. | | | Structure | Name |
| --- | --- | --- | --- | --- |
| | | | RIPK1 inhibitors. II. | |
| 79 | A-4 | B-4 | 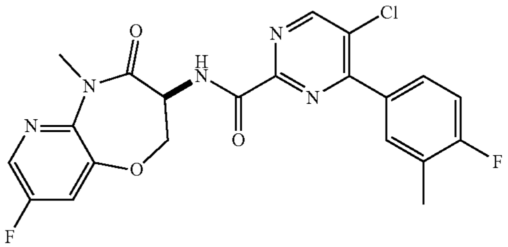 [SMILES: Cc1cc(-c2nc(C(=O)N[C@H]3COc4cc(F)cnc4N(C)C3=O)ncc2Cl)ccc1F] | (S)-5-chloro-4-(4-fluoro-3-methylphenyl)-N-(8-fluoro-5-methyl-4-oxo-2,3,4,5-tetrahydropyrido[3,2-b]-[1,4]oxazepin-3-yl)pyrimidine-2-carboxamide |
| 80 | A-6 | B-4 | 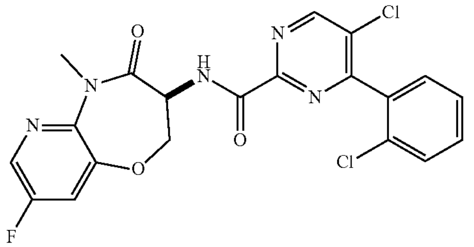 [SMILES: CN1C(=O)[C@@H](NC(=O)c2ncc(Cl)c(-c3ccccc3Cl)n2)COc2cc(F)cnc21] | (S)-5-chloro-4-(2-chlorophenyl)-N-(8-fluoro-5-methyl-4-oxo-2,3,4,5-tetrahydropyrido[3,2-b]-[1,4]oxazepin-3-yl)pyrimidine-2-carboxamide |
| 81 | A-22 | B-4 | 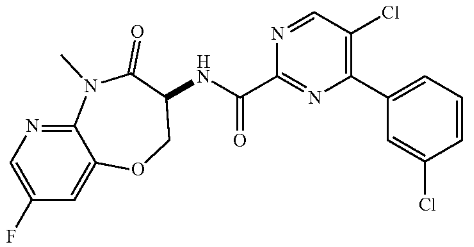 [SMILES: CN1C(=O)[C@@H](NC(=O)c2ncc(Cl)c(-c3cccc(Cl)c3)n2)COc2cc(F)cnc21] | (S)-5-chloro-4-(3-chlorophenyl)-N-(8-fluoro-5-methyl-4-oxo-2,3,4,5-tetrahydropyrido[3,2-b]-[1,4]oxazepin-3-yl)pyrimidine-2-carboxamide |
| 82 | A-7 | B-4 | 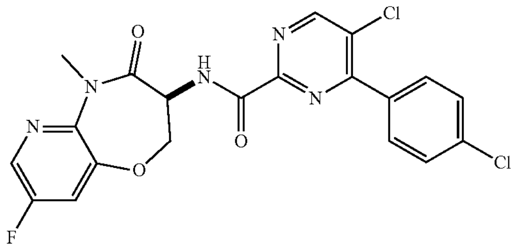 [SMILES: CN1C(=O)[C@@H](NC(=O)c2ncc(Cl)c(-c3ccc(Cl)cc3)n2)COc2cc(F)cnc21] | (S)-5-chloro-4-(4-chlorophenyl)-N-(8-fluoro-5-methyl-4-oxo-2,3,4,5-tetrahydropyrido[3,2-b]-[1,4]oxazepin-3-yl)pyrimidine-2-carboxamide |
| 83 | A-15 | B-4 | 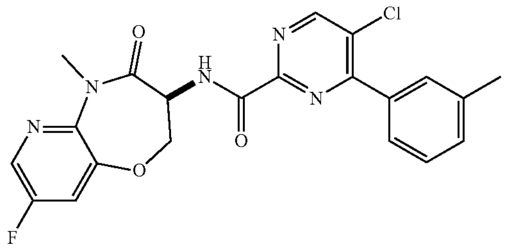 [SMILES: Cc1cccc(-c2nc(C(=O)N[C@H]3COc4cc(F)cnc4N(C)C3=O)ncc2Cl)c1] | (S)-5-chloro-N-(8-fluoro-5-methyl-4-oxo-2,3,4,5-tetrahydropyrido[3,2-b]-[1,4]oxazepin-3-yl)-4-(m-tolyl)-pyrimidine-2-carboxamide |
| 84 | A-9 | B-4 | 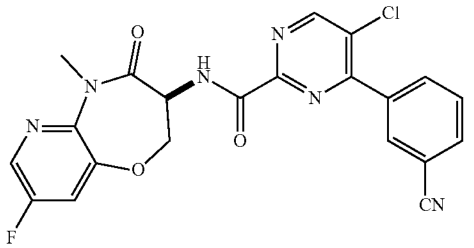 [SMILES: CN1C(=O)[C@@H](NC(=O)c2ncc(Cl)c(-c3cccc(C#N)c3)n2)COc2cc(F)cnc21] | (S)-5-chloro-4-(3-cyanophenyl)-N-(8-fluoro-5-methyl-4-oxo-2,3,4,5-tetrahydropyrido[3,2-b]-[1,4]oxazepin-3-yl)pyrimidine-2-carboxamide |

TABLE 7-continued

RIPK1 inhibitors. II.

| Ex. No. | | | Structure | Name |
|---|---|---|---|---|
| 85 | A-27 | B-4 | 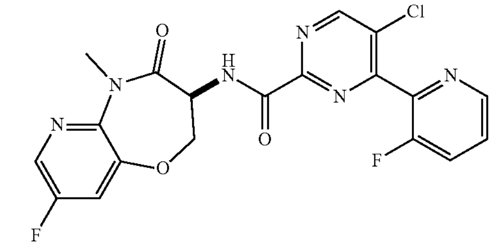 [SMILES: CN1C(=O)[C@@H](NC(=O)c2ncc(Cl)c(-c3ncccc3F)n2)COc2cc(F)cnc21] | (S)-5-chloro-N-(8-fluoro-5-methyl-4-oxo-2,3,4,5-tetrahydropyrido[3,2-b]-[1,4]oxazepin-3-yl)-4-(3-fluoropyridin-2-yl)pyrimidine-2-carboxamide |
| 86 | A-45 | B-4 | 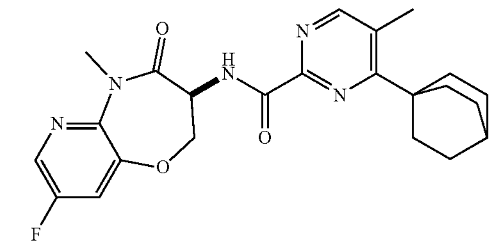 [SMILES: Cc1cnc(C(=O)N[C@H]2COc3cc(F)cnc3N(C)C2=O)nc1C12CCC(CC1)CC2] | (S)-4-(bicyclo[2.2.2]octan-1-yl)-N-(8-fluoro-5-methyl-4-oxo-2,3,4,5-tetrahydro-pyrido[3,2-b][1,4]oxazepin-3-yl)-5-methylpyrimidine-2-carboxamide |
| 87 | A-46 | B-4 | 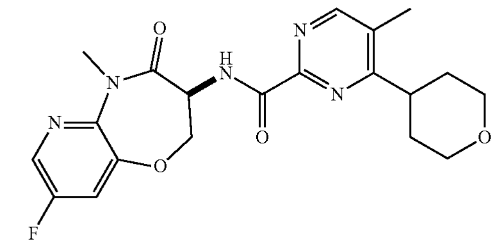 [SMILES: Cc1cnc(C(=O)N[C@H]2COc3cc(F)cnc3N(C)C2=O)nc1C1CCOCC1] | (S)-N-(8-fluoro-5-methyl-4-oxo-2,3,4,5-tetrahydro-pyrido[3,2-b][1,4]oxazepin-3-yl)-5-methyl-4-(tetrahydro-2H-pyran-4-yl)pyrimidine-2-carboxamide |
| 88 | A-47 | B-4 | 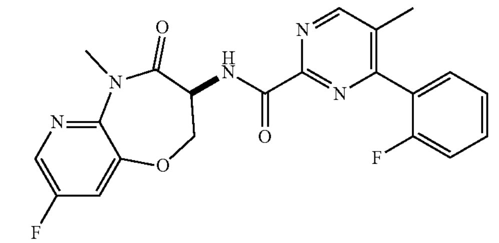 [SMILES: Cc1cnc(C(=O)N[C@H]2COc3cc(F)cnc3N(C)C2=O)nc1-c1ccccc1F] | (S)-N-(8-fluoro-5-methyl-4-oxo-2,3,4,5-tetrahydro-pyrido[3,2-b][1,4]oxazepin-3-yl)-4-(2-fluorophenyl)-5-methylpyrimidine-2-carboxamide |
| 89 | A-41 | B-5 | 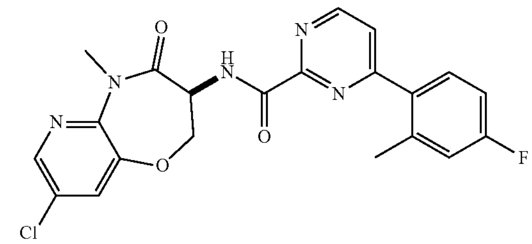 [SMILES: Cc1cc(F)ccc1-c1ccnc(C(=O)N[C@H]2COc3cc(Cl)cnc3N(C)C2=O)n1] | (S)-N-(8-chloro-5-methyl-4-oxo-2,3,4,5-tetrahydro-pyrido[3,2-b][1,4]oxazepin-3-yl)-4-(4-fluoro-2-methylphenyl)pyrimidine-2-carboxamide |
| 90 | A-38 | B-5 | 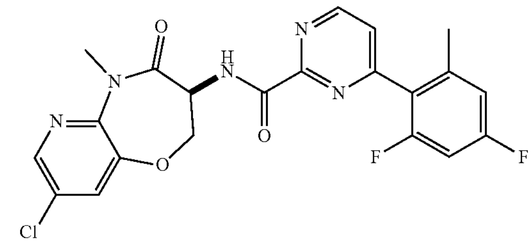 [SMILES: Cc1cc(F)cc(F)c1-c1ccnc(C(=O)N[C@H]2COc3cc(Cl)cnc3N(C)C2=O)n1] | (S)-N-(8-chloro-5-methyl-4-oxo-2,3,4,5-tetrahydro-pyrido[3,2-b][1,4]oxazepin-3-yl)-4-(2,4-difluoro-6-methylphenyl)pyrimidine-2-carboxamide |

TABLE 7-continued

| Ex. No. | | | Structure | Name |
|---|---|---|---|---|
| | | | RIPK1 inhibitors. II. | |
| 91 | A-17 | B-5 | 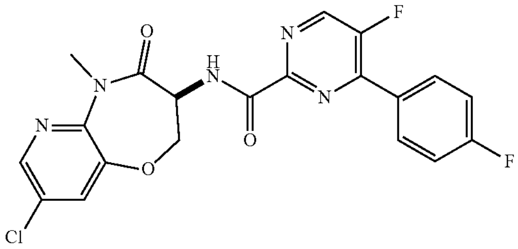 [SMILES: CN1C(=O)[C@@H](NC(=O)c2ncc(F)c(-c3ccc(F)cc3)n2)COc2cc(Cl)cnc21] | (S)-N-(8-chloro-5-methyl-4-oxo-2,3,4,5-tetrahydro-pyrido[3,2-b][1,4]oxazepin-3-yl)-5-fluoro-4-(4-fluorophenyl)-pyrimidine-2-carboxamide |
| 92 | A-16 | B-5 | 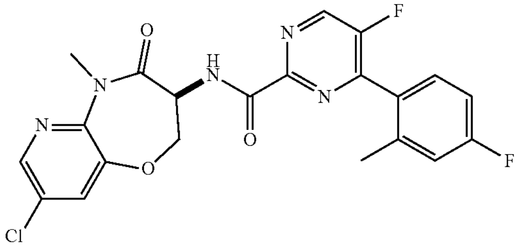 [SMILES: Cc1cc(F)ccc1-c1nc(C(=O)N[C@H]2COc3cc(Cl)cnc3N(C)C2=O)ncc1F] | (S)-N-(8-chloro-5-methyl-4-oxo-2,3,4,5-tetrahydro-pyrido[3,2-b][1,4]oxazepin-3-yl)-5-fluoro-4-(4-fluoro-2-methylphenyl)pyrimidine-2-carboxamide |
| 93 | A-20 | B-5 | 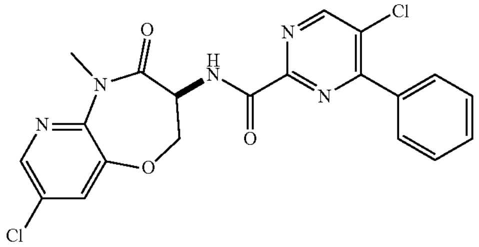 | (S)-5-chloro-N-(8-chloro-5-methyl-4-oxo-2,3,4,5-tetrahydropyrido[3,2-b]-[1,4]oxazepin-3-yl)-4-phenylpyrimidine-2-carboxamide |
| 94 | A-5 | B-5 | 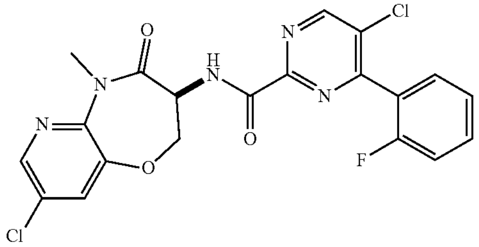 | (S)-5-chloro-N-(8-chloro-5-methyl-4-oxo-2,3,4,5-tetrahydropyrido[3,2-b]-[1,4]oxazepin-3-yl)-4-(2-fluorophenyl)pyrimidine-2-carboxamide |
| 95 | A-8 | B-5 | 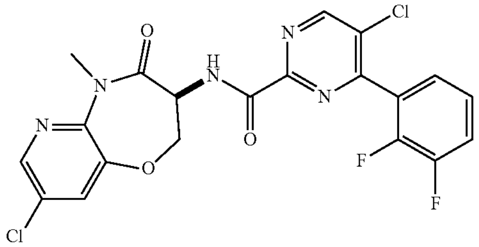 [SMILES: CN1C(=O)[C@@H](NC(=O)c2ncc(Cl)c(-c3cccc(F)c3F)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(2,3-difluorophenyl)pyrimidine-2-carboxamide |
| 96 | A-23 | B-5 | 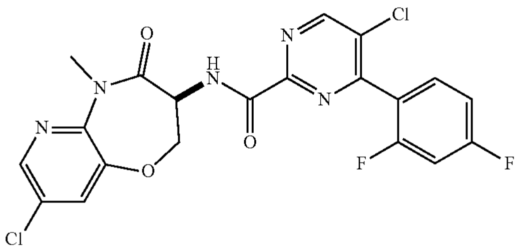 [SMILES: CN1C(=O)[C@@H](NC(=O)c2ncc(Cl)c(-c3ccc(F)cc3F)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(2,4-difluorophenyl)pyrimidine-2-carboxamide |

TABLE 7-continued

RIPK1 inhibitors. II.

| Ex. No. | | | Structure | Name |
|---|---|---|---|---|
| 97 | A-11 | B-5 | 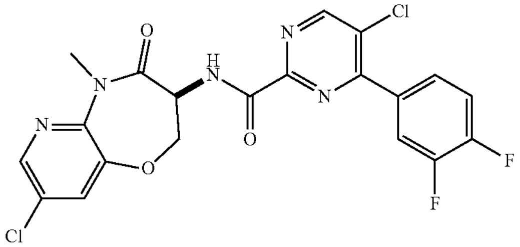 [SMILES: CN1C(=O)[C@@H](NC(=O)c2ncc(Cl)c(-c3ccc(F)c(F)c3)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(3,4-difluorophenyl)pyrimidine-2-carboxamide |
| 98 | A-13 | B-5 | 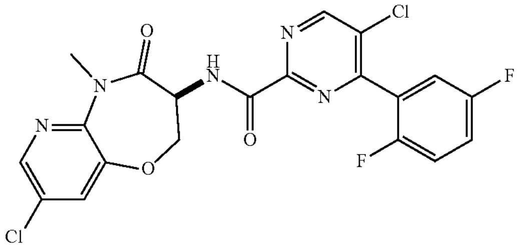 [SMILES: CN1C(=O)[C@@H](NC(=O)c2ncc(Cl)c(-c3cc(F)ccc3F)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(2,5-difluorophenyl)pyrimidine-2-carboxamide |
| 99 | A-12 | B-5 | 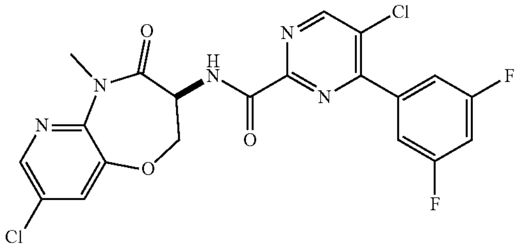 [SMILES: CN1C(=O)[C@@H](NC(=O)c2ncc(Cl)c(-c3cc(F)cc(F)c3)n2)COc2cc(Cl)cnc21] | (S)-5-chloro-N-(8-chloro-5-methyl-4-oxo-2,3,4,5-tetrahydropyrido [3,2-b]-[1,4]oxazepin-3-yl)-4-(3,5-difluorophenyl)pyrimidine-2-carboxamide |
| 100 | A-4 | B-5 | 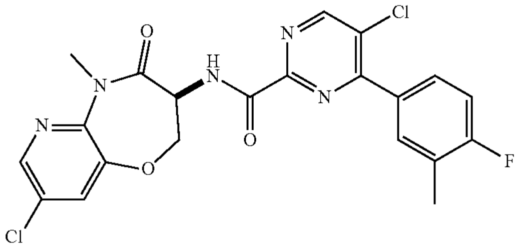 [SMILES: Cc1cc(-c2nc(C(=O)N[C@H]3COc4cc(Cl)cnc4N(C)C3=O)ncc2Cl)ccc1F] | (S)-5-chloro-N-(8-chloro-5-methyl-4-oxo-2,3,4,5-tetrahydropyrido[3,2-b]-[1,4]oxazepin-3-yl)-4-(4-fluoro-3-methylphenyl)pyrimidine-2-carboxamide |
| 101 | A-6 | B-5 | 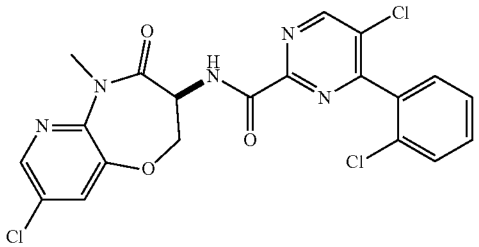 | (S)-5-chloro-N-(8-chloro-5-methyl-4-oxo-2,3,4,5-tetrahydropyrido[3,2-b]-[1,4]oxazepin-3-yl)-4-(2-chlorophenyl)pyrimidine-2-carboxamide |
| 102 | A-22 | B-5 | 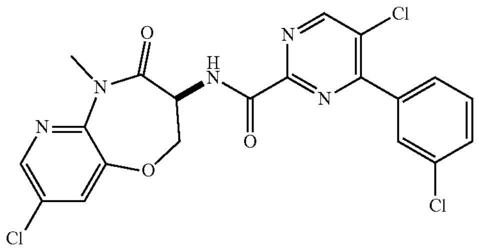 [SMILES: CN1C(=O)[C@@H](NC(=O)c2ncc(Cl)c(-c3cccc(Cl)c3)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(3-chlorophenyl)pyrimidine-2-carboxamide |

TABLE 7-continued

RIPK1 inhibitors. II.

| Ex. No. | | | Structure | Name |
|---|---|---|---|---|
| 103 | A-7 | B-5 | 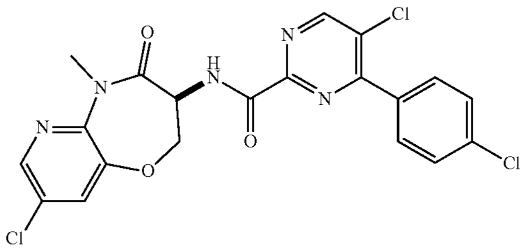 [SMILES: CN1C(=O)[C@@H](NC(=O)c2ncc(Cl)c(-c3ccc(Cl)cc3)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(4-chlorophenyl)pyrimidine-2-carboxamide |
| 104 | A-9 | B-5 | 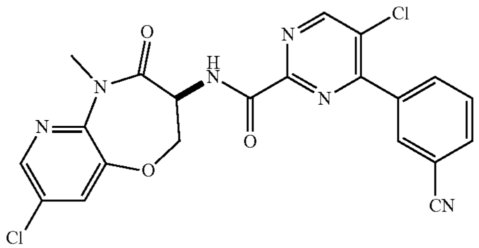 [SMILES: CN1C(=O)[C@@H](NC(=O)c2ncc(Cl)c(-c3cccc(C#N)c3)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(3-cyanophenyl)pyrimidine-2-carboxamide |
| 105 | A-10 | B-5 | 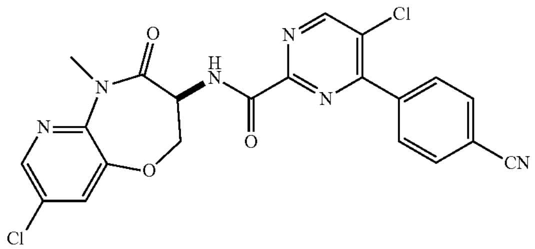 [SMILES: CN1C(=O)[C@@H](NC(=O)c2ncc(Cl)c(-c3ccc(C#N)cc3)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(4-cyanophenyl)pyrimidine-2-carboxamide |
| 106 | A-15 | B-5 | 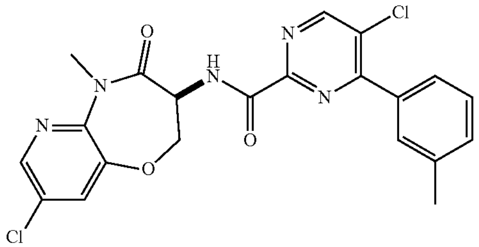 [SMILES: Cc1cccc(-c2nc(C(=O)N[C@H]3COc4cc(Cl)cnc4N(C)C3=O)ncc2Cl)c1] | (S)-5-chloro-N-(8-chloro-5-methyl-4-oxo-2,3,4,5-tetrahydropyrido[3,2-b]-[1,4]oxazepin-3-yl)-4-(m-tolyl)-pyrimidine-2-carboxamide |
| 107 | A-51 | B-5 | 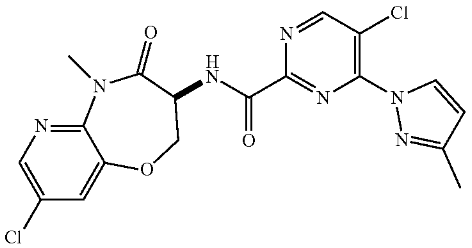 [SMILES: Cc1ccn(-c2nc(C(=O)N[C@H]3COc4cc(Cl)cnc4N(C)C3=O)ncc2Cl)n1] | (S)-5-chloro-N-(8-chloro-5-methyl-4-oxo-2,3,4,5-tetrahydropyrido [3,2-b]-[1,4]oxazepin-3-yl)-4-(3-methyl-1H-pyrazol-1-yl)-pyrimidine-2-carboxamide |
| 108 | A-27 | B-5 | 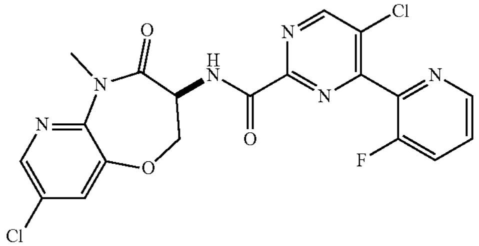 [SMILES: CN1C(=O)[C@@H](NC(=O)c2ncc(Cl)c(-c3ncccc3F)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(3-fluoropyridin-2-yl)pyrimidine-2-carboxamide |

TABLE 7-continued

RIPK1 inhibitors. II.

| Ex. No. | | | Structure | Name |
|---|---|---|---|---|
| 109 | A-14 | B-5 | 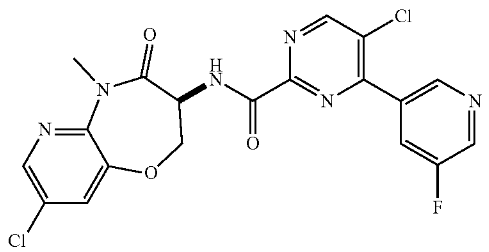 [SMILES: CN1C(=O)[C@@H](NC(=O)c2ncc(Cl)c(-c3cncc(F)c3)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(5-fluoropyridin-3-yl)pyrimidine-2-carboxamide |
| 110 | A-49 | B-5 | 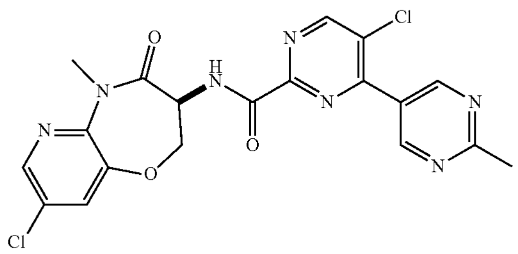 [SMILES: Cc1ncc(-c2nc(C(=O)N[C@H]3COc4cc(Cl)cnc4N(C)C3=O)ncc2Cl)cn1] | (S)-5-chloro-N-(8-chloro-5-methyl-4-oxo-2,3,4,5-tetrahydropyrido[3,2-b]-[1,4]oxazepin-3-yl)-2'-methyl-[4,5'-bipyrimidine]-2-carboxamide |
| 111 | A-50 | B-5 | 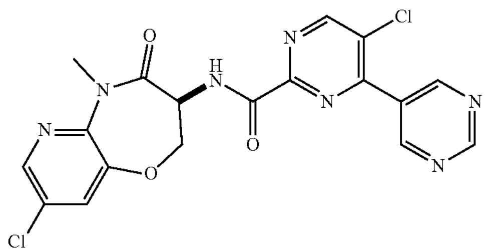 [SMILES: CN1C(=O)[C@@H](NC(=O)c2ncc(Cl)c(-c3cncnc3)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-[4,5'-bipyrimidine]-2-carboxamide |
| 112 | A-28 | B-5 | 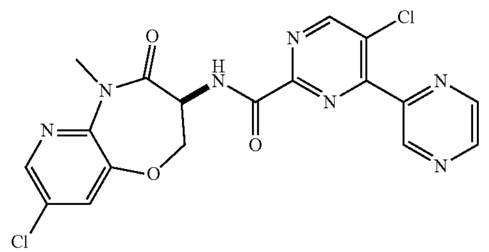 [SMILES: CN1C(=O)[C@@H](NC(=O)c2ncc(Cl)c(-c3cnccn3)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(pyrazin-2-yl)pyrimidine-2-carboxamide |
| 113 | A-54 | B-5 | 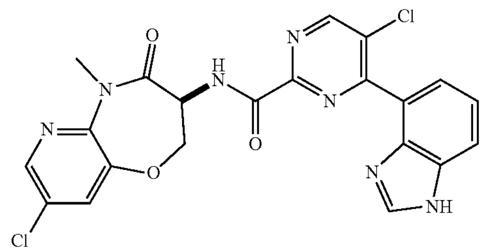 [SMILES: CN1C(=O)[C@@H](NC(=O)c2ncc(Cl)c(-c3cccc4[nH]cnc34)n2)COc2cc(Cl)cnc21] | (S)-4-(1H-benzo[d]imidazol-4-yl)-5-chloro-N-(8-chloro-5-methyl-4-oxo-2,3,4,5-tetrahydropyrido[3,2-b]-[1,4]oxazepin-3-yl)pyrimidine-2-carboxamide |
| 114 | A-57 | B-5 | 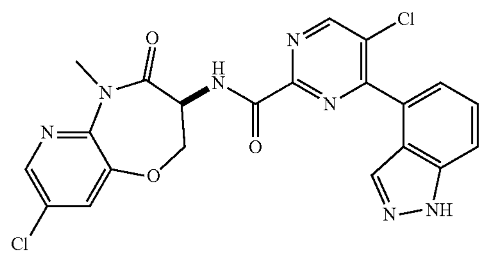 [SMILES: CN1C(=O)[C@@H](NC(=O)c2ncc(Cl)c(-c3cccc4[nH]ncc34)n2)COc2cc(Cl)cnc21] | (S)-5-chloro-N-(8-chloro-5-methyl-4-oxo-2,3,4,5-tetrahydropyrido[3,2-b]-[1,4]oxazepin-3-yl)-4-(1H-indazol-4-yl)pyrimidine-2-carboxamide |

TABLE 7-continued

RIPK1 inhibitors. II.

| Ex. No. | | | Structure | Name |
|---|---|---|---|---|
| 115 | A-59 | B-5 | 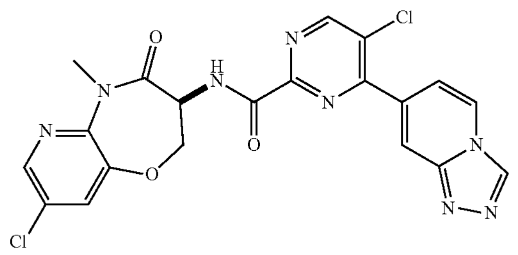 [SMILES: CN1C(=O)[C@@H](NC(=O)c2ncc(Cl)c(-c3ccn4cnnc4c3)n2)COc2cc(Cl)cnc21] | (S)-4-([1,2,4]triazolo[4,3-a]pyridin-7-yl)-5-chloro-N-(8-chloro-5-methyl-4-oxo-2,3,4,5-tetrahydropyrido[3,2-b]-[1,4]oxazepin-3-yl)pyrimidine-2-carboxamide |
| 116 | A-47 | B-5 | 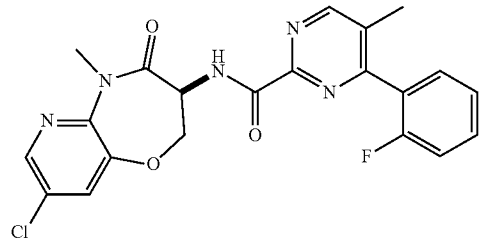 [SMILES: Cc1cnc(C(=O)N[C@H]2COc3cc(Cl)cnc3N(C)C2=O)nc1-c1ccccc1F] | (S)-N-(8-chloro-5-methyl-4-oxo-2,3,4,5-tetrahydro-pyrido[3,2-b][1,4]oxazepin-3-yl)-4-(2-fluorophenyl)-5-methylpyrimidine-2-carboxamide |
| 117 | A-31 | B-5 | 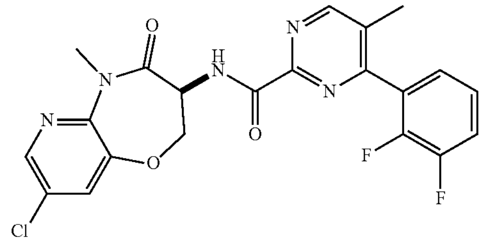 [SMILES: Cc1cnc(C(=O)N[C@H]2COc3cc(Cl)cnc3N(C)C2=O)nc1-c1cccc(F)c1F] | (S)-N-(8-chloro-5-methyl-4-oxo-2,3,4,5-tetrahydro-pyrido[3,2-b][1,4]oxazepin-3-yl)-4-(2,3-difluorophenyl)-5-methylpyrimidine-2-carboxamide |
| 118 | A-43 | B-5 | 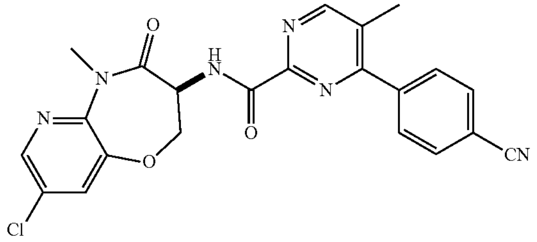 [SMILES: Cc1cnc(C(=O)N[C@H]2COc3cc(Cl)cnc3N(C)C2=O)nc1-c1ccc(C#N)cc1] | (S)-N-(8-chloro-5-methyl-4-oxo-2,3,4,5-tetrahydro-pyrido[3,2-b][1,4]oxazepin-3-yl)-4-(4-cyanophenyl)-5-methylpyrimidine-2-carboxamide |
| 119 | A-44 | B-5 | 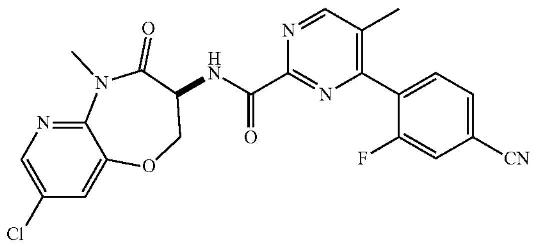 [SMILES: Cc1cnc(C(=O)N[C@H]2COc3cc(Cl)cnc3N(C)C2=O)nc1-c1ccc(C#N)cc1F] | (S)-N-(8-chloro-5-methyl-4-oxo-2,3,4,5-tetrahydro-pyrido[3,2-b][1,4]oxazepin-3-yl)-4-(4-cyano-2-fluorophenyl)-5-methylpyrimidine-2-carboxamide |
| 120 | A-18 | B-5 | 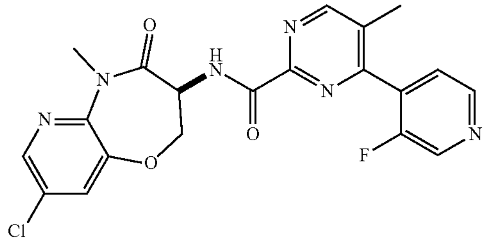 [SMILES: Cc1cnc(C(=O)N[C@H]2COc3cc(Cl)cnc3N(C)C2=O)nc1-c1ccncc1F] | (S)-N-(8-chloro-5-methyl-4-oxo-2,3,4,5-tetrahydro-pyrido[3,2-b][1,4]oxazepin-3-yl)-4-(3-fluoropyridin-4-yl)-5-methylpyrimidine-2-carboxamide |

TABLE 7-continued

| RIPK1 inhibitors. II. | | | | |
|---|---|---|---|---|
| Ex. No. | | | Structure | Name |
| 121 | A-26 | B-5 | 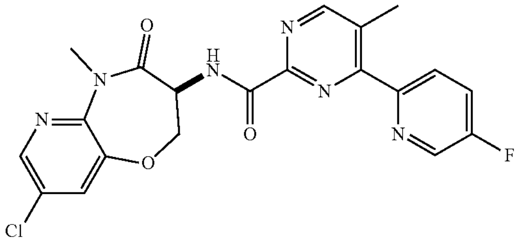 [SMILES: Cc1cnc(C(=O)N[C@H]2COc3cc(Cl)cnc3N(C)C2=O)nc1-c1ccc(F)cn1] | (S)-N-(8-chloro-5-methyl-4-oxo-2,3,4,5-tetrahydro-pyrido[3,2-b][1,4]oxazepin-3-yl)-4-(5-fluoropyridin-2-yl)-5-methylpyrimidine-2-carboxamide |
| 122 | A-39 | B-5 | 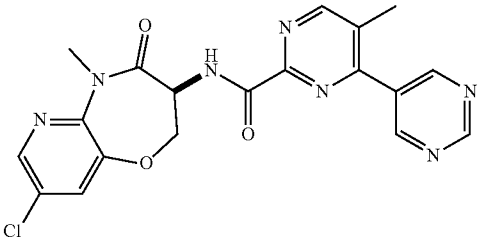 [SMILES: Cc1cnc(C(=O)N[C@H]2COc3cc(Cl)cnc3N(C)C2=O)nc1-c1cncnc1] | (S)-N-(8-chloro-5-methyl-4-oxo-2,3,4,5-tetrahydro-pyrido[3,2-b][1,4]oxazepin-3-yl)-5-methyl-[4,5'-bipyrimidine]-2-carboxamide |
| 123 | A-37 | B-5 | 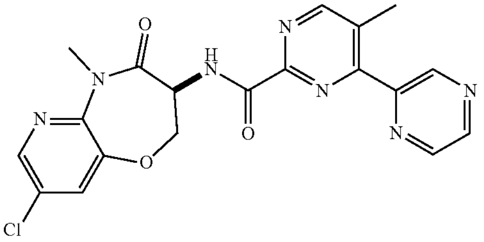 [SMILES: Cc1cnc(C(=O)N[C@H]2COc3cc(Cl)cnc3N(C)C2=O)nc1-c1cnccn1] | (S)-N-(8-chloro-5-methyl-4-oxo-2,3,4,5-tetrahydro-pyrido[3,2-b][1,4]oxazepin-3-yl)-5-methyl-4-(pyrazin-2-yl)-pyrimidine-2-carboxamide |
| 124 | A-58 | B-5 | 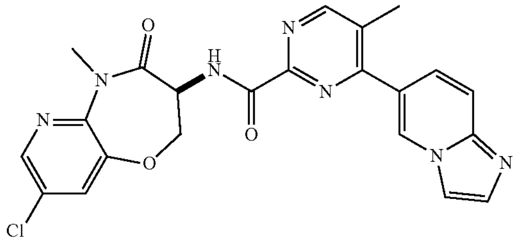 [SMILES: Cc1cnc(C(=O)N[C@H]2COc3cc(Cl)cnc3N(C)C2=O)nc1-c1ccc2nccn2c1] | (S)-N-(8-chloro-5-methyl-4-oxo-2,3,4,5-tetrahydropyrido[3,2-b][1,4]oxazepin-3-yl)-4-(imidazo[1,2-a]pyridin-6-yl)-5-methylpyrimidine-2-carboxamide |
| 125 | A-40 | B-5 | 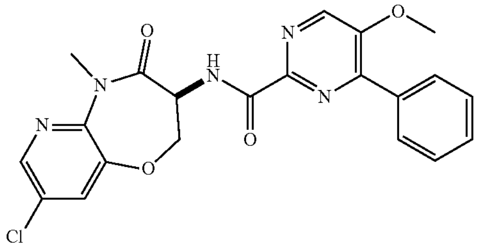 [SMILES: COc1cnc(C(=O)N[C@H]2COc3cc(Cl)cnc3N(C)C2=O)nc1-c1ccccc1] | (S)-N-(8-chloro-5-methyl-4-oxo-2,3,4,5-tetrahydro-pyrido[3,2-b][1,4]oxazepin-3-yl)-5-methoxy-4-phenylpyrimidine-2-carboxamide |
| 126 | A-63 | B-5 | 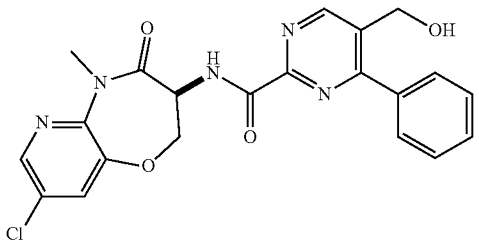 [SMILES: CN1C(=O)[C@@H](NC(=O)c2ncc(CO)c(-c3ccccc3)n2)COc2cc(Cl)cnc21] | (S)-N-(8-chloro-5-methyl-4-oxo-2,3,4,5-tetrahydro-pyrido[3,2-b][1,4]oxazepin-3-yl)-5-(hydroxymethyl)-4-phenylpyrimidine-2-carboxamide |

TABLE 7-continued

| RIPK1 inhibitors. II. | | | | |
|---|---|---|---|---|
| Ex. No. | | | Structure | Name |
| 127 | A-55 | B-5 | 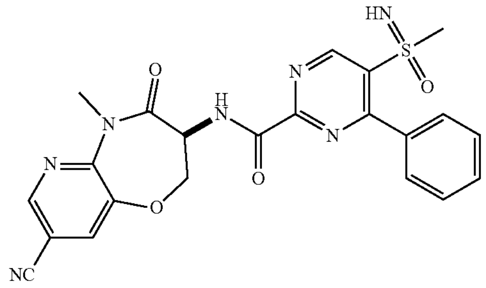 [SMILES: CN1C(=O)[C@@H](NC(=O)c2ncc(S(C)(=N)=O)c(-c3ccccc3)n2)COc2cc(C#N)cnc21] | N-((S)-8-chloro-5-methyl-4-oxo-2,3,4,5-tetrahydro-pyrido[3,2-b][1,4]oxazepin-3-yl)-5-(S-methylsulfonimidoyl)-4-phenylpyrimidine-2-carboxamide |
| 128 | A-64 | B-3 | 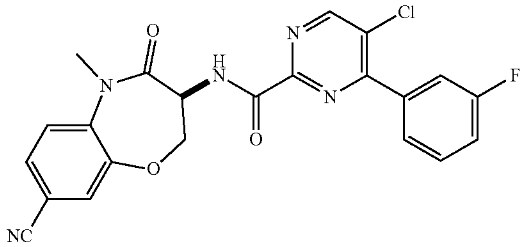 [SMILES: CN1C(=O)[C@@H](NC(=O)c2ncc(Cl)c(-c3cccc(F)c3)n2)COc2cc(C#N)ccc21] | (S)-5-chloro-N-(8-cyano-5-methyl-4-oxo-2,3,4,5-tetrahydrobenzo[b]-[1,4]oxazepin-3-yl)-4-(3-fluorophenyl)pyrimidine-2-carboxamide |
| 129 | A-21 | B-3 | 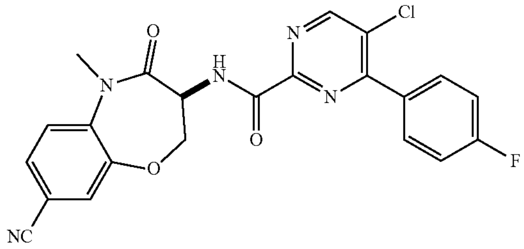 [SMILES: CN1C(=O)[C@@H](NC(=O)c2ncc(Cl)c(-c3ccc(F)cc3)n2)COc2cc(C#N)ccc21] | (S)-5-chloro-N-(8-cyano-5-methyl-4-oxo-2,3,4,5-tetrahydrobenzo[b]-[1,4]oxazepin-3-yl)-4-(4-fluorophenyl)pyrimidine-2-carboxamide |
| 130 | A-13 | B-3 | 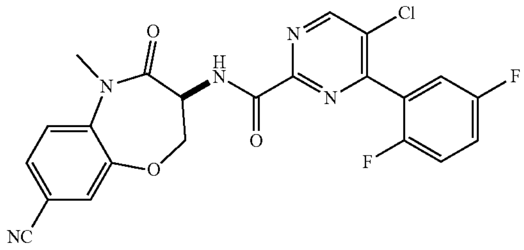 [SMILES: CN1C(=O)[C@@H](NC(=O)c2ncc(Cl)c(-c3cc(F)ccc3F)n2)COc2cc(C#N)ccc21] | (S)-5-chloro-N-(8-cyano-5-methyl-4-oxo-2,3,4,5-tetrahydrobenzo[b]-[1,4]oxazepin-3-yl)-4-(2,5-difluorophenyl)pyrimidine-2-carboxamide |
| 131 | A-7 | B-3 | 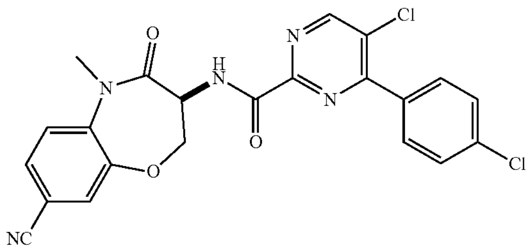 [SMILES: CN1C(=O)[C@@H](NC(=O)c2ncc(Cl)c(-c3ccc(Cl)cc3)n2)COc2cc(C#N)ccc21] | (S)-5-chloro-4-(4-chlorophenyl)-N-(8-cyano-5-methyl-4-oxo-2,3,4,5-tetrahydrobenzo[b]-[1,4]oxazepin-3-yl)pyrimidine-2-carboxamide |

TABLE 7-continued

| RIPK1 inhibitors. II. | | | | |
|---|---|---|---|---|
| Ex. No. | | | Structure | Name |
| 132 | A-25 | B-3 | 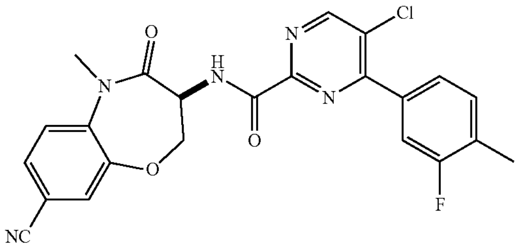 [SMILES: Cc1ccc(-c2nc(C(=O)N[C@H]3COc4cc(C#N)ccc4N(C)C3=O)ncc2Cl)cc1F] | (S)-5-chloro-N-(8-cyano-5-methyl-4-oxo-2,3,4,5-tetrahydrobenzo[b]-[1,4]oxazepin-3-yl)-4-(3-fluoro-4-methylphenyl)pyrimidine-2-carboxamide |
| 133 | A-45 | B-3 | 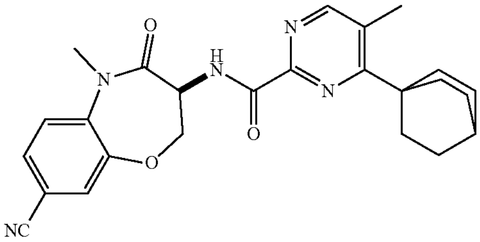 [SMILES: Cc1cnc(C(=O)N[C@H]2COc3cc(C#N)ccc3N(C)C2=O)nc1C12CCC(CC1)CC2] | (S)-4-(bicyclo[2.2.2]octan-1-yl)-N-(8-cyano-5-methyl-4-oxo-2,3,4,5-tetrahydrobenzo[b]-[1,4]oxazepin-3-yl)-5-methylpyrimidine-2-carboxamide |
| 134 | A-46 | B-3 | 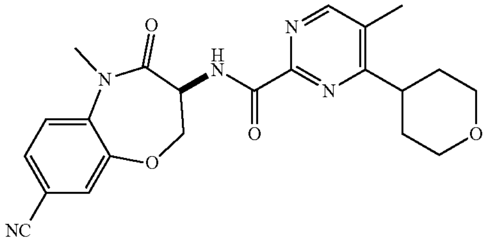 | (S)-N-(8-cyano-5-methyl-4-oxo-2,3,4,5-tetrahydrobenzo[b]-[1,4]oxazepin-3-yl)-5-methyl-4-(tetrahydro-2H-pyran-4-yl)-pyrimidine-2-carboxamide |
| 135 | A-65 | B-3 | 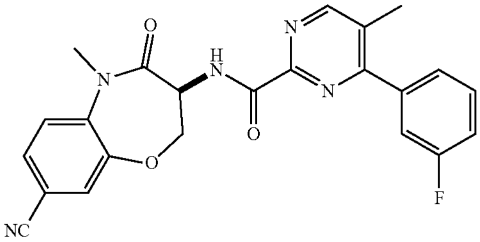 [SMILES: Cc1cnc(C(=O)N[C@H]2COc3cc(C#N)ccc3N(C)C2=O)nc1-c1cccc(F)c1] | (S)-N-(8-cyano-5-methyl-4-oxo-2,3,4,5-tetrahydrobenzo[b]-[1,4]oxazepin-3-yl)-4-(3-fluorophenyl)-5-methylpyrimidine-2-carboxamide |
| 136 | A-34 | B-3 | 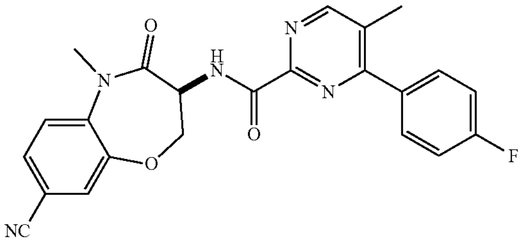 [SMILES: Cc1cnc(C(=O)N[C@H]2COc3cc(C#N)ccc3N(C)C2=O)nc1-c1ccc(F)cc1] | (S)-N-(8-cyano-5-methyl-4-oxo-2,3,4,5-tetrahydrobenzo[b]-[1,4]oxazepin-3-yl)-4-(4-fluorophenyl)-5-methylpyrimidine-2-carboxamide |
| 137 | A-35 | B-3 | 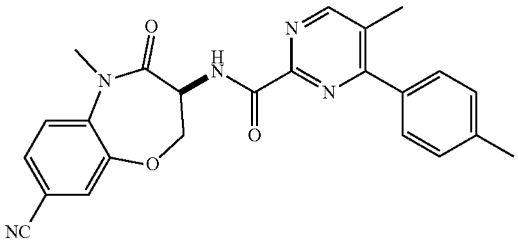 [SMILES: Cc1ccc(-c2nc(C(=O)N[C@H]3COc4cc(C#N)ccc4N(C)C3=O)ncc2C)cc1] | (S)-N-(8-cyano-5-methyl-4-oxo-2,3,4,5-tetrahydrobenzo[b]-[1,4]oxazepin-3-yl)-5-methyl-4-(p-tolyl)pyrimidine-2-carboxamide |

TABLE 7-continued

RIPK1 inhibitors. II.

| Ex. No. | | | Structure | Name |
|---|---|---|---|---|
| 138 | A-23 | B-3 | 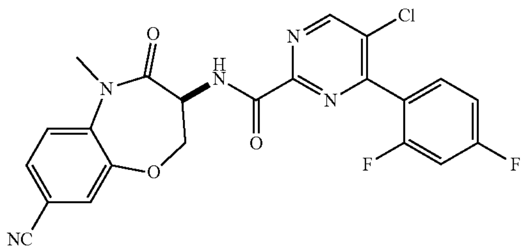 [SMILES: CN1C(=O)[C@@H](NC(=O)c2ncc(Cl)c(-c3ccc(F)cc3F)n2)COc2cc(C#N)ccc21] | (S)-5-chloro-N-(8-cyano-5-methyl-4-oxo-2,3,4,5-tetrahydrobenzo[b]-[1,4]oxazepin-3-yl)-4-(2,4-difluorophenyl)pyrimidine-2-carboxamide |
| 139 | A-24 | B-3 | 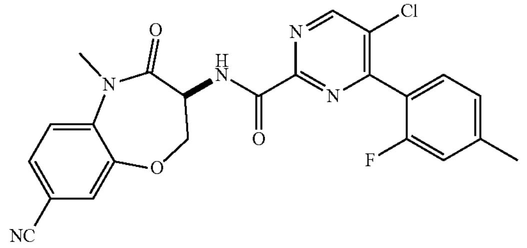 [SMILES: Cc1ccc(-c2nc(C(=O)N[C@H]3COc4cc(C#N)ccc4N(C)C3=O)ncc2Cl)c(F)c1] | (S)-5-chloro-N-(8-cyano-5-methyl-4-oxo-2,3,4,5-tetrahydrobenzo[b]-[1,4]oxazepin-3-yl)-4-(2-fluoro-4-methylphenyl)pyrimidine-2-carboxamide |
| 140 | A-23 | | 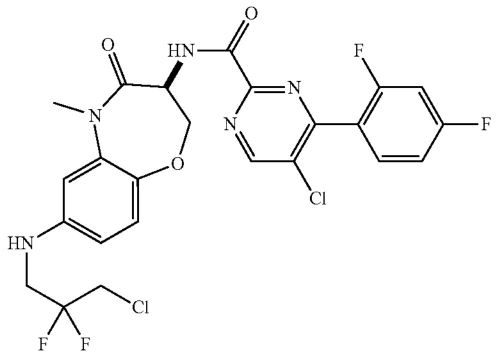 [SMILES: CN1C(=O)[C@@H](NC(=O)c2ncc(Cl)c(-c3ccc(F)cc3F)n2)COc2ccc(NCC(F)(F)CCl)cc21] | (S)-5-chloro-N-(7-((3-chloro-2,2-difluoropropyl)amino)-5-methyl-4-oxo-2,3,4,5-tetrahydrobenzo[b]-[1,4]oxazepin-3-yl)-4-(2,4-difluorophenyl)pyrimidine-2-carboxamide |
| 141 | A-23 | B-9 | 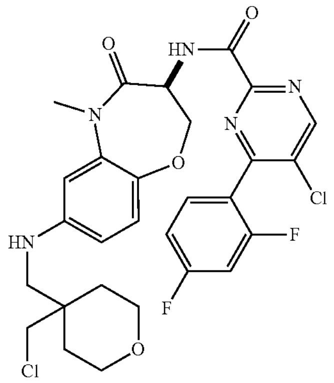 [SMILES: CN1C(=O)[C@@H](NC(=O)c2ncc(Cl)c(-c3ccc(F)cc3F)n2)COc2ccc(NCC3(CCl)CCOCC3)cc21] | (S)-5-chloro-N-(7-(((4-(chloromethyl)tetrahydro-2H-pyran-4-yl)methyl)amino)-5-methyl-4-oxo-2,3,4,5-tetrahydrobenzo[b]-[1,4]oxazepin-3-yl)-4-(2,4-difluorophenyl)pyrimidine-2-carboxamide |

TABLE 7-continued

| RIPK1 inhibitors. II. | | | | |
|---|---|---|---|---|
| Ex. No. | | | Structure | Name |
| 142 | A-13 | B-9 | 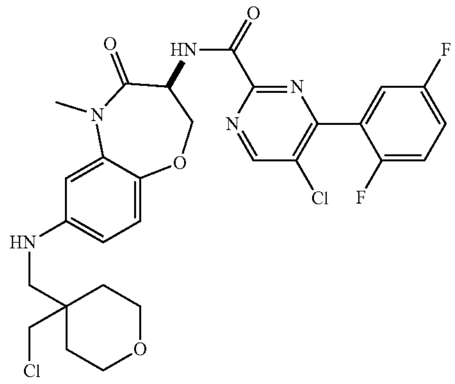 [SMILES: CN1C(=O)[C@@H](NC(=O)c2ncc(Cl)c(-c3cc(F)ccc3F)n2)COc2ccc(NCC3(CCl)CCOCC3)cc21] | (S)-5-chloro-N-(7-(((4-(chloromethyl)tetrahydro-2H-pyran-4-yl)methyl)amino)-5-methyl-4-oxo-2,3,4,5-tetrahydrobenzo[b]-[1,4]oxazepin-3-yl)-4-(2,5-difluorophenyl)pyrimidine-2-carboxamide |
| 143 | A-23 | B-18 | 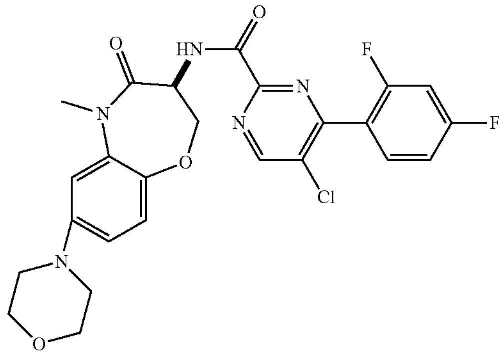 | (S)-5-chloro-4-(2,4-difluorophenyl)-N-(5-methyl-7-morpholino-4-oxo-2,3,4,5-tetrahydrobenzo[b]-[1,4]oxazepin-3-yl)pyrimidine-2-carboxamide |
| 144 | A-13 | B-8 | 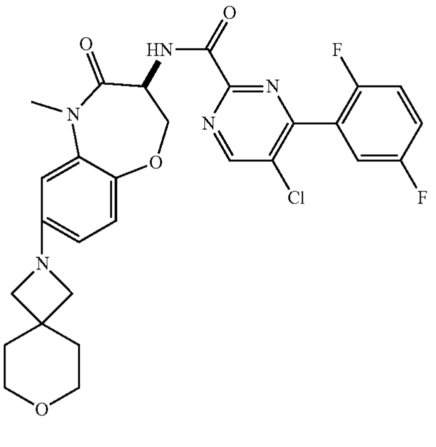 | (S)-5-chloro-4-(2,5-difluorophenyl)-N-(5-methyl-4-oxo-7-(7-oxa-2-azaspiro[3.5]nonan-2-yl)-2,3,4,5-tetrahydrobenzo[b]-[1,4]oxazepin-3-yl)pyrimidine-2-carboxamide |

TABLE 7-continued

RIPK1 inhibitors. II.

| Ex. No. | | | Structure | Name |
|---|---|---|---|---|
| 145 | A-3 | B-8 | 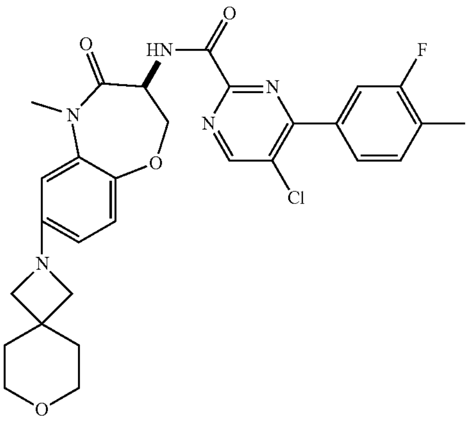 | (S)-5-chloro-4-(3-fluoro-4-methylphenyl)-N-(5-methyl-4-oxo-7-(7-oxa-2-azaspiro[3.5]nonan-2-yl)-2,3,4,5-tetrahydrobenzo[b]-[1,4]oxazepin-3-yl)pyrimidine-2-carboxamide |
| 146 | A-23 | B-12 | 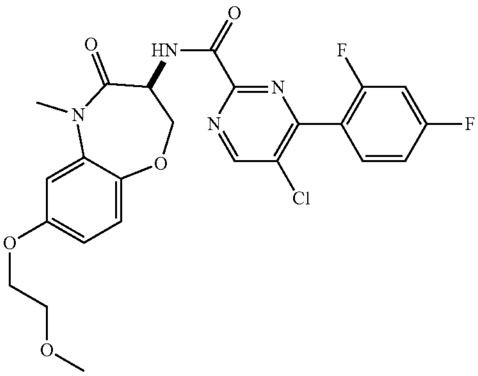 | (S)-5-chloro-4-(2,4-difluorophenyl)-N-(7-(2-methoxyethoxy)-5-methyl-4-oxo-2,3,4,5-tetrahydrobenzo[b]-[1,4]oxazepin-3-yl)pyrimidine-2-carboxamide |
| 147 | A-23 | B-19 | 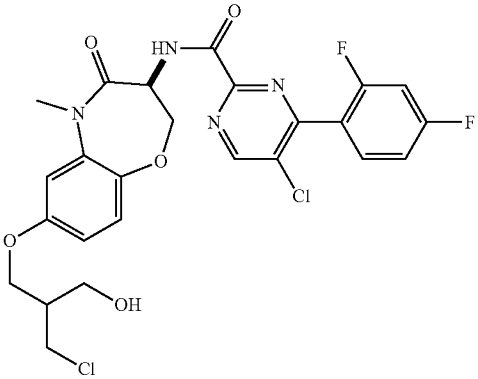 | 5-chloro-N-((3S)-7-(3-chloro-2-(hydroxymethyl)propoxy)-5-methyl-4-oxo-2,3,4,5-tetrahydrobenzo[b]-[1,4]oxazepin-3-yl)-4-(2,4-difluorophenyl)pyrimidine-2-carboxamide |

TABLE 7-continued

RIPK1 inhibitors. II.

| Ex. No. | | | Structure | Name |
|---|---|---|---|---|
| 148 | A-23 | B-15 | 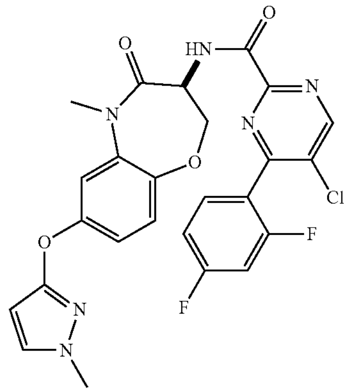 [SMILES: CN1C(=O)[C@@H](NC(=O)c2ncc(Cl)c(-c3ccc(F)cc3F)n2)COc2ccc(Oc3ccn(C)n3)cc21] | (S)-5-chloro-4-(2,4-difluorophenyl)-N-(5-methyl-7-((1-methyl-1H-pyrazol-3-yl)oxy)-4-oxo-2,3,4,5-tetrahydrobenzo[b]-[1,4]oxazepin-3-yl)pyrimidine-2-carboxamide |
| 149 | A-23 | B-13 | 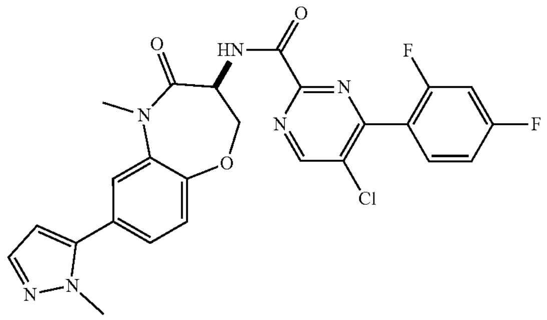 [SMILES: CN1C(=O)[C@@H](NC(=O)c2ncc(Cl)c(-c3ccc(F)cc3F)n2)COc2ccc(-c3ccnn3C)cc21] | (S)-5-chloro-4-(2,4-difluorophenyl)-N-(5-methyl-7-(1-methyl-1H-pyrazol-5-yl)-4-oxo-2,3,4,5-tetrahydrobenzo[b]-[1,4]oxazepin-3-yl)pyrimidine-2-carboxamide |
| 150 | A-23 | B-20 | 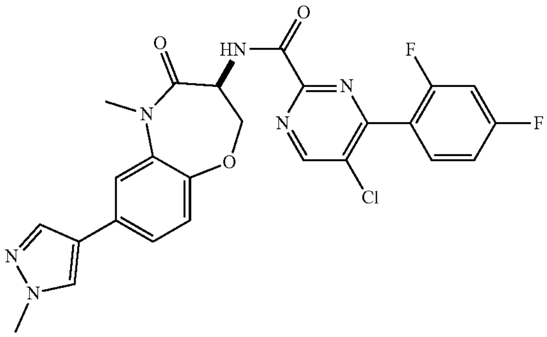 [SMILES: CN1C(=O)[C@@H](NC(=O)c2ncc(Cl)c(-c3ccc(F)cc3F)n2)COc2ccc(-c3cnn(C)c3)cc21] | (S)-5-chloro-4-(2,4-difluorophenyl)-N-(5-methyl-7-(1-methyl-1H-pyrazol-4-yl)-4-oxo-2,3,4,5-tetrahydrobenzo[b]-[1,4]oxazepin-3-yl)pyrimidine-2-carboxamide |
| 151 | A-23 | B-21 | 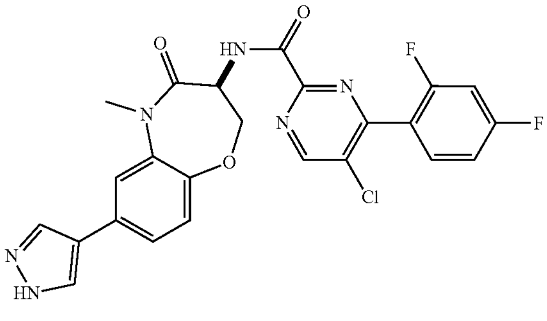 [SMILES: CN1C(=O)[C@@H](NC(=O)c2ncc(Cl)c(-c3ccc(F)cc3F)n2)COc2ccc(-c3cn[nH]c3)cc21] | (S)-5-chloro-4-(2,4-difluorophenyl)-N-(5-methyl-4-oxo-8-(1H-pyrazol-4-yl)-2,3,4,5-tetrahydropyrido[3,2-b]-[1,4]oxazepin-3-yl)pyrimidine-2-carboxamide |

TABLE 7-continued

RIPK1 inhibitors. II.

| Ex. No. | | | Structure | Name |
|---|---|---|---|---|
| 152 | A-23 | B-14 | 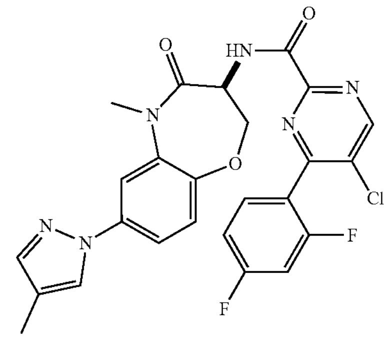 [SMILES: Cc1cnn(-c2ccc3c(c2)N(C)C(=O)[C@@H](NC(=O)c2ncc(Cl)c(-c4ccc(F)cc4F)n2)CO3)c1] | (S)-5-chloro-4-(2,4-difluorophenyl)-N-(5-methyl-7-(4-methyl-1H-pyrazol-1-yl)-4-oxo-2,3,4,5-tetrahydrobenzo[b]-[1,4]oxazepin-3-yl)pyrimidine-2-carboxamide |
| 153 | A-25 | B-7 | 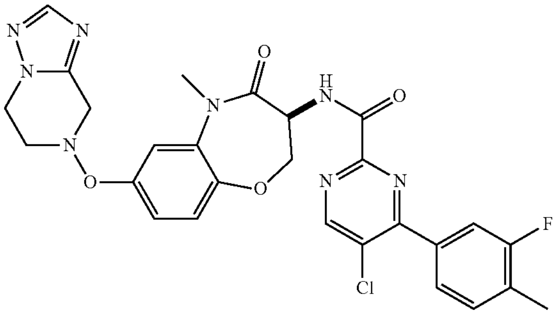 [SMILES: Cc1ccc(-c2nc(C(=O)N[C@H]3COc4ccc(ON5CCn6ncnc6C5)cc4N(C)C3=O)ncc2Cl)cc1F] | (S)-5-chloro-N-(7-((5,6-dihydro-[1,2,4]triazolo[1,5-a]pyrazin-7(8H)-yl)methyl)-5-methyl-4-oxo-2,3,4,5-tetrahydrobenzo[b]-[1,4]oxazepin-3-yl)-4-(3-fluoro-4-methylphenyl)pyrimidine-2-carboxamide |
| 154 | A-23 | B-7 | 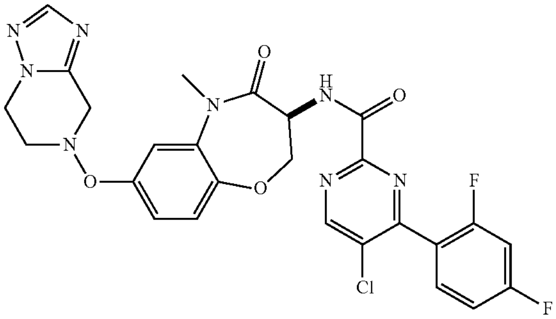 [SMILES: CN1C(=O)[C@@H](NC(=O)c2ncc(Cl)c(-c3ccc(F)cc3F)n2)COc2ccc(ON3CCn4ncnc4C3)cc21] | (S)-5-chloro-4-(2,4-difluorophenyl)-N-(8-((5,6-dihydro-[1,2,4]triazolo[1,5-a]pyrazin-7(8H)-yl)methyl)-5-methyl-4-oxo-2,3,4,5-tetrahydrobenzo[b]-[1,4]oxazepin-3-yl)pyrimidine-2-carboxamide |
| 155 | A-13 | B-7 | 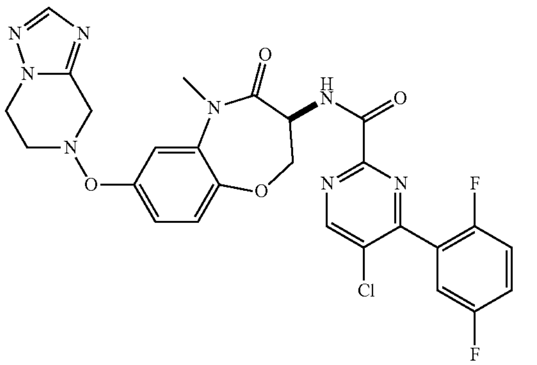 [SMILES: CN1C(=O)[C@@H](NC(=O)c2ncc(Cl)c(-c3cc(F)ccc3F)n2)COc2ccc(ON3CCn4ncnc4C3)cc21] | (S)-5-chloro-4-(2,5-difluorophenyl)-N-(8-((5,6-dihydro-[1,2,4]triazolo[1,5-a]pyrazin-7(8H)-yl)methyl)-5-methyl-4-oxo-2,3,4,5-tetrahydrobenzo[b]-[1,4]oxazepin-3-yl)pyrimidine-2-carboxamide |

TABLE 7-continued

RIPK1 inhibitors. II.

| Ex. No. | | | Structure | Name |
|---|---|---|---|---|
| 156 | A-47 | B-7 | 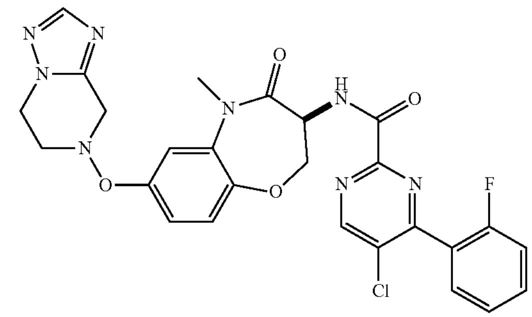 [SMILES: CN1C(=O)[C@@H](NC(=O)c2ncc(Cl)c(-c3ccccc3F)n2)COc2ccc(ON3CCn4ncnc4C3)cc21] | (S)-N-(7-((5,6-dihydro-[1,2,4]triazolo[1,5-a]pyrazin-7(8H)-yl)methyl)-5-methyl-4-oxo-2,3,4,5-tetrahydrobenzo[b]-[1,4]oxazepin-3-yl)-4-(2-fluorophenyl)-5-methylpyrimidine-2-carboxamide |
| 157 | A-61 | B-5 | 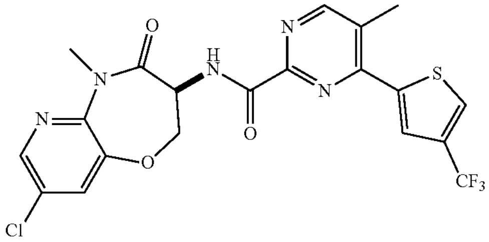 [SMILES: Cc1cnc(C(=O)N[C@H]2COc3cc(Cl)cnc3N(C)C2=O)nc1-c1cc(C(F)(F)F)cs1] | (S)-N-(8-chloro-5-methyl-4-oxo-2,3,4,5-tetrahydro-pyrido[3,2-b][1,4]oxazepin-3-yl)-5-methyl-4-(4-(trifluoromethyl)thiophen-2-yl)-pyrimidine-2-carboxamide |
| 158 | A-62 | B-5 | 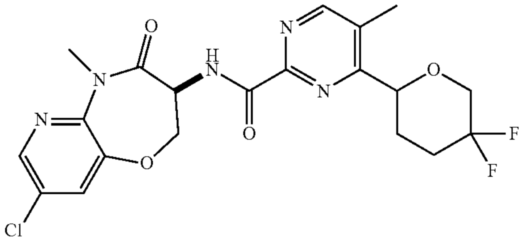 [SMILES: Cc1cnc(C(=O)N[C@H]2COc3cc(Cl)cnc3N(C)C2=O)nc1C1CCC(F)(F)CO1] | N-((S)-8-chloro-5-methyl-4-oxo-2,3,4,5-tetrahydro-pyrido[3,2-b][1,4]oxazepin-3-yl)-4-(5,5-difluorotetrahydro-2H-pyran-2-yl)-5-methylpyrimidine-2-carboxamide |
| 159 | A-47 | B-11 | 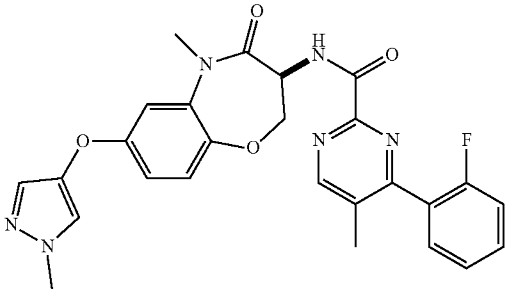 [SMILES: Cc1cnc(C(=O)N[C@H]2COc3ccc(Oc4cnn(C)c4)cc3N(C)C2=O)nc1-c1ccccc1F] | (S)-4-(2-fluorophenyl)-5-methyl-N-(5-methyl-7-((1-methyl-1H-pyrazol-4-yl)oxy)-4-oxo-2,3,4,5-tetrahydrobenzo[b]-[1,4]oxazepin-3-yl)pyrimidine-2-carboxamide |
| 160 | A-43 | B-11 | 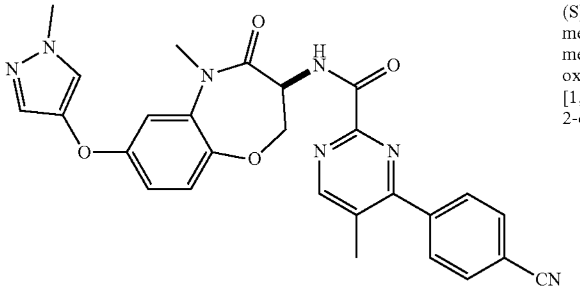 | (S)-4-(4-cyanophenyl)-5-methyl-N-(5-methyl-7-((1-methyl-1H-pyrazol-4-yl)oxy)-4-oxo-2,3,4,5-tetrahydrobenzo[b]-[1,4]oxazepin-3-yl)pyrimidine-2-carboxamide |

TABLE 7-continued

RIPK1 inhibitors. II.

| Ex. No. | Structure | Name |
|---|---|---|
| 161 A-13 B-11 | 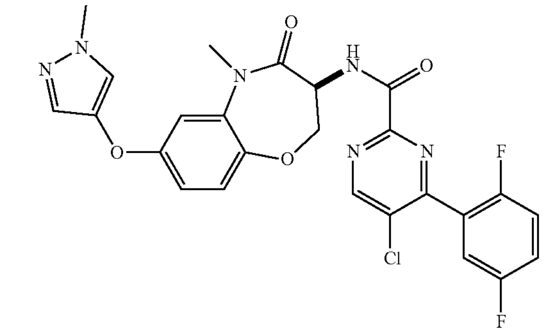 [SMILES: CN1C(=O)[C@@H](NC(=O)c2ncc(Cl)c(-c3cc(F)ccc3F)n2)COc2ccc(Oc3cnn(C)c3)cc21] | (S)-5-chloro-4-(2,5-difluorophenyl)-N-(5-methyl-7-((1-methyl-1H-pyrazol-4-yl)oxy)-4-oxo-2,3,4,5-tetrahydrobenzo[b]-[1,4]oxazepin-3-yl)pyrimidine-2-carboxamide |

EXAMPLE 162

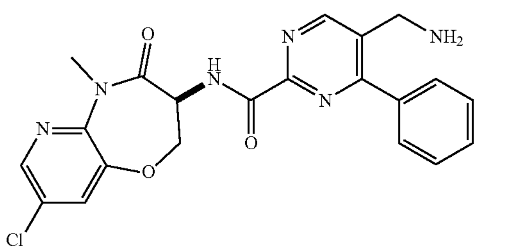

(S)-5-(aminomethyl)-N-(8-chloro-5-methyl-4-oxo-2,3,4,5-tetrahydropyrido[3,2-b][1,4]oxazepin-3-yl)-4-phenylpyrimidine-2-carboxamide

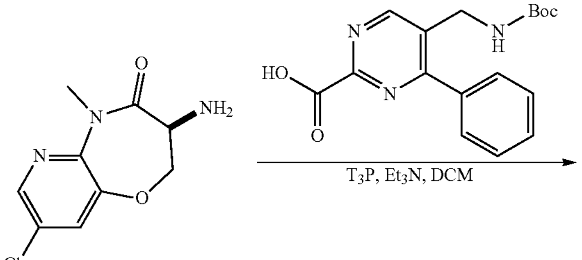

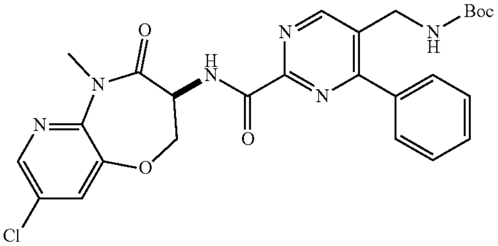

tert-Butyl (S)-((2-((8-chloro-5-methyl-4-oxo-2,3,4,5-tetrahydropyrido[3,2-b][1,4]oxazepin-3-yl)carbamoyl)-4-phenylpyrimidin-5-yl)methyl)carbamate To a solution of Intermediate A-30 (40 mg, 121.45 μmol, 1 eq) and Intermediate B-5 hydrochloride (54.48 mg, 121.45 μmol, 67% purity, 1 eq) in $CH_2Cl_2$ (4 mL) were added $Et_3N$ (36.87 mg, 364.35 μmol, 50.71 μL, 3 eq) and $T_3P$ (115.93 mg, 182.18 μmol, 108.35 μL of a 50% solution in EtOAc, 1.5 eq). After stirring at 25° C. for 0.5 h, the mixture was diluted with $H_2O$ (10 mL) and extracted with $CH_2Cl_2$ (10 mL×2). The combined organic layer was concentrated under reduced pressure. The residue which was purified by prep-TLC (Petroleum ether/EtOAc=1/1) to afford the title compound (20 mg, 20.41 μmol, 16% yield) as a yellow oil. MS (ES+) $C_{26}H_{27}N_6O_5Cl$ requires: 538 and 540, found: 539 and 541 $[M+H]^+$.

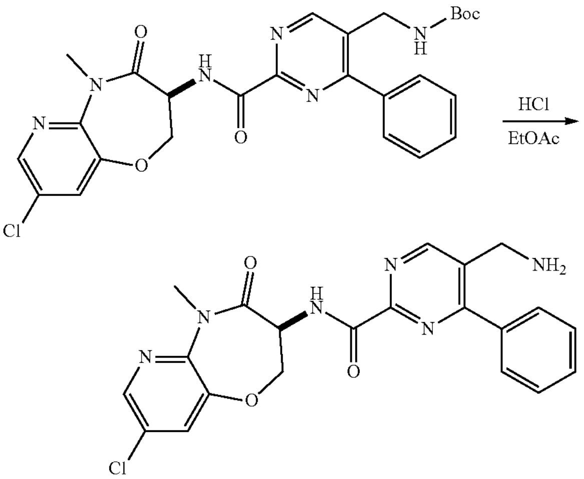

(S)-5-(aminomethyl)-N-(8-chloro-5-methyl-4-oxo-2,3,4,5-tetrahydropyrido[3,2-b][1,4]oxazepin-3-yl)-4-phenylpyrimidine-2-carboxamide To a solution of the product from the previous step (20 mg, 20.41 μmol, 1 eq) in EtOAc (1 mL) was added HCl/EtOAc (4 M, 0.3 mL, 58.80 eq). After stirring at 0° C. for 0.5 h, the mixture was poured into saturated $Na_2CO_3$ aqueous solution (5 mL) and extracted with EtOAc (5 mL×2), and the combined organic layer was concentrated under reduced pressure. The residue was purified by prep-HPLC (column: Waters Xbridge 150*25 mm*5 um; mobile phase: [water (10 mM $NH_4HCO_3$) —$CH_3CN$]; B %: 30%-60%, 10 min), and the eluent was concentrated under reduced pressure and freeze dried to afford the title compound (3.4 mg, 7.05 μmol, 34% yield) as a white solid.

MS (ES+) $C_{21}H_{19}N_6O_3Cl$ requires: 438 and 440, found: 439 and 441 $[M+H]^+$. $^1H$ NMR (400 MHz, $CD_3OD$) δ=9.09

(s, 1H), 8.35 (d, J=2.2 Hz, 1H), 7.78 (d, J=2.3 Hz, 1H), 7.75-7.67 (m, 2H), 7.62-7.53 (m, 3H), 5.11 (dd, J=7.0, 11.4 Hz, 1H), 4.78 (dd, J=7.0, 9.8 Hz, 1H), 4.56 (dd, J=10.0, 11.3 Hz, 1H), 4.03 (s, 2H), 3.48 (s, 3H).

EXAMPLES 163a and 163b

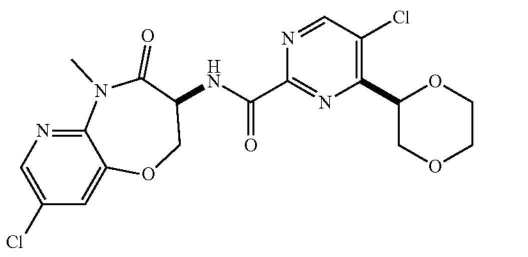

5-chloro-N—((S)-8-chloro-5-methyl-4-oxo-2,3,4,5-tetrahydropyrido[3,2-b][1,4]oxazepin-3-yl)-4-((R)-1,4-dioxan-2-yl)pyrimidine-2-carboxamide

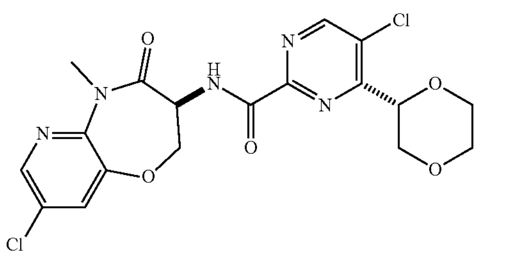

5-chloro-N—((S)-8-chloro-5-methyl-4-oxo-2,3,4,5-tetrahydropyrido[3,2-b][1,4]oxazepin-3-yl)-4-((S)-1,4-dioxan-2-yl)pyrimidine-2-carboxamide

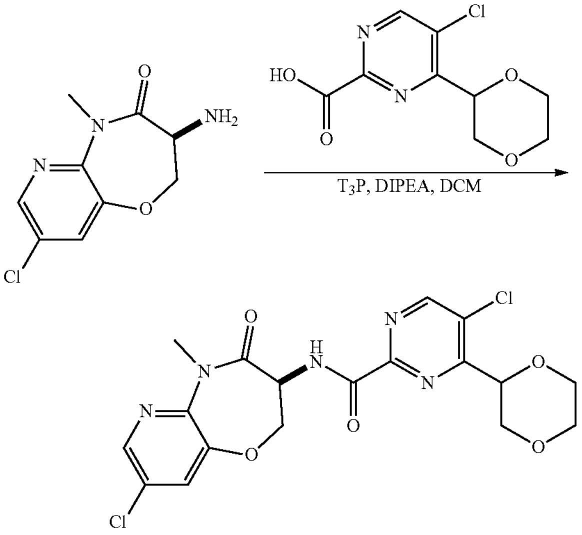

5-Chloro-N—((S)-8-chloro-5-methyl-4-oxo-2,3,4,5-tetrahydropyrido[3,2-b][1,4]oxazepin-3-yl)-4-(1,4-dioxan-2-yl)pyrimidine-2-carboxamide To a solution of Intermediate B-5 hydrochloride salt (110 mg, 245.20 μmol, 1 eq), Intermediate A-52 (59.98 mg, 245.20 μmol, 1 eq) in $CH_2Cl_2$ (1 mL) were added $T_3P$ (156.04 mg, 490.40 μmol, 145.83 μL of a 50% solution in EtOAc, 2 eq), i-$Pr_2NEt$ (158.45 mg, 1.23 mmol, 213.54 μL, 5 eq). After stirring at 25° C. for 16 h, the mixture was concentrated under reduced pressure. The residue was purified by prep-HPLC (column: Unisil 3-100 $C_{18}$ μLtra 150*50 mm*3 um; mobile phase: [water (0.225% FA) —$CH_3CN$]; B %: 50%-70%, 10 min) to afford the a mixture of two diastereomers which was further purified by chiral prep-HPLC (column: DAICEL CHIRALPAK AS-H (250 mm*30 mm, 5 um); mobile phase: [Neu-MeOH]; B %: 30%-30%, 4.7;30 min) to afford the title compound (7.2 mg, 15.69 μmol, 6% yield) (peakA) as a white solid.

MS (ES+) $C_{18}H_{17}N_5Cl_2O_5$ requires: 453 and 455, found: 454 and 456 $[M+H]^+$. $^1$H NMR (400 MHz, $CDCl_3$) δ=8.91-8.84 (m, 2H), 8.30 (d, J=2.2 Hz, 1H), 7.59 (d, J=2.2 Hz, 1H), 5.16-5.04 (m, 2H), 4.92 (dd, J=7.0, 9.7 Hz, 1H), 4.38 (dd, J=9.9, 11.0 Hz, 1H), 4.13-3.97 (m, 4H), 3.90-3.85 (m, 2H), 3.55 (s, 3H).

Also obtained was 5-chloro-N-[(3S)-8-chloro-5-methyl-4-oxo-2,3-dihydropyrido[3,2-b][1,4]oxazepin-3-yl]-4-(1,4-dioxan-2-yl)pyrimidine-2-carboxamide (8.3 mg, 18.09 μmol, 7% yield) (peak B) as a white solid. MS (ES+) $C_{18}H_{17}N_5Cl_2O_5$ requires: 453 and 455, found: 454 and 456 $[M+H]^+$. $^1$H NMR (400 MHz, $CDCl_3$) δ=8.89-8.82 (m, 2H), 8.29 (d, J=2.0 Hz, 1H), 7.57 (d, J=2.0 Hz, 1H), 5.17-5.04 (m, 2H), 4.94-4.85 (m, 1H), 4.40 (br t, J=10.7 Hz, 1H), 4.12-3.95 (m, 4H), 3.92-3.79 (m, 2H), 3.53 (s, 3H).

EXAMPLES 164A AND 164B

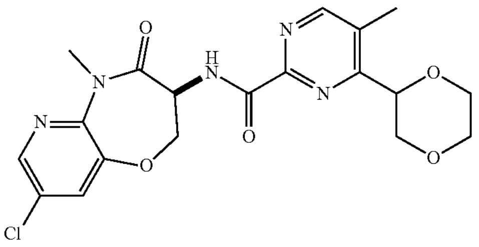

N—((S)-8-chloro-5-methyl-4-oxo-2,3,4,5-tetrahydropyrido[3,2-b][1,4]oxazepin-3-yl)-4-(1,4-dioxan-2-yl)-5-methylpyrimidine-2-carboxamide

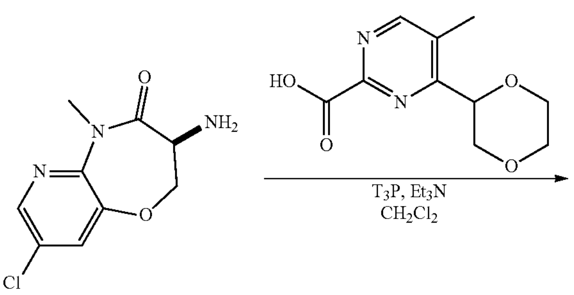

-continued

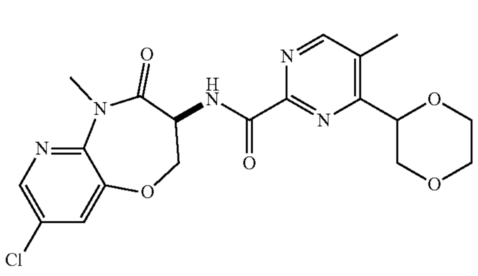 [SMILES: Cc1cnc(C(=O)N[C@H]2COc3cc(Cl)cnc3N(C)C2=O)nc1C1COCCO1]

To a solution of Intermediate A-53 (40 mg, 178.40 μmol, 1 eq) in $CH_2Cl_2$ (1 mL) were added Intermediate B-5 hydrochloride (53.62 mg, 178.40 μmol, 1 eq), $T_3P$ (340.58 mg, 535.21 μmol, 318.30 μL of a 50% solution in EtOAc, 3 eq) and i-$Pr_2NEt$ (115.29 mg, 892.01 μmol, 155.37 μL, 5 eq). After stirring at 25° C. for 16 h, the mixture was poured into water (10 mL), extracted with EtOAc (10 mL×3), dried over $Na_2SO_4$, filtered and concentrated under reduced pressure. The residue was purified by prep-HPLC (column: Phenomenex Synergi C18 150*25 mm*10 um; mobile phase: [water (0.225% FA) —$CH_3CN$]; B %: 24%-54%, 10 min). The eluent was concentrated and freeze dried to afford the title compound (40 mg, 92.20 μmol, 51% yield) as a white solid.

MS (ES+) $C_{19}H_{20}N_5O_5Cl$ requires: 433 and 435, found: 434 and 436 $[M+H]^+$. $^1H$ NMR (400 MHz, $CDCl_3$) δ=8.81 (br d, J=5.6 Hz, 1H), 8.62 (d, J=5.8 Hz, 1H), 8.20 (d, J=2.3 Hz, 1H), 7.49 (d, J=2.3 Hz, 1H), 5.06-4.92 (m, 1H), 4.88-4.74 (m, 2H), 4.35-4.22 (m, 1H), 4.13-3.98 (m, 2H), 3.93-3.81 (m, 2H), 3.80-3.71 (m, 2H), 3.45 (d, J=1.1 Hz, 3H), 2.43 (s, 3H)

The mixture (40 mg, mixture of two epimers) was purified by chiral prep-HPLC (column: Daicel ChiralPak IG (250*30 mm, 10 um); mobile phase: [Neu-MeOH]; B %: 70%-70%, 3.9; 20 min) to afford two fractions of undetermined stereochemistry:

Peak A; Rt 1.486 min; white solid (3.4 mg, 7.84 μmol, 8% yield); MS (ES+) $C_{19}H_{20}N_5O_5Cl$ requires: 433 and 435, found: 434 and 436 $[M+H]^{+1}H$ NMR (400 MHz, $CDCl_3$) δ=8.80 (br d, J=6.2 Hz, 1H), 8.62 (s, 1H), 8.20 (d, J=2.2 Hz, 1H), 7.49 (d, J=2.2 Hz, 1H), 5.09-4.91 (m, 1H), 4.88-4.76 (m, 2H), 4.27 (dd, J=9.8, 11.2 Hz, 1H), 4.14-4.00 (m, 2H), 3.90-3.81 (m, 2H), 3.79-3.69 (m, 2H), 3.45 (s, 3H), 2.43 (s, 3H).

Peak B; Rt: 2.252 min; white solid (5.2 mg, 11.99 μmol, 13% yield); MS (ES+) $C_{19}H_{20}N_5O_5Cl$ requires: 433 and 435, found: 434 and 436 $[M+H]^{+1}H$ NMR (400 MHz, $CDCl_3$) δ=8.89 (br d, J=6.8 Hz, 1H), 8.71 (s, 1H), 8.28 (d, J=2.3 Hz, 1H), 7.57 (d, J=2.2 Hz, 1H), 5.14-5.03 (m, 1H), 4.95-4.85 (m, 2H), 4.38 (dd, J=9.8, 11.2 Hz, 1H), 4.14 (d, J=6.5 Hz, 2H), 3.98-3.93 (m, 2H), 3.88-3.81 (m, 2H), 3.53 (s, 3H), 2.51 (s, 3H).

EXAMPLE 165

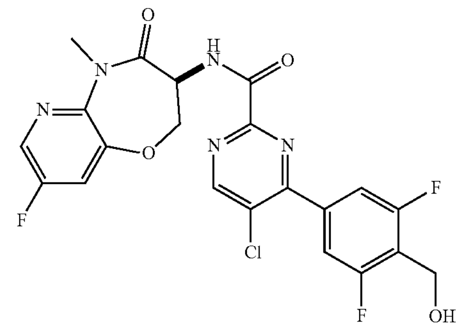

(S)-5-chloro-N-(8-chloro-5-methyl-4-oxo-2,3,4,5-tetrahydropyrido[3,2-b][1,4]oxazepin-3-yl)-4-(2,4-difluoro-3-(hydroxymethyl)phenyl)pyrimidine-2-carboxamide

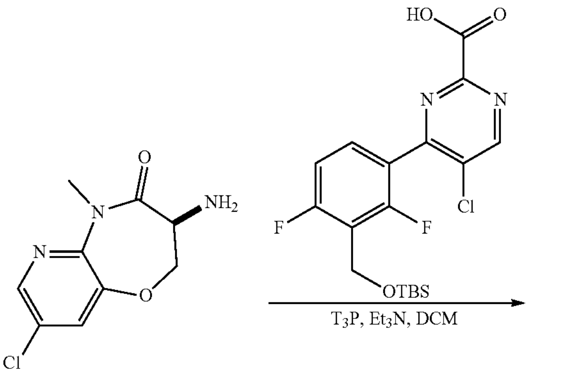

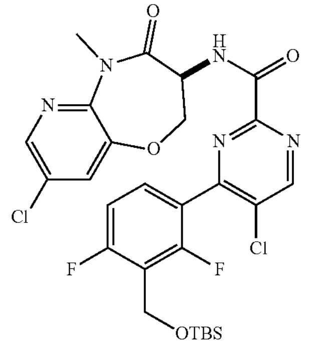

(S)-4-(3-(((tert-butyldimethylsilyl)oxy)methyl)-2,4-difluorophenyl)-5-chloro-N-(8-chloro-5-methyl-4-oxo-2,3,4,5-tetrahydropyrido[3,2-b][1,4]oxazepin-3-yl)-pyrimidine-2-carboxamide To a solution of Intermediate B-5 (50 mg, 219.64 μmol, 1 eq) and Intermediate A-55 (87.18 mg, 219.64 μmol, 1 eq) in $CH_2Cl_2$ (4 mL) were added $Et_3N$ (111.12 mg, 1.10 mmol, 152.85 μL, 5 eq) and $T_3P$ (209.65 mg, 329.46 μmol, 195.94 μL of a 50% solution in EtOAc, 1.5 eq). After stirring at 25° C. for 16 h, the reaction mixture was diluted with water (10 mL), extracted with $CH_2Cl_2$ (10 mL×2) and concentrated under reduced pressure. The residue was purified by prep-TLC (eluent Petroluem ether/EtOAc=3/1) to afford the title compound (50 mg, 80.06 μmol, 36% yield) as a yellow solid. MS(ES+)$C_{27}H_{29}N_5O_4Cl_2F_2Si$ requires: 623 and 625, found: 624 and 626 $[M+H]^+$,

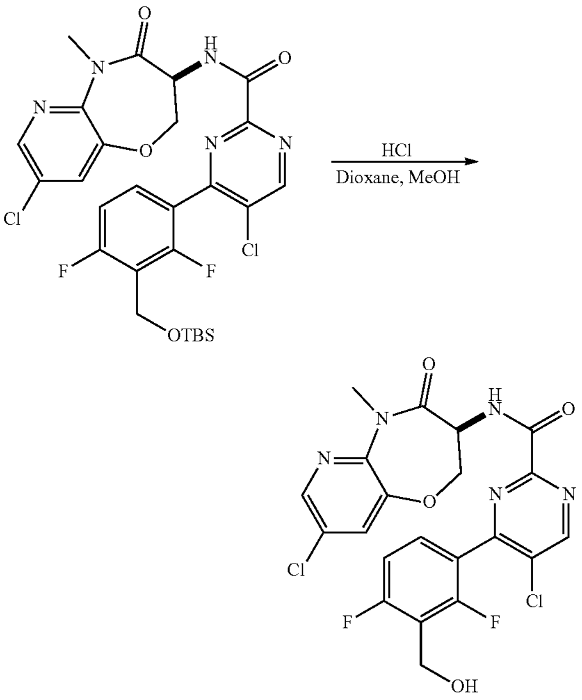

(S)-5-chloro-N-(8-chloro-5-methyl-4-oxo-2,3,4,5-tetrahydropyrido[3,2-b][1,4]oxazepin-3-yl)-4-(2,4-difluoro-3-(hydroxymethyl)phenyl)pyrimidine-2-carboxamide To a solution of the product from the previous step (40 mg, 64.05 μmol, 1 eq) in MeOH (2 mL) was added HCl/dioxane (4 M in dioxane, 4.00 mL, 249.81 eq). After stirring at 25° C. for 30 min, the reaction mixture was concentrated under reduced pressure. The residue was purified by prep-HPLC (column: 3_Phenomenex Luna $C_{18}$ 75*30 mm*3 um; mobile phase: [water (0.05% HCl) —$CH_3CN$]; B %: 37%-57%, 6.5 min). The eluent was concentrated and freeze-dried to afford the HCl salt of the title compound (17.7 mg, 34.69 μmol, 50% yield) as a white solid.

MS (ES+) $C_{21}H_{15}Cl_2F_2N_5O_4$ requires: 509 and 511, found: 510 and 512 $[M+H]^+$. $^1H$ NMR (400 MHz, DMSO-$d_6$) δ=9.26 (s, 1H), 9.15 (d, J=7.7 Hz, 1H), 8.45 (d, J=2.3 Hz, 1H), 7.95 (d, J=2.3 Hz, 1H), 7.70-7.60 (m, 1H), 7.39-7.31 (m, 1H), 5.06-4.94 (m, 1H), 4.81-4.70 (m, 1H), 4.65-4.62 (m, 1H), 4.61-4.57 (m, 2H), 3.36 (s, 3H).

EXAMPLE 166

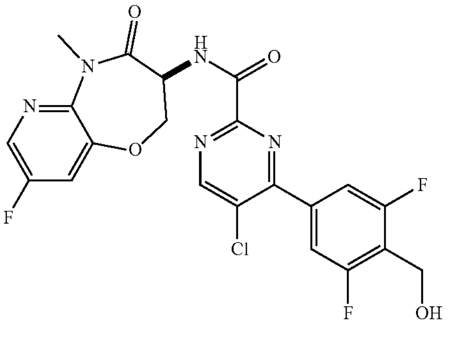

(S)-5-chloro-4-(3,5-difluoro-4-(hydroxymethyl)phenyl)-N-(8-fluoro-5-methyl-4-oxo-2,3,4,5-tetrahydropyrido[3,2-b][1,4]oxazepin-3-yl)pyrimidine-2-carboxamide The compound was prepared with a procedure similar to that used for Example 165.

MS ($ES^+$) $C_{21}H_{15}ClF_3N_5O_4$ requires: 493, found: 494 $[M+H]^+$. $^1H$ NMR (600 MHz, DMSO-$d_6$) δ 9.26 (s, 1H), 9.13 (d, J=7.6 Hz, 1H), 8.45-8.41 (m, 1H), 7.83 (d, J=8.7 Hz, 1H), 7.65 (q, J=7.7 Hz, 1H), 7.34 (t, J=8.7 Hz, 1H), 5.41 (dd, J=6.4, 4.9 Hz, 1H), 5.01-4.93 (m, 1H), 4.74 (t, J=10.7 Hz, 1H), 4.61 (dd, J=9.7, 7.4 Hz, 1H), 4.58 (d, J=5.7 Hz, 2H), 3.35 (d, J=1.3 Hz, 3H).

EXAMPLE 167

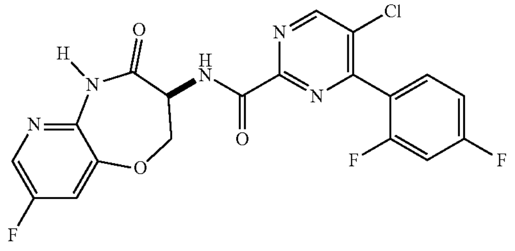

(S)-5-chloro-4-(2,4-difluorophenyl)-N-(8-fluoro-4-oxo-2,3,4,5-tetrahydropyrido[3,2-b][1,4]oxazepin-3-yl)pyrimidine-2-carboxamide

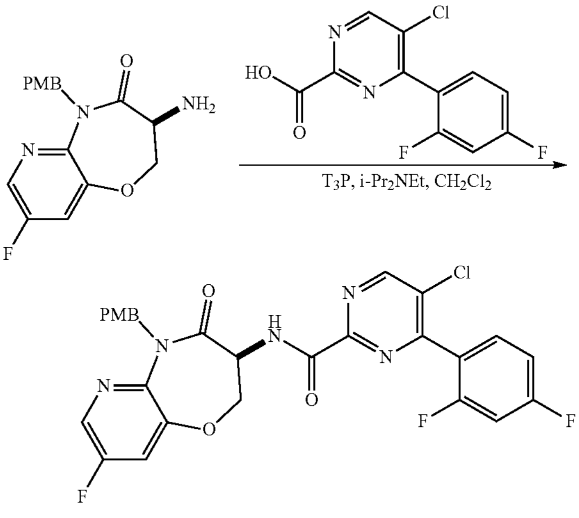

(S)-5-chloro-4-(2,4-difluorophenyl)-N-(8-fluoro-5-(4-methoxybenzyl)-4-oxo-2,3,4,5-tetrahydropyrido[3,2-b][1,4]oxazepin-3-yl)pyrimidine-2-carboxamide To a solution of Intermediate B-6 (3S)-3-amino-8-fluoro-5-[(4-methoxyphenyl) methyl]-2, 3-dihydropyrido[3, 2-b][1, 4]oxazepin-4-one hydrochloride (100 mg, 315.15 μmol, 1 eq) and Intermediate A-23 (85.28 mg, 315.15 μmol, 1 eq) in $CH_2Cl_2$ (2 mL) were added $T_3P$ (200.55 mg, 630.29 μmol, 187.43 μL of a 50% solution in EtOAc, 2 eq), i-$Pr_2NEt$ (203.65 mg, 1.58 mmol, 274.46 μL, 5 eq). After stirring at 25° C. for 6 h, HATU (239.66 mg, 630.29 μmol, 2 eq) was added and the mixture was stirred at 25° C. for another 16 h. The the mixture was diluted with $H_2O$ (5 mL) and then extracted with $CH_2Cl_2$ (5 mL×3). The combined organic phase was dried over $Na_2SO_4$, filtered and concentrated under reduced pressure. The residue was purified by chromatography on silica gel (eluent Petroleum ether/EtOAc=20/1 to 10/1) to afford the title compound (140 mg, 240.74 μmol, 76% yield) as white solid.

MS (ES+) $C_{27}H_{19}ClF_3N_5O_4$ requires: 569 and 571, found: 570 and 572 $[M+H]^+$. $^1H$ NMR (400 MHz, $CDCl_3$) δ=8.86 (s, 1H), 8.78 (br d, J=6.8 Hz, 1H), 8.15 (d, J=2.7 Hz, 1H), 7.54-7.46 (m, 1H), 7.22 (dd, J=2.6, 7.9 Hz, 1H), 7.14 (d, J=8.6 Hz, 2H), 7.03-6.99 (m, 1H), 6.94-6.88 (m, 1H), 6.71 (d, J=8.7 Hz, 2H), 5.29 (d, J=14.8 Hz, 1H), 5.09-5.03 (m, 2H), 4.81 (dd, J=7.1, 9.8 Hz, 1H), 4.31 (dd, J=10.1, 11.1 Hz, 1H), 3.67 (s, 3H)

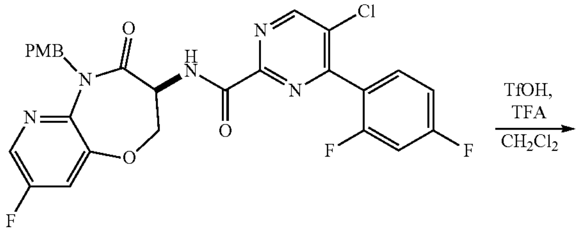

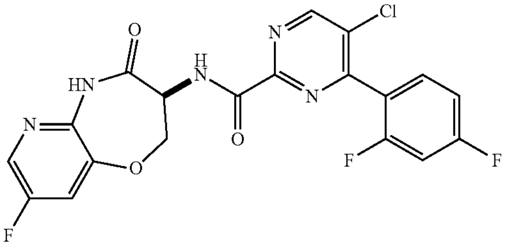

(S)-5-chloro-4-(2,4-difluorophenyl)-N-(8-fluoro-4-oxo-2,3,4,5-tetrahydropyrido[3,2-b][1,4]oxazepin-3-yl)pyrimidine-2-carboxamide To a solution of the product from the previous step in $CH_2Cl_2$ (1 mL) were added TfOH (158.00 mg, 1.05 mmol, 92.94 μL, 6 eq) and TFA (80.03 mg, 701.85 μmol, 51.96 μL, 4 eq). After stirring at 25° C. for 1 h, the mixture was concentrated under reduced pressure. The residue was purified by prep-HPLC (column: Unisil 3-100 C18 μLtra 150*50 mm*3 um; mobile phase: [water (0.225% FA)—$CH_3CN$]; B %: 50%-70%, 10 min). The eluent was concentrated and freeze-dried to afford the title compound (46 mg, 101.25 μmol, 57% yield) as a white solid.

MS (ES+) $C_{19}H_{11}N_5O_3ClF_3$ requires: 449 and 451, found: 450 and 452 $[M+H]^+$. $^1H$ NMR (400 MHz, $CDCl_3$) δ=8.98 (s, 1H), 8.83 (br d, J=5.8 Hz, 1H), 8.14 (br s, 1H), 8.03 (d, J=2.4 Hz, 1H), 7.61 (dt, J=6.3, 8.3 Hz, 1H), 7.27 (d, J=2.5 Hz, 1H), 7.11 (dt, J=2.4, 8.0 Hz, 1H), 7.04-6.98 (m, 1H), 5.06 (ddd, J=3.8, 5.9, 9.4 Hz, 1H), 4.85 (dd, J=3.8, 11.0 Hz, 1H), 4.32 (dd, J=9.6, 10.9 Hz, 1H).

EXAMPLE 168

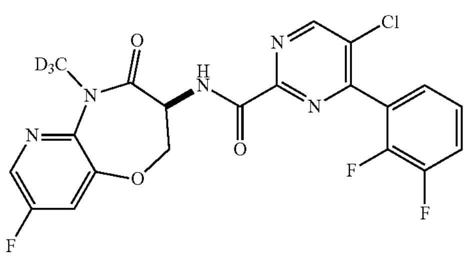

(S)-5-chloro-4-(2,3-difluorophenyl)-N-(8-fluoro-5-(methyl-$d_3$)-4-oxo-2,3,4,5-tetrahydropyrido[3,2-b][1,4]oxazepin-3-yl)pyrimidine-2-carboxamide

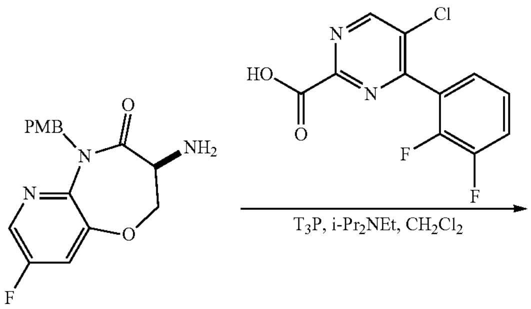

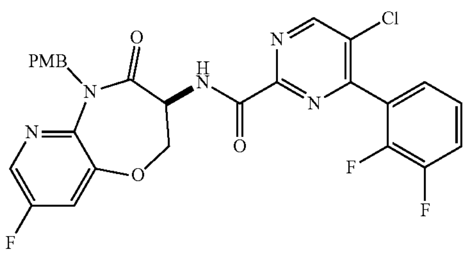

(S)-5-chloro-4-(2,3-difluorophenyl)-N-(8-fluoro-5-(4-methoxybenzyl)-4-oxo-2,3,4,5-tetrahydropyrido[3,2-b][1,4]oxazepin-3-yl)pyrimidine-2-carboxamide To a solution of Intermediate B-6 hydrochloride (100 mg, 315.15 μmol, 1 eq) and Intermediate A-8 (85.28 mg, 315.15 μmol, 1 eq) in $CH_2Cl_2$ (6 mL) were added $Et_3N$ (95.67 mg, 945.44 μmol, 131.59 μL, 3 eq) and $T_3P$ (300.82 mg, 472.72 μmol, 281.14 μL of a 50% solution in EtOAc, 1.5 eq). After stirring at 25° C. for 16 h, the mixture was diluted with $H_2O$ (20 mL) and extracted with $CH_2Cl_2$ (20 mL×2). The combined organic layer was dried over $Na_2SO_4$, filtered and concentrated to afford the title compound (240 mg, crude) as a yellow solid.

MS (ES+) $C_{27}H_{19}ClF_3N_5O_4$ requires: 569 and 571, found: 570 and 572 $[M+H]^+$. $^1H$ NMR (400 MHz, DMSO-$d_6$) δ=9.35 (s, 1H), 9.26 (d, J=7.7 Hz, 1H), 8.49 (d, J=2.7 Hz, 1H), 7.87 (dd, J=2.7, 8.6 Hz, 1H), 7.83-7.74 (m, 1H), 7.56-7.49 (m, 2H), 7.23-7.15 (m, 2H), 6.90-6.84 (m, 2H), 5.30-5.19 (m, 1H), 5.17-5.07 (m, 2H), 4.93-4.81 (m, 1H), 4.69 (dd, J=7.6, 9.8 Hz, 1H), 3.74 (s, 3H).

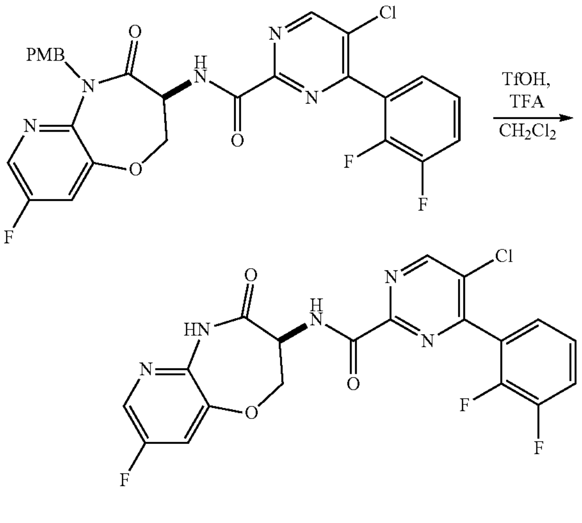

(S)-5-chloro-4-(2,3-difluorophenyl)-N-(8-fluoro-4-oxo-2,3,4,5-tetrahydropyrido[3,2-b][1,4]oxazepin-3-yl)pyrimidine-2-carboxamide To a solution of the product from the previous step (100 mg, 175.46 μmol, 1 eq) in $CH_2Cl_2$ (1 mL) were added TfOH (158.00 mg, 1.05 mmol, 92.94 μL, 6 eq) and TFA (80.03 mg, 701.86 μmol, 51.97 μL, 4 eq). After stirring at 25° C. for 1 h, the mixture was quenched with saturated $Na_2CO_3$ aqueous solution (5 mL), extracted with $CH_2Cl_2$ (5 mL×2), dried over $Na_2SO_4$, filtered and concentrated under reduced pressure to afford the title compound (80 mg, crude) as a yellow solid. MS (ES+) $C_{19}H_{11}ClF_3N_5O_3$ requires: 449 and 451, found: 450 and 452 $[M+H]^+$.

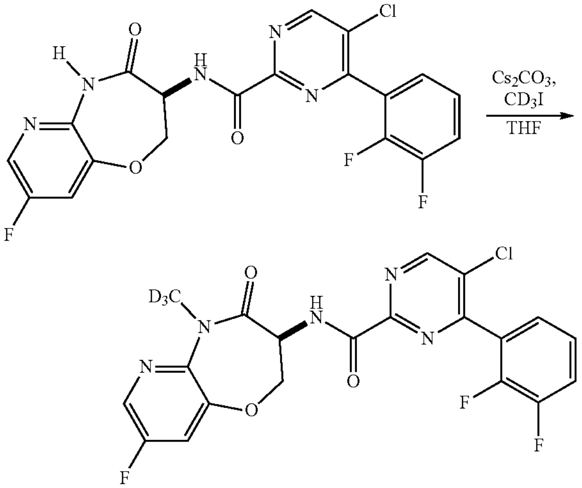

(S)-5-chloro-4-(2,3-difluorophenyl)-N-(8-fluoro-5-(methyl-$d_3$)-4-oxo-2,3,4,5-tetrahydropyrido[3,2-b][1,4]oxazepin-3-yl)pyrimidine-2-carboxamide To a solution of the product from the previous step (40 mg, 88.93 μmol, 1 eq) in THF (2 mL) were added $CD_3I$ (15.47 mg, 106.72 μmol, 1.2 eq) and $Cs_2CO_3$ (57.95 mg, 177.87 μmol, 2 eq). After stirring at 25° C. for 16 h, the mixture was diluted with $H_2O$ (10 mL), extracted with $CH_2Cl_2$ (10 mL×2) and concentrated under reduced pressure. The residue was purified by prep-HPLC (column: Waters Xbridge 150*25 mm*5 um; mobile phase: [water (0.05% $NH_4OH$ v/v) —$CH_3CN$]; B %:

38%-68%, 10 min) to afford the title compound (1.3 mg, 2.67 μmol, 3% yield) as a white solid.

MS (ES+) $C_{20}H_{10}D_3ClF_3N_5O_3$ requires: 466 and 468, found: 467 and 469 $[M+H]^+$. $^1H$ NMR (400 MHz, DMSO-$d_6$) δ=9.29 (s, 1H), 9.15 (d, J=7.5 Hz, 1H), 8.43 (d, J=2.6 Hz, 1H), 7.82 (dd, J=2.4, 8.3 Hz, 1H), 7.77-7.67 (m, 1H), 7.52-7.44 (m, 2H), 5.03-4.90 (m, 1H), 4.79-4.70 (m, 1H), 4.67-4.57 (m, 1H).

EXAMPLE 169

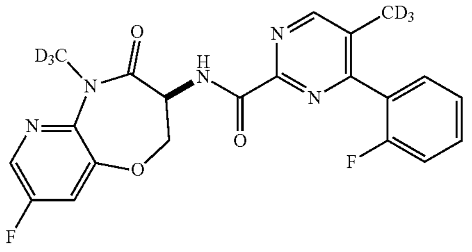

(S)—N-(8-fluoro-5-(methyl-$d_3$)-4-oxo-2,3,4,5-tetrahydropyrido[3,2-b][1,4]oxazepin-3-yl)-4-(2-fluorophenyl)-5-(methyl-$d_3$)pyrimidine-2-carboxamide

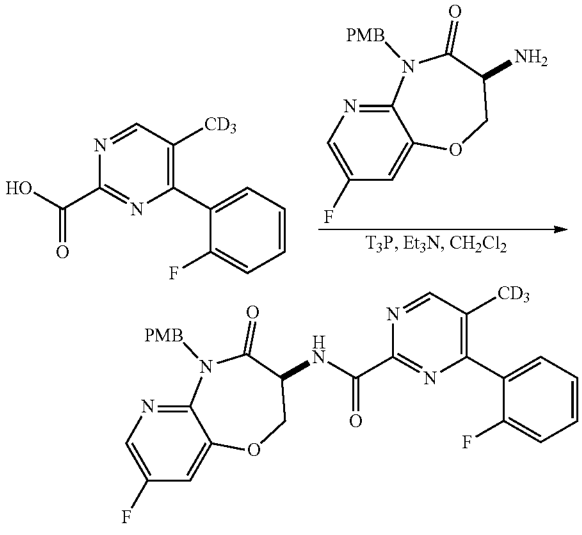

(S)—N-(8-fluoro-5-(4-methoxybenzyl)-4-oxo-2,3,4,5-tetrahydropyrido[3,2-b][1,4]oxazepin-3-yl)-4-(2-fluorophenyl)-5-(methyl-$d_3$)pyrimidine-2-carboxamide To a solution of Intermediate A-42 (30 mg, 127.54 umol, 1 eq) and Intermediate B-6 hydrochloride (49.77 mg, 127.54 umol, 1 eq) in $CH_2Cl_2$ (2 mL) were added $Et_3N$ (77.43 mg, 765.21 umol, 106.51 uL, 6 eq) and $T_3P$ (202.90 mg, 318.84 umol, 189.62 uL of a 50% solution in EtOAc, 2.5 eq). After stirring at 15° C. for 30 min, the mixture was diluted with $H_2O$ (10 mL) and extracted with $CH_2Cl_2$ (10 mL×2). The combined organic layer was washed with brine, dried over $Na_2SO_4$ and filtered. The filtrate was concentrated to afford the title compound (80 mg, crude) as a yellow oil. MS(ES+) $C_{28}H_{20}D_3N_5O_4F_2$ requires:534, found: 535 $[M+H]^+$.

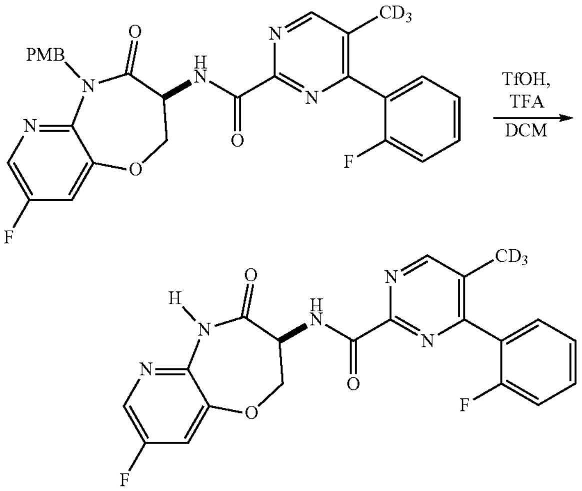

(S)—N-(8-fluoro-4-oxo-2,3,4,5-tetrahydropyrido[3,2-b][1,4]oxazepin-3-yl)-4-(2-fluorophenyl)-5-(methyl-$d_3$)pyrimidine-2-carboxamide To a solution of the product from the previous step (80 mg, 149.66 umol, 1 eq) in $CH_2Cl_2$ (1 mL) were added TFA (77.00 mg, 675.30 umol, 0.05 mL, 4.51 eq) and TfOH (170.00 mg, 1.13 mmol, 0.1 mL, 7.57 eq). The mixture was stirred at 15° C. for 1 h. The pH of mixture was adjusted to 7 with 1M NaOH aqueous solution. The residue was diluted with $H_2O$ (5 mL) and extracted with dichoromethane (5 mLx2). The combined organic layer was washed with brine, dried over $Na_2SO_4$ and filtered. The filtrate was concentrated and purified by prep-TLC (eluent $CH_2Cl_2$:methanol=10:1) to afford the title compound (20 mg, 46.33 umol, 30% yield) as a yellow oil. MS(ES+) $C_{20}H_{12}D_3N_5O_3F_2$ requires:414, found: 415 $[M+H]^+$.

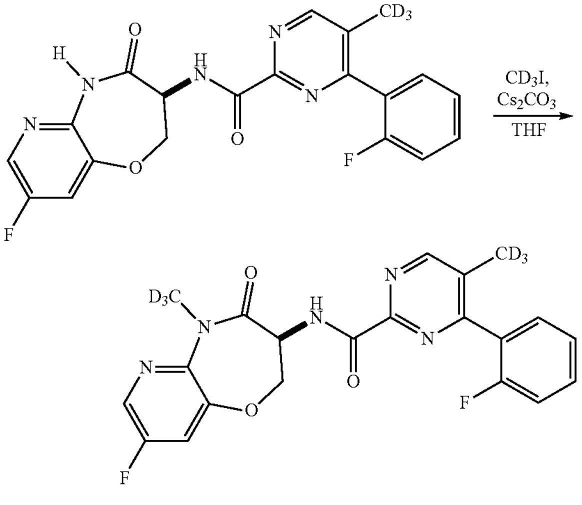

(S)—N-(8-fluoro-5-(methyl-$d_3$)-4-oxo-2,3,4,5-tetrahydropyrido[3,2-b][1,4]oxazepin-3-yl)-4-(2-fluorophenyl)-5-(methyl-$d_3$)pyrimidine-2-carboxamide To a solution of the product from the previous step (20 mg, 48.26 umol, 1 eq) in THF (1.5 mL) were added $CD_3I$ (10.49 mg, 72.40 umol, 1.5 eq) and $Cs_2CO_3$ (31.45 mg, 96.53 umol, 2 eq). After stirring at 15° C. for 16 h, the mixture was filtrated and the filtrate was concentrated. The resulting yellow oil was purified by prep-HPLC (column: 3_Phenomenex Luna C18 75*30 mm*3 um; mobile phase: [water (0.05% HCl)— $CH_3CN$]; B %: 39%-59%, 6.5 min). The eluent was concentrated and freeze-dried to afford the HCl salt of the title compound (5.0 mg, 11.36 umol, 23% yield) as a colorless oil.

MS(ES+) $C_{21}H_{11}D_6F_2N_5O_3$ requires:431, found: 432$[M+H]^+$. $^1H$ NMR (400 MHz, DMSO-$d_6$) δ=9.06 (d, J=7.6 Hz, 1H), 8.97 (s, 1H), 8.42 (d, J=2.6 Hz, 1H), 7.82 (dd, J=2.7, 8.7 Hz, 1H), 7.67-7.52 (m, 2H), 7.45-7.39 (m, 2H), 5.01-4.91 (m, 1H), 4.77-4.69 (m, 1H), 4.65-4.58 (m, 1H).

EXAMPLE 170

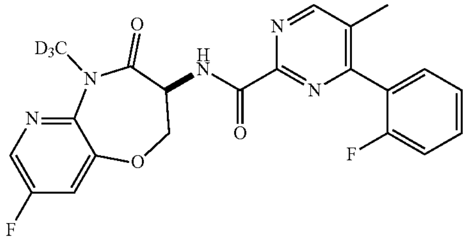

(S)—N-(8-fluoro-5-(methyl-$d_3$)-4-oxo-2,3,4,5-tetrahydropyrido[3,2-b][1,4]oxazepin-3-yl)-4-(2-fluorophenyl)-5-methylpyrimidine-2-carboxamide This compound was prepared by a procedure similar to that used for example 169.

MS(ES+) $C_{21}H_{14}D_3F_2N_5O_3$ requires:428, found: 429$[M+H]^+$. $^1H$ NMR (400 MHz, DMSO-$d_6$) δ=9.06 (d, J=7.7 Hz, 1H), 8.98 (s, 1H), 8.43 (d, J=2.7 Hz, 1H), 7.83 (dd, J=2.6, 8.7 Hz, 1H), 7.68-7.53 (m, 2H), 7.47-7.39 (m, 2H), 5.03-4.91 (m, 1H), 4.79-4.69 (m, 1H), 4.68-4.58 (m, 1H), 2.26 (s, 3H).

EXAMPLE 171

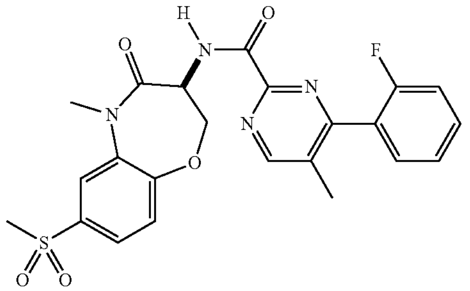

(S)-4-(2-fluorophenyl)-5-methyl-N-(5-methyl-7-(methylsulfonyl)-4-oxo-2,3,4,5-tetrahydrobenzo[b][1,4]oxazepin-3-yl)pyrimidine-2-carboxamide To a solution of Intermediate A-47 (43.60 mg, 187.77 μmol, 1.2 eq) and Intermediate B-16 (48 mg, 156.47 μmol, 1 eq) in $CH_2Cl_2$ (2 mL) were added $T_3P$ (149.36 mg, 234.71 μmol, 139.59 μL of a 50% solution in EtOAc, 1.5 eq) and i-$Pr_2NEt$ (80.89 mg, 625.89 μmol, 109.02 μL, 4 eq). After stirring at 15° C. for 20 min, the mixture was concentrated under reduced pressure. The residue was purified by prep-HPLC (column: 3_Phenomenex Luna C18 75*30 mm*3 um; mobile phase: [water (0.05% HCl) —$CH_3CN$]; B %:

34%-54%, 6.5 min), the eluent was concentrated and freeze-dried to afford the title compound (22.4 mg, 44.38 μmol, 28% yield) as a white solid.

MS (ES+) $C_{23}H_{21}N_4O_5SF$ requires: 484, found 485 $[M+H]^+$. $^1H$ NMR (400 MHz, DMSO-$d_6$) δ=9.00 (d, J=7.7 Hz, 1H), 8.97 (s, 1H), 8.03 (d, J=2.2 Hz, 1H), 7.84 (dd, J=2.2, 8.4 Hz, 1H), 7.66-7.54 (m, 2H), 7.50 (d, J=8.4 Hz, 1H), 7.45-7.38 (m, 2H), 4.99-4.90 (m, 1H), 4.74-4.66 (m, 1H), 4.57 (dd, J=7.5, 9.8 Hz, 1H), 3.39 (s, 3H), 3.31 (s, 3H), 2.25 (s, 3H).

EXAMPLE 172

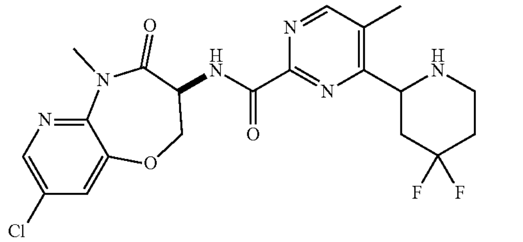

N—((S)-8-chloro-5-methyl-4-oxo-2,3,4,5-tetrahydropyrido[3,2-b][1,4]oxazepin-3-yl)-4-(4,4-difluoropiperidin-2-yl)-5-methylpyrimidine-2-carboxamide

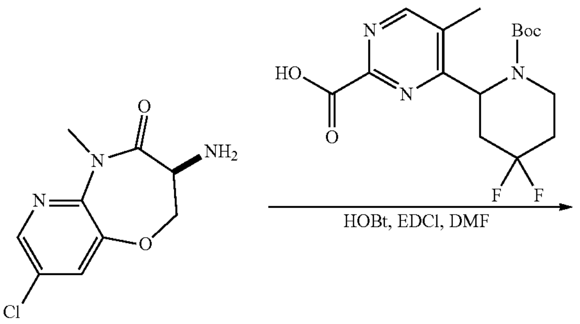

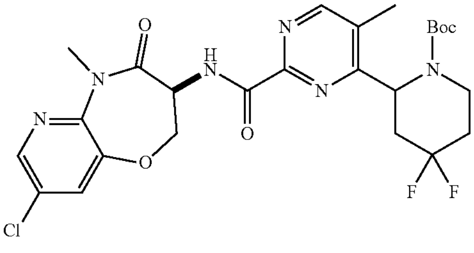

tert-Butyl 2-(2-(((S)-8-chloro-5-methyl-4-oxo-2,3,4,5-tetrahydropyrido[3,2-b]-[1,4]oxazepin-3-yl)carbamoyl)-5-methylpyrimidin-4-yl)-4,4-difluoropiperidine-1-carboxylate To a solution of Intermediate A-60 (40 mg, 111.93 μmol, 6.73e-1 eq) and Intermediate B-5 hydrochloride (50 mg, 166.35 μmol, 1 eq) in DMF (2 mL) were added HOBT (22.48 mg, 166.35 μmol, 1 eq) and EDCI (95.67 mg, 499.05 μmol, 3 eq). After stirring at 20° C. for 16 h, the reaction mixture was filtered and the filtrate was concentrated under reduced pressure. The residue was purified by prep-HPLC (column: Phenomenex Gemini-NX C18 75*30 mm*3 um; mobile phase: [water (0.225% FA) —$CH_3CN$]; B %: 52%-62%, 7 min). The eluent was concentrated and freeze-dried to afford the title compound (50 mg, 88.19 μmol, 53% yield) as a white solid.

MS (ES+) $C_{25}H_{29}ClF_2N_6O_5$ requires: 566 and 568, found 567 and 569 $[M+H]^+$. $^1H$ NMR (400 MHz, DMSO-$d_6$) δ=8.93-8.84 (m, 1H), 8.80-8.75 (m, 1H), 8.45 (d, J=2.3 Hz, 1H), 7.99-7.94 (m, 1H), 5.52-5.39 (m, 1H), 5.04-4.92 (m, 1H), 4.71-4.50 (m, 2H), 4.11-3.94 (m, 2H), 3.38 (s, 3H), 2.72-2.60 (m, 1H), 2.46-2.42 (m, 1H), 2.40 (s, 3H), 2.21-2.06 (m, 2H), 1.22 (br s, 9H).

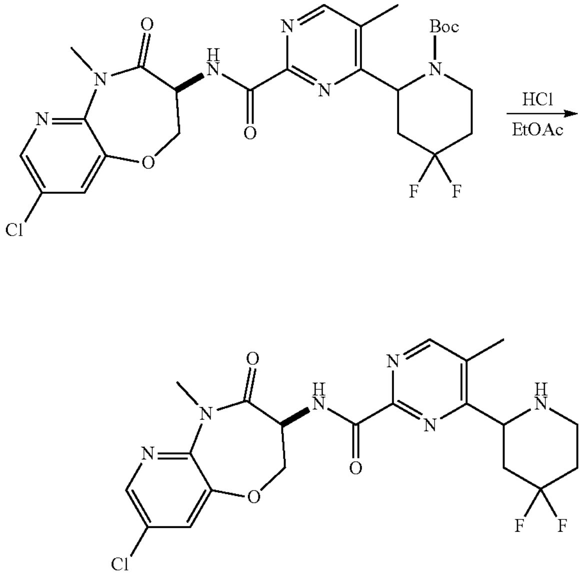

N—((S)-8-chloro-5-methyl-4-oxo-2,3,4,5-tetrahydropyrido[3,2-b][1,4]oxazepin-3-yl)-4-(4,4-difluoropiperidin-2-yl)-5-methylpyrimidine-2-carboxamide A solution of the product from the previous step (30 mg, 52.91 μmol, 1 eq) in HCl/EtOAc (4 M, 10 mL) was stirred at 20° C. for 2 h. The reaction mixture was concentrated under reduced pressure. The residue was purified by prep-HPLC (column: Waters Xbridge 150*25 mm*5 um; mobile phase: [water (10 mM $NH_4HCO_3$) —$CH_3CN$]; B %: 32%-62%, 9 min). The eluent was concentrated and freeze-dried to afford the title compound (8 mg, 17.14 μmol, 32% yield) as a white solid.

MS (ES+) $C_{20}H_{21}ClF_2N_6O_3$ requires: 466 and 468, found 467 and 469 $[M+H]^+$. $^1H$ NMR (400 MHz, DMSO-$d_6$) δ=9.10-9.03 (m, 1H), 8.78 (s, 1H), 8.48-8.42 (m, 1H), 7.98-7.93 (m, 1H), 5.04-4.95 (m, 1H), 4.81-4.72 (m, 1H), 4.67-4.59 (m, 1H), 4.14-4.01 (m, 1H), 3.36 (s, 3H), 3.26-3.17 (i, 1H), 2.84-2.71 (i, 1H), 2.41 (s, 3H), 2.27-2.16 (i, 1H), 2.13-1.98 (1, 2H), 1.95-1.79 (mi, 1H).

TABLE 8

Analytical data for RIPK1 inhibitors. I.

| Ex. No. | NMR | M + 1 |
|---|---|---|
| 1 | (500 MHz, DMSO-$d_6$) δ 9.04-9.01 (m, 1H), 8.91-8.89 (m, 1H), 7.86-7.79 (m, 2H), 7.73-7.70 (m, 1H), 7.70-7.67 (m, 1H), 7.66-7.59 (m, 1H), 7.37-7.30 (m, 1H), 4.97-4.88 (m, 1H), 4.74-4.66 (m, 1H), 4.60-4.53 (m, 1H), 3.36 (s, 3H), 2.43 (s, 3H), 2.36-2.32 (m, 3H). | 446 |
| 2 | (500 MHz, DMSO-$d_6$) δ 10.06 (s, 1H), 8.82 (d, J = 7.6 Hz, 1H), 8.64 (s, 1H), 7.84-7.76 (m, 2H), 7.62-7.52 (m, 3H), 7.38-7.32 (m, 1H), 7.32-7.26 (m, 1H), 7.21-7.14 (m, 1H), 7.08-7.02 (m, 1H), 4.43-4.34 (m, 1H), 2.85-2.75 (m, 1H), 2.75-2.68 (m, 1H), 2.61-2.51 (m, 1H), 2.24-2.14 (m, 1H), 2.06-1.97 (m, 1H), 1.08-0.98 (m, 2H), 0.96-0.89 (m, 2H). | 399 |
| 3 | (500 MHz, DMSO-$d_6$) δ 10.06 (s, 1H), 8.89 (s, 1H), 8.85 (d, J = 7.6 Hz, 1H), 7.76-7.69 (m, 2H), 7.61-7.52 (m, 3H), 7.38-7.33 (m, 1H), 7.33-7.26 (m, 1H), 7.21-7.14 (m, 1H), 7.08-7.03 (m, 1H), 4.44-4.35 (m, 1H), 2.85-2.76 (m, 1H), 2.76-2.69 (m, 1H), 2.61-2.51 (m, 1H), 2.42 (s, 3H), 2.25-2.16 (m, 1H). | 373 |
| 4 | (500 MHz, DMSO-$d_6$) δ 10.07 (s, 1H), 9.04-8.97 (m, 2H), 8.37-8.30 (m, 2H), 8.26 (d, J = 5.3 Hz, 1H), 7.66-7.57 (m, 3H), 7.39-7.33 (m, 1H), 7.33-7.28 (m, 1H), 7.22-7.15 (m, 1H), 7.10-7.04 (m, 1H), 4.48-4.38 (m, 1H), 2.88-2.78 (m, 1H), 2.78-2.71 (m, 1H), 2.62-2.51 (m, 1H), 2.33-2.24 (m, 1H). | 359 |
| 5 | (600 MHz, DMSO-$d_6$) δ 9.02 (d, J = 7.8 Hz, 1H), 8.91 (s, 1H), 7.84-7.78 (m, 2H), 7.76-7.72 (m, 2H), 7.70 (d, J = 8.3 Hz, 1H), 7.61-7.53 (m, 3H), 4.96-4.89 (m, 1H), 4.72-4.65 (m, 1H), 4.59-4.53 (m, 1H), 3.36 (s, 3H), 2.43 (s, 3H). | 414 |
| 6 | (600 MHz, DMSO-$d_6$) δ 9.06 (d, J = 7.7 Hz, 1H), 8.91 (s, 1H), 8.40-8.35 (m, 1H), 7.77-7.71 (m, 3H), 7.61-7.53 (m, 3H), 7.37-7.32 (m, 1H), 4.97-4.89 (m, 1H), 4.74-4.67 (m, 1H), 4.63-4.57 (m, 1H), 3.38 (s, 3H), 2.43 (s, 3H). | 390 |
| 7 | (600 MHz, DMSO-$d_6$) δ 10.01 (s, 1H), 8.89 (s, 1H), 8.85 (d, J = 7.5 Hz, 1H), 7.76-7.71 (m, 2H), 7.60-7.54 (m, 3H), 7.32-7.25 (m, 1H), 7.19-7.14 (m, 1H), 4.45-4.37 (m, 1H), 2.84-2.76 (m, 2H), 2.58-2.52 (m, 1H), 2.42 (s, 3H), 2.28-2.19 (m, 1H). | 409 |
| 8 | (600 MHz, DMSO-$d_6$) δ 9.93 (s, 1H), 8.85 (d, J = 7.9 Hz, 1H), 8.42 (s, 1H), 7.75-7.71 (m, 2H), 7.57-7.49 (m, 3H), 7.35-7.26 (m, 2H), 7.19-7.13 (m, 1H), 7.05 (d, J = 7.8 Hz, 1H), 4.42-4.35 (m, 1H), 2.82-2.72 (m, 1H), 2.74-2.68 (m, 1H), 2.48-2.38 (m, 1H), 2.20-2.11 (m, 1H). | 427 |
| 9 | (600 MHz, DMSO-$d_6$) δ 10.05 (s, 1H), 8.89 (s, 1H), 8.84 (d, J = 7.7 Hz, 1H), 7.85-7.79 (m, 2H), 7.43-7.37 (m, 2H), 7.35 (d, J = 7.4 Hz, 1H), 7.29 (t, J = 7.5 Hz, 1H), 7.17 (t, J = 7.4 Hz, 1H), 7.05 (d, J = 7.8 Hz, 1H), 4.43-4.36 (m, 1H), 2.85-2.76 (m, 1H), 2.76-2.69 (m, 1H), 2.59-2.51 (m, 1H), 2.42 (s, 3H), 2.25-2.17 (m, 1H). | 391 |
| 10 | (600 MHz, DMSO-$d_6$) δ 10.04 (s, 1H), 8.91 (s, 1H), 8.87 (d, J = 7.7 Hz, 1H), 7.93-7.87 (m, 1H), 7.68-7.61 (m, 2H), 7.35 (d, J = 7.4 Hz, 1H), 7.29 (t, J = 7.6 Hz, 1H), 7.17 (t, J = 7.4 Hz, 1H), 7.05 (d, J = 7.8 Hz, 1H), 4.44-4.36 (m, 1H), 2.85-2.76 (m, 1H), 2.76-2.70 (m, 1H), 2.58-2.51 (m, 1H), 2.43 (s, 3H), 2.28-2.19 (m, 1H). | 409 |
| 11 | (500 MHz, DMSO-$d_6$) δ 8.92-8.88 (m, 2H), 7.82-7.77 (m, 1H), 7.76-7.71 (m, 2H), 7.60-7.55 (m, 3H), 6.89-6.84 (m, 1H), 4.49-4.40 (m, 1H), 3.90 (s, 3H), 3.28 (s, 3H), 3.05-2.94 (m, 1H), 2.72-2.54 (m, 2H), 2.42 (s, 3H), 2.29-2.18 (m, 1H). | 418 |
| 12 | (600 MHz, DMSO-$d_6$) δ 10.05 (s, 1H), 8.92 (s, 1H), 8.86 (d, J = 7.6 Hz, 1H), 7.65-7.55 (m, 3H), 7.44-7.38 (m, 1H), 7.35 (d, J = 7.5 Hz, 1H), 7.30 (t, J = 7.6 Hz, 1H), 7.17 (t, J = 7.5 Hz, 1H), 7.06 (d, J = 7.8 Hz, 1H), 4.44-4.36 (m, 1H), 2.85-2.76 (m, 1H), 2.76-2.70 (m, 1H), 2.59-2.50 (m, 1H), 2.43 (s, 3H), 2.27-2.19 (m, 1H). | 391 |
| 13 | (600 MHz, DMSO-$d_6$) δ 10.06 (s, 1H), 8.87-8.82 (m, 2H), 7.65 (d, J = 8.0 Hz, 2H), 7.40-7.33 (m, 3H), 7.32-7.27 (m, 1H), 7.17 (t, J = 7.4 Hz, 1H), 7.05 (d, J = 7.8 Hz, 1H), 4.43-4.35 (m, 1H), 2.85-2.76 (m, 1H), 2.76-2.69 (m, 1H), 2.60-2.52 (m, 1H), 2.41 (d, J = 8.9 Hz, 6H), 2.24-2.16 (m, 1H). | 387 |
| 14 | (500 MHz, DMSO-$d_6$) δ 8.92 (d, J = 8.0 Hz, 1H), 8.20 (s, 1H), 7.91-7.78 (m, 2H), 7.70 (d, J = 8.3 Hz, 1H), 4.92-4.83 (m, 1H), 4.73-4.59 (m, 1H), 4.58-4.51 (m, 1H), 3.71-3.66 (m, 4H), 3.36 (s, 3H), 2.31 (s, 3H), 1.67 (s, 6H). | 421 |
| 15 | (500 MHz, DMSO-$d_6$) δ 9.08-9.02 (m, 1H), 8.90 (d, J = 2.4 Hz, 1H), 7.77-7.71 (m, 2H), 7.61-7.53 (m, 3H), 6.95 (d, J = 2.4 Hz, 1H), 4.56-4.45 (m, 1H), 4.45-4.30 (m, 2H), 3.30 (d, J = 2.5 Hz, 3H), 2.81-2.69 (m, 1H), 2.52-2.44 (m, 1H), 2.43 (d, J = 2.4 Hz, 3H). | 445 |
| 16 | (600 MHz, DMSO-$d_6$) δ 8.92 (s, 1H), 8.81 (d, J = 6.8 Hz, 1H), 8.39-8.35 (m, 1H), 7.80-7.75 (m, 1H), 7.75-7.70 (m, 2H), 7.62-7.54 (m, 3H), 7.39-7.34 (m, 1H), 5.07-5.00 (m, 1H), 4.99-4.94 (m, 1H), 3.41 (s, 3H), 2.43 (s, 3H), 1.34 (d, J = 6.2 Hz, 3H). | 404 |

TABLE 8-continued

| Ex. No. | NMR | M + 1 |
| --- | --- | --- |
| | Analytical data for RIPK1 inhibitors. I. | |
| 17 | (600 MHz, DMSO-$d_6$) δ 9.04 (d, J = 7.9 Hz, 1H), 8.93 (s, 1H), 7.89 (s, 1H), 7.84-7.78 (m, 2H), 7.71 (d, J = 8.3 Hz, 1H), 7.66-7.62 (m, 2H), 4.98-4.89 (m, 1H), 4.74-4.67 (m, 1H), 4.59-4.53 (m, 1H), 3.38 (s, 3H), 2.44 (s, 3H). | 450 |
| 18 | (600 MHz, DMSO-$d_6$) δ 10.61 (s, 1H), 8.99 (s, 1H), 7.97-7.92 (m, 1H), 7.84-7.80 (m, 2H), 7.63-7.55 (m, 3H), 7.48-7.42 (m, 1H), 7.33-7.27 (m, 1H), 2.48 (s, 3H). | 342 |
| 19 | (500 MHz, DMSO-$d_6$) δ 8.99-8.94 (m, 1H), 8.35-8.31 (m, 1H), 7.86-7.79 (m, 2H), 7.73-7.68 (m, 1H), 4.94-4.85 (m, 1H), 4.72-4.64 (m, 1H), 4.58-4.51 (m, 1H), 3.82-3.76 (m, 4H), 3.37 (s, 3H), 2.34 (s, 3H), 2.21-2.06 (m, 4H). | 457 |
| 20 | (600 MHz, DMSO-d6) δ 8.93-8.89 (m, 1H), 8.06 (s, 1H), 7.86-7.80 (m, 2H), 7.72-7.68 (m, 1H), 4.92-4.84 (m, 1H), 4.71-4.64 (m, 1H), 4.60-4.54 (m, 1H), 3.93-3.86 (m, 4H), 3.37 (s, 6H), 2.45 (s, 3H), 1.98-1.92 (m, 4H). | 407 |
| 21 | (600 MHz, DMSO-$d_6$) δ 9.08 (d, J = 7.9 Hz, 1H), 8.94 (s, 1H), 8.40-8.36 (m, 1H), 7.94-7.88 (m, 1H), 7.76-7.71 (m, 1H), 7.69-7.61 (m, 2H), 7.37-7.32 (m, 1H), 4.97-4.90 (m, 1H), 4.76-4.69 (m, 1H), 4.63-4.57 (m, 1H), 3.38 (s, 3H), 2.45 (s, 3H). | 426 |
| 22 | (600 MHz, DMSO-$d_6$) δ 8.97 (d, J = 7.8 Hz, 1H), 8.91 (s, 1H), 7.77 (d, J = 2.4 Hz, 1H), 7.76-7.72 (m, 2H), 7.59-7.54 (m, 3H), 7.51-7.46 (m, 1H), 7.23 (d, J = 8.5 Hz, 1H), 4.95-4.87 (m, 1H), 4.63-4.56 (m, 1H), 4.53-4.47 (m, 1H), 3.37 (s, 3H), 2.43 (s, 3H). | 468 |
| 23 | (500 MHz, DMSO-d6) δ 8.87 (d, J = 7.9 Hz, 1H), 8.17 (s, 1H), 7.86-7.78 (m, 2H), 7.70 (d, J = 8.3 Hz, 1H), 4.87 (dt, J = 11.4, 7.8 Hz, 1H), 4.67 (dd, J = 11.4, 9.9 Hz, 1H), 4.53 (dd, J = 9.9, 7.7 Hz, 1H), 4.27 (t, J = 13.1 Hz, 2H), 4.06 (t, J = 7.4 Hz, 2H), 3.36 (s, 3H), 2.55 (dd, J = 14.2, 7.5 Hz, 2H), 2.42 (s, 3H). | 443 |
| 24 | (500 MHz, DMSO-d6) δ 9.17 (s, 1H), 9.10 (d, J = 7.9 Hz, 1H), 7.93-7.86 (m, 2H), 7.85-7.78 (m, 2H), 7.71 (d, J = 8.2 Hz, 1H), 7.61 (dd, J = 5.2, 1.9 Hz, 3H), 4.93 (dt, J = 11.4, 7.8 Hz, 1H), 4.71 (dd, J = 11.5, 9.8 Hz, 1H), 4.56 (dd, J = 9.8, 7.6 Hz, 1H), 3.36 (s, 3H). | 434 |
| 25 | (500 MHz, Methanol-d4) δ 10.30 (s, 1H), 8.07 (d, J = 7.7 Hz, 1H), 8.03 (dd, J = 7.7, 0.9 Hz, 1H), 7.90-7.84 (m, 1H), 7.48-7.40 (m, 1H), 7.31-7.23 (m, 1H), 2.45 (s, 3H) | 344 |
| 26 | (600 MHz, DMSO-$d_6$) δ 8.94-8.89 (m, 2H), 7.76-7.71 (m, 2H), 7.60-7.54 (m, 3H), 7.06 (d, J = 8.6 Hz, 1H), 6.48 (d, J = 2.7 Hz, 1H), 6.35-6.30 (m, 1H), 4.91-4.83 (m, 1H), 4.45-4.35 (m, 2H), 3.66-3.60 (m, 4H), 3.58-3.51 (m, 4H), 3.31 (s, 3H), 2.42 (s, 3H), 1.78-1.73 (m, 4H). | 514 |
| 27 | (600 MHz, DMSO-$d_6$) δ 9.17 (s, 1H), 9.13 (d, J = 7.8 Hz, 1H), 8.40-8.36 (m, 1H), 7.92-7.87 (m, 2H), 7.76-7.71 (m, 1H), 7.64-7.56 (m, 3H), 7.38-7.32 (m, 1H), 4.97-4.90 (m, 1H), 4.75-4.68 (m, 1H), 4.63-4.57 (m, 1H), 3.38 (s, 3H). | 410 |
| 28 | | |
| 29 | (600 MHz, DMSO-$d_6$) δ 9.06 (d, J = 7.6 Hz, 1H), 8.91 (s, 1H), 8.51 (d, J = 2.2 Hz, 1H), 8.05 (d, J = 2.2 Hz, 1H), 7.74 (dd, J = 7.5, 2.2 Hz, 2H), 7.61-7.54 (m, 3H), 5.03-4.96 (m, 1H), 4.77-4.71 (m, 1H), 4.67-4.61 (m, 1H), 3.36 (s, 3H), 2.43 (s, 3H). | 469 |
| 30 | (500 MHz, DMSO-d6) δ 9.03-8.98 (m, 1H), 8.93 (s, 1H), 7.83-7.77 (m, 2H), 7.71-7.66 (m, 1H), 7.47-7.40 (m, 1H), 7.27-7.20 (m, 2H), 4.95-4.86 (m, 1H), 4.70-4.63 (m, 1H), 4.59-4.52 (m, 1H), 3.35 (s, 3H), 2.42 (s, 3H), 2.26-2.22 (m, 3H) | 446 |
| 31 | (600 MHz, DMSO-d6) δ 9.82 (s, 1H), 8.84 (d, J = 7.8 Hz, 1H), 8.40 (s, 1H), 7.83 (dd, J = 8.4, 1.9 Hz, 1H), 7.80 (d, J = 1.9 Hz, 1H), 7.70 (d, J = 8.4 Hz, 1H), 4.87 (dt, J = 11.4, 7.7 Hz, 1H), 4.64 (dd, J = 11.5, 9.9 Hz, 1H), 4.53 (dd, J = 9.9, 7.6 Hz, 1H), 4.24 (d, J = 14.3 Hz, 2H), 3.55-3.51 (m, 2H), 3.36 (s, 3H), 3.28 (t, J = 13.3 Hz, 2H), 3.21-3.10 (m, 2H), 2.86 (s, 3H), 2.30 (s, 3H). | 436 |
| 32 | (600 MHz, DMSO-d6) δ 8.84 (d, J = 7.8 Hz, 1H), 8.22 (s, 1H), 7.82 (dd, J = 8.3, 1.9 Hz, 1H), 7.80 (d, J = 1.9 Hz, 1H), 7.69 (d, J = 8.3 Hz, 1H), 4.85 (dt, J = 11.4, 7.8 Hz, 1H), 4.78 (t, J = 12.6 Hz, 4H), 4.64 (dd, J = 11.4, 9.9 Hz, 1H), 4.53 (dd, J = 9.8, 7.7 Hz, 1H), 3.35 (s, 3H), 2.23 (s, 3H) | 429 |
| 33 | (600 MHz, DMSO-d6) δ 8.76 (d, J = 7.8 Hz, 1H), 7.97-7.93 (m, 1H), 7.91 (d, J = 7.7 Hz, 1H), 7.82 (dd, J = 8.3, 1.9 Hz, 1H), 7.80 (d, J = 1.9 Hz, 1H), 7.69 (d, J = 8.3 Hz, 1H), 4.90 (dt, J = 11.5, 7.7 Hz, 1H), 4.73 (dd, J = 11.5, 9.8 Hz, 1H), 4.53 (dd, J = 9.8, 7.6 Hz, 1H), 3.36 (s, 3H), 2.42 (s, 3H). | 416 |
| 34 | (600 MHz, DMSO-d6) δ 10.44 (s, 1H), 8.10-8.05 (m, 2H), 8.03 (d, J = 7.9 Hz, 1H), 7.74-7.70 (m, 2H), 7.58-7.53 (m, 2H), 7.52-7.47 (m, 1H), 7.42-7.37 (m, 1H), 7.30-7.25 (m, 1H), 2.45 (s, 3H). | 341 |
| 35 | (600 MHz, DMSO-d6) δ 10.38 (s, 1H), 8.14 (d, J = 7.9 Hz, 1H), 8.07 (d, J = 7.9 Hz, 1H), 7.97-7.91 (m, 1H), 7.56-7.51 (m, 1H), 7.50-7.39 (m, 3H), 7.30-7.24 (m, 1H), 2.31 (s, 3H). | 377 |

TABLE 8-continued

| Analytical data for RIPK1 inhibitors. I. | | |
|---|---|---|
| Ex. No. | NMR | M + 1 |
| 36 | (600 MHz, DMSO-$d_6$) δ 8.80 (d, J = 7.8 Hz, 1H), 7.93 (d, J = 7.9 Hz, 1H), 7.89 (d, J = 7.9 Hz, 1H), 7.84-7.78 (m, 2H), 7.72-7.66 (m, 3H), 7.41-7.34 (m, 2H), 4.96-4.88 (m, 1H), 4.69-4.63 (m, 1H), 4.58-4.52 (m, 1H), 3.35 (s, 3H), 2.39 (s, 3H). | 431 |
| 37 | (600 MHz, DMSO-$d_6$) δ 8.87 (d, J = 7.8 Hz, 1H), 8.24 (d, J = 8.3 Hz, 1H), 7.96 (d, J = 8.3 Hz, 1H), 7.88-7.83 (m, 2H), 7.83-7.78 (m, 2H), 7.69 (d, J = 8.3 Hz, 1H), 7.44-7.38 (m, 2H), 4.96-4.88 (m, 1H), 4.73-4.66 (m, 1H), 4.58-4.52 (m, 1H), 3.35 (s, 3H). | 450 |
| 38 | (500 MHz, DMSO-$d_6$) δ 9.04-9.01 (m, 1H), 9.00-8.96 (m, 1H), 7.84-7.79 (m, 2H), 7.73-7.69 (m, 1H), 7.69-7.63 (m, 1H), 7.54-7.46 (m, 1H), 7.37-7.29 (m, 1H), 4.97-4.88 (m, 1H), 4.73-4.65 (m, 1H), 4.59-4.52 (m, 1H), 3.36 (s, 3H), 2.28-2.22 (m, 3H). | 450 |
| 39 | (600 MHz, DMSO-$d_6$) δ 8.96 (d, J = 7.8 Hz, 1H), 8.90 (s, 1H), 7.96 (s, 1H), 7.76-7.71 (m, 2H), 7.61-7.53 (m, 4H), 7.35 (d, J = 8.2 Hz, 1H), 7.28 (d, J = 8.2 Hz, 1H), 4.97-4.89 (m, 1H), 4.61-4.55 (m, 1H), 4.55-4.49 (m, 1H), 4.25-4.19 (m, 2H), 4.00 (s, 4H), 3.35 (s, 3H), 3.23 (s, 2H), 2.43 (s, 3H). | 525 |
| 40 | (600 MHz, $CD_3OD$) δ 7.93 (d, J = 7.9 Hz, 1H), 7.85-7.83 (m, 1H), 7.60-7.54 (m, 3H), 7.43 (dd, J = 8.4, 1.9 Hz, 2H), 7.29-7.25 (m, 3H), 5.03 (dd, J = 11.3, 7.3 Hz, 1H), 4.67 (dd, J = 9.9, 7.4 Hz, 1H), 4.48-4.42 (m, 1H), 3.42 (s, 3H), 2.41 (s, 3H). | 413 |
| 41 | (500 MHz, DMSO-d6) δ 8.78 (d, J = 7.9 Hz, 1H), 8.00-7.94 (m, 2H), 7.84-7.78 (m, 2H), 7.69 (d, J = 8.2 Hz, 1H), 7.48-7.40 (m, 3H), 4.92 (dt, J = 11.5, 7.7 Hz, 1H), 4.68 (dd, J = 11.5, 9.9 Hz, 1H), 4.53 (dd, J = 9.9, 7.6 Hz, 1H), 3.36 (s, 3H), 2.25 (d, J = 1.6 Hz, 3H). | 449 |
| 42 | (500 MHz, DMSO-$d_6$) δ 9.02 (d, J = 7.8 Hz, 1H), 8.97 (s, 1H), 7.84-7.78 (m, 2H), 7.70 (d, J = 8.3 Hz, 1H), 7.67-7.59 (m, 1H), 7.59-7.53 (m, 1H), 7.46-7.39 (m, 2H), 4.96-4.87 (m, 1H), 4.72-4.65 (m, 1H), 4.58-4.51 (m, 1H), 3.35 (s, 3H), 2.25 (d, J = 1.5 Hz, 3H). | 432 |
| 43 | (500 MHz, DMSO-$d_6$) δ 8.93-8.87 (m, 1H), 8.70 (s, 1H), 7.85-7.79 (m, 2H), 7.70 (d, J = 8.1 Hz, 1H), 4.93-4.84 (m, 1H), 4.70-4.62 (m, 1H), 4.61-4.54 (m, 1H), 3.96-3.88 (m, 2H), 3.60-3.53 (m, 2H), 3.37 (s, 3H), 3.22-3.16 (m, 1H), 2.39 (s, 3H), 1.93-1.84 (m, 2H), 1.77-1.66 (m, 2H). | 422 |
| 44 | (500 MHz, DMSO-$d_6$) δ 9.05-8.95 (m, 1H), 8.02 (s, 1H), 7.87-7.79 (m, 2H), 7.74-7.67 (m, 1H), 5.23 (s, 1H), 4.94-4.84 (m, 1H), 4.77-4.66 (m, 1H), 4.60-4.51 (m, 1H), 3.90 (s, 2H), 3.37 (s, 3H), 2.73-2.69 (m, 1H), 2.40 (s, 3H), 1.87-1.66 (m, 4H), 1.61 (d, J = 10.0 Hz, 1H), 1.52-1.43 (m, 1H). | 433 |
| 45 | (500 MHz, DMSO-$d_6$) δ 9.06 (d, J = 7.7 Hz, 1H), 8.97 (s, 1H), 8.40-8.35 (m, 1H), 7.76-7.70 (m, 1H), 7.67-7.53 (m, 2H), 7.46-7.39 (m, 2H), 7.38-7.31 (m, 1H), 4.96-4.87 (m, 1H), 4.74-4.66 (m, 1H), 4.62-4.55 (m, 1H), 3.37 (s, 3H), 2.25 (s, 3H). | 408 |

TABLE 9

| Analytical data for RIPK1 inhibitors. II. | | |
|---|---|---|
| Ex. No | MS ($ES^+$) | $^1H$ NMR |
| 46 | $C_{21}H_{15}ClF2N_4O_3$ requires: 444, found: 445 $[M + H]^+$. | 600 MHz, DMSO-$d_6$: δ 9.24 (s, 1H), 9.03 (d, J = 8.0 Hz, 1H), 7.73 (q, J = 7.8 Hz, 1H), 7.57-7.50 (m, 2H), 7.40-7.28 (m, 3H), 7.26 (d, J = 7.8 Hz, 1H), 4.88 (dt, J = 11.6, 8.0 Hz, 1H), 4.58 (t, J = 10.7 Hz, 1H), 4.48 (dd, J = 9.9, 7.8 Hz, 1H), 3.33 (s, 3H). |
| 47 | $C_{20}H_{15}ClFN_5O_3$ requires: 427, found: 428 $[M + H]^+$. | 500 MHz, DMSO-$d_6$: δ 9.25 (s, 1H), 9.15 (d, J = 7.8 Hz, 1H), 8.41-8.36 (m, 1H), 7.76-7.61 (m, 3H), 7.49-7.42 (m, 2H), 7.38-7.32 (m, 1H), 4.98-4.89 (m, 1H), 4.76-4.68 (m, 1H), 4.63-4.56 (m, 1H), 3.38 (s, 3H). |
| 48 | $C_{20}H_{15}ClFN_5O_3$ requires: 427 and 429, found: 428 and 430 $[M + H]^+$. | 400 MHz, DMSO-$d_6$: δ = 9.21 (s, 1H), 9.17 (d, J = 7.9 Hz, 1H), 8.38 (dd, J = 1.6, 4.7 Hz, 1H), 7.80-7.71 (m, 3H), 7.70-7.61 (m, 1H), 7.53-7.43 (m, 1H), 7.35 (dd, J = 4.7, 8.0 Hz, 1H), 5.00-4.88 (m, 1H), 4.74 (dd, J = 9.9, 11.4 Hz, 1H), 4.60 (dd, J = 7.5, 9.8 Hz, 1H), 3.43 (s, 3H). |
| 49 | $C_{20}H_{15}ClFN_5O_3$ requires: 427 and 429, found: 428 and 430 $[M + H]^+$. | 400 MHz, DMSO-$d_6$: δ = 9.17 (s, 1H), 9.14 (br d, J = 7.9 Hz, 1H), 8.42-8.35 (m, 1H), 8.04-7.96 (m, 2H), 7.76-7.70 (m, 1H), 7.48-7.42 (m, 2H), 7.35 (br d, J = 4.8 Hz, 1H), 4.96-4.89 (m, 1H), 4.80-4.65 (m, 1H), 4.65-4.55 (m, 1H), 2.67 (s, 3H). |
| 50 | $C_{20}H_{14}ClF_2N_5O_3$ requires: 445 and 447, found: 446 and 448 $[M + H]^+$. | 400 MHz, DMSO-$d_6$: δ = 9.25 (s, 1H), 9.16 (d, J = 7.8 Hz, 1H), 8.38 (dd, J = 1.5, 4.8 Hz, 1H), 7.78-7.70 (m, 2H), 7.58-7.51 (m, 1H), 7.40-7.33 (m, 2H), 4.97-4.89 (m, 1H), 4.75-4.68 (m, 1H), 4.59 (dd, J = 7.5, 9.7 Hz, 1H), 3.38 (s, 3H) |

TABLE 9-continued

Analytical data for RIPK1 inhibitors. II.

| Ex. No | MS ($ES^+$) | $^1H$ NMR |
|---|---|---|
| 51 | $C_{20}H_{14}ClF2N_5O_3$ requires: 445 and 447, found: 446 and 448 $[M + H]^+$. | 400 MHz, DMSO-$d_6$: δ = 9.28 (s, 1H), 9.18 (d, J = 7.8 Hz, 1H), 8.38 (dd, J = 1.5, 4.6 Hz, 1H), 7.73 (dd, J = 1.4, 8.0 Hz, 1H), 7.63-7.48 (m, 3H), 7.35 (dd, J = 4.7, 8.0 Hz, 1H), 4.99-4.88 (m, 1H), 4.77-4.68 (m, 1H), 4.59 (dd, J = 7.5, 9.8 Hz, 1H) 3.38 (s, 3H). |
| 52 | $C_{20}H_{15}Cl_2N_5O_3$ requires: 443 and 445, found: 444 and 446 $[M + H]^+$. | 400 MHz, $CDCl_3$: δ = 9.05-8.90 (m, 2H), 8.37 (d, J = 4.8 Hz, 1H), 7.95 (d, J = 8.5 Hz, 2H), 7.62 (br d, J = 7.9 Hz, 1H), 7.56 (d, J = 8.4 Hz, 2H), 7.27-7.23 (m, 1H), 5.19-5.06 (m, 1H), 4.98-4.88 (m, 1H), 4.41-4.33 (m, 1H), 3.58 (s, 3H). |
| 53 | $C_{21}H_{17}ClFN_5O_3$ requires: 441 and 443, found: 442 and 444 $[M + H]^+$. | 400 MHz, DMSO-$d_6$: δ = 9.21 (s, 1H), 9.13 (d, J = 7.8 Hz, 1H), 8.37 (dd, J = 1.6, 4.7 Hz, 1H), 7.72 (dd, J = 1.6, 8.0 Hz, 1H), 7.51 (t, J = 7.9 Hz, 1H), 7.34 (dd, J = 4.7, 8.0 Hz, 1H), 7.29-7.23 (m, 2H), 4.97-4.86 (m, 1H), 4.73-4.66 (m, 1H), 4.61-4.56 (m, 1H), 3.40 (br s, 3H), 2.43 (s, 3H). |
| 54 | $C_{21}H_{17}ClFN_5O_3$. requires: 441, found: 442 $[M + H]^+$. | 500 MHz, DMSO-$d_6$: δ 9.11 (s, 1H), 9.08 (d, J = 7.8 Hz, 1H), 8.31 (dd, J = 4.7, 1.6 Hz, 1H), 7.68-7.60 (m, 3H), 7.45 (t, J = 7.9 Hz, 1H), 7.28 (dd, J = 7.9, 4.7 Hz, 1H), 4.87 (dt, J = 11.5, 7.6 Hz, 1H), 4.66 (dd, J = 11.5, 9.8 Hz, 1H), 4.53 (dd, J = 9.8, 7.5 Hz, 1H), 3.31 (s, 3H), 2.28 (s, 3H). |
| 55 | $C_{21}H_{16}ClF_2N_5O_3$ requires: 459, found: 460 $[M + H]^+$. | 500 MHz, DMSO-$d_6$: δ 9.26 (s, 1H), 8.75 (d, J = 6.7 Hz, 1H), 8.37 (dd, J = 4.7, 1.6 Hz, 1H), 7.80-7.68 (m, 2H), 7.59-7.51 (m, 1H), 7.41-7.33 (m, 2H), 5.02 (p, J = 6.2 Hz, 1H), 4.96 (t, J = 6.5 Hz, 1H), 3.41 (s, 3H), 1.34 (d, J = 6.2 Hz, 3H). |
| 56 | $C_{19}H_{14}ClFN_6O_3$ requires: 428, found: 429 $[M + H]^+$. | 600 MHz, DMSO-$d_6$: δ 9.27 (s, 1H), 9.21 (d, J = 7.9 Hz, 1H), 8.99 (s, 1H), 8.84 (s, 1H), 8.41-8.37 (m, 1H), 8.33-8.28 (m, 1H), 7.76-7.71 (m, 1H), 7.38-7.33 (m, 1H), 4.99-4.94 (m, 1H), 4.79-4.72 (m, 1H), 4.63-4.57 (m, 1H), 3.39 (s, 3H). |
| 57 | $C_{23}H_{27}N_5O_3$ requires: 421 and 423, found: 422 and 424 $[M + H]^+$. | 400 MHz, $CDCl_3$: δ = 9.04 (br d, J = 6.8 Hz, 1H), 8.53 (s, 1H), 8.34 (dd, J = 1.6, 4.7 Hz, 1H), 7.57 (dd, J = 1.6, 8.0 Hz, 1H), 7.22 (dd, J = 4.8, 7.9 Hz, 1H), 5.15-5.07 (m, 1H), 4.91 (dd, J = 7.2, 9.7 Hz, 1H), 4.40-4.32 (m, 1H), 3.58 (s, 3H), 2.55 (s, 3H), 2.08-2.03 (m, 6H), 1.77-1.72 (m, 7H). |
| 58 | $C_{20}H_{23}N_5O_4$ requires: 397, found: 398 $[M + H]^+$. | 400 MHz, DMSO-$d_6$: δ = 9.00 (d, J = 7.7 Hz, 1H), 8.71 (s, 1H), 8.38 (dd, J = 1.6, 4.7 Hz, 1H), 7.75 (dd, J = 1.6, 8.0 Hz, 1H), 7.36 (dd, J = 4.7, 8.0 Hz, 1H), 4.94-4.86 (m, 1H), 4.76-4.56 (m, 2H), 4.05-3.85 (m, 2H), 3.53-3.48 (m, 2H), 3.4 (s, 3H), 3.30-3.19 (m, 1H), 2.40 (s, 3H), 2.02-1.86 (m, 2H), 1.70-1.57 (m, 2H). |
| 59 | $C_{21}H_{17}F_2N_5O_3$ requires: 425, found: 426 $[M + H]^+$. | 400 MHz, DMSO-$d_6$: δ = 9.07 (d, J = 7.8 Hz, 1H), 9.01 (s, 1H), 8.37 (dd, J = 1.5, 4.6 Hz, 1H), 7.73 (dd, J = 1.5, 7.9 Hz, 1H), 7.70-7.62 (m, 1H), 7.46-7.37 (m, 2H), 7.36-7.32 (m, 1H), 4.97-4.86 (m, 1H), 4.76-4.66 (m, 1H), 4.62-4.54 (m, 1H), 3.37 (s, 3H), 2.27 (s, 3H). |
| 60 | $C_{21}H_{17}F_2N_5O_3$• requires: 425, found: 426 $[M + H]^+$. | 500 MHz, DMSO-$d_6$: δ 9.07 (d, J = 7.8 Hz, 1H), 8.98 (s, 1H), 8.38 (dd, J = 4.7, 1.5 Hz, 1H), 7.73 (dd, J = 8.0, 1.5 Hz, 1H), 7.70-7.62 (m, 1H), 7.54-7.46 (m, 1H), 7.38-7.28 (m, 2H), 4.92 (dt, J = 11.5, 7.6 Hz, 1H), 4.70 (dd, J = 11.5, 9.8 Hz, 1H), 4.59 (dd, J = 9.8, 7.4 Hz, 1H), 3.38 (s, 3H), 2.26 (s, 3H). |
| 61 | $C_{22}H_{20}FN_5O_3$• requires: 421, found: 422 $[M + H]^+$. | 500 MHz, DMSO-$d_6$: δ 9.05 (d, J = 7.7 Hz, 1H), 8.95 (s, 1H), 8.38 (dd, J = 4.7, 1.6 Hz, 1H), 7.73 (dd, J = 7.9, 1.6 Hz, 1H), 7.45 (t, J = 7.8 Hz, 1H), 7.35 (dd, J = 7.9, 4.7 Hz, 1H), 7.28-7.21 (m, 2H), 4.96-4.87 (m, 1H), 4.73-4.66 (m, 1H), 4.63-4.56 (m, 1H), 3.38 (s, 3H), 2.43 (s, 3H), 2.25 (s, 3H). |
| 62 | $C_{22}H_{20}FN_5O_3$• requires: 421, found: 422 $[M + H]^+$. | 500 MHz, DMSO-$d_6$: δ 9.06 (d, J = 7.8 Hz, 1H), 8.90 (s, 1H), 8.38 (d, J = 4.8 Hz, 1H), 7.73 (d, J = 7.6 Hz, 1H), 7.69 (d, J = 7.6 Hz, 1H), 7.66-7.59 (m, 1H), 7.38-7.30 (m, 2H), 4.93 (dt, J = 11.5, 7.6 Hz, 1H), 4.75-4.67 (m, 1H), 4.60 (dd, J = 9.9, 7.4 Hz, 1H), 3.38 (s, 3H), 2.43 (s, 3H), 2.34 (s, 3H). |
| 63 | $C_{21}H_{17}F_2N_5O_3$ requires: 425, found: 426 $[M + H]^+$. | 600 MHz, $CDCl_3$: δ 9.02 (d, J = 6.7 Hz, 1H), 8.95 (d, J = 5.1 Hz, 1H), 8.21 (s, 1H), 7.56 (d, J = 5.1 Hz, 1H), 7.54-7.49 (m, 1H), 7.34 (d, J = 8.0 Hz, 1H), 7.09-7.02 (m, 2H), 5.15-5.08 (m, 1H), 4.92 (dd, J = 9.8, 7.0 Hz, 1H), 4.36 (t, J = 10.6 Hz, 1H), 3.52 (s, 3H), 2.54 (s, 3H). |
| 64 | $C_{21}H_{16}F_3N_5O_3$ requires: 443, found: 444 $[M + H]^+$. | 600 MHz, DMSO-$d_6$: δ 9.14-9.09 (m, 2H), 8.43 (s, 1H), 7.87 (d, J = 5.0 Hz, 1H), 7.83 (d, J = 8.7 Hz, 1H), 7.31 (t, J = 9.7 Hz, 1H), 7.21 (d, J = 9.5 Hz, 1H), 5.02-4.94 (m, 1H), 4.74 (t, J = 10.6 Hz, 1H), 4.66-4.60 (m, 1H), 3.36 (s, 3H), 2.25 (s, 3H). |
| 65 | $C_{21}H_{18}FN_5O_3$ requires: 407, found: 408 $[M + H]^+$. | 600 MHz, $CDCl_3$: δ 9.04 (d, J = 6.7 Hz, 1H), 8.96 (d, J = 5.1 Hz, 1H), 8.21 (s, 1H), 7.59 (d, J = 5.1 Hz, 1H), 7.51 (d, J = 7.6 Hz, 1H), 7.42 (t, J = 7.6 Hz, 1H), 7.38-7.31 (m, 3H), 5.16-5.09 (m, 1H), 4.94-4.89 (m, 1H), 4.36 (t, J = 10.6 Hz, 1H), 3.51 (s, 3H), 2.54 (s, 3H). |
| 66 | $C_{20}H_{14}F_3N_5O_3$ requires: 429, found: 430 $[M + H]^+$. | 600 MHz, $CDCl_3$: δ 8.93 (d, J = 6.6 Hz, 1H), 8.76 (d, J = 3.1 Hz, 1H), 8.30-8.24 (m, 2H), 8.22 (s, 1H), 7.35 (d, J = 7.9 Hz, 1H), 7.28 (s, 1H), 5.13-5.06 (m, 1H), 4.93 (dd, J = 9.8, 7.0 Hz, 1H), 4.39 (t, J = 10.6 Hz, 1H), 3.54 (s, 3H). |

TABLE 9-continued

Analytical data for RIPK1 inhibitors. II.

| Ex. No | MS (ES+) | 1H NMR |
| --- | --- | --- |
| 67 | $C_{21}H_{16}F_3N_5O_3$ requires: 443, found: 444 $[M + H]^+$. | 600 MHz, $CDCl_3$: δ 8.85 (d, J = 6.8 Hz, 1H), 8.79 (s, 1H), 8.21 (s, 1H), 7.47 (t, J = 7.2 Hz, 1H), 7.34 (d, J = 7.9 Hz, 1H), 7.10-7.02 (m, 2H), 5.12-5.05 (m, 1H), 4.93-4.87 (m, 1H), 4.36 (t, J = 10.5 Hz, 1H), 3.51 (s, 3H), 2.38 (s, 3H). |
| 68 | $C_{19}H_{19}N_5Cl_2O_4$ requires: 451 and 453, found: 452 and 454 $[M + H]^+$. | 400 MHz, $CDCl_3$: δ = 8.88-8.79 (m, 1H), 8.74 (d, J = 8.8 Hz, 1H), 8.21 (d, J = 2.3 Hz, 1H), 7.49 (d, J = 2.3 Hz, 1H), 5.11-4.94 (m, 1H), 4.88-4.66 (m, 2H), 4.37-4.26 (m, 1H), 4.18-4.04 (m, 1H), 3.65-3.55 (m, 1H), 3.45 (s, 3H), 2.14-1.89 (m, 2H), 1.86-1.57 (m, 4H). |
| 69 | $C_{20}H_{15}ClN_5O_3F$ requires: 427 and 429, found: 428 and 430 $[M + H]^+$. | 400 MHz, DMSO-$d_6$: δ = 9.18 (s, 1H), 9.14 (d, J = 7.7 Hz, 1H), 8.44 (d, J = 2.6 Hz, 1H), 7.92-7.88 (m, 2H), 7.84 (dd, J = 2.6, 8.7 Hz, 1H), 7.63-7.59 (m, 3H), 5.03-4.92 (m, 1H), 4.80-4.70 (m, 1H), 4.64 (dd, J = 7.3, 9.7 Hz, 1H), 3.36 (s, 3H). |
| 70 | $C_{20}H_{14}N_5O_3F_2Cl$ requires: 445 and 447, found: 446 and 448 $[M + H]^+$. | 400 MHz, DMSO-$d_6$: δ = 9.21 (s, 1H), 9.17 (d, J = 7.7 Hz, 1H), 8.44 (d, J = 2.6 Hz, 1H), 7.84 (dd, J = 2.6, 8.7 Hz, 1H), 7.78-7.73 (m, 2H), 7.70-7.61 (m, 1H), 7.52-7.45 (m, 1H), 5.04-4.94 (m, 1H), 4.83-4.73 (m, 1H), 4.63 (dd, J = 7.3, 9.7 Hz, 1H), 3.36 (s, 3H). |
| 71 | $C_{20}H_{14}N_5O_3F_2Cl$ requires: 445 and 447, found: 446 and 448 $[M + H]^+$. | 400 MHz, DMSO-$d_6$: δ = 9.18 (s, 1H), 9.15 (d, J = 7.7 Hz, 1H), 8.44 (d, J = 2.8 Hz, 1H), 8.04-7.96 (m, 2H), 7.84 (dd, J = 2.7, 8.7 Hz, 1H), 7.50-7.42 (m, 2H), 5.03-4.94 (m, 1H), 4.80-4.71 (m, 1H), 4.63 (dd, J = 7.4 Hz, 9.8 Hz, 1H), 3.36 (s, 3H). |
| 72 | $C_{20}H_{13}ClF_3N_5O_3$ requires: 463, found: 464 $[M + H]^+$. | 600 MHz, DMSO-$d_6$: δ 9.29 (s, 1H), 9.15 (d, J = 7.7 Hz, 1H), 8.43 (s, 1H), 7.83 (d, J = 8.7 Hz, 1H), 7.72 (d, J = 8.1 Hz, 1H), 7.50-7.43 (m, 2H), 5.01-4.94 (m, 1H), 4.74 (t, J = 10.6 Hz, 1H), 4.65-4.59 (m, 1H), 3.35 (s, 3H). |
| 73 | $C_{20}H_{13}N_5O_3F_3Cl$ requires: 463 and 465, found: 464 and 466 $[M + H]^+$. | 400 MHz, DMSO-$d_6$: δ= 9.25 (s, 1H), 9.14 (d, J = 7.7 Hz, 1H), 8.43 (d, J = 2.6 Hz, 1H), 7.83 (dd, J = 2.8, 8.7 Hz, 1H), 7.76-7.71 (m, 1H), 7.58-7.50 (m, 1H), 7.39-7.34 (m, 1H), 5.02-4.93 (m, 1H), 4.79-4.72 (m, 1H), 4.61 (dd, J = 7.3 Hz, 9.8 Hz, 1H), 3.35 (s, 3H). |
| 74 | $C_{20}H_{13}N_5O_3F_3Cl$ requires: 463 and 465, found: 464 and 466 $[M + H]^+$. | 400 MHz, DMSO-$d_6$: δ = 9.29 (s, 1H), 9.17 (d, J = 7.8 Hz, 1H), 8.44 (d, J = 2.8 Hz, 1H), 7.83 (dd, J = 2.6, 8.7 Hz, 1H), 7.64-7.46 (m, 3H), 5.05-4.92 (m, 1H), 4.82-4.72 (m, 1H), 4.62 (dd, J = 7.3, 9.8 Hz, 1H), 3.36 (s, 3H). |
| 75 | $C_{20}H_{13}ClF_3N_5O_3$ requires: 463, found: 464 $[M + H]^+$. | 600 MHz, DMSO-$d_6$: δDMSO-d6: 8 9.21 (s, 1H), 9.16 (d, J = 7.8 Hz, 1H), 8.43(s, 1H), 8.07-8.00 (m, 1H), 7.86-7.79 (m, 2H), 7.74-7.66 (m, 1H), 5.02-4.95 (m, 1H), 4.77 (t, J = 10.7 Hz, 1H), 4.63 (dd, J = 9.8, 7.4 Hz, 1H), 3.36 (s, 3H). |
| 76 | $C_{20}H_{13}ClF_3N_5O_3$ requires: 463, found: 464 $[M + H]^+$. | 600 MHz, $CDCl_3$: δ 8.95 (s, 1H), 8.87 (d, J = 6.4 Hz, 1H), 8.22 (s, 1H), 7.52-7.45 (m, 2H), 7.35 (d, J = 7.9 Hz, 1H), 7.05-6.99 (m, 1H), 5.12-5.05 (m, 1H), 4.93-4.88 (m, 1H), 4.41-4.35 (m, 1H), 3.52 (s, 3H). |
| 77 | $C_{21}H_{16}N_5O_3F_2Cl$ requires: 459 and 461, found: 460 and 463 $[M + H]^+$. | 400 MHz, DMSO-$d_6$: δ = 9.23 (s, 1H), 9.13 (d, J = 7.5 Hz, 1H), 8.43 (d, J = 2.6 Hz, 1H), 7.83 (dd, J = 2.7, 8.7 Hz, 1H), 7.52 (t, J = 7.9 Hz, 1H), 7.34-7.22 (m, 2H), 5.01-4.92 (m, 1H), 4.77-4.69 (m, 1H), 4.62 (dd, J = 7.3, 9.7 Hz, 1H), 3.36 (br s, 3H), 2.44 (s, 3H). |
| 78 | $C_{21}H_{16}N_5O_3F_2Cl$ requires: 459 and 461, found: 460 and 462 $[M + H]^+$. | 400 MHz, DMSO-$d_6$: δ = 9.18 (s, 1H), 9.14 (d, J = 7.7 Hz, 1H), 8.44 (d, J = 2.8 Hz, 1H), 7.84 (dd, J = 2.7, 8.7 Hz, 1H), 7.76-7.67 (m, 2H), 7.53 (t, J = 7.9 Hz, 1H), 5.03-4.95 (m, 1H), 4.80-4.73 (m, 1H), 4.63 (dd, J = 7.3, 9.7 Hz, 1H), 3.37 (br s, 3H), 2.36 (d, J = 1.2 Hz, 3H). |
| 79 | $C_{21}H_{16}ClF_2N_5O_3$ requires: 459, found: 460 $[M + H]^+$. | 600 MHz, DMSO-$d_6$: δ 9.17 (s, 1H), 9.12 (d, J = 7.7 Hz, 1H), 8.43 (s, 1H), 7.86-7.77 (m, 3H), 7.40-7.35 (m, 1H), 5.01-4.94 (m, 1H), 4.76 (t, J = 10.6 Hz, 1H), 4.66-4.60 (m, 1H), 3.36 (s, 3H), 2.35 (s, 3H). |
| 80 | $C_{20}H_{14}Cl_2FN_5O_3$ requires: 462, found: 463 $[M + H]^+$. | 600 MHz, DMSO-$d_6$: δ 9.28 (s, 1H), 9.14 (d, J = 7.7 Hz, 1H), 8.43 (s, 1H), 7.85-7.80 (m, 1H), 7.68 (d, J = 8.0 Hz, 1H), 7.64-7.59 (m, 1H), 7.58-7.53 (m, 2H), 5.01-4.93 (m, 1H), 4.76 (dd, J = 11.6, 9.7 Hz, 1H), 4.61 (dd, J = 9.8, 7.3 Hz, 1H), 3.35 (s, 3H). |
| 81 | $C_{20}H_{14}Cl_2FN_5O_3$ requires: 462, found: 463 $[M + H]^+$. | 600 MHz, DMSO-$d_6$: δ 9.21 (s, 1H), 9.16 (d, J = 7.7 Hz, 1H), 8.43 (s, 1H), 7.93 (s, 1H), 7.87-7.81 (m, 2H), 7.72-7.67 (m, 1H), 7.64 (t, J = 7.9 Hz, 1H), 5.02-4.95 (m, 1H), 4.77 (t, J = 10.6 Hz, 1H), 4.65-4.60 (m, 1H), 3.36 (s, 3H). |
| 82 | $C_{20}H_{14}N_5O_3FCl_2$ requires: 461 and 463, found: 462 and 464 $[M + H]^+$. | 400 MHz, DMSO-$d_6$: δ = 9.19 (s, 1H), 9.14 (d, J = 7.7 Hz, 1H), 8.44 (d, J = 2.7 Hz, 1H), 7.97-7.92 (m, 2H), 7.84 (dd, J = 2.7, 8.7 Hz, 1H), 7.72-7.67 (m, 2H), 5.05-4.92 (m, 1H), 4.79-4.72 (m, 1H), 4.63 (dd, J = 7.3, 9.8 Hz, 1H), 3.36 (br s, 3H). |
| 83 | $C_{21}H_{17}ClFN_5O_3$ requires: 441, found: 442 $[M + H]^+$. | 600 MHz, DMSO-$d_6$: δ 9.16 (d, J = 1.3 Hz, 1H), 9.12 (d, J = 7.6 Hz, 1H), 8.43 (s, 1H), 7.86-7.81 (m, 1H), 7.67 (s, 2H), 7.48 (t, J = 7.9 Hz, 1H), 7.43 (d, J = 7.7 Hz, 1H), 5.01-4.94 (m, 1H), 4.79-4.72 (m, 1H), 4.66-4.60 (m, 1H), 3.36 (s, 3H), 2.42 (s, 3H). |
| 84 | $C_{21}H_{14}ClFN_6O_3$ requires: 452, found: 453 $[M + H]^+$. | 600 MHz, $CDCl_3$: δ 8.97 (s, 1H), 8.88 (d, J = 6.7 Hz, 1H), 8.25-8.20 (m, 2H), 8.17 (d, J = 8.0 Hz, 1H), 7.85 (d, J = 7.8 Hz, 1H), 7.70 (t, J = 7.8 Hz, 1H), 7.37-7.33 (m, 1H), 5.12-5.05 (m, 1H), 4.94-4.88 (m, 1H), 4.38 (t, J = 10.6 Hz, 1H), 3.52 (s, 3H). |

TABLE 9-continued

Analytical data for RIPK1 inhibitors. II.

| Ex. No | MS ($ES^+$) | $^1H$ NMR |
|---|---|---|
| 85 | $C_{19}H_{13}ClF_2N_6O_3$ requires: 446, found: 447 $[M + H]^+$. | 600 MHz, DMSO-$d_6$: δ 9.34 (d, J = 1.9 Hz, 1H), 9.15 (d, J = 7.6 Hz, 1H), 8.66 (d, J = 4.5 Hz, 1H), 8.44-8.39 (m, 1H), 8.08-8.02 (m, 1H), 7.82 (dd, J = 8.6, 2.9 Hz, 1H), 7.80-7.74 (m, 1H), 5.01-4.93 (m, 1H), 4.77-4.69 (m, 1H), 4.62 (t, J = 8.3 Hz, 1H), 3.35 (s, 3H). |
| 86 | $C_{23}H_{26}N_5O_3F$ requires: 439 and 441, found: 440 and 442 $[M + H]^+$. | 400 MHz, DMSO-$d_6$: δ = 8.89 (d, J = 7.3 Hz, 1H), 8.63 (s, 1H), 8.43 (d, J = 2.8 Hz, 1H), 7.85 (dd, J = 2.6, 8.7 Hz, 1H), 5.00-4.89 (m, 1H), 4.70-4.63 (m, 2H), 3.38 (s, 3H), 2.53 (s, 3H), 2.02-1.94 (m, 6H), 1.72-1.63 (m, 7H). |
| 87 | $C_{20}H_{22}FN_5O_4$ requires: 415 and 417, found: 416 and 418 $[M + H]^+$. | 400 MHz, DMSO-$d_6$: δ = 8.99 (d, J = 7.3 Hz, 1H), 8.71 (s, 1H), 8.43 (d, J = 2.7 Hz, 1H), 7.89-7.82 (m, 1H), 5.00-4.89 (m, 1H), 4.76-4.68 (m, 1H), 4.68-4.61 (m, 1H), 3.99 (br dd, J = 3.3, 11.4 Hz, 2H), 3.56-3.45 (m, 2H), 3.38 (s, 3H), 3.26-3.18 (m, 1H), 2.40 (s, 3H), 2.03-1.82 (m, 2H), 1.70-1.56 (m, 2H). |
| 88 | $C_{21}H_{17}F_2N_5O_3$ requires: 425, found: 426 $[M + H]^+$. | 600 MHz, $CDCl_3$: δ 8.94 (d, J = 6.8 Hz, 1H), 8.79 (s, 1H), 8.20 (s, 1H), 7.55-7.48 (m, 2H), 7.33 (t, J = 7.4 Hz, 2H), 7.20 (t, J = 9.2 Hz, 1H), 5.16-5.09 (m, 1H), 4.92-4.86 (m, 1H), 4.37 (t, J = 10.6 Hz, 1H), 3.50 (s, 3H), 2.33 (s, 3H). |
| 89 | $C_{21}H_{17}N_5O_3FCl$ requires: 441 and 443, found: 442 and 444 $[M + H]^+$. | 400 MHz, DMSO-$d_6$: δ = 9.13 (d, J = 7.6 Hz, 1H), 9.05 (d, J = 5.3 Hz, 1H), 8.45 (d, J = 2.3 Hz, 1H), 7.97 (d, J = 2.3 Hz, 1H), 7.91 (d, J = 5.3 Hz, 1H), 7.67 (dd, J = 6.1, 8.5 Hz, 1H), 7.33-7.20 (m, 2H), 5.07-4.96 (m, 1H), 4.79-4.70 (m, 1H), 4.69-4.61 (m, 1H), 3.34 (s, 3H), 2.46 (s, 3H). |
| 90 | $C_{21}H_{16}O_3N_5ClF_2$ requires: 459 and 461, found: 460 and 462 $[M + H]^+$. | 400 MHz, DMSO-$d_6$: δ = 9.16-9.09 (m, 2H), 8.44 (d, J = 2.3 Hz, 1H), 7.95 (d, J = 2.3 Hz, 1H), 7.87 (dd, J = 1.6, 5.0 Hz, 1H), 7.36-7.26 (m, 1H), 7.21 (d, J = 9.5 Hz, 1H), 5.08-4.94 (m, 1H), 4.80-4.70 (m, 1H), 4.68-4.59 (m, 1H), 3.36 (s, 3H), 2.25 (s, 3H). |
| 91 | $C_{20}H_{14}N_5O_3F_2Cl$ requires: 445 and 447, found: 446 and 448 $[M + H]^+$. | 400 MHz, $CDCl_3$: δ = 8.99-8.93 (m, 1H), 8.79 (d, J = 3.2 Hz, 1H), 8.33-8.26 (m, 3H), 7.60 (d, J = 2.2 Hz, 1H), 7.33-7.28 (m, 2H), 5.20-5.05 (m, 1H), 4.94 (dd, J = 6.9, 9.7 Hz, 1H), 4.41 (dd, J = 9.8, 11.2 Hz, 1H), 3.56 (s, 3H). |
| 92 | $C_{21}H_{16}N_5O_3F_2Cl$ requires: 459 and 461, found: 460 and 462. $[M + H]^+$. | 400 MHz, $CDCl_3$: δ = 8.87 (br d, J = 6.8 Hz, 1H), 8.80 (d, J = 1.1 Hz, 1H), 8.29 (d, J = 2.2 Hz, 1H), 7.58 (d, J = 2.3 Hz, 1H), 7.50-7.45 (m, 1H), 7.11-7.03 (m, 2H), 5.11-5.08 (m, 1H), 4.90 (dd, J = 6.9, 9.7 Hz, 1H), 4.37 (dd, J = 9.8, 11.2 Hz, 1H), 3.52 (s, 3H), 2.38 (s, 3H). |
| 93 | $C_{20}H_{15}Cl_2N_5O_3$ requires: 443 and 445, found: 444 and 446 $[M + H]^+$. | 400 MHz, DMSO-$d_6$: δ = 9.18 (s, 1H), 9.15 (d, J = 7.8 Hz, 1H), 8.45 (d, J = 2.3 Hz, 1H), 7.96 (d, J = 2.3 Hz, 1H), 7.93-7.87 (m, 2H), 7.64-7.59 (m, 3H), 5.08-4.95 (m, 1H), 4.82-4.71 (m, 1H), 4.64 (dd, J = 7.4, 9.8 Hz, 1H), 3.37 (s, 3H). |
| 94 | $C_{20}H_{14}O_3N_5Cl_2F$ requires: 461 and 463, found: 462 and 464 $[M + H]^+$. | 400 MHz, DMSO-$d_6$: δ = 9.25 (s, 1H), 9.16 (d, J = 7.6 Hz, 1H), 8.44 (d, J = 2.2 Hz, 1H), 7.95 (d, J = 2.3 Hz, 1H), 7.73-7.60 (m, 2H), 7.49-7.41 (m, 2H), 5.05-4.93 (m, 1H), 4.80-4.69 (m, 1H), 4.62 (dd, J = 7.5, 9.8 Hz, 1H), 3.35 (s, 3H). |
| 95 | $C_{20}H_{13}N_5O_3Cl_2F_2$ requires: 479 and 481, found: 480 and 482 $[M + H]^+$. | 400 MHz, $CDCl_3$: δ = 8.99 (s, 1H), 8.87 (br d, J = 6.5 Hz, 1H), 8.31 (d, J = 2.3 Hz, 1H), 7.59 (d, J = 2.3 Hz, 1H), 7.46-7.30 (m, 3H), 5.18-5.07 (m, 1H), 4.91 (dd, J = 7.0, 9.8 Hz, 1H), 4.39 (dd, J = 9.8, 11.2 Hz, 1H), 3.53 (s, 3H). |
| 96 | $C_{20}H_{13}O_3N_5Cl_2F_2$ requires: 479 and 481, found: 480 and 482 $[M + H]^+$. | 400 MHz, DMSO-$d_6$: δ = 9.26 (s, 1H), 9.16 (d, J = 7.6 Hz, 1H), 8.45 (d, J = 2.3 Hz, 1H), 7.95 (d, J = 2.3 Hz, 1H), 7.80-7.69 (m, 1H), 7.60-7.48 (m, 1H), 7.44-7.32 (m, 1H), 5.06-4.94 (m, 1H), 4.80-4.70 (m, 1H), 4.63 (dd, J = 7.4, 9.8 Hz, 1H), 3.36 (s, 3H). |
| 97 | $C_{20}H_{13}Cl_2F_2N_5O_3$ requires:479 and 481, found: 480 and 482 $[M + H]^+$. | 400 MHz, DMSO-$d_6$: δ = 9.23-9.16 (m, 2H), 8.47-8.44 (m, 1H), 8.08-8.01 (m, 1H), 7.98-7.94 (m, 1H), 7.85-7.79 (m, 1H), 7.75-7.66 (m, 1H), 5.06-4.97 (m, 1H), 4.78 (dd, J = 9.9, 11.3 Hz, 1H), 4.64 (dd, J = 7.4, 9.7 Hz, 1H), 3.37 (s, 3H). |
| 98 | $C_{20}H_{13}Cl_2F_2N_5O_3$ requires: 479 and 481, found: 480 and 482 $[M + H]^+$. | 400 MHz, DMSO-$d_6$: δ = 9.28 (s, 1H), 9.17 (d, J = 7.8 Hz, 1H), 8.44 (d, J = 2.3 Hz, 1H), 7.95 (d, J = 2.3 Hz, 1H), 7.61-7.50 (m, 3H), 5.08-4.92 (m, 1H), 4.81-4.71 (m, 1H), 4.62 (dd, J = 7.4, 9.7 Hz, 1H), 3.35 (s, 3H). |
| 99 | $C_{20}H_{13}N_5O_3Cl_2F_2$ requires: 479 and 481, found: 480 and 482 $[M + H]^+$. | 400 MHz, $CDCl_3$: δ = 8.99-8.94 (m, 1H), 8.92-8.84 (m, 1H), 8.32-8.27 (m, 1H), 7.60 (s, 1H), 7.54-7.44 (m, 2H), 7.08-7.00 (m, 1H), 5.14-5.06 (m, 1H), 4.95-4.86 (m, 1H), 4.43-4.35 (m, 1H), 3.57-3.49 (m, 3H). |
| 100 | $C_{21}H_{16}N_5O_3Cl_2F$ requires: 475 and 477, found: 476 and 478 $[M + H]^+$. | 400 MHz, $CDCl_3$: δ = 8.93-8.86 (m, 2H), 8.31-8.26 (m, 1H), 7.85-7.76 (m, 2H), 7.59-7.55 (m, 1H), 7.21-7.14 (m, 1H), 5.15-5.06 (m, 1H), 4.95-4.85 (m, 1H), 4.43-4.33 (m, 1H), 3.52 (s, 3H), 2.39 (d, J = 1.8 Hz, 3H). |
| 101 | $C_{20}H_{14}N_5O_3Cl_3$ requires: 477 and 479, found: 478 and 480 $[M + H]^+$. | 400 MHz, $CDCl_3$: δ = 8.96 (s, 1H), 8.85 (br d, J = 6.6 Hz, 1H), 8.29 (d, J = 2.3 Hz, 1H), 7.60-7.37 (m, 5H), 5.15-5.05 (m, 1H), 4.89 (dd, J = 7.0, 9.8 Hz, 1H), 4.37 (dd, J = 9.9, 11.2 Hz, 1H), 3.51 (s, 3H). |

TABLE 9-continued

Analytical data for RIPK1 inhibitors. II.

| Ex. No | MS ($ES^+$) | $^1H$ NMR |
|---|---|---|
| 102 | $C_{20}H_{14}O_3N_5Cl_3$ requires: 477 and 479, found: 478 and 480 $[M + H]^+$. | 400 MHz, $CD_3OD$: δ = 9.06 (s, 1H), 8.34 (d, J = 2.3 Hz, 1H), 7.97 (t, J = 1.7 Hz, 1H), 7.92-7.85 (m, 1H), 7.78 (d, J = 2.3 Hz, 1H), 7.64-7.52 (m, 2H), 5.10 (dd, J = 7.0, 11.4 Hz, 1H), 4.77 (dd, J = 7.0, 9.8 Hz, 1H), 4.63-4.59 (m, 1H), 3.48 (s, 3H). |
| 103 | $C_{20}H_{14}O_3N_5Cl_3$ requires: 477 and 479, found: 478 and 480 $[M + H]^+$. | 400 MHz, DMSO-$d_6$: δ = 9.18 (s, 1H), 9.15 (d, J = 7.6 Hz, 1H), 8.44 (d, J = 2.3 Hz, 1H), 7.98-7.89 (m, 3H), 7.74-7.63 (m, 2H), 5.06-4.94 (m, 1H), 4.80-4.72 (m, 1H), 4.63 (dd, J = 7.4, 9.8 Hz, 1H), 3.36 (s, 3H). |
| 104 | $C_{21}H_{14}O_3N_6Cl_2$ requires:468 and 470, found: 469 and 471 $[M + H]^+$. | 400 MHz, DMSO-$d_6$: δ = 9.24 (s, 1H), 9.19 (d, J = 7.8 Hz, 1H), 8.45 (d, J = 2.4 Hz, 1H), 8.34 (t, J = 1.5 Hz, 1H), 8.25-8.19 (m, 1H), 8.13-8.07 (m, 1H), 7.95 (d, J = 2.3 Hz, 1H), 7.83 (t, J = 7.9 Hz, 1H), 5.08-4.95 (m, 1H), 4.78 (dd, J = 9.9, 11.3 Hz, 1H), 4.63 (dd, J = 7.4, 9.8 Hz, 1H), 3.36 (s, 3H). |
| 105 | $C_{21}H_{14}N_6Cl_2O_3$ requires: 468 and 470, found: 469 and 471 $[M + H]^+$. | 400 MHz, DMSO-$d_6$: δ = 9.24 (s, 1H), 9.17 (d, J = 7.7 Hz, 1H), 8.45 (d, J = 2.3 Hz, 1H), 8.12-8.08 (m, 2H), 8.08-8.04 (m, 2H), 7.96 (d, J = 2.3 Hz, 1H), 5.01 (td, J = 7.5, 11.4 Hz, 1H), 4.80-4.73 (m, 1H), 4.64 (dd, J = 7.3, 9.8 Hz, 1H), 3.37 (s, 3H). |
| 106 | $C_{21}H_{17}N_5O_3Cl_2$ requires: 457 and 459, found: 458 and 460 $[M + H]^+$. | 400 MHz, $CDCl_3$: δ = 8.83 (s, 2H), 8.21 (d, J = 2.3 Hz, 1H), 7.69-7.61 (m, 2H), 7.49 (d, J = 2.3 Hz, 1H), 7.40-7.25 (m, 2H), 5.12-4.98 (m, 1H), 4.81 (dd, J = 6.9, 9.8 Hz, 1H), 4.35-4.25 (m, 1H), 3.44 (s, 3H), 2.40 (s, 3H). |
| 107 | $C_{18}H_{15}N_7O_3Cl_2$ requires: 447 and 449, found: 448 and 450 $[M + H]^+$. | 400 MHz, $CDCl_3$: δ = 8.91 (s, 1H), 8.87 (br d, J = 6.7 Hz, 1H), 8.60 (d, J = 2.7 Hz, 1H), 8.31 (d, J = 2.2 Hz, 1H), 7.60 (d, J = 2.3 Hz, 1H), 6.41 (d, J = 2.8 Hz, 1H), 5.12-5.03 (m, 1H), 4.92 (dd, J = 6.9, 9.7 Hz, 1H), 4.39 (dd, J = 9.8, 11.2 Hz, 1H), 3.55 (s, 3H), 2.44 (s, 3H). |
| 108 | $C_{19}H_{13}N_6O_3Cl_2F$ requires: 462 and 464, found: 463 and 465 $[M + H]^+$. | 400 MHz, $CDCl_3$: δ = 9.02 (s, 1H), 8.86 (br d, J = 6.4 Hz, 1H), 8.68-8.59 (m, 1H), 8.28 (d, J = 2.3 Hz, 1H), 7.68-7.60 (m, 1H), 7.59-7.52 (m, 2H), 5.16-5.05 (m, 1H), 4.93-4.85 (m, 1H), 4.43-4.32 (m, 1H), 3.51 (s, 3H). |
| 109 | $C_{19}H_{13}O_3N_6Cl_2F$ requires: 462 and 464, found: 463 and 465 $[M + H]^+$. | 400 MHz, DMSO-$d_6$: δ = 9.26 (s, 1H), 9.22 (d, J = 7.9 Hz, 1H), 8.98 (t, J = 1.6 Hz, 1H), 8.84 (d, J = 2.9 Hz, 1H), 8.45 (d, J = 2.3 Hz, 1H), 8.34-8.26 (m, 1H), 7.95 (d, J = 2.3 Hz, 1H), 5.07-4.96 (m, 1H), 4.83-4.75 (m, 1H), 4.63 (dd, J = 7.4, 9.8 Hz, 1H), 3.36 (s, 3H). |
| 110 | $C_{19}H_{15}N_7O_3Cl_2$ requires: 459 and 461, found: 460 and 462 $[M + H]^+$. | 400 MHz, DMSO-$d_6$: δ = 9.29-9.21 (m, 4H), 8.45 (d, J = 2.3 Hz, 1H), 7.96 (d, J = 2.3 Hz, 1H), 5.06-4.98 (m, 1H), 4.84-4.76 (m, 1H), 4.63 (dd, J = 7.4, 9.7 Hz, 1H), 3.37 (s, 3H), 2.76 (s, 3H). |
| 111 | $C_{18}H_{13}Cl_2N_7O_3$ requires: 445 and 447, found: 446 and 448 $[M + H]^+$. | 400 MHz, DMSO-$d_6$: δ = 9.41 (s, 1H), 9.37 (s, 2H), 9.28 (s, 1H), 9.25 (d, J = 7.9 Hz, 1H), 8.45 (d, J = 2.3 Hz, 1H), 7.95 (d, J = 2.3 Hz, 1H), 5.06-4.98 (m, 1H), 4.83-4.76 (m, 1H), 4.66-4.59 (m, 1H), 3.36 (s, 3H). |
| 112 | $C_{18}H_{13}N_7O_3Cl_2$ requires:445 and 447, found: 446 and 448 $[M + H]^+$. | 400 MHz, $CD_3OD$: δ = 9.34 (d, J = 1.4 Hz, 1H), 9.16 (s, 1H), 8.87-8.76 (m, 2H), 8.35 (d, J = 2.3 Hz, 1H), 7.78 (d, J = 2.3 Hz, 1H), 5.12 (dd, J = 7.0, 11.5 Hz, 1H), 4.77 (dd, J = 7.0, 9.9 Hz, 1H), 4.64-4.57 (m, 1H), 3.48 (s, 3H). |
| 113 | $C_{21}H_{15}N_7Cl_2O_3$ requires: 483 and 485, found: 484 and 486 $[M + H]^+$. | 400 MHz, $CDCl_3$: δ = 9.29 (s, 1H), 8.95-8.91 (m, 1H), 8.89-8.80 (m, 1H), 8.45-8.32 (m, 1H), 8.26-8.22 (m, 1H), 7.96 (br d, J = 8.3 Hz, 1H), 7.59-7.51 (m, 1H), 7.46 (t, J = 8.1 Hz, 1H), 5.05-4.99 (m, 1H), 4.83 (dd, J = 6.8, 9.8 Hz, 1H), 4.39 (t, J = 10.6 Hz, 1H), 3.63 (s, 3H). |
| 114 | $C_{21}H_{15}N_7O_3Cl_2$ requires: 483 and 485, found: 484 and 486 $[M + H]^+$. | 400 MHz, $CDCl_3$: δ = 13.38 (s, 1H), 9.25 (s, 1H), 9.11 (d, J = 7.7 Hz, 1H), 8.45 (d, J = 2.3 Hz, 1H), 8.17 (s, 1H), 7.96 (d, J = 2.3 Hz, 1H), 7.80 (d, J = 8.2 Hz, 1H), 7.63-7.60 (m, 1H), 7.58-7.53 (m, 1H), 5.06-4.97 (m, 1H), 4.76-4.70 (m, 1H), 4.68-4.63 (m, 1H), 3.37 (s, 3H) |
| 115 | $C_{20}H_{14}Cl_2N_8O_3$ requires: 484 and 486, found: 485 and 487 $[M + H]^+$. | 400 MHz, DMSO-$d_6$: δ = 9.66-9.63 (m, 1H), 9.27-9.22 (m, 2H), 8.69 (s, 1H), 8.45 (d, J = 2.3 Hz, 1H), 8.21 (dd, J = 1.8, 9.3 Hz, 1H), 8.07 (d, J = 9.4 Hz, 1H), 7.95 (d, J = 2.3 Hz, 1H), 5.07-4.98 (m, 1H), 4.82-4.75 (m, 1H), 4.64 (dd, J= 7.5, 9.7 Hz, 1H), 3.36 (s, 3H). |
| 116 | $C_{21}H_{17}ClFN_5O_3$ requires: 441 and 443, found: 442 and 444 $[M + H]^+$. | 400 MHz, DMSO-$d_6$: δ = 9.07 (d, J = 7.7 Hz, 1H), 8.98 (s, 1H), 8.45 (d, J = 2.3 Hz, 1H), 7.96 (d, J = 2.3 Hz, 1H), 7.67-7.60 (m, 1H), 7.57 (dt, J = 1.5, 7.5 Hz, 1H), 7.46-7.40 (m, 2H), 4.99 (td, J = 7.6, 11.3 Hz, 1H), 4.79-4.71 (m, 1H), 4.63 (dd, J = 7.3, 9.7 Hz, 1H), 3.36 (s, 3H), 2.26 (d, J = 0.6 Hz, 3H). |
| 117 | $C_{21}H_{16}ClF_2N_5O_3$ requires: 459, found: 460 $[M + H]^+$. | 400 MHz, DMSO-$d_6$: δ = 9.09 (d, J = 7.8 Hz, 1H), 9.02 (s, 1H), 8.45 (d, J = 2.3 Hz, 1H), 7.96 (d, J = 2.3 Hz, 1H), 7.72-7.62 (m, 1H), 7.47-7.38 (m, 2H), 5.03-4.96 (m, 1H), 4.78-4.73 (m, 1H), 4.66-4.60 (m, 1H), 3.36 (s, 3H), 2.29 (s, 3H) |

TABLE 9-continued

Analytical data for RIPK1 inhibitors. II.

| Ex. No | MS ($ES^+$) | $^1H$ NMR |
|---|---|---|
| 118 | MS (ES+) $C_{27}H_{23}N_7O_4$ requires: 509, found: 510 $[M + H]^+$. | 400 MHz, DMSO-$d_6$: δ = 9.02-8.96 (m, 2H), 8.07 (d, J = 8.4 Hz, 2H), 7.94 (d, J = 8.6 Hz, 2H), 7.81 (s, 1H), 7.43 (s, 1H), 7.24-7.18 (m, 2H), 6.88 (dd, J = 2.9, 8.8 Hz, 1H), 4.96-4.88 (m, 1H), 4.58-4.43 (m, 2H), 3.82 (s, 3H), 3.30 (s, 3H), 2.42 (s, 3H). |
| 119 | MS (ES+) $C_{12}H_7ClFN_3$ requires: 247 and 249, found: 248 and 250 $[M + H]^+$. | (400 MHz, DMSO-$d_6$) δ = 8.85 (s, 1H), 8.12 (dd, J = 1.2, 10.0 Hz, 1H), 7.95-7.88 (m, 1H), 7.84-7.75 (m, 1H), 2.18 (d, J = 0.9 Hz, 3H) |
| 120 | $C_{20}H_{16}N_6O_3ClF$ requires: 442 and 444, found: 443 and $[M + H]^+$. | 400 MHz, $CD_3OD$: δ = 8.97 (s, 1H), 8.69 (d, J = 1.6 Hz, 1H), 8.62 (d, J = 4.9 Hz, 1H), 8.34 (d, J = 2.2 Hz, 1H), 7.77 (d, J = 2.2 Hz, 1H), 7.69-7.63 (m, 1H), 5.10 (dd, J = 6.9, 11.4 Hz, 1H), 4.77 (dd, J = 7.0, 9.8 Hz, 1H), 4.61-4.53 (m, 1H), 3.47 (s, 3H), 2.35 (d, J = 1.3 Hz, 3H). |
| 121 | $C_{20}H_{16}N_6O_3ClF$ requires: 442 and 444, found: 443 and 445 $[M + H]^+$. | 400 MHz, DMSO-$d_6$: δ = 9.14 (d, J = 7.8 Hz, 1H), 8.96 (s, 1H), 8.77 (d, J = 2.9 Hz, 1H), 8.45 (d, J = 2.3 Hz, 1H), 8.36 (dd, J = 4.7, 8.8 Hz, 1H), 8.06-7.98 (m, 1H), 7.96 (d, J = 2.3 Hz, 1H), 5.07-4.94 (m, 1H), 4.84-4.73 (m, 1H), 4.65 (dd, J = 7.5, 9.7 Hz, 1H), 3.37 (s, 3H), 2.61 (s, 3H). |
| 122 | $C_{19}H_{16}N_7O_3Cl$ requires: 425 and 427, found: 426 and 428 $[M + H]^+$. | 400 MHz, DMSO-$d_6$: δ = 9.37 (s, 1H), 9.26 (s, 2H), 9.16 (d, J = 7.8 Hz, 1H), 9.00 (s, 1H), 8.50-8.40 (m, 1H), 8.01-7.90 (m, 1H), 5.06-4.96 (m, 1H), 4.82-4.75 (m, 1H), 4.66-4.59 (m, 1H), 3.36 (s, 3H), 2.50 (s, 3H). |
| 123 | $C_{19}H_{16}ClN_7O_3$ requires: 425 and 427, found: 426 and 428 $[M + H]^+$. | 400 MHz, DMSO-$d_6$: δ = 9.51 (s, 1H), 9.20 (d, J = 7.9 Hz, 1H), 9.02 (s, 1H), 8.84 (s, 2H), 8.45 (d, J = 2.3 Hz, 1H), 7.96 (d, J = 2.1 Hz, 1H), 5.07-4.99 (m, 1H), 4.85-4.77 (m, 1H), 4.67-4.61 (m, 1H), 3.37 (s, 3H), 2.63 (s, 3H). |
| 124 | $C_{21}H_{15}Cl_2N_7O_3$ requires: 483 and 485, found: 484 and 486 $[M + H]^+$. | 400 MHz, DMSO-$d_6$: δ = 9.30 (s, 1H), 9.24-9.14 (m, 2H), 8.45 (d, J = 2.2 Hz, 1H), 8.17 (s, 1H), 7.95 (d, J = 2.2 Hz, 1H), 7.81-7.73 (m, 2H), 7.72-7.69 (m, 1H), 5.07-4.97 (m, 1H), 4.83-4.73 (m, 1H), 4.69-4.60 (m, 1H), 3.37 (s, 3H). |
| 125 | $C_{21}H_{18}N_5O_4Cl$ requires: 439, found: 440 $[M + H]^+$. | 400 MHz, DMSO-$d_6$: δ = 8.98 (d, J = 7.7 Hz, 1H), 8.81 (s, 1H), 8.44 (d, J = 2.1 Hz, 1H), 8.17-8.07 (m, 2H), 7.95 (d, J = 2.1 Hz, 1H), 7.60-7.51 (m, 3H), 5.04-4.96 (m, 1H), 4.85-4.70 (m, 1H), 4.67-4.62 (m, 1H), 4.08 (s, 3H), 3.37 (s, 3H). |
| 126 | $C_{21}H_{18}N_5O_4Cl$ requires: 439 and 441, found: 440 and 442 $[M + H]^+$. | 400 MHz, DMSO-$d_6$: δ = 9.13 (d, J = 7.6 Hz, 1H), 9.07 (s, 1H), 8.44 (d, J = 2.3 Hz, 1H), 7.96 (d, J = 2.3 Hz, 1H), 7.82-7.76 (m, 2H), 7.62-7.54 (m, 3H), 5.71 (s, 1H), 5.08-4.95 (m, 1H), 4.81-4.72 (m, 1H), 4.69-4.61 (m, 3H), 3.36 (s, 3H). |
| 127 | $C_{21}H_{19}N_6SO_4Cl$ requires: 486 and 488, found: 487 and 489 $[M + H]^+$. | 400 MHz, DMSO-$d_6$: δ = 9.49 (s, 1H), 9.23 (d, J = 7.6 Hz, 1H), 8.44 (d, J = 2.3 Hz, 1H), 7.94 (d, J = 2.3 Hz, 1H), 7.75-7.68 (m, 2H), 7.61-7.51 (m, 3H), 5.01 (td, J = 7.4, 11.4 Hz, 1H), 4.79-4.73 (m, 1H), 4.63 (dd, J = 7.4, 9.8 Hz, 1H), 3.36 (s, 3H), 2.91 (s, 3H) |
| 128 | $C_{22}H_{15}O_3N5FCl$ requires: 451 and 453, found: 452 and 454 $[M + H]^+$. | 400 MHz, DMSO-$d_6$: δ: 9.20 (s, 1H), 9.12 (d, J = 7.9 Hz, 1H), 7.84-7.78 (m, 2H), 7.77-7.62 (m, 4H), 7.51-7.43 (m, 1H), 4.96-4.90 (m, 1H), 4.76-4.67 (m, 1H), 4.55 (dd, J = 7.7, 9.8 Hz, 1H), 3.36 (s, 3H). |
| 129 | $C_{22}H_{15}O_3N_5ClF$ requires: 451 and 453, found: 452 and 454 $[M + H]^+$. | 400 MHz, DMSO-$d_6$: δ: 9.17 (s, 1H), 9.10 (d, J = 7.8 Hz, 1H), 8.03-7.94 (m, 2H), 7.86-7.78 (m, 2H), 7.74-7.67 (m, 1H), 7.50-7.39 (m, 2H), 5.00-4.87 (m, 1H), 4.77-4.64 (m, 1H), 4.56 (dd, J = 7.7, 9.8 Hz, 1H), 3.36 (s, 3H). |
| 130 | $C_{22}H_{14}O_3N_5ClF_2$ requires: 469 and 471, found: 470 and 472 $[M + H]^+$. | 400 MHz, DMSO-$d_6$: δ: 9.28 (s, 1H), 9.13 (d, J = 7.9 Hz, 1H), 7.86-7.78 (m, 2H), 7.75-7.68 (m, 1H), 7.62-7.48 (m, 3H), 4.99-4.88 (m, 1H), 4.78-4.66 (m, 1H), 4.55 (dd, J = 7.8, 9.7 Hz, 1H), 3.36 (s, 3H). |
| 131 | $C_{22}H_{15}O_3N5Cl_2$ requires: 467, 468 and 469, found: 468, 469 and 470 $[M + H]^+$. | 400 MHz, DMSO-$d_6$: δ = 9.18 (s, 1H), 9.11 (d, J = 7.9 Hz, 1H), 7.98-7.88 (m, 2H), 7.86-7.78 (m, 2H), 7.76-7.63 (m, 3H), 5.02-4.84 (m, 1H), 4.78-4.64 (m, 1H), 4.62-4.49 (m, 1H), 3.36 (s, 3H). |
| 132 | $C_{23}H_{17}O_3N_5ClF$ requires: 465 and 467, found: 466 and 468 $[M + H]^+$. | 400 MHz, DMSO-$d_6$: δ = 9.17 (s, 1H), 9.10 (d, J = 7.9 Hz, 1H), 7.85-7.78 (m, 2H), 7.76-7.66 (m, 3H), 7.52 (t, J = 7.9 Hz, 1H), 4.99-4.86 (m, 1H), 4.77-4.67 (m, 1H), 4.56 (dd, J = 7.7, 9.7 Hz, 1H), 3.36 (s, 3H), 2.34 (s, 3H). |
| 133 | $C_{25}H_{27}O_3N_5$ requires: 445, found: 446 $[M + H]^+$. | 400 MHz, DMSO-$d_6$: δ: 8.84 (d, J = 7.5 Hz, 1H), 8.60 (s, 1H), 7.85-7.76 (m, 2H), 7.73-7.62 (m, 1H), 4.96-4.79 (m, 1H), 4.65-4.53 (m, 2H), 3.36 (s, 3H), 2.51 (s, 3H), 2.02-1.89 (m, 6H), 1.73-1.59 (m, 7H). |
| 134 | $C_{22}H_{23}O_4N_5$ requires: 421, found: 422 $[M + H]^+$. | 400 MHz, DMSO-$d_6$: δ = 8.95 (d, J = 7.6 Hz, 1H), 8.70 (s, 1H), 7.87-7.78 (m, 2H), 7.75-7.65 (m, 1H), 4.97-4.84 (m, 1H), 4.74-4.52 (m, 2H), 3.98 (dd, J = 3.4, 11.0 Hz, 2H), 3.54-3.52 (m, 1H), 3.37 (s, 3H), 3.34-3.11 (m, 2H), 2.39 (s, 3H), 2.01-1.85 (m, 2H), 1.63 (d, J = 12.8 Hz, 2H). |
| 135 | $C_{23}H_{18}FN_5O_3$ requires: 431, found: | 500 MHz, DMSO-$d_6$: δ 9.05 (d, J = 7.9 Hz, 1H), 8.94 (s, 1H), 7.85-7.78 (m, 2H), 7.71 (d, J = 8.3 Hz, 1H), 7.66-7.56 (m, 3H), 7.45- |

TABLE 9-continued

| Ex. No | MS ($ES^+$) | $^1H$ NMR |
|---|---|---|
| Analytical data for RIPK1 inhibitors. II. | | |
| | 432 $[M+H]^+$. | 7.37 (m, 1H), 4.93 (dt, J = 11.5, 7.7 Hz, 1H), 4.71 (dd, J = 11.5, 9.8 Hz, 1H), 4.56 (dd, J = 9.8, 7.7 Hz, 1H), 3.36 (s, 3H), 2.44 (s, 3H). |
| 136 | $C_{23}H_{18}FN_5O_3$ requires: 431, found: 432 $[M+H]^+$. | 500 MHz, DMSO-$d_6$: δ 9.03 (d, J = 7.8 Hz, 1H), 8.91 (s, 1H), 7.87-7.77 (m, 4H), 7.71 (d, J = 8.3 Hz, 1H), 7.45-7.37 (m, 2H), 4.97-4.88 (m, 1H), 4.73-4.65 (m, 1H), 4.56 (dd, J = 9.8, 7.6 Hz, 1H), 3.24 (s, 3H), 2.43 (s, 3H). |
| 137 | $C_{24}H_{21}N_5O_3$ requires: 427, found: 428 $[M+H]^+$. | 500 MHz, DMSO-$d_6$: δ 8.96 (d, J = 7.7 Hz, 1H), 8.83 (s, 1H), 7.80-7.74 (m, 2H), 7.63 (dd, J = 20.6, 7.9 Hz, 3H), 7.33 (d, J = 8.0 Hz, 2H), 4.92-4.83 (m, 1H), 4.67-4.60 (m, 1H), 4.55-4.50 (m, 1H), 3.24 (s, 3H), 2.40-2.34 (m, 6H). |
| 138 | $C_{22}H_{14}O_3N_5ClF_2$ requires:469 and 471, found: 470 and 472 $[M+H]^+$. | 400 MHz, DMSO-$d_6$: δ: 9.24 (s, 1H), 9.10 (d, J = 7.8 Hz, 1H), 7.84-7.78 (m, 2H), 7.77-7.68 (m, 2H), 7.57-7.49 (m, 1H), 7.39-7.32 (m, 1H), 4.96-4.87 (m, 1H), 4.74-4.64 (m, 1H), 4.55 (dd, J = 7.7, 9.8 Hz, 1H), 3.35 (s, 3H). |
| 139 | $C_{23}H_{17}ClFN_5O_3$. requires: 465, found: 466 $[M+H]^+$. | 500 MHz, DMSO-$d_6$: δ 9.22 (s, 1H), 9.09 (d, J = 7.8 Hz, 1H), 7.85-7.78 (m, 2H), 7.71 (d, J = 8.3 Hz, 1H), 7.52 (t, J = 7.7 Hz, 1H), 7.31-7.24 (m, 2H), 4.96-4.87 (m, 1H), 4.69 (dd, J = 11.5, 9.9 Hz, 1H), 4.55 (dd, J = 9.9, 7.7 Hz, 1H), 3.36 (s, 3H), 2.44 (s, 3H). |
| 140 | $C_{24}H_{19}Cl_2FAN_5O_3$ requires: 572, found: 573 $[M+H]^+$. | 600 MHz, $CDCl_3$: δ 8.94-8.90 (m, 1H), 8.80 (d, J = 7.4 Hz, 1H), 7.58 (d, J = 8.0 Hz, 1H), 7.10-7.03 (m, 2H), 6.97 (s, 1H), 6.60-6.53 (m, 2H), 5.14-5.08 (m, 1H), 4.78-4.72 (m, 1H), 4.22-4.15 (m, 1H), 3.84-3.77 (m, 1H), 3.75-3.69 (m, 1H), 3.45-3.39 (m, 3H), 2.95 (s, 1H), 1.25 (s, 2H). |
| 141 | $C_{28}H_{27}Cl_2F_2N_5O_4$ requires: 606, found: 607 $[M+H]^+$. | 600 MHz, DMSO-$d_6$: δ 9.24 (d, J = 1.2 Hz, 1H), 8.98 (d, J = 7.9 Hz, 1H), 7.77-7.70 (m, 1H), 7.57-7.51 (m, 1H), 7.40-7.34 (m, 1H), 6.97 (d, J = 8.7 Hz, 1H), 6.73 (d, J = 2.7 Hz, 1H), 6.63-6.58 (m, 1H), 5.63-5.58 (m, 1H), 4.92-4.85 (m, 1H), 4.44-4.34 (m, 2H), 3.82 (s, 2H), 3.64-3.56 (m, 4H), 3.29 (s, 3H), 3.18-3.10 (m, 2H), 1.63-1.50 (m, 4H). |
| 142 | $C_{28}H_{27}Cl_2F_2N_5O_4$ requires: 606, found: 607 $[M+H]^+$. | 600 MHz, DMSO-$d_6$: δ 9.27 (s, 1H), 9.00 (d, J = 8.0 Hz, 1H), 7.60-7.51 (m, 3H), 6.97 (d, J = 8.6 Hz, 1H), 6.74 (d, J = 2.6 Hz, 1H), 6.63-6.58 (m, 1H), 4.93-4.86 (m, 1H), 4.46-4.39 (m, 1H), 4.39-4.33 (m, 1H), 3.82 (s, 2H), 3.64-3.59 (m, 4H), 3.29 (s, 3H), 3.19-3.11 (m, 2H), 2.08 (s, 1H), 1.63-1.48 (m, 4H). |
| 143 | $C_{25}H_{22}ClF_2N_5O_4$ requires: 529, found: 530 $[M+H]^+$. | 600 MHz, DMSO-$d_6$: δ 9.24 (s, 1H), 9.00 (d, J = 7.9 Hz, 1H), 7.77-7.71 (m, 1H), 7.58-7.51 (m, 1H), 7.40-7.32 (m, 1H), 7.11 (d, J = 8.8 Hz, 1H), 7.03 (d, J = 2.8 Hz, 1H), 6.89-6.83 (m, 1H), 4.93-4.84 (m, 1H), 4.48 (t, J = 10.6 Hz, 1H), 4.40 (t, J = 8.8 Hz, 1H), 4.08-3.41 (m, 6H), 3.32 (s, 3H), 3.15 (s, 2H). |
| 144 | $C_{28}H_{26}ClF_2N_5O_4$ requires: 569, found: 570 $[M+H]^+$. | 600 MHz, DMSO-$d_6$: δ 9.20 (s, 1H), 8.94 (d, J = 8.0 Hz, 1H), 7.53-7.42 (m, 3H), 6.98 (d, J = 8.6 Hz, 1H), 6.42 (d, J = 2.7 Hz, 1H), 6.25 (dd, J = 8.6, 2.7 Hz, 1H), 4.84-4.77 (m, 1H), 4.42-4.35 (m, 1H), 4.32-4.26 (m, 1H), 3.56 (d, J = 2.5 Hz, 8H), 3.23 (s, 3H), 1.68 (t, J = 5.2 Hz, 4H). |
| 145 | $C_{29}H_{29}ClFN_5O_4$ requires: 566, found: 567 $[M+H]^+$. | 600 MHz, DMSO-$d_6$: δ 9.17 (s, 1H), 9.01 (d, J = 8.1 Hz, 1H), 7.73 (d, J = 10.7 Hz, 1H), 7.69 (d, J = 7.8 Hz, 1H), 7.53 (t, J = 7.9 Hz, 1H), 7.06 (d, J = 8.6 Hz, 1H), 6.49 (d, J = 2.7 Hz, 1H), 6.33 (dd, J = 8.6, 2.7 Hz, 1H), 4.92-4.84 (m, 1H), 4.50-4.43 (m, 1H), 4.41-4.35 (m, 1H), 3.66-3.60 (m, 4H), 3.56 (t, J = 5.2 Hz, 4H), 3.31 (s, 3H), 2.35 (s, 3H), 1.76 (t, J = 5.2 Hz, 4H). |
| 146 | $C_{24}H_{21}ClF_2N_4O_5$ requires: 518, found: 519 $[M+H]^+$. | 500 MHz, DMSO-$d_6$: δ 9.24 (s, 1H), 9.02 (d, J = 8.0 Hz, 1H), 7.77-7.69 (m, 1H), 7.58-7.50 (m, 1H), 7.40-7.33 (m, 1H), 7.16 (d, J = 8.8 Hz, 1H), 7.10 (d, J = 2.9 Hz, 1H), 6.86 (dd, J = 8.8, 2.9 Hz, 1H), 4.93-4.84 (m, 1H), 4.51 (t, J = 9.9 Hz, 1H), 4.42 (d, J = 9.9 Hz, 1H), 4.16-4.11 (m, 2H), 3.69-3.64 (m, 2H), 3.32 (d, J = 2.5 Hz, 6H). |
| 147 | $C_{25}H_{22}Cl_2F_2N_4O_5$ requires: 567, found: 568 $[M+H]^+$. | 600 MHz, DMSO-$d_6$: δ 9.24 (s, 1H), 9.02 (d, J = 8.2 Hz, 1H), 7.73 (q, J = 8.0 Hz, 1H), 7.54 (t, J = 9.7 Hz, 2H), 7.36 (t, J = 8.4 Hz, 1H), 7.17 (d, J = 8.6 Hz, 1H), 7.11 (s, 1H), 6.90-6.85 (m, 1H), 4.92-4.77 (m, 3H), 4.54-4.48 (m, 1H), 4.45-4.39 (m, 1H), 4.10-4.07 (m, 1H), 4.06-4.02 (m, 1H), 3.81 (d, J = 5.6 Hz, 2H), 3.58 (s, 3H), 2.30-2.21 (m, 1H). |
| 148 | $C_{25}H_{19}ClF_2N_6O_4$ requires: 540, found: 541 $[M+H]^+$. | 600 MHz, DMSO-$d_6$: δ 9.25 (s, 1H), 9.03 (d, J = 7.9 Hz, 1H), 7.79 (s, 1H), 7.73 (td, J = 8.5, 8.0, 6.4 Hz, 1H), 7.54 (t, J = 10.1 Hz, 1H), 7.42 (s, 1H), 7.36 (t, J = 8.5 Hz, 1H), 7.23-7.17 (m, 2H), 6.87 (d, J = 9.0 Hz, 1H), 4.91 (dt, J = 10.7, 7.8 Hz, 1H), 4.53 (t, J = 10.6 Hz, 1H), 4.45 (dd, J = 10.0, 7.7 Hz, 1H), 3.82 (s, 3H), 3.30 (s, 3H). |
| 149 | $C_{25}H_{19}ClF_2N_6O_3$ requires: 524, found: 525 $[M+H]^+$. | 600 MHz, $CDCl_3$: δ 8.94 (s, 1H), 8.84 (d, J = 7.1 Hz, 1H), 7.59 (q, J = 7.8 Hz, 1H), 7.54 (s, 1H), 7.31 (s, 2H), 7.27 (s, 1H), 7.12-7.05 (m, 1H), 7.02-6.95 (m, 1H), 6.33 (s, 1H), 5.20 (dt, J = 11.0, 7.3 Hz, 1H), 4.88-4.82 (m, 1H), 4.34 (t, J = 10.5 Hz, 1H), 3.93 (s, 3H), 3.48 (s, 3H). |

TABLE 9-continued

| Analytical data for RIPK1 inhibitors. II. | | |
|---|---|---|
| Ex. No | MS ($ES^+$) | $^1H$ NMR |
| 150 | $C_{25}H_{19}ClF_2N_6O_3$ requires: 524, found: 525 $[M + H]^+$. | 600 MHz, DMSO-$d_6$: δ 9.24 (s, 1H), 9.04 (d, J = 7.9 Hz, 1H), 8.20 (s, 1H), 7.93 (s, 1H), 7.77-7.70 (m, 2H), 7.54 (t, J = 10.2 Hz, 1H), 7.47 (d, J = 8.2 Hz, 1H), 7.36 (t, J = 8.5 Hz, 1H), 7.22 (d, J = 8.3 Hz, 1H), 4.97-4.89 (m, 1H), 4.57 (t, J = 10.7 Hz, 1H), 4.47 (t, J = 9.9, 7.7 Hz, 1H), 3.87 (s, 3H), 3.37 (s, 3H). |
| 151 | $C_{24}H_{17}ClF_2N_6O_3$ requires: 510, found: 511 $[M + H]^+$. | 600 MHz, DMSO-$d_6$: δ 9.24 (s, 1H), 9.04 (d, J = 7.9 Hz, 1H), 8.13 (s, 2H), 7.77-7.70 (m, 2H), 7.57-7.50 (m, 2H), 7.36 (t, J = 8.4 Hz, 1H), 7.22 (d, J = 8.4 Hz, 1H), 4.97-4.89 (m, 1H), 4.58 (t, J = 10.7 Hz, 1H), 4.47 (t, J = 9.9 Hz, 1H) 2.50 (s, 3H). |
| 152 | $C_{25}H_{19}ClF_2N_6O_3$ requires: 524, found: 525 $[M + H]^+$. | 600 MHz, DMSO-$d_6$: δ 9.25 (s, 1H), 9.06 (d, J = 7.9 Hz, 1H), 8.35 (s, 1H), 7.88 (s, 1H), 7.77-7.67 (m, 2H), 7.59 (s, 1H), 7.54 (t, J = 9.8 Hz, 1H), 7.39-7.32 (m, 2H), 4.99-4.92 (m, 1H), 4.61 (t, J = 10.7 Hz, 1H), 4.51 (t, J = 8.8 Hz, 1H), 3.39 (s, 3H), 2.11 (s, 3H). |
| 153 | $C_{28}H_{26}ClFN_8O_3$• requires: 577, found: 578 $[M + H]^+$. | 500 MHz, DMSO-$d_6$: δ 9.18 (s, 1H), 9.05 (d, J = 7.9 Hz, 1H), 7.96 (s, 1H), 7.75-7.66 (m, 2H), 7.56-7.50 (m, 2H), 7.34 (d, J = 8.2 Hz, 1H), 7.28 (d, J = 8.2 Hz, 1H), 4.98-4.89 (m, 1H), 4.61 (t, J = 10.6 Hz, 1H), 4.52 (t, J = 10.0 Hz, 1H), 4.21 (s, 2H), 3.97-3.93 (m, 4H), 3.36 (s, 3H), 3.17 (s, 2H), 2.36 (s, 3H). |
| 154 | $C_{27}H_{23}ClF_2N_8O_3$ requires: 580, found: 581 $[M + H]^+$. | 600 MHz, DMSO-$d_6$: δ 9.25 (s, 1H), 9.02 (d, J = 7.8 Hz, 1H), 7.91 (s, 1H), 7.74 (q, J = 8.1 Hz, 1H), 7.58-7.51 (m, 1H), 7.51-7.48 (m, 1H), 7.40-7.34 (m, 1H), 7.33-7.28 (m, 1H), 7.24 (d, J = 8.1 Hz, 1H), 4.95-4.88 (m, 1H), 4.60-4.54 (m, 1H), 4.53-4.47 (m, 1H), 4.17-4.11 (m, 2H), 3.81 (s, 2H), 3.76 (d, J = 3.9 Hz, 2H), 3.34 (s, 3H), 3.03-2.96 (m, 2H). |
| 155 | $C_{27}H_{23}ClF_2N_8O_3$ requires: 580, found: 581 $[M + H]^+$. | 600 MHz, DMSO-$d_6$: δ 9.28 (s, 1H), 9.04 (d, J = 7.9 Hz, 1H), 7.91 (s, 1H), 7.60-7.48 (m, 4H), 7.30 (dd, J = 8.3, 1.9 Hz, 1H), 7.24 (d, J = 8.1 Hz, 1H), 4.96-4.88 (m, 1H), 4.62-4.56 (m, 1H), 4.53-4.47 (m, 1H), 4.17-4.13 (m, 2H), 3.82-3.72 (m, 3H), 3.35 (s, 3H), 3.06-2.95 (m, 2H), 2.17-1.86 (m, 1H). |
| 156 | $C_{28}H_{27}FN_8O_3$ requires: 542, found: 543 $[M + H]^+$. | 600 MHz, DMSO-$d_6$: δ 8.99-8.93 (m, 2H), 7.91 (s, 1H), 7.63 (q, J = 7.3 Hz, 1H), 7.57 (t, J = 7.6 Hz, 1H), 7.49 (s, 1H), 7.43 (t, J = 8.0 Hz, 2H), 7.30 (d, J = 8.2 Hz, 1H), 7.25 (d, J = 8.2 Hz, 1H), 4.95-4.88 (m, 1H), 4.59-4.48 (m, 2H), 4.17-4.12 (m, 2H), 3.81 (s, 2H), 3.76 (s, 2H), 3.32 (s, 3H), 3.06-2.93 (m, 2H), 2.25 (s, 3H). |
| 157 | $C_{20}H_{15}N_5O_3ClSF_3$ requires: 497 and 499, found: 498 and 500 $[M + H]^+$. | 400 MHz, DMSO-$d_6$: δ = 9.07 (d, J = 7.5 Hz, 1H), 8.95 (s, 1H), 8.63 (s, 1H), 8.46 (d, J = 2.3 Hz, 1H), 8.13 (s, 1H), 7.98 (d, J = 2.2 Hz, 1H), 5.06-4.94 (m, 1H), 4.77-4.65 (m, 2H), 3.39 (s, 3H), 2.66 (s, 3H). |
| 158 | $C_{20}H_{20}N_5O_4ClF_2$ requires: 467 and 469, found: 468 and 470 $[M + H]^+$. | 400 MHz, $CDCl_3$ δ = 8.93 (br d, J = 6.1 Hz, 1H), 8.71 (d, J = 5.9 Hz, 1H), 8.30 (d, J = 2.1 Hz, 1H), 7.59 (s, 1H), 5.18-5.04 (m, 1H), 4.97-4.86 (m, 1H), 4.82-4.72 (m, 1H), 4.47-4.32 (m, 1H), 4.16-4.01 (m, 1H), 3.83-3.63 (m, 1H), 3.54 (d, J = 1.3 Hz, 3H), 2.54-2.37 (m, 5H), 2.26-2.07 (m, 2H). |
| 159 | MS (ES+) $C_{26}H_{23}O_4N_6F$ requires: 502, found: 503 $[M + H]^+$. | (400 MHz, DMSO-$d_6$) δ = 9.00-8.93 (m, 2H), 7.80 (s, 1H), 7.67-7.60 (m, 1H), 7.57 (dt, J = 1.4, 7.5 Hz, 1H), 7.47-7.39 (m, 3H), 7.23-7.17 (m, 2H), 6.88 (dd, J = 2.9, 8.8 Hz, 1H), 4.96-4.85 (m, 1H), 4.60-4.38 (m, 2H), 3.82 (s, 3H), 3.30 (s, 3H), 2.26 (s, 3H). |
| 160 | MS (ES+) $C_{27}H_{23}N_7O_4$ requires: 509, found: 510 $[M + H]^+$. | 400 MHz, DMSO-$d_6$: δ = 9.02-8.96 (m, 2H), 8.07 (d, J = 8.4 Hz, 2H), 7.94 (d, J = 8.6 Hz, 2H), 7.81 (s, 1H), 7.43 (s, 1H), 7.24-7.18 (m, 2H), 6.88 (dd, J = 2.9, 8.8 Hz, 1H), 4.96-4.88 (m, 1H), 4.58-4.43 (m, 2H), 3.82 (s, 3H), 3.30 (s, 3H), 2.42 (s, 3H). |
| 161 | MS (ES+) $C_{25}H_{19}ClF_2N_6O_4$ requires: 540 and 542, found: 541 and 543 $[M + H]^+$. | 400 MHz, DMSO-$d_6$: δ = 9.27 (s, 1H), 9.06 (d, J = 8.0 Hz, 1H), 7.81-7.77 (s, 1H), 7.60-7.49 (m, 3H), 7.42 (d, J = 0.6 Hz, 1H), 7.24-7.17 (m, 2H), 6.91-6.83 (m, 1H), 4.96-4.86 (m, 1H), 4.59-4.50 (m, 1H), 4.48-4.40 (m, 1H), 3.81 (s, 3H), 3.29 (s, 3H). |

The following compounds can generally be made using the procedures described above. It is expected that these compounds when made will have activity similar to those that have been made in the examples above.

| Structure | Name | MS |
|---|---|---|
| 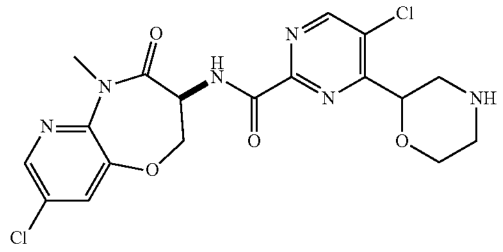 [SMILES: CN1C(=O)[C@@H](NC(=O)c2ncc(Cl)c(C3CNCCO3)n2)COc2cc(Cl)cnc21] | 5-chloro-N-((S)-8-chloro-5-methyl-4-oxo-2,3,4,5-tetrahydropyrido[3,2-b][1,4]oxazepin-3-yl)-4-(morpholin-2-yl)pyrimidine-2-carboxamide | $C_{18}H_{18}Cl_2N_6O_4$ m/z = 452.08 |
| 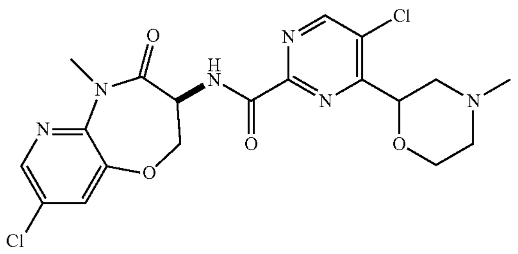 [SMILES: CN1CCOC(c2nc(C(=O)N[C@H]3COc4cc(Cl)cnc4N(C)C3=O)ncc2Cl)C1] | 5-chloro-N-((S)-8-chloro-5-methyl-4-oxo-2,3,4,5-tetrahydropyrido[3,2-b][1,4]oxazepin-3-yl)-4-(4-methylmorpholin-2-yl)-pyrimidine-2-carboxamide | $C_{19}H_{20}Cl_2N_6O_4$ m/z = 466.09 |
| 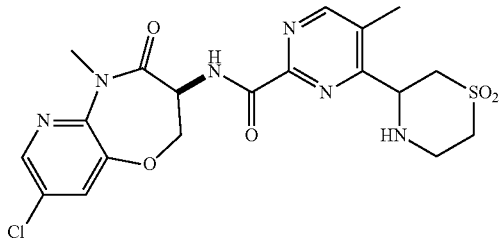 [SMILES: Cc1cnc(C(=O)N[C@H]2COc3cc(Cl)cnc3N(C)C2=O)nc1C1CS(=O)(=O)CCN1] | N-((S)-8-chloro-5-methyl-4-oxo-2,3,4,5-tetrahydropyrido[3,2-b][1,4]oxazepin-3-yl)-4-(1,1-dioxidothiomorpholin-3-yl)-5-methylpyrimidine-2-carboxamide | $C_{19}H_{21}ClN_6O_5S$ m/z = 480.10 |
| 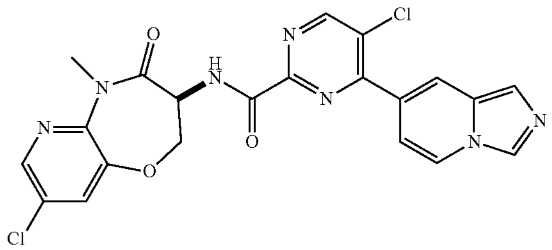 [SMILES: CN1C(=O)[C@@H](NC(=O)c2ncc(Cl)c(-c3ccn4cncc4c3)n2)COc2cc(Cl)cnc21] | (S)-5-chloro-N-(8-chloro-5-methyl-4-oxo-2,3,4,5-tetrahydropyrido[3,2-b][1,4]oxazepin-3-yl)-4-(imidazo[1,5-a]pyridin-7-yl)-pyrimidine-2-carboxamide | $C_{21}H_{15}Cl_2N_7O_3$ m/z = 483.06 |
| 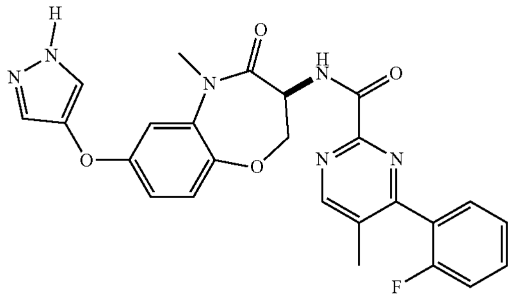 [SMILES: Cc1cnc(C(=O)N[C@H]2COc3ccc(Oc4cn[nH]c4)cc3N(C)C2=O)nc1-c1ccccc1F] | (S)-N-(7-((1H-pyrazol-4-yl)oxy)-5-methyl-4-oxo-2,3,4,5-tetrahydrobenzo[b][1,4]oxazepin-3-yl)-4-(2-fluorophenyl)-5-methylpyrimidine-2-carboxamide | $C_{25}H_{21}ClFN_6O_4$ m/z = 488.16 |

-continued

| Structure | Name | MS |
|---|---|---|
| 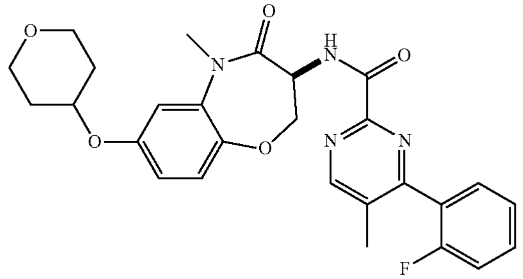 [SMILES: Cc1cnc(C(=O)N[C@H]2COc3ccc(OC4CCOCC4)cc3N(C)C2=O)nc1-c1ccccc1F] | (S)-4-(2-fluorophenyl)-5-methyl-N-(5-methyl-4-oxo-7-((tetrahydro-2H-pyran-4-yl)oxy)-2,3,4,5-tetrahydrobenzo[b][1,4]oxazepin-3-yl)pyrimidine-2-carboxamide | $C_{27}H_{27}FN_4O_5$ m/z = 506.20 |
| 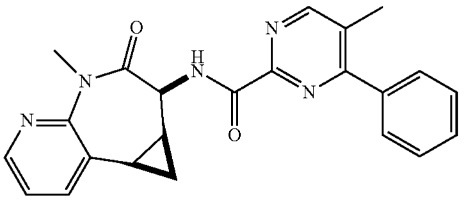 | 5-methyl-N-((1aS,2S,8bR)-4-methyl-3-oxo-1,1a,2,3,4,8b-hexahydrocyclopropa[d]pyrido[2,3-b]azepin-2-yl)-4-phenylpyrimidine-2-carboxamide | $C_{23}H_{21}N_5O_2$ m/z = 399.17 |
| 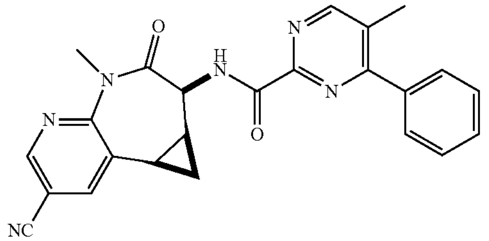 | N-((1aS,2S,8bR)-7-cyano-4-methyl-3-oxo-1,1a,2,3,4,8b-hexahydrocyclopropa[d]pyrido[2,3-b]azepin-2-yl)-5-methyl-4-phenylpyrimidine-2-carboxamide | $C_{24}H_{20}N_6O_2$ m/z = 424.16 |
| 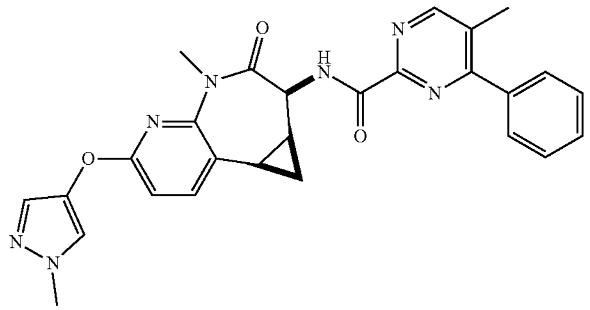 | 5-methyl-N-((1aS,2S,8bR)-4-methyl-6-((1-methyl-1H-pyrazol-4-yl)oxy)-3-oxo-1,1a,2,3,4,8b-hexahydrocyclopropa[d]pyrido[2,3-b]azepin-2-yl)-4-phenylpyrimidine-2-carboxamide | $C_{27}H_{25}N_7O_3$ m/z = 495.20 |

The activity of the compounds in Examples 1-154 as RIPK1 inhibitors is illustrated in the following assays.

Biological Activity Assays

Compounds described herein have been shown to bind RIPK1 in vitro, and to inhibit phosphorylation of a downstream molecular target in a cellular assay.

ADP-Glo Kinase Assay

In order to measure RIPK1 activity the ADP-Glo kinase assay (Promega, Catalog #V7002) was used to measure the conversion of ATP to ADP. This enzymatic assay was performed in a 384-well white, Optiplate (Perkin Elmer, Catalog #6007299) with assay buffer consisting of 50 mM HEPES pH 7.5 (Gibco, Catalog #15630-080), 50 mM NaCl (Teknova, Catalog #S0252), 30 mM $MgCl_2$ (Ambion, Catalog #AM9530G), 1 mM DTT (Santa Cruz Biotechnology, Catalog #sc-29089), 0.05% BSA (Sigma, Catalog #A3059-50G) and 0.02% CHAPS (Sigma, Catalog #$C_{5070\text{-}5}$G). Stock solutions of the test compounds were prepared in 100% DMSO (Sigma, Catalog #D2650) and serially diluted 1:3 using 100% DMSO. Compounds were additionally diluted 1:40 in assay buffer, and 2 μL/well were transferred to the assay plate. 4 μL/well (final concentration of 5 nM) of RIPK1 protein (SignalChem, Catalog #R07-11G-05) diluted in assay buffer and added to the assay plate followed by a 10 minute preincubation at room temperature. 4 μL/well of ATP (Promega, Catalog #V7002) (final concentration of 50 μM) diluted in assay buffer were then added to the assay plate followed by a 6 hr reaction time. Final concentrations of RIPK1 and ATP refer to a 10 μL volume. Luminescence was measured using a BioTek Synergy™ NEO plate reader. $IC_{50}$ values were calculated using a four-parameter logistic curve fit using Genedata Screener software.

Human U937 Cellular Necroptosis Assay

The human monocytic cell line U937 (CRL-1593.2) may be purchased from ATCC. The cells are routinely maintained in RPMI-1640 Medium (Gibco, Catalog #11875-093) supplemented with 10% heat inactivated fetal bovine serum (Gibco, Catalog #16140-071), 100 units/mL penicillin and 100 μg/mL streptomycin (Gibco, Catalog #15140-122), in a humidified incubator (37° C., 5% $CO_2$). For the assay, cells are resuspended in RPMI-1640 phenol red free Media (Gibco, Catalog #11835-030) supplemented with 10% fetal bovine serum (Sigma, Catalog #F2442), 100 units/mL penicillin and 100 ug/mL streptomycin. Cells are stimulated with 25 ng/mL human TNFalpha (Cell Sciences, Catalog #CSI15659B) and 25 μM z-VAD-FMK (R&D Systems, Catalog #FMK001) followed by seeding 5000 cells per well in a volume of 40 μL to a white, CulturPlate-384 (Perkin Elmer, Catalog #6007680). Stock solutions of the test compounds are prepared in 100% DMSO (Sigma, Catalog #D2650) and serially diluted 1:3 using 100% DMSO. Compounds are additionally diluted 1:40 in assay medium, and 10 μL/well was transferred to the plate. Following the compound addition, the plate is incubated at 37° C. and 5% $CO_2$ for 22 hr. After 22 hr, viability is assessed with the addition of 20 μL of Cell Titer-Glo 2.0 (Promega, Catalog #G9243). The tissue culture plate is shaken on an orbital shaker at 300 RPM for 15 minutes at room temperature in the dark. Luminescence is measured using a PerkinElmer Envision™ plate reader. $IC_{50}$ values are calculated using a four-parameter logistic curve fit using Genedata Screener software. Compounds disclosed herein are expected to have activity in this assay.

RIPK1 Kd Determinations

Compounds with lower dissociation constants bind with more affinity to the target. Compounds disclosed herein, particularly (but not exclusively) those with with lower dissociation constants, can be expected to inhibit target activity and to be useful in the treatment of RIPK1-mediated disease.

TABLE 10 hU937 activity

| Ex. No. | hU937 IC50, nM |
|---|---|
| 1 | 12.42 |
| 2 | 509.10 |
| 3 | 18.47 |
| 4 | 2158.75 |
| 5 | 15.13 |
| 6 | 12.52 |
| 7 | 22.16 |
| 8 | 353.90 |
| 9 | 10.25 |
| 10 | 15.39 |
| 11 | 459.03 |
| 12 | 14.57 |
| 13 | 27.62 |
| 14 | 119.25 |
| 15 | 497.63 |
| 16 | 36.09 |
| 17 | 40.82 |
| 18 | 1893.50 |
| 19 | 747.70 |
| 20 | 482.35 |
| 21 | 14.76 |
| 22 | 12.14 |
| 23 | 830 |
| 24 | 19.16 |
| 25 | 10000.00 |
| 26 | 14.60 |
| 27 | 26.71 |
| 28 | 19.00 |
| 29 | 11.67 |
| 30 | 32.30 |
| 31 | 10000.00 |
| 32 | 1115.75 |
| 33 | 10000.00 |
| 34 | 10000.00 |
| 35 | 10000.00 |
| 36 | 260.25 |

TABLE 10-continued hU937 activity

| Ex. No. | hU937 IC50, nM |
|---|---|
| 37 | 1561.00 |
| 38 | 18.93 |
| 39 | 12.91 |
| 40 | 1568.50 |
| 41 | 594.45 |
| 42 | 19.41 |
| 43 | 153.60 |
| 44 | 789.35 |
| 45 | 10 |
| 46 | 11.83 |
| 47 | 29.76 |
| 48 | 13.18 |
| 49 | 8.35 |
| 50 | 9.29 |
| 51 | 10.57 |
| 52 | 11.96 |
| 53 | 11.66 |
| 54 | 13.63 |
| 55 | 34.42 |
| 56 | 180.15 |
| 57 | 90.87 |
| 58 | 228.65 |
| 59 | 13.93 |
| 60 | 16.24 |
| 61 | 16.08 |
| 62 | 10.44 |
| 63 | 116.79 |
| 64 | 189.25 |
| 65 | 177.20 |
| 66 | 106.06 |
| 67 | 24.67 |
| 68 | 59.45 |
| 69 | 7.41 |
| 70 | 9.94 |
| 71 | 8.83 |
| 72 | 25.49 |
| 73 | 11.42 |
| 74 | 10.98 |
| 75 | 11.89 |
| 76 | 16.49 |
| 77 | 9.14 |
| 78 | 8.30 |
| 79 | 18.90 |
| 80 | 15.25 |
| 81 | 29.64 |
| 82 | 13.64 |
| 83 | 15.11 |
| 84 | 33.45 |
| 85 | 611.15 |
| 86 | 67.47 |
| 87 | 156.60 |
| 88 | 13.66 |
| 89 | 136.13 |
| 90 | 83.48 |
| 91 | 33.22 |
| 92 | 15.18 |
| 93 | 6.23 |
| 94 | 13.46 |
| 95 | 15.17 |
| 96 | 8.33 |
| 97 | 11.04 |
| 98 | 7.25 |
| 99 | 13.90 |
| 100 | 12.19 |
| 101 | 14.66 |
| 102 | 12.74 |
| 103 | 6.69 |
| 104 | 32.08 |
| 105 | 19.61 |
| 106 | 14.84 |
| 107 | 605.55 |
| 108 | 121.00 |
| 109 | 59.20 |
| 110 | 3565.00 |
| 111 | 485.35 |

TABLE 10-continued

| hU937 activity | |
|---|---|
| Ex. No. | hU937 IC50, nM |
| 112 | 92.89 |
| 113 | 7764.50 |
| 114 | 63.06 |
| 115 | 329.50 |
| 116 | 8.42 |
| 117 | 14.11 |
| 120 | 134.03 |
| 121 | 30.24 |
| 122 | 144.35 |
| 123 | 48.55 |
| 124 | 164.68 |
| 125 | 128.20 |
| 126 | 29.96 |
| 127 | 3953.75 |
| 128 | 16.19 |
| 129 | 13.77 |
| 130 | 16.10 |
| 131 | 22.05 |
| 132 | 20.16 |
| 133 | 160.35 |
| 134 | 245.55 |
| 135 | 17.63 |
| 136 | 14.32 |
| 137 | 18.81 |
| 138 | 16.40 |
| 139 | 32.64 |
| 140 | 35.38 |
| 141 | 14.49 |
| 142 | 18.98 |
| 143 | 71.01 |
| 144 | 15.77 |
| 145 | 10.99 |
| 146 | 19.43 |
| 147 | 20.91 |
| 148 | 8.58 |
| 149 | 19.75 |
| 150 | 14.24 |
| 151 | 13.00 |
| 152 | 29.23 |
| 153 | 10.03 |
| 154 | 32.14 |
| 155 | 24.82 |
| 156 | 17.13 |
| 157 | 423 |
| 158 | 149 |
| 159 | 9 |
| 160 | 24 |
| 161 | 9 |
| 162 | 121.65 |
| 163a | 171.70 |
| 163b | 87.94 |
| 164 | 356.80 |
| 165 | 108.63 |
| 166 | 196.37 |
| 167 | 463.85 |
| 168 | 45.25 |
| 169 | 20.95 |
| 170 | 15.85 |
| 171 | 120 |
| 172 | 175 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having structural Formula (VI):

(VI)

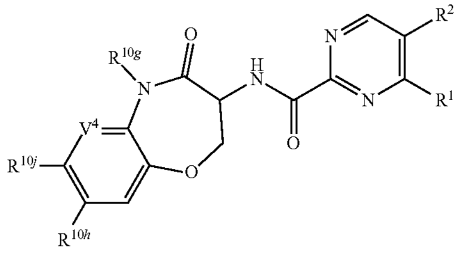

or a salt or tautomer thereof, wherein:

$V^4$ is N;

$R^1$ is chosen from CN, halo, hydroxy, alkyl, cycloalkyl, heterocycloalkyl, aryl, heteroaryl, (cycloalkyl)alkyl, (heterocycloalkyl)alkyl, (aryl)alkyl, and (heteroaryl) alkyl, any one of which is optionally substituted with one or more $R^6$;

$R^2$ is chosen from halo, cyano, alkyl, (alkyl)oxy, (alkyl) thio, (alkyl)sulfonimidoyl, (alkyl)sulfonyl, cycloalkyl, and (cycloalkyl)oxy, any one of which is optionally substituted with one or more $R^7$;

each $R^6$ and $R^7$ is independently chosen from CN, halo, hydroxy, oxo, alkyl, and (alkyl)oxy;

$R^{10g}$ is chosen from H and $C_{1-4}$alkyl;

$R^{10h}$ is chosen from H, F, Cl, and CN;

$R^{10j}$ is H or is chosen from CN, halo, hydroxy, oxo, alkyl, cycloalkyl, heterocycloalkyl, aryl, heteroaryl, (alkyl)oxy, (cycloalkyl)oxy, (heterocycloalkyl)oxy, (aryl)oxy, and (heteroaryl)oxy, any one of which is optionally substituted with one or more $R^{11}$;

each $R^{11}$ is independently chosen from CN, halo, hydroxy, oxo, alkyl, cycloalkyl, heterocycloalkyl, alkylsulfonyl, haloalkylsulfonyl, aryl, heteroaryl, (alkyl)oxy, (cycloalkyl)oxy, (heterocycloalkyl)oxy, (alkylsulfonyl)oxy, (haloalkylsulfonyl)oxy, (aryl) oxy, (heteroaryl)oxy, (alkyl)NH, (cycloalkyl)NH, (heterocycloalkyl)NH, (alkylsulfonyl)NH, (haloalkylsulfonyl)NH, (aryl)NH, and (heteroaryl)NH, any one of which is optionally substituted with one or more $R^{12}$, two $R^{11}$ can combine to form a $C_{5-7}$cycloalkyl or 5- to 7-membered heterocycloalkyl; and each $R^{12}$ is chosen from CN, halo, hydroxy, alkyl, (alkyl)oxy, and oxo.

2. The compound as recited in claim 1, or a salt or tautomer thereof, wherein $R^{10j}$ is H.

3. The compound as recited in claim 1, or a salt or tautomer thereof, wherein $R^{10h}$ is chosen from H, F, and Cl.

4. The compound as recited in claim 1, or a salt or tautomer thereof, wherein $R^2$ is chosen from Cl and $CH_3$.

5. The compound as recited in claim 1, or a salt or tautomer thereof, wherein $R^1$ is chosen from:

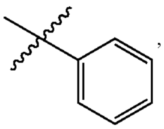

,

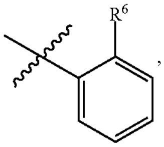

,

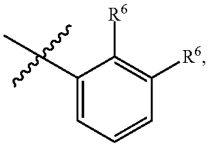

,

-continued
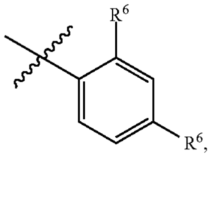
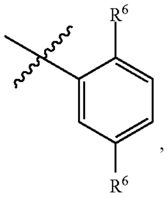
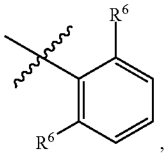
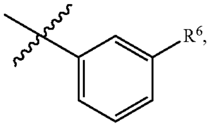
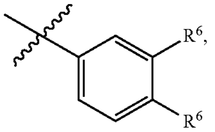
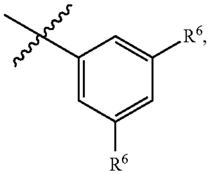
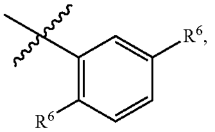
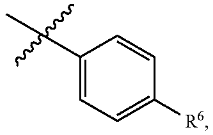
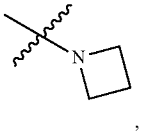
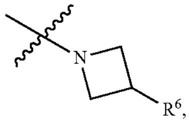
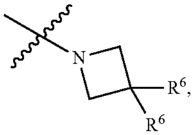
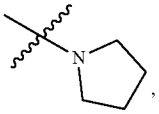
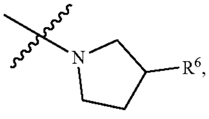
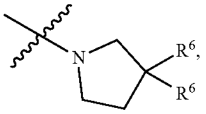
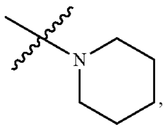
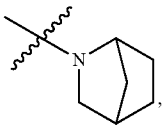
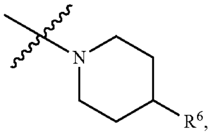
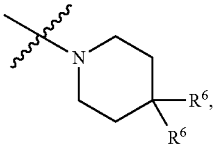
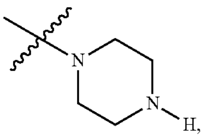
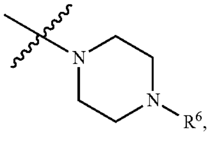
and
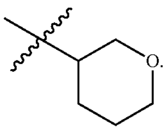
6. A compound selected from the group consisting of:
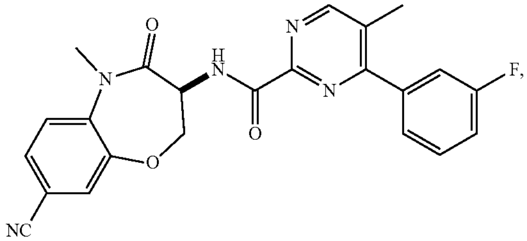
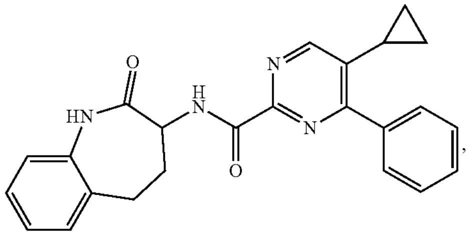
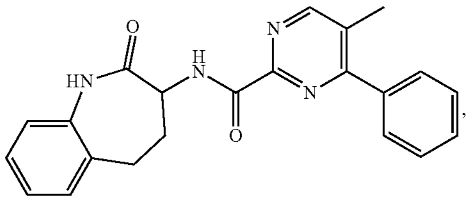
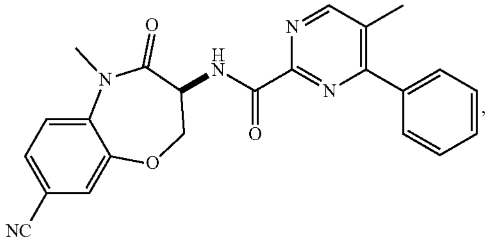
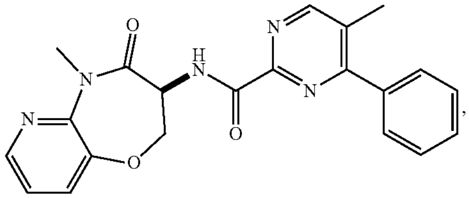
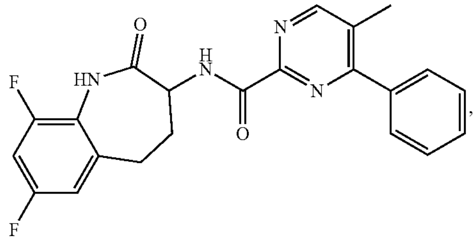
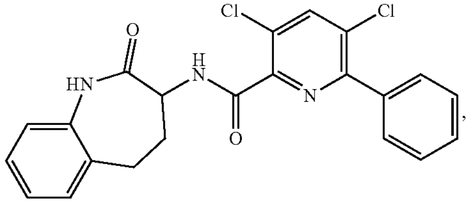

-continued
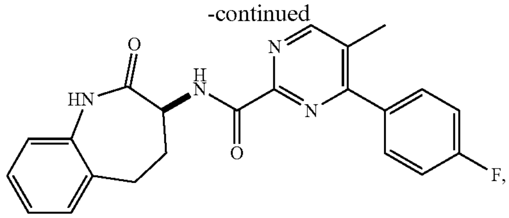
,
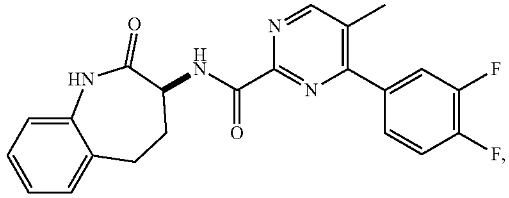
,
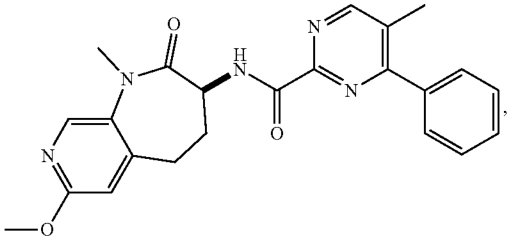
,
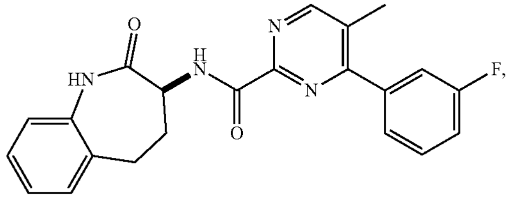
,
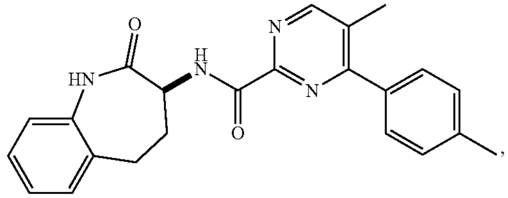
,
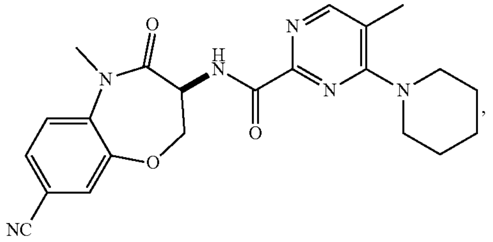
,
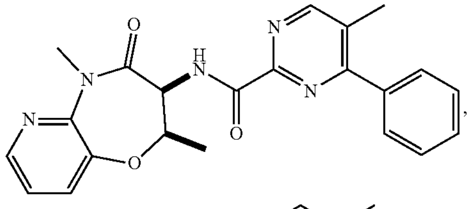
,
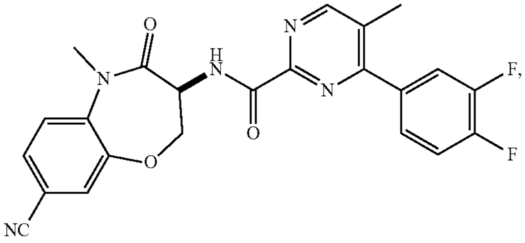
,
-continued
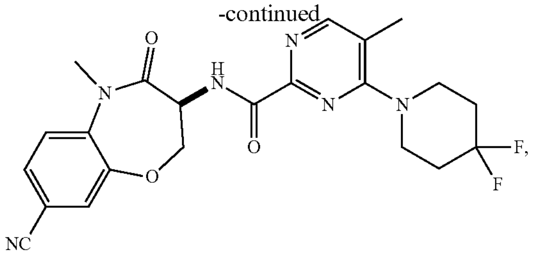
,
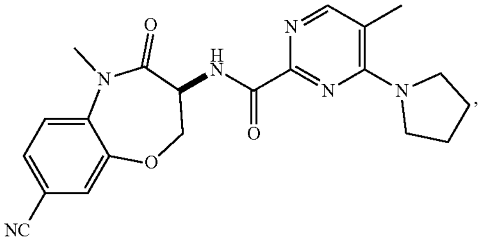
,
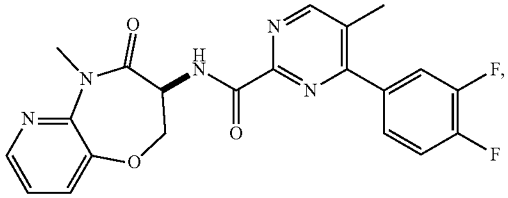
,
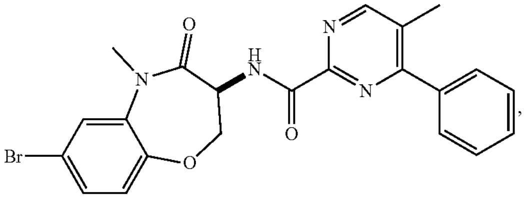
,
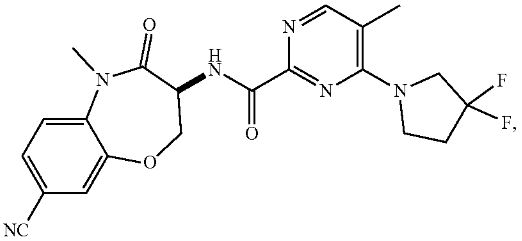
,
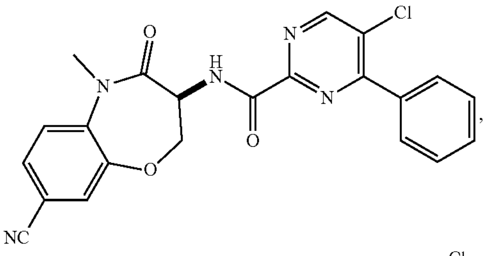
,
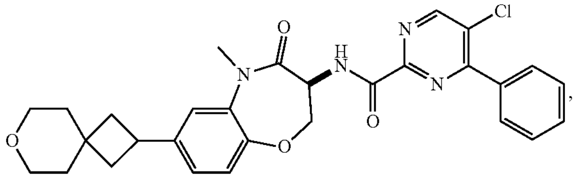
, -continued
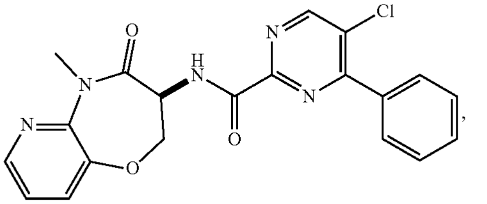
,
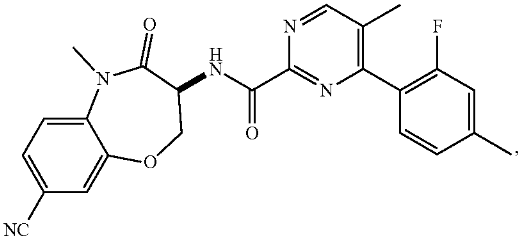
,
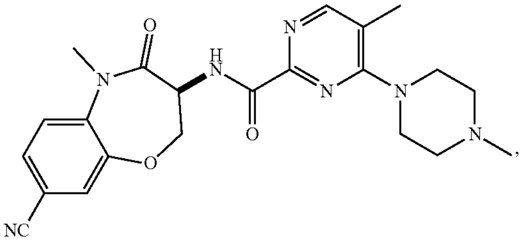
,
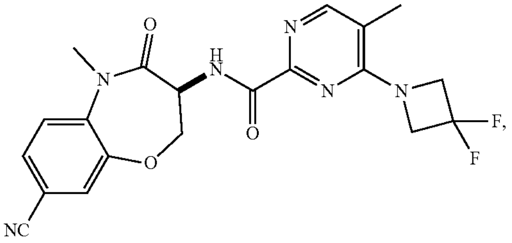
,
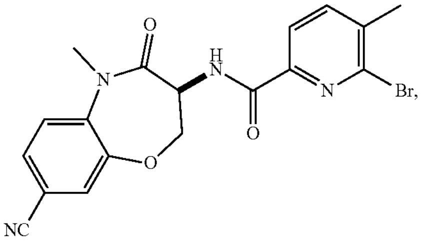
,
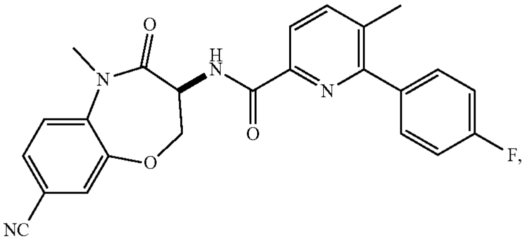
,
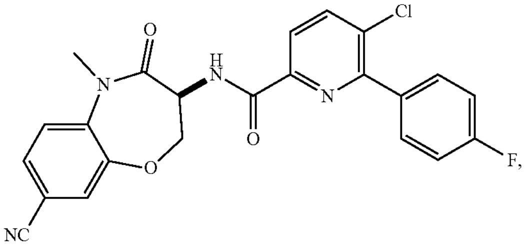
,
-continued
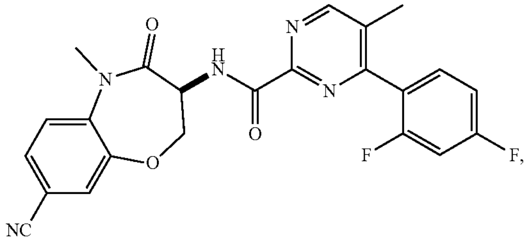
,
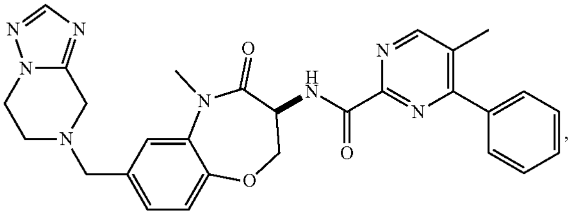 [SMILES: Cc1cnc(C(=O)N[C@H]2COc3ccc(CN4CCn5ncnc5C4)nc3N(C)C2=O)nc1-c1ccccc1]
,
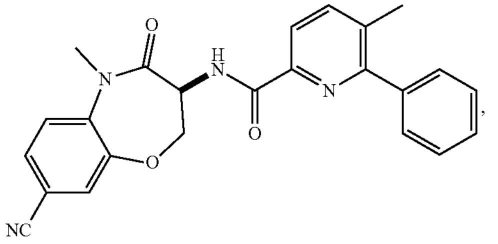
,
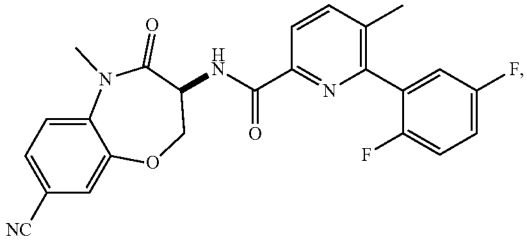
,
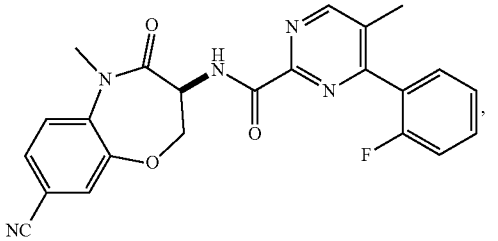
,
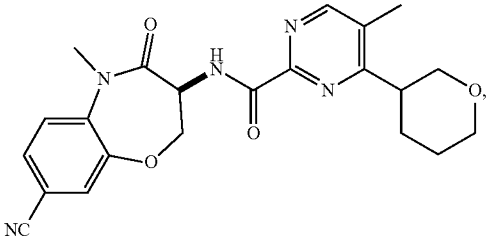
,
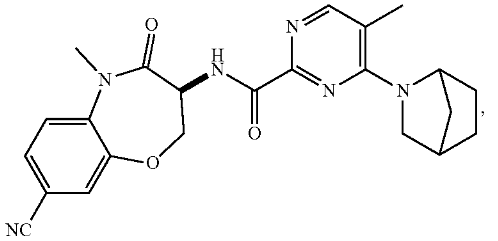
, -continued
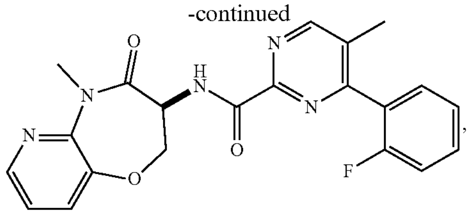
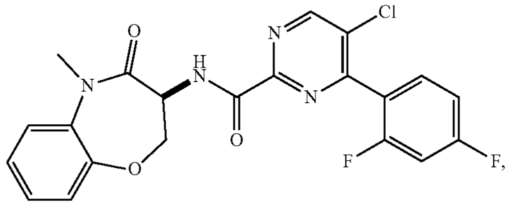
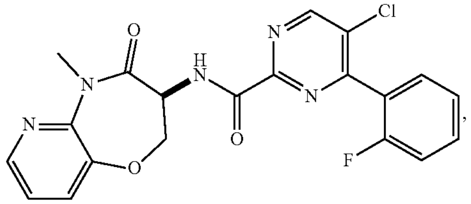
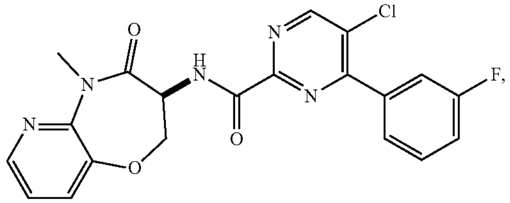
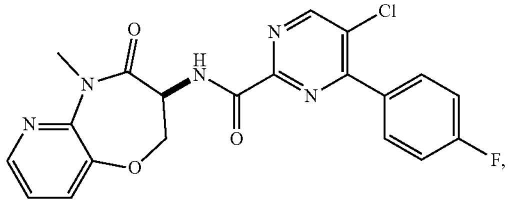
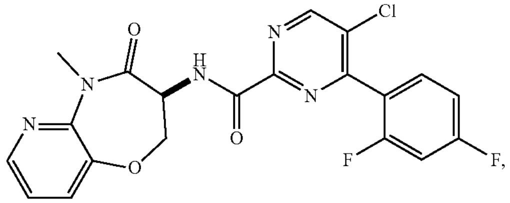
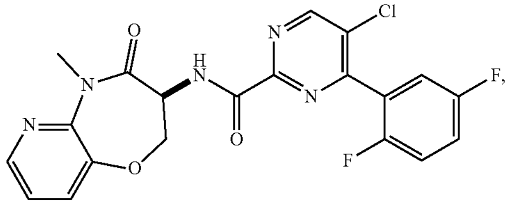
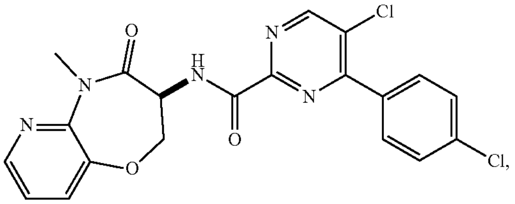
-continued
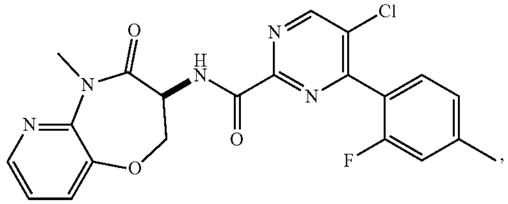
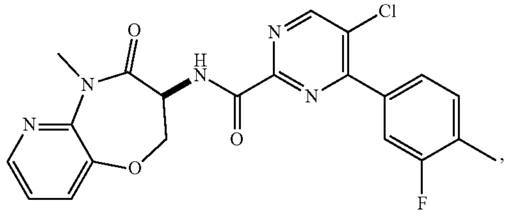
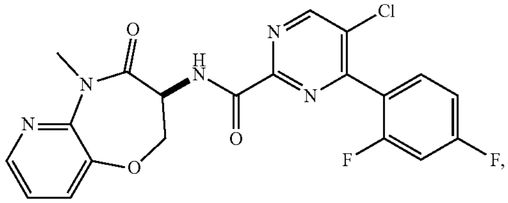
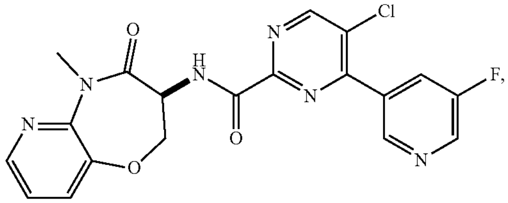
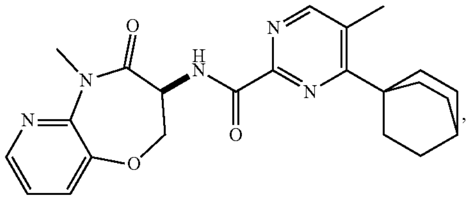
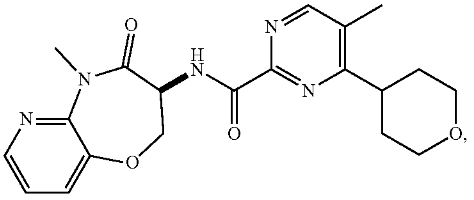
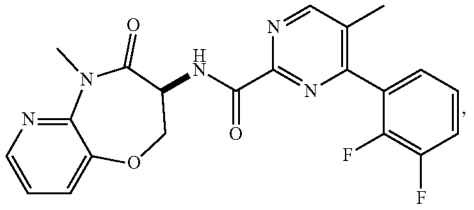
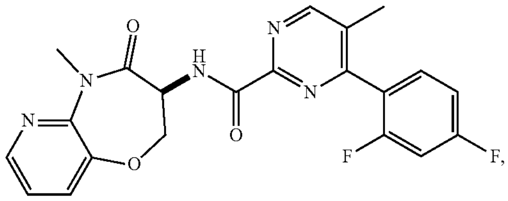

-continued
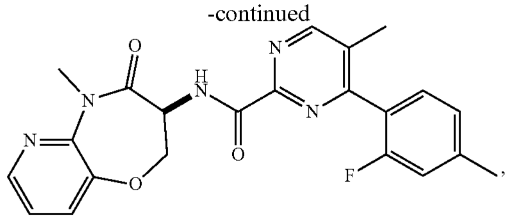
,
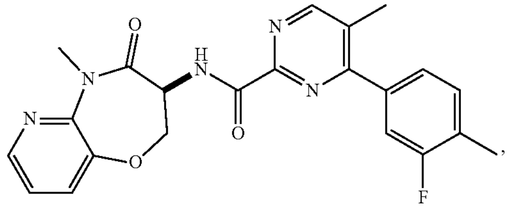
,
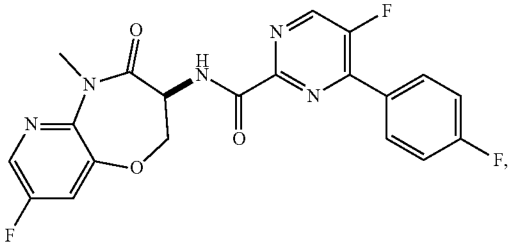
,
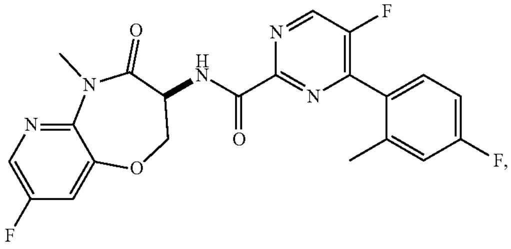
,
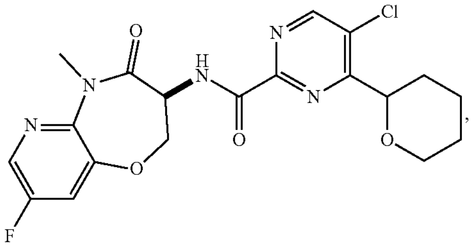
,
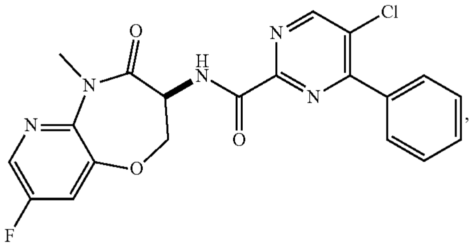
,
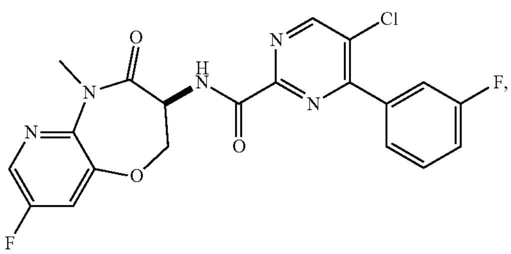
,
-continued
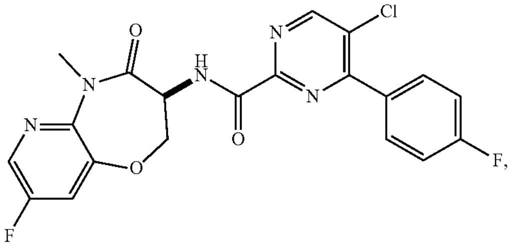
,
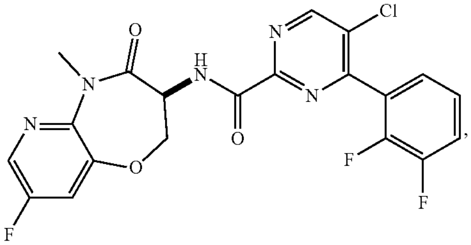
,
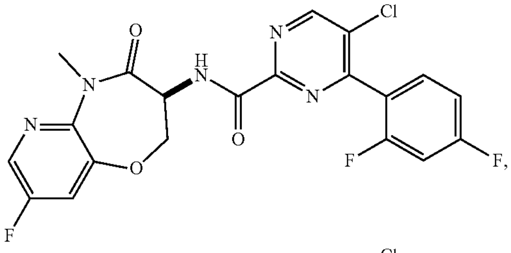
,
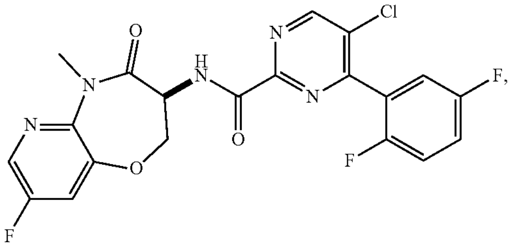
,
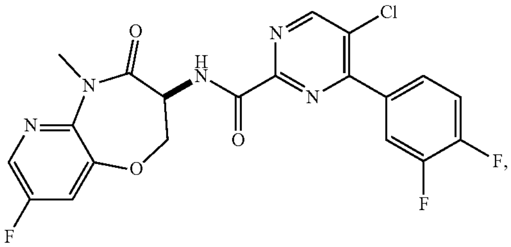
,
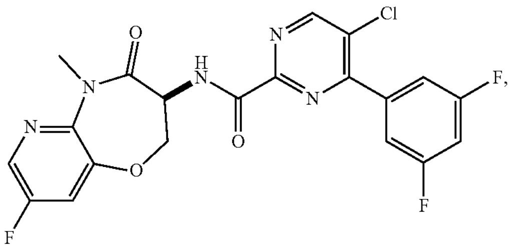
,
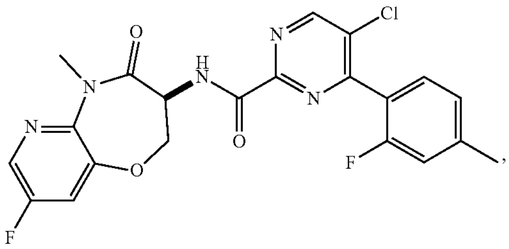
, -continued
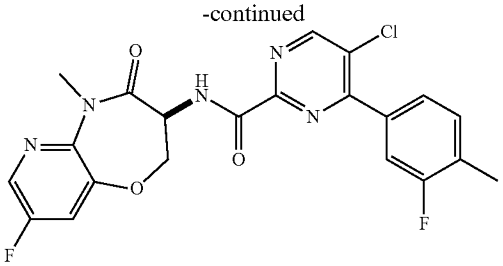
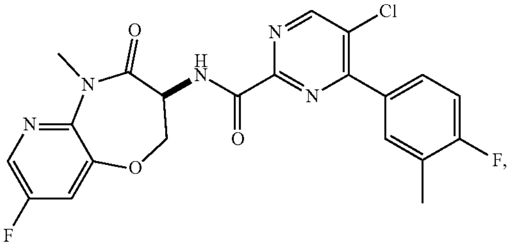,
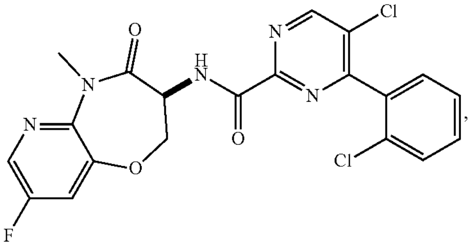,
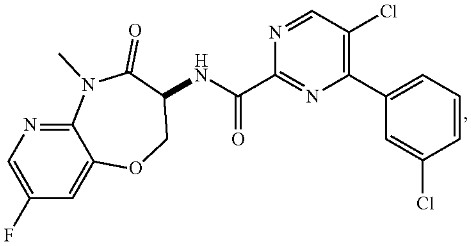,
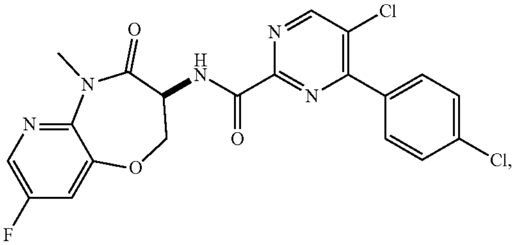,
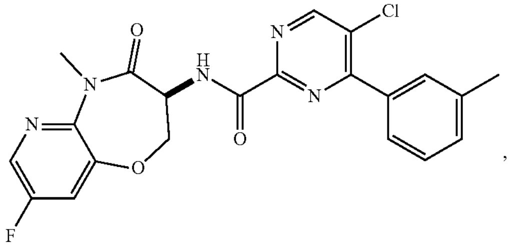,
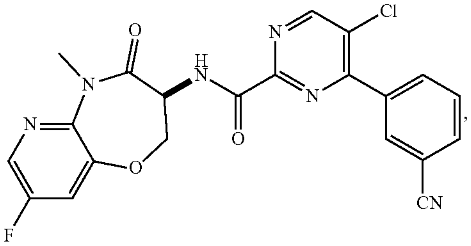,
-continued
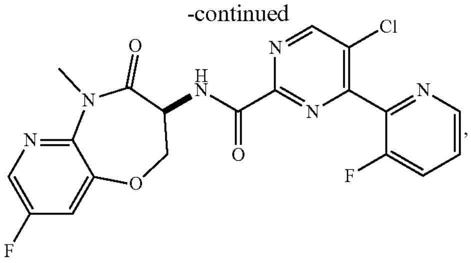,
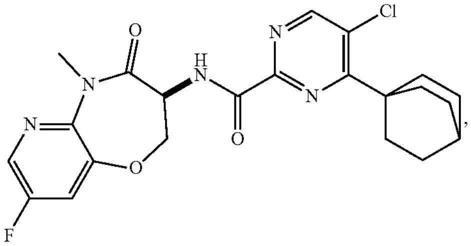,
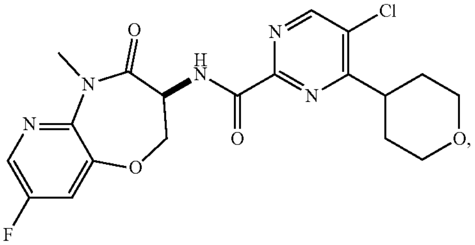,
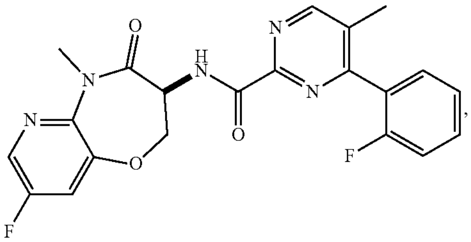,
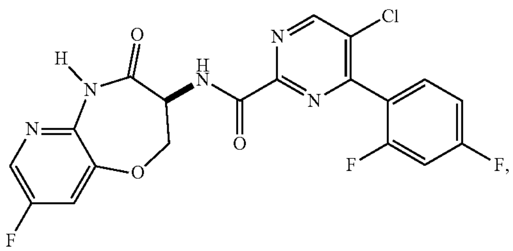,
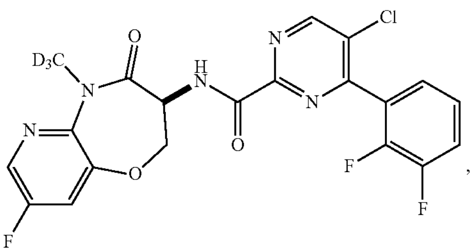,
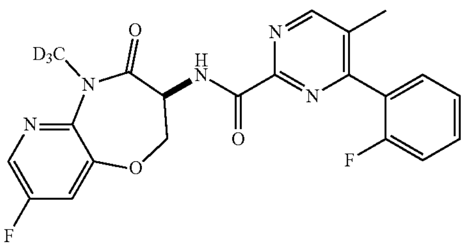, and -continued
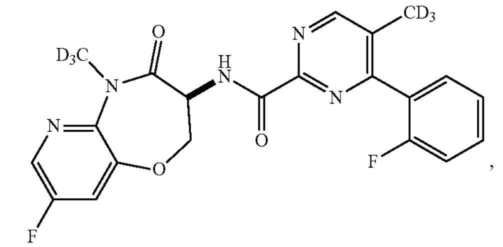
,
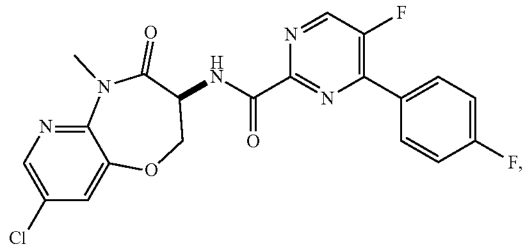
,
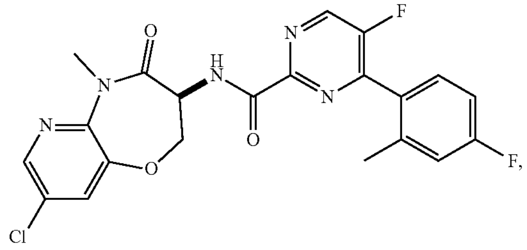
,
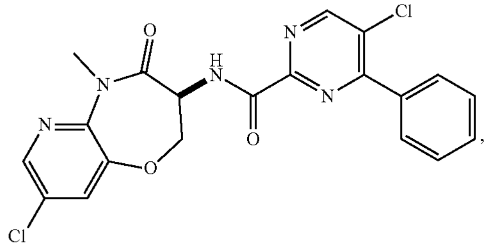
,
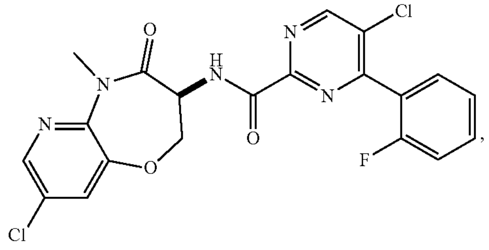
,
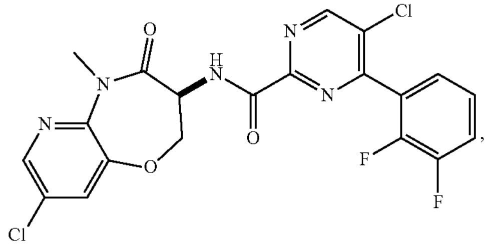
,
-continued
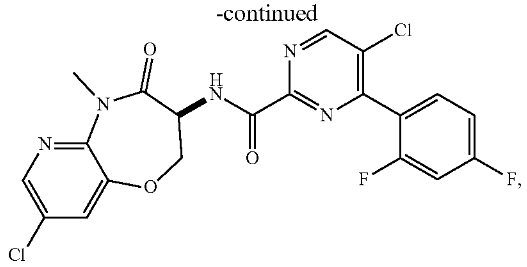
,
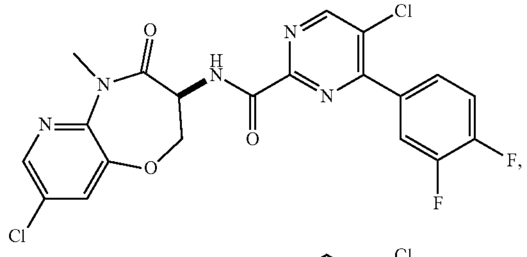
,
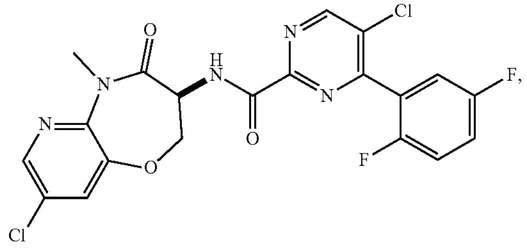
,
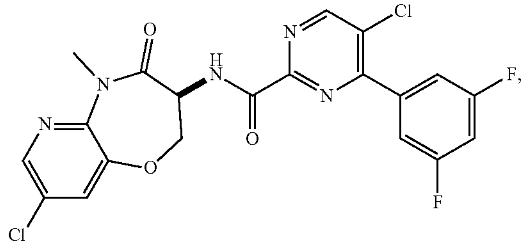
,
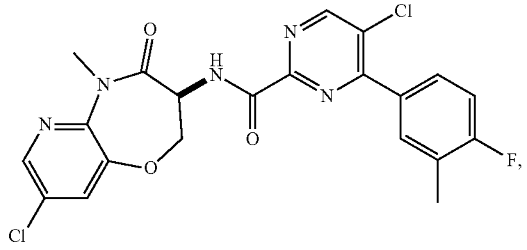
,
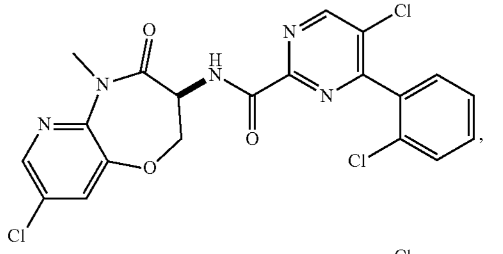
,
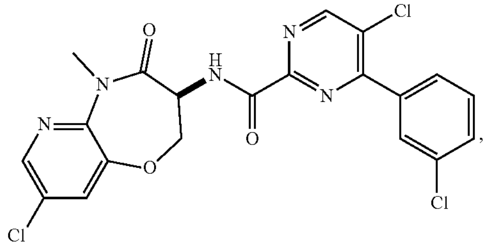
, -continued
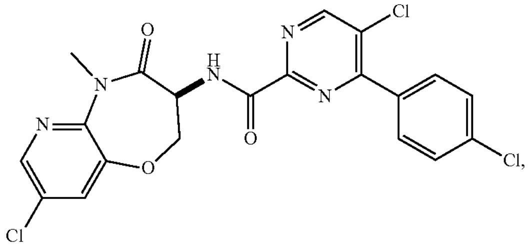
,
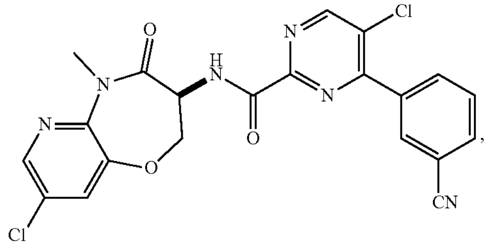
,
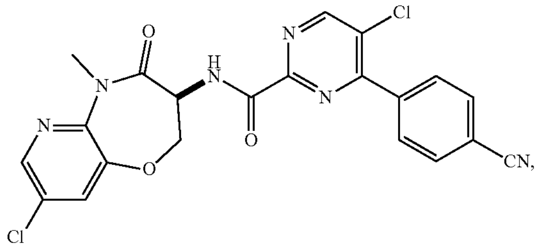
,
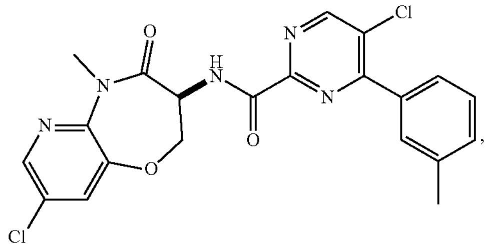
,
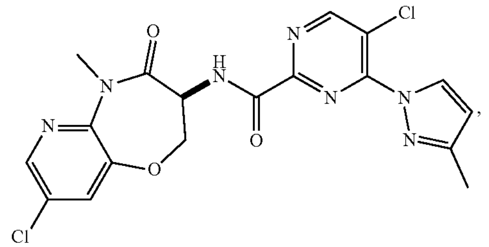
,
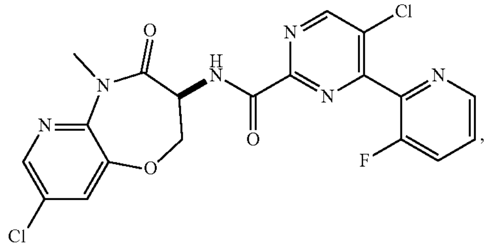
,
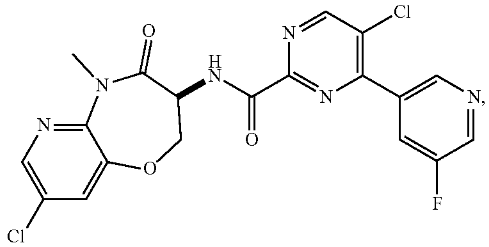
,
-continued
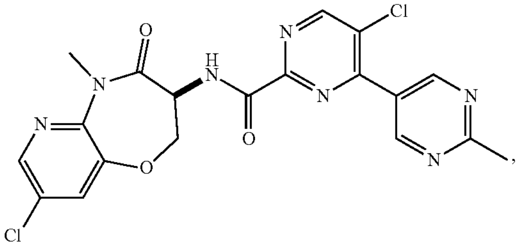
,
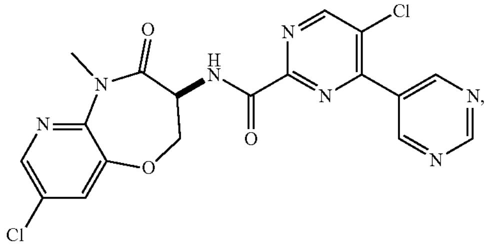
,
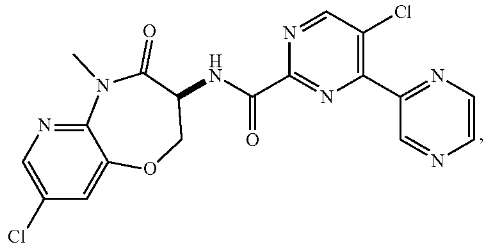
,
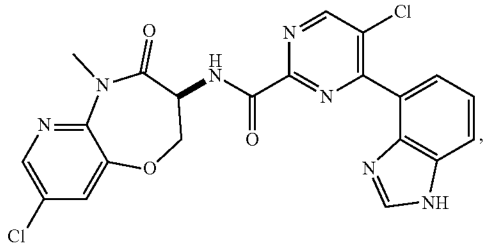
,
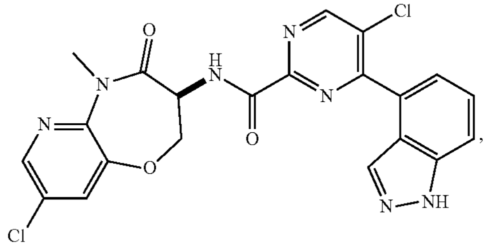
,
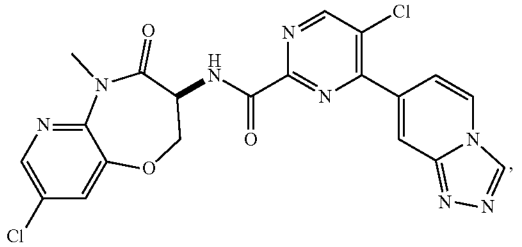
,
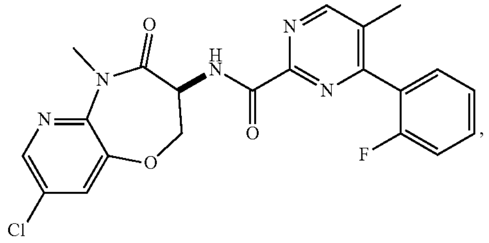 [SMILES: Cc1cnc(C(=O)N[C@H]2COc3cc(Cl)cnc3N(C)C2=O)nc1-c1ccccc1F]
, -continued
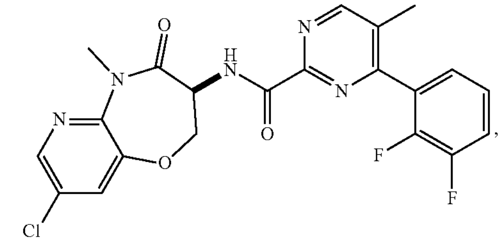 [SMILES: Cc1cnc(C(=O)N[C@H]2COc3cc(Cl)cnc3N(C)C2=O)nc1-c1cccc(F)c1F]
,
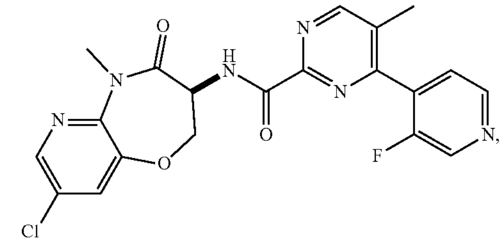
,
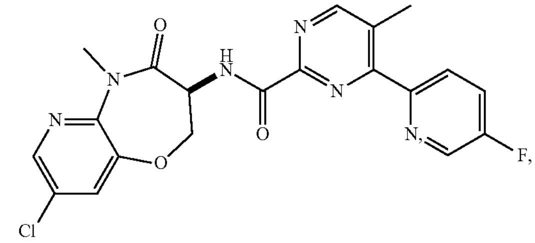
,
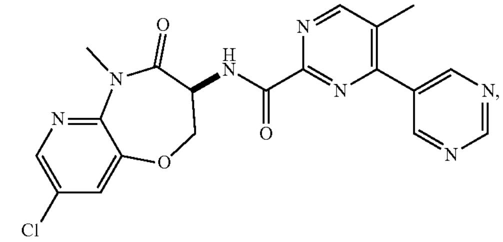
,
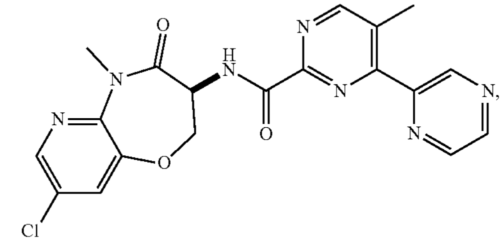
,
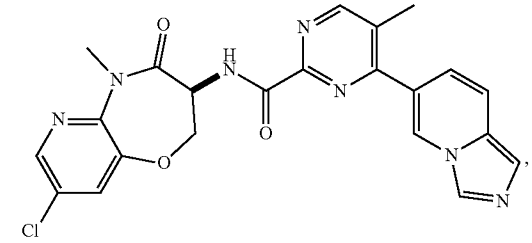
,
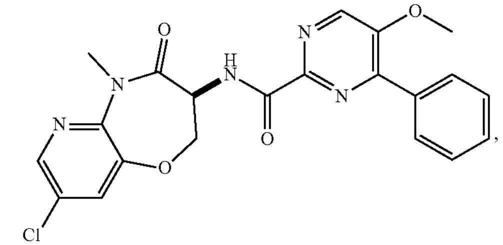
,
-continued
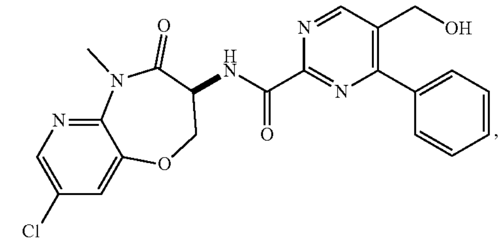 [SMILES: CN1C(=O)[C@@H](NC(=O)c2ncc(CO)c(-c3ccccc3)n2)COc2cc(Cl)cnc21]
,
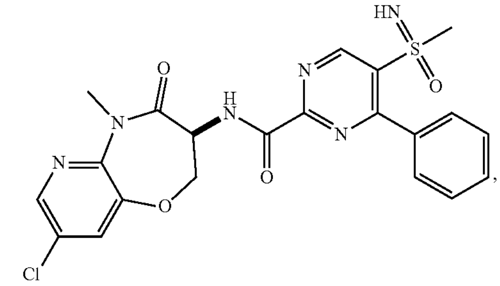
,
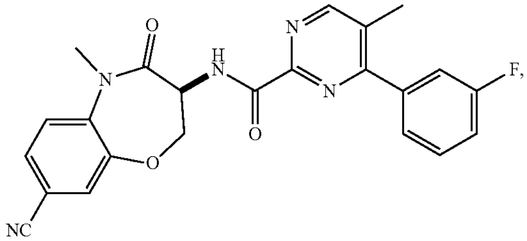
,
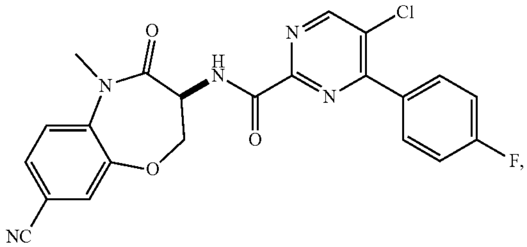
,
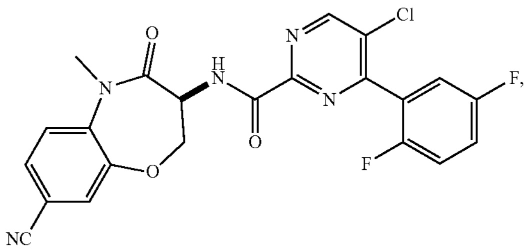
,
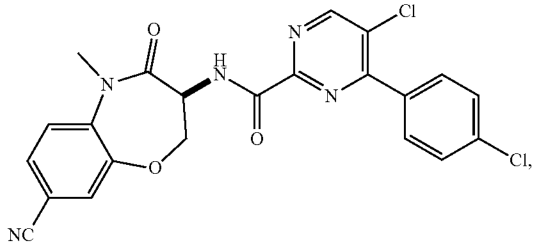
, -continued
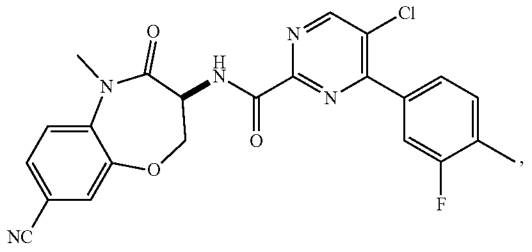
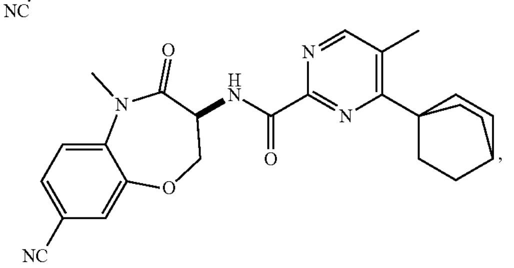
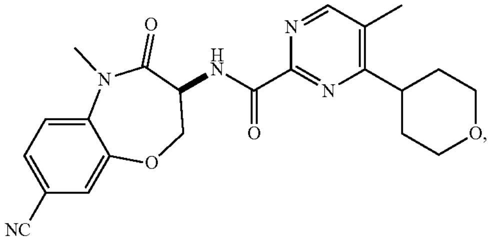
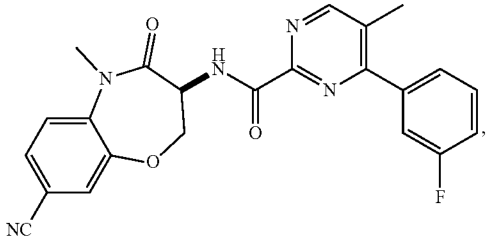
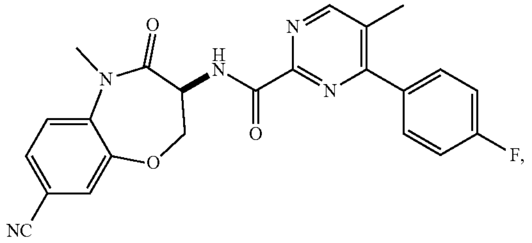
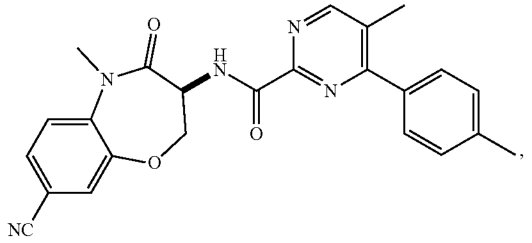
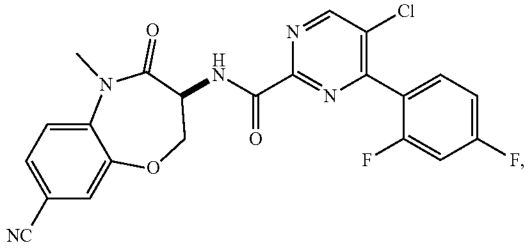
-continued
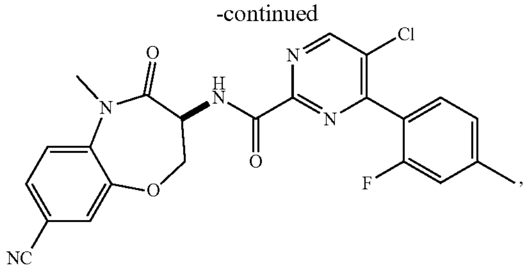
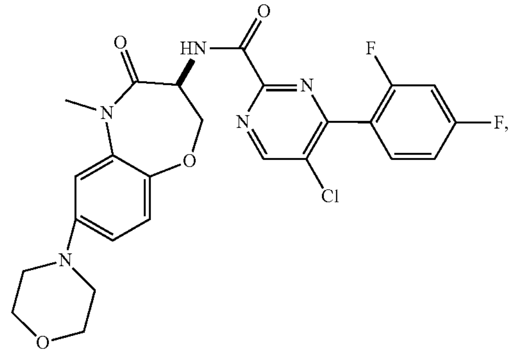
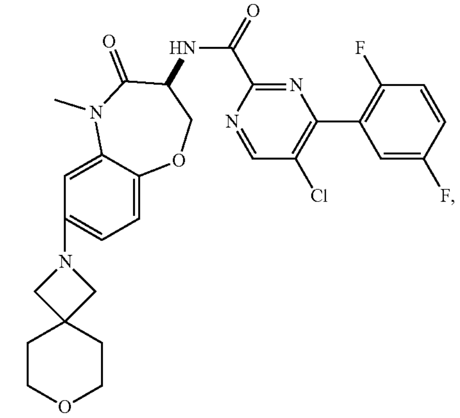
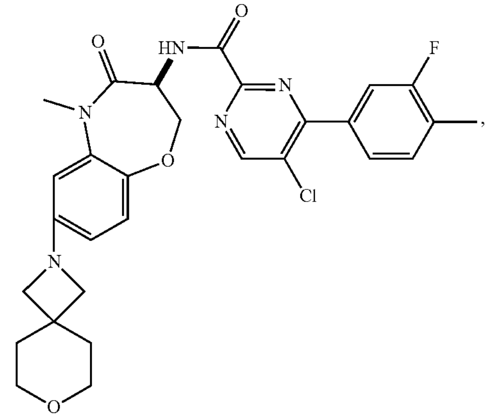

-continued
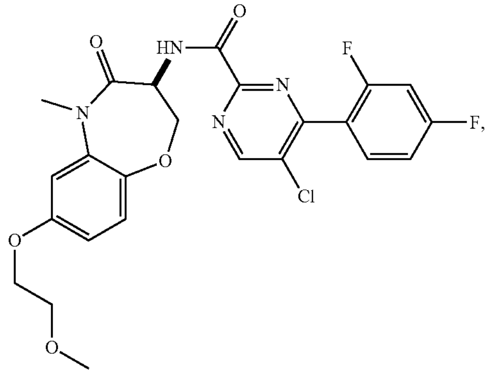
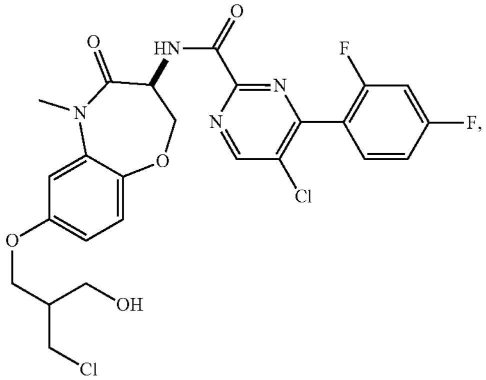
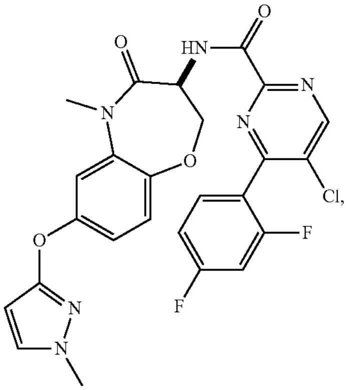 [SMILES: CN1C(=O)[C@@H](NC(=O)c2ncc(Cl)c(-c3ccc(F)cc3F)n2)COc2ccc(Oc3ccn(C)n3)cc21]
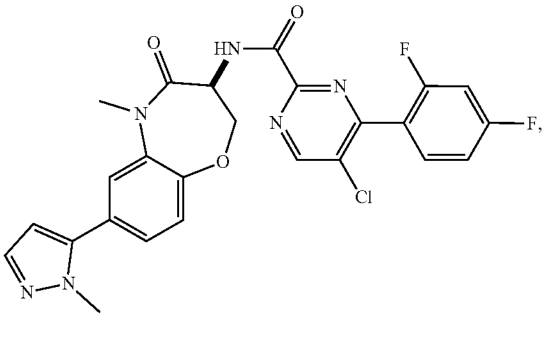
-continued
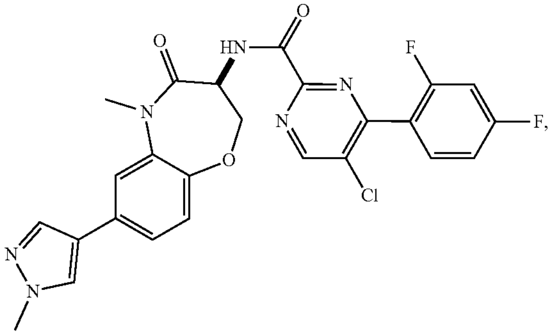
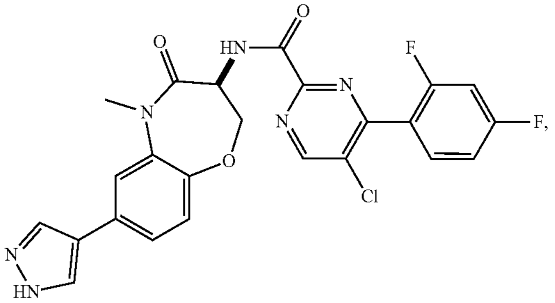
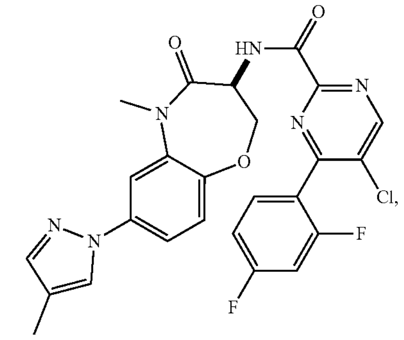
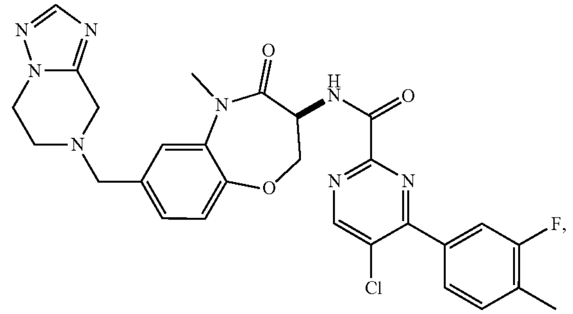
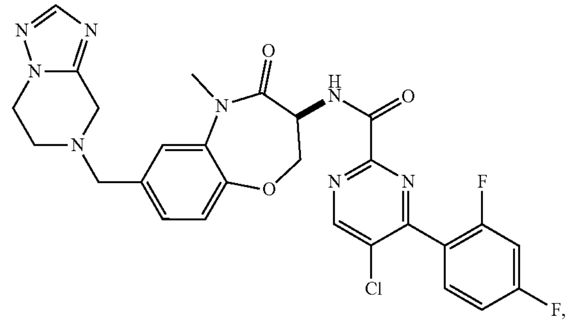

-continued

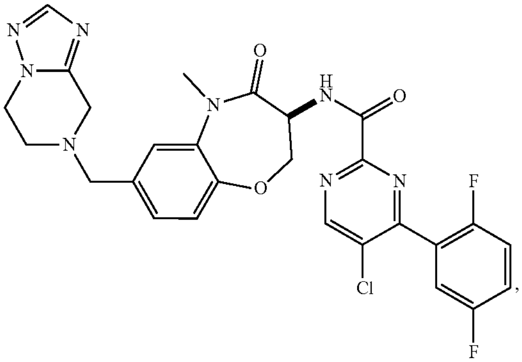
,

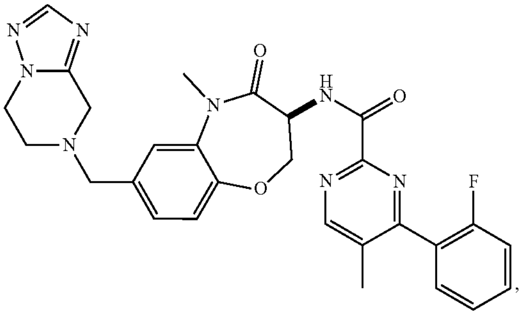
,

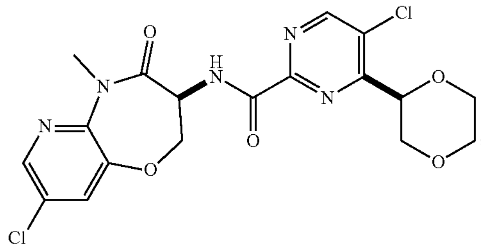
,

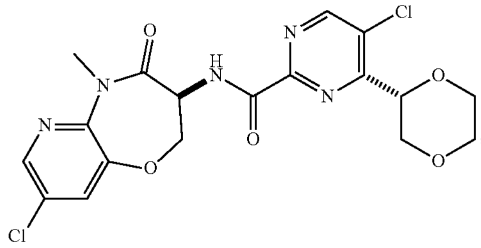
,

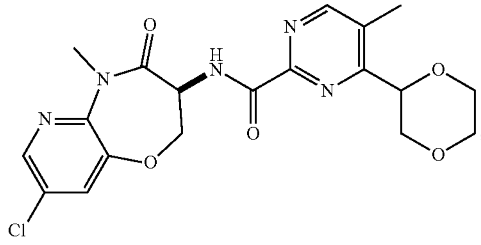
,

-continued

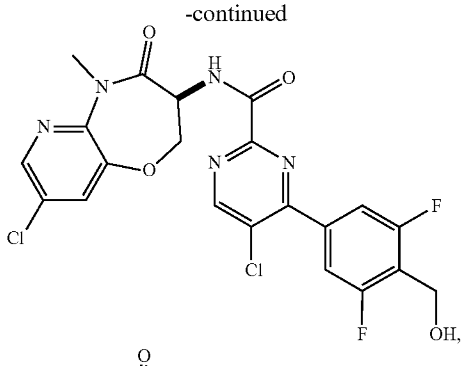

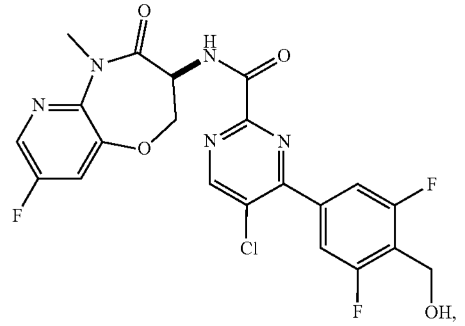

tautomer thereof.

7. A pharmaceutical composition comprising a compound as recited in claim 1, or a salt or tautomer thereof, together with a pharmaceutically acceptable carrier.

8. A method of inhibition of RIPK1 comprising contacting RIPK1 with a compound as recited in claim 1, or a salt or tautomer thereof.

9. A method of treatment of a RIPK1-mediated disease comprising the administration of a therapeutically effective amount of a compound as recited in claim 1, or a salt or tautomer thereof, to a patient in need thereof.

10. A method of treatment of injury to the CNS comprising the administration of a therapeutically effective amount of a compound as recited in claim 1, or a salt or tautomer thereof, to a patient in need thereof.

11. The method as recited in claim 10, wherein said injury is chosen from traumatic brain injury and stroke.

12. The method as recited in claim 9, wherein said disease is a neurological disease.

13. The method as recited in claim 12, wherein said neurological disease is accompanied by an inflammatory component of cellular stress.

14. The method as recited in claim 13, wherein said neurological disease is chosen from Multiple Sclerosis, Neimanm-Pick disease, Alzheimers disease, Parkinson's disease, amyotrophic lateral sclerosis, Lewy body dementia, frontotemporal dementia, and glutamine expansion diseases such as Huntington's disease, Kennedy's disease, spinocerebellar ataxia.

15. The method as recited in claim 9, wherein said disease is a neuropathy.

16. The method as recited in claim 15, wherein said neuropathy is chosen from diabetic neuropathy and chemotherapy induced neuropathy.

17. The method as recited in claim 9, wherein said disease is a retinal disease.

18. The method as recited in claim 17, wherein said retinal disease is chosen from macular degeneration and retinitis.

19. The method as recited in claim 9, wherein said disease is an auto-immune disorder.

20. The method as recited in claim 19, wherein said auto-immune disorder is chosen from ulcerative colitis, rheumatoid arthritis, psoriasis, lupus, and inflammatory bowel disease.

21. The method as recited in claim 9, wherein said disease is an inflammatory disease.

22. The method as recited in claim 21, wherein said inflammatory disease is in one or more organs chosen from lung, heart, kidney, and liver.

23. The method as recited in claim 9, wherein said disease is cancer.

24. The method as recited in claim 23, wherein the cancer is treated by promoting an appropriate immune response to the tumor.

25. The method as recited in claim 9, wherein said disease is a myelodysplastic syndrome (MDS).

26. The method as recited in claim 9, wherein said disease is acute myeloid leukemia (AML).

27. The compound as recited in claim 6, having the structure:

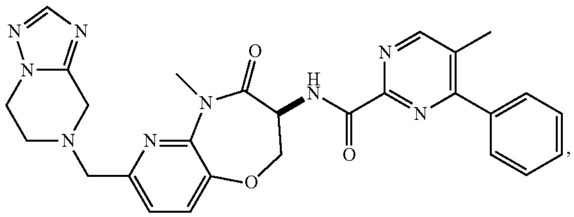

or a salt or tautomer thereof.

28. The compound as recited in claim 6, having the structure:

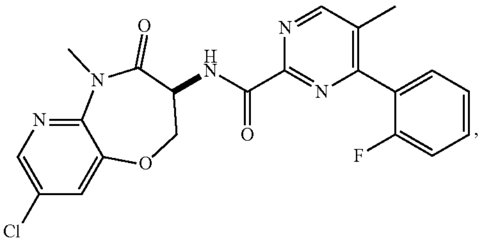

or a salt or tautomer thereof.

29. The compound as recited in claim 6, having the structure:

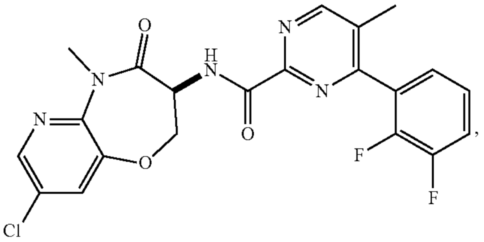

or a salt or tautomer thereof.

30. The compound as recited in claim 6, having the structure:

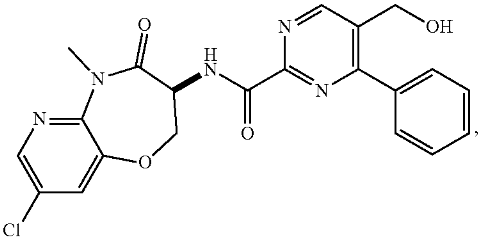

or a salt or tautomer thereof.

31. The compound as recited in claim 6, having the structure:

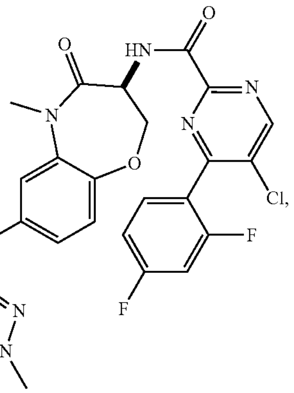

or a salt or tautomer thereof.

* * * * *